US012234271B2

(12) United States Patent
Ptacin et al.

(10) Patent No.: US 12,234,271 B2
(45) Date of Patent: Feb. 25, 2025

(54) IL-2 CONJUGATES AND METHODS OF USE TO TREAT AUTOIMMUNE DISEASES

(71) Applicant: Synthorx, Inc., La Jolla, CA (US)

(72) Inventors: Jerod Ptacin, La Jolla, CA (US); Carolina E. Caffaro, La Jolla, CA (US); Marcos Milla, La Jolla, CA (US)

(73) Assignee: Synthorx, Inc., La Jolla, CA (US)

( * ) Notice: Subject to any disclaimer, the term of this patent is extended or adjusted under 35 U.S.C. 154(b) by 841 days.

(21) Appl. No.: 17/016,003

(22) Filed: Sep. 9, 2020

(65) Prior Publication Data

US 2021/0070827 A1    Mar. 11, 2021

Related U.S. Application Data

(60) Provisional application No. 63/042,393, filed on Jun. 22, 2020, provisional application No. 62/953,075, filed on Dec. 23, 2019, provisional application No. 62/930,987, filed on Nov. 5, 2019, provisional application No. 62/900,488, filed on Sep. 14, 2019, provisional application No. 62/898,478, filed on Sep. 10, 2019.

(51) Int. Cl.
*C07K 14/55* (2006.01)
*A61P 37/06* (2006.01)
*C07D 487/04* (2006.01)

(52) U.S. Cl.
CPC .............. *C07K 14/55* (2013.01); *A61P 37/06* (2018.01); *C07D 487/04* (2013.01)

(58) Field of Classification Search
CPC ............................ C07K 14/55; C07D 487/04
See application file for complete search history.

(56) References Cited

U.S. PATENT DOCUMENTS

| | | |
|---|---|---|
| 3,687,808 A | 8/1972 | Merigan, Jr. et al. |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Dinh et al. |
| 4,849,513 A | 7/1989 | Smith et al. |
| 4,876,335 A | 10/1989 | Yamane et al. |
| 4,904,582 A | 2/1990 | Tullis |
| 4,910,300 A | 3/1990 | Urdea et al. |
| 4,948,882 A | 8/1990 | Ruth |
| 4,958,013 A | 9/1990 | Letsinger |
| 4,981,957 A | 1/1991 | Lebleu et al. |
| 5,015,733 A | 5/1991 | Smith et al. |
| 5,023,243 A | 6/1991 | Tullis |
| 5,034,506 A | 7/1991 | Summerton et al. |
| 5,082,830 A | 1/1992 | Brakel et al. |
| 5,093,232 A | 3/1992 | Urdea et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren, III et al. |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |

(Continued)

FOREIGN PATENT DOCUMENTS

| | | |
|---|---|---|
| CN | 102260353 A | 11/2011 |
| CN | 102665754 A | 9/2012 |

(Continued)

OTHER PUBLICATIONS

International Search Report and Written Opinion, International Application No. PCT/US2020/049954, Nov. 24, 2020, 10 pages.

(Continued)

*Primary Examiner* — Vanessa L. Ford
*Assistant Examiner* — Sandra Carter
(74) *Attorney, Agent, or Firm* — McNeill PLLC

(57) ABSTRACT

Disclosed herein are compositions, kits, and methods comprising interleukin (IL) conjugates (e.g., IL-2 conjugates) useful for the treatment of one or more indications. Also described herein are pharmaceutical compositions and kits comprising one or more of the interleukin conjugates (e.g., IL-2 conjugates).

57 Claims, 29 Drawing Sheets

Specification includes a Sequence Listing.

(56) References Cited

U.S. PATENT DOCUMENTS

| | | |
|---|---|---|
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Ness et al. |
| 5,519,126 A | 5/1996 | Hecht |
| 5,519,134 A | 5/1996 | Acevedo et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,722 A | 1/1997 | Montgomery et al. |
| 5,594,121 A | 1/1997 | Froehler et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,658,873 A | 8/1997 | Bertsch-Frank et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,525,191 B1 | 2/2003 | Ramasamy |
| 6,770,748 B2 | 8/2004 | Imanishi et al. |
| 6,794,499 B2 | 9/2004 | Wengel et al. |
| 6,955,807 B1 | 10/2005 | Shanafelt et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 7,744,861 B2 | 6/2010 | Zhao et al. |
| 7,803,777 B2 | 9/2010 | DeFrees |
| 8,012,465 B2 | 9/2011 | Elias et al. |
| 8,273,833 B2 | 9/2012 | Bentley et al. |
| 8,501,805 B2 | 8/2013 | Seth et al. |
| 8,546,556 B2 | 10/2013 | Seth et al. |
| 9,682,934 B2 | 6/2017 | Stafford et al. |
| 9,732,134 B2 | 8/2017 | Gavin et al. |
| 9,840,493 B2 | 12/2017 | Yang et al. |
| 9,861,705 B2 | 1/2018 | Bossard et al. |
| 9,938,516 B2 | 4/2018 | Zimmerman et al. |
| 9,988,619 B2 | 6/2018 | Zimmerman et al. |
| 10,610,571 B2 | 4/2020 | Ptacin et al. |
| 10,851,144 B2 | 12/2020 | Butz et al. |
| 10,960,079 B2 | 3/2021 | Bossard et al. |
| 11,077,195 B2 | 8/2021 | Ptacin et al. |
| 11,622,993 B2 | 4/2023 | Ptacin et al. |
| 11,701,407 B2 | 7/2023 | Ptacin et al. |
| 2004/0171570 A1 | 9/2004 | Allerson et al. |
| 2005/0130923 A1 | 6/2005 | Bhat et al. |
| 2006/0074035 A1 | 4/2006 | Hong et al. |
| 2007/0287831 A1 | 12/2007 | Seth et al. |
| 2008/0039618 A1 | 2/2008 | Allerson et al. |
| 2008/0300163 A1 | 12/2008 | Cho et al. |
| 2010/0316595 A1 | 12/2010 | Elias et al. |
| 2012/0244112 A1 | 9/2012 | Ast et al. |
| 2012/0315245 A1 | 12/2012 | Leon et al. |
| 2017/0044229 A1 | 2/2017 | Garcia et al. |
| 2017/0260137 A1 | 9/2017 | Stafford et al. |
| 2017/0313753 A1 | 11/2017 | Gavin et al. |
| 2018/0086734 A1 | 3/2018 | Yang et al. |
| 2020/0181220 A1 | 6/2020 | Ptacin et al. |
| 2020/0188484 A1 | 6/2020 | Ptacin et al. |
| 2020/0231644 A1 | 7/2020 | Ptacin et al. |
| 2020/0246467 A1 | 8/2020 | Ptacin et al. |
| 2020/0299349 A1 | 9/2020 | Garcia et al. |
| 2020/0330601 A1 | 10/2020 | Ptacin et al. |
| 2020/0368293 A1 | 11/2020 | Olle |
| 2020/0399338 A1 | 12/2020 | Caffaro et al. |
| 2021/0023230 A1 | 1/2021 | Bossard et al. |
| 2021/0024602 A1 | 1/2021 | Sprogøe et al. |
| 2021/0046160 A1 | 2/2021 | Ptacin et al. |
| 2021/0054040 A1 | 2/2021 | Caffaro et al. |
| 2021/0060169 A1 | 3/2021 | Ikeda et al. |
| 2021/0139554 A1 | 5/2021 | Butz et al. |

(56) References Cited

U.S. PATENT DOCUMENTS

| | | | |
|---|---|---|---|
| 2021/0196796 | A1 | 7/2021 | Penaflor-Aspuria et al. |
| 2021/0221863 | A1 | 7/2021 | Kang et al. |
| 2021/0299222 | A1 | 9/2021 | Rodriguez et al. |
| 2021/0338829 | A1 | 11/2021 | Caffaro et al. |
| 2022/0016249 | A1 | 1/2022 | Ptacin et al. |
| 2022/0016252 | A1 | 1/2022 | Abbadessa et al. |
| 2022/0273767 | A1 | 9/2022 | Caffaro et al. |
| 2022/0324792 | A1 | 10/2022 | Aerni et al. |
| 2023/0265148 | A1 | 8/2023 | Hu et al. |
| 2023/0277627 | A1 | 9/2023 | Caffaro et al. |
| 2023/0302089 | A1 | 9/2023 | Caffaro et al. |
| 2023/0416327 | A1 | 12/2023 | Caffaro et al. |
| 2024/0082359 | A1 | 3/2024 | Ptacin et al. |

FOREIGN PATENT DOCUMENTS

| | | | |
|---|---|---|---|
| CN | 104231068 | A | 12/2014 |
| EP | 0614907 | A1 | 9/1994 |
| EP | 0629633 | A2 | 12/1994 |
| EP | 2382228 | B1 | 8/2020 |
| EP | 3280725 | B1 | 8/2020 |
| EP | 4011388 | A1 | 6/2022 |
| EP | 4209503 | A1 | 7/2023 |
| JP | 2008509651 | A | 4/2008 |
| JP | 2014506116 | A | 3/2014 |
| WO | 9213869 | A1 | 8/1992 |
| WO | 9422890 | A1 | 10/1994 |
| WO | 9735869 | A1 | 10/1997 |
| WO | 1999014226 | A3 | 8/1999 |
| WO | 9962923 | A2 | 12/1999 |
| WO | 0105801 | A1 | 1/2001 |
| WO | 02070533 | A2 | 9/2002 |
| WO | 2004007713 | A1 | 1/2004 |
| WO | 2004106356 | A1 | 12/2004 |
| WO | 2005021570 | A1 | 3/2005 |
| WO | 2005026187 | A1 | 3/2005 |
| WO | 2005086751 | A2 | 9/2005 |
| WO | 2006049297 | A1 | 5/2006 |
| WO | 2007015557 | A1 | 2/2007 |
| WO | 2007066737 | A1 | 6/2007 |
| WO | 2007090071 | A2 | 8/2007 |
| WO | 2007134181 | A3 | 1/2008 |
| WO | 2008101157 | A1 | 8/2008 |
| WO | 2008106186 | A3 | 10/2008 |
| WO | 2009006478 | A2 | 1/2009 |
| WO | 2008150729 | A3 | 3/2009 |
| WO | 2008154401 | A3 | 3/2009 |
| WO | 2009123216 | A1 | 10/2009 |
| WO | 2011043385 | A1 | 4/2011 |
| WO | 2012065086 | A1 | 5/2012 |
| WO | 2011139699 | A3 | 7/2013 |
| WO | 2015021432 | A1 | 2/2015 |
| WO | 2016025385 | A1 | 2/2016 |
| WO | 2015157555 | | 3/2016 |
| WO | 2016115168 | A1 | 7/2016 |
| WO | 2016164937 | A2 | 10/2016 |
| WO | 2017106767 | A1 | 6/2017 |
| WO | 2017223528 | A1 | 12/2017 |
| WO | 2019014262 | A1 | 1/2019 |
| WO | 2019014267 | A1 | 1/2019 |
| WO | 2019028419 | A1 | 2/2019 |
| WO | 2019028425 | A1 | 2/2019 |
| WO | 2019165453 | A1 | 8/2019 |
| WO | 2019173832 | A2 | 9/2019 |
| WO | 2020020783 | A1 | 1/2020 |
| WO | 2020056066 | A1 | 3/2020 |
| WO | 2020097325 | A1 | 5/2020 |
| WO | 2020146221 | A1 | 7/2020 |
| WO | 2020163532 | A1 | 8/2020 |
| WO | 2020201095 | A1 | 10/2020 |
| WO | 2020219943 | A1 | 10/2020 |
| WO | 2020252418 | A2 | 12/2020 |
| WO | 2021030374 | A1 | 2/2021 |
| WO | 2021030483 | A1 | 2/2021 |
| WO | 2021030602 | A1 | 2/2021 |
| WO | 2021030706 | A1 | 2/2021 |
| WO | 2021041206 | A1 | 3/2021 |
| WO | 2021091986 | A1 | 5/2021 |
| WO | 2021093633 | A1 | 5/2021 |
| WO | 2021133839 | A1 | 7/2021 |
| WO | 2021140416 | A2 | 7/2021 |
| WO | 2021263026 | A1 | 12/2021 |
| WO | 2022076853 | A1 | 4/2022 |
| WO | 2022076859 | A1 | 4/2022 |
| WO | 2022174101 | A1 | 8/2022 |
| WO | 2022256538 | A1 | 12/2022 |
| WO | 2023122750 | A1 | 6/2023 |
| WO | 2023137401 | A1 | 7/2023 |

OTHER PUBLICATIONS

Zhang et al., "Site-specific PEGylation of interleukin-2 enhances immunosuppression via the sustained activation of regulatory T cells," Nature Biomedical Engineering, Nov. 2021, 1288-1135, vol. 5.

Malyshev et al. Efficient and sequence-independent replication of DNA containing a third base pair establishes a functional six-letter genetic alphabet. PNAS USA 109: 12005-12010 (2012).

Manoharan et al. Chemical Modifications to Improve Uptake and Bioavailability of Antisense Oligonucleotides. Ann. N.Y. Acad. Scie 660:306-309 (1992).

Manoharan et al. Cholic Acid-Oligonucleotide Conjugates for Antisense Applications. Bioorg. Med. Chem. Let 4:1053-1060 (1994).

Manoharan et al. Introduction of a Lipophilic Thioether in the Minor Groove of Nucleic Acids for Antisense Applications. Bioorg. Med. Chem. Let 3:2765-2770 (1993).

Manoharan et al. Lipidic Nucleic Acids. Tetrahedron Lett 36:3651-3654 (1995).

Manoharan et al. Oligonucleotide Conjugates: Alteration of the Pharmacokinetic Properties of Antisense Agents. Nucleosides & Nucleotides 14:969-973 (1995).

Matteucci. Oligonucleotide Analogs: an Overview in Oligonucleotides as Therapeutic Agents, (Chadwick and Cardew, ed.) John Wiley and Sons, New York, NY; Zon, 1993, Oligonucleoside Phosphorothioates in Protocols for Oligonucleotides and Analogs, Synthesis and Properties, Humana Press, pp. 165-190 (1997).

Micklefield. Backbone Modification of Nucleic Acids: Synthesis, Structure and Therapeutic Applications. Current Medicinal Chemistry 8:1157-1179 (2001).

Mikhailov et al. Substrate Properties of C'-Methylnucleoside and C'-Methyl-2'-deoxynucleoside 5'-Triphosphates in RNA and DNA Synthesis Reactions Catalysed by RNA and DNA Polymerases Nucleosides & Nucleotides 10(1-3):339-343 (1991).

Miller et al. Conformation and interaction of dinucleoside mono- and diphosphates. V. Syntheses and properties of adenine and thymine nucleoside alkyl phosphotriesters, the neutral analogs of dinucleoside monophosphates. JACS 93:6657-6665 (1971).

Mishra et al. Improved leishmanicidal effect of phosphorotioate antisense oligonucleotides by LDL-mediated delivery. Biochem Biophys Acta 1264:229-237 (1995).

Napolitano et al. Emergent rules for codon choice elucidated by editing rare arginine codons in *Escherichia coli*. PNAS 113(38): E5588-5597 (2016).

Nawrot et al. A novel class of DNA analogs bearing 5'-C-phosphonothymidine units: synthesis and physicochemical and biochemical properties. Oligonucleotides16(1):68-82 (2006).

Nelson et al. N3'-> PS' Oligodeoxyribonucleotide Phosphoramidates: A New Method of Synthesis Based on a Phosphoramidite Amine-Exchange Reaction. J Org Chem 62:7278-7287 (1997).

Neumann et al. Encoding multiple unnatural amino acids via evolution of a quadruplet-decoding ribosome. Nature 464(7287):441-444 (2010).

Nielsen et al. Sequence-selective recognition of DNA by strand displacement with a thymine-substituted polyamide. Science 254:1497-1500 (1991).

Oberhauser et al. Effective incorporation of 2'-O-methyl-oligoribonucleotides into liposomes and enhanced cell association through modification with thiocholesterol. Nucl. Acids Res. 20:533-538 (1992).

(56) References Cited

OTHER PUBLICATIONS

Orum et al. Locked nucleic acids: a promising molecular family for gene-function analysis and antisense drug development. Curr Opinion Mol Ther 3:239-243 (2001).
Ostrov et al. Design, synthesis, and testing toward a 57-codon genome. Science 353(6301): 819-822 (2016).
Peyrottes et al. Oligodeoxynucleoside phosphoramidates (P-NH2): synthesis and thermal stability of duplexes with DNA and RNA targets. Nucleic Acids Res 24:1841-1848 (1996).
Saha et al. 5'-Methyl-DNA—A New Oligonucleotide Analog: Synthesis and Biochemical Properties. J Org Chem 60:788-789 (1995).
Saison-Behmoaras et al. Short modified antisense oligonucleotides directed against Ha-ras point mutation induce selective cleavage of the mRNA and inhibit T24 cells proliferation. EMBO J. 10:1111-1118 (1991).
Sanghvi. Chapter 15: Heterocyclic Base Modifications In Nucleic Acids And Their Applications In Antisense Oligonucleotides. Antisense Research and Applications, Crookeand Lebleu Eds., CRC Press (pp. 273-288) (1993).
Schultz et al. Oligo-2'-fluoro-2'-deoxynucleotide N3'-> PS' phosphoramidates: synthesis and properties. Nucleic Acids Res 24:2966-2973 (1996).
Shea et al., Nucl. Acids Res., 1990, 18, 3777-3783.
Singh et al. LNA (locked nucleic acids): synthesis and high-affinity nucleic acid recognition. Chem Commun 4:455-456 (1998).
Singh et al. Synthesis of 2'-amino-LNA: A novel conformationally restricted high-affinity oligonucleotide analogues with a handle. J Bio Chem 63:10035-10039 (1998).
Srivastava et al. Five- and six-membered conformationally locked 2',4'-carbocyclic ribo-thymidines: synthesis, structure, and biochemical studies. J Am Chem Soc 129(26):8362-8379 (2007).
Svinarchuk et al. Inhibition of HIV proliferation in MT-4 cells by antisense oligonucleotide conjugated to lipophilic groups. Biochimie 75:49-54 (1993).
Vrudhula et al. Isozyme-specific enzyme inhibitors. 13. S-[5'(R)-[(N-triphosphoamino)methyl]adenosyl]-L-homocysteine, a potent inhibitor of rat methionine adenosyltransferases. J Med Chem 30:888-894 (1987).
Wahlestedt et al. Potent and nontoxic antisense oligonucleotides containing locked nucleic acids. PNAS USA 97:5633-5638 (2000).
Wang et al. Biophysical and biochemical properties of oligodeoxynucleotides containing 4'-C-and 5'-C-substituted thymidines. Bioorg Med Chem Lett 9:885-890 (1999).
Wang et al. Synthesis of Azole Nucleoside 5'-Monophosphate Mimics (P1 Ms) and Their Inhibitory Properties of IMP Dehydrogenases. Nucleosides Nucleotides & Nucleic Acids 23(1 & 2):317-337 (2004).
Wu et al. Functionalization of the sugar moiety of oligoribonucleotides on solid support. Bioconjugate Chem 10:921-924 (1999).
Wu et al. Synthesis of 5'-C- and 2'-O-(Bromoalkyl)-Substituted Ribonucleoside Phosphoramidites for the Post-synthetic Functionalization of Oligonucleotides on Solid Support. Helvetica Chimica Acta 83:1127-1143 (2000).
Wurm et al. Squaric acid mediated synthesis and biological activity of a library of linear and hyperbranched poly (glycerol)-protein conjugates. Biomacromolecules 13: 1161-1171 (2012).
Zhang et al. A semisynthetic organism engineered for the stable expansion of the genetic alphabet. PNAS USA 114(6):1317-1322 (2017).
Zhang et al. A Semi-Synthetic Organism that Stores and Retrieves Increased Genetic Information. Nature 551(7682):644-647 (2017).
Zon. Chapter 8: Oligonucleotide Phosphorothioates in Protocols for Oligonucleotides and Analogs, Synthesis and Properties. Humana Press (pp. 165-190) (1993).
Beigelman et al. Synthesis of 5'-C-Methyl-D-allo- & L-Talo-ribonucleoside 3'-0-Phosphoramidites & Their Incorporation into Hammerhead Ribozymes. Nucleosides and Nucleotides 14(3-5):901-905 (1995).
Betz et al. Structural insights into DNA replication without hydrogen bonds. J Am Chem Soc 135:18637-18643 (2013).
Bohringer et al. Synthesis of 5'-deoxy-5'-methylphosphonate linked thymidine oligonucleotides. Tet Lett 34:2723-2726 (1993).
Braasch et al. Locked nucleic acid (LNA): fine-tuning the recognition of DNA and RNA. Chem Bio 8:1-7 (2001).
Chattopadhyay et al. Structural Basis of Inducible Costimulator Ligand Costimulatory Function: State and Functional Mapping of the Determination of the Cell Surface Oligomeric Receptor Binding Site of the Protein. J Immunol; 177:3920-3929 (2006).
Chaturvedi et al. Stabilization of triple-stranded oligonucleotide complexes: use of probes containing alternating phosphodiester and stereo-uniform cationic phosphoramidate linkages. Nucleic Acids Res. 24:2318-2323 (1996).
Chen et al. Phosphonate Analogues of Cytosine Arabinoside Monophosphate. Phosphorus, Sulfur and Silicon 177:1783-1786 (2002).
Chen et al. Selective chemical labeling of proteins. Org. Biomol. Chem. 14:5417 (2016).
Collingwood et al. The Synthesis and Incorporation in Oligonucleotides of a Thymidine Dimer Containing an Internucleoside Phosphinate Linkage. Synlett 7:703-705 (1995).
Co-pending U.S. Appl. No. 16/634,487, filed Jan. 27, 2020; also cited herein as US 2020/0231644.
Co-pending U.S. Appl. No. 16/803,816, filed Feb. 27, 2020; also cited herein as US 2020/0188484.
Co-pending U.S. Appl. No. 16/918,930, filed Jul. 1, 2020; also cited herein as US 2020/0330601.
Co-pending U.S. Appl. No. 16/993,967, filed Aug. 14, 2020.
Co-pending U.S. Appl. No. 16/999,638, filed Aug. 21, 2020.
Co-pending U.S. Appl. No. 17/001,965, filed Aug. 25, 2020.
Crooke et al. Pharmacokinetic properties of several novel oligonucleotide analogs in mice. J Pharmacol Exp Ther 277:923-937 (1996).
De Mesmaeker et al. Amide-Modified Oligonucleotides with Preorganized Backbone and Furanose Rings: Highly Increased Thermodynamic Stability of the Duplexes Formed with their RNA and DNA Complements. Synlett 1997(11) 1287-1290 (1997).
Dhami et al. Systematic exploration of a class of hydrophobic unnatural base pairs yields multiple new candidates for the expansion of the genetic alphabet. Nucleic Acids Res 42:10235-10244 (2014).
Dien et al. Progress Toward a Semi-Synthetic Organism with an Unrestricted Expanded Genetic Alphabet. J Am Chem Soc. 140:16115-16123 (2018).
Dumas et al. Designing logical codon reassignment—Expanding the chemistry in biology. Chem Sci 6:50-69 (2015).
Elayadi et al. Application of PNA and LNA oligomers to chemotherapy. Curr Opinion Invens Drugs 2:558-561 (2001).
Englisch et al. Chemically Modified Oligonucleotides as Probes and Inhibitors. Angew. Chem. Int. Ed. Eng. 30:613-629 (1991).
Eppacher et al. Synthesis and Incorporation of C(5')-Ethynylated Uracil-Derived Phosphoramidites into RNA. Helvetica Chimica Acta 87:3004-3020 (2004).
Fairhurst et al. Synthesis and Hybridisation Properties of Phosphonamidate Ester Modified Nucleic Acid. Synlett 4:467-472 (2001).
Feldman et al. A Tool for the Import of Natural and Unnatural Nucleoside Triphosphates into Bacteria. J Am Chem Soc 140(4):1447-1454 (2018).
Feldman et al. In Vivo Structure-Activity Relationships and Optimization of an Unnatural Base Pair for Replication in a Semi-Synthetic Organism. J Am Chem Soc 139:11427-11433 (2017).
Gallier et al. Ex-Chiral-Pool Synthesis of 13-Hydroxyphosphonate Nucleoside Analogues. Eur J Org Chem 6:925-933 (2007).
Geze et al. J. Am. Chem. Soc., 1983, 105(26), 7638-7640.
Gong et al. Recent advances in bioorthogonal reactions for site-specific protein labeling and engineering. Tetrahedron Letters 56:2123-2131 (2015).
Hampton et al. Design of substrate-site-directed inhibitors of adenylate kinase and hexokinase. Effect of substrate substituents on affinity on affinity for the adenine nucleotide sites. J Med Chem 19:1371-1377 (1976).

(56) References Cited

OTHER PUBLICATIONS

Hampton et al. Design of substrate-site-directed irreversible inhibitors of adenosine 5'-phosphate aminohydrolase. Effect of substrate substituents on affinity for the substrate site. J Med Chem 19(8):1029-1033 (1976).
Hampton et al. Synthesis of 6'-cyano-6'-deoxyhomoadenosine-6'-phosphonic acid and its phosphoryl and byrophosphoryl an hydrides and studies of their interactions with adenine nucleotide utilizing enzymes. J Am Chem Soc 95(13):4404-4414 (1973).
Hutter et al. From Phosphate to Bis(methylene) Sulfone: Non-Ionic Backbone Linkers in DNA. Helvetica Chimica Acta 85:2777-2806 (2002).
Imran et al. Influence of architecture of high molecular weight linear and branched poly glycerolspolyglycerols on their biocompatibility and biodistribution. Biomaterials 33:9135-914 7 (2012).
Jager et al. Oligonucleotide N-alkylphosphoramidates: synthesis and binding to polyn ucleotides. Biochemistry 27 :724 7-7246 (1988).
Jung et al. Synthesis of phosphonate derivatives of uridine, cytidine, and cytosine arabinoside. Bioorg Med Chem 8:2501-2509 (2000).
Kabanov et al. A new class of antivirals: antisense oligonucleotides combined with a hydrophobic substituent effectively inhibit influenza virus reproduction and synthesis of virus-specific proteins in MOCK cells. FEBS Lett 259:327-330 (1990).
Kandimalla et al. Effect of chemical modifications of cytosine and guanine in a CpG-motif of oligonucleotides: structure-immunostimulatory activity relationships. Bioorg. Med. Chem. 9:807-813 (2001).
Kappler et al. Isozyme-specific enzyme inhibitors. 11. L-homocysteine-ATP S-C5' covalent adducts as inhibitors of at methionine adenosyltransferases. J Med Chem 29:1030-1038 (1986).
Kappler et al. Species- or isozyme-specific enzyme inhibitors. 8. Synthesis of disubstituted two-substrate condensation products as inhibitors of rat adenylate kinases. J Med Chem 25:1179-1184 (1982).
Koshkin et al. LNA (locked nucleic acids): synthesis of the adenine, cytosine, guanine 5-methylcytosine, thymine and uracil bicyclonucleoside monomers, oligomerisation, and unprecedented nucleic acid recognition. Tetrahedron 54(14):3607-3630 (1998).
Kroschwitz, J.I. The Concise Encyclopedia of Polymer Science and Engineering, Ed., John Wiley & Sons pp. 858-859 (1990).
Kumar et al. The First Analogues of LNA (Locked Nucleic Acids): Phosphorothioate LNA and 2'-Thio-LNA. Bioorg Med Chem Lett 8:2219-2222 (1998).
Lavergne et al. Expanding the scope of replicable unnatural DNA: Stepwise optimization of a predominantly hydrophobic base pair. JACS 135:5408-5419 (2013).
Ledbetter et al. Reprograming the Replisome of a Semisynthetic Organism for the Expansion of the Genetic Alphabet. J Am Chem Soc. 140:758-765 (2018).
Letsinger et al. Cholesteryl-conjugated oligonucleotides: Synthesis, properties, and activity as inhibitors of replication of human immunodeficiency virus in cell culture. PNAS 86:6553-6556 (1989).
Li et al. Synthesis of linear polyether polyol derivatives as new materials for bioconjugation. Bioconjugate Chem. 20:780-789 (2009).
Malyshev et al. A semi-synthetic organism with an expanded genetic alphabet. Nature 509(7500):385-388 (2014).
Caffaro et al., Co-pending U.S. Appl. No. 17/313,579, filed Nov. 7, 2019; also cited herein as US 2021/0338829.
Caffaro et al., Co-pending U.S. Appl. No. 17/735,564, filed May 3, 2022; also cited herein as US 2022/0273767.
Abbadessa et al., Co-pending U.S. Appl. No. 17/357,615, filed Jun. 24, 2021; also cited herein as US 2022/0016252.
Aerni et al., Co-pending U.S. Appl. No. 17/845,495, filed Dec. 22, 2020; also cited herein as US 2022/0324792.
Ptacin et al., Co-pending U.S. Appl. No. 17/350,672, filed Jun. 17, 2021; also cited herein as US 2022/0016249.
Caffaro et al., Pending U.S. Appl. No. 18/179,198, filed Mar. 6, 2023; also cited herein as US 2023/0302089.
Caffaro et al., Pending U.S. Appl. No. 18/296,710, filed Apr. 6, 2023; also cited herein as US 2023/0277627.
Caffaro et al., Pending U.S. Appl. No. 18/296,711, filed Apr. 6, 2023; also cited herein as US 2023/0416327.
Caffaro et al., Pending U.S. Appl. No. 18/415,445, filed Jan. 17, 2024.
Caffaro et al., Pending U.S. Appl. No. 18/424,573, filed Jan. 26, 2024.
Ptacin et al., Pending U.S. Appl. No. 18/327,535, filed Jun. 1, 2023.
Abbadessa, Giovanni, et al., Pending U.S. Appl. No. 18/524,157, filed Nov. 30, 2023.
Emerson et al., "NMR Characterization of Interleukin-2 in Complexes with the IL-2R Receptor Component, and with Low Molecular Weight Compounds that Inhibit the IL-2/IL-R interaction", Protein Science, vol. 12 (Dec. 31, 2003).
Ghelani et al., "Defining the Threshold IL-2 Signal Required for Induction of Selective Treg Cell Responses Using Engineered IL-2 Muteins", Frontiers in Immunology, vol. 11, Article 1106 (Jun. 30, 2020).
Levin et al., "Exploiting a Natural Conformational Switch to Engineer an Interleukin-2 Superkine", Nature, vol. 484, No. 7359, (Apr. 26, 2012).
Mei et al., "Site-Mutation of Hydrophobic Core Residues Synchronically Poise Super Interleukin 2 for Signaling: Identifying Distant Structural Effects through Affordable Computations", International Journal of Molecular Science, vol. 19, No. 3, Article 916 (Mar. 20, 2018).
Prometheus Laboratories Inc., FDA Label for Proleukin (Aldesleukin), 19 pages (2011).
Ptacin et al., "A CD25-biased interleukin-2 for autoimmune therapy engineered via a semi-synthetic organism", Communications Medicine, 4:58, pp. 1-16, (2024).
Ptacin, Jerod, et al., Pending U.S. Appl. No. 18/886,814, filed Sep. 16, 2024.
Rao et al., "Interleukin-2 Mutants with Enhanced A-Receptor Subunit Binding Affinity", Protein Engineering, vol. 16, No. 12, (Dec. 31, 2003).

IL-2 CONJUGATES AND METHODS OF USE TO TREAT AUTOIMMUNE DISEASES

This application claims the benefit of priority to U.S. Provisional Application No. 62/898,478, filed Sep. 10, 2019, U.S. Provisional Application No. 62/900,488, filed Sep. 14, 2019, U.S. Provisional Application No. 62/930,987, filed Nov. 5, 2019, U.S. Provisional Application No. 62/953,075, filed Dec. 23, 2019, and U.S. Provisional Application No. 63/042,393, filed Jun. 22, 2020, the contents of each of which are incorporated herein by reference in their entirety for all purposes.

SEQUENCE LISTING

The present application is filed with a Sequence Listing in electronic format. The Sequence Listing is provided as a file entitled "01183-0072-00US_ST25.txt" created on Sep. 7, 2020, which is 335,872 bytes in size. The information in the electronic format of the sequence listing is incorporated herein by reference in its entirety.

INTRODUCTION AND SUMMARY

Distinct populations of T cells modulate the immune system to maintain immune homeostasis and tolerance. For example, regulatory T (Treg) cells prevent inappropriate responses by the immune system by preventing pathological self-reactivity. In some instances, modulation of the different populations of T cells provides an option for treatment of a disease or indication.

Described herein are IL-2 conjugates comprising the amino acid sequence of SEQ ID NO: 3 in which at least one amino acid residue in the IL-2 conjugate is replaced by the structure of Formula (I):

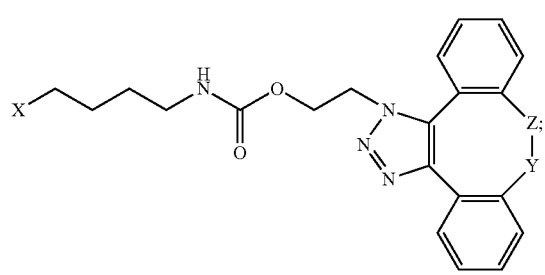

Formula (I)

wherein:

Z is $CH_2$ and Y is

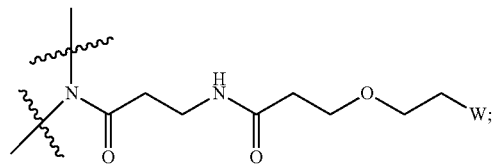

Y is $CH_2$ and Z is

Z is $CH_2$ and Y is or

Y is $CH_2$ and Z is

W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and X has the structure:

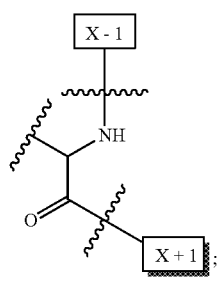

X−1 indicates the point of attachment to the preceding amino acid residue; and

X+1 indicates the point of attachment to the following amino acid residue. In some embodiments, the IL-2 conjugate is a pharmaceutically acceptable salt, solvate, or hydrate thereof. Further provided herein are IL-2 conjugates wherein Z is $CH_2$ and Y is

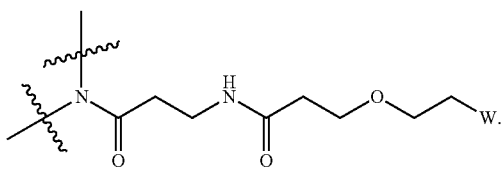

Further provided herein are IL-2 conjugates wherein Y is CH₂ and Z is

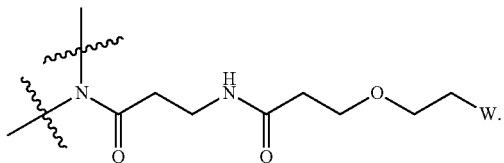

Further provided herein are IL-2 conjugates wherein Z is CH₂ and Y is

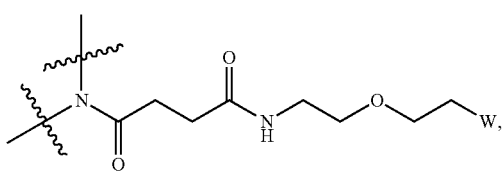

or a pharmaceutically acceptable salt, solvate, or hydrate thereof. Further provided herein are IL-2 conjugates wherein Z is CH₂ and Y is

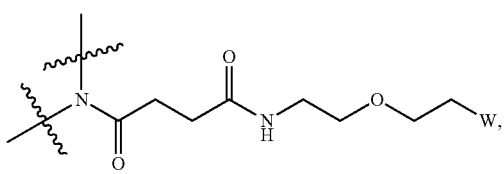

and W is a PEG group having an average molecular weight selected from 15 kDa, 20 kDa, 25 kDa, 30 kDa, 35 kDa, 40 kDa, 45 kDa, 50 kDa, 55 kDa, and 60 kDa. Further provided herein are IL-2 conjugates wherein Y is CH₂ and Z is

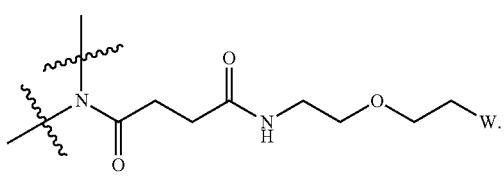

Further provided herein are IL-2 conjugates wherein the PEG group has an average molecular weight selected from 5 kDa, 10 kDa, 20 kDa, 30 kDa, 40 kDa, or 50 kDa. Further provided herein are IL-2 conjugates wherein the PEG group has an average molecular weight of 5 kDa. Here and throughout, embodiments of Z and Y also encompass a pharmaceutically acceptable salt, solvate, or hydrate thereof. Further provided herein are IL-2 conjugates wherein the PEG group has an average molecular weight of 30 kDa. Further provided herein are IL-2 conjugates wherein the PEG group has an average molecular weight of 35 kDa. Further provided herein are IL-2 conjugates wherein the PEG group has an average molecular weight of 40 kDa. Further provided herein are IL-2 conjugates wherein the PEG group has an average molecular weight of 45 kDa. Further provided herein are IL-2 conjugates wherein the PEG group has an average molecular weight of 50 kDa. Further provided herein are IL-2 conjugates wherein the PEG group has an average molecular weight of 55 kDa. Further provided herein are IL-2 conjugates wherein the PEG group has an average molecular weight of 60 kDa. Further provided herein are IL-2 conjugates wherein the position of the structure of Formula (I) in the amino acid sequence of the IL-2 conjugate is selected from P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, I88, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, and T132. Further described herein are IL-2 conjugates wherein the position of the structure of Formula (I) in the amino acid sequence of the IL-2 conjugate is selected from K8, H15, L18, D19, M22, N25, N87, V90, I91, L93, E94, K96, G97, S98, E99, D108 in the N87R variant, N118, T122, S124, Q125, S126, S129, and T130. Further described herein are IL-2 conjugates wherein the position of the structure of Formula (I) in the amino acid sequence of the IL-2 conjugate is selected from K8, H15, L18, D19, M22, N25, N87, V90, E99, D108 in the N87R variant, N118, T122, S124, and T130. Further described herein are IL-2 conjugates wherein the position of the structure of Formula (I) in the amino acid sequence of the IL-2 conjugate is K8. Further described herein are IL-2 conjugates wherein the position of the structure of Formula (I) in the amino acid sequence of the IL-2 conjugate is H15. Further described herein are IL-2 conjugates wherein the position of the structure of Formula (I) in the amino acid sequence of the IL-2 conjugate is L18. Further described herein are IL-2 conjugates wherein the position of the structure of Formula (I) in the amino acid sequence of the IL-2 conjugate is D19. Further described herein are IL-2 conjugates wherein the position of the structure of Formula (I) in the amino acid sequence of the IL-2 conjugate is M22. Further described herein are IL-2 conjugates wherein the position of the structure of Formula (I) in the amino acid sequence of the IL-2 conjugate is N25. Further described herein are IL-2 conjugates wherein the position of the structure of Formula (I) in the amino acid sequence of the IL-2 conjugate is N87. Further described herein are IL-2 conjugates wherein the position of the structure of Formula (I) in the amino acid sequence of the IL-2 conjugate is V90. Further described herein are IL-2 conjugates wherein the position of the structure of Formula (I) in the amino acid sequence of the IL-2 conjugate is E99. Further described herein are IL-2 conjugates wherein the position of the structure of Formula (I) in the amino acid sequence of the IL-2 conjugate is D108 in the N87R variant. Further described herein are IL-2 conjugates wherein the position of the structure of Formula (I) in the amino acid sequence of the IL-2 conjugate is N118. Further described herein are IL-2 conjugates wherein the position of the structure of Formula (I) in the amino acid sequence of the IL-2 conjugate is T122. Further described herein are IL-2 conjugates wherein the position of the structure of Formula (I) in the amino acid sequence of the IL-2 conjugate is S124. Further described herein are IL-2 conjugates wherein the position of the structure of Formula (I) in the amino acid sequence of the IL-2 conjugate is T130.

Described herein are IL-2 conjugates comprising the amino acid sequence of SEQ ID NO: 4 in which at least one amino acid residue in the IL-2 conjugate is replaced by the structure of Formula (I):

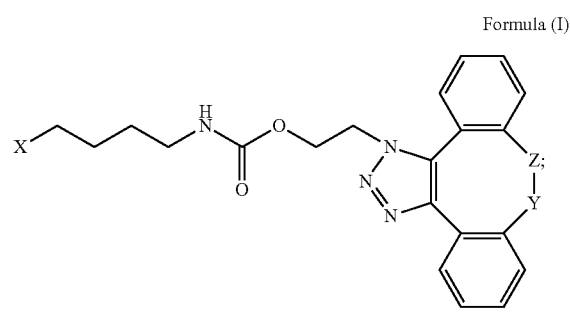

Formula (I)

wherein:

Z is CH$_2$ and Y is

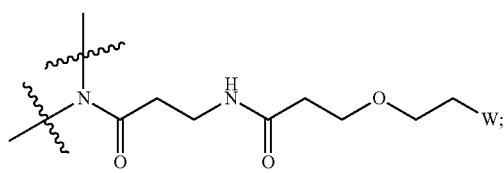

Y is CH$_2$ and Z is

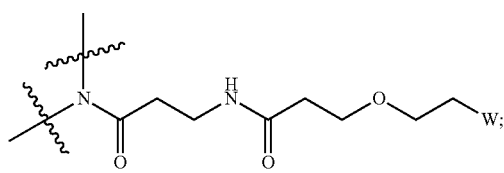

Z is CH$_2$ and Y is

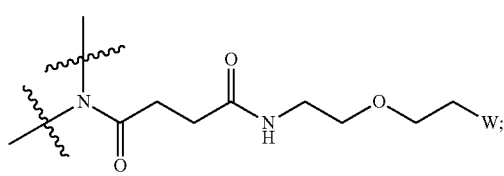

or
Y is CH$_2$ and Z is

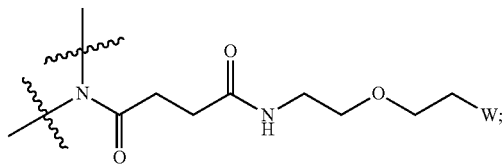

W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa;
X has the structure:

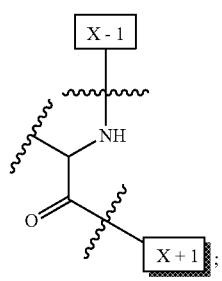

X−1 indicates the point of attachment to the preceding amino acid residue; and
X+1 indicates the point of attachment to the following amino acid residue. In some embodiments, the IL-2 conjugate is a pharmaceutically acceptable salt, solvate, or hydrate thereof. Further provided herein are IL-2 conjugates wherein Z is CH$_2$ and Y is

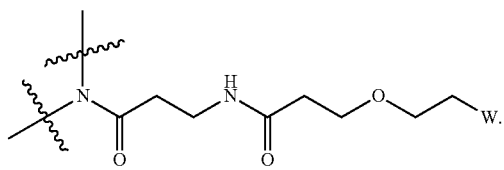

Further provided herein are IL-2 conjugates wherein Y is CH$_2$ and Z is

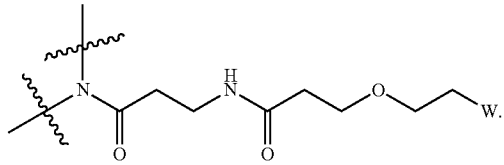

Further provided herein are IL-2 conjugates wherein Z is CH$_2$ and Y is

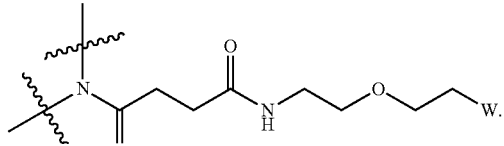

Further provided herein are IL-2 conjugates wherein Z is CH₂ and Y is

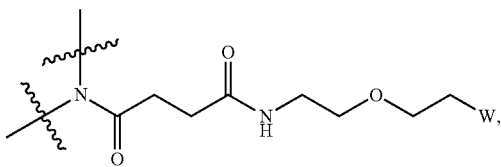

and W is a PEG group having an average molecular weight selected from 15 kDa, 20 kDa, 25 kDa, 30 kDa, 35 kDa, 40 kDa, 45 kDa, 50 kDa, 55 kDa, and 60 kDa. Further provided herein are IL-2 conjugates wherein Y is CH₂ and Z is

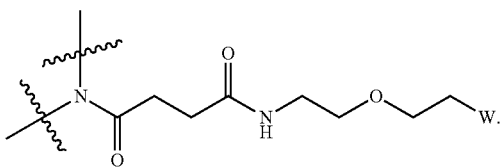

Further provided herein are IL-2 conjugates wherein the PEG group has an average molecular weight selected from 5 kDa, 10 kDa, 20 kDa, 30 kDa, 40 kDa, or 50 kDa. Further provided herein are IL-2 conjugates wherein the PEG group has an average molecular weight of 5 kDa. Further provided herein are IL-2 conjugates wherein the PEG group has an average molecular weight of 30 kDa. Further provided herein are IL-2 conjugates wherein the PEG group has an average molecular weight of 35 kDa. Further provided herein are IL-2 conjugates wherein the PEG group has an average molecular weight of 40 kDa. Further provided herein are IL-2 conjugates wherein the PEG group has an average molecular weight of 45 kDa. Further provided herein are IL-2 conjugates wherein the PEG group has an average molecular weight of 50 kDa. Further provided herein are IL-2 conjugates wherein the PEG group has an average molecular weight of 55 kDa. Further provided herein are IL-2 conjugates wherein the PEG group has an average molecular weight of 60 kDa. Further provided herein are IL-2 conjugates wherein the position of the structure of Formula (I) in the amino acid sequence of the IL-2 conjugate is selected from A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133. Further described herein are IL-2 conjugates wherein the position of the structure of Formula (I) in the amino acid sequence of the IL-2 conjugate is selected from K9, H16, L19, D20, M23, N26, N88, V91, I92, L94, E95, K97, G98, S99, E100, D109 in the N88R variant, N119, T123, S125, Q126, S127, S130, and T131. Further described herein are IL-2 conjugates wherein the position of the structure of Formula (I) in the amino acid sequence of the IL-2 conjugate is selected from K9, H16, L19, D20, M23, N26, N88, V91, E100, D109 in the N88R variant, N119, T123, S125, and T131. Further described herein are IL-2 conjugates wherein the position of the structure of Formula (I) in the amino acid sequence of the IL-2 conjugate is K9. Further described herein are IL-2 conjugates wherein the position of the structure of Formula (I) in the amino acid sequence of the IL-2 conjugate is H16. Further described herein are IL-2 conjugates wherein the position of the structure of Formula (I) in the amino acid sequence of the IL-2 conjugate is L19. Further described herein are IL-2 conjugates wherein the position of the structure of Formula (I) in the amino acid sequence of the IL-2 conjugate is D20. Further described herein are IL-2 conjugates wherein the position of the structure of Formula (I) in the amino acid sequence of the IL-2 conjugate is M23. Further described herein are IL-2 conjugates wherein the position of the structure of Formula (I) in the amino acid sequence of the IL-2 conjugate is N26. Further described herein are IL-2 conjugates wherein the position of the structure of Formula (I) in the amino acid sequence of the IL-2 conjugate is N88. Further described herein are IL-2 conjugates wherein the position of the structure of Formula (I) in the amino acid sequence of the IL-2 conjugate is V91. Further described herein are IL-2 conjugates wherein the position of the structure of Formula (I) in the amino acid sequence of the IL-2 conjugate is E100. Further described herein are IL-2 conjugates wherein the position of the structure of Formula (I) in the amino acid sequence of the IL-2 conjugate is D109 in the N88R variant. Further described herein are IL-2 conjugates wherein the position of the structure of Formula (I) in the amino acid sequence of the IL-2 conjugate is N119. Further described herein are IL-2 conjugates wherein the position of the structure of Formula (I) in the amino acid sequence of the IL-2 conjugate is T123. Further described herein are IL-2 conjugates wherein the position of the structure of Formula (I) in the amino acid sequence of the IL-2 conjugate is 5125. Further described herein are IL-2 conjugates wherein the position of the structure of Formula (I) in the amino acid sequence of the IL-2 conjugate is and T131.

Described herein are IL-2 conjugates comprising the amino acid sequence of any one of SEQ ID NOS: 34-48, and 199-213, wherein [AzK_PEG] has the structure of Formula (II) or Formula (III), or a mixture of Formula (ID and Formula (III):

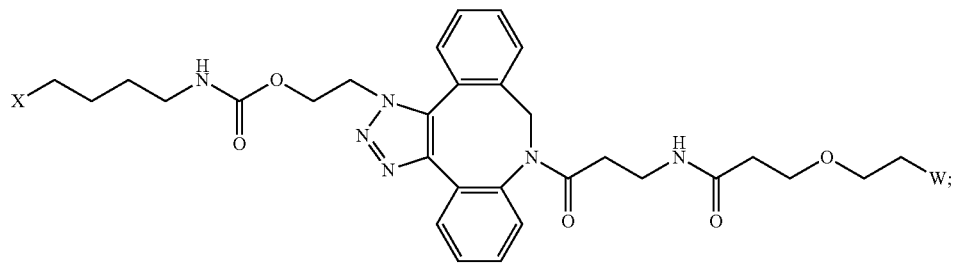

Formula (II)

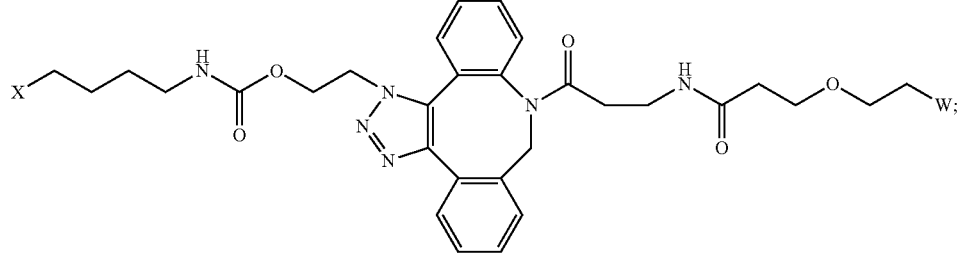

Formula (III)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and
X has the structure:

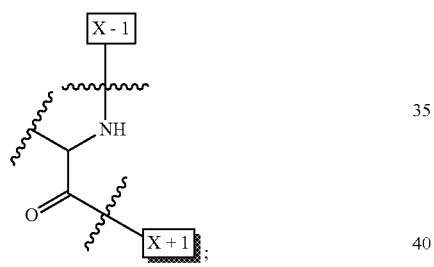

X−1 indicates the point of attachment to the preceding amino acid residue; and
X+1 indicates the point of attachment to the following amino acid residue. In some embodiments, the IL-2 conjugate is a pharmaceutically acceptable salt, solvate, or hydrate thereof. Here and throughout, embodiments of Formula (II) and/or (III) also encompass a pharmaceutically acceptable salt, solvate, or hydrate thereof. Further described herein are IL-2 conjugates wherein the [AzK_PEG] is a mixture of Formula (II) and Formula (III). Further described herein are IL-2 conjugates wherein the [AzK_PEG] has the structure of formula (II):

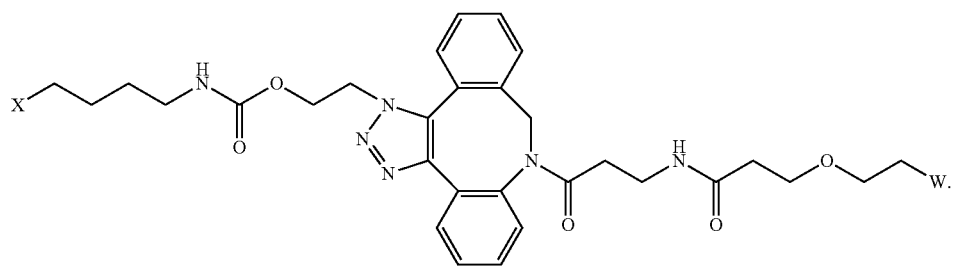

Formula (II)

Here and throughout, the structure of Formula (II) encompasses pharmaceutically acceptable salts, solvates, or hydrates thereof. Further described herein are IL-2 conjugates wherein the IL-2 conjugate has the amino acid sequence of any one of SEQ ID NOS: 34-48. Further described herein are IL-2 conjugates wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa. Further described herein are IL-2 conjugates wherein W is a PEG group having an average molecular weight selected from 25 kDa, 30 kDa, 35 kDa, 40 kDa, 45 kDa, 50 kDa, 55 kDa, or 60 kDa. Further described herein are IL-2 conjugates wherein W is a PEG group having an average molecular weight of 5 kDa. Further described herein are IL-2 conjugates wherein W is a PEG group having an average molecular weight of 30 kDa. Further provided herein are IL-2 conjugates wherein the PEG group has an average molecular weight of 35 kDa. Further provided herein are IL-2 conjugates wherein the PEG group has an average molecular weight of 40 kDa. Further provided herein are IL-2 conjugates wherein the PEG group has an average molecular weight of 45 kDa. Further provided herein are IL-2 conjugates wherein the PEG group has an average molecular weight of 50 kDa. Further provided herein are IL-2 conjugates wherein the PEG group has an average molecular weight of 55 kDa. Further provided herein are IL-2 conjugates wherein the PEG group has an average molecular weight of 60 kDa. Further described herein are IL-2 conjugates wherein the IL-2 conjugate has the amino acid sequence of SEQ ID NO: 35 or 200. Further described herein are IL-2 conjugates wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa. Further described herein are IL-2 conjugates wherein W is a PEG group having an average molecular weight selected from 50 kDa and 30 kDa. Further described herein are IL-2 conjugates wherein W is a PEG group having an average molecular weight of 5 kDa. Further described herein are IL-2 conjugates wherein W is a PEG group having an average molecular weight of 30 kDa. Further provided herein are IL-2 conjugates wherein the PEG group has an average molecular weight of 35 kDa. Further provided herein are IL-2 conjugates wherein the PEG group has an average molecular weight of 40 kDa. Further provided herein are IL-2 conjugates wherein the PEG group has an average molecular weight of 45 kDa. Further provided herein are IL-2 conjugates wherein the PEG group has an average molecular weight of 50 kDa. Further provided herein are IL-2 conjugates wherein the PEG group has an average molecular weight of 55 kDa. Further provided herein are IL-2 conjugates wherein the PEG group has an average molecular weight of 60 kDa. Further described herein are IL-2 conjugates wherein the [AzK_PEG] has the structure of formula (III)

Formula (III)

$$X-(CH_2)_4-NH-C(=O)-O-CH_2CH_2-[\text{triazole-dibenzocyclooctene}]-N-C(=O)-CH_2-NH-C(=O)-CH_2CH_2-O-CH_2CH_2-W$$

Further described herein are IL-2 conjugates wherein the IL-2 conjugate has the amino acid sequence of any one of SEQ ID NOS: 199-213. Further described herein are IL-2 conjugates wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa. Further described herein are IL-2 conjugates wherein W is a PEG group having an average molecular weight selected from 50 kDa and 30 kDa. Further described herein are IL-2 conjugates wherein W is a PEG group having an average molecular weight of 5 kDa. Further described herein are IL-2 conjugates wherein W is a PEG group having an average molecular weight of 30 kDa. Further provided herein are IL-2 conjugates wherein the PEG group has an average molecular weight of 35 kDa. Further provided herein are IL-2 conjugates wherein the PEG group has an average molecular weight of 40 kDa. Further provided herein are IL-2 conjugates wherein the PEG group has an average molecular weight of 45 kDa. Further provided herein are IL-2 conjugates wherein the PEG group has an average molecular weight of 50 kDa. Further provided herein are IL-2 conjugates wherein the PEG group has an average molecular weight of 55 kDa. Further provided herein are IL-2 conjugates wherein the Here and throughout, the structure of Formula (III) encompasses pharmaceutically acceptable salts, solvates, or hydrates thereof. Further described herein are IL-2 conjugates wherein the IL-2 conjugate has the amino acid sequence of any one of SEQ ID NOS: 34-48. Further described herein are IL-2 conjugates wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa. Further described herein are IL-2 conjugates wherein W is a PEG group having an average molecular weight selected from 50 kDa and 30 kDa. Further described herein are IL-2 conjugates wherein W is a PEG group having an average molecular weight of 5 kDa. Further described herein are IL-2 conjugates wherein W is a PEG group having an average molecular weight of 30 kDa. Further provided herein are IL-2 conjugates wherein the PEG group has an average molecular weight of 35 kDa. Further provided herein are IL-2 conjugates wherein the PEG group has an average molecular weight of 40 kDa. Further provided herein are IL-2 conjugates wherein the PEG group has an average molecular weight of 45 kDa. Further provided herein are IL-2 conjugates wherein the PEG group has an average molecular weight of 50 kDa. Further provided herein are IL-2 conjugates wherein the PEG group has an average molecular weight of 55 kDa. Further provided herein are IL-2 conjugates wherein the PEG group has an average molecular weight of 60 kDa. Further described herein are IL-2 conjugates wherein the IL-2 conjugate has the amino acid sequence of any one of SEQ ID NOS: 199-213. Further described herein are IL-2 conjugates wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa. Further described herein are IL-2 conjugates wherein W is a PEG group having an average molecular weight selected from 50 kDa and 30 kDa. Further described herein are IL-2 conjugates wherein W is a PEG group having an average molecular weight of 5 kDa. Further described herein are IL-2 conjugates wherein W is a PEG group having an average molecular weight of 30 kDa. Further provided herein are IL-2 conjugates wherein the PEG group has an average molecular weight of 35 kDa. Further provided herein are IL-2 conjugates wherein the PEG group has an average molecular weight of 40 kDa. Further provided herein are IL-2 conjugates wherein the PEG group has an average molecular weight of 45 kDa. Further provided herein are IL-2 conjugates wherein the PEG group has an average molecular weight of 50 kDa. Further provided herein are IL-2 conjugates wherein the PEG group has an average molecular weight of 55 kDa. Further provided herein are IL-2 conjugates wherein the PEG group has an average molecular weight of 60 kDa. Further provided herein are IL-2 conjugates wherein W is a linear or branched PEG group. Further provided herein are IL-2 conjugates wherein W is a linear PEG group. Further provided herein are IL-2 conjugates wherein W is a branched PEG group. Further provided herein are IL-2 conjugates wherein W is a methoxy PEG group. Further described herein are IL-2 conjugates wherein the methoxy PEG group is linear or branched. Further described herein are IL-2 conjugates wherein the methoxy PEG group is linear. Further described herein are IL-2 conjugates wherein the methoxy PEG group is branched.

Described herein are IL-2 conjugates comprising the amino acid sequence of any one of SEQ ID NOS: 49-63 and 214-228, wherein [AzK_PEG50 kDa] has the structure of Formula (II) or Formula (III), or a mixture of Formula (II) and Formula (III):

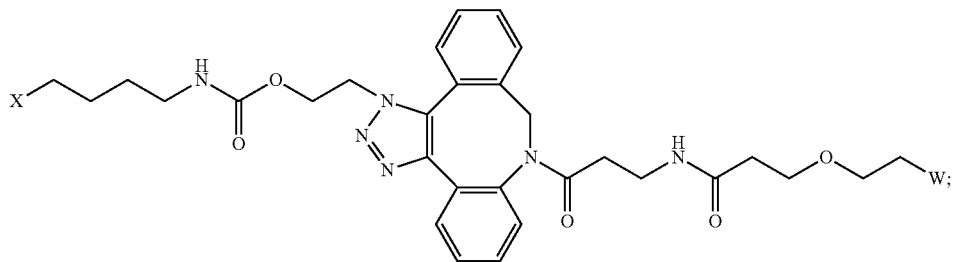

Formula (II)

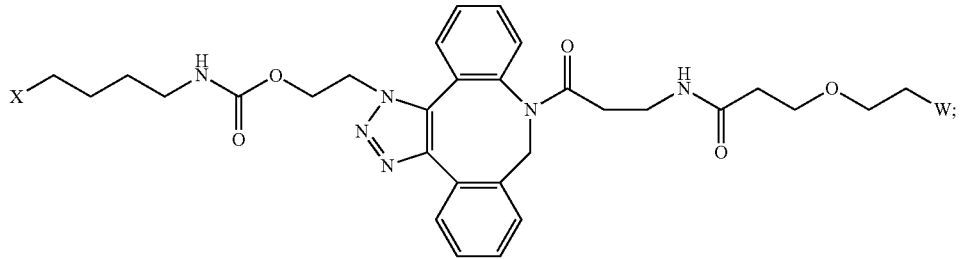

Formula (III)

wherein:
W is a PEG group having an average molecular weight of 50 kDa; and
X has the structure:

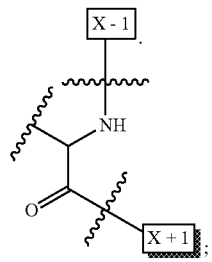

X−1 indicates the point of attachment to the preceding amino acid residue; and
X+1 indicates the point of attachment to the following amino acid residue. In some embodiments, the IL-2 conjugate is a pharmaceutically acceptable salt, solvate, or hydrate thereof. Further described herein are IL-2 conjugates wherein the IL-2 conjugate has the amino acid sequence of any one of SEQ ID NOS: 49-63. Further described herein are IL-2 conjugates wherein the IL-2 conjugate has the amino acid sequence of any one of SEQ ID NOS: 214-228. Further described herein are IL-2 conjugates wherein the IL-2 conjugate has the amino acid sequence of SEQ ID NO: 50 or 215. Further described herein are IL-2 conjugates wherein the [AzK_PEG50 kDa] has the structure of formula (II)

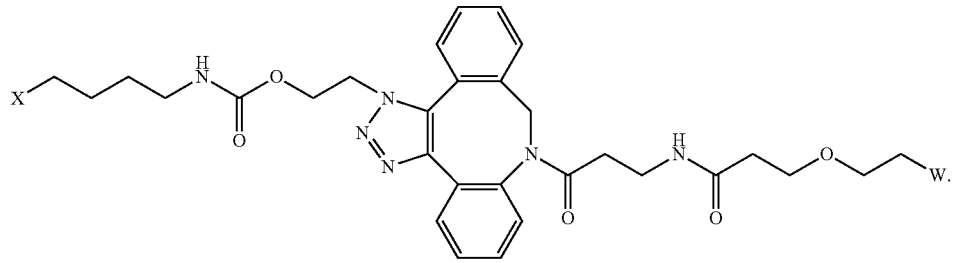

Formula (II)

Further described herein are IL-2 conjugates wherein the IL-2 conjugate has the amino acid sequence of any one of SEQ ID NOS: 49-63. Further described herein are IL-2 conjugates wherein the IL-2 conjugate has the amino acid sequence of any one of SEQ ID NOS: 214-228. Further described herein are IL-2 conjugates wherein the IL-2 conjugate has the amino acid sequence of SEQ ID NO: 50 or 215. Further described herein are IL-2 conjugates wherein the [AzK_PEG50 kDa] has the structure of formula (III)

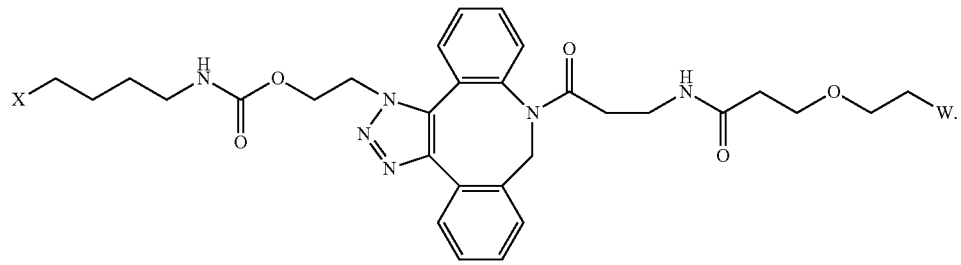

Formula (III)

Further described herein are IL-2 conjugates wherein the IL-2 conjugate has the amino acid sequence of any one of SEQ ID NOS: 49-63. Further described herein are IL-2 conjugates wherein the IL-2 conjugate has the amino acid sequence of any one of SEQ ID NOS: 214-228. Further described herein are IL-2 conjugates wherein the IL-2 conjugate has the amino acid sequence of SEQ ID NO: 50 or 215.

Described herein are IL-2 conjugates comprising the amino acid sequence of any one of SEQ ID NOS: 64-78 and 229-243, wherein [AzK_PEG30 kDa] has the structure of Formula (II) or Formula (III), or is a mixture of the structures of Formula (II) and Formula (III):

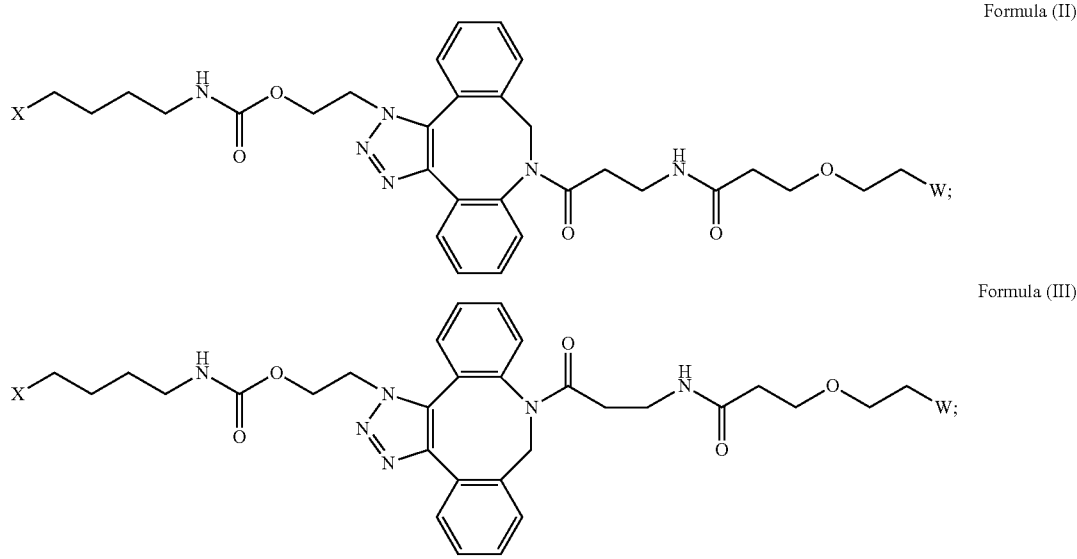

wherein:
W is a PEG group having an average molecular weight of 30 kDa; and
X has the structure:

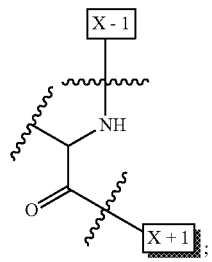

X−1 indicates the point of attachment to the preceding amino acid residue; and
X+1 indicates the point of attachment to the following amino acid residue. In some embodiments, the IL-2 conjugate is a pharmaceutically acceptable salt, solvate, or hydrate thereof. Further described herein are IL-2 conjugates wherein the IL-2 conjugate has the amino acid sequence of any one of SEQ ID NOS: 64-78. Further described herein are IL-2 conjugates wherein the IL-2 conjugate has the amino acid sequence of any one of SEQ ID NOS: 229-243. Further described herein are IL-2 conjugates wherein the IL-2 conjugate has the amino acid sequence of SEQ ID NO: 65 or 230. Further described herein are IL-2 conjugates wherein the [AzK_PEG30 kDa] has the structure of formula (II):

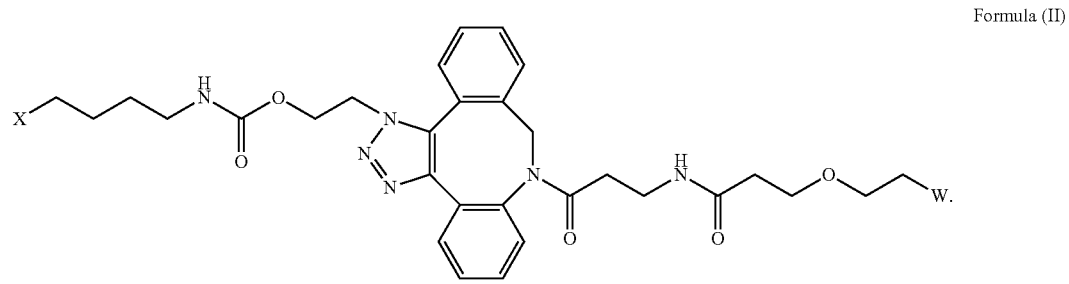

Further described herein are IL-2 conjugates wherein the IL-2 conjugate has the amino acid sequence of any one of SEQ ID NOS: 64-78. Further described herein are IL-2 conjugates wherein the IL-2 conjugate has the amino acid sequence of any one of SEQ ID NOS: 229-243. Further described herein are IL-2 conjugates wherein the IL-2 conjugate has the amino acid sequence of SEQ ID NO: 65 or 230. Further described herein are IL-2 conjugates wherein the [AzK_PEG30 kDa] has the structure of formula (III)

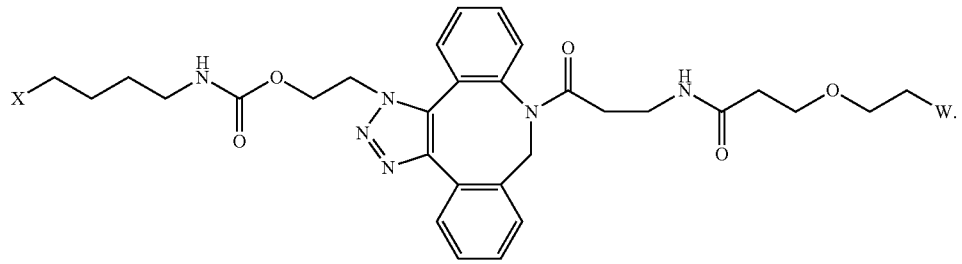

Formula (III)

Further described herein are IL-2 conjugates wherein the IL-2 conjugate has the amino acid sequence of any one of SEQ ID NOS: 64-78. Further described herein are IL-2 conjugates wherein the IL-2 conjugate has the amino acid sequence of any one of SEQ ID NOS: 229-243. Further described herein are IL-2 conjugates wherein the IL-2 conjugate has the amino acid sequence of SEQ ID NO: 65 or 230.

Described herein are IL-2 conjugates comprising the amino acid sequence of any one of SEQ ID NOS: 34-48 and 199-213, wherein [AzK_PEG] is a mixture of the structures of Formula (II) and Formula (III):

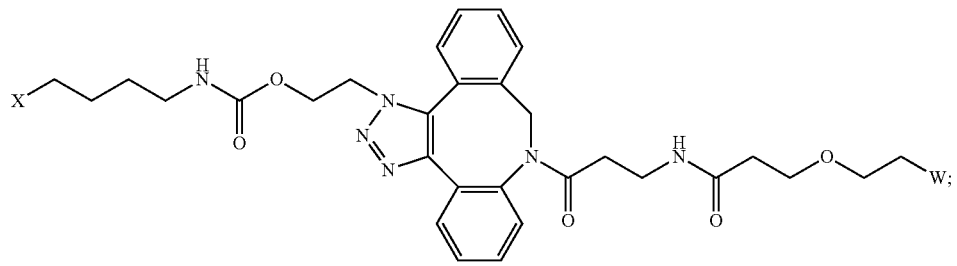

Formula (II)

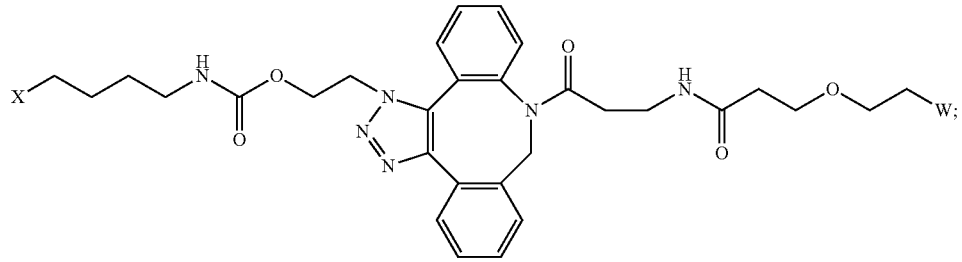

Formula (III)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and
X has the structure:

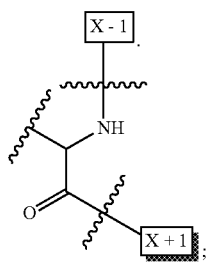

X−1 indicates the point of attachment to the preceding amino acid residue; and
X+1 indicates the point of attachment to the following amino acid residue. In some embodiments, the IL-2 conjugate is a pharmaceutically acceptable salt, solvate, or hydrate thereof. Further described herein are IL-2 conjugates wherein the ratio of the amount of the structure of Formula (II) to the amount of the structure of Formula (III) comprising the total amount of [AzK_PEG] in the IL-2 conjugate is about 1:1. Further described herein are IL-2 conjugates wherein the ratio of the amount of the structure of Formula (II) to the amount of the structure of Formula (III) comprising the total amount of [AzK_PEG] in the IL-2 conjugate is greater than 1:1. Further described herein are IL-2 conjugates wherein the ratio of the amount of the structure of Formula (II) to the amount of the structure of Formula (III) comprising the total amount of [AzK_PEG] in the IL-2 conjugate is less than 1:1. Further described herein are IL-2 conjugates wherein W is a linear or branched PEG group. Further described herein are IL-2 conjugates wherein W is a linear PEG group. Further described herein are IL-2 conjugates wherein W is a branched PEG group. Further described herein are IL-2 conjugates wherein W is a methoxy PEG group. Further described herein are IL-2 conjugates wherein the methoxy PEG group is linear or branched. Further described herein are IL-2 conjugates wherein the methoxy PEG group is linear. Further described herein are IL-2 conjugates wherein the methoxy PEG group is branched.

Described herein are IL-2 conjugates comprising the amino acid sequence of any one of SEQ ID NOS: 49-63 and 214-228, wherein [AzK_PEG50 kDa] is a mixture of the structures of Formula (II) and Formula (III):

Formula (II)

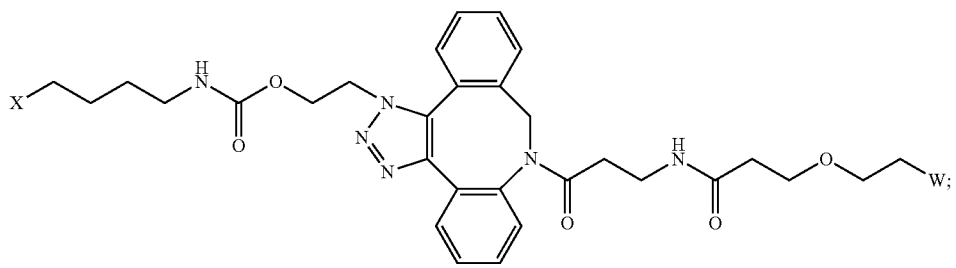

Formula (III)

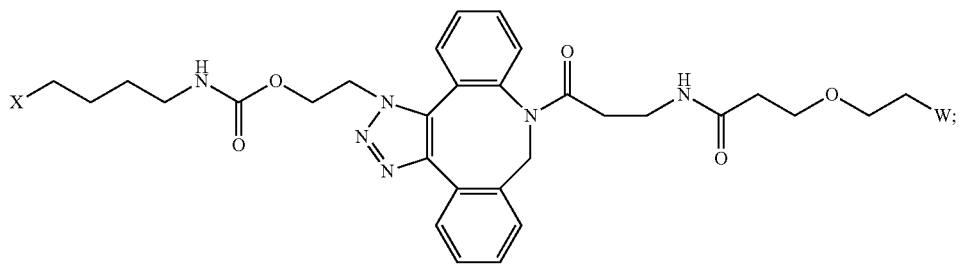

wherein:

W is a PEG group having an average molecular weight of 50 kDa; and

X has the structure:

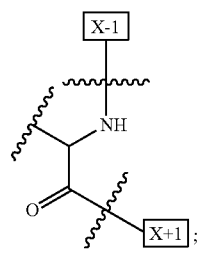

X−1 indicates the point of attachment to the preceding amino acid residue; and

X+1 indicates the point of attachment to the following amino acid residue. In some embodiments, the IL-2 conjugate is a pharmaceutically acceptable salt, solvate, or hydrate thereof. Further described herein are IL-2 conjugates wherein the ratio of the amount of the structure of Formula (II) to the amount of the structure of Formula (III) comprising the total amount of [AzK_PEG50 kDa] in the IL-2 conjugate is about 1:1. Further described herein are IL-2 conjugates wherein the ratio of the amount of the structure of Formula (II) to the amount of the structure of Formula (III) comprising the total amount of [AzK_PEG50 kDa] in the IL-2 conjugate is greater than 1:1. Further described herein are IL-2 conjugates wherein the ratio of the amount of the structure of Formula (II) to the amount of the structure of Formula (III) comprising the total amount of [AzK_PEG50 kDa] in the IL-2 conjugate is less than 1:1.

Described herein are IL-2 conjugates comprising the amino acid sequence of any one of SEQ ID NOS: 64-78 and 229-243, wherein [AzK_PEG30 kDa] is a mixture of the structures of Formula (II) and Formula (III):

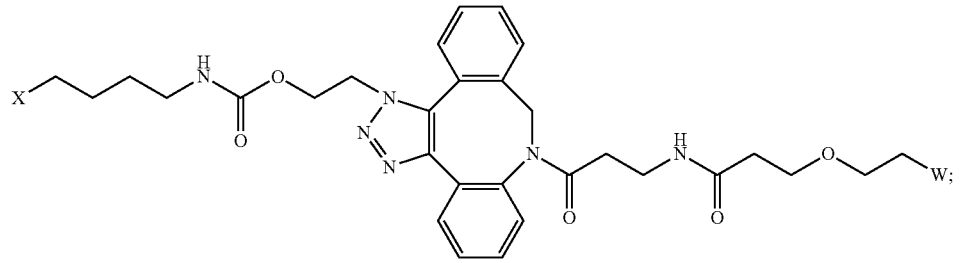

Formula (II)

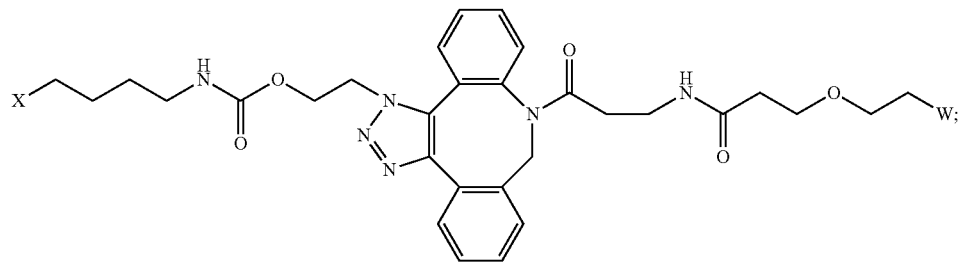

Formula (III)

wherein:

W is a PEG group having an average molecular weight of 30 kDa; and

X has the structure:

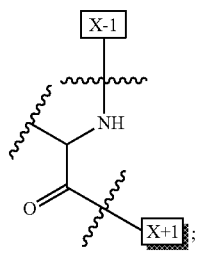

X−1 indicates the point of attachment to the preceding amino acid residue; and

X+1 indicates the point of attachment to the following amino acid residue. In some embodiments, the IL-2 conjugate is a pharmaceutically acceptable salt, solvate, or hydrate thereof. Further described herein are IL-2 conjugates wherein the ratio of the amount of the structure of Formula (II) to the amount of the structure of Formula (III) comprising the total amount of [AzK_PEG30 kDa] in the IL-2 conjugate is about 1:1. Further described herein are IL-2 conjugates wherein the ratio of the amount of the structure of Formula (II) to the amount of the structure of Formula (III) comprising the total amount of [AzK_PEG30 kDa] in the IL-2 conjugate is greater than 1:1. Further described herein are IL-2 conjugates wherein the ratio of the amount of the structure of Formula (II) to the amount of the structure of Formula (III) comprising the total amount of [AzK_PEG30 kDa] in the IL-2 conjugate is less than 1:1.

Described herein are IL-2 conjugates comprising the amino acid sequence of any one of SEQ ID NOS: 154-168 and 109-123, wherein [AzK_L1_PEG] has the structure of Formula (IV) or Formula (V), or a mixture of Formula (IV) and Formula (V):

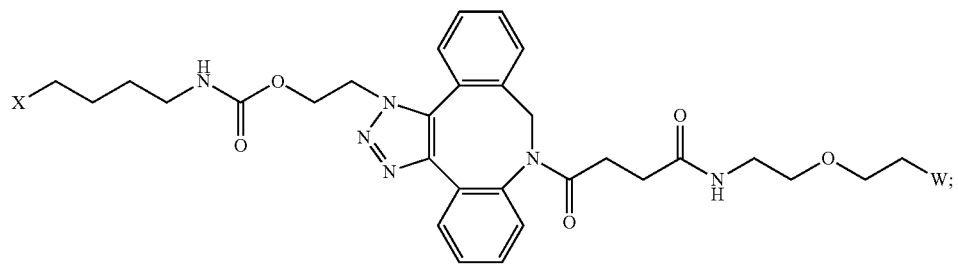

Formula (IV)

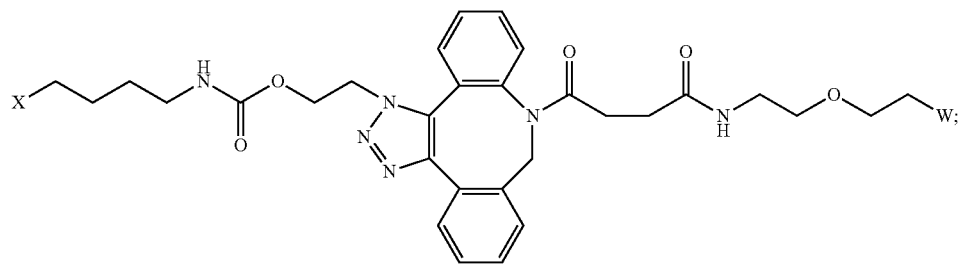

Formula (V)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and
X has the structure:

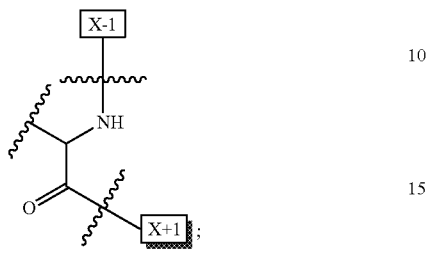

X−1 indicates the point of attachment to the preceding amino acid residue; and
X+1 indicates the point of attachment to the following amino acid residue. In some embodiments, the IL-2 conjugate is a pharmaceutically acceptable salt, solvate, or hydrate thereof. Here and throughout, embodiments of Formula (IV) and/or (V) also encompass a pharmaceutically acceptable salt, solvate, or hydrate thereof. Further described herein are IL-2 conjugates wherein the [AzK_L1_PEG] is a mixture of Formula (IV) and Formula (V). Further described herein are IL-2 conjugates wherein the [AzK_L1_PEG] has the structure of Formula (IV):

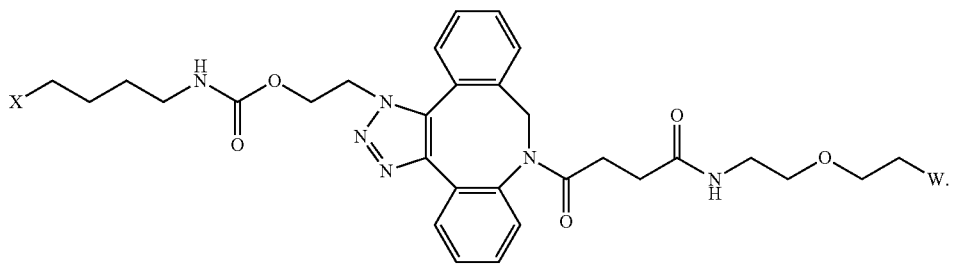

Formula (IV)

Here and throughout, the structure of Formula (IV) encompasses pharmaceutically acceptable salts, solvates, or hydrates thereof. Further described herein are IL-2 conjugates wherein the IL-2 conjugate has the amino acid sequence of any one of SEQ ID NOS: 109-123. Further described herein are IL-2 conjugates wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa. Further described herein are IL-2 conjugates wherein W is a PEG group having an average molecular weight selected from 50 kDa and 30 kDa. Further described herein are IL-2 conjugates wherein W is a PEG group having an average molecular weight of 5 kDa. Further described herein are IL-2 conjugates wherein W is a PEG group having an average molecular weight of 30 kDa. Further described herein are IL-2 conjugates wherein the IL-2 conjugate has the amino acid sequence of SEQ ID NO: 155 or 110. Further described herein are IL-2 conjugates wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa. Further described herein are IL-2 conjugates wherein W is a PEG group having an average molecular weight selected from 5 kDa and 30 kDa. Further described herein are IL-2 conjugates wherein W is a PEG group having an average molecular weight of 5 kDa. Further described herein are IL-2 conjugates wherein W is a PEG group having an average molecular weight of 30 kDa. Further provided herein are IL-2 conjugates wherein the PEG group has an average molecular weight of 35 kDa. Further provided herein are IL-2 conjugates wherein the PEG group has an average molecular weight of 40 kDa. Further provided herein are IL-2 conjugates wherein the PEG group has an average molecular weight of 45 kDa. Further provided herein are IL-2 conjugates wherein the PEG group has an average molecular weight of 50 kDa. Further provided herein are IL-2 conjugates wherein the PEG group has an average molecular weight of 55 kDa. Further provided herein are IL-2 conjugates wherein the PEG group has an average molecular weight of 60 kDa. Further described herein are IL-2 conjugates wherein the [AzK_L1_PEG] has the structure of Formula (V)

Formula (V)

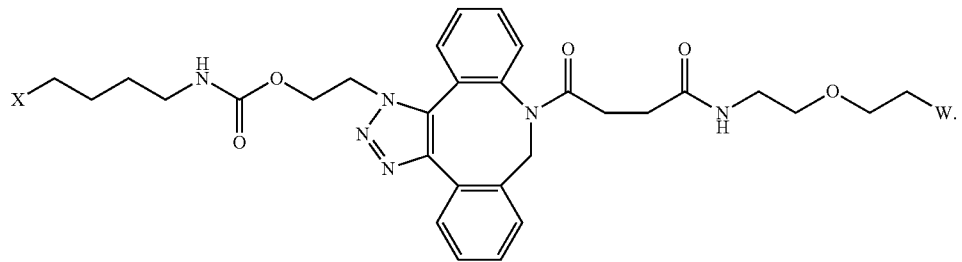

Here and throughout, the structure of Formula (V) encompasses pharmaceutically acceptable salts, solvates, or hydrates thereof. Further described herein are IL-2 conjugates wherein the IL-2 conjugate has the amino acid sequence of any one of SEQ ID NOS: 109-123. Further described herein are IL-2 conjugates wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa. Further described herein are IL-2 conjugates wherein W is a PEG group having an average molecular weight selected from 50 kDa and 30 kDa. Further described herein are IL-2 conjugates wherein W is a PEG group having an average molecular weight of 5 kDa. Further described herein are IL-2 conjugates wherein W is a PEG group having an average molecular weight of 30 kDa. Further provided herein are IL-2 conjugates wherein the PEG group has an average molecular weight of 35 kDa. Further provided herein are IL-2 conjugates wherein the PEG group has an average molecular weight of 40 kDa. Further provided herein are IL-2 conjugates wherein the PEG group has an average molecular weight of 45 kDa. Further provided herein are IL-2 conjugates wherein the PEG group has an average molecular weight of 50 kDa. Further provided herein are IL-2 conjugates wherein the PEG group has an average molecular weight of 55 kDa. Further provided herein are IL-2 conjugates wherein the PEG group has an average molecular weight of 60 kDa. Further described herein are IL-2 conjugates wherein the IL-2 conjugate has the amino acid sequence of SEQ ID NO: 155 or 110. Further described herein are IL-2 conjugates wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa. Further described herein are IL-2 conjugates wherein W is a PEG group having an average molecular weight selected from 50 kDa and 30 kDa. Further described herein are IL-2 conjugates wherein W is a PEG group having an average molecular weight of 5 kDa. Further described herein are IL-2 conjugates wherein W is a PEG group having an average molecular weight of 30 kDa. Further provided herein are IL-2 conjugates wherein the PEG group has an average molecular weight of 35 kDa. Further provided herein are IL-2 conjugates wherein the PEG group has an average molecular weight of 40 kDa. Further provided herein are IL-2 conjugates wherein the PEG group has an average molecular weight of 45 kDa. Further provided herein are IL-2 conjugates wherein the PEG group has an average molecular weight of 50 kDa. Further provided herein are IL-2 conjugates wherein the PEG group has an average molecular weight of 55 kDa. Further provided herein are IL-2 conjugates wherein the PEG group has an average molecular weight of 60 kDa. Further described herein are IL-2 conjugates wherein W is a linear or branched PEG group. Further described herein are IL-2 conjugates wherein W is a linear PEG group. Further described herein are IL-2 conjugates wherein W is a branched PEG group. Further described herein are IL-2 conjugates wherein W is a methoxy PEG group. Further described herein are IL-2 conjugates wherein the methoxy PEG group is linear or branched. Further described herein are IL-2 conjugates wherein the methoxy PEG group is linear. Further described herein are IL-2 conjugates wherein the methoxy PEG group is branched.

Described herein are IL-2 conjugates comprising the amino acid sequence of any one of SEQ ID NOS: 169-183 and 124-138, wherein [AzK_L1_PEG50 kDa] has the structure of Formula (IV) or Formula (V), or a mixture of Formula (IV) and Formula (V):

Formula (IV)

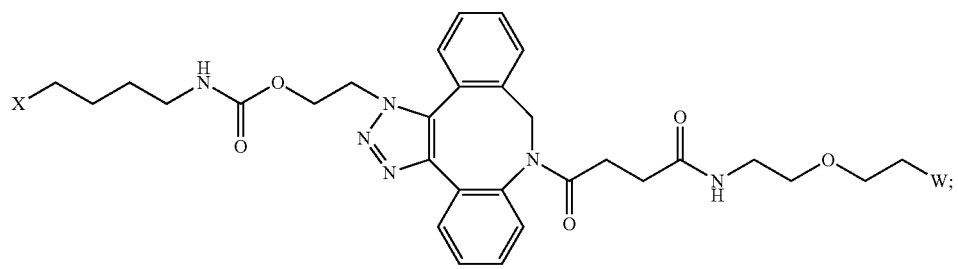

Formula (V)

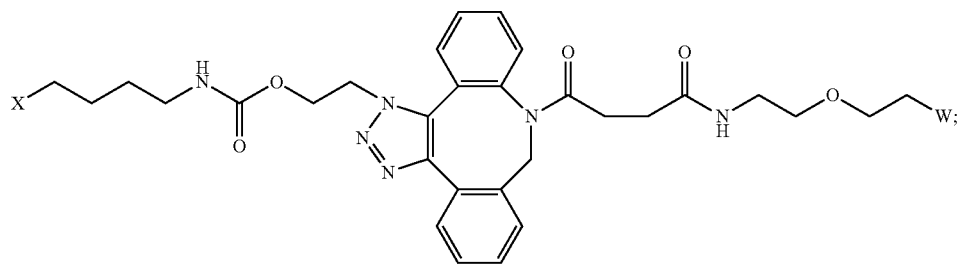

wherein:
W is a PEG group having an average molecular weight of 50 kDa; and
X has the structure:

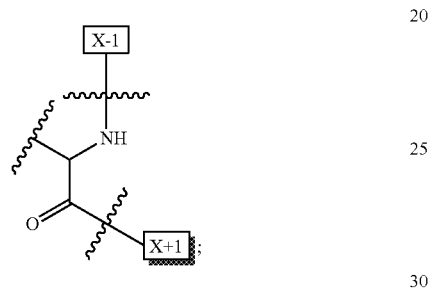

X-1 indicates the point of attachment to the preceding amino acid residue; and
X+1 indicates the point of attachment to the following amino acid residue. In some embodiments, the IL-2 conjugate is a pharmaceutically acceptable salt, solvate, or hydrate thereof. Further described herein are IL-2 conjugates wherein the IL-2 conjugate has the amino acid sequence of any one of SEQ ID NOS: 169-183. Further described herein are IL-2 conjugates wherein the IL-2 conjugate has the amino acid sequence of any one of SEQ ID NOS: 124-138. Further described herein are IL-2 conjugates wherein the IL-2 conjugate has the amino acid sequence of SEQ ID NO: 170 or 125. Further described herein are IL-2 conjugates wherein the [AzK_L1_PEG50 kDa] has the structure of Formula (IV)

Formula (IV)

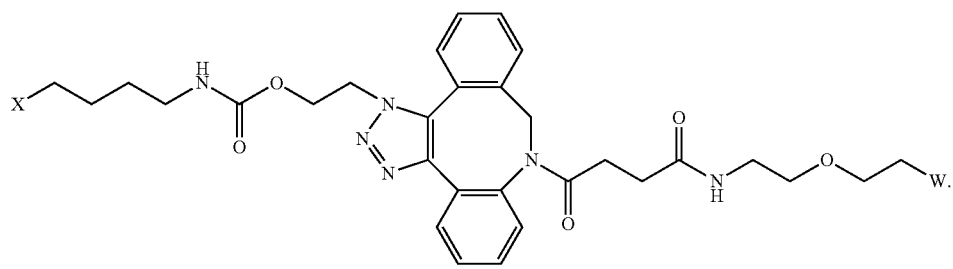

Further described herein are IL-2 conjugates wherein the IL-2 conjugate has the amino acid sequence of any one of SEQ ID NOS: 169-183. Further described herein are IL-2 conjugates wherein the IL-2 conjugate has the amino acid sequence of any one of SEQ ID NOS: 124-138. Further described herein are IL-2 conjugates wherein the IL-2 conjugate has the amino acid sequence of SEQ ID NO: 170 or 125. Further described herein are IL-2 conjugates wherein the [AzK_L1_PEG50 kDa] has the structure of Formula (V)

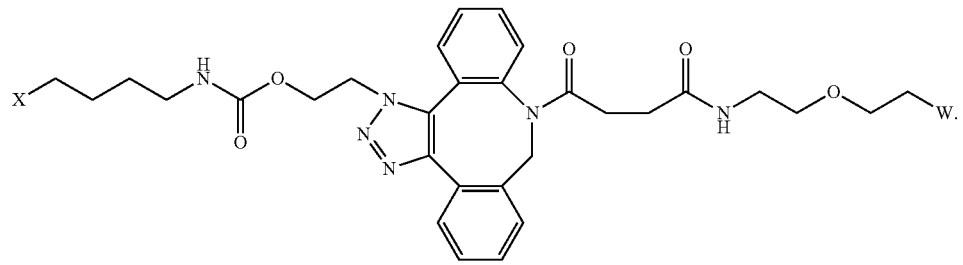

Formula (V)

Further described herein are IL-2 conjugates wherein the IL-2 conjugate has the amino acid sequence of any one of SEQ ID NOS: 169-183. Further described herein are IL-2 conjugates wherein the IL-2 conjugate has the amino acid sequence of any one of SEQ ID NOS: 124-138. Further described herein are IL-2 conjugates wherein the IL-2 conjugate has the amino acid sequence of SEQ ID NO: 170 or 125.

Described herein are IL-2 conjugates comprising the amino acid sequence of any one of SEQ ID NOS: 184-198 and 139-153, wherein [AzK_L1_PEG30 kDa] has the structure of Formula (IV) or Formula (V), or is a mixture of the structures of Formula (IV) and Formula (V):

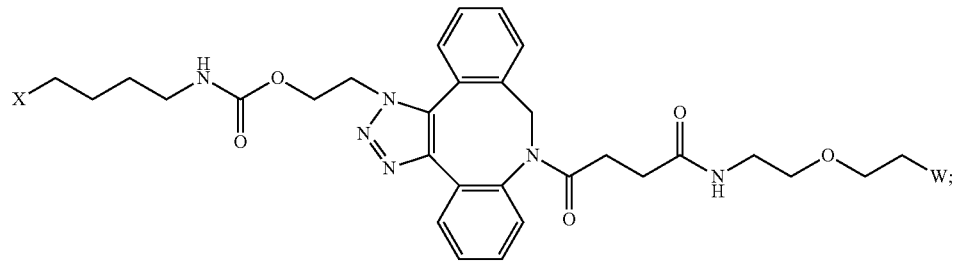

Formula (IV)

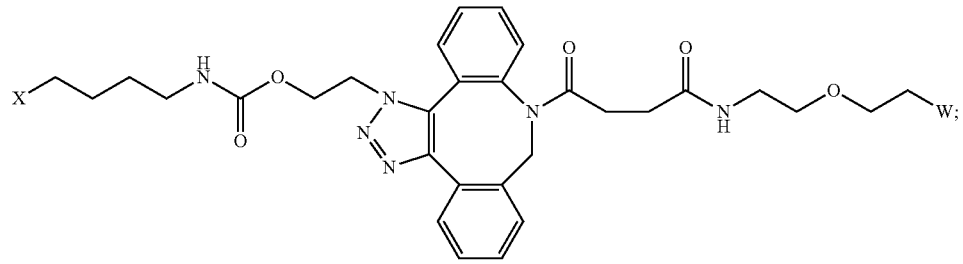

Formula (V)

wherein:
W is a PEG group having an average molecular weight of 30 kDa; and
X has the structure:

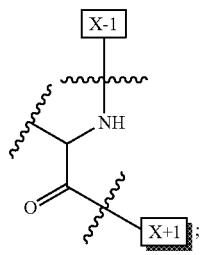

X−1 indicates the point of attachment to the preceding amino acid residue; and

X+1 indicates the point of attachment to the following amino acid residue. In some embodiments, the IL-2 conjugate is a pharmaceutically acceptable salt, solvate, or hydrate thereof. Further described herein are IL-2 conjugates wherein the IL-2 conjugate has the amino acid sequence of any one of SEQ ID NOS: 184-198. Further described herein are IL-2 conjugates wherein the IL-2 conjugate has the amino acid sequence of any one of SEQ ID NOS: 139-153. Further described herein are IL-2 conjugates wherein the IL-2 conjugate has the amino acid sequence of SEQ ID NO: 185 or 140. Further described herein are IL-2 conjugates wherein the [AzK_L1_PEG30 kDa] has the structure of Formula (IV):

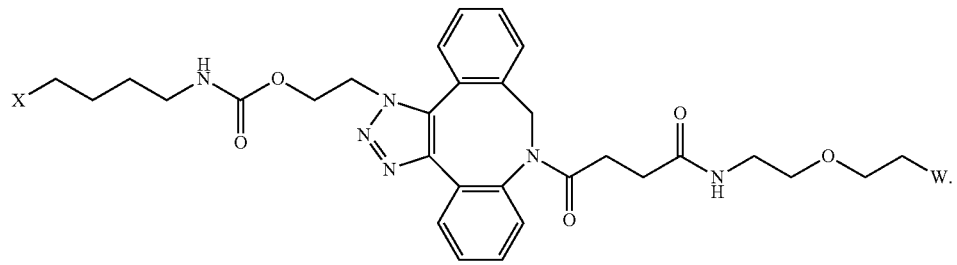

Formula (IV)

Further described herein are IL-2 conjugates wherein the IL-2 conjugate has the amino acid sequence of any one of SEQ ID NOS: 184-198. Further described herein are IL-2 conjugates wherein the IL-2 conjugate has the amino acid sequence of any one of SEQ ID NOS: 139-153. Further described herein are IL-2 conjugates wherein the IL-2 conjugate has the amino acid sequence of SEQ ID NO: 185 or 140. Further described herein are IL-2 conjugates wherein the [AzK_L1_PEG30 kDa] has the structure of Formula (V)

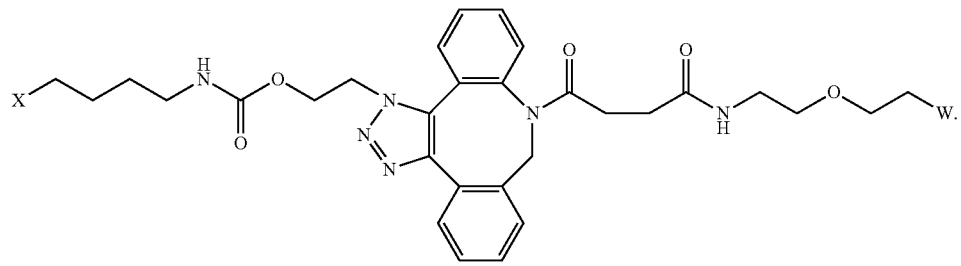

Formula (V)

Further described herein are IL-2 conjugates wherein the IL-2 conjugate has the amino acid sequence of any one of SEQ ID NOS: 184-198. Further described herein are IL-2 conjugates wherein the IL-2 conjugate has the amino acid sequence of any one of SEQ ID NOS: 139-153. Further described herein are IL-2 conjugates wherein the IL-2 conjugate has the amino acid sequence of SEQ ID NO: 185 or 140.

Described herein are IL-2 conjugates comprising the amino acid sequence of any one of SEQ ID NOS: 154-168 and 109-123, wherein [Azk_L1 PEG] is a mixture of the structures of Formula (IV) and Formula (V):

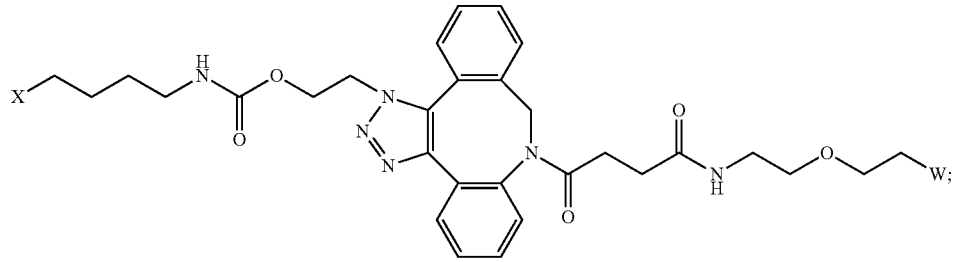

Formula (IV)

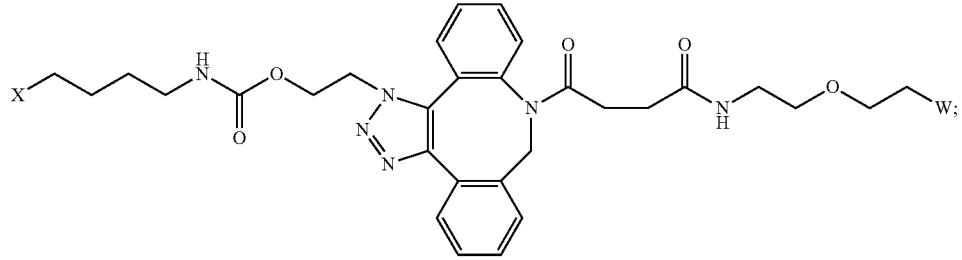

Formula (V)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and
X has the structure:

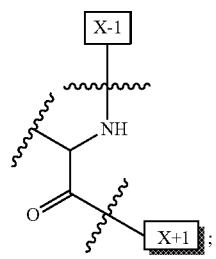

X-1 indicates the point of attachment to the preceding amino acid residue; and
X+1 indicates the point of attachment to the following amino acid residue. In some embodiments, the IL-2 conjugate is a pharmaceutically acceptable salt, solvate, or hydrate thereof. Further described herein are IL-2 conjugates wherein the ratio of the amount of the structure of Formula (IV) to the amount of the structure of Formula (V) comprising the total amount of [AzK_L1_PEG] in the IL-2 conjugate is about 1:1. Further described herein are IL-2 conjugates wherein the ratio of the amount of the structure of Formula (IV) to the amount of the structure of Formula (V) comprising the total amount of [AzK_L1_PEG] in the IL-2 conjugate is greater than 1:1. Further described herein are IL-2 conjugates wherein the ratio of the amount of the structure of Formula (IV) to the amount of the structure of Formula (V) comprising the total amount of [AzK_L1_PEG] in the IL-2 conjugate is less than 1:1. Further described herein are IL-2 conjugates wherein W is a linear or branched PEG group. Further described herein are IL-2 conjugates wherein W is a linear PEG group. Further described herein are IL-2 conjugates wherein W is a branched PEG group. Further described herein are IL-2 conjugates wherein W is a methoxy PEG group. Further described herein are IL-2 conjugates wherein the methoxy PEG group is linear or branched. Further described herein are IL-2 conjugates wherein the methoxy PEG group is linear. Further described herein are IL-2 conjugates wherein the methoxy PEG group is branched.

Described herein are IL-2 conjugates comprising the amino acid sequence of any one of SEQ ID NOS: 169-183 and 124-138, wherein [AzK_L1_PEG50 kDa] is a mixture of the structures of Formula (IV) and Formula (V):

Formula (IV)

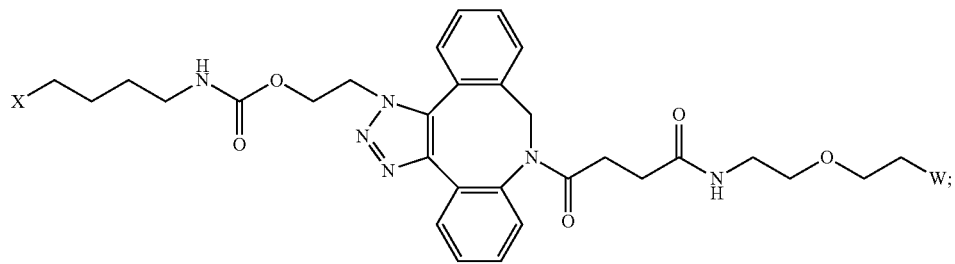

Formula (V)

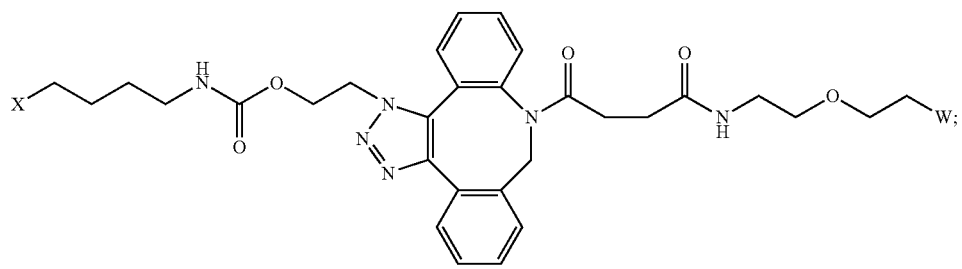

wherein:

W is a PEG group having an average molecular weight of 50 kDa; and

X has the structure:

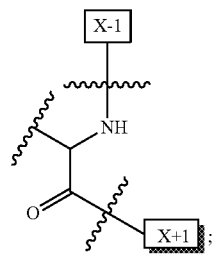

X−1 indicates the point of attachment to the preceding amino acid residue; and

X+1 indicates the point of attachment to the following amino acid residue. In some embodiments, the IL-2 conjugate is a pharmaceutically acceptable salt, solvate, or hydrate thereof. Further described herein are IL-2 conjugates wherein the ratio of the amount of the structure of Formula (IV) to the amount of the structure of Formula (V) comprising the total amount of [AzK_L1_PEG50 kDa] in the IL-2 conjugate is about 1:1. Further described herein are IL-2 conjugates wherein the ratio of the amount of the structure of Formula (IV) to the amount of the structure of Formula (V) comprising the total amount of [AzK_L1_PEG50 kDa] in the IL-2 conjugate is greater than 1:1. Further described herein are IL-2 conjugates wherein the ratio of the amount of the structure of Formula (IV) to the amount of the structure of Formula (V) comprising the total amount of [AzK_L1_PEG50 kDa] in the IL-2 conjugate is less than 1:1.

Described herein are IL-2 conjugates comprising the amino acid sequence of any one of SEQ ID NOS: 184-198 and 139-153, wherein [AzK_L1_PEG30 kDa] is a mixture of the structures of Formula (IV) and Formula (V):

Formula (IV)

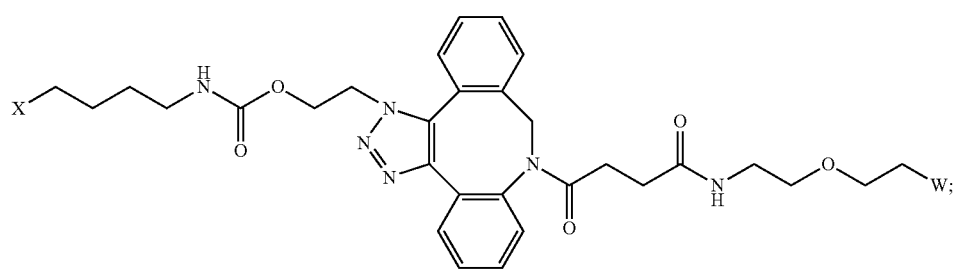

Formula (V)

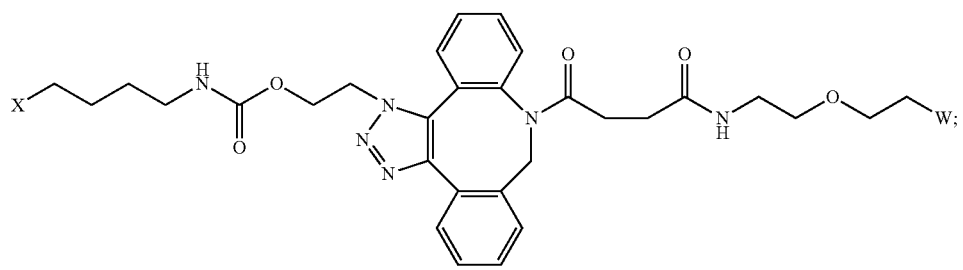

wherein:
W is a PEG group having an average molecular weight of 30 kDa; and
X has the structure:

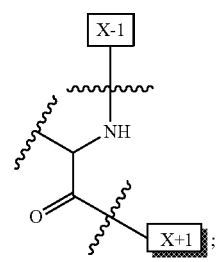

X−1 indicates the point of attachment to the preceding amino acid residue; and
X+1 indicates the point of attachment to the following amino acid residue. In some embodiments, the IL-2 conjugate is a pharmaceutically acceptable salt, solvate, or hydrate thereof. Further described herein are IL-2 conjugates wherein the ratio of the amount of the structure of Formula (IV) to the amount of the structure of Formula (V) comprising the total amount of [AzK_L1_PEG30 kDa] in the IL-2 conjugate is about 1:1. Further described herein are IL-2 conjugates wherein the ratio of the amount of the structure of Formula (IV) to the amount of the structure of Formula (V) comprising the total amount of [AzK_L1_PEG30 kDa] in the IL-2 conjugate is greater than 1:1. Further described herein are IL-2 conjugates wherein the ratio of the amount of the structure of Formula (IV) to the amount of the structure of Formula (V) comprising the total amount of [AzK_L1_PEG30 kDa] in the IL-2 conjugate is less than 1:1.

Described herein are IL-2 conjugates comprising the amino acid sequence of SEQ ID NO: 3 in which at least one amino acid residue in the IL-2 conjugate is replaced by the structure of Formula (VI) or (VII), or a mixture of (VI) and (VII):

Formula (VI)

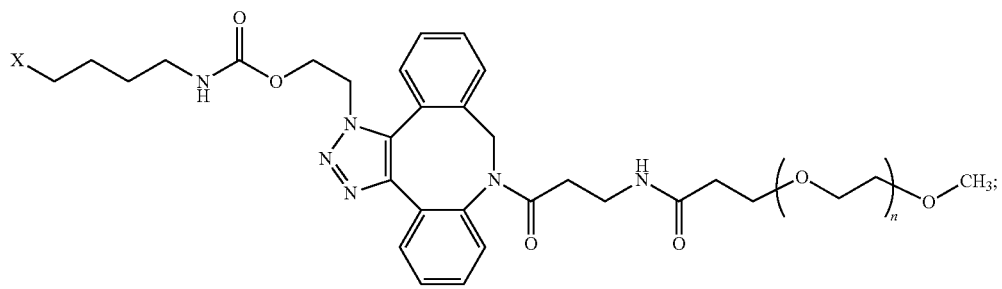

(VII)

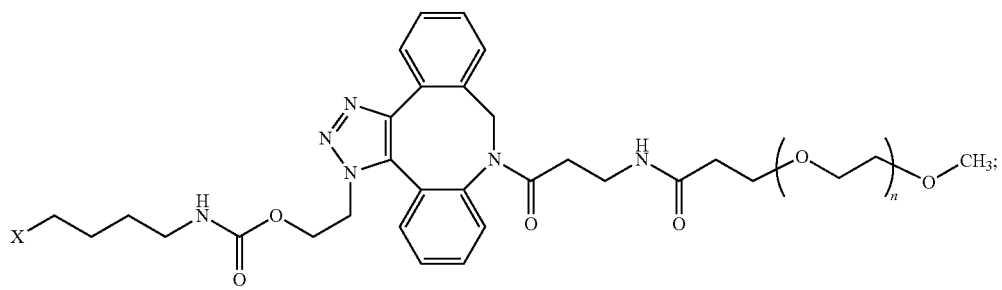

wherein:
n is an integer in the range from about 2 to about 5000; and
X has the structure:

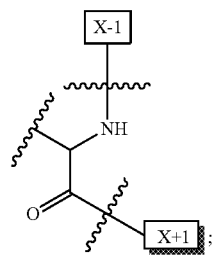

X−1 indicates the point of attachment to the preceding amino acid residue; and
X+1 indicates the point of attachment to the following amino acid residue. In some embodiments, the IL-2 conjugate is a pharmaceutically acceptable salt, solvate, or hydrate thereof. Here and throughout, embodiments of Formula (VI) and/or (VII) also encompass a pharmaceutically acceptable salt, solvate, or hydrate thereof. Further described herein are IL-2 conjugates wherein the position of the structure of Formula (VI) or (VII), or a mixture of (VI) and (VII), in the amino acid sequence of the IL-2 conjugate is selected from P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, I88, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, and T132. Further described herein are IL-2 conjugates wherein the position of the structure of Formula (VI) or (VII), or a mixture of (VI) and (VII), in the amino acid sequence of the IL-2 conjugate is selected from K8, H15, L18, D19, M22, N25, N87, V90, I91, L93, E94, K96, G97, S98, E99, D108 in the N87R variant, N118, T122, S124, Q125, S126, S129, and T130. Further described herein are IL-2 conjugates wherein the position of the structure of Formula (VI) or (VII), or a mixture of (VI) and (VII), in the amino acid sequence of the IL-2 conjugate is selected from K8, H15, L18, D19, M22, N25, N87, V90, E99, D108 in the N87R variant, N118, T122, S124, and T130. Further described herein are IL-2 conjugates wherein the position of the structure of Formula (VI) or (VII), or a mixture of (VI) and (VII), in the amino acid sequence of the IL-2 conjugate is selected from in the amino acid sequence of the IL-2 conjugate is K8. Further described herein are IL-2 conjugates wherein the position of the structure of Formula (VI) or (VII), or a mixture of (VI) and (VII), in the amino acid sequence of the IL-2 conjugate is H15. Further described herein are IL-2 conjugates wherein the position of the structure of Formula (VI) or (VII), or a mixture of (VI) and (VII), in the amino acid sequence of the IL-2 conjugate is L18. Further described herein are IL-2 conjugates wherein the position of the structure of Formula (VI) or (VII), or a mixture of (VI) and (VII), in the amino acid sequence of the IL-2 conjugate is D19. Further described herein are IL-2 conjugates wherein the position of the structure of Formula (VI) or (VII), or a mixture of (VI) and (VII), in the amino acid sequence of the IL-2 conjugate is M22. Further described herein are IL-2 conjugates wherein the position of the structure of Formula (VI) or (VII), or a mixture of (VI) and (VII), in the amino acid sequence of the IL-2 conjugate is N25. Further described herein are IL-2 conjugates wherein the position of the structure of Formula (VI) or (VII), or a mixture of (VI) and (VII), in the amino acid sequence of the IL-2 conjugate is N87. Further described herein are IL-2 conjugates wherein the position of the structure of Formula (VI) or (VII), or a mixture of (VI) and (VII), in the amino acid sequence of the IL-2 conjugate is V90. Further described herein are IL-2 conjugates wherein the position of the structure of Formula (VI) or (VII), or a mixture of (VI) and (VII), in the amino acid sequence of the IL-2 conjugate is E99. Further described herein are IL-2 conjugates wherein the position of the structure of Formula (VI) or (VII), or a mixture of (VI) and (VII), in the amino acid sequence of the IL-2 conjugate is D108 in the N87R variant. Further described herein are IL-2 conjugates wherein the position of the structure of Formula (VI) or (VII), or a mixture of (VI) and (VII), in the amino acid sequence of the IL-2 conjugate is N118. Further described herein are IL-2 conjugates wherein the position of the structure of Formula (VI) or (VII), or a mixture of (VI) and (VII), in the amino acid sequence of the IL-2 conjugate is T122. Further described herein are IL-2 conjugates wherein the position of the structure of Formula (VI) or (VII), or a mixture of (VI) and (VII), in the amino acid sequence of the IL-2 conjugate is S124. Further described herein are IL-2 conjugates wherein the position of the structure of Formula (VI) or (VII), or a mixture of (VI) and (VII), in the amino acid sequence of the IL-2 conjugate is T130. Further described herein are IL-2 conjugates wherein n is about 75 to about 1000. Further described herein are IL-2 conjugates wherein n is about 100 to about 1000. Further described herein are IL-2 conjugates wherein n is about 200 to about 5000. Further described herein are IL-2 conjugates wherein n is about 500 to about 1000. Further described herein are IL-2 conjugates wherein n is about 400 to about 800.

Described herein are IL-2 conjugates comprising the amino acid sequence of SEQ ID NO: 3 in which at least one amino acid residue in the IL-2 conjugate is replaced by the structure of Formula (VIII) or (IX), or a mixture of (VIII) and (IX):

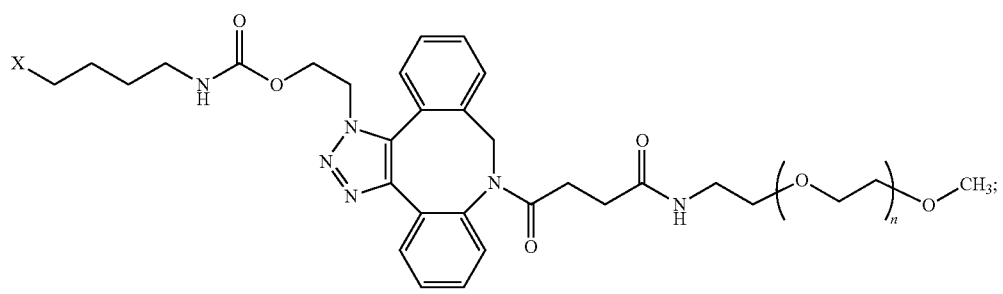

Formula (VIII)


Formula (IX)

wherein:

n is an integer in the range from about 2 to about 5000; and
X has the structure:

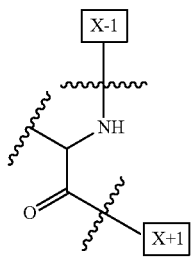

X−1 indicates the point of attachment to the preceding amino acid residue; and

X+1 indicates the point of attachment to the following amino acid residue. In some embodiments, the IL-2 conjugate is a pharmaceutically acceptable salt, solvate, or hydrate thereof. Here and throughout, embodiments of Formula (VIII) and/or (IX) also encompass a pharmaceutically acceptable salt, solvate, or hydrate thereof. Further described herein are IL-2 conjugates wherein the position of the structure of Formula (VIII) or (IX), or a mixture of (VIII) and (IX), in the amino acid sequence of the IL-2 conjugate is selected from P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, I88, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, and T132. Further described herein are IL-2 conjugates wherein the position of the structure of Formula (VIII) or (IX), or a mixture of (VIII) and (IX), in the amino acid sequence of the IL-2 conjugate is selected from K8, H15, L18, D19, M22, N25, N87, V90, I91, L93, E94, K96, G97, S98, E99, D108 in the N87R variant, N118, T122, S124, Q125, S126, S129, and T130. Further described herein are IL-2 conjugates wherein the position of the structure of Formula (VIII) or (IX), or a mixture of (VIII) and (IX), in the amino acid sequence of the IL-2 conjugate is selected from K8, H15, L18, D19, M22, N25, N87, V90, E99, D108 in the N87R variant, N118, T122, S124, and T130. Further described herein are IL-2 conjugates wherein the position of the structure of Formula (VIII) or (IX), or a mixture of (VIII) and (IX), in the amino acid sequence of the IL-2 conjugate is K8. Further described herein are IL-2 conjugates wherein the position of the structure of Formula (VIII) or (IX), or a mixture of (VIII) and (IX), in the amino acid sequence of the IL-2 conjugate is H15. Further described herein are IL-2 conjugates wherein the position of the structure of Formula (VIII) or (IX), or a mixture of (VIII) and (IX), in the amino acid sequence of the IL-2 conjugate is L18. Further described herein are IL-2 conjugates wherein the position of the structure of Formula (VIII) or (IX), or a mixture of (VIII) and (IX), in the amino acid sequence of the IL-2 conjugate is D19. Further described herein are IL-2 conjugates wherein the position of the structure of Formula (VIII) or (IX), or a mixture of (VIII) and (IX), in the amino acid sequence of the IL-2 conjugate is M22. Further described herein are IL-2 conjugates wherein the position of the structure of Formula (VIII) or (IX), or a mixture of (VIII) and (IX), in the amino acid sequence of the IL-2 conjugate is N25. Further described herein are IL-2 conjugates wherein the position of the structure of Formula (VIII) or (IX), or a mixture of (VIII) and (IX), in the amino acid sequence of the IL-2 conjugate is N87. Further described herein are IL-2 conjugates wherein the position of the structure of Formula (VIII) or (IX), or a mixture of (VIII) and (IX), in the amino acid sequence of the IL-2 conjugate is V90. Further described herein are IL-2 conjugates wherein the position of the structure of Formula (VIII) or (IX), or a mixture of (VIII) and (IX), in the amino acid sequence of the IL-2 conjugate is E99. Further described herein are IL-2 conjugates wherein the position of the structure of Formula (VIII) or (IX), or a mixture of (VIII)

and (IX), in the amino acid sequence of the IL-2 conjugate is D108 in the N87R variant. Further described herein are IL-2 conjugates wherein the position of the structure of Formula (VIII) or (IX), or a mixture of (VIII) and (IX), in the amino acid sequence of the IL-2 conjugate is N118. Further described herein are IL-2 conjugates wherein the position of the structure of Formula (VIII) or (IX), or a mixture of (VIII) and (IX), in the amino acid sequence of the IL-2 conjugate is T122. Further described herein are IL-2 conjugates wherein the position of the structure of Formula (VIII) or (IX), or a mixture of (VIII) and (IX), in the amino acid sequence of the IL-2 conjugate is S124. Further described herein are IL-2 conjugates wherein the position of the structure of Formula (VIII) or (IX), or a mixture of (VIII) and (IX), in the amino acid sequence of the IL-2 conjugate is T130. Further described herein are IL-2 conjugates wherein n is about 75 to about 1000. Further described herein are IL-2 conjugates wherein n is about 100 to about 1000. Further described herein are IL-2 conjugates wherein n is about 200 to about 5000. Further described herein are IL-2 conjugates wherein n is about 500 to about 1000. Further described herein are IL-2 conjugates wherein n is about 400 to about 800.

Described herein are IL-2 conjugates comprising the amino acid sequence of SEQ ID NO: 3 in which at least one amino acid residue in the IL-2 conjugate is replaced by the structure of Formula (X) or (XI), or a mixture of (X) and (XI):

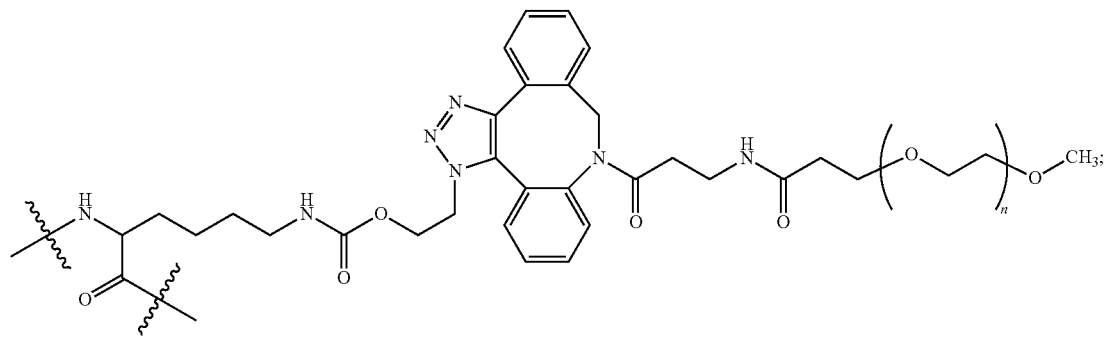

Formula (X)

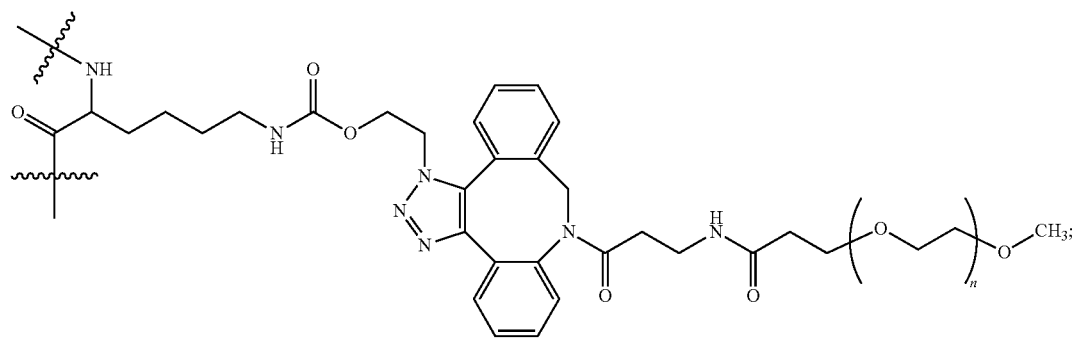

Formula (XI)

wherein:

n is an integer in the range from about 2 to about 5000; and the wavy lines indicate covalent bonds to amino acid residues within SEQ ID NO: 3 that are not replaced. Here and throughout, embodiments of Formula (X) and/or (XI) also encompass a pharmaceutically acceptable salt, solvate, or hydrate thereof. Further described herein are IL-2 conjugates wherein the position of the structure of Formula (X) or (XI), or a mixture of (X) and (XI), in the amino acid sequence of the IL-2 conjugate is selected from P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, I88, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, and T132. Further described herein are IL-2 conjugates wherein the position of the structure of Formula (X) or (XI), or a mixture of (X) and (XI), in the amino acid sequence of the IL-2 conjugate is selected from K8, H15, L18, D19, M22, N25, N87, V90, I91, L93, E94, K96, G97, S98, E99, D108 in the N87R variant, N118, T122, S124, Q125, S126, S129, and T130. Further described herein are IL-2 conjugates wherein the position of the structure of Formula (X) or (XI), or a mixture of (X) and (XI), in the amino acid sequence of the IL-2 conjugate is selected from K8, H15, L18, D19, M22, N25, N87, V90, E99, D108 in the N87R variant, N118, T122, S124, and T130. Further described herein are IL-2 conjugates wherein the position of the structure of Formula (X) or (XI), or a mixture of (X) and (XI), in the amino acid sequence of the IL-2 conjugate is K8. Further described herein are IL-2 conjugates wherein the position of the structure of Formula (X) or (XI), or a mixture of (X) and (XI), in the amino acid sequence of the IL-2 conjugate is H15. Further described herein are IL-2 conjugates wherein the position of the structure of Formula (X) or (XI), or a mixture of (X) and (XI), in the amino acid sequence of the IL-2 conjugate is L18. Further described herein are IL-2 conjugates wherein the position of the structure of Formula (X) or (XI), or a mixture of (X) and (XI), in the amino acid sequence of the IL-2 conjugate is D19. Further described herein are IL-2 conjugates wherein the position of the structure of Formula (X) or (XI), or a mixture of (X) and (XI), in the amino acid sequence of the IL-2 conjugate is M22. Further described herein are IL-2 conjugates wherein the position of the structure of Formula (X) or (XI), or a mixture of (X) and (XI), in the amino acid sequence of the IL-2 conjugate is N25. Further described herein are IL-2 conjugates wherein the position of the structure of Formula (X) or (XI), or a mixture of (X) and (XI), in the amino acid sequence of the IL-2 conjugate is N87. Further described herein are IL-2 conjugates wherein the position of the structure of Formula (X) or (XI), or a mixture of (X) and (XI), in the amino acid sequence of the IL-2 conjugate is V90. Further described herein are IL-2 conjugates wherein the position of the structure of Formula (X) or (XI), or a mixture of (X) and (XI), in the amino acid sequence of the IL-2 conjugate is E99. Further described herein are IL-2 conjugates wherein the position of the structure of Formula (X) or (XI), or a mixture of (X) and (XI), in the amino acid sequence of the IL-2 conjugate is D108 in the N87R variant. Further described herein are IL-2 conjugates wherein the position of the structure of Formula (X) or (XI), or a mixture of (X) and (XI), in the amino acid sequence of the IL-2 conjugate is N118. Further described herein are IL-2 conjugates wherein the position of the structure of Formula (X) or (XI), or a mixture of (X) and (XI), in the amino acid sequence of the IL-2 conjugate is T122. Further described herein are IL-2 conjugates wherein the position of the structure of Formula (X) or (XI), or a mixture of (X) and (XI), in the amino acid sequence of the IL-2 conjugate ate is S124. Further described herein are IL-2 conjugates wherein the position of the structure of Formula (X) or (XI), or a mixture of (X) and (XI), in the amino acid sequence of the IL-2 conjugate is T130. Further described herein are IL-2 conjugates wherein n is about 75 to about 1000. Further described herein are IL-2 conjugates wherein n is about 100 to about 1000. Further described herein are IL-2 conjugates wherein n is about 200 to about 5000. Further described herein are IL-2 conjugates wherein n is about 500 to about 1000. Further described herein are IL-2 conjugates wherein n is about 400 to about 800.

Described herein are IL-2 conjugates comprising the amino acid sequence of SEQ ID NO: 3 in which at least one amino acid residue in the IL-2 conjugate is replaced by the structure of Formula (XII) or (XIII), or a mixture of (XII) and (XIII):

Formula (XII)

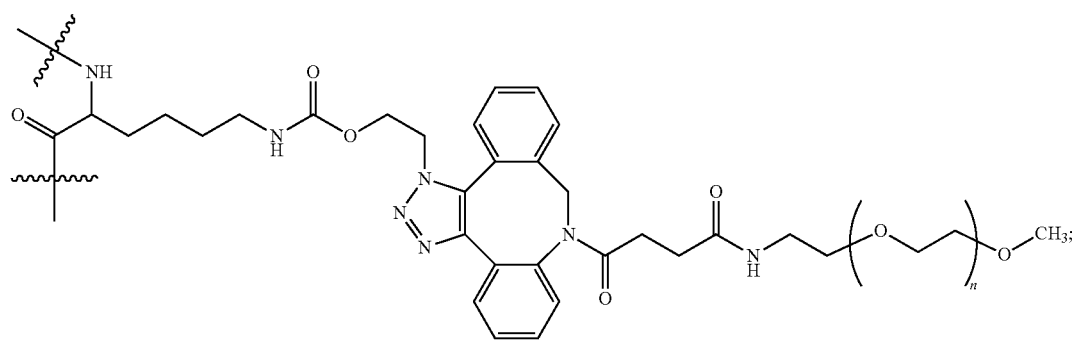

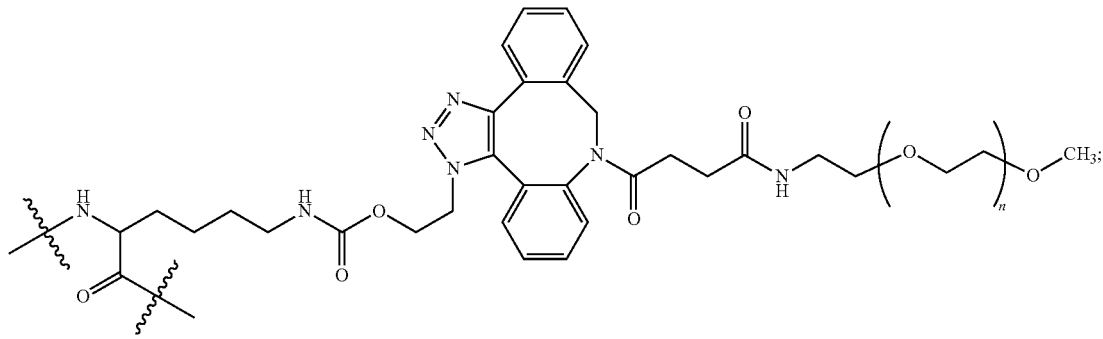

Formula (XIII)

wherein:

n is an integer in the range from about 2 to about 5000; and the wavy lines indicate covalent bonds to amino acid residues within SEQ ID NO: 3 that are not replaced. Here and throughout, embodiments of Formula (XII) and/or (XIII) also encompass a pharmaceutically acceptable salt, solvate, or hydrate thereof. Further described herein are IL-2 conjugates wherein the position of the structure of Formula (XII) or (XIII), or a mixture of (XII) and (XIII), in the amino acid sequence of the IL-2 conjugate is selected from P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, I88, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, and T132. Further described herein are IL-2 conjugates wherein the position of the structure of Formula (XII) or (XIII), or a mixture of (XII) and (XIII), in the amino acid sequence of the IL-2 conjugate is selected from K8, H15, L18, D19, M22, N25, N87, V90, I91, L93, E94, K96, G97, S98, E99, D108 in the N87R variant, N118, T122, S124, Q125, S126, S129, and T130. Further described herein are IL-2 conjugates wherein the position of the structure of Formula (XII) or (XIII), or a mixture of (XII) and (XIII), in the amino acid sequence of the IL-2 conjugate is selected from K8, H15, L18, D19, M22, N25, N87, V90, E99, D108 in the N87R variant, N118, T122, S124, and T130. Further described herein are IL-2 conjugates wherein the position of the structure of Formula (XII) or (XIII), or a mixture of (XII) and (XIII), in the amino acid sequence of the IL-2 conjugate is K8. Further described herein are IL-2 conjugates wherein the position of the structure of Formula (XII) or (XIII), or a mixture of (XII) and (XIII), in the amino acid sequence of the IL-2 conjugate is H15. Further described herein are IL-2 conjugates wherein the position of the structure of Formula (XII) or (XIII), or a mixture of (XII) and (XIII), in the amino acid sequence of the IL-2 conjugate is L18. Further described herein are IL-2 conjugates wherein the position of the structure of Formula (XII) or (XIII), or a mixture of (XII) and (XIII), in the amino acid sequence of the IL-2 conjugate is D19. Further described herein are IL-2 conjugates wherein the position of the structure of Formula (XII) or (XIII), or a mixture of (XII) and (XIII), in the amino acid sequence of the IL-2 conjugate is M22. Further described herein are IL-2 conjugates wherein the position of the structure of Formula (XII) or (XIII), or a mixture of (XII) and (XIII), in the amino acid sequence of the IL-2 conjugate is N25. Further described herein are IL-2 conjugates wherein the position of the structure of Formula (XII) or (XIII), or a mixture of (XII) and (XIII), in the amino acid sequence of the IL-2 conjugate is N87. Further described herein are IL-2 conjugates wherein the position of the structure of Formula (XII) or (XIII), or a mixture of (XII) and (XIII), in the amino acid sequence of the IL-2 conjugate is V90. Further described herein are IL-2 conjugates wherein the position of the structure of Formula (XII) or (XIII), or a mixture of (XII) and (XIII), in the amino acid sequence of the IL-2 conjugate is E99. Further described herein are IL-2 conjugates wherein the position of the structure of Formula (XII) or (XIII), or a mixture of (XII) and (XIII), in the amino acid sequence of the IL-2 conjugate is D108 in the N87R variant. Further described herein are IL-2 conjugates wherein the position of the structure of Formula (XII) or (XIII), or a mixture of (XII) and (XIII), in the amino acid sequence of the IL-2 conjugate is N118. Further described herein are IL-2 conjugates wherein the position of the structure of Formula (XII) or (XIII), or a mixture of (XII) and (XIII), in the amino acid sequence of the IL-2 conjugate is T122. Further described herein are IL-2 conjugates wherein the position of the structure of Formula (XII) or (XIII), or a mixture of (XII) and (XIII), in the amino acid sequence of the IL-2 conjugate is S124. Further described herein are IL-2 conjugates wherein the position of the structure of Formula (XII) or (XIII), or a mixture of (XII) and (XIII), in the amino acid sequence of the IL-2 conjugate is T130. Further described herein are IL-2 conjugates wherein n is about 75 to about 1000. Further described herein are IL-2 conjugates wherein n is about 100 to about 1000. Further described herein are IL-2 conjugates wherein n is about 200 to about 5000. Further described herein are IL-2 conjugates wherein n is about 500 to about 1370. Further described herein are IL-2 conjugates wherein n is about 400 to about 800. Further described herein are IL-2 conjugates wherein n is about 400 to about 1370. Further described herein are IL-2 conjugates wherein n is about 400 to about 1250. Further described herein are IL-2 conjugates wherein n is about 600 to about 1370. Further described herein are IL-2 conjugates wherein n is about 600 to about 1250. Further described herein are IL-2 conjugates wherein n is about 675 to about 1250. Further described herein are IL-2 conjugates wherein n is about 680 to about 1250. Further described herein are IL-2 conjugates wherein n is about 680 to about 1140. Further described herein are IL-2 conjugates wherein n is about 450. Further described herein are IL-2 conjugates wherein n is about 568. Further described herein are IL-2 conjugates wherein n is about 682.

Further described herein are IL-2 conjugates wherein n is about 795. Further described herein are IL-2 conjugates wherein n is about 909. Further described herein are IL-2 conjugates wherein n is about 1022. Further described herein are IL-2 conjugates wherein n is about 1136. Further described herein are IL-2 conjugates wherein n is about 1250. Further described herein are IL-2 conjugates wherein n is about 1363.

Described herein are IL-2 conjugates comprising the amino acid sequence of SEQ ID NO: 4 in which at least one amino acid residue in the IL-2 conjugate is replaced by the structure of Formula (VI) or (VII), or a mixture of (VI) and (VII):

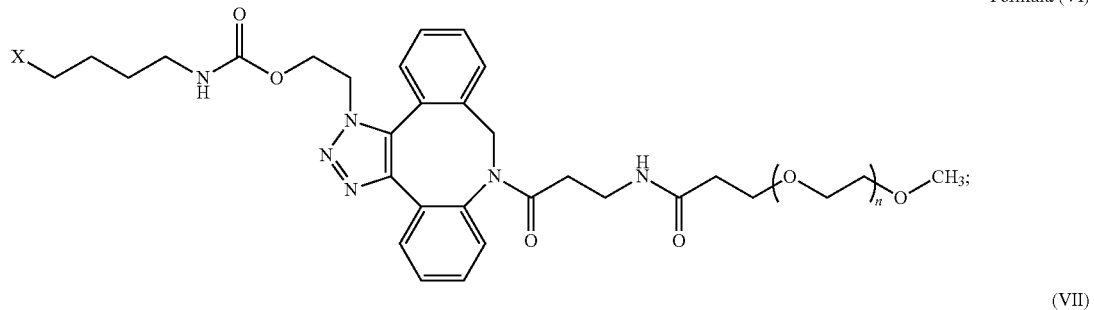

Formula (VI)

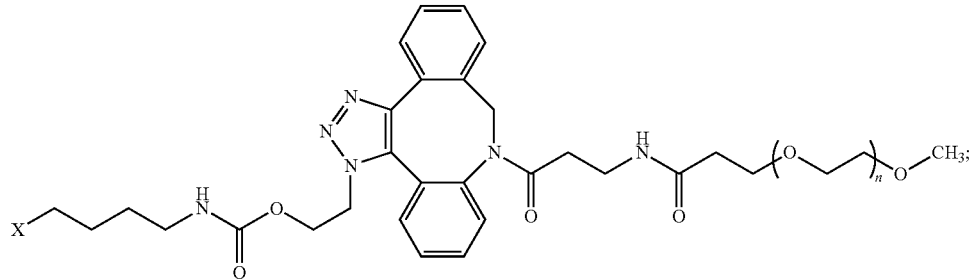

(VII)

wherein:
n is an integer in the range from about 2 to about 5000; and
X has the structure:

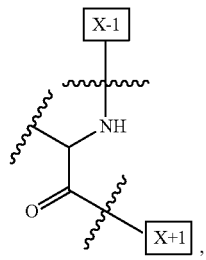

X−1 indicates the point of attachment to the preceding amino acid residue; and
X+1 indicates the point of attachment to the following amino acid residue. In some embodiments, the IL-2 conjugate is a pharmaceutically acceptable salt, solvate, or hydrate thereof.

Further described herein are IL-2 conjugates wherein the position of the structure of Formula (VI) or (VII), or a mixture of (VI) and (VII), in the amino acid sequence of the IL-2 conjugate is selected from A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133. Further described herein are IL-2 conjugates wherein the position of the structure of Formula (VI) or (VII), or a mixture of (VI) and (VII), in the amino acid sequence of the IL-2 conjugate is selected from K9, H16, L19, D20, M23, N26, N88, V91, I92, L94, E95, K97, G98, S99, E100, D109 in the N88R variant, N119, T123, S125, Q126, S127, S130, and T131. Further described herein are IL-2 conjugates wherein the position of the structure of Formula (VI) or (VII), or a mixture of (VI) and (VII), in the amino acid sequence of the IL-2 conjugate is selected from K9, H16, L19, D20, M23, N26, N88, V91, E100, D109 in the N88R variant, N119, T123, S125, and T131. Further described herein are IL-2 conjugates wherein the position of the structure of Formula (VI) or (VII), or a mixture of (VI) and (VII), in the amino acid sequence of the IL-2 conjugate is K9. Further described herein are IL-2 conjugates wherein the position of the structure of Formula (VI) or (VII), or a mixture of (VI) and (VII), in the amino acid sequence of the IL-2 conjugate is H16. Further described herein are IL-2 conjugates wherein the position of the structure of Formula (VI) or (VII), or a mixture of (VI) and (VII), in the amino acid sequence of the IL-2 conjugate is L19. Further described herein are IL-2 conjugates wherein the position of the structure of Formula (VI) or (VII), or a mixture of (VI) and (VII), in the amino acid sequence of the IL-2 conjugate is D20. Further described herein are IL-2 conjugates wherein the position of the structure of Formula (VI) or (VII), or a mixture of (VI) and (VII), in the amino acid sequence of the IL-2 conjugate is M23. Further described herein are IL-2 conjugates wherein the position of the structure of Formula (VI) or (VII), or a mixture of (VI) and (VII), in the amino acid sequence of the IL-2 conjugate is N26. Further described herein are IL-2 conjugates wherein the position of the structure of Formula (VI) or (VII), or a mixture of (VI) and (VII), in the amino acid sequence of the IL-2 conjugate is N88. Further described herein are IL-2 conjugates wherein the position of the structure of Formula (VI) or (VII), or a mixture of (VI) and (VII), in the amino acid sequence of the IL-2 conjugate is V91. Further described herein are IL-2 conjugates wherein the position of the structure of Formula (VI) or (VII), or a mixture of (VI) and (VII), in the amino acid sequence of the IL-2 conjugate is E100. Further described herein are IL-2 conjugates wherein the position of the structure of Formula (VI) or (VII), or a mixture of (VI) and (VII), in the amino acid sequence of the IL-2 conjugate is D109 in the N88R variant. Further described herein are IL-2 conjugates wherein the position of the structure of Formula (VI) or (VII), or a mixture of (VI) and (VII), in the amino acid sequence of the IL-2 conjugate is N119. Further described herein are IL-2 conjugates wherein the position of the structure of Formula (VI) or (VII), or a mixture of (VI) and (VII), in the amino acid sequence of the IL-2 conjugate is T123. Further described herein are IL-2 conjugates wherein the position of the structure of Formula (VI) or (VII), or a mixture of (VI) and (VII), in the amino acid sequence of the IL-2 conjugate is S125. Further described herein are IL-2 conjugates wherein the position of the structure of Formula (VI) or (VII), or a mixture of (VI) and (VII), in the amino acid sequence of the IL-2 conjugate is T131. Further described herein are IL-2 conjugates wherein n is about 75 to about 1000. Further described herein are IL-2 conjugates wherein n is about 100 to about 1000. Further described herein are IL-2 conjugates wherein n is about 200 to about 5000. Further described herein are IL-2 conjugates wherein n is about 500 to about 1370. Further described herein are IL-2 conjugates wherein n is about 400 to about 800. Further described herein are IL-2 conjugates wherein n is about 400 to about 1370. Further described herein are IL-2 conjugates wherein n is about 400 to about 1250. Further described herein are IL-2 conjugates wherein n is about 600 to about 1370. Further described herein are IL-2 conjugates wherein n is about 600 to about 1250. Further described herein are IL-2 conjugates wherein n is about 675 to about 1250. Further described herein are IL-2 conjugates wherein n is about 680 to about 1250. Further described herein are IL-2 conjugates wherein n is about 680 to about 1140. Further described herein are IL-2 conjugates wherein n is about 450. Further described herein are IL-2 conjugates wherein n is about 568. Further described herein are IL-2 conjugates wherein n is about 682. Further described herein are IL-2 conjugates wherein n is about 795. Further described herein are IL-2 conjugates wherein n is about 909. Further described herein are IL-2 conjugates wherein n is about 1022. Further described herein are IL-2 conjugates wherein n is about 1136. Further described herein are IL-2 conjugates wherein n is about 1250. Further described herein are IL-2 conjugates wherein n is about 1363.

Described herein are IL-2 conjugates comprising the amino acid sequence of SEQ ID NO: 4 in which at least one amino acid residue in the IL-2 conjugate is replaced by the structure of Formula (VIII) or (IX), or a mixture of (VIII) and (IX):

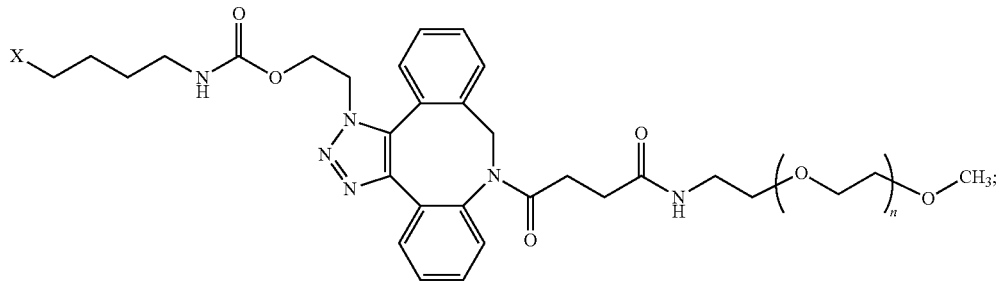

Formula (VIII)

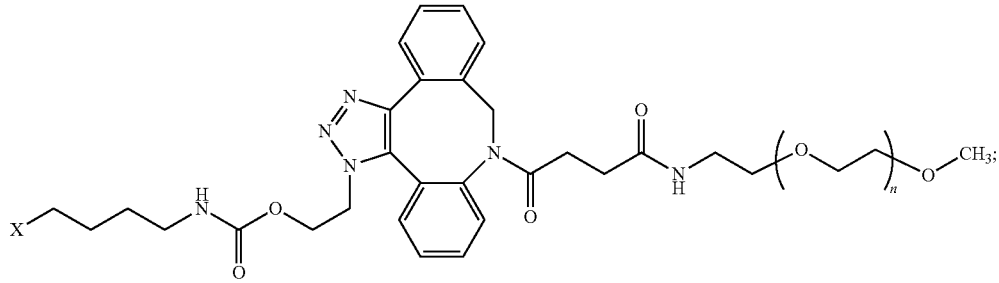

Formula (IX)

wherein:

n is an integer in the range from about 2 to about 5000; and
X has the structure:

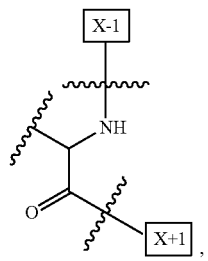

X−1 indicates the point of attachment to the preceding amino acid residue; and

X+1 indicates the point of attachment to the following amino acid residue. In some embodiments, the IL-2 conjugate is a pharmaceutically acceptable salt, solvate, or hydrate thereof. Further described herein are IL-2 conjugates wherein the position of the structure of Formula (VIII) or (IX), or a mixture of (VIII) and (IX), in the amino acid sequence of the IL-2 conjugate is selected from A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133. Further described herein are IL-2 conjugates wherein the position of the structure of Formula (VIII) or (IX), or a mixture of (VIII) and (IX), in the amino acid sequence of the IL-2 conjugate is selected from K9, H16, L19, D20, M23, N26, N88, V91, I92, L94, E95, K97, G98, S99, E100, D109 in the N88R variant, N119, T123, S125, Q126, S127, S130, and T131. Further described herein are IL-2 conjugates wherein the position of the structure of Formula (VIII) or (IX), or a mixture of (VIII) and (IX), in the amino acid sequence of the IL-2 conjugate is selected from K9, H16, L19, D20, M23, N26, N88, V91, E100, D109 in the N88R variant, N119, T123, S125, and T131. Further described herein are IL-2 conjugates wherein the position of the structure of Formula (VIII) or (IX), or a mixture of (VIII) and (IX), in the amino acid sequence of the IL-2 conjugate is K9. Further described herein are IL-2 conjugates wherein the position of the structure of Formula (VIII) or (IX), or a mixture of (VIII) and (IX), in the amino acid sequence of the IL-2 conjugate is H16. Further described herein are IL-2 conjugates wherein the position of the structure of Formula (VIII) or (IX), or a mixture of (VIII) and (IX), in the amino acid sequence of the IL-2 conjugate is L19. Further described herein are IL-2 conjugates wherein the position of the structure of Formula (VIII) or (IX), or a mixture of (VIII) and (IX), in the amino acid sequence of the IL-2 conjugate is D20. Further described herein are IL-2 conjugates wherein the position of the structure of Formula (VIII) or (IX), or a mixture of (VIII) and (IX), in the amino acid sequence of the IL-2 conjugate is M23. Further described herein are IL-2 conjugates wherein the position of the structure of Formula (VIII) or (IX), or a mixture of (VIII) and (IX), in the amino acid sequence of the IL-2 conjugate is N26. Further described herein are IL-2 conjugates wherein the position of the structure of Formula (VIII) or (IX), or a mixture of (VIII) and (IX), in the amino acid sequence of the IL-2 conjugate is N88. Further described herein are IL-2 conjugates wherein the position of the structure of Formula (VIII) or (IX), or a mixture of (VIII) and (IX), in the amino acid sequence of the IL-2 conjugate is V91. Further described herein are IL-2 conjugates wherein the position of the structure of Formula (VIII) or (IX), or a mixture of (VIII) and (IX), in the amino acid sequence of the IL-2 conjugate is E100. Further described herein are IL-2 conjugates wherein the position of the structure of Formula (VIII) or (IX), or a mixture of (VIII) and (IX), in the amino acid sequence of the IL-2 conjugate is D109 in the N88R variant. Further described herein are IL-2 conjugates wherein the position of the structure of Formula (VIII) or (IX), or a mixture of (VIII) and (IX), in the amino acid sequence of the IL-2 conjugate is N119. Further described herein are IL-2 conjugates wherein the position of the structure of Formula (VIII) or (IX), or a mixture of (VIII) and (IX), in the amino acid sequence of the IL-2 conjugate is T123. Further described herein are IL-2 conjugates wherein the position of the structure of Formula (VIII) or (IX), or a mixture of (VIII) and (IX), in the amino acid sequence of the IL-2 conjugate is S125. Further described herein are IL-2 conjugates wherein the position of the structure of Formula (VIII) or (IX), or a mixture of (VIII) and (IX), in the amino acid sequence of the IL-2 conjugate is T131. Further described herein are IL-2 conjugates wherein n is about 75 to about 1000. Further described herein are IL-2 conjugates wherein n is about 100 to about 1000. Further described herein are IL-2 conjugates wherein n is about 200 to about 5000. Further described herein are IL-2 conjugates wherein n is about 500 to about 1370. Further described herein are IL-2 conjugates wherein n is about 400 to about 800. Further described herein are IL-2 conjugates wherein n is about 400 to about 1370. Further described herein are IL-2 conjugates wherein n is about 400 to about 1250. Further described herein are IL-2 conjugates wherein n is about 600 to about 1370. Further described herein are IL-2 conjugates wherein n is about 600 to about 1250. Further described herein are IL-2 conjugates wherein n is about 675 to about 1250. Further described herein are IL-2 conjugates wherein n is about 680 to about 1250. Further described herein are IL-2 conjugates wherein n is about 680 to about 1140. Further described herein are IL-2 conjugates wherein n is about 450. Further described herein are IL-2 conjugates wherein n is about 568. Further described herein are IL-2 conjugates wherein n is about 682. Further described herein are IL-2 conjugates wherein n is about 795. Further described herein are IL-2 conjugates wherein n is about 909. Further described herein are IL-2 conjugates wherein n is about 1022. Further described herein are IL-2 conjugates wherein n is about 1136. Further described herein are IL-2 conjugates wherein n is about 1250. Further described herein are IL-2 conjugates wherein n is about 1363.

Described herein are IL-2 conjugates comprising the amino acid sequence of SEQ ID NO: 4 in which at least one amino acid residue in the IL-2 conjugate is replaced by the structure of Formula (X) or (XI), or a mixture of (X) and (XI):

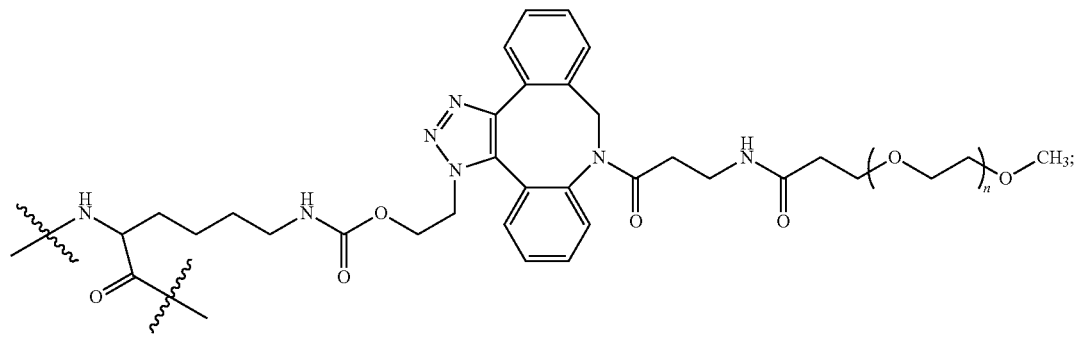

Formula (X)

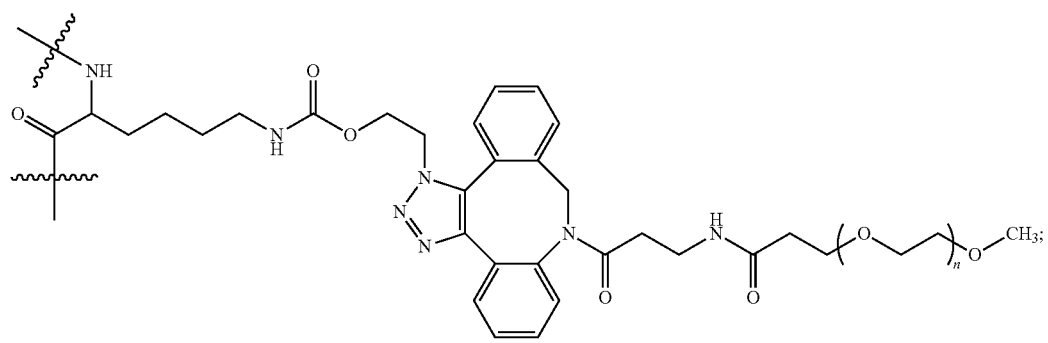

Formula (XI)

wherein:
n is an integer in the range from about 2 to about 5000; and the wavy lines indicate covalent bonds to amino acid residues within SEQ ID NO: 4 that are not replaced. Further described herein are IL-2 conjugates wherein the position of the structure of Formula (X) or (XI), or a mixture of (X) and (XI), in the amino acid sequence of the IL-2 conjugate is selected from A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133. Further described herein are IL-2 conjugates wherein the position of the structure of Formula (X) or (XI), or a mixture of (X) and (XI), in the amino acid sequence of the IL-2 conjugate is selected from K9, H16, L19, D20, M23, N26, N88, V91, I92, L94, E95, K97, G98, S99, E100, D109 in the N88R variant, N119, T123, S125, Q126, S127, S130, and T131. Further described herein are IL-2 conjugates wherein the position of the structure of Formula (X) or (XI), or a mixture of (X) and (XI), in the amino acid sequence of the IL-2 conjugate is selected from K9, H16, L19, D20, M23, N26, N88, V91, E100, D109 in the N88R variant, N119, T123, S125, and T131. Further described herein are IL-2 conjugates wherein the position of the structure of Formula (X) or (XI), or a mixture of (X) and (XI), in the amino acid sequence of the IL-2 conjugate is K9. Further described herein are IL-2 conjugates wherein the position of the structure of Formula (X) or (XI), or a mixture of (X) and (XI), in the amino acid sequence of the IL-2 conjugate is H16. Further described herein are IL-2 conjugates wherein the position of the structure of Formula (X) or (XI), or a mixture of (X) and (XI), in the amino acid sequence of the IL-2 conjugate is L19. Further described herein are IL-2 conjugates wherein the position of the structure of Formula (X) or (XI), or a mixture of (X) and (XI), in the amino acid sequence of the IL-2 conjugate is D20. Further described herein are IL-2 conjugates wherein the position of the structure of Formula (X) or (XI), or a mixture of (X) and (XI), in the amino acid sequence of the IL-2 conjugate is M23. Further described herein are IL-2 conjugates wherein the position of the structure of Formula (X) or (XI), or a mixture of (X) and (XI), in the amino acid sequence of the IL-2 conjugate is N26. Further described herein are IL-2 conjugates wherein the position of the structure of Formula (X) or (XI), or a mixture of (X) and (XI), in the amino acid sequence of the IL-2 conjugate is N88. Further described herein are IL-2 conjugates wherein the position of the structure of Formula (X) or (XI), or a mixture of (X) and (XI), in the amino acid sequence of the IL-2 conjugate is V91. Further described herein are IL-2 conjugates wherein the position of the structure of Formula (X) or (XI), or a mixture of (X) and (XI), in the amino acid sequence of the IL-2 conjugate is E100. Further described herein are IL-2 conjugates wherein the position of the structure of Formula (X) or (XI), or a mixture of (X) and (XI), in the amino acid sequence of the IL-2 conjugate is D109 in the N88R variant. Further described herein are IL-2 conjugates wherein the position of the structure of Formula (X) or (XI), or a mixture of (X) and (XI), in the amino acid sequence of the IL-2 conjugate is N119. Further described herein are IL-2 conjugates wherein the position of the structure of Formula (X) or (XI), or a mixture of (X) and (XI), in the amino acid sequence of the IL-2 conjugate is T123. Further described herein are IL-2 conjugates wherein the position of the structure of Formula (X) or (XI), or a mixture of (X) and (XI), in the amino acid sequence of the IL-2 conjugate is S125. Further described herein are IL-2 conjugates wherein the position of the structure of Formula (X) or (XI), or a mixture of (X) and (XI), in the amino acid sequence of the IL-2 conjugate is T131. Further described herein are IL-2 conjugates wherein n is about 75 to about 1000. Further described herein are IL-2 conjugates wherein n is about 100 to about 1000. Further described herein are IL-2 conjugates wherein n is about 200 to about 5000. Further described herein are IL-2 conjugates wherein n is about 500 to about 1370. Further described herein are IL-2 conjugates wherein n is about 400 to about 800. Further described herein are IL-2 conjugates wherein n is about 400 to about 1370. Further described herein are IL-2 conjugates wherein n is about 400 to about 1250. Further described herein are IL-2 conjugates wherein n is about 600 to about 1370. Further described herein are IL-2 conjugates wherein n is about 600 to about 1250. Further described herein are IL-2 conjugates wherein n is about 675 to about 1250. Further described herein are IL-2 conjugates wherein n is about 680 to about 1250. Further described herein are IL-2 conjugates wherein n is about 680 to about 1140. Further described herein are IL-2 conjugates wherein n is about 450. Further described herein are IL-2 conjugates wherein n is about 568. Further described herein are IL-2 conjugates wherein n is about 682. Further described herein are IL-2 conjugates wherein n is about 795. Further described herein are IL-2 conjugates wherein n is about 909. Further described herein are IL-2 conjugates wherein n is about 1022. Further described herein are IL-2 conjugates wherein n is about 1136. Further described herein are IL-2 conjugates wherein n is about 1250. Further described herein are IL-2 conjugates wherein n is about 1363.

Described herein are IL-2 conjugates comprising the amino acid sequence of SEQ ID NO: 4 in which at least one amino acid residue in the IL-2 conjugate is replaced by the structure of Formula (XII) or (XIII), or a mixture of (XII) and (XIII):

Formula (XII)

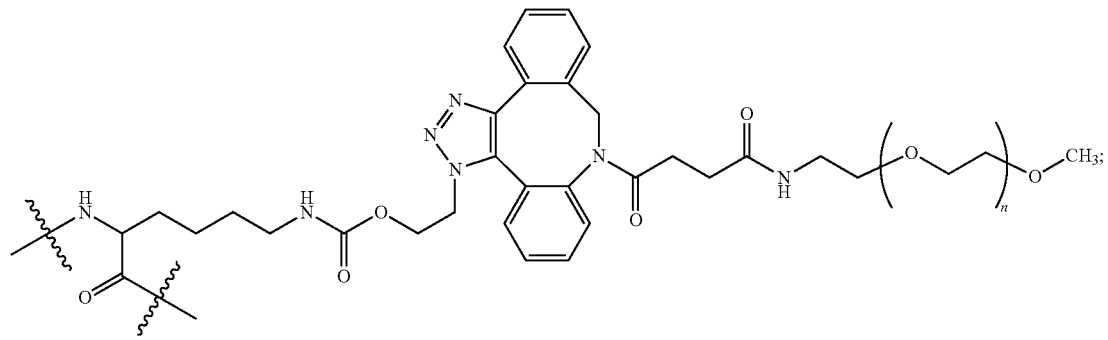

Formula (XIII)

wherein:

n is an integer in the range from about 2 to about 5000; and the wavy lines indicate covalent bonds to amino acid residues within SEQ ID NO: 4 that are not replaced. Further described herein are IL-2 conjugates wherein the position of the structure of Formula (XII) or (XIII), or a mixture of (XII) and (XIII), in the amino acid sequence of the IL-2 conjugate is selected from A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133. Further described herein are IL-2 conjugates wherein the position of the structure of Formula (XII) or (XIII), or a mixture of (XII) and (XIII), in the amino acid sequence of the IL-2 conjugate is selected from K9, H16, L19, D20, M23, N26, N88, V91, I92, L94, E95, K97, G98, S99, E100, D109 in the N88R variant, N119, T123, S125, Q126, S127, S130, and T131. Further described herein are IL-2 conjugates wherein the position of the structure of Formula (XII) or (XIII), or a mixture of (XII) and (XIII), in the amino acid sequence of the IL-2 conjugate is selected from K9, H16, L19, D20, M23, N26, N88, V91, E100, D109 in the N88R variant, N119, T123, S125, and T131. Further described herein are IL-2 conjugates wherein the position of the structure of Formula (XII) or (XIII), or a mixture of (XII) and (XIII), in the amino acid sequence of the IL-2 conjugate is K9. Further described herein are IL-2 conjugates wherein the position of the structure of Formula (XII) or (XIII), or a mixture of (XII) and (XIII), in the amino acid sequence of the IL-2 conjugate is H16. Further described herein are IL-2 conjugates wherein the position of the structure of Formula (XII) or (XIII), or a mixture of (XII) and (XIII), in the amino acid sequence of the IL-2 conjugate is L19. Further described herein are IL-2 conjugates wherein the position of the structure of Formula (XII) or (XIII), or a mixture of (XII) and (XIII), in the amino acid sequence of the IL-2 conjugate is D20. Further described herein are IL-2 conjugates wherein the position of the structure of Formula (XII) or (XIII), or a mixture of (XII) and (XIII), in the amino acid sequence of the IL-2 conjugate is M23. Further described herein are IL-2 conjugates wherein the position of the structure of Formula (XII) or (XIII), or a mixture of (XII) and (XIII), in the amino acid sequence of the IL-2 conjugate is N26. Further described herein are IL-2 conjugates wherein the position of the structure of Formula (XII) or (XIII), or a mixture of (XII) and (XIII), in the amino acid sequence of the IL-2 conjugate is N88. Further described herein are IL-2 conjugates wherein the position of the structure of Formula (XII) or (XIII), or a mixture of (XII) and (XIII), in the amino acid sequence of the IL-2 conjugate is V91. Further described herein are IL-2 conjugates wherein the position of the structure of Formula (XII) or (XIII), or a mixture of (XII) and (XIII), in the amino acid sequence of the IL-2 conjugate is E100. Further described herein are IL-2 conjugates wherein the position of the structure of Formula (XII) or (XIII), or a mixture of (XII) and (XIII), in the amino acid sequence of the IL-2 conjugate is D109 in the N88R variant. Further described herein are IL-2 conjugates wherein the position of the structure of Formula (XII) or (XIII), or a mixture of (XII) and (XIII), in the amino acid sequence of the IL-2 conjugate is N119. Further described herein are IL-2 conjugates wherein the position of the structure of Formula (XII) or (XIII), or a mixture of (XII) and (XIII), in the amino acid sequence of the IL-2 conjugate is T123. Further described herein are IL-2 conjugates wherein the position of the structure of Formula (XII) or (XIII), or a mixture of (XII) and (XIII), in the amino acid sequence of the IL-2 conjugate is S125. Further described herein are IL-2 conjugates wherein the position of the structure of Formula (XII) or (XIII), or a mixture of (XII) and (XIII), in the amino acid sequence of the IL-2 conjugate is T131. Further described herein are IL-2 conjugates wherein n is about 75 to about 1000. Further described herein are IL-2 conjugates wherein n is about 100 to about 1000. Further described herein are IL-2 conjugates wherein n is about 200 to about 5000. Further described herein are IL-2 conjugates wherein n is about 500 to about 1370. Further described herein are IL-2 conjugates wherein n is about 400 to about 800. Further described herein are IL-2 conjugates wherein n is about 400 to about 1370. Further described herein are IL-2 conjugates wherein n is about 400 to about 1250. Further described herein are IL-2 conjugates wherein n is about 600 to about 1370. Further described herein are IL-2 conjugates wherein n is about 600 to about 1250. Further described herein are IL-2 conjugates wherein n is about 675 to about 1250. Further described herein are IL-2 conjugates wherein n is about 680 to about 1250. Further described herein are IL-2 conjugates wherein n is about 680 to about 1140. Further described herein are IL-2 conjugates wherein n is about 450. Further described herein are IL-2 conjugates wherein n is about 568. Further described herein are IL-2 conjugates wherein n is about 682. Further described herein are IL-2 conjugates wherein n is about 795. Further described herein are IL-2 conjugates wherein n is about 909. Further described herein are IL-2 conjugates wherein n is about 1022. Further described herein are IL-2 conjugates wherein n is about 1136. Further described herein are IL-2 conjugates wherein n is about 1250. Further described herein are IL-2 conjugates wherein n is about 1363.

Described herein are IL-2 conjugates comprising the amino acid sequence of SEQ ID NO: 3 or SEQ ID NO: 4 in which at least one amino acid residue in the IL-2 conjugate is replaced by the structure of Formula (XIV) or (XV), or a mixture of (XIV) and (XV):

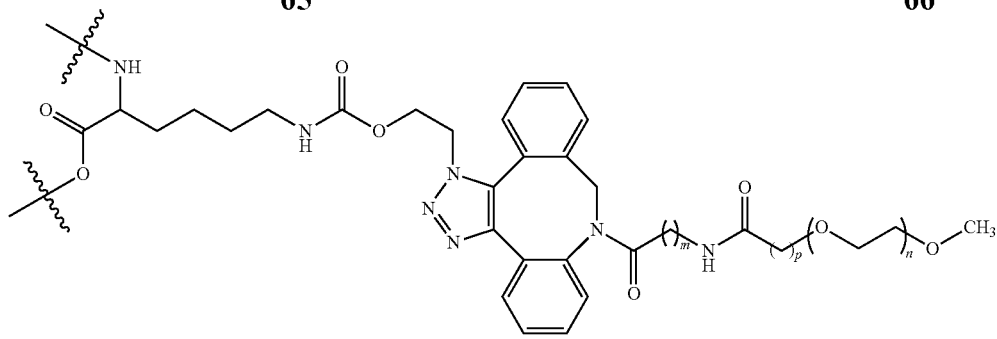

Formula (XIV)

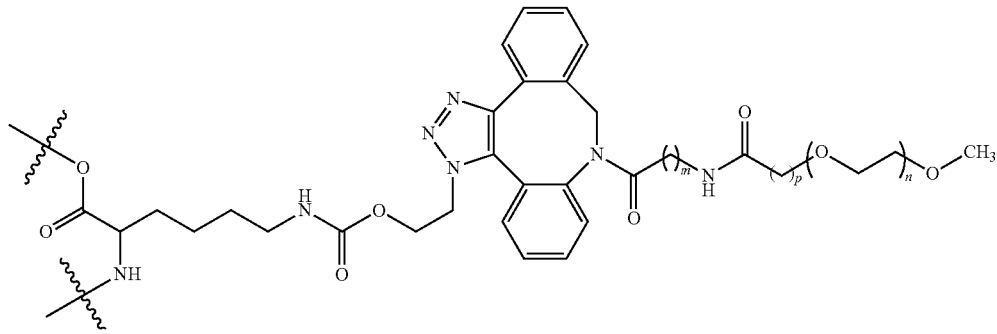

Formula (XV)

wherein:

m is an integer from 0 to 20;
p is an integer from 0 to 20;
n is an integer in the range from about 2 to about 5000; and
the wavy lines indicate covalent bonds to amino acid residues within SEQ ID NO: 3 or SEQ ID NO: 4 that are not replaced. Here and throughout, embodiments of Formula (XIV) and/or (XV) also encompass a pharmaceutically acceptable salt, solvate, or hydrate thereof. In some embodiments described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein m, p, n, and the meaning of the wavy line are as described above. In some embodiments described herein are IL-2 conjugates comprising the amino acid sequence of SEQ ID NO: 4 in which at least one amino acid residue in the IL-2 conjugate is replaced by the structure of Formula (XIV) or (XV), or a mixture of (XIV) and (XV), wherein m, p, n, and the meaning of the wavy line are as described above.

In some embodiments, the stereochemistry of the chiral center within Formula (XIV) and Formula (XV) is racemic, is enriched in (R), is enriched in (S), is substantially (R), is substantially (S), is (R) or is (S). In some embodiments, the stereochemistry of the chiral center within Formula (XIV) and Formula (XV) is racemic. In some embodiments, the stereochemistry of the chiral center within Formula (XIV) and Formula (XV) is enriched in (R). In some embodiments, the stereochemistry of the chiral center within Formula (XIV) and Formula (XV) is enriched in (S). In some embodiments, the stereochemistry of the chiral center within Formula (XIV) and Formula (XV) is substantially (R). In some embodiments, the stereochemistry of the chiral center within Formula (XIV) and Formula (XV) is substantially (S). In some embodiments, the stereochemistry of the chiral center within Formula (XIV) and Formula (XV) is (R). In some embodiments, the stereochemistry of the chiral center within Formula (XIV) and Formula (XV) is (S).

In some embodiments of an IL-2 conjugate described herein, m in the compounds of Formula (XIV) and (XV) is from 0 to 20, or from 1 to 18, or from 1 to 16, or from 1 to 14, or from 1 to 12, or from 1 to 10, or from 1 to 9, or from 1 to 8, or from 1 to 7, or from 1 to 6, or from 1 to 5, or from 1 to 4, or from 1 to 3, or from 1 to 2. In some embodiments of an IL-2 conjugate described herein, m in the compounds of Formula (XIV) and (XV) is 1. In some embodiments of an IL-2 conjugate described herein, m in the compounds of Formula (XIV) and (XV) is 2. In some embodiments of an IL-2 conjugate described herein, m in the compounds of Formula (XIV) and (XV) is 3. In some embodiments of an IL-2 conjugate described herein, m in the compounds of Formula (XIV) and (XV) is 4. In some embodiments of an IL-2 conjugate described herein, m in the compounds of Formula (XIV) and (XV) is 5. In some embodiments of an IL-2 conjugate described herein, m in the compounds of Formula (XIV) and (XV) is 6. In some embodiments of an IL-2 conjugate described herein, m in the compounds of Formula (XIV) and (XV) is 7. In some embodiments of an IL-2 conjugate described herein, m in the compounds of Formula (XIV) and (XV) is 8. In some embodiments of an IL-2 conjugate described herein, m in the compounds of Formula (XIV) and (XV) is 9. In some embodiments of an IL-2 conjugate described herein, m in the compounds of Formula (XIV) and (XV) is 10. In some embodiments of an IL-2 conjugate described herein, m in the compounds of Formula (XIV) and (XV) is 11. In some embodiments of an IL-2 conjugate described herein, m in the compounds of Formula (XIV) and (XV) is 12. In some embodiments of an IL-2 conjugate described herein, m in the compounds of Formula (XIV) and (XV) is 13. In some embodiments of an IL-2 conjugate described herein, m in the compounds of Formula (XIV) and (XV) is 14. In some embodiments of an IL-2 conjugate described herein, m in the compounds of Formula (XIV) and (XV) is 15. In some embodiments of an IL-2 conjugate described herein, m in the compounds of Formula (XIV) and (XV) is 16. In some embodiments of an IL-2 conjugate described herein, m in the compounds of Formula (XIV) and (XV) is 17. In some embodiments of an IL-2 conjugate described herein, m in the compounds of Formula (XIV) and (XV) is 18. In some embodiments of an IL-2 conjugate described herein, m in the compounds of Formula (XIV) and (XV) is 19. In some embodiments of an IL-2 conjugate described herein, m in the compounds of Formula (XIV) and (XV) is 20.

In some embodiments of an IL-2 conjugate described herein, p in the compounds of Formula (XIV) and (XV) is from 1 to 20, or from 1 to 18, or from 1 to 16, or from 1 to 14, or from 1 to 12, or from 1 to 10, or from 1 to 9, or from 1 to 8, or from 1 to 7, or from 1 to 6, or from 1 to 5, or from 1 to 4, or from 1 to 3, or from 1 to 2. In some embodiments of an IL-2 conjugate described herein, p in the compounds of Formula (XIV) and (XV) is 1. In some embodiments of an IL-2 conjugate described herein, p in the compounds of Formula (XIV) and (XV) is 2. In some embodiments of an IL-2 conjugate described herein, p in the compounds of Formula (XIV) and (XV) is 3. In some embodiments of an IL-2 conjugate described herein, p in the compounds of Formula (XIV) and (XV) is 4. In some embodiments of an IL-2 conjugate described herein, p in the compounds of Formula (XIV) and (XV) is 5. In some embodiments of an IL-2 conjugate described herein, p in the compounds of Formula (XIV) and (XV) is 6. In some embodiments of an IL-2 conjugate described herein, p in the compounds of Formula (XIV) and (XV) is 7. In some embodiments of an IL-2 conjugate described herein, p in the compounds of Formula (XIV) and (XV) is 8. In some embodiments of an IL-2 conjugate described herein, p in the compounds of Formula (XIV) and (XV) is 9. In some embodiments of an IL-2 conjugate described herein, p in the compounds of Formula (XIV) and (XV) is 10. In some embodiments of an IL-2 conjugate described herein, p in the compounds of Formula (XIV) and (XV) is 11. In some embodiments of an IL-2 conjugate described herein, p in the compounds of Formula (XIV) and (XV) is 12. In some embodiments of an IL-2 conjugate described herein, p in the compounds of Formula (XIV) and (XV) is 13. In some embodiments of an IL-2 conjugate described herein, p in the compounds of Formula (XIV) and (XV) is 14. In some embodiments of an IL-2 conjugate described herein, p in the compounds of Formula (XIV) and (XV) is 15. In some embodiments of an IL-2 conjugate described herein, m in the compounds of Formula (XIV) and (XV) is 16. In some embodiments of an IL-2 conjugate described herein, p in the compounds of Formula (XIV) and (XV) is 17. In some embodiments of an IL-2 conjugate described herein, p in the compounds of Formula (XIV) and (XV) is 18. In some embodiments of an IL-2 conjugate described herein, p in the compounds of Formula (XIV) and (XV) is 19. In some embodiments of an IL-2 conjugate described herein, p in the compounds of Formula (XIV) and (XV) is 20.

In some embodiments of an IL-2 conjugate described herein, n in the compounds of Formula (XIV) and (XV) is in the range from about 5 to about 4600, or from about 10 to about 4000, or from about 20 to about 3000, or from about 100 to about 3000, or from about 100 to about 2900, or from about 150 to about 2900, or from about 125 to about 2900, or from about 100 to about 2500, or from about 100 to about 2000, or from about 100 to about 1900, or from about 100 to about 1850, or from about 100 to about 1750, or from about 100 to about 1650, or from about 100 to about 1500, or from about 100 to about 1400, or from about 100 to about 1300, or from about 100 to about 1250, or from about 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575.

In some embodiments of an IL-2 conjugate described herein in the compounds of Formula (XIV) and (XV), m is an integer from 1 to 6, p is an integer from 1 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is an integer from 2 to 6, p is an integer from 2 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is an integer from 2 to 4, p is an integer from 2 to 4, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 1, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 2, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 3, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 4, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 5, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 6, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 7, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 8, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 9, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 10, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 11, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 12, p is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XIV) and (XV), m is 2, p is 2, and n is an integer selected from 680, 681, 682, 794, 795, 796, 908, 909, 910, 1021, 1022, 1023, 1135, 1136, and 1137.

In some embodiments of an IL-2 conjugate described herein, n in the compounds of Formula (XIV) and (XV) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments of an IL-2 conjugate described herein, when the IL-2 conjugate comprises SEQ ID NO: 3, the position of the structure of Formula (XIV) and (XV) or a mixture of Formula (XIV) and (XV) in the amino acid sequence of the IL-2 conjugate is selected from P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, I88, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, and T132. Further described herein are IL-2 conjugates wherein the position of the structure of Formula (XIV) or (XV), or a mixture of (XIV) and (XV), in the amino acid sequence of the IL-2 conjugate is selected from K8, H15, L18, D19, M22, N25, N87, V90, I91, L93, E94, K96, G97, S98, E99, D108 in the N87R variant, N118, T122, S124, Q125, S126, S129, and T130. Further described herein are IL-2 conjugates wherein the position of the structure of Formula (XIV) or (XV), or a mixture of (XIV) and (XV), in the amino acid sequence of the IL-2 conjugate is selected from K8, H15, L18, D19, M22, N25, N87, V90, E99, D108 in the N87R variant, N118, T122, S124, and T130. Further described herein are IL-2 conjugates wherein the position of the structure of Formula (XIV) or (XV), or a mixture of (XIV) and (XV), in the amino acid sequence of the IL-2 conjugate is K8. Further described herein are IL-2 conjugates wherein the position of the structure of Formula (XIV) or (XV), or a mixture of (XIV) and (XV), in the amino acid sequence of the IL-2 conjugate is H15. Further described herein are IL-2 conjugates wherein the position of the structure of Formula (XIV) or (XV), or a mixture of (XIV) and (XV), in the amino acid sequence of the IL-2 conjugate is L18. Further described herein are IL-2 conjugates wherein the position of the structure of Formula (XIV) or (XV), or a mixture of (XIV) and (XV), in the amino acid sequence of the IL-2 conjugate is D19. Further described herein are IL-2 conjugates wherein the position of the structure of Formula (XIV) or (XV), or a mixture of (XIV) and (XV), in the amino acid sequence of the IL-2 conjugate is M22. Further described herein are IL-2 conjugates wherein the position of the structure of Formula (XIV) or (XV), or a mixture of (XIV) and (XV), in the amino acid sequence of the IL-2 conjugate is N25. Further described herein are IL-2 conjugates wherein the position of the structure of Formula (XIV) or (XV), or a mixture of (XIV) and (XV), in the amino acid sequence of the IL-2 conjugate is N87. Further described herein are IL-2 conjugates wherein the position of the structure of Formula (XIV) or (XV), or a mixture of (XIV) and (XV), in the amino acid sequence of the IL-2 conjugate is V90. Further described herein are IL-2 conjugates wherein the position of the structure of Formula (XIV) or (XV), or a mixture of (XIV) and (XV), in the amino acid sequence of the IL-2 conjugate is E99. Further described herein are IL-2 conjugates wherein the position of the structure of Formula (XIV) or (XV), or a mixture of (XIV) and (XV), in the amino acid sequence of the IL-2 conjugate is D108 in the N87R variant. Further described herein are IL-2 conjugates wherein the position of the structure of Formula (XIV) or (XV), or a mixture of (XIV) and (XV), in the amino acid sequence of the IL-2 conjugate is N118. Further described herein are IL-2 conjugates wherein the position of the structure of Formula (XIV) or (XV), or a mixture of (XIV) and (XV), in the amino acid sequence of the IL-2 conjugate is T122. Further described herein are IL-2 conjugates wherein the position of the structure of Formula (XIV) or (XV), or a mixture of (XIV) and (XV), in the amino acid sequence of the IL-2 conjugate is S124. Further described herein are IL-2 conjugates wherein the position of the structure of Formula (XIV) or (XV), or a mixture of (XIV) and (XV), in the amino acid sequence of the IL-2 conjugate is T130. In some embodiments of an IL-2 conjugate described herein, the ratio of the amount of the structure of Formula (XIV) to the amount of the structure of Formula (XV) comprising the total amount of the IL-2 conjugate is about 1:1. In some embodiments of an IL-2 conjugate described herein, the ratio of the amount of the structure of Formula (XIV) to the amount of the structure of Formula (XV) comprising the total amount of the IL-2 conjugate is greater than 1:1. In some embodiments of an IL-2 conjugate described herein, the ratio of the amount of the structure of Formula (XIV) to the amount of the structure of Formula (XV) comprising the total amount of the IL-2 conjugate is less than 1:1.

In some embodiments of an IL-2 conjugate described herein, when the IL-2 conjugate comprises SEQ ID NO: 4, the position of the structure of Formula (XIV) and (XV) or a mixture of Formula (XIV) and (XV) in the amino acid sequence of the IL-2 conjugate is selected from A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133. Further described herein are IL-2 conjugates wherein the position of the structure of Formula (XIV) or (XV), or a mixture of (XIV) and (XV), in the amino acid sequence of the IL-2 conjugate is selected from K9, H16, L19, D20, M23, N26, N88, V91, I92, L94, E95, K97, G98, S99, E100, D109 in the N88R variant, N119, T123, S125, Q126, S127, S130, and T131. Further described herein are IL-2 conjugates wherein the position of the structure of Formula (XIV) or (XV), or a mixture of (XIV) and (XV), in the amino acid sequence of the IL-2 conjugate is selected from K9, H16, L19, D20, M23, N26, N88, V91, E100, D109 in the N88R variant, N119, T123, S125, and T131. Further described herein are IL-2 conjugates wherein the position of the structure of Formula (XIV) or (XV), or a mixture of (XIV) and (XV), in the amino acid sequence of the IL-2 conjugate is K9. Further described herein are IL-2 conjugates wherein the position of the structure of Formula (XIV) or (XV), or a mixture of (XIV) and (XV), in the amino acid sequence of the IL-2 conjugate is H16. Further described herein are IL-2 conjugates wherein the position of the structure of Formula (XIV) or (XV), or a mixture of (XIV) and (XV), in the amino acid sequence of the IL-2 conjugate is L19. Further described herein are IL-2 conjugates wherein the position of the structure of Formula (XIV) or (XV), or a mixture of (XIV) and (XV), in the amino acid sequence of the IL-2 conjugate is D20. Further described herein are IL-2 conjugates wherein the position of the structure of Formula (XIV) or (XV), or a mixture of (XIV) and (XV), in the amino acid sequence of the IL-2 conjugate is M23. Further described herein are IL-2 conjugates wherein the position of the structure of Formula (XIV) or (XV), or a mixture of (XIV) and (XV), in the amino acid sequence of the IL-2 conjugate is N26. Further described herein are IL-2 conjugates wherein the position of the structure of Formula (XIV) or (XV), or a mixture of (XIV) and (XV), in the amino acid sequence of the IL-2 conjugate is N88. Further described herein are IL-2 conjugates wherein the position of the structure of Formula (XIV) or (XV), or a mixture of (XIV) and (XV), in the amino acid sequence of the IL-2 conjugate is V91. Further described herein are IL-2 conjugates wherein the position of the structure of Formula (XIV) or (XV), or a mixture of (XIV) and (XV), in the amino acid sequence of the IL-2 conjugate is E100. Further described herein are IL-2 conjugates wherein the position of the structure of Formula (XIV) or (XV), or a mixture of (XIV) and (XV), in the amino acid sequence of the IL-2 conjugate is D109 in the N88R variant. Further described herein are IL-2 conjugates wherein the position of the structure of Formula (XIV) or (XV), or a mixture of (XIV) and (XV), in the amino acid sequence of the IL-2 conjugate is N119. Further described herein are IL-2 conjugates wherein the position of the structure of Formula (XIV) or (XV), or a mixture of (XIV) and (XV), in the amino acid sequence of the IL-2 conjugate is T123. Further described herein are IL-2 conjugates wherein the position of the structure of Formula (XIV) or (XV), or a mixture of (XIV) and (XV), in the amino acid sequence of the IL-2 conjugate is S125. Further described herein are IL-2 conjugates wherein the position of the structure of Formula (XIV) or (XV), or a mixture of (XIV) and (XV), in the amino acid sequence of the IL-2 conjugate is T131. In some embodiments of an IL-2 conjugate described herein, the ratio of the amount of the structure of Formula (XIV) to the amount of the structure of Formula (XV) comprising the total amount of the IL-2 conjugate is about 1:1. In some embodiments of an IL-2 conjugate described herein, the ratio of the amount of the structure of Formula (XIV) to the amount of the structure of Formula (XV) comprising the total amount of the IL-2 conjugate is greater than 1:1. In some embodiments of an IL-2 conjugate described herein, the ratio of the amount of the structure of Formula (XIV) to the amount of the structure of Formula (XV) comprising the total amount of the IL-2 conjugate is less than 1:1.

In some embodiments described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein the amino acid residue in in SEQ ID NO: 3 that is replaced is selected from K8, H15, L18, D19, M22, N25, N87, V90, E99, D108 in the N87R variant, N118, T122, S124, and T130, and wherein n is an integer from 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-2 conjugate described herein, n in the compounds of formula (XIV) and (XV) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments described herein are IL-2 conjugates comprising the amino acid sequence of SEQ ID NO: 4 in which at least one amino acid residue in the IL-2 conjugate is replaced by the structure of Formula (XIV) or (XV), or a mixture of (XIV) and (XV), wherein the amino acid residue in in SEQ ID NO: 3 that is replaced is selected from K9, H16, L19, D20, M23, N26, N88, V91, I92, L94, E95, K97, G98, S99, E100, D109 in the N88R variant, N119, T123, S125, Q126, S127, S130, and T131, and wherein n is an integer from 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-2 conjugate described herein, n in the compounds of formula (XIV) and (XV) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

Described herein are IL-2 conjugates comprising the amino acid sequence of SEQ ID NO: 3 or SEQ ID NO: 4 in which at least one amino acid residue in the IL-2 conjugate is replaced by the structure of Formula (XIV) or (XV), or a mixture of (XIV) and (XV), wherein n is an integer such that the molecular weight of the PEG moiety is in the range from about 1,000 Daltons about 200,000 Daltons, or from about 2,000 Daltons to about 150,000 Daltons, or from about 3,000 Daltons to about 125,000 Daltons, or from about 4,000 Daltons to about 100,000 Daltons, or from about 5,000 Daltons to about 100,000 Daltons, or from about 6,000 Daltons to about 90,000 Daltons, or from about 7,000 Daltons to about 80,000 Daltons, or from about 8,000 Daltons to about 70,000 Daltons, or from about 5,000 Daltons to about 70,000 Daltons, or from about 5,000 Daltons to about 65,000 Daltons, or from about 5,000 Daltons to about 60,000 Daltons, or from about 5,000 Daltons to about 50,000 Daltons, or from about 6,000 Daltons to about 50,000 Daltons, or from about 7,000 Daltons to about 50,000 Daltons, or from about 7,000 Daltons to about 45,000 Daltons, or from about 7,000 Daltons to about 40,000 Daltons, or from about 8,000 Daltons to about 40,000 Daltons, or from about 8,500 Daltons to about 40,000 Daltons, or from about 8,500 Daltons to about 35,000 Daltons, or from about 9,000 Daltons to about 50,000 Daltons, or from about 9,000 Daltons to about 45,000 Daltons, or from about 9,000 Daltons to about 40,000 Daltons, or from about 9,000 Daltons to about 35,000 Daltons, or from about 9,500 Daltons to about 30,000 Daltons, or from about 9,500 Daltons to about 35,000 Daltons, or from about 10,000 Daltons to about 30,000 Daltons, or from about 10,000 Daltons to about 50,000 Daltons, or from about 10,000 Daltons to about 45,000 Daltons, or from about 10,000 Daltons to about 40,000 Daltons, or from about 10,000 Daltons to about 35,000 Daltons, or from about 15,000 Daltons to about 30,000 Daltons, or from about 15,000 Daltons to about 50,000 Daltons, or from about 15,000 Daltons to about 45,000 Daltons, or from about 15,000 Daltons to about 40,000 Daltons, or from about 15,000 Daltons to about 35,000 Daltons, or from about 20,000 Daltons to about 30,000 Daltons, or from about 20,000 Daltons to about 50,000 Daltons, or from about 20,000 Daltons to about 45,000 Daltons, or from about 20,000 Daltons to about 40,000 Daltons, or from about 20,000 Daltons to about 35,000 Daltons, or from about 20,000 Daltons to about 30,000 Daltons. Described herein are IL-2 conjugates comprising the amino acid sequence of SEQ ID NO: 3 or SEQ ID NO: 4 in which at least one amino acid residue in the IL-2 conjugate is replaced by the structure of Formula (XIV) or (XV), or a mixture of (XIV) and (XV), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 60,000 Daltons, about 70,000 Daltons, about 80,000 Daltons, about 90,000 Daltons, about 100,000 Daltons, about 125,000 Daltons, about 150,000 Daltons, about 175,000 Daltons or about 200,000 Daltons. Described herein are IL-2 conjugates comprising the amino acid sequence of SEQ ID NO: 3 or SEQ ID NO: 4 in which at least one amino acid residue in the IL-2 conjugate is replaced by the structure of Formula (XIV) or (XV), or a mixture of (XIV) and (XV), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, or about 50,000 Daltons.

In some embodiments described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein the amino acid residue in SEQ ID NO: 3 that is replaced is H15, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-2 conjugate described herein in the compounds of formula (XIV) and (XV), m is 2, p is 2, and n is an integer selected from 454, 455, 568, 569, 680, 681, 682, 794, 795, 796, 908, 909, and 910.

In some embodiments described herein are IL-2 conjugates comprising the amino acid sequence of SEQ ID NO: 3 in which at least one amino acid residue in the IL-2 conjugate is replaced by the structure of Formula (XIV) or (XV), or a mixture of (XIV) and (XV), wherein the amino acid residue in SEQ ID NO: 3 that is replaced is H15, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-2 conjugate described herein in the compounds of formula (XIV) and (XV), m is 2, p is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

In some embodiments described herein are IL-2 conjugates comprising the amino acid sequence of SEQ ID NO: 4 in which at least one amino acid residue in the IL-2 conjugate is replaced by the structure of Formula (XIV) or (XV), or a mixture of (XIV) and (XV), wherein the amino acid residue in SEQ ID NO: 4 that is replaced is H16, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-2 conjugate described herein in the compounds of formula (XIV) and (XV), m is 2, p is 2, and n is an integer selected from 454, 455, 568, 569, 680, 681, 682, 794, 795, 796, 908, 909, and 910.

In some embodiments described herein are IL-2 conjugates comprising the amino acid sequence of SEQ ID NO: 4 in which at least one amino acid residue in the IL-2 conjugate is replaced by the structure of Formula (XIV) or (XV), or a mixture of (XIV) and (XV), wherein the amino acid residue in SEQ ID NO: 4 that is replaced is H16, and wherein m is an integer from 1 to 6, p is an integer from 1 to 6, and n is an integer from about 450 to about 800, or from about 454 to about 796, or from about 454 to about 682, or from about 568 to about 909. In some embodiments of an IL-2 conjugate described herein in the compounds of formula (XIV) and (XV), m is 2, p is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

Described herein are IL-2 conjugates comprising the amino acid sequence of SEQ ID NO: 3 or SEQ ID NO: 4 in which at least one amino acid residue in the IL-2 conjugate is replaced by the structure of Formula (XVI) or (XVII), or a mixture of (XVI) and (XVII):

Formula (XVI)

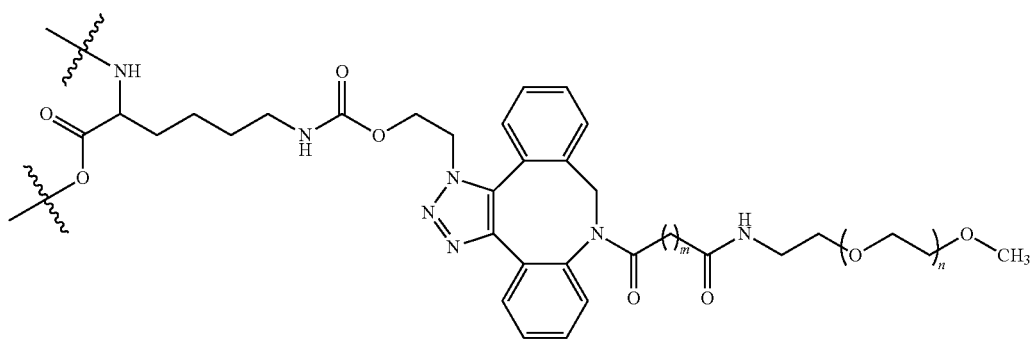

Formula (XVII)

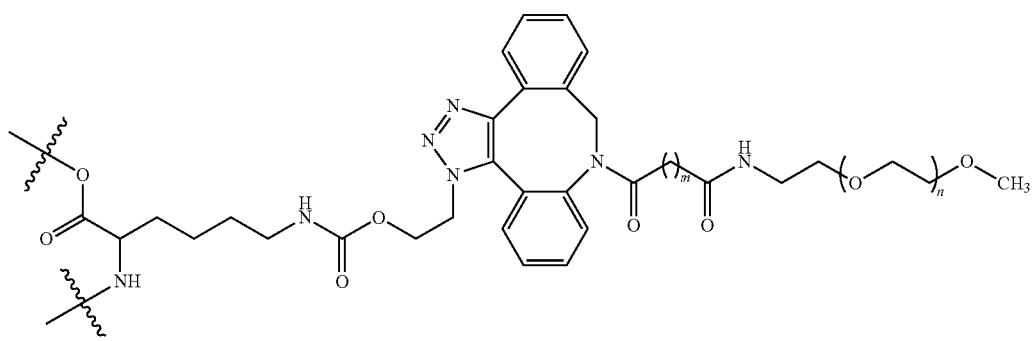

wherein:

m is an integer from 0 to 20;

n is an integer in the range from about 2 to about 5000; and the wavy lines indicate covalent bonds to amino acid residues within SEQ ID NO: 3 or SEQ ID NO: 4 that are not replaced. Here and throughout, embodiments of Formula (XVI) and/or (XVII) also encompass a pharmaceutically acceptable salt, solvate, or hydrate thereof. In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein m, p, n, and the meaning of the wavy line are as described above. In some embodiments described herein are IL-2 conjugates comprising the amino acid sequence of SEQ ID NO: 4 in which at least one amino acid residue in the IL-2 conjugate is replaced by the structure of Formula (XVI) or (XVII), or a mixture of (XVI) and (XVII), wherein m, p, n, and the meaning of the wavy line are as described above.

In some embodiments, the stereochemistry of the chiral center within Formula (XVI) and Formula (XVII) is racemic, is enriched in (R), is enriched in (S), is substantially (R), is substantially (S), is (R) or is (S). In some embodiments, the stereochemistry of the chiral center within Formula (XVI) and Formula (XVII) is racemic. In some embodiments, the stereochemistry of the chiral center within Formula (XVI) and Formula (XVII) is enriched in (R). In some embodiments, the stereochemistry of the chiral center within Formula (XVI) and Formula (XVII) is enriched in (S). In some embodiments, the stereochemistry of the chiral center within Formula (XVI) and Formula (XVII) is substantially (R). In some embodiments, the stereochemistry of the chiral center within Formula (XVI) and Formula (XVII) is substantially (S). In some embodiments, the stereochemistry of the chiral center within Formula (XVI) and Formula (XVII) is (R). In some embodiments, the stereochemistry of the chiral center within Formula (XVI) and Formula (XVII) is (S).

In some embodiments of an IL-2 conjugate described herein, m in the compounds of Formula (XVI) and (XVII) is from 1 to 20, or from 1 to 18, or from 1 to 16, or from 1 to 14, or from 1 to 12, or from 1 to 10, or from 1 to 9, or from 1 to 8, or from 1 to 7, or from 1 to 6, or from 1 to 5, or from 1 to 4, or from 1 to 3, or from 1 to 2. In some embodiments of an IL-2 conjugate described herein, m in the compounds of Formula (XVI) and (XVII) is 1. In some embodiments of an IL-2 conjugate described herein, m in the compounds of Formula (XVI) and (XVII) is 2. In some embodiments of an IL-2 conjugate described herein, m in the compounds of Formula (XVI) and (XVII) is 3. In some embodiments of an IL-2 conjugate described herein, m in the compounds of Formula (XVI) and (XVII) is 4. In some embodiments of an IL-2 conjugate described herein, m in the compounds of Formula (XVI) and (XVII) is 5. In some embodiments of an IL-2 conjugate described herein, m in the compounds of Formula (XVI) and (XVII) is 6. In some embodiments of an IL-2 conjugate described herein, m in the compounds of Formula (XVI) and (XVII) is 7. In some embodiments of an IL-2 conjugate described herein, m in the compounds of Formula (XVI) and (XVII) is 8. In some embodiments of an IL-2 conjugate described herein, m in the compounds of Formula (XVI) and (XVII) is 9. In some embodiments of an IL-2 conjugate described herein, m in the compounds of Formula (XVI) and (XVII) is 10. In some embodiments of an IL-2 conjugate described herein, m in the compounds of Formula (XVI) and (XVII) is 11. In some embodiments of an IL-2 conjugate described herein, m in the compounds of Formula (XVI) and (XVII) is 12. In some embodiments of an IL-2 conjugate described herein, m in the compounds of Formula (XVI) and (XVII) is 13. In some embodiments of an IL-2 conjugate described herein, m in the compounds of Formula (XVI) and (XVII) is 14. In some embodiments of an IL-2 conjugate described herein, m in the compounds of Formula (XVI) and (XVII) is 15. In some embodiments of an IL-2 conjugate described herein, m in the compounds of Formula (XVI) and (XVII) is 16. In some embodiments of an IL-2 conjugate described herein, m in the compounds of Formula (XVI) and (XVII) is 17. In some embodiments of an IL-2 conjugate described herein, m in the compounds of Formula (XVI) and (XVII) is 18. In some embodiments of an IL-2 conjugate described herein, m in the compounds of Formula (XVI) and (XVII) is 19. In some embodiments of an IL-2 conjugate described herein, m in the compounds of Formula (XVI) and (XVII) is 20.

In some embodiments of an IL-2 conjugate described herein, n in the compounds of Formula (XVI) and (XVII) is in the range from about 5 to about 4600, or from about 10 to about 4000, or from about 20 to about 3000, or from about 100 to about 3000, or from about 100 to about 2900, or from about 150 to about 2900, or from about 125 to about 2900, or from about 100 to about 2500, or from about 100 to about 2000, or from about 100 to about 1900, or from about 100 to about 1850, or from about 100 to about 1750, or from about 100 to about 1650, or from about 100 to about 1500, or from about 100 to about 1400, or from about 100 to about 1300, or from about 100 to about 1250, or from about 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575.

In some embodiments of an IL-2 conjugate described herein in the compounds of Formula (XVI) and (XVII), m is an integer from 1 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is an integer from 2 to 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is an integer from 2 to 4, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 1, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 2, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 3, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 4, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 5, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 6, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 7, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 8, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 9, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 10, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 11, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 12, and n is an integer selected from 113, 114, 227, 228, 340, 341, 454, 455, 568, 569, 680, 681, 682, 794, 795, 796, 908, 909, 910, 1021, 1022, 1023, 1135, 1136, and 1137. In some embodiments of an IL-2 conjugate described herein in the compounds of Formula (XVI) and (XVII), m is 2, and n is an integer selected from 680, 681, 682, 794, 795, 796, 908, 909, 910, 1021, 1022, 1023, 1135, 1136, and 1137.

In some embodiments of an IL-2 conjugate described herein, n in the compounds of Formula (XVI) and (XVII) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments of an IL-2 conjugate described herein, the position of the structure of Formula (XVI) and (XVII) or a mixture of Formula (XVI) and (XVII) in the amino acid sequence of the IL-2 conjugate comprising SEQ ID NO: 3 is selected from P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, I88, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, and T132. In some embodiments of an IL-2 conjugate described herein, the position of the structure of Formula (XVI) and (XVII) or a mixture of Formula (XVI) and (XVII) in the amino acid sequence of the IL-2 conjugate of SEQ ID NO: 3 is selected from K8, H15, L18, D19, M22, N25, N87, V90, I91, L93, E94, K96, G97, S98, E99, D108 in the N87R variant, N118, T122, S124, Q125, S126, S129, and T130. Further described herein are IL-2 conjugates wherein the position of the structure of Formula (XVI) or (XVII), or a mixture of (XVI) and (XVII), in the amino acid sequence of the IL-2 conjugate is selected from K8, H15, L18, D19, M22, N25, N87, V90, E99, D108 in the N87R variant, N118, T122, S124, and T130. Further described herein are IL-2 conjugates wherein the position of the structure of Formula (XVI) or (XVII), or a mixture of (XVI) and (XVII), in the amino acid sequence of the IL-2 conjugate is K8. Further described herein are IL-2 conjugates wherein the position of the structure of Formula (XVI) or (XVII), or a mixture of (XVI) and (XVII), in the amino acid sequence of the IL-2 conjugate is H15. Further described herein are IL-2 conjugates wherein the position of the structure of Formula (XVI) or (XVII), or a mixture of (XVI) and (XVII), in the amino acid sequence of the IL-2 conjugate is L18. Further described herein are IL-2 conjugates wherein the position of the structure of Formula (XVI) or (XVII), or a mixture of (XVI) and (XVII), in the amino acid sequence of the IL-2 conjugate is D19. Further described herein are IL-2 conjugates wherein the position of the structure of Formula (XVI) or (XVII), or a mixture of (XVI) and (XVII), in the amino acid sequence of the IL-2 conjugate is M22. Further described herein are IL-2 conjugates wherein the position of the structure of Formula (XVI) or (XVII), or a mixture of (XVI) and (XVII), in the amino acid sequence of the IL-2 conjugate is N25. Further described herein are IL-2 conjugates wherein the position of the structure of Formula (XVI) or (XVII), or a mixture of (XVI) and (XVII), in the amino acid sequence of the IL-2 conjugate is N87. Further described herein are IL-2 conjugates wherein the position of the structure of Formula (XVI) or (XVII), or a mixture of (XVI) and (XVII), in the amino acid sequence of the IL-2 conjugate is V90. Further described herein are IL-2 conjugates wherein the position of the structure of Formula (XVI) or (XVII), or a mixture of (XVI) and (XVII), in the amino acid sequence of the IL-2 conjugate is E99. Further described herein are IL-2 conjugates wherein the position of the structure of Formula (XVI) or (XVII), or a mixture of (XVI) and (XVII), in the amino acid sequence of the IL-2 conjugate is D108 in the N87R variant. Further described herein are IL-2 conjugates wherein the position of the structure of Formula (XVI) or (XVII), or a mixture of (XVI) and (XVII), in the amino acid sequence of the IL-2 conjugate is N118. Further described herein are IL-2 conjugates wherein the position of the structure of Formula (XVI) or (XVII), or a mixture of (XVI) and (XVII), in the amino acid sequence of the IL-2 conjugate is T122. Further described herein are IL-2 conjugates wherein the position of the structure of Formula (XVI) or (XVII), or a mixture of (XVI) and (XVII), in the amino acid sequence of the IL-2 conjugate is S124. Further described herein are IL-2 conjugates wherein the position of the structure of Formula (XVI) or (XVII), or a mixture of (XVI) and (XVII), in the amino acid sequence of the IL-2 conjugate is T130. In some embodiments of an IL-2 conjugate described herein, the ratio of the amount of the structure of Formula (XVI) to the amount of the structure of Formula (XVII) comprising the total amount of the IL-2 conjugate is about 1:1. In some embodiments of an IL-2 conjugate described herein, the ratio of the amount of the structure of Formula (XVI) to the amount of the structure of Formula (XVII) comprising the total amount of the IL-2 conjugate is greater than 1:1. In some embodiments of an IL-2 conjugate described herein, the ratio of the amount of the structure of Formula (XVI) to the amount of the structure of Formula (XVII) comprising the total amount of the IL-2 conjugate is less than 1:1.

In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein the amino acid residue in in SEQ ID NO: 3 that is replaced is selected from K8, H15, L18, D19, M22, N25, N87, V90, E99, D108 in the N87R variant, N118, T122, S124, and T130, and wherein n is an integer from 100 to about 1150, or from about 100 to about 1100, or from about 100 to about 1000, or from about 100 to about 900, or from about 100 to about 750, or from about 100 to about 700, or from about 100 to about 600, or from about 100 to about 575, or from about 100 to about 500, or from about 100 to about 450, or from about 100 to about to about 350, or from about 100 to about 275, or from about 100 to about 230, or from about 150 to about 475, or from about 150 to about 340, or from about 113 to about 340, or from about 450 to about 800, or from about 454 to about 796, or from about 454 to about 682, or from about 340 to about 795, or from about 341 to about 682, or from about 568 to about 909, or from about 227 to about 1500, or from about 225 to about 2280, or from about 460 to about 2160, or from about 460 to about 2050, or from about 341 to about 1820, or from about 341 to about 1710, or from about 341 to about 1250, or from about 225 to about 1250, or from about 341 to about 1250, or from about 341 to about 1136, or from about 341 to about 1023, or from about 341 to about 910, or from about 341 to about 796, or from about 341 to about 682, or from about 341 to about 568, or from about 114 to about 1000, or from about 114 to about 950, or from about 114 to about 910, or from about 114 to about 800, or from about 114 to about 690, or from about 114 to about 575. In some embodiments of an IL-2 conjugate described herein, n in the compounds of formula (XVI) and (XVII) is an integer selected from 2, 5, 10, 11, 22, 23, 113, 114, 227, 228, 340, 341, 454, 455, 568, 569, 680, 681, 682, 794, 795, 796, 908, 909, 910, 1021, 1022, 1023, 1135, 1136, 1137, 1249, 1250, 1251, 1362, 1363, 1364, 1476, 1477, 1478, 1589, 1590, 1591, 1703, 1704, 1705, 1817, 1818, 1819, 1930, 1931, 1932, 2044, 2045, 2046, 2158, 2159, 2160, 2271, 2272, 2273, 2839, 2840, 2841, 2953, 2954, 2955, 3408, 3409, 3410, 3976, 3977, 3978, 4544, 4545, and 4546.

In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein the amino acid residue in in SEQ ID NO: 3 that is replaced is selected from H15, and wherein n is an integer from about 450 to about 800, or from about 454 to about 796, or from about 454 to about 682, or from about 568 to about 909. In some embodiments of an IL-2 conjugate described herein, n in the compounds of formula (XVI) and (XVII) is an integer selected from 454, 455, 568, 569, 680, 681, 682, 794, 795, 796, 908, 909, 910, 1021, 1022, 1023, 1135, 1136, 1137, and 1249.

In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein the amino acid residue in SEQ ID NO: 3 that is replaced is selected from H15, and wherein n is an integer from about 450 to about 800, or from about 454 to about 796, or from about 454 to about 682, or from about 568 to about 909. In some embodiments of an IL-2 conjugate described herein, n in the compounds of formula (XVI) and (XVII) is an integer selected from 454, 455, 568, 569, 680, 681, 682, 794, 795, 796, 908, 909, and 910.

In some embodiments described herein are IL-2 conjugates comprising the amino acid sequence of SEQ ID NO: 3 in which at least one amino acid residue in the IL-2 conjugate is replaced by the structure of Formula (XVI) or (XVII), or a mixture of (XVI) and (XVII), wherein the amino acid residue in SEQ ID NO: 3 that is replaced is H15, and wherein n is an integer from about 450 to about 800, or from about 454 to about 796, or from about 454 to about 682, or from about 568 to about 909. In some embodiments of an IL-2 conjugate described herein, n in the compounds of formula (XVI) and (XVII) is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

In some embodiments of an IL-2 conjugate described herein, the position of the structure of Formula (XVI) and (XVII) or a mixture of Formula (XVI) and (XVII) in the amino acid sequence of the IL-2 conjugate comprising SEQ ID NO: 4 is selected from A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133. Further described herein are IL-2 conjugates wherein the position of the structure of Formula (XVI) or (XVII), or a mixture of (XVI) and (XVII), in the amino acid sequence of the IL-2 conjugate is selected from K9, H16, L19, D20, M23, N26, N88, V91, I92, L94, E95, K97, G98, S99, E100, D109 in the N88R variant, N119, T123, S125, Q126, S127, S130, and T131. Further described herein are IL-2 conjugates wherein the position of the structure of Formula (XVI) or (XVII), or a mixture of (XVI) and (XVII), in the amino acid sequence of the IL-2 conjugate is selected from K9, H16, L19, D20, M23, N26, N88, V91, E100, D109 in the N88R variant, N119, T123, S125, and T131. Further described herein are IL-2 conjugates wherein the position of the structure of Formula (XVI) or (XVII), or a mixture of (XVI) and (XVII), in the amino acid sequence of the IL-2 conjugate is K9. Further described herein are IL-2 conjugates wherein the position of the structure of Formula (XVI) or (XVII), or a mixture of (XVI) and (XVII), in the amino acid sequence of the IL-2 conjugate is H16. Further described herein are IL-2 conjugates wherein the position of the structure of Formula (XVI) or (XVII), or a mixture of (XVI) and (XVII), in the amino acid sequence of the IL-2 conjugate is L19. Further described herein are IL-2 conjugates wherein the position of the structure of Formula (XVI) or (XVII), or a mixture of (XVI) and (XVII), in the amino acid sequence of the IL-2 conjugate is D20. Further described herein are IL-2 conjugates wherein the position of the structure of Formula (XVI) or (XVII), or a mixture of (XVI) and (XVII), in the amino acid sequence of the IL-2 conjugate is M23. Further described herein are IL-2 conjugates wherein the position of the structure of Formula (XVI) or (XVII), or a mixture of (XVI) and (XVII), in the amino acid sequence of the IL-2 conjugate is N26. Further described herein are IL-2 conjugates wherein the position of the structure of Formula (XVI) or (XVII), or a mixture of (XVI) and (XVII), in the amino acid sequence of the IL-2 conjugate is N88. Further described herein are IL-2 conjugates wherein the position of the structure of Formula (XVI) or (XVII), or a mixture of (XVI) and (XVII), in the amino acid sequence of the IL-2 conjugate is V91. Further described herein are IL-2 conjugates wherein the position of the structure of Formula (XVI) or (XVII), or a mixture of (XVI) and (XVII), in the amino acid sequence of the IL-2 conjugate is E100. Further described herein are IL-2 conjugates wherein the position of the structure of Formula (XVI) or (XVII), or a mixture of (XVI) and (XVII), in the amino acid sequence of the IL-2 conjugate is D109 in the N88R variant. Further described herein are IL-2 conjugates wherein the position of the structure of Formula (XVI) or (XVII), or a mixture of (XVI) and (XVII), in the amino acid sequence of the IL-2 conjugate is N119. Further described herein are IL-2 conjugates wherein the position of the structure of Formula (XVI) or (XVII), or a mixture of (XVI) and (XVII), in the amino acid sequence of the IL-2 conjugate is T123. Further described herein are IL-2 conjugates wherein the position of the structure of Formula (XVI) or (XVII), or a mixture of (XVI) and (XVII), in the amino acid sequence of the IL-2 conjugate is 5125. Further described herein are IL-2 conjugates wherein the position of the structure of Formula (XVI) or (XVII), or a mixture of (XVI) and (XVII), in the amino acid sequence of the IL-2 conjugate is T131.

Described herein are IL-2 conjugates comprising the amino acid sequence of SEQ ID NO: 3 or SEQ ID NO: 4 in which at least one amino acid residue in the IL-2 conjugate is replaced by the structure of Formula (XVI) or (XVII), or a mixture of (XVI) and (XVII), wherein n is an integer such that the molecular weight of the PEG moiety is in the range from about 1,000 Daltons about 200,000 Daltons, or from about 2,000 Daltons to about 150,000 Daltons, or from about 3,000 Daltons to about 125,000 Daltons, or from about 4,000 Daltons to about 100,000 Daltons, or from about 5,000 Daltons to about 100,000 Daltons, or from about 6,000 Daltons to about 90,000 Daltons, or from about 7,000 Daltons to about 80,000 Daltons, or from about 8,000 Daltons to about 70,000 Daltons, or from about 5,000 Daltons to about 70,000 Daltons, or from about 5,000 Daltons to about 65,000 Daltons, or from about 5,000 Daltons to about 60,000 Daltons, or from about 5,000 Daltons to about 50,000 Daltons, or from about 6,000 Daltons to about 50,000 Daltons, or from about 7,000 Daltons to about 50,000 Daltons, or from about 7,000 Daltons to about 45,000 Daltons, or from about 7,000 Daltons to about 40,000 Daltons, or from about 8,000 Daltons to about 40,000 Daltons, or from about 8,500 Daltons to about 40,000 Daltons, or from about 8,500 Daltons to about 35,000 Daltons, or from about 9,000 Daltons to about 50,000 Daltons, or from about 9,000 Daltons to about 45,000 Daltons, or from about 9,000 Daltons to about 40,000 Daltons, or from about 9,000 Daltons to about 35,000 Daltons, or from about 9,000 Daltons to about 30,000 Daltons, or from about 9,500 Daltons to about 35,000 Daltons, or from about 9,500 Daltons to about 30,000 Daltons, or from about 10,000 Daltons to about 50,000 Daltons, or from about 10,000 Daltons to about 45,000 Daltons, or from about 10,000 Daltons to about 40,000 Daltons, or from about 10,000 Daltons to about 35,000 Daltons, or from about 10,000 Daltons to about 30,000 Daltons, or from about 15,000 Daltons to about 50,000 Daltons, or from about 15,000 Daltons to about 45,000 Daltons, or from about 15,000 Daltons to about 40,000 Daltons, or from about 15,000 Daltons to about 35,000 Daltons, or from about 15,000 Daltons to about 30,000 Daltons, or from about 20,000 Daltons to about 50,000 Daltons, or from about 20,000 Daltons to about 45,000 Daltons, or from about 20,000 Daltons to about 40,000 Daltons, or from about 20,000 Daltons to about 35,000 Daltons, or from about 20,000 Daltons to about 30,000 Daltons. Described herein are IL-2 conjugates comprising the amino acid sequence of SEQ ID NO: 3 or SEQ ID NO: 4 in which at least one amino acid residue in the IL-2 conjugate is replaced by the structure of Formula (XVI) or (XVII), or a mixture of (XVI) and (XVII), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, about 50,000 Daltons, about 60,000 Daltons, about 70,000 Daltons, about 80,000 Daltons, about 90,000 Daltons, about 100,000 Daltons, about 125,000 Daltons, about 150,000 Daltons, about 175,000 Daltons or about 200,000 Daltons. Described herein are IL-2 conjugates comprising the amino acid sequence of SEQ ID NO: 3 or SEQ ID NO: 4 in which at least one amino acid residue in the IL-2 conjugate is replaced by the structure of Formula (XVI) or (XVII), or a mixture of (XVI) and (XVII), wherein n is an integer such that the molecular weight of the PEG moiety is about 5,000 Daltons, about 7,500 Daltons, about 10,000 Daltons, about 15,000 Daltons, about 20,000 Daltons, about 25,000 Daltons, about 30,000 Daltons, about 35,000 Daltons, about 40,000 Daltons, about 45,000 Daltons, or about 50,000 Daltons.

In some embodiments described herein are IL-2 conjugates comprising the amino acid sequence of SEQ ID NO: 4 in which at least one amino acid residue in the IL-2 conjugate is replaced by the structure of Formula (XVI) or (XVII), or a mixture of (XVI) and (XVII), wherein the amino acid residue in in SEQ ID NO: 4 that is H16, m is an integer from 1 to 6, and n is an integer from about 450 to about 800, or from about 454 to about 796, or from about 454 to about 682, or from about 568 to about 909. In some embodiments of an IL-2 conjugate described herein in the compounds of formula (XVI) and (XVII), m is 2, and n is an integer selected from 454, 455, 568, 569, 680, 681, 682, 794, 795, 796, 908, 909, 910, 1021, 1022, 1023, 1135, 1136, 1137, and 1249.

In some embodiments described herein are IL-2 conjugates comprising the amino acid sequence of SEQ ID NO: 4 in which at least one amino acid residue in the IL-2 conjugate is replaced by the structure of Formula (XVI) or (XVII), or a mixture of (XVI) and (XVII), wherein the amino acid residue in SEQ ID NO: 4 that is replaced is H16, and wherein m is an integer from 1 to 6, and n is an integer from about 450 to about 800, or from about 454 to about 796, or from about 454 to about 682, or from about 568 to about 909. In some embodiments of an IL-2 conjugate described herein in the compounds of formula (XVI) and (XVII), m is 2, and n is an integer selected from 454, 455, 568, 569, 680, 681, 682, 794, 795, 796, 908, 909, and 910.

In some embodiments described herein are IL-2 conjugates comprising the amino acid sequence of SEQ ID NO: 4 in which at least one amino acid residue in the IL-2 conjugate is replaced by the structure of Formula (XVI) or (XVII), or a mixture of (XVI) and (XVII), wherein the amino acid residue in SEQ ID NO: 4 that is replaced is E61, and wherein m is an integer from 1 to 6, and n is an integer from about 450 to about 800, or from about 454 to about 796, or from about 454 to about 682, or from about 568 to about 909. In some embodiments of an IL-2 conjugate described herein in the compounds of formula (XVI) and (XVII), m is 2, and n is an integer selected from 454, 455, 568, 569, 680, 681, 682, 794, 795, 796, 908, 909, and 910. In some embodiments, n is from about 500 to about 1000. In some embodiments, n is from about 550 to about 800. In some embodiments, n is about 681.

Described herein are methods of treating an autoimmune disease in a subject, comprising administering to a subject in need thereof a therapeutically effective amount of an IL-2 conjugate described herein. Further described herein are methods wherein the autoimmune disease is selected from the group consisting of graft versus host disease (GVHD), atopic dermatitis, Crohn's disease, alopecia areata, autoimmune hemolytic anemia, autoimmune hepatitis, dermatomyositis, type 1 diabetes, juvenile/pediatric type 1 diabetes, juvenile idiopathic arthritis, glomerulonephritis, Graves' disease, Guillain-Barré syndrome, idiopathic thrombocytopenic purpura, myasthenia gravis, multiple sclerosis, pemphigus/pemphigoid, pernicious anemia, polyarteritis nodosa, polymyositis, primary biliary cholangitis, primary biliary cirrhosis, nonalcoholic steatohepatitis (NASH), psoriasis, rheumatoid arthritis, scleroderma, CREST syndrome, Sjögren's syndrome, systemic lupus erythematosus, thyroiditis, uveitis, vitiligo, Wegener's granulomatosis, Addison's disease (adrenal insufficiency), Hashimoto thyroiditis, autoimmune hepatitis, infertility, ANCA-associated vasculitis, psoriatic arthritis, Celiac disease, ulcerative colitis, lichen sclerosus, and Behcet's disease. Further described herein are methods wherein the autoimmune disease is selected from the group consisting of graft versus host disease (GVHD), atopic dermatitis, Crohn's disease, type 1 diabetes, multiple sclerosis, rheumatoid arthritis, myasthenia gravis, primary biliary cirrhosis, nonalcoholic steatohepatitis (NASH), glomerulonephritis, idiopathic thrombocytopenic purpura, systemic lupus erythematosus, scleroderma, CREST syndrome, psoriasis, Celiac disease, ulcerative colitis, pemphigus, psoriatic arthritis, and infertility. Further described herein are methods wherein the autoimmune disease is graft versus host disease (GVHD). Further described herein are methods wherein the autoimmune disease is atopic dermatitis. Further described herein are methods wherein the autoimmune disease is Crohn's disease. Further described herein are methods wherein the autoimmune disease is type 1 diabetes. Further described herein are methods wherein the autoimmune disease is multiple sclerosis. Further described herein are methods wherein the autoimmune disease is rheumatoid arthritis. Further described herein are methods wherein the autoimmune disease is myasthenia gravis. Further described herein are methods wherein the autoimmune disease is primary biliary cholangitis or primary biliary cirrhosis. Further described herein are methods wherein the autoimmune disease is nonalcoholic steatohepatitis (NASH). Further described herein are methods wherein the autoimmune disease is glomerulonephritis. Further described herein are methods wherein the autoimmune disease is idiopathic thrombocytopenic purpura. Further described herein are methods wherein the autoimmune disease is systemic lupus erythematosus. Further described herein are methods wherein the autoimmune disease is scleroderma. Further described herein are methods wherein the autoimmune disease is CREST syndrome. Further described herein are methods wherein the autoimmune disease is infertility. Further described herein are methods wherein the IL-2 conjugate is administered to the subject in need thereof once per week, once every two weeks, once every three weeks, once every 4 weeks, once every 5 weeks, once every 6 weeks, once every 7 weeks, or once every 8 weeks. Further described herein are methods wherein the IL-2 conjugate is administered to the subject in need thereof once per week, once every two weeks, once every three weeks, or once every 4 weeks. Further described herein are methods wherein the IL-2 conjugate is administered to the subject in need thereof once per week. Further described herein are methods wherein the IL-2 conjugate is administered to the subject in need thereof once every two weeks. Further described herein are methods wherein the IL-2 conjugate is administered to the subject in need thereof once every three weeks. Further described herein are methods wherein the IL-2 conjugate is administered to the subject in need thereof once every four weeks. Further described herein are methods wherein the subject in need thereof is determined to exhibit an increased concentration of rheumatoid factor in the blood of the subject prior to administration to the subject of the therapeutically effective amount of the IL-2 conjugate. Further described herein are methods wherein the increased concentration of rheumatoid factor in the blood of the subject is about 14 IU/mL or higher, or about 15 IU/mL or higher. Further described herein are methods wherein the increased concentration of rheumatoid factor in the blood of the subject is about 14 IU/mL or higher. Further described herein are methods wherein the increased concentration of rheumatoid factor in the blood of the subject is about 15 IU/mL or higher.

Described herein are methods of treating rheumatoid arthritis in a subject in need thereof, comprising: (a) determining the concentration of rheumatoid factor in the blood of the subject; and (b) administering to the subject in need thereof a therapeutically effective amount of an IL-2 conjugate described herein if the concentration of rheumatoid factor in the blood of the subject is greater than about 14 IU/mL. Further described herein are methods wherein a therapeutically effective amount of the IL-2 conjugate is administered to the subject in need thereof if the concentration of rheumatoid factor in the blood of the subject is greater than about 15 IU/mL.

Described herein are methods of treating rheumatoid arthritis in a subject in need thereof, comprising administering to the subject in need thereof a therapeutically effective amount of an IL-2 conjugate described herein if the concentration of rheumatoid factor in the blood of the subject is determined to be greater than about 14 IU/mL.

Described herein are methods of treating rheumatoid arthritis in a subject in need thereof, comprising administering to the subject in need thereof a therapeutically effective amount of an IL-2 conjugate described herein if the concentration of rheumatoid factor in the blood of the subject is determined to be greater than about 15 IU/mL. Further provided herein are methods wherein the subject in need thereof is determined to exhibit an abnormal erythrocyte sedimentation rate (ESR) test prior to administration to the subject of the therapeutically effective amount of the IL-2 conjugate. Further described herein are methods wherein the subject is determined to exhibit an abnormal erythrocyte sedimentation rate (ESR) test using the Westergren rate method prior to administration to the subject of the therapeutically effective amount of the IL-2 conjugate. Further described herein are methods wherein the subject is determined to exhibit an abnormal erythrocyte sedimentation rate (ESR) test using the Wintrobe rate method prior to administration to the subject of the therapeutically effective amount of the IL-2 conjugate. Further provided herein are methods wherein the subject is a woman under age 50 and exhibits a Westergren rate greater than about 20 mm/hr. Further provided herein are methods wherein the subject is a woman greater than age 50 and exhibits a Westergren rate greater than about 30 mm/hr. Further provided herein are methods wherein the subject is a man under age 50 and exhibits a Westergren rate greater than about 15 mm/hr. Further provided herein are methods wherein the subject is a man greater than age 50 and exhibits a Westergren rate greater than 20 mm/hr. Further provided herein are methods wherein the subject is a child and exhibits a Westergren rate greater than about 10 mm/hr.

Described herein are methods of treating an autoimmune disease in a subject in need thereof, comprising: (a) determining the erythrocyte sedimentation rate (ESR) in the subject; and (b) administering to the subject in need thereof a therapeutically effective amount of an IL-2 conjugate described herein if the ESR is determined to be abnormal. Further described herein are methods wherein the subject is determined to exhibit an abnormal erythrocyte sedimentation rate (ESR) test using the Wintrobe rate method. Further described herein are methods wherein the subject is determined to exhibit an abnormal erythrocyte sedimentation rate (ESR) test using the Westergren rate method. Further described herein are methods wherein the subject is a woman under age 50 and exhibits a Westergren rate greater than about 20 mm/hr. Further described herein are methods wherein the subject is a woman greater than age 50 and exhibits a Westergren rate greater than about 30 mm/hr. Further described herein are methods wherein the subject is a man under age 50 and exhibits a Westergren rate greater than about 15 mm/hr. Further described herein are methods wherein the subject is a man greater than age 50 and exhibits a Westergren rate greater than 20 mm/hr. Further described herein are methods wherein the subject is a child and exhibits a Westergren rate greater than about 10 mm/hr. Further provided herein are methods wherein the subject in need thereof is determined to exhibit an increased concentration of C-reactive protein (CRP) in the blood of the subject prior to administration to the subject the therapeutically effective amount of the IL-2 conjugate. Further described herein are methods wherein the subject in need thereof is determined to exhibit a concentration of C-reactive protein (CRP) in the blood greater than 10 mg/L prior to administration to the subject the therapeutically effective amount of the IL-2 conjugate.

Described herein are methods of treating an autoimmune disease in a subject in need thereof, comprising: (a) determining the concentration of C-reactive protein (CRP) in the blood of the subject; and (b) administering to the subject in need thereof a therapeutically effective amount of an IL-2 conjugate described herein if the concentration of C-reactive protein (CRP) in the blood of the subject is determined to be abnormal. Further described herein are methods wherein the subject in need thereof is determined to exhibit a concentration of C-reactive protein (CRP) in the blood greater than 10 mg/L prior to administration to the subject of the therapeutically effective amount of the IL-2 conjugate.

Described herein are methods of treating rheumatoid arthritis in a subject in need thereof, comprising: (a) determining the concentration of anti-cyclic citrullinated peptide (anti-CCP) in the blood of the subject; and (b) administering to the subject in need thereof a therapeutically effective amount of an IL-2 conjugate described herein if the concentration of rheumatoid factor in the blood of the subject is determined to be abnormal. Further described herein are methods wherein a therapeutically effective amount of the IL-2 conjugate is administered to the subject in need thereof if the concentration of anti-cyclic citrullinated peptide (anti-CCP) in the blood of the subject is determined to be greater than about 20 Iu/mL.

Described herein are methods of treating rheumatoid arthritis in a subject in need thereof, comprising administering to the subject in need thereof a therapeutically effective amount of an IL-2 conjugate described herein if the concentration of anti-cyclic citrullinated peptide (anti-CCP) in the blood of the subject is determined to be abnormal.

Described herein are methods of treating rheumatoid arthritis in a subject in need thereof, comprising administering to the subject in need thereof a therapeutically effective amount of an IL-2 conjugate described herein if the concentration of anti-cyclic citrullinated peptide (anti-CCP) in the blood of the subject is determined to be greater than about 20 Iu/mL. Further described herein are methods wherein the autoimmune disease is psoriasis. Further described herein are methods wherein the autoimmune disease is Celiac disease. Further described herein are methods wherein the autoimmune disease is ulcerative colitis. Further described herein are methods wherein the autoimmune disease is pemphigus.

Described herein are methods of alleviating or eliminating an autoimmune condition modeled by, represented by, and/or characterized by delayed-type hypersensitivity (DTH) in a subject in need thereof, comprising administering to the subject a therapeutically effective amount of an IL-2 conjugate described herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A illustrates exemplary lysine derivatives. FIG. 2B illustrates exemplary phenylalanine derivatives.

FIG. 3B—UAA #43-89; FIG. 3C—UAA #90-128; FIG. 3D—UAA #129-167). FIGS. 3A-3D are adopted from Table 1 of Dumas et al., *Chemical Science* 2015, 6, 50-69.

FIG. 5A shows plots generated from assays with IL-2 and IL-2 conjugate D20_30 kD. FIG. 5B shows plots generated from assays with IL-2 conjugates H16_30 kD and L19_30 kD. FIG. 5C shows plots generated from assays with IL-2 conjugates N88_30 kD and L12_30 kD. X-axis: in pg/ml; Y-axis: % of maximal response.

FIG. 17A shows Area Under Curve (AUC) of increased ear thickness as compared to the mice with KLH challenge on Day 7 only. FIG. 17B shows changes in ear thickness measurements in the C57BL/6 mice prior to KLH challenge (on Day 7) and then subsequently on Days 8, 9 and 10. FIG. 17C shows changes over time in the relative percentage of CD4+ T cells within CD25+ FoxP3+ cell population in whole blood samples from the mice. "KLH only" indicates KLH challenge on Day 7 only (without sensitization on Day 1) with dosing of vehicle only. "Vehicle" indicates KLH sensitization (Day 1) and challenge (Day 7) with dosing of vehicle only. "0.03" indicates KLH sensitization and challenge with dosing of H16_50 kD at a dose of 0.03 mg/kg. "0.1" indicates KLH sensitization and challenge with dosing of H16_50 kD at a dose of 0.1 mg/kg. "0.3" indicates KLH sensitization and challenge with dosing of H16_50 kD at a dose of 0.3 mg/kg. "CsA" indicates KLH sensitization and challenge with dosing of Cyclosporine A. See also Table 10 in Example 7.

DETAILED DESCRIPTION OF THE DISCLOSURE

Figure 1:
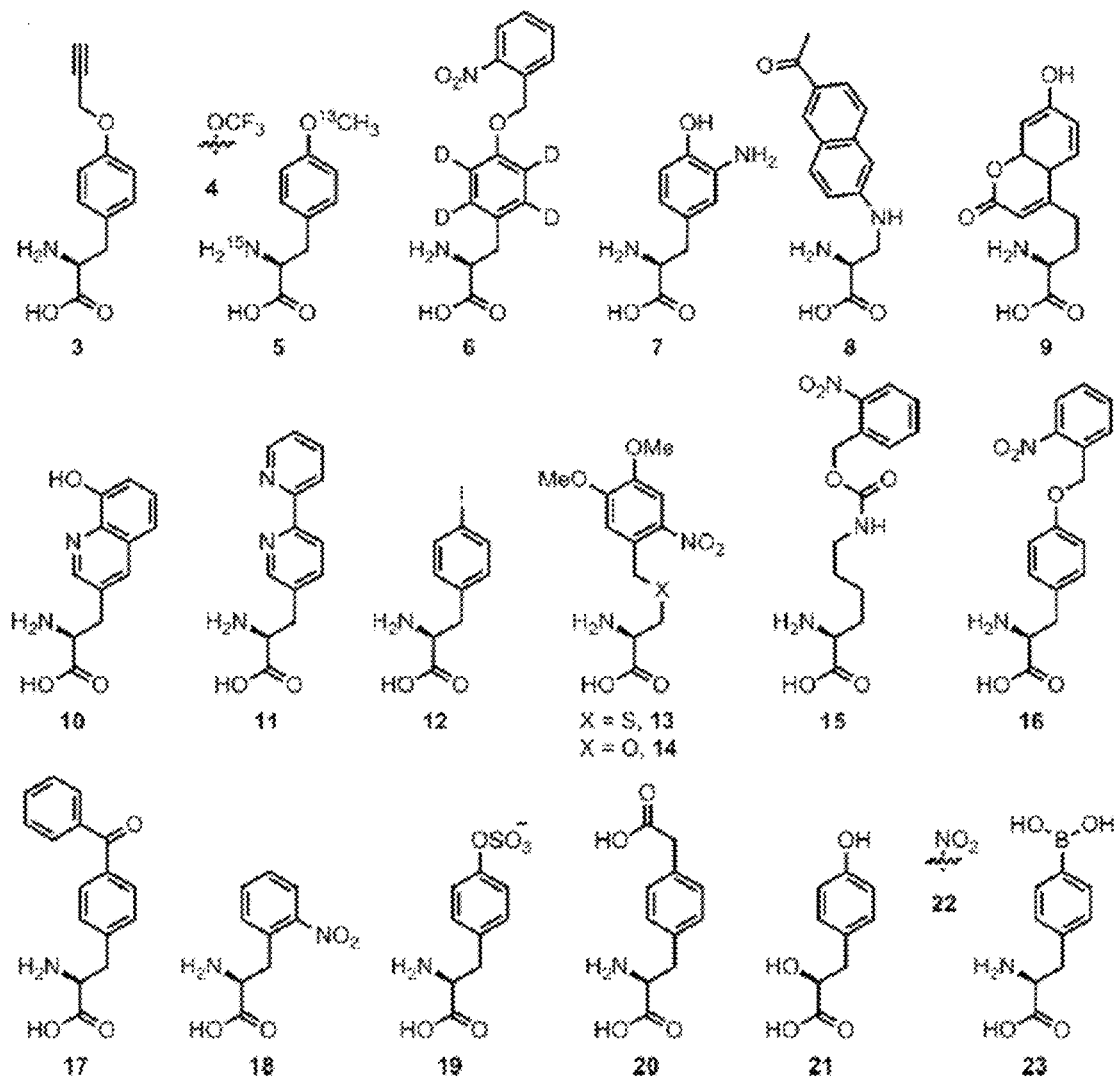
FIG. 1 shows exemplary unnatural amino acids. This figure is adapted from FIG. 2 of Young et al., "Beyond the canonical 20 amino acids: expanding the genetic lexicon," *J. of Biological Chemistry* 285(15): 11039-11044 (2010).

Cytokines comprise a family of cell signaling proteins such as chemokines, interferons, interleukins, lymphokines, tumor necrosis factors, and other growth factors playing roles in innate and adaptive immune cell homeostasis. Cytokines are produced by immune cells such as macrophages, B lymphocytes, T lymphocytes and mast cells, endothelial cells, fibroblasts, and different stromal cells. In some instances, cytokines modulate the balance between humoral and cell-based immune responses.

Interleukins are signaling proteins which modulate the development and differentiation of T and B lymphocytes, cell of the monocytic lineage, neutrophils, basophils, eosinophils, megakaryocytes, and hematopoietic cells. Interleukins are produced by helper CD4 T and B lymphocytes, monocytes, macrophages, endothelial cells, and other tissue residents.

Interleukin 2 (IL-2) is a pleiotropic type-1 cytokine whose structure comprises a 15.5 kDa four α-helix bundle. The precursor form of IL-2 is 153 amino acid residues in length, with the first 20 amino acids forming a signal peptide and residues 21-153 forming the mature form. IL-2 is produced primarily by CD4+ T cells post antigen stimulation and to a lesser extent, by CD8+ cells, Natural Killer (NK) cells, and Natural killer T (NKT) cells, activated dendritic cells (DCs), and mast cells. IL-2 signaling occurs through interaction with specific combinations of IL-2 receptor (IL-2R) subunits, IL-2Rα (also known as CD25), IL-2Rβ (also known as CD122), and IL-2Rγ (also known as CD132). Interaction of IL-2 with the IL-2Rα forms the "low-affinity" IL-2 receptor complex with a $K_d$ of about $10^{-8}$ M. Interaction of IL-2 with IL-2Rβ and IL-2Rγ forms the "intermediate-affinity" IL-2 receptor complex with a $K_d$ of about $10^{-9}$ M. Interaction of IL-2 with all three subunits, IL-2Rα, IL-2Rβ, and IL-2Rγ, forms the "high-affinity" IL-2 receptor complex with a $K_d$ of about $>10^{-11}$M.

In some instances, IL-2 signaling via the "high-affinity" IL-2Rαβγ complex modulates the activation and proliferation of regulatory T cells. Regulatory T cells, or CD4+ CD25+Foxp3+ regulatory T (Treg) cells, mediate maintenance of immune homeostasis by suppression of effector cells such as CD4+ T cells, CD8+ T cells, B cells, NK cells, and NKT cells. In some instances, Treg cells are generated from the thymus (tTreg cells) or are induced from naïve T cells in the periphery (pTreg cells). In some cases, Treg cells are considered as the mediator of peripheral tolerance. Indeed, in one study, transfer of CD25-depleted peripheral CD4+ T cells produced a variety of autoimmune diseases in nude mice, whereas cotransfer of CD4+CD25+ T cells suppressed the development of autoimmunity (Sakaguchi, et al., "Immunologic self-tolerance maintained by activated T cells expressing IL-2 receptor alpha-chains (CD25)," *J. Immunol.* 155(3): 1151-1164 (1995)). Augmentation of the Treg cell population down-regulates effector T cell proliferation and suppresses autoimmunity and T cell anti-tumor responses.

Disclosed herein, in certain embodiments, is a method of selectively upregulating distinct population(s) of lymphocytes (e.g., CD4+ helper cells, CD8+ effector naïve and memory cells, NK cells, or NKT cells) through cytokine/cytokine receptor signaling. In some instances, the cytokine comprises an interleukin, an interferon, or a tumor necrosis factor. In some cases, the cytokine is a cytokine conjugate, e.g., an interleukin conjugate, an interferon conjugate, or a tumor necrosis factor conjugate. In additional cases, described herein comprise pharmaceutical compositions and kits comprising one or more cytokine conjugates described herein.

In some embodiments, also described herein is a method of selectively upregulating CD4+ helper cell, CD8+ effector naïve and memory cell, NK cell, and/or NKT cell populations through IL-2/IL-2R signaling. In some instances, IL-2 is an IL-2 conjugate, which interacts with the "intermediate-affinity" IL-2Rβγ complex, optionally with a similar potency as the IL-2Rαβγ complex, and with a weakened IL-2Rα interaction relative to wild-type IL-2. In some embodiments, further described herein are methods of treating a cancer with use of an IL-2 conjugate described herein. In additional embodiments, described herein are pharmaceutical compositions and kits which comprise one or more IL-2 conjugates described herein. In some embodiments, the IL-2 conjugates comprise conjugating moieties (e.g., a PEG) that contribute to an increase or a decrease in "clearance rate," or plasma half-life in a subject, without affecting the pharmacokinetics, including the desired cytokine-receptor interactions and immune cell expansion.

Cytokine Conjugates

In some embodiments, described herein are cytokine conjugates. In some instances, the cytokine comprises an interleukins, a tumor necrosis factor, an interferon, a chemokine, a lymphokine, or a growth factor. In some instances, the cytokine is an interleukin. In some cases, the cytokine is an interferon. In additional cases, the cytokine is a tumor necrosis factor. In further cases, the cytokine is a growth factor.

In some embodiments, described herein is an interleukin conjugate. Exemplary interleukins include, but are not limited to interleukin 2 (IL-2).

IL-2 Conjugates

Described herein are polypeptides shown in Table 1. In some embodiments, IL-2 conjugates described herein are exemplified in Table 1.

TABLE 1

| Name | Sequence | SEQ ID NO: |
|---|---|---|
| IL-2<br>(homo sapiens)<br>(mature form) | APTSSSTKKTQLQLEHLLLDLQMILNGINNYKNPKLTRMLTF<br>KFYMPKKATELKHLQCLEEELKPLEEVLNLAQSKNFHLRPRD<br>LISNINVIVLELKGSETTFMCEYADETATIVEFLNRWITFCQSII<br>STLT | 1 |
| IL-2<br>(homo sapiens)<br>(precursor)<br>NCBI Accession No.:<br>AAB46883.1 | MYRMQLLSCIALSLALVTNSAPTSSSTKKTQLQLEHLLLDLQ<br>MILNGINNYKNPKLTRMLTFKFYMPKKATELKHLQCLEEELK<br>PLEEVLNLAQSKNFHLRPRDLISNINVIVLELKGSETTFMCEY<br>ADETATIVEFLNRWITFCQSIISTLT | 2 |
| aldesleukin | PTSSSTKKTQLQLEHLLLDLQMILNGINNYKNPKLTRMLTFKF<br>YMPKKATELKHLQCLEEELKPLEEVLNLAQSKNFHLRPRDLI<br>SNINVIVLELKGSETTFMCEYADETATIVEFLNRWITFSQSIIST<br>LT | 3 |
| IL-2_C125S | APTSSSTKKTQLQLEHLLLDLQMILNGINNYKNPKLTRMLTF<br>KFYMPKKATELKHLQCLEEELKPLEEVLNLAQSKNFHLRPRD<br>LISNINVIVLELKGSETTFMCEYADETATIVEFLNRWITFSQSII<br>STLT | 4 |

TABLE 1-continued

| Name | Sequence | SEQ ID NO: |
|---|---|---|
| IL-2_K9X | APTSSSTKXTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQSII STLT | 5 |
| IL-2_H16X | APTSSSTKKTQLQLEXLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQSII STLT | 6 |
| IL-2_L19X | APTSSSTKKTQLQLEHLLXDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQSII STLT | 7 |
| IL-2_D20X | APTSSSTKKTQLQLEHLLLXLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQSII STLT | 8 |
| IL-2_M23X | APTSSSTKKTQLQLEHLLLDLQXILNGINNYKNPKLTRMLTFK FYMPKKATELKHLQCLEEELKPLEEVLNLAQSKNFHLRPRDL ISNINVIVLELKGSETTFMCEYADETATIVEFLNRWITFSQSIIS TLT | 9 |
| IL-2_N26X | APTSSSTKKTQLQLEHLLLDLQMILXGINNYKNPKLTRMLTF KFYMPKKATELKHLQCLEEELKPLEEVLNLAQSKNFHLRPRD LISNINVIVLELKGSETTFMCEYADETATIVEFLNRWITFSQSII STLT | 10 |
| IL-2_N88X | APTSSSTKKTQLQLEHLLLDLQMILNGINNYKNPKLTRMLTF KFYMPKKATELKHLQCLEEELKPLEEVLNLAQSKNFHLRPRD LISXINVIVLELKGSETTFMCEYADETATIVEFLNRWITFSQSII STLT | 11 |
| IL-2_E100X | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSXTTFMCEYADETATIVEFLNRWITFSQSII STLT | 12 |
| IL-2_N119X | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLXRWITFSQSII STLT | 13 |
| IL-2_T123X | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWIXFSQSII STLT | 14 |
| IL-2_Q126X | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSXII STLT | 15 |
| IL-2_S127X | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQXII STLT | 16 |
| IL-2_T131X | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQSII SXLT | 17 |
| IL-2_N88R_D109X | APTSSSTKKTQLQLEHLLLDLQMILNGINNYKNPKLTRMLTF KFYMPKKATELKHLQCLEEELKPLEEVLNLAQSKNFHLRPRD LISRINVIVLELKGSETTFMCEYAXETATIVEFLNRWITFSQSII STLT | 18 |
| IL-2_V91X | APTSSSTKKTQLQLEHLLLDLQMILNGINNYKNPKLTRMLTF KFYMPKKATELKHLQCLEEELKPLEEVLNLAQSKNFHLRPRD LISNINXIVLELKGSETTFMCEYADETATIVEFLNRWITFSQSII STLT | 19 |

TABLE 1-continued

| Name | Sequence | SEQ ID NO: |
|---|---|---|
| IL-2_K9[AzK] | APTSSSTK[AzK]TQLQLEHLLLDLQMILNGINNYKNPKLTRM LTFKFYMPKKATELKHLQCLEEELKPLEEVLNLAQSKNFHLR PRDLISNINVIVLELKGSETTFMCEYADETATIVEFLNRWITFS QSIISTLT | 20 |
| IL-2_H16[AzK] | APTSSSTKKTQLQLE[AzK]LLLDLQMILNGINNYKNPKLTRM LTFKFYMPKKATELKHLQCLEEELKPLEEVLNLAQSKNFHLR PRDLISNINVIVLELKGSETTFMCEYADETATIVEFLNRWITFS QSIISTLT | 21 |
| IL-2_L19[AzK] | APTSSSTKKTQLQLEHLL[AzK]DQMILNGINNYKNPKLTRM LTFKFYMPKKATELKHLQCLEEELKPLEEVLNLAQSKNFHLR PRDLISNINVIVLELKGSETTFMCEYADETATIVEFLNRWITFS QSIISTLT | 22 |
| IL-2_D20[AzK] | APTSSSTKKTQLQLEHLLL[AzK]LQMILNGINNYKNPKLTRM LTFKFYMPKKATELKHLQCLEEELKPLEEVLNLAQSKNFHLR PRDLISNINVIVLELKGSETTFMCEYADETATIVEFLNRWITFS QSIISTLT | 23 |
| IL-2_M23[AzK] | APTSSSTKKTQLQLEHLLLDLQ[AzK]ILNGINNYKNPKLTRML TFKFYMPKKATELKHLQCLEEELKPLEEVLNLAQSKNFHLRP RDLISNINVIVLELKGSETTFMCEYADETATIVEFLNRWITFSQ SIISTLT | 24 |
| IL-2_N26[AzK] | APTSSSTKKTQLQLEHLLLDLQMIL[AzK]GINNYKNPKLTRM LTFKFYMPKKATELKHLQCLEEELKPLEEVLNLAQSKNFHLR PRDLISNINVIVLELKGSETTFMCEYADETATIVEFLNRWITFS QSIISTLT | 25 |
| IL-2_N88[AzK] | APTSSSTKKTQLQLEHLLLDLQMILNGINNYKNPKLTRMLTF KFYMPKKATELKHLQCLEEELKPLEEVLNLAQSKNFHLRPRD LIS[AzK]INVIVLELKGSETTFMCEYADETATIVEFLNRWITFS QSIISTLT | 26 |
| IL-2_E100[AzK] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGS[AzK]TTFMCEYADETATIVEFLNRWITFS QSIISTLT | 27 |
| IL-2_N119[AzK] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFL[AzK]RWITFS QSIISTLT | 28 |
| IL-2_T123[AzK] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWI[AzK]FS QSIISTLT | 29 |
| IL-2_Q126[AzK] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFS[AzK] SIISTLT | 30 |
| IL-2_S127[AzK] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQ[AzK] IISTLT | 31 |
| IL-2_T131[AzK] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQSII S[AzK]LT | 32 |
| IL-2_N88R_D109[AzK] | APTSSSTKKTQLQLEHLLLDLQMILNGINNYKNPKLTRMLTF KFYMPKKATELKHLQCLEEELKPLEEVLNLAQSKNFHLRPRD LISRINVIVLELKGSETTFMCEYA[AzK]ETATIVEFLNRWITFS QSIISTLT | 33 |
| IL-2_K9[AzK_PEG] | APTSSSTK[AzK_PEG]TQLQLEHLLLDLQMILNGINNYKNPKL TRMLTFKFYMPKKATELKHLQCLEEELKPLEEVLNLAQSKNF HLRPRDLISNINVIVLELKGSETTFMCEYADETATIVEFLNRWI TFSQSIISTLT | 34 |

TABLE 1-continued

| Name | Sequence | SEQ ID NO: |
| --- | --- | --- |
| IL-2_H16[AzK_PEG] | APTSSSTKKTQLQLE[AzK_PEG]LLLDLQMILNGINNYKNPKL<br>TRMLTFKFYMPKKATELKHLQCLEEELKPLEEVLNLAQSKNF<br>HLRPRDLISNINVIVLELKGSETTFMCEYADETATIVEFLNRWI<br>TFSQSIISTLT | 35 |
| IL-2_L19[AzK_PEG] | APTSSSTKKTQLQLEHLL[AzK_PEG]DLQMILNGINNYKNPKL<br>TRMLTFKFYMPKKATELKHLQCLEEELKPLEEVLNLAQSKNF<br>HLRPRDLISNINVIVLELKGSETTFMCEYADETATIVEFLNRWI<br>TFSQSIISTLT | 36 |
| IL-2_D20[AzK_PEG] | APTSSSTKKTQLQLEHLLL[AzK_PEG]LQMILNGINNYKNPKL<br>TRMLTFKFYMPKKATELKHLQCLEEELKPLEEVLNLAQSKNF<br>HLRPRDLISNINVIVLELKGSETTFMCEYADETATIVEFLNRWI<br>TFSQSIISTLT | 37 |
| IL-2_M23[AzK_PEG] | APTSSSTKKTQLQLEHLLLDLQ[AzK_PEG]ILNGINNYKNPKL<br>TRMLTFKFYMPKKATELKHLQCLEEELKPLEEVLNLAQSKNF<br>HLRPRDLISNINVIVLELKGSETTFMCEYADETATIVEFLNRWI<br>TFSQSIISTLT | 38 |
| IL-2_N26[AzK_PEG] | APTSSSTKKTQLQLEHLLLDLQMIL[AzK_PEG]GINNYKNPKL<br>TRMLTFKFYMPKKATELKHLQCLEEELKPLEEVLNLAQSKNF<br>HLRPRDLISNINVIVLELKGSETTFMCEYADETATIVEFLNRWI<br>TFSQSIISTLT | 39 |
| IL-2_N88[AzK_PEG] | APTSSSTKKTQLQLEHLLLDLQMILNGINNYKNPKLTRMLTF<br>KFYMPKKATELKHLQCLEEELKPLEEVLNLAQSKNFHLRPRD<br>LIS[AzK_PEG]INVIVLELKGSETTFMCEYADETATIVEFLNR<br>WITFSQSIISTLT | 40 |
| IL-2_E100[AzK_PEG] | APTSSSTKKTQLQLEHLLLDLQMILNGINNYKNPKLTRMLTF<br>KFYMPKKATELKHLQCLEEELKPLEEVLNLAQSKNFHLRPRD<br>LISNINVIVLELKGS[AzK_PEG]TTFMCEYADETATIVEFLNR<br>WITFSQSIISTLT | 41 |
| IL-2_N119[AzK_PEG] | APTSSSTKKTQLQLEHLLLDLQMILNGINNYKNPKLTRMLTF<br>KFYMPKKATELKHLQCLEEELKPLEEVLNLAQSKNFHLRPRD<br>LISNINVIVLELKGSETTFMCEYADETATIVEFL[AzK_PEG]R<br>WITFSQSIISTLT | 42 |
| IL-2_T123[AzK_PEG] | APTSSSTKKTQLQLEHLLLDLQMILNGINNYKNPKLTRMLTF<br>KFYMPKKATELKHLQCLEEELKPLEEVLNLAQSKNFHLRPRD<br>LISNINVIVLELKGSETTFMCEYADETATIVEFLNRWI[AzK_PEG]<br>FSQSIISTLT | 43 |
| IL-2_Q126[AzK_PEG] | APTSSSTKKTQLQLEHLLLDLQMILNGINNYKNPKLTRMLTF<br>KFYMPKKATELKHLQCLEEELKPLEEVLNLAQSKNFHLRPRD<br>LISNINVIVLELKGSETTFMCEYADETATIVEFLNRWITFS<br>[AzK_PEG]SIISTLT | 44 |
| IL-2_S127[AzK_PEG] | APTSSSTKKTQLQLEHLLLDLQMILNGINNYKNPKLTRMLTF<br>KFYMPKKATELKHLQCLEEELKPLEEVLNLAQSKNFHLRPRD<br>LISNINVIVLELKGSETTFMCEYADETATIVEFLNRWITFSQ<br>[AzK_PEG]IISTLT | 45 |
| IL-2_T131[AzK_PEG] | APTSSSTKKTQLQLEHLLLDLQMILNGINNYKNPKLTRMLTF<br>KFYMPKKATELKHLQCLEEELKPLEEVLNLAQSKNFHLRPRD<br>LISNINVIVLELKGSETTFMCEYADETATIVEFLNRWITFSQSII<br>S[AzK_PEG]LT | 46 |
| IL-2_N88R_D109[AzK_PEG] | APTSSSTKKTQLQLEHLLLDLQMILNGINNYKNPKLTRMLTF<br>KFYMPKKATELKHLQCLEEELKPLEEVLNLAQSKNFHLRPRD<br>LISRINVIVLELKGSETTFMCEYA[AzK_PEG]ETATIVEFLNR<br>WITFSQSIISTLT | 47 |
| IL-2_V91[AzK_PEG] | APTSSSTKKTQLQLEHLLLDLQMILNGINNYKNPKLTRMLTF<br>KFYMPKKATELKHLQCLEEELKPLEEVLNLAQSKNFHLRPRD<br>LISNIN[AzK_PEG]IVLELKGSETTFMCEYADETATIVEFLNR<br>WITFSQSIISTLT | 48 |
| IL-2_K9[AzK_PEG50kDa] | APTSSSTK[AzK_PEG50kDa]TQLQLEHLLLDLQMILNGINNY<br>KNPKLTRMLTFKFYMPKKATELKHLQCLEEELKPLEEVLNLA<br>QSKNFHLRPRDLISNINVIVLELKGSETTFMCEYADETATIVEF<br>LNRWITFSQSIISTLT | 49 |

TABLE 1-continued

| Name | Sequence | SEQ ID NO: |
|---|---|---|
| IL-2_H16[AzK_PEG50kDa] | APTSSSTKKTQLQLE[AzK_PEG50kDa]LLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLT | 50 |
| IL-2_L19[AzK_PEG50kDa] | APTSSSTKKTQLQLEHLL[AzK_PEG50kDa]DLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLT | 51 |
| IL-2_D20[AzK_PEG50kDa] | APTSSSTKKTQLQLEHLLL[AzK_PEG50kDa]LQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLT | 52 |
| IL-2_M23[AzK_PEG50kDa] | APTSSSTKKTQLQLEHLLLDLQ[AzK_PEG50kDa]ILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLT | 53 |
| IL-2_N26[AzK_PEG50kDa] | APTSSSTKKTQLQLEHLLLDLQMIL[AzK_PEG50kDa]GINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLT | 54 |
| IL-2_N88[AzK_PEG50kDa] | APTSSSTKKTQLQLEHLLLDLQMILNGINNYKNPKLTRMLTFKFYMPKKATELKHLQCLEEELKPLEEVLNLAQSKNFHLRPRDLIS[AzK_PEG50kDa]INVIVLELKGSETTFMCEYADETATIVEFLNRWITFSQSIISTLT | 55 |
| IL-2_E100[AzK_PEG50kDa] | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGS[AzK_PEG50kDa]TTFMCEYADETATIVEFLNRWITFSQSIISTLT | 56 |
| IL-2_N119[AzK_PEG50kDa] | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFL[AzK_PEG50kDa]RWITFSQSIISTLT | 57 |
| IL-2_T123[AzK_PEG50kDa] | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWI[AzK_PEG50kDa]FSQSIISTLT | 58 |
| IL-2_Q126[AzK_PEG50kDa] | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFS[AzK_PEG50kDa]SIISTLT | 59 |
| IL-2_S127[AzK_PEG50kDa] | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQ[AzK_PEG50kDa]IISTLT | 60 |
| IL-2_T131[AzK_PEG50kDa] | APTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIIS[AzK_PEG50kDa]LT | 61 |
| IL-2_N88R_D109[AzK_PEG50kDa] | APTSSSTKKTQLQLEHLLLDLQMILNGINNYKNPKLTRMLTFKFYMPKKATELKHLQCLEEELKPLEEVLNLAQSKNFHLRPRDLISRINVIVLELKGSETTFMCEYA[AzK_PEG50kDa]ETATIVEFLNRWITFSQSIISTLT | 62 |
| IL-2_V91[AzK_PEG50kDa] | APTSSSTKKTQLQLEHLLLDLQMILNGINNYKNPKLTRMLTFKFYMPKKATELKHLQCLEEELKPLEEVLNLAQSKNFHLRPRDLISNIN[AzK_PEG50kDa]IVLELKGSETTFMCEYADETATIVEFLNRWITFSQSIISTLT | 63 |
| IL-2_K9[AzK_PEG30kDa] | APTSSSTK[AzK_PEG30kDa]TQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLT | 64 |

TABLE 1-continued

| Name | Sequence | SEQ ID NO: |
|---|---|---|
| IL-2_H16[AzK_PEG30kDa] | APTSSSTKKTQLQLE[AzK_PEG30kDa]LLLDLQMILNGINNY KNPKLTRMLTFKFYMPKKATELKHLQCLEEELKPLEEVLNLA QSKNFHLRPRDLISNINVIVLELKGSETTFMCEYADETATIVEF LNRWITFSQSIISTLT | 65 |
| IL-2_L19[AzK_PEG30kDa] | APTSSSTKKTQLQLEHLL[AzK_PEG30kDa]DLQMILNGINNY KNPKLTRMLTFKFYMPKKATELKHLQCLEEELKPLEEVLNLA QSKNFHLRPRDLISNINVIVLELKGSETTFMCEYADETATIVEF LNRWITFSQSIISTLT | 66 |
| IL-2_D20[AzK_PEG30kDa] | APTSSSTKKTQLQLEHLLL[AzK_PEG30kDa]LQMILNGINNY KNPKLTRMLTFKFYMPKKATELKHLQCLEEELKPLEEVLNLA QSKNFHLRPRDLISNINVIVLELKGSETTFMCEYADETATIVEF LNRWITFSQSIISTLT | 67 |
| IL-2_M23[AzK_PEG30kDa] | APTSSSTKKTQLQLEHLLLDLQ[AzK_PEG30kDa]ILNGINNYK NPKLTRMLTFKFYMPKKATELKHLQCLEEELKPLEEVLNLAQ SKNFHLRPRDLISNINVIVLELKGSETTFMCEYADETATIVEFL NRWITFSQSIISTLT | 68 |
| IL-2_N26[AzK_PEG30kDa] | APTSSSTKKTQLQLEHLLLDLQMIL[AzK_PEG30kDa]GINNY KNPKLTRMLTFKFYMPKKATELKHLQCLEEELKPLEEVLNLA QSKNFHLRPRDLISNINVIVLELKGSETTFMCEYADETATIVEF LNRWITFSQSIISTLT | 69 |
| IL-2_N88[AzK_PEG30kDa] | APTSSSTKKTQLQLEHLLLDLQMILNGINNYKNPKLTRMLTF KFYMPKKATELKHLQCLEEELKPLEEVLNLAQSKNFHLRPRD LIS[AzK_PEG30kDa]INVIVLELKGSETTFMCEYADETATIVEF LNRWITFSQSIISTLT | 70 |
| IL-2_E100[AzK_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGS[AzK_PEG30kDa]TTFMCEYADETATIVEF LNRWITFSQSIISTLT | 71 |
| IL-2_N119[AzK_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFL[AzK_PEG30kDa]RWITFSQSIISTLT | 72 |
| IL-2_T123[AzK_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWI[AzK_PEG30kDa]FSQSIISTLT | 73 |
| IL-2_Q126[AzK_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFS[AzK_PEG30kDa]SIISTLT | 74 |
| IL-2_S127[AzK_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQ[AzK_PEG30kDa]IISTLT | 75 |
| IL-2_T131[AzK_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQSII S[AzK_PEG30kDa]LT | 76 |
| IL-2_N88R_D109[AzK_PEG30kDA] | APTSSSTKKTQLQLEHLLLDLQMILNGINNYKNPKLTRMLTF KFYMPKKATELKHLQCLEEELKPLEEVLNLAQSKNFHLRPRD LISRINVIVLELKGSETTFMCEYA[AzK_PEG30kDa]ETATIVEF LNRWITFSQSIISTLT | 77 |
| IL-2_V91[AzK_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNIN[AzK_PEG30kDa]IVLELKGSETTFMCEYADETATIVEF LNRWITFSQSIISTLT | 78 |
| IL-2_K8X | PTSSTKXTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFSQSIIST LT | 79 |

TABLE 1-continued

| Name | Sequence | SEQ ID NO: |
|---|---|---|
| IL-2_H15X | PTSSSTKKTQLQLEXLLLDLQMILNGINNYKNPKLTRMLTFKF YMPKKATELKHLQCLEEELKPLEEVLNLAQSKNFHLRPRDLI SNINIVIVLELKGSETTFMCEYADETATIVEFLNRWITFSQSIIST LT | 80 |
| IL-2_L18X | PTSSSTKKTQLQLEHLLXDLQMILNGINNYKNPKLTRMLTFK FYMPKKATELKHLQCLEEELKPLEEVLNLAQSKNFHLRPRDL ISNINIVIVLELKGSETTFMCEYADETATIVEFLNRWITFSQSIIS TLT | 81 |
| IL-2_D19X | PTSSSTKKTQLQLEHLLLXLQMILNGINNYKNPKLTRMLTFKF YMPKKATELKHLQCLEEELKPLEEVLNLAQSKNFHLRPRDLI SNINIVIVLELKGSETTFMCEYADETATIVEFLNRWITFSQSIIST LT | 82 |
| IL-2_M22X | PTSSSTKKTQLQLEHLLLDLQXILNGINNYKNPKLTRMLTFKF YMPKKATELKHLQCLEEELKPLEEVLNLAQSKNFHLRPRDLI SNINIVIVLELKGSETTFMCEYADETATIVEFLNRWITFSQSIIST LT | 83 |
| IL-2_N25X | PTSSSTKKTQLQLEHLLLDLQMILXGINNYKNPKLTRMLTFKF YMPKKATELKHLQCLEEELKPLEEVLNLAQSKNFHLRPRDLI SNINIVIVLELKGSETTFMCEYADETATIVEFLNRWITFSQSIIST LT | 84 |
| IL-2_N87X | PTSSSTKKTQLQLEHLLLDLQMILNGINNYKNPKLTRMLTFKF YMPKKATELKHLQCLEEELKPLEEVLNLAQSKNFHLRPRDLI SXINVIVLELKGSETTFMCEYADETATIVEFLNRWITFSQSIIST LT | 85 |
| IL-2_E99X | PTSSSTKKTQLQLEHLLLDLQMILNGINNYKNPKLTRMLTFKF YMPKKATELKHLQCLEEELKPLEEVLNLAQSKNFHLRPRDLI SNINIVIVLELKGSXTTFMCEYADETATIVEFLNRWITFSQSIIST LT | 86 |
| IL-2_N118X | PTSSSTKKTQLQLEHLLLDLQMILNGINNYKNPKLTRMLTFKF YMPKKATELKHLQCLEEELKPLEEVLNLAQSKNFHLRPRDLI SNINIVIVLELKGSETTFMCEYADETATIVEFLXRWITFSQSIIST LT | 87 |
| IL-2_T122X | PTSSSTKKTQLQLEHLLLDLQMILNGINNYKNPKLTRMLTFKF YMPKKATELKHLQCLEEELKPLEEVLNLAQSKNFHLRPRDLI SNINIVIVLELKGSETTFMCEYADETATIVEFLNRWIXFSQSIIST LT | 88 |
| IL-2_Q125X | PTSSSTKKTQLQLEHLLLDLQMILNGINNYKNPKLTRMLTFKF YMPKKATELKHLQCLEEELKPLEEVLNLAQSKNFHLRPRDLI SNINIVIVLELKGSETTFMCEYADETATIVEFLNRWITFSXSIIST LT | 89 |
| IL-2_S126X | PTSSSTKKTQLQLEHLLLDLQMILNGINNYKNPKLTRMLTFKF YMPKKATELKHLQCLEEELKPLEEVLNLAQSKNFHLRPRDLI SNINIVIVLELKGSETTFMCEYADETATIVEFLNRWITFSQXIIST LT | 90 |
| IL-2_T130X | PTSSSTKKTQLQLEHLLLDLQMILNGINNYKNPKLTRMLTFKF YMPKKATELKHLQCLEEELKPLEEVLNLAQSKNFHLRPRDLI SNINIVIVLELKGSETTFMCEYADETATIVEFLNRWITFSQSIISX LT | 91 |
| IL-2_N87R_D108X | PTSSSTKKTQLQLEHLLLDLQMILNGINNYKNPKLTRMLTFKF YMPKKATELKHLQCLEEELKPLEEVLNLAQSKNFHLRPRDLI SRINVIVLELKGSETTFMCEYAXETATIVEFLNRWITFSQSIIST LT | 92 |
| IL-2_V90X | PTSSSTKKTQLQLEHLLLDLQMILNGINNYKNPKLTRMLTFKF YMPKKATELKHLQCLEEELKPLEEVLNLAQSKNFHLRPRDLI SNINXIVLELKGSETTFMCEYADETATIVEFLNRWITFSQSIIST LT | 93 |
| IL-2_K8[AzK] | PTSSSTK[AzK]TQLQLEHLLLDLQMILNGINNYKNPKLTRMLT FKFYMPKKATELKHLQCLEEELKPLEEVLNLAQSKNFHLRPR DLISNINIVIVLELKGSETTFMCEYADETATIVEFLNRWITFSQSI ISTLT | 94 |

TABLE 1-continued

| Name | Sequence | SEQ ID NO: |
|---|---|---|
| IL-2_H15[AzK] | PTSSSTKKTQLQLE[AzK]LLLDLQMILNGINNYKNPKLTRMLT FKFYMPKKATELKHLQCLEEELKPLEEVLNLAQSKNFHLRPR DLISNINVIVLELKGSETTFMCEYADETATIVEFLNRWITFSQSI ISTLT | 95 |
| IL-2_L18[AzK] | PTSSSTKKTQLQLEHLL[AzK]DLQMILNGINNYKNPKLTRML TFKFYMPKKATELKHLQCLEEELKPLEEVLNLAQSKNFHLRP RDLISNINVIVLELKGSETTFMCEYADETATIVEFLNRWITFSQ SIISTLT | 96 |
| IL-2_D19[AzK] | PTSSSTKKTQLQLEHLLL[AzK]LQMILNGINNYKNPKLTRMLT FKFYMPKKATELKHLQCLEEELKPLEEVLNLAQSKNFHLRPR DLISNINVIVLELKGSETTFMCEYADETATIVEFLNRWITFSQSI ISTLT | 97 |
| IL-2_M22[AzK] | PTSSSTKKTQLQLEHLLLDLQ[AzK]ILNGINNYKNPKLTRMLT FKFYMPKKATELKHLQCLEEELKPLEEVLNLAQSKNFHLRPR DLISNINVIVLELKGSETTFMCEYADETATIVEFLNRWITFSQSI ISTLT | 98 |
| IL-2_N25[AzK] | PTS SSTKKTQLQLEHLLLDLQMIL[AzK]GINNYKNPKLTRMLT FKFYMPKKATELKHLQCLEEELKPLEEVLNLAQSKNFHLRPR DLISNINVIVLELKGSETTFMCEYADETATIVEFLNRWITFSQSI ISTLT | 99 |
| IL-2_N87[AzK] | PTSSSTKKTQLQLEHLLLDLQMILNGINNYKNPKLTRMLTFKF YMPKKATELKHLQCLEEELKPLEEVLNLAQSKNFHLRPRDLI S[AzK]INVIVLELKGSETTFMCEYADETATIVEFLNRWITFSQS IISTLT | 100 |
| IL-2_E99[AzK] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGS[AzK]TFMCEYADETATIVEFLNRWITFSQS IISTLT | 101 |
| IL-2_N118[AzK]-1 | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFL[AzK]RWITFSQS IISTLT | 102 |
| IL-2_T122[AzK]-1 | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWI[AzK]FSQS IISTLT | 103 |
| IL-2_Q125[AzK] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFS[AzK]S IISTLT | 104 |
| IL-2_S126[AzK] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFSQ[AzK] IISTLT | 105 |
| IL-2_T130[AzK] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFSQSIIS [AzK]LT | 106 |
| IL-2_N87R_D108[AzK] | PTSSSTKKTQLQLEHLLLDLQMILNGINNYKNPKLTRMLTFKF YMPKKATELKHLQCLEEELKPLEEVLNLAQSKNFHLRPRDLI SRINVIVLELKGSETTFMCEYA[AzK]ETATIVEFLNRWITFSQS IISTLT | 107 |
| IL-2_V90[AzK] | PTSSSTKKTQLQLEHLLLDLQMILNGINNYKNPKLTRMLTFKF YMPKKATELKHLQCLEEELKPLEEVLNLAQSKNFHLRPRDLI SNIN[AzK]IVLELKGSETTFMCEYADETATIVEFLNRWITFSQS IISTLT | 108 |
| IL-2_K8[AzK_L1_PEG] | PTSSSTK[AzK_L1_PEG]TQLQLEHLLLDLQMILNGINNYKNP KLTRMLTFKFYMPKKATELKHLQCLEEELKPLEEVLNLAQSK NFHLRPRDLISNINVIVLELKGSETTFMCEYADETATIVEFLNR WITFSQSIISTLT | 109 |

TABLE 1-continued

| Name | Sequence | SEQ ID NO: |
|---|---|---|
| IL-2_H15[AzK_L1_PEG] | PTSSSTKKTQLQLE[AzK_L1_PEG]LLLDLQMILNGINNYKNP KLTRMLTFKFYMPKKATELKHLQCLEEELKPLEEVLNLAQSK NFHLRPRDLISNINVIVLELKGSETTFMCEYADETATIVEFLNR WITFSQSIISTLT | 110 |
| IL-2_L18[AzK_L1_PEG] | PTSSSTKKTQLQLEHLL[AzK_L1_PEG]DLQMILNGINNYKNP KLTRMLTFKFYMPKKATELKHLQCLEEELKPLEEVLNLAQSK NFHLRPRDLISNINVIVLELKGSETTFMCEYADETATIVEFLNR WITFSQSIISTLT | 111 |
| IL-2_D19[AzK_L1_PEG] | PTSSSTKKTQLQLEHLLL[AzK_L1_PEG]LQMILNGINNYKNP KLTRMLTFKFYMPKKATELKHLQCLEEELKPLEEVLNLAQSK NFHLRPRDLISNINVIVLELKGSETTFMCEYADETATIVEFLNR WITFSQSIISTLT | 112 |
| IL-2_M22[AzK_L1_PEG] | PTSSSTKKTQLQLEHLLLDLQ[AzK_L1_PEG]ILNGINNYKNP KLTRMLTFKFYMPKKATELKHLQCLEEELKPLEEVLNLAQSK NFHLRPRDLISNINVIVLELKGSETTFMCEYADETATIVEFLNR WITFSQSIISTLT | 113 |
| IL-2_N25[AzK_L1_PEG] | PTSSSTKKTQLQLEHLLLDLQMIL[AzK_L1_PEG]GINNYKNP KLTRMLTFKFYMPKKATELKHLQCLEEELKPLEEVLNLAQSK NFHLRPRDLISNINVIVLELKGSETTFMCEYADETATIVEFLNR WITFSQSIISTLT | 114 |
| IL-2_N87[AzK_L1_PEG] | PTSSSTKKTQLQLEHLLLDLQMILNGINNYKNPKLTRMLTFKF YMPKKATELKHLQCLEEELKPLEEVLNLAQSKNFHLRPRDLI S[AzK_L1_PEG]INVIVLELKGSETTFMCEYADETATIVEFLNR WITFSQSIISTLT | 115 |
| IL-2_E99[AzK_L1_PEG] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGS[AzK_L1_PEG]TTFMCEYADETATIVEFLNR WITFSQSIISTLT | 116 |
| IL-2_N118[AzK_L1_PEG] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFL[AzK_L1_PEG]R WITFSQSIISTLT | 117 |
| IL-2_T122[AzK_L1_PEG] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWI [AzK_L1_PEG]FSQSIISTLT | 118 |
| IL-2_Q125[AzK_L1_PEG] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFS [AzK_L1_PEG]SIISTLT | 119 |
| IL-2_S126[AzK_L1_PEG] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFSQ [AzK_L1_PEG]IISTLT | 120 |
| IL-2_T130[AzK_L1_PEG] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFSQSIIS [AzK_L1_PEG]LT | 121 |
| IL-2_N87R_D108[AzK_L1_PEG] | PTSSSTKKTQLQLEHLLLDLQMILNGINNYKNPKLTRMLTFKF YMPKKATELKHLQCLEEELKPLEEVLNLAQSKNFHLRPRDLI SRINVIVLELKGSETTFMCEYA[AzK_L1_PEG]ETATIVEFLNR WITFSQSIISTLT | 122 |
| IL-2_V90[AzK_L1_PEG] | PTSSSTKKTQLQLEHLLLDLQMILNGINNYKNPKLTRMLTFKF YMPKKATELKHLQCLEEELKPLEEVLNLAQSKNFHLRPRDLI SNIN[AzK_L1_PEG]IVLELKGSETTFMCEYADETATIVEFLNR WITFSQSIISTLT | 123 |
| IL-2_K8[AzK_L1_PEG50kDa] | PTSSSTK[AzK_L1_PEG50kDa]TQLQLEHLLLDLQMILNGINN YKNPKLTRMLTFKFYMPKKATELKHLQCLEEELKPLEEVLNL AQSKNFHLRPRDLISNINVIVLELKGSETTFMCEYADETATIV EFLNRWITFSQSIISTLT | 124 |

TABLE 1-continued

| Name | Sequence | SEQ ID NO: |
|---|---|---|
| IL-2_H15[AzK_L1_PEG50kDa] | PTSSSTKKTQLQLE[AzK_L1_PEG50kDa]LLLDLQMILNGINN YKNPKLTRMLTFKFYMPKKATELKHLQCLEEELKPLEEVLNL AQSKNFHLRPRDLISNINVIVLELKGSETTFMCEYADETATIV EFLNRWITFSQSIISTLT | 125 |
| IL-2_L18[AzK_L1_PEG50kDa] | PTSSSTKKTQLQLEHLL[AzK_L1_PEG50kDa]DLQMILNGINN YKNPKLTRMLTFKFYMPKKATELKHLQCLEEELKPLEEVLNL AQSKNFHLRPRDLISNINVIVLELKGSETTFMCEYADETATIV EFLNRWITFSQSIISTLT | 126 |
| IL-2_D19[AzK_L1_PEG50kDa]-1 | PTSSSTKKTQLQLEHLLL[AzK_L1_PEG50kDa]LQMILNGINN YKNPKLTRMLTFKFYMPKKATELKHLQCLEEELKPLEEVLNL AQSKNFHLRPRDLISNINVIVLELKGSETTFMCEYADETATIV EFLNRWITFSQSIISTLT | 127 |
| IL-2_M22[AzK_L1_PEG50kDa] | PTSSSTKKTQLQLEHLLLDLQ[AzK_L1_PEG50kDa]ILNGINN YKNPKLTRMLTFKFYMPKKATELKHLQCLEEELKPLEEVLNL AQSKNFHLRPRDLISNINVIVLELKGSETTFMCEYADETATIV EFLNRWITFSQSIISTLT | 128 |
| IL-2_N25[AzK_L1_PEG50kDa] | PTSSSTKKTQLQLEHLLLDLQMIL[AzK_L1_PEG50kDa]GINN YKNPKLTRMLTFKFYMPKKATELKHLQCLEEELKPLEEVLNL AQSKNFHLRPRDLISNINVIVLELKGSETTFMCEYADETATIV EFLNRWITFSQSIISTLT | 129 |
| IL-2_N87[AzK_L1_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI S[AzK_L1_PEG50kDa]INVIVLELKGSETTFMCEYADETATIV EFLNRWITFSQSIISTLT | 130 |
| IL-2_E99[AzK_L1_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGS[AzK_L1_PEG50kDa]TTFMCEYADETATIV EFLNRWITFSQSIISTLT | 131 |
| IL-2_N118[AzK_L1_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFL[AzK_L1_PEG50kDa] RWITFSQSIISTLT | 132 |
| IL-2_T122[AzK_L1_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWI [AzK_L1_PEG50kDa]FSQSIISTLT | 133 |
| IL-2_Q125[AzK_L1_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFS [AzK_L1_PEG50kDa]SIISTLT | 134 |
| IL-2_S126[AzK_L1_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFSQ [AzK_L1_PEG50kDa]IISTLT | 135 |
| IL-2_T130[AzK_L1_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFSQSIIS [AzK_L1_PEG50kDa]LT | 136 |
| IL-2_N87R_D108[AzK_L1_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SRINVIVLELKGSETTFMCEYA[AzK_L1_PEG50kDa]ETATIV EFLNRWITFSQSIISTLT | 137 |
| IL-2_V91[AzK_L1_PEG50kDa]-1 | PTSSSTKKTQLQLEHLLLDLQMILNGINNYKNPKLTRMLTFKF YMPKKATELKHLQCLEEELKPLEEVLNLAQSKNFHLRPRDLI SNIN[AzK_L1_PEG50kDa]IVLELKGSETTFMCEYADETATIV EFLNRWITFSQSIISTLT | 138 |
| IL-2_K8[AzK_L1_PEG30kDa] | PTSSSTK[AzK_L1_PEG30kDa]TQLQLEHLLLDLQMILNGINN YKNPKLTRMLTFKFYMPKKATELKHLQCLEEELKPLEEVLNL AQSKNFHLRPRDLISNINVIVLELKGSETTFMCEYADETATIV EFLNRWITFSQSIISTLT | 139 |

TABLE 1-continued

| Name | Sequence | SEQ ID NO: |
|---|---|---|
| IL-2_H15[AzK_L1_PEG30kDa] | PTSSSTKKTQLQLE[AzK_L1_PEG30kDa]LLLDLQMILNGINN YKNPKLTRMLTFKFYMPKKATELKHLQCLEEELKPLEEVLNL AQSKNFHLRPRDLISNINVIVLELKGSETTFMCEYADETATIV EFLNRWITFSQSIISTLT | 140 |
| IL-2_L18[AzK_L1_PEG30kDa] | PTSSSTKKTQLQLEHLL[AzK_L1_PEG30kDa]DLQMILNGINN YKNPKLTRMLTFKFYMPKKATELKHLQCLEEELKPLEEVLNL AQSKNFHLRPRDLISNINVIVLELKGSETTFMCEYADETATIV EFLNRWITFSQSIISTLT | 141 |
| IL-2_D19[AzK_L1_PEG30kDa] | PTSSSTKKTQLQLEHLLL[AzK_L1_PEG30kDa]LQMILNGINN YKNPKLTRMLTFKFYMPKKATELKHLQCLEEELKPLEEVLNL AQSKNFHLRPRDLISNINVIVLELKGSETTFMCEYADETATIV EFLNRWITFSQSIISTLT | 142 |
| IL-2_M22[AzK_L1_PEG30kDa] | PTSSSTKKTQLQLEHLLLDLQ[AzK_L1_PEG30kDa]ILNGINN YKNPKLTRMLTFKFYMPKKATELKHLQCLEEELKPLEEVLNL AQSKNFHLRPRDLISNINVIVLELKGSETTFMCEYADETATIV EFLNRWITFSQSIISTLT | 143 |
| IL-2_N25[AzK_L1_PEG30kDa] | PTSSSTKKTQLQLEHLLLDLQMIL[AzK_L1_PEG30kDa]GINN YKNPKLTRMLTFKFYMPKKATELKHLQCLEEELKPLEEVLNL AQSKNFHLRPRDLISNINVIVLELKGSETTFMCEYADETATIV EFLNRWITFSQSIISTLT | 144 |
| IL-2_N87[AzK_L1_PEG30kDa] | PTSSSTKKTQLQLEHLLLDLQMILNGINNYKNPKLTRMLTFKF YMPKKATELKHLQCLEEELKPLEEVLNLAQSKNFHLRPRDLI S[AzK_L1_PEG30kDa]INVIVLELKGSETTFMCEYADETATIV EFLNRWITFSQSIISTLT | 145 |
| IL-2_E99[AzK_L1_PEG30kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGS[AzK_L1_PEG30kDa]TTFMCEYADETATIV EFLNRWITFSQSIISTLT | 146 |
| IL-2_N118[AzK_L1_PEG30kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFL[AzK_L1_PEG30kDa] RWITFSQSIISTLT | 147 |
| IL-2_T122[AzK_L1_PEG30kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWI [AzK_L1_PEG30kDa]FSQSIISTLT | 148 |
| IL-2_Q125[AzK_L1_PEG30kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFS [AzK_L1_PEG30kDa]SIISTLT | 149 |
| IL-2_S126[AzK_L1_PEG30kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFSQ [AzK_L1_PEG30kDa]IISTLT | 150 |
| IL-2_T130[AzK_L1_PEG30kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFSQSIIS [AzK_L1_PEG30kDa]LT | 151 |
| IL-2_N87R_D108[AzK_L1_PEG30kDa] | PTSSSTKKTQLQLEHLLLDLQMILNGINNYKNPKLTRMLTFKF PYMPKKATELKHLQCLEEELKPLEEVLNLAQSKNFHLRPRDLI SRINVIVLELKGSETTFMCEYA[AzK_L1_PEG30kDa]ETATIV EFLNRWITFSQSIISTLT | 152 |
| IL-2_V90[AzK_L1_PEG30kDa] | PTSSSTKKTQLQLEHLLLDLQMILNGINNYKNPKLTRMLTFKF YMPKKATELKHLQCLEEELKPLEEVLNLAQSKNFHLRPRDLI SNIN[AzK_L1_PEG30kDa]IVLELKGSETTFMCEYADETATIV EFLNRWITFSQSIISTLT | 153 |
| IL-2_K9[AzK_L1_PEG] | APTSSSTK[AzK_L1_PEG]TQLQLEHLLLDLQMILNGINNYKN PKLTRMLTFKFYMPKKATELKHLQCLEEELKPLEEVLNLAQS KNFHLRPRDLISNINVIVLELKGSETTFMCEYADETATIVEFLN RWITFSQSIISTLT | 154 |

TABLE 1-continued

| Name | Sequence | SEQ ID NO: |
|---|---|---|
| IL-2_H16[AzK_L1_PEG] | APTSSSTKKTQLQLE[AzK_L1_PEG]LLLDLQMILNGINNYKN PKLTRMLTFKFYMPKKATELKHLQCLEEELKPLEEVLNLAQS KNFHLRPRDLISNINVIVLELKGSETTFMCEYADETATIVEFLN RWITFSQSIISTLT | 155 |
| IL-2_L19[AzK_L1_PEG] | APTSSSTKKTQLQLEHLL[AzK_L1_PEG]DLQMILNGINNYKN PKLTRMLTFKFYMPKKATELKHLQCLEEELKPLEEVLNLAQS KNFHLRPRDLISNINVIVLELKGSETTFMCEYADETATIVEFLN RWITFSQSIISTLT | 156 |
| IL-2_D20[AzK_L1_PEG] | APTSSSTKKTQLQLEHLLL[AzK_L1_PEG]LQMILNGINNYKN PKLTRMLTFKFYMPKKATELKHLQCLEEELKPLEEVLNLAQS KNFHLRPRDLISNINVIVLELKGSETTFMCEYADETATIVEFLN RWITFSQSIISTLT | 157 |
| IL-2_M23[AzK_L1_PEG] | APTSSSTKKTQLQLEHLLLDLQ[AzK_L1_PEG]ILNGINNYKN PKLTRMLTFKFYMPKKATELKHLQCLEEELKPLEEVLNLAQS KNFHLRPRDLISNINVIVLELKGSETTFMCEYADETATIVEFLN RWITFSQSIISTLT | 158 |
| IL-2_N26[AzK_L1_PEG] | APTSSSTKKTQLQLEHLLLDLQMIL[AzK_L1_PEG]GINNYKN PKLTRMLTFKFYMPKKATELKHLQCLEEELKPLEEVLNLAQS KNFHLRPRDLISNINVIVLELKGSETTFMCEYADETATIVEFLN RWITFSQSIISTLT | 159 |
| IL-2_N88[AzK_L1_PEG] | APTSSSTKKTQLQLEHLLLDLQMILNGINNYKNPKLTRMLTF KFYMPKKATELKHLQCLEEELKPLEEVLNLAQSKNFHLRPRD LIS[AzK_L1_PEG]INVIVLELKGSETTFMCEYADETATIVEFL NRWITFSQSIISTLT | 160 |
| IL-2_E100[AzK_L1_PEG] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGS[AzK_L1_PEG]TTFMCEYADETATIVEFL NRWITFSQSIISTLT | 161 |
| IL-2_N119[AzK_L1_PEG] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFL[AzK_L1_PEG] RWITFSQSIISTLT | 162 |
| IL-2_T123[AzK_L1_PEG] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWI [AzK_L1_PEG]FSQSIISTLT | 163 |
| IL-2_Q126[AzK_L1_PEG] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFS [AzK_L1_PEG]SIISTLT | 164 |
| IL-2_S127[AzK_L1_PEG] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQ [AzK_L1_PEG]IISTLT | 165 |
| IL-2_T131[AzK_L1_PEG] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQSII S[AzK_L1_PEG]LT | 166 |
| IL-2_N88R_D109[AzK_L1_PEG] | APTSSSTKKTQLQLEHLLLDLQMILNGINNYKNPKLTRMLTF KFYMPKKATELKHLQCLEEELKPLEEVLNLAQSKNFHLRPRD LISRINVIVLELKGSETTFMCEYA[AzK_L1_PEG]ETATIVEFL NRWITFSQSIISTLT | 167 |
| IL-2_V91[AzK_L1_PEG] | APTSSSTKKTQLQLEHLLLDLQMILNGINNYKNPKLTRMLTF KFYMPKKATELKHLQCLEEELKPLEEVLNLAQSKNFHLRPRD LISNIN[AzK_L1_PEG]IVLELKGSETTFMCEYADETATIVEFL NRWITFSQSIISTLT | 168 |
| IL-2_K9[AzK_L1_PEG50kDa] | APTSSSTK[AzK_L1_PEG50kDa]TQLQLEHLLLDLQMILNGIN NYKNPKLTRMLTFKFYMPKKATELKHLQCLEEELKPLEEVL NLAQSKNFHLRPRDLISNINVIVLELKGSETTFMCEYADETAT IVEFLNRWITFSQSIISTLT | 169 |

TABLE 1-continued

| Name | Sequence | SEQ ID NO: |
|---|---|---|
| IL-2_H16[AzK_L1_PEG50kDa] | APTSSSTKKTQLQLE[AzK_L1_PEG50kDa]LLLDLQMILNGIN NYKNPKLTRMLTFKFYMPKKATELKHLQCLEEELKPLEEVL NLAQSKNFHLRPRDLISNINVIVLELKGSETTFMCEYADETAT IVEFLNRWITFSQSIISTLT | 170 |
| IL-2_L19[AzK_L1_PEG50kDA] | APTSSSTKKTQLQLEHLL[AzK_L1_PEG50kDa]DLQMILNGIN NYKNPKLTRMLTFKFYMPKKATELKHLQCLEEELKPLEEVL NLAQSKNFHLRPRDLISNINVIVLELKGSETTFMCEYADETAT IVEFLNRWITFSQSIISTLT | 171 |
| IL-2_D20[AzK_L1_PEG50kDa]-2 | APTSSSTKKTQLQLEHLLL[AzK_L1_PEG50kDa]LQMILNGIN NYKNPKLTRMLTFKFYMPKKATELKHLQCLEEELKPLEEVL NLAQSKNFHLRPRDLISNINVIVLELKGSETTFMCEYADETAT IVEFLNRWITFSQSIISTLT | 172 |
| IL-2_M23[AzK_L1_PEG50kDa] | APTSSSTKKTQLQLEHLLLDLQ[AzK_L1_PEG50kDa]ILNGIN NYKNPKLTRMLTFKFYMPKKATELKHLQCLEEELKPLEEVL NLAQSKNFHLRPRDLISNINVIVLELKGSETTFMCEYADETAT IVEFLNRWITFSQSIISTLT | 173 |
| IL-2_N26[AzK_L1_PEG50kDA] | APTSSSTKKTQLQLEHLLLDLQMIL[AzK_L1_PEG50kDa]GIN NYKNPKLTRMLTFKFYMPKKATELKHLQCLEEELKPLEEVL NLAQSKNFHLRPRDLISNINVIVLELKGSETTFMCEYADETAT IVEFLNRWITFSQSIISTLT | 174 |
| IL-2_N88[AzK_L1_PEG50kDa] | APTSSSTKKTQLQLEHLLLDLQMILNGINNYKNPKLTRMLTF KFYMPKKATELKHLQCLEEELKPLEEVLNLAQSKNFHLRPRD LIS[AzK_L1_PEG50kDa]INVIVLELKGSETTFMCEYADETATI VEFLNRWITFSQSIISTLT | 175 |
| IL-2_E100[AzK_L1_PEG50kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGS[AzK_L1_PEG50kDa]TTFMCEYADETATI VEFLNRWITFSQSIISTLT | 176 |
| IL-2_N119[AzK_L1_PEG50kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFL [AzK_L1_PEG50kDa]RWITFSQSIISTLT | 177 |
| IL-2_T123[AzK_L1_PEG50kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWI [AzK_L1_PEG50kDa]FSQSIISTLT | 178 |
| IL-2_Q126[AzK_L1_PEG50kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFS [AzK_L1_PEG50kDa]SIISTLT | 179 |
| IL-2_S127[AzK_L1_PEG50kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQ [AzK_L1_PEG50kDa]IISTLT | 180 |
| IL-2_T131[AzK_L1_PEG50kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQSII S[AzK_L1_PEG50kDa]LT | 181 |
| IL-2_N88R_D109[AzK_L1_PEG50kDa] | APTSSSTKKTQLQLEHLLLDLQMILNGINNYKNPKLTRMLTF KFYMPKKATELKHLQCLEEELKPLEEVLNLAQSKNFHLRPRD LISRINVIVLELKGSETTFMCEYA[AzK_L1_PEG50kDa]ETATI VEFLNRWITFSQSIISTLT | 182 |
| IL-2_V91[AzK_L1_PEG50kDa] | APTSSSTKKTQLQLEHLLLDLQMILNGINNYKNPKLTRMLTF KFYMPKKATELKHLQCLEEELKPLEEVLNLAQSKNFHLRPRD LISNIN[AzK_L1_PEG50kDa]IVLELKGSETTFMCEYADETATI VEFLNRWITFSQSIISTLT | 183 |
| IL-2_K9[AzK_L1_PEG30kDa] | APTSSSTK[AzK_L1_PEG30kDa]TQLQLEHLLLDLQMILNGIN NYKNPKLTRMLTFKFYMPKKATELKHLQCLEEELKPLEEVL NLAQSKNFHLRPRDLISNINVIVLELKGSETTFMCEYADETAT IVEFLNRWITFSQSIISTLT | 184 |

TABLE 1-continued

| Name | Sequence | SEQ ID NO: |
|---|---|---|
| IL-2_H16[AzK_L1_PEG30kDa] | APTSSSTKKTQLQLE[AzK_L1_PEG30kDa]LLLDLQMILNGIN NYKNPKLTRMLTFKFYMPKKATELKHLQCLEEELKPLEEVL NLAQSKNFHLRPRDLISNINVIVLELKGSETTFMCEYADETAT IVEFLNRWITFSQSIISTLT | 185 |
| IL-2_L19[AzK_L1_PEG30kDa] | APTSSSTKKTQLQLEHLL[AzK_L1_PEG30kDa]DLQMILNGIN NYKNPKLTRMLTFKFYMPKKATELKHLQCLEEELKPLEEVL NLAQSKNFHLRPRDLISNINVIVLELKGSETTFMCEYADETAT IVEFLNRWITFSQSIISTLT | 186 |
| IL-2_D20[AzK_L1_PEG30kDa] | APTSSSTKKTQLQLEHLLL[AzK_L1_PEG30kDa]LQMILNGIN NYKNPKLTRMLTFKFYMPKKATELKHLQCLEEELKPLEEVL NLAQSKNFHLRPRDLISNINVIVLELKGSETTFMCEYADETAT IVEFLNRWITFSQSIISTLT | 187 |
| IL-2_M23[AzK_L1_PEG30kDa] | APTSSSTKKTQLQLEHLLLDLQ[AzK_L1_PEG30kDa]ILNGIN NYKNPKLTRMLTFKFYMPKKATELKHLQCLEEELKPLEEVL NLAQSKNFHLRPRDLISNINVIVLELKGSETTFMCEYADETAT IVEFLNRWITFSQSIISTLT | 188 |
| IL-2_N26[AzK_L1_PEG30kDa] | APTSSSTKKTQLQLEHLLLDLQMIL[AzK_L1_PEG30kDa]GIN NYKNPKLTRMLTFKFYMPKKATELKHLQCLEEELKPLEEVL NLAQSKNFHLRPRDLISNINVIVLELKGSETTFMCEYADETAT IVEFLNRWITFSQSIISTLT | 189 |
| IL-2_N88[AzK_L1_PEG30kDa] | APTSSSTKKTQLQLEHLLLDLQMILNGINNYKNPKLTRMLTF KFYMPKKATELKHLQCLEEELKPLEEVLNLAQSKNFHLRPRD LIS[AzK_L1_PEG30kDa]INVIVLELKGSETTFMCEYADETATI VEFLNRWITFSQSIISTLT | 190 |
| IL-2_E100[AzK_L1_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGS[AzK_L1_PEG30kDa]TTFMCEYADETATI VEFLNRWITFSQSIISTLT | 191 |
| IL-2_N119[AzK_L1_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFL[AzK_L1_PEG30kDa]RWITFSQSIISTLT | 192 |
| IL-2_T123[AzK_L1_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWI[AzK_L1_PEG30kDa]FSQSIISTLT | 193 |
| IL-2_Q126[AzK_L1_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFS[AzK_L1_PEG30kDa]SIISTLT | 194 |
| IL-2_S127[AzK_L1_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQ[AzK_L1_PEG30kDa]IISTLT | 195 |
| IL-2_T131[AzK_L1_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNINVIVLELKGSETTFMCEYADETATIVEFLNRWITFSQSII S[AzK_L1_PEG30kDa]LT | 196 |
| IL-2_N88R_D109[AzK_L1_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISRIVKIVLELKGSETTFMCEYA[AzK_L1_PEG30kDa]ETATI VEFLNRWITFSQSIISTLT | 197 |
| IL-2_V91[AzK_L1_PEG30kDa] | APTSSSTKKTQLQLEHLLLDLQMILNGINNYKNPKLTRMLTF KFYMPKKATELKHLQCLEEELKPLEEVLNLAQSKNFHLRPRD LISNIN[AzK_L1_PEG30kDa]IVLELKGSETTFMCEYADETATI VEFLNRWITFSQSIISTLT | 198 |
| IL-2_K8[AzK_PEG] | PTSSSTK[AzK_PEG]TQLQLEHLLLDLQMILNGINNYKNPKLT RMLTFKFYMPKKATELKHLQCLEEELKPLEEVLNLAQSKNF HLRPRDLISNINVIVLELKGSETTFMCEYADETATIVEFLNRWI TFSQSIISTLT | 199 |

TABLE 1-continued

| Name | Sequence | SEQ ID NO: |
|---|---|---|
| IL-2_H15[AzK_PEG] | PTSSSTKKTQLQLE[AzK_PEG]LLLDLQMILNGINNYKNPKLT RMLTFKFYMPKKATELKHLQCLEEELKPLEEVLNLAQSKNF HLRPRDLISNINVIVLELKGSETTFMCEYADETATIVEFLNRWI TFSQSIISTLT | 200 |
| IL-2_L18[AzK_PEG] | PTSSSTKKTQLQLEHLL[AzK_PEG]DLQMILNGINNYKNPKLT RMLTFKFYMPKKATELKHLQCLEEELKPLEEVLNLAQSKNF HLRPRDLISNINVIVLELKGSETTFMCEYADETATIVEFLNRWI TFSQSIISTLT | 201 |
| IL-2_D19[AzK_PEG] | PTSSSTKKTQLQLEHLLL[AzK_PEG]LQMILNGINNYKNPKLT RMLTFKFYMPKKATELKHLQCLEEELKPLEEVLNLAQSKNF HLRPRDLISNINVIVLELKGSETTFMCEYADETATIVEFLNRWI TFSQSIISTLT | 202 |
| IL-2_M22[AzK_PEG] | PTSSSTKKTQLQLEHLLLDLQ[AzK_PEG]ILNGINNYKNPKLT RMLTFKFYMPKKATELKHLQCLEEELKPLEEVLNLAQSKNF HLRPRDLISNINVIVLELKGSETTFMCEYADETATIVEFLNRWI TFSQSIISTLT | 203 |
| IL-2_N25[AzK_PEG] | PTSSSTKKTQLQLEHLLLDLQMIL[AzK_PEG]GINNYKNPKLT RMLTFKFYMPKKATELKHLQCLEEELKPLEEVLNLAQSKNF HLRPRDLISNINVIVLELKGSETTFMCEYADETATIVEFLNRWI TFSQSIISTLT | 204 |
| IL-2_N87[AzK_PEG] | PTSSSTKKTQLQLEHLLLDLQMILNGINNYKNPKLTRMLTFKF YMPKKATELKHLQCLEEELKPLEEVLNLAQSKNFHLRPRDLI S[AzK_PEG]INVIVLELKGSETTFMCEYADETATIVEFLNRWI TFSQSIISTLT | 205 |
| IL-2_E99[AzK_PEG] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGS[AzK_PEG]TTFMCEYADETATIVEFLNRWI TFSQSIISTLT | 206 |
| IL-2_N118[AzK_PEG] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFL[AzK_PEG]RWI TFSQSIISTLT | 207 |
| IL-2_T122[AzK_PEG] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWI[AzK_PEG] FSQSIISTLT | 208 |
| IL-2_Q125[AzK_PEG] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFS[AzK_PEG] SIISTLT | 209 |
| IL-2_S126[AzK_PEG] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFSQ [AzK_PEG]IISTLT | 210 |
| IL-2_T130[AzK_PEG] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFSQSIIS [AzK_PEG]LT | 211 |
| IL-2_N87R_D109[AzK_PEG]-1 | PTS SSTKKTQLQLEHLLLDLQMILNGINNYKNPKLTRMLTFKF YMPKKATELKHLQCLEEELKPLEEVLNLAQSKNFHLRPRDLI SRINVIVLELKGSETTFMCEYA[AzK_PEG]ETATIVEFLNRWI TFSQSIISTLT | 212 |
| IL-2_V90[AzK_PEG] | PTSSSTKKTQLQLEHLLLDLQMILNGINNYKNPKLTRMLTFKF YMPKKATELKHLQCLEEELKPLEEVLNLAQSKNFHLRPRDLI SNIN[AzK_PEG]IVLELKGSETTFMCEYADETATIVEFLNRWI TFSQSIISTLT | 213 |
| IL-2_K8[AzK_PEG50kDa] | PTSSSTK[AzK_PEG50kDa]TQLQLEHLLLDLQMILNGINNYK NPKLTRMLTFKFYMPKKATELKHLQCLEEELKPLEEVLNLAQ SKNFHLRPRDLISNINVIVLELKGSETTFMCEYADETATIVEFL NRWITFSQSIISTLT | 214 |

TABLE 1-continued

| Name | Sequence | SEQ ID NO: |
|---|---|---|
| IL-2_H15[AzK_PEG50kDa] | PTSSSTKKTQLQLE[AzK_PEG50kDa]LLLDLQMILNGINNYK NPKLTRMLTFKFYMPKKATELKHLQCLEEELKPLEEVLNLAQ SKNFHLRPRDLISNINVIVLELKGSETTFMCEYADETATIVEFL NRWITFSQSIISTLT | 215 |
| IL-2-L18[AzK_PEG50kDa] | PTSSSTKKTQLQLEHLL[AzK_PEG50kDa]DLQMILNGINNYK NPKLTRMLTFKFYMPKKATELKHLQCLEEELKPLEEVLNLAQ SKNFHLRPRDLISNINVIVLELKGSETTFMCEYADETATIVEFL NRWITFSQSIISTLT | 216 |
| IL-2_D19[AzK_PEG50kDa] | PTSSSTKKTQLQLEHLLL[AzK_PEG50kDa]LQMILNGINNYK NPKLTRMLTFKFYMPKKATELKHLQCLEEELKPLEEVLNLAQ SKNFHLRPRDLISNINVIVLELKGSETTFMCEYADETATIVEFL NRWITFSQSIISTLT | 217 |
| IL-2_M22[AzK_PEG50kDa] | PTSSSTKKTQLQLEHLLLDLQ[AzK_PEG50kDa]ILNGINNYKN PKLTRMLTFKFYMPKKATELKHLQCLEEELKPLEEVLNLAQS KNFHLRPRDLISNINVIVLELKGSETTFMCEYADETATIVEFLN RWITFSQSIISTLT | 218 |
| IL-2_N25[AzK_PEG50kDa] | PTSSSTKKTQLQLEHLLLDLQMIL[AzK_PEG50kDa]GINNYK NPKLTRMLTFKFYMPKKATELKHLQCLEEELKPLEEVLNLAQ SKNFHLRPRDLISNINVIVLELKGSETTFMCEYADETATIVEFL NRWITFSQSIISTLT | 219 |
| IL-2_N87[AzK_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI S[AzK_PEG50kDa]INVIVLELKGSETTFMCEYADETATIVEFL NRWITFSQSIISTLT | 220 |
| IL-2_E99[AzK_PEG50kDa]-1 | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGS[AzK_PEG50kDa]TTFMCEYADETATIVEFL NRWITFSQSIISTLT | 221 |
| IL-2_N118[AzK_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFL[AzK_PEG50kDa] RWITFSQSIISTLT | 222 |
| IL-2_T122[AzK_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWI [AzK_PEG50kDa]FSQSIISTLT | 223 |
| IL-2_Q125[AzK_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFS [AzK_PEG50kDa]SIISTLT | 224 |
| IL-2_S126[AzK_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFSQ [AzK_PEG50kDa]IISTLT | 225 |
| IL-2_T130[AzK_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SNINVIVLELKGSETTFMCEYADETATIVEFLNRWITFSQSIIS [AzK_PEG50kDa]LT | 226 |
| IL-2_N87R_D108[AzK_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SRINVIVLELKGSETTFMCEYA[AzK_PEG50kDa]ETATIVEFL NRWITFSQSIISTLT | 227 |
| IL-2_V90[AzK_PEG50kDa] | PTSSSTKKTQLQLEHLLLDLQMILNGINNYKNPKLTRMLTFKF YMPKKATELKHLQCLEEELKPLEEVLNLAQSKNFHLRPRDLI SNIN[AzK_PEG50kDa]IVLELKGSETTFMCEYADETATIVEFL NRWITFSQSIISTLT | 228 |
| IL-2_K8[AzK_PEG30kDa] | PTSSSTK[AzK_PEG30kDa]TQLQLEHLLLDLQMILNGINNYK NPKLTRMLTFKFYMPKKATELKHLQCLEEELKPLEEVLNLAQ SKNFHLRPRDLISNINVIVLELKGSETTFMCEYADETATIVEFL NRWITFSQSIISTLT | 229 |

TABLE 1-continued

| Name | Sequence | SEQ ID NO: |
|---|---|---|
| IL-2_H15[AzK_PEG30kDa] | PTSSSTKKTQLQLE[AzK_PEG30kDa]LLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLT | 230 |
| IL-2_L18[AzK_PEG30kDa] | PTSSSTKKTQLQLEHLL[AzK_PEG30kDa]DLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLT | 231 |
| IL-2_D19[AzK_PEG30kDa] | PTSSSTKKTQLQLEHLLL[AzK_PEG30kDa]LQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLT | 232 |
| IL-2_M22[AzK_PEG30kDa] | PTSSSTKKTQLQLEHLLLDLQ[AzK_PEG30kDa]ILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLT | 233 |
| IL-2_N25[AzK_PEG30kDa] | PTSSSTKKTQLQLEHLLLDLQMIL[AzK_PEG30kDa]GINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLT | 234 |
| IL-2_N87[AzK_PEG30kDa] | PTSSSTKKTQLQLEHLLLDLQMILNGINNYKNPKLTRMLTFKFYMPKKATELKHLQCLEEELKPLEEVLNLAQSKNFHLRPRDLIS[AzK_PEG30kDa]INVIVLELKGSETTFMCEYADETATIVEFLNRWITFSQSIISTLT | 235 |
| IL-2_E99[AzK_PEG30kDa] | PTSSSTKKTQLQLEHLLLDLQMILNGINNYKNPKLTRMLTFKFYMPKKATELKHLQCLEEELKPLEEVLNLAQSKNFHLRPRDLISNINVIVLELKGS[AzK_PEG30kDa]TTFMCEYADETATIVEFLNRWITFSQSIISTLT | 236 |
| IL-2_N118[AzK_PEG30kDa] | PTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFL[AzK_PEG30kDa]RWITFSQSIISTLT | 237 |
| IL-2_T122[AzK_PEG30kDa] | PTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWI[AzK_PEG30kDa]FSQSIISTLT | 238 |
| IL-2_Q125[AzK_PEG30kDa] | PTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFS[AzK_PEG30kDa]SIISTLT | 239 |
| IL-2_S126[AzK_PEG30kDa] | PTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQ[AzK_PEG30kDa]IISTLT | 240 |
| IL-2-T130[AzK_PEG30kDa] | PTSSSTKKTQLQLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIIS[AzK_PEG30kDa]LT | 241 |
| IL-2_N87R_D108[AzK_PEG30kDa] | PTSSSTKKTQLQLEHLLLDLQMILNGINNYKNPKLTRMLTFKFYMPKKATELKHLQCLEEELKPLEEVLNLAQSKNFHLRPRDLISRINVIVLELKGSETTFMCEYA[AzK_PEG30kDa]ETATIVEFLNRWITFSQSIISTLT | 242 |
| IL-2_V90[AzK_PEG30kDa] | PTSSSTKKTQLQLEHLLLDLQMILNGINNYKNPKLTRMLTFKFYMPKKATELKHLQCLEEELKPLEEVLNLAQSKNFHLRPRDLISNIN[AzK_PEG30kDa]IVLELKGSETTFMCEYADETATIVEFLNRWITFSQSIISTLT | 243 |
| IL-2_L12[AzK_PEG30kDa] | APTSSSTKKTQ[AzK_PEG30kDa]QLEHLLLDLQMILNGINNYKNPKLTRMLTFKFYMPKKATELKHLQCLEEELKPLEEVLNLAQSKNFHLRPRDLISNINVIVLELKGSETTFMCEYADETATIVEFLNRWITFSQSIISTLT | 244 |

TABLE 1-continued

| Name | Sequence | SEQ ID NO: |
|---|---|---|
| IL-2_E15[AzK_PEG30kDa] | APTSSSTKKTQLQL[AzK_PEG30kDa]HLLLDLQMILNGINNY KNPKLTRMLTFKFYMPKKATELKHLQCLEEELKPLEEVLNLA QSKNFHLRPRDLISNINVIVLELKGSETTFMCEYADETATIVEF LNRWITFSQSIISTLT | 245 |
| IL-2_V91K_C125S | APTSSSTKKTQLQLEHLLLDLQMILNGINNYKNPKLTRMLTF KFYMPKKATELKHLQCLEEELKPLEEVLNLAQSKNFHLRPRD LISNINKIVLELKGSETTFMCEYADETATIVEFLNRWITFSQSII STLT | 246 |
| IL-2_N88R_C125S | APTSSSTKKTQLQLEHLLLDLQMILNGINNYKNPKLTRMLTF KFYMPKKATELKHLQCLEEELKPLEEVLNLAQSKNFHLRPRD LISRINVIVLELKGSETTFMCEYADETATIVEFLNRWITFSQSII STLT | 247 |
| CTP Peptide (30 amino acids) | FQSSSSKAPPPSLPSPSRLPGPSDTPILPQ | 248 |
| CTP Peptide (31 amino acids) | FQDSSSSKAPPPSLPSPSRLPGPSDTPILPQ | 249 |

Figure 3A:
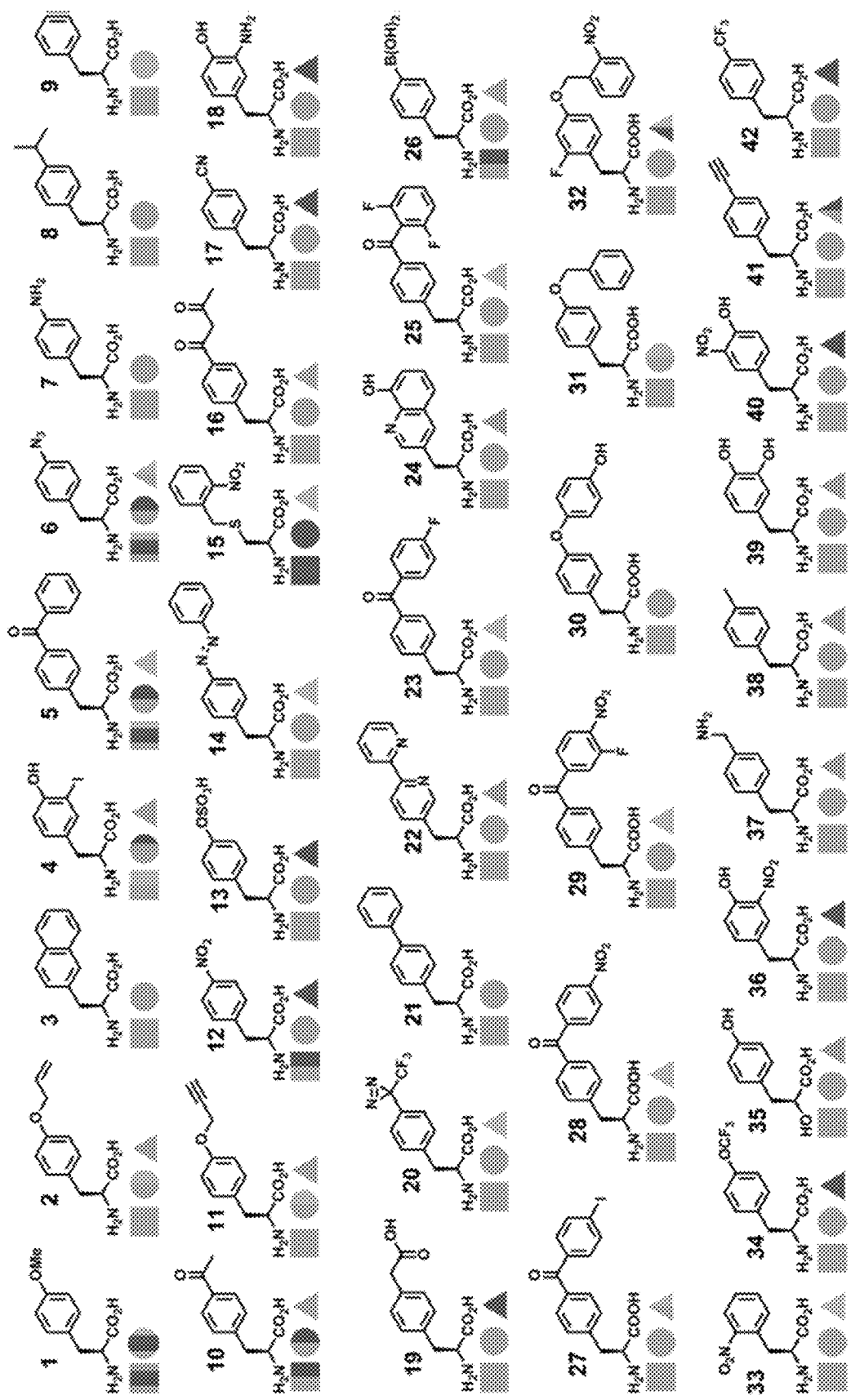
FIGS. 3A-FIG. 3D illustrate exemplary unnatural amino acids. These unnatural amino acids (UAAs) have been genetically encoded in proteins (FIG. 3A—UAA #1-42.
Figure 3B:
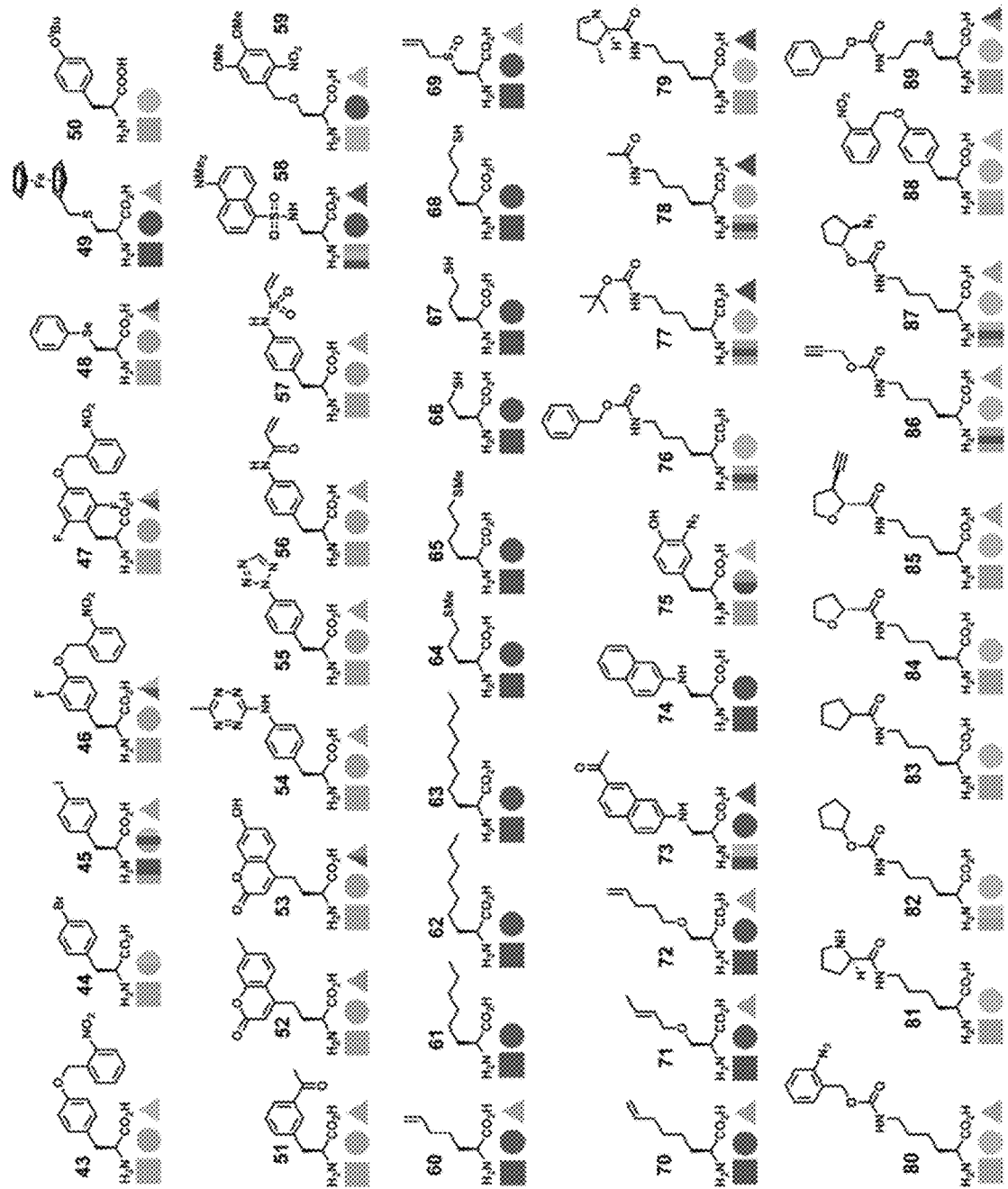
Figure 3C:
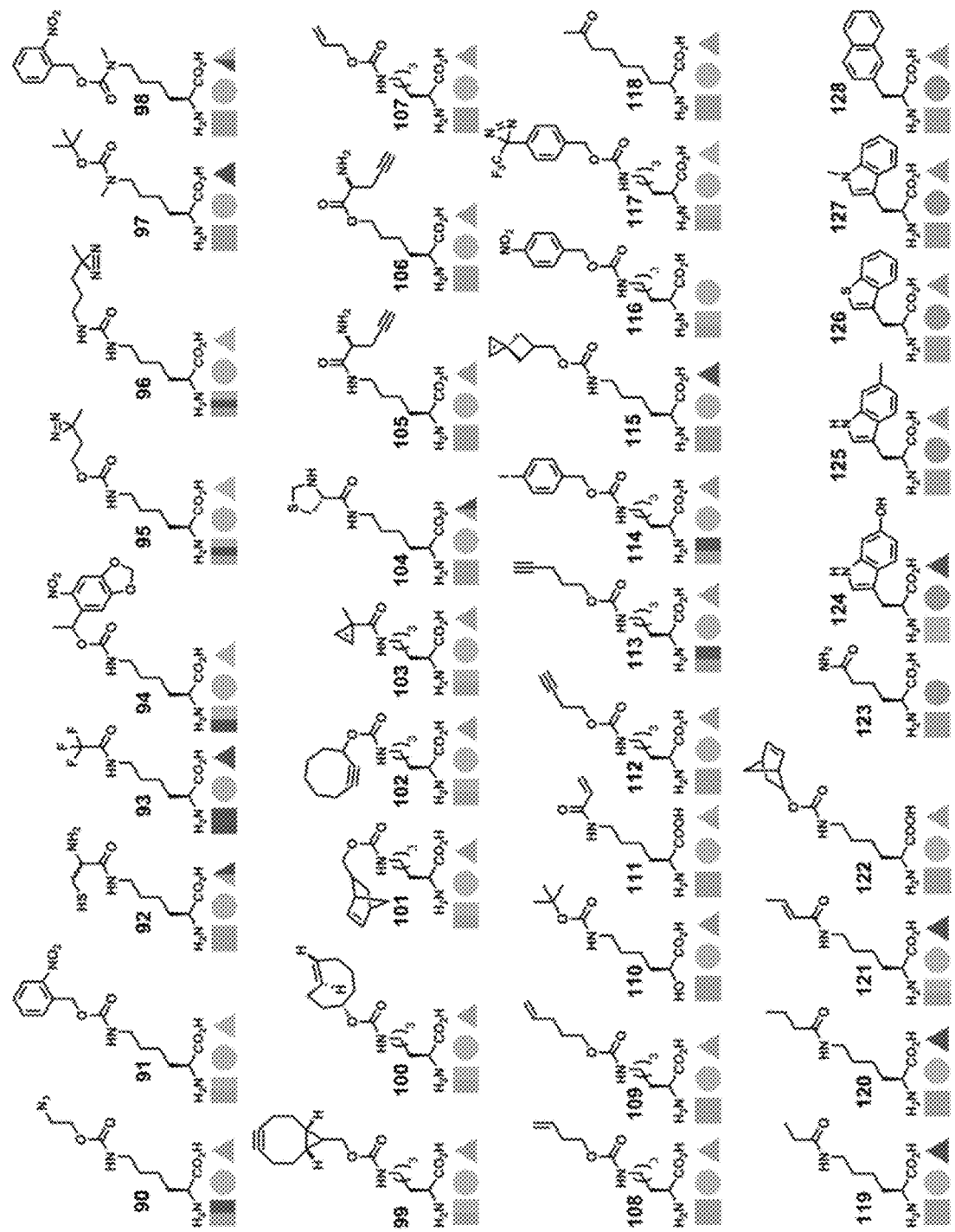
Figure 3D:
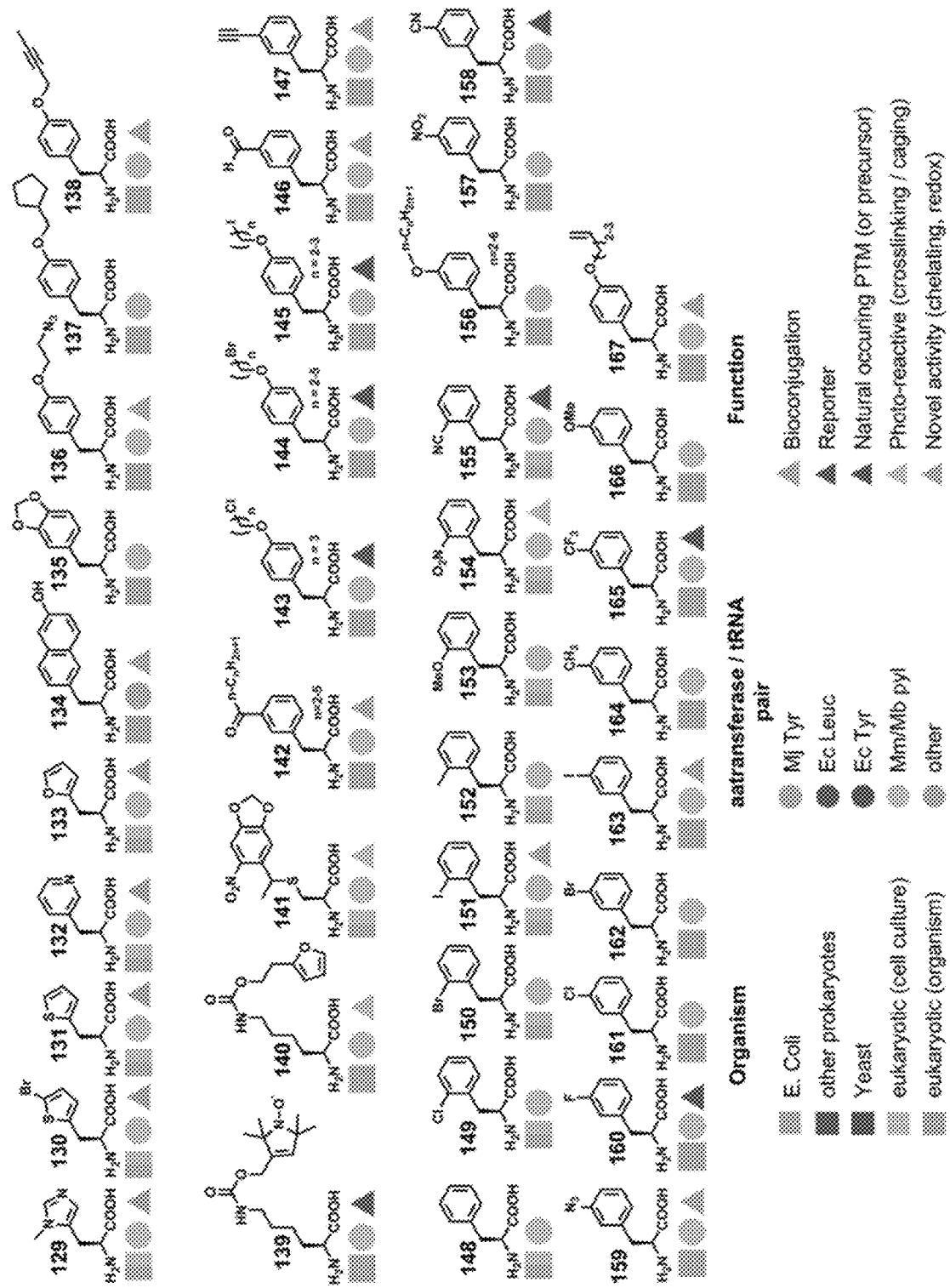

X = site comprising an unnatural amino acid.
[AzK] = N6-((2-azidoethoxy)-carbonyl)-L-lysine (the structure of which is disclosed as compound 90 in FIG. 3C), having Chemical Abstracts Registry No. 1167421-25-1.
[AzK_PEG] = N6-((2-azidoethoxy)-carbonyl)-L-lysine stably-conjugated to PEG via DBCO-mediated click chemistry, to form a compound comprising a structure of Formula (II) or Formula (III). For example, if specified, PEG50kD indicates a linear polyethylene glycol chain with an average molecular weight of 50 kDa, capped with a methoxy group. The ratio of regioisomers generated from the click reaction is about 1:1 or greater than 1:1. The term "DBCO" means a chemical moiety comprising a dibenzocyclooctyne group, such as comprising the mPEG-DBCO compound illustrated in Scheme 1 of Example 1. An exemplary structure of a methoxy PEG group is illustrated in the mPEG-DBCO structure in Scheme 1 of Example 1.
[AzK_L1_PEG] = N6-((2-azidoethoxy)-carbonyl)-L-lysine stably-conjugated to PEG via DBCO-mediated click chemistry to form a compound comprising a structure of Formula (IV) or Formula (V). For example, if specified, PEG50kD indicates a linear polyethylene glycol chain with an average molecular weight of 50 kDa, capped with a methoxy group. The ratio of regioisomers generated from the click reaction is about 1:1 or greater than 1:1. The term "DBCO" means a chemical moiety comprising a dibenzocyclooctyne group, such as comprising the mPEG-DBCO compound illustrated in Scheme 1 of Example 1.

In some embodiments, described herein are IL-2 conjugates modified at an amino acid position. In some instances, the modification is to a natural amino acid. In some instances, the modification is to an unnatural amino acid. In some instances, described herein is an isolated and modified IL-2 polypeptide that comprises at least one unnatural amino acid. In some instances, the IL-2 polypeptide is an isolated and purified mammalian IL-2, for example, a rodent IL-2 protein, or a human IL-2 protein. In some cases, the IL-2 polypeptide is a human IL-2 protein. In some cases, the IL-2 polypeptide comprises about 80%, 85%, 90%, 95%, 96%, 97%, 98%, or 99% sequence identity to SEQ ID NO: 1. In some cases, the IL-2 polypeptide comprises the sequence of SEQ ID NO: 1. In some cases, the IL-2 polypeptide consists of the sequence of SEQ ID NO: 1. In additional cases, the IL-2 polypeptide comprises about 80%, 85%, 90%, 95%, 96%, 97%, 98%, or 99% sequence identity to SEQ ID NO: 2. In additional cases, the IL-2 polypeptide comprises the sequence of SEQ ID NO: 2. In additional cases, the IL-2 polypeptide consists of the sequence of SEQ ID NO: 2. In some cases, the IL-2 polypeptide comprises about 80%, 85%, 90%, 95%, 96%, 97%, 98%, or 99% sequence identity to SEQ ID NO: 3. In some cases, the IL-2 polypeptide comprises the sequence of SEQ ID NO: 3. In some cases, the IL-2 polypeptide consists of the sequence of SEQ ID NO: 3. In additional cases, the IL-2 polypeptide comprises about 80%, 85%, 90%, 95%, 96%, 97%, 98%, or 99% sequence identity to SEQ ID NO: 4. In additional cases, the IL-2 polypeptide comprises the sequence of SEQ ID NO: 4. In additional cases, the IL-2 polypeptide consists of the sequence of SEQ ID NO: 4. In some cases, the IL-2 polypeptide comprises about 80%, 85%, 90%, 95%, 96%, 97%, 98%, or 99% sequence identity to SEQ ID NO: 34-48. In some cases, the IL-2 polypeptide comprises the sequence of SEQ ID NO: 34-48. In some cases, the IL-2 polypeptide consists of the sequence of SEQ ID NO: 34-48. In additional cases, the IL-2 polypeptide comprises about 80%, 85%, 90%, 95%, 96%, 97%, 98%, or 99% sequence identity to SEQ ID NO: 199-213. In additional cases, the IL-2 polypeptide comprises the sequence of SEQ ID NO: 199-213. In additional cases, the IL-2 polypeptide consists of the sequence of SEQ ID NO: 199-213. In some cases, the IL-2 polypeptide comprises about 80%, 85%, 90%, 95%, 96%, 97%, 98%, or 99% sequence identity to SEQ ID NO: 49-63. In some cases, the IL-2 polypeptide comprises the sequence of SEQ ID NO: 49-63. In some cases, the IL-2 polypeptide consists of the sequence of SEQ ID NO: 49-63. In additional cases, the IL-2 polypeptide comprises about 80%, 85%, 90%, 95%, 96%, 97%, 98%, or 99% sequence identity to SEQ ID NO: 213-228. In additional cases, the IL-2 polypeptide comprises the sequence of SEQ ID NO: 213-228. In additional cases, the IL-2 polypeptide consists of the sequence of SEQ ID NO: 213-228. In some cases, the IL-2 polypeptide comprises about 80%, 85%, 90%, 95%, 96%, 97%, 98%, or 99% sequence identity to SEQ ID NO: 64-78. In some cases, the IL-2 polypeptide comprises the sequence of SEQ ID NO: 64-78. In some cases, the IL-2 polypeptide consists of the sequence of SEQ ID NO: 64-78. In some cases, the IL-2 polypeptide comprises about 80%, 85%, 90%, 95%, 96%, 97%, 98%, or 99% sequence identity to SEQ ID NO: 229-243. In some cases, the IL-2 polypeptide comprises the sequence of SEQ ID NO: 229-243. In some cases, the IL-2 polypeptide consists of the sequence of SEQ ID NO: 229-243. In some cases, the IL-2 polypeptide comprises about 80%, 85%, 90%, 95%, 96%, 97%, 98%, or 99% sequence identity to SEQ ID NO: 154-168. In some cases, the IL-2 polypeptide comprises the sequence of SEQ ID NO: 154-168. In some cases, the IL-2 polypeptide consists of the sequence of SEQ ID NO: 154-168. In some cases, the IL-2 polypeptide comprises about 80%, 85%, 90%, 95%, 96%, 97%, 98%, or 99% sequence identity to SEQ ID NO: 109-123. In some cases, the IL-2 polypeptide comprises the sequence of SEQ ID NO: 109-123. In some cases, the IL-2 polypeptide consists of the sequence of SEQ ID NO: 109-123. In some cases, the IL-2 polypeptide comprises about 80%, 85%, 90%, 95%, 96%, 97%, 98%, or 99% sequence identity to SEQ ID NO: 169-183. In some cases, the IL-2 polypeptide comprises the sequence of SEQ ID NO: 169-183. In some cases, the IL-2 polypeptide consists of the sequence of SEQ ID NO: 169-183. In some cases, the IL-2 polypeptide comprises about 80%, 85%, 90%, 95%, 96%, 97%, 98%, or 99% sequence identity to SEQ ID NO: 123-138. In some cases, the IL-2 polypeptide comprises the sequence of SEQ ID NO: 123-138. In some cases, the IL-2 polypeptide consists of the sequence of SEQ ID NO: 123-138. In some cases, the IL-2 polypeptide comprises about 80%, 85%, 90%, 95%, 96%, 97%, 98%, or 99% sequence identity to SEQ ID NO: 184-198. In some cases, the IL-2 polypeptide comprises the sequence of SEQ ID NO: 184-198. In some cases, the IL-2 polypeptide consists of the sequence of SEQ ID NO: 184-198. In some cases, the IL-2 polypeptide comprises about 80%, 85%, 90%, 95%, 96%, 97%, 98%, or 99% sequence identity to SEQ ID NO: 139-153. In some cases, the IL-2 polypeptide comprises the sequence of SEQ ID NO: 139-153. In some cases, the IL-2 polypeptide consists of the sequence of SEQ ID NO: 139-153.

In some instances, the IL-2 polypeptide is a truncated variant. In some instances, the truncation is an N-terminal deletion. In other instances, the truncation is a C-terminal deletion. In additional instances, the truncation comprises both N-terminal and C-terminal deletions. For example, the truncation can be a deletion of at least or about 1, 2, 3, 4, 5, 6, 7, 8, 9, 10, 11, 12, 13, 14, 15, 20, or more residues from either the N-terminus or the C-terminus, or both termini. In some cases, the IL-2 polypeptide comprises an N-terminal deletion of at least or about 1, 2, 3, 4, 5, 6, 7, 8, 9, 10, 11, 12, 13, 14, 15, 20, or more residues. In some cases, the IL-2 polypeptide comprises an N-terminal deletion of at least or about 1, 2, 3, 4, 5, 6, 7, 8, 9, or 10 residues. In some cases, the IL-2 polypeptide comprises an N-terminal deletion of at least or about 2 residues. In some cases, the IL-2 polypeptide comprises an N-terminal deletion of at least or about 3 residues. In some cases, the IL-2 polypeptide comprises an N-terminal deletion of at least or about 4 residues. In some cases, the IL-2 polypeptide comprises an N-terminal deletion of at least or about 5 residues. In some cases, the IL-2 polypeptide comprises an N-terminal deletion of at least or about 6 residues. In some cases, the IL-2 polypeptide comprises an N-terminal deletion of at least or about 7 residues. In some cases, the IL-2 polypeptide comprises an N-terminal deletion of at least or about 8 residues. In some cases, the IL-2 polypeptide comprises an N-terminal deletion of at least or about 9 residues. In some cases, the IL-2 polypeptide comprises an N-terminal deletion of at least or about 10 residues.

In some embodiments, the IL-2 polypeptide is a functionally active fragment. In some cases, the functionally active fragment comprises IL-2 region 10-133, 20-133, 30-133, 10-130, 20-130, 30-130, 10-125, 20-125, 30-125, 1-130, or 1-125, wherein the residue positions are in reference to the positions in SEQ ID NO: 1. In some cases, the functionally active fragment comprises IL-2 region 10-133, wherein the residue positions are in reference to the positions in SEQ ID NO: 1. In some cases, the functionally active fragment comprises IL-2 region 20-133, wherein the residue positions are in reference to the positions in SEQ ID NO: 1. In some cases, the functionally active fragment comprises IL-2 region 30-133, wherein the residue positions are in reference to the positions in SEQ ID NO: 1. In some cases, the functionally active fragment comprises IL-2 region 10-125, wherein the residue positions are in reference to the positions in SEQ ID NO: 1. In some cases, the functionally active fragment comprises IL-2 region 20-125, wherein the residue positions are in reference to the positions in SEQ ID NO: 1. In some cases, the functionally active fragment comprises IL-2 region 1-130, wherein the residue positions are in reference to the positions in SEQ ID NO: 1. In some cases, the functionally active fragment comprises IL-2 region 1-125, wherein the residue positions are in reference to the positions in SEQ ID NO: 1.

In some embodiments, described herein is an IL-2 conjugate that comprises an isolated, purified, and modified IL-2 polypeptide and a conjugating moiety. In some instances, the IL-2 conjugate has a decreased affinity to an IL-2 receptor α (IL-2Rα) subunit relative to a wild-type IL-2 polypeptide. In some cases, the conjugating moiety is bound to an amino acid residue that interacts with IL-2Rα (e.g., at the IL-2/IL-2Rα interface). In some cases, the conjugating moiety is bound to an amino acid residue that is proximal to the IL-2/IL-2Rα interface (e.g., about 5 Å, about 10 Å, about 15 Å, or about 20 Å away from the IL-2/IL-2Rα interface). As used herein, the residues involved in the IL-2/IL-2Rα interface comprise IL-2 residues that form hydrophobic interactions, hydrogen bonds, or ionic interactions with residues from the IL-2Rα subunit.

In some instances, the conjugating moiety is bound to an amino acid residue selected from an amino acid position A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, or T133, in which the numbering of the amino acid residues corresponds to SEQ ID NO: 1. In some instances, the amino acid position is selected from A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133. In some instances, the amino acid position is selected from A1, P2, T3, S4, S5, S6, T7, K8, K9, Q11, L12, E15, H16, L18, L19, D20, Q22, M23, N26, G27, N29, N30, and Y31. In some instances, the amino acid position is selected from K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133. In some instances, the amino acid position is selected from K9, Q11, L12, E15, H16, L18, L19, K35, T37, M46, P47, K48, A50, K76, N77, F78, H79, R81, P82, R83, D84, S87, N88, F103, M104, C105, E106, Y107, A108, D109, D109 in the N88R variant. In some instances, the amino acid position is selected from S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133. In some instances, the amino acid position is selected from K8, H15, L18, D19, M22, N25, N87, V90, I91, L93, E94, K96, G97, S98, E99, D108 in the N87R variant, N118, T122, S124, Q125, S126, S129, and T130.

In some instances, the IL-2 conjugate further comprises an additional mutation. In some cases, the additional mutation is at an amino acid position selected from K8, H15, L18, D19, M22, N25, N87, V90, I91, L93, E94, K96, G97, S98, E99, D108 in the N87R variant, N118, T122, S124, Q125, 5126, S129, and T130. In such cases, the amino acid is conjugated to an additional conjugating moiety for increase in serum half-life, stability, or a combination thereof. Alternatively, the amino acid is first mutated to a natural amino acid such as lysine, cysteine, histidine, arginine, aspartic acid, glutamic acid, serine, threonine, or tyrosine; or to an unnatural amino acid prior to binding to the additional conjugating moiety.

In some instances, the receptor signaling potency is measured by an ED50 value. In some instances, the modified IL-2 polypeptide provides a first ED50 value for activating IL-2βγ signaling complex and a second ED50 value for activating IL-2αβγ signaling complex, and wherein a difference between the first ED50 and the second ED50 value is less than 10-fold. In some instances, the modified IL-2 polypeptide provides a first ED50 value for activating IL-2βγ signaling complex and a second ED50 value for activating IL-2αβγ signaling complex, and wherein a difference between the first ED50 and the second ED50 value is less than 5-fold. In some cases, the difference is less than 9-fold, less than 8-fold, less than 7-fold, less than 6-fold, less than 5-fold, less than 4-fold, less than 3-fold, less than 2-fold, or less than 1-fold.

In some embodiments, the conjugating moiety is linked to the N-terminus or the C-terminus of an IL-2 polypeptide, either directly or indirectly through a linker peptide. In some cases, the conjugating moiety (e.g., a polymer, a protein, or a peptide) is genetically fused to the IL-2, at the N-terminus or the C-terminus of IL-2, and either directly or indirectly through a linker peptide. In some instances, the conjugating moiety is linked to the N-terminus or the C-terminus amino acid residue. In some instances, the conjugating moiety is linked to a reactive group that is bound to the N-terminus or C-terminus amino acid residue.

In some embodiments, the IL-2 conjugate with reduced binding affinity to IL-2Rα is capable of expanding CD4+ helper cell, CD8+ effector naïve and memory T cell, Natural Killer (NK) cell, or Natural killer T (NKT) cell populations. In some cases, the conjugating moiety impairs or blocks binding of IL-2 with IL-2Rα.

In some cases, activation of CD4+ helper cell, CD8+ effector naïve and memory cell, Natural Killer (NK) cell, or Natural killer T (NKT) cell population via the IL-2Rβγ complex by the modified IL-2 polypeptide retains significant potency of activation of said cell population relative to a wild-type IL-2 polypeptide. In some instances, the activation by the modified IL-2 polypeptide is equivalent to that of the wild-type IL-2 polypeptide. In other instances, the activation by the modified IL-2 polypeptide is higher than that of the wild-type IL-2 polypeptide. In some cases, the receptor signaling potency of the modified IL-2 polypeptide to the IL-2Rβγ complex is higher than a receptor signaling potency of the wild-type IL-2 polypeptide to the IL-2Rβγ complex. In some cases, the receptor signaling potency of the modified IL-2 polypeptide is at least 1-fold higher than the respective potency of the wild-type IL-2 polypeptide. In some cases, the receptor signaling potency of the modified IL-2 polypeptide is about or at least 2-fold, 3-fold, 4-fold, 5-fold, 6-fold, 7-fold, 8-fold, 9-fold, 10-fold, 15-fold, 20-fold, 25-fold, 30-fold, 40-fold, 50-fold, 60-fold, 70-fold, 80-fold, 90-fold, 100-fold, 150-fold, 200-fold, 300-fold, 400-fold, 500-fold, 1,000-fold, or higher than the respective potency of the wild-type IL-2 polypeptide. In such cases, the dose or concentration of the modified IL-2 polypeptide used for achieving a similar level of activation of the CD4+ helper cell, CD8+ effector naïve and memory cell, Natural Killer (NK) cell, or Natural killer T (NKT) cell population as a wild-type 11-2 polypeptide is lower than a dose or concentration used for the wild-type IL-2 polypeptide.

In some embodiments, activation of CD4+ helper cell, CD8+ effector naïve and memory cell, Natural Killer (NK) cell, or Natural killer T (NKT) cell population via the IL-2Rβγ complex by the modified IL-2 polypeptide retains significant potency of activation of said cell population by a wild-type IL-2 polypeptide. In some cases, the receptor signaling potency of the modified IL-2 polypeptide the IL-2Rβγ complex is lower than a receptor signaling potency of the wild-type IL-2 polypeptide the IL-2Rβγ complex. In some cases, the receptor signaling potency of the modified IL-2 polypeptide is about or at least 1-fold, 2-fold, 3-fold, 4-fold, 5-fold, 10-fold, 20-fold, or 50-fold lower than the respective potency of the wild-type IL-2 polypeptide.

In some embodiments, the modified IL-2 polypeptide exhibits a first receptor signaling potency to IL-2Rβγ and a second receptor signaling potency to IL-2Rαβγ. In some instances, the first receptor signaling potency to IL-2Rβγ is an improved potency relative to a wild-type IL-2 polypeptide. In some instances, the second receptor signaling potency to IL-2Rαβγ is an impaired potency relative to the wild-type IL-2 polypeptide. In some embodiments, the modified IL-2 polypeptide exhibits a first receptor signaling potency to IL-2Rβγ and a second receptor signaling potency to IL-2Rαβγ, and wherein the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, 1000-fold, or higher than the second receptor signaling potency. In some instances, the first receptor signaling potency is at least 1-fold or higher than the second receptor signaling potency. In some instances, the first receptor signaling potency is at least 2-fold or higher than the second receptor signaling potency. In some instances, the first receptor signaling potency is at least 5-fold or higher than the second receptor signaling potency. In some instances, the first receptor signaling potency is at least 10-fold or higher than the second receptor signaling potency. In some instances, the first receptor signaling potency is at least 20-fold or higher than the second receptor signaling potency. In some instances, the first receptor signaling potency is at least 50-fold or higher than the second receptor signaling potency. In some instances, the first receptor signaling potency is at least 100-fold or higher than the second receptor signaling potency. In some instances, the first receptor signaling potency is at least 500-fold or higher than the second receptor signaling potency. In some instances, the first receptor signaling potency is at least 1000-fold or higher than the second receptor signaling potency. In some instances, the first receptor signaling potency of the modified IL-2 polypeptide is higher than a receptor signaling potency of the wild-type IL-2 polypeptide to the IL-2Rβγ, and the second receptor signaling potency of the modified IL-2 polypeptide is lower than a receptor signaling potency of the wild-type IL-2 polypeptide to the IL-2Rαβγ. In some cases, both receptor signaling potencies are lower than their respective potencies in a wild-type IL-2 polypeptide. In other cases, both receptor signaling potencies are higher than their respective potencies in a wild-type IL-2 polypeptide.

In some embodiments, the IL-2 conjugate decreases a toxic adverse event in a subject administered with the IL-2 conjugate. Exemplary toxic adverse events include eosinophilia, capillary leak, and vascular leak syndrome (VLS). In some instances, the IL-2 conjugate decreases the occurrence of a toxic adverse event in the subject by about 10%, 20%, 30%, 40%, 50%, 60%, 70%, 80%, 90%, 95%, 99%, or about 100%, relative to a second subject administered with a wild-type IL-2 or aldesleukin. In some instances, the IL-2 conjugate decreases the severity of a toxic adverse event in the subject by about 10%, 20%, 30%, 40%, 50%, 60%, 70%, 80%, 90%, 95%, 99%, or about 100%, relative to a second subject administered with a wild-type IL-2 or aldesleukin.

In some instances, the toxic adverse event is eosinophilia. In some cases, the IL-2 conjugate decreases the occurrence of eosinophilia in the subject by about 10%, 20%, 30%, 40%, 50%, 60%, 70%, 80%, 90%, 95%, 99%, or about 100%, relative to a second subject administered with a wild-type IL-2 or aldesleukin. In some cases, the IL-2 conjugate decreases the severity of eosinophilia in the subject by about 10%, 20%, 30%, 40%, 50%, 60%, 70%, 80%, 90%, 95%, 99%, or about 100%, relative to a second subject administered with a wild-type IL-2 or aldesleukin.

In some instances, the toxic adverse event is capillary leak. In some cases, the IL-2 conjugate decreases the occurrence of capillary leak in the subject by about 10%, 20%, 30%, 40%, 50%, 60%, 70%, 80%, 90%, 95%, 99%, or about 100%, relative to a second subject administered with a wild-type IL-2 or aldesleukin. In some cases, the IL-2 conjugate decreases the severity of capillary leak in the subject by about 10%, 20%, 30%, 40%, 50%, 60%, 70%, 80%, 90%, 95%, 99%, or about 100%, relative to a second subject administered with a wild-type IL-2 or aldesleukin.

In some instances, the toxic adverse event is VLS. In some cases, the IL-2 conjugate decreases the occurrence of VLS in the subject by about 10%, 20%, 30%, 40%, 50%, 60%, 70%, 80%, 90%, 95%, 99%, or about 100%, relative to a second subject administered with a wild-type IL-2 or aldesleukin. In some cases, the IL-2 conjugate decreases the severity of VLS in the subject by about 10%, 20%, 30%, 40%, 50%, 60%, 70%, 80%, 90%, 95%, 99%, or about 100%, relative to a second subject administered with a wild-type IL-2 or aldesleukin.

In some embodiments, the IL-2 conjugate comprises a plasma half-life of greater than 1 hour, 2 hours, 3 hours, 4 hours, 5 hours, 6 hours, 7 hours, 8 hours, 9 hours, 10 hours, 12 hours, 18 hours, 24 hours, 2 days, 3 days, 4 days, 5 days, 6 days, 7 days, or more. In some embodiments, the IL-2 conjugate comprises a plasma half-life of greater than 1 hour, 2 hours, 3 hours, 4 hours, 5 hours, 6 hours, 7 hours, 8 hours, 9 hours, 10 hours, or more. In some embodiments, the IL-2 conjugate comprises a plasma half-life of greater than 1 hour. In some embodiments, the IL-2 conjugate comprises a plasma half-life of greater than 2 hours. In some embodiments, the IL-2 conjugate comprises a plasma half-life of greater than 3 hours. In some embodiments, the IL-2 conjugate comprises a plasma half-life of greater than 4 hours. In some embodiments, the IL-2 conjugate comprises a plasma half-life of greater than 5 hours. In some embodiments, the IL-2 conjugate comprises a plasma half-life of greater than 6 hours. In some embodiments, the IL-2 conjugate comprises a plasma half-life of greater than 7 hours. In some embodiments, the IL-2 conjugate comprises a plasma half-life of greater than 8 hours. In some embodiments, the IL-2 conjugate comprises a plasma half-life of greater than 9 hours. In some embodiments, the IL-2 conjugate comprises a plasma half-life of greater than 10 hours. In some embodiments, the IL-2 conjugate comprises a plasma half-life of greater than 12 hours. In some embodiments, the IL-2 conjugate comprises a plasma half-life of greater than 18 hours. In some embodiments, the IL-2 conjugate comprises a plasma half-life of greater than 24 hours.

In some embodiments, the IL-2 conjugate comprises a plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more. In some embodiments, the IL-2 conjugate comprises a plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, or more. In some embodiments, the IL-2 conjugate comprises a plasma half-life of at least 1 hour. In some embodiments, the IL-2 conjugate comprises a plasma half-life of at least 2 hours. In some embodiments, the IL-2 conjugate comprises a plasma half-life of at least 3 hours. In some embodiments, the IL-2 conjugate comprises a plasma half-life of at least 4 hours. In some embodiments, the IL-2 conjugate comprises a plasma half-life of at least 5 hours. In some embodiments, the IL-2 conjugate comprises a plasma half-life of at least 6 hours. In some embodiments, the IL-2 conjugate comprises a plasma half-life of at least 7 hours. In some embodiments, the IL-2 conjugate comprises a plasma half-life of at least 8 hours. In some embodiments, the IL-2 conjugate comprises a plasma half-life of at least 9 hours. In some embodiments, the IL-2 conjugate comprises a plasma half-life of at least 10 hours. In some embodiments, the IL-2 conjugate comprises a plasma half-life of at least 12 hours. In some embodiments, the IL-2 conjugate comprises a plasma half-life of at least 18 hours. In some embodiments, the IL-2 conjugate comprises a plasma half-life of at least 24 hours.

In some embodiments, the IL-2 conjugate comprises a plasma half-life of from about 1 hour to about 7 days, from about 12 hours to about 7 days, from about 18 hours to about 7 days, from about 24 hours to about 7 days, from about 1 hours to about 5 days, from about 12 hours to about 5 days, from about 24 hours to about 5 days, from about 2 days to about 5 days, or from about 2 days to about 3 days.

In some embodiments, the IL-2 conjugate comprises a plasma half-life of from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours.

In some embodiments, the IL-2 conjugate comprises a plasma half-life that is capable of proliferating and/or expanding a CD4+ helper cell, CD8+ effector naïve and memory T cell, NK cell, NKT cell, or a combination thereof, but does not exert a deleterious effect such as apoptosis.

In some embodiments, the IL-2 conjugate comprises an extended plasma half-life, e.g., by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more relative to a wild-type IL-2. In some embodiments, the IL-2 conjugate comprises an extended plasma half-life, e.g., by at least 1 hour, 2 hours, 3 hours, 4 hours, 5 hours, 6 hours, 7 hours, 8 hours, 9 hours, 10 hours, 12 hours, 15 hours, 18 hours, 24 hours, or more relative to a wild-type IL-2.

In some embodiments, the IL-2 conjugate comprises an extended plasma half-life, e.g., from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours relative to a wild-type IL-2.

In some embodiments, the IL-2 conjugate comprises an extended plasma half-life, e.g., by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more relative to aldesleukin. In some embodiments, the IL-2 conjugate comprises an extended plasma half-life, e.g., by at least 1 hour, 2 hours, 3 hours, 4 hours, 5 hours, 6 hours, 7 hours, 8 hours, 9 hours, 10 hours, 12 hours, 15 hours, 18 hours, 24 hours, or more relative to aldesleukin.

In some embodiments, the IL-2 conjugate comprises an extended plasma half-life, e.g., from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours relative to aldesleukin.

In some embodiments, the IL-2 conjugate comprises an extended plasma half-life with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, or more with a reduced toxicity. In some instances, the IL-2 conjugate comprises an extended plasma half-life of from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours with a reduced toxicity. In some cases, the reduced toxicity is at least 1-fold, 2-fold, 3-fold, 4-fold, 5-fold, 6-fold, 7-fold, 8-fold, 9-fold, 10-fold, 20-fold, 30-fold, 50-fold, 100-fold, or more reduced relative to a wild-type IL2. In some cases, the reduced toxicity is at least 10%, 20%, 30%, 40%, 50%, 60%, 70%, 80%, 90%, 100%, 200%, 300%, 400%, 500%, or more reduced relative to a wild-type IL-2.

In some embodiments, the IL-2 conjugate comprises an extended plasma half-life with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more with a reduced toxicity. In some instances, the IL-2 conjugate comprises an extended plasma half-life of at least 1 hour, 2 hours, 3 hours, 4 hours, 5 hours, 6 hours, 7 hours, 8 hours, 9 hours, 10 hours, 12 hours, 15 hours, 18 hours, 24 hours, or more with a reduced toxicity. In some instances, the IL-2 conjugate comprises an extended plasma half-life of from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours with a reduced toxicity. In some cases, the reduced toxicity is at least 1-fold, 2-fold, 3-fold, 4-fold, 5-fold, 6-fold, 7-fold, 8-fold, 9-fold, 10-fold, 20-fold, 30-fold, 50-fold, 100-fold, or more reduced relative to aldesleukin. In some cases, the reduced toxicity is at least 10%, 20%, 30%, 40%, 50%, 60%, 70%, 80%, 90%, 100%, 200%, 300%, 400%, 500%, or more reduced relative to aldesleukin.

In some embodiments, the IL-2 conjugate comprises a conjugating moiety in which the size (e.g., the volume or length) of the conjugating moiety enhances plasma stability but does not reduce potency. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, or more. In some instances, the size of the conjugating moiety extends plasma half-life from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours. In some instances, the size of the conjugating moiety reduces the potency by less than 5%, 4%, 3%, 2%, 1%, or less relative to aldesleukin.

In some embodiments, the IL-2 conjugate comprises a conjugating moiety in which the size (e.g., the volume or length) of the conjugating moiety enhances plasma stability and potency. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, 2 days, 3 days, 4 days, 5 days, 6 days, 7 days, or more. In some instances, the size of the conjugating moiety extends plasma half-life by at least 1 hour, 2 hours, 3 hours, 4 hours, 5 hours, 6 hours, 7 hours, 8 hours, 9 hours, 10 hours, 12 hours, 15 hours, 18 hours, 24 hours, or more. In some instances, the size of the conjugating moiety extends plasma half-life from about 1 hour to about 18 hours, from about 1 hour to about 12 hours, from about 2 hours to about 10 hours, from about 2 hours to about 8 hours, from about 4 hours to about 18 hours, from about 4 hours to about 12 hours, from about 4 hours to about 10 hours, from about 4 hours to about 8 hours, from about 6 hours to about 18 hours, from about 6 hours to about 12 hours, from about 6 hours to about 10 hours, from about 6 hours to about 8 hours, from about 8 hours to about 18 hours, from about 8 hours to about 12 hours, or from about 8 hours to about 10 hours. In some instances, the size of the conjugating moiety further enhances the potency by more than 5%, 10%, 20%, 30%, 40%, 50%, 60%, 70%, 80%, 90%, 100%, 200%, or more relative to aldesleukin.

In some embodiments, described herein is an IL-2 conjugate comprising an unnatural amino acid covalently attached to a conjugating moiety, wherein the unnatural amino acid is located in region 35-107, and wherein the region 35-107 corresponds to residues K35-Y107 of SEQ ID NO: 1.

In some embodiments, described herein is an interleukin 2 βγ receptor (IL-2Rβγ) binding protein, wherein the binding affinity for an interleukin 2 α receptor (IL-2Rα) of said binding protein is less than that of wild-type human IL-2 (hIL-2), wherein the binding affinity for an interleukin 2 α receptor (IL-2Rα) of said binding protein is less than that of wild-type human IL-2 (hIL-2). In some embodiments, described herein is an interleukin 2 βγ receptor (IL-2Rβγ) binding protein, wherein the binding affinity for an interleukin 2 α receptor (IL-2Rα) of said binding protein is less than that of wild-type human IL-2 (hIL-2), and wherein said binding protein comprises at least one unnatural amino acid. In some instances, said binding protein is a modified IL-2 polypeptide or a functionally active fragment thereof, wherein the modified IL-2 polypeptide comprises at least one unnatural amino acid. In some instances, the at least one unnatural amino acid is located in region 35-107, and wherein the region 35-107 corresponds to residues K35-Y107 of SEQ ID NO: 1.

In some embodiments, described herein is an IL-2/IL-2Rβγ complex comprising a modified IL-2 polypeptide comprising a mutation and an IL-2Rβγ, wherein the modified IL-2 polypeptide has a reduced binding affinity toward IL-2Rα, and wherein the reduced binding affinity is compared to a binding affinity between a wild-type IL-2 polypeptide and IL-2Rα. In some instances, the modified IL-2 polypeptide further comprises a conjugating moiety covalently attached to site of mutation. In some instances, the site of mutation comprises an amino acid mutated to a natural amino acid. In some cases, the site of mutation comprises an amino acid mutated to a cysteine residue. In other cases, the site of mutation comprises an amino acid mutated to a lysine residue.

In some embodiments, described herein is an IL-2/IL-2Rβγ complex comprising a modified IL-2 polypeptide comprising an unnatural amino acid and an IL-2Rβγ, wherein the modified IL-2 polypeptide has a reduced binding affinity toward IL-2Rα, and wherein the reduced binding affinity is compared to a binding affinity between a wild-type IL-2 polypeptide and IL-2Rα. In some instances, the modified IL-2 polypeptide further comprises a conjugating moiety covalently attached to the unnatural amino acid.

In some embodiments, described herein is an IL-2/IL-2Rβγ complex comprising a modified IL-2 polypeptide comprising an unnatural amino acid and an IL-2Rβγ, wherein the modified IL-2 polypeptide has a reduced receptor signaling potency toward IL-2Rα, and wherein the reduced receptor signaling potency is compared to a receptor signaling potency between a wild-type IL-2 polypeptide and IL-2Rα. In some instances, the modified IL-2 polypeptide further comprises a conjugating moiety covalently attached to the unnatural amino acid.

In some embodiments, described herein is an activator of a CD4+ helper cell, CD8+ effector naïve and memory T cell, Natural Killer (NK) cell, or a Natural killer T (NKT) cell that selectively expands CD4+ helper cells, CD8+ effector naïve and memory T cells, NK cells, NKT cells, or a combination thereof in a cell population, wherein said activator comprises a modified interleukin 2 (IL-2) polypeptide comprising at least one mutation. In some instances, the mutation is to a natural amino acid. In other instances, the mutation is to an unnatural amino acid. In some embodiments, described herein is an activator of a CD4+ helper cell, CD8+ effector naïve and memory T cell, Natural Killer (NK) cell, or a Natural killer T (NKT) cell that selectively expands CD4+ helper cells, CD8+ effector naïve and memory T cells, NK cells, NKT cells, or a combination thereof in a cell population, wherein said activator comprises a modified interleukin 2 (IL-2) polypeptide comprising at least one unnatural amino acid. In some instances, said activator expands CD4+ T regulatory (Treg) cells by less than 20%, 15%, 10%, 5%, 1%, or less than 0.1% when said activator is in contact with said CD3+ cell population compared to an expansion of CD4+ Treg cells in the CD3+ cell population contacted with a wild-type IL-2 polypeptide. In some instances, said activator does not expand Treg cells in said cell population. In some instances, said cell population is an in vivo cell population. In some instances, said cell population is an in vitro cell population. In some instances, said cell population is an ex vivo cell population.

In some instances, also described herein is a method of expanding a CD4+ helper cell, CD8+ effector naïve and memory T cell, Natural Killer (NK) cell, or a Natural killer T (NKT) cell population, comprising contacting said cell population with a therapeutically effective amount of a CD4+ helper cell, CD8+ effector naïve and memory T cell, Natural Killer (NK) cell, or a Natural killer T (NKT) cell activator, in which said activator comprises a modified interleukin 2 (IL-2) polypeptide comprising at least one mutation, thereby expanding the CD4+ helper cell, CD8+ effector naïve and memory T cell, Natural Killer (NK) cell, or Natural killer T (NKT) cell population. In some instances, the mutation is to a natural amino acid. In other instances, the mutation is to an unnatural amino acid. In some instances, also described herein is a method of expanding a CD4+ helper cell, CD8+ effector naïve and memory T cell, Natural Killer (NK) cell, or a Natural killer T (NKT) cell population, comprising contacting said cell population with a therapeutically effective amount of a CD4+ helper cell, CD8+ effector naïve and memory T cell, Natural Killer (NK) cell, or a Natural killer T (NKT) cell activator, in which said activator comprises a modified interleukin 2 (IL-2) polypeptide comprising at least one unnatural amino acid, thereby expanding the CD4+ helper cell, CD8+ effector naïve and memory T cell, Natural Killer (NK) cell, or Natural killer T (NKT) cell population.

In some embodiments, the modified IL-2 polypeptide comprising a mutation at K35 corresponding to residue position 35, of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue T37 corresponding to a position 37 of SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some instances, the conjugating moiety is bound to an amino acid residue selected from an amino acid position A1, P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, I92, L94, E95, K97, G98, S99, E100, T101, T102, F103, M104, C105, E106, Y107, A108, D109, E110, T111, A112, T113, E116, N119, R120, T123, A125, Q126, S127, S130, T131, L132, and T133, in which the numbering of the amino acid residues corresponds to SEQ ID NO: 1. In some instances, the amino acid position is selected from K8, K9, Q11, L12, E15, H16, L18, L19, D20, Q22, M23, N26, R81, D84, S87, N88, V91, I92, L94, E95, E116, N119, R120, T123, A125, Q126, S127, S130, T131, L132, and T133. In some instances, the amino acid position is selected from A1, P2, T3, S4, S5, S6, T7, G27, N29, N30, Y31, K32, K35, T37, M46, K47, K48, A50, T51, E52, K53, H55, Q57, E60, E67, N71, Q74, S75, K76, N77, F78, H79, P82, R83, N89, K97, G98, S99, E100, T101, T102, F103, M104, C105, E106, Y107, A108, D109, E110, T111, A112, and T113. In some instances, the amino acid position is selected from K8, K9, L12, E15, H16, L19, D20, Q22, M23, N26, D84, N88, E95, and Q126. In some instances, the amino acid position is selected from K8, K9, and H16. In some instances, the amino acid position is selected from Q22, N26, N88, and Q126. In some instances, the amino acid position is selected from E15, D20, D84, and E95. In some instances, the amino acid position is selected from L12, L19, and M23. In some instances, the amino acid position is selected from Q22 and N26. In some cases, the amino acid position is at K8. In some cases, the amino acid position is at K9. In some cases, the amino acid position is at Q11. In some cases, the amino acid position is at L12. In some cases, the amino acid position is at E15. In some cases, the amino acid position is at H16. In some cases, the amino acid position is at L18. In some cases, the amino acid position is at L19. In some cases, the amino acid position is at D20. In some cases, the amino acid position is at Q22. In some cases, the amino acid position is at M23. In some cases, the amino acid position is at N26. In some cases, the amino acid position is at R81. In some cases, the amino acid position is at D84. In some cases, the amino acid position is at S87. In some cases, the amino acid position is at N88. In some cases, the amino acid position is at V91. In some cases, the amino acid position is at I92. In some cases, the amino acid position is at L94. In some cases, the amino acid position is at E95. In some cases, the amino acid position is at E116. In some cases, the amino acid position is at N119.

In some cases, the amino acid position is at R120. In some cases, the amino acid position is at T123. In some cases, the amino acid position is at A125. In some cases, the amino acid position is at Q126. In some cases, the amino acid position is at 5127. In some cases, the amino acid position is at S130. In some cases, the amino acid position is at T131. In some cases, the amino acid position is at L132. In some cases, the amino acid position is at T133.

In some instances, the IL-2 conjugate further comprises an additional mutation. In such cases, the amino acid is conjugated to an additional conjugating moiety for increase in serum half-life, stability, or a combination thereof. Alternatively, the amino acid is first mutated to a natural amino acid such as lysine, cysteine, histidine, arginine, aspartic acid, glutamic acid, serine, threonine, or tyrosine; or to an unnatural amino acid prior to binding to the additional conjugating moiety.

In some embodiments, the IL-2 conjugate has a decreased binding affinity to IL-2 receptor β (IL-2Rβ) subunit, IL-2 receptor α (IL-2Rγ) subunit, or a combination thereof, of the IL-2Rαβγ complex, relative to a wild-type IL-2 polypeptide. In some instances, the decreased affinity of the IL-2 conjugate to IL-2 receptor β. (IL-2Rβ) subunit, IL-2 receptor γ (IL-2Rγ) subunit, or a combination thereof, relative to a wild-type IL-2 polypeptide, is about 10%, 20%, 30%, 40%, 50%, 60%, 70%, 80%, 90%, 95%, 99%, or greater than 99%. In some cases, the decreased affinity is about 10%. In some cases, the decreased affinity is about 20%. In some cases, the decreased affinity is about 40%. In some cases, the decreased affinity is about 50%. In some cases, the decreased affinity is about 60%. In some cases, the decreased affinity is about 80%. In some cases, the decreased affinity is about 90%. In some cases, the decreased affinity is about 99%. In some cases, the decreased affinity is greater than 99%. In some cases, the decreased affinity is about 80%. In some cases, the decreased affinity is about 100%.

In some embodiments, the decreased binding affinity of the IL-2 conjugate to IL-2 receptor β(IL-2Rβ) subunit, IL-2 receptor γ (IL-2Rγ) subunit, or a combination thereof, relative to a wild-type IL-2 polypeptide, is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1,000-fold, or more. In some cases, the decreased affinity is about 1-fold. In some cases, the decreased affinity is about 2-fold. In some cases, the decreased affinity is about 4-fold. In some cases, the decreased affinity is about 5-fold. In some cases, the decreased affinity is about 6-fold. In some cases, the decreased affinity is about 8-fold. In some cases, the decreased affinity is about 10-fold. In some cases, the decreased affinity is about 30-fold. In some cases, the decreased affinity is about 50-fold. In some cases, the decreased affinity is about 100-fold. In some cases, the decreased affinity is about 300-fold. In some cases, the decreased affinity is about 500-fold. In some cases, the decreased affinity is about 1000-fold. In some cases, the decreased affinity is more than 1,000-fold.

In some embodiments, the IL-2 conjugate has a reduced IL-2Rγ subunit recruitment to the IL-2/IL-2Rβ complex. In some cases, the reduced recruitment is compared to an IL-2Rγ subunit recruitment by an equivalent IL-2 polypeptide without the unnatural amino acid (e.g., a wild-type IL-2 polypeptide). In some cases, the decrease in IL-2Rγ subunit recruitment is about 10%, 20%, 30%, 40%, 50%, 60%, 70%, 80%, 90%, 95%, 99%, or greater than 99% decrease relative to an equivalent IL-2 polypeptide without the unnatural amino acid modification. In some cases, the decrease in IL-2Rγ subunit recruitment is about 10%. In some cases, the decrease in IL-2Rγ subunit recruitment is about 20%. In some cases, the decrease in IL-2Rγ subunit recruitment is about 40%. In some cases, the decrease in IL-2Rγ subunit recruitment is about 50%. In some cases, the decrease in IL-2Rγ subunit recruitment is about 60%. In some cases, the decrease in IL-2Rγ subunit recruitment is about 70%. In some cases, the decrease in IL-2Rγ subunit recruitment is about 80%. In some cases, the decrease in IL-2Rγ subunit recruitment is about 90%. In some cases, the decrease in IL-2Rγ subunit recruitment is about 99%. In some cases, the decrease in IL-2Rγ subunit recruitment is greater than 99%. In some cases, the decrease in IL-2Rγ subunit recruitment is about 100%. In some instances, the IL-2 conjugate further has an increase in IL-2Rα subunit recruitment.

In some embodiments, the decrease in IL-2Rγ subunit recruitment is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1,000-fold, or more relative to an equivalent IL-2 polypeptide without the unnatural amino acid modification (e.g., a wild-type IL-2 polypeptide). In some cases, the decrease in IL-2Rγ subunit recruitment is about 1-fold. In some cases, the decrease in IL-2Rγ subunit recruitment is about 2-fold. In some cases, the decrease in IL-2Rγ subunit recruitment is about 4-fold. In some cases, the decrease in IL-2Rγ subunit recruitment is about 5-fold. In some cases, the decrease in IL-2Rγ subunit recruitment is about 6-fold. In some cases, the decrease in IL-2Rγ subunit recruitment is about 8-fold. In some cases, the decrease in IL-2Rγ subunit recruitment is about 10-fold. In some cases, the decrease in IL-2Rγ subunit recruitment is about 30-fold. In some cases, the decrease in IL-2Rγ subunit recruitment is about 50-fold. In some cases, the decrease in IL-2Rγ subunit recruitment is about 100-fold. In some cases, the decrease in IL-2Rγ subunit recruitment is about 300-fold. In some cases, the decrease in IL-2Rγ subunit recruitment is about 500-fold. In some cases, the decrease in IL-2Rγ subunit recruitment is about 1000-fold. In some cases, the decrease in IL-2Rγ subunit recruitment is more than 1,000-fold. In some instances, the IL-2 conjugate further has an increase in IL-2Rα subunit recruitment.

In some embodiments, the IL-2 conjugate has an increase in IL-2Rα subunit recruitment to the IL-2 polypeptide. In some cases, the reduced recruitment is compared to an IL-2Rα subunit recruitment by an equivalent IL-2 polypeptide without the unnatural amino acid (e.g., a wild-type IL-2 polypeptide). In some cases, the increase in IL-2Rα subunit recruitment is about 10%, 20%, 30%, 40%, 50%, 60%, 70%, 80%, 90%, 95%, 99%, or greater than 99% increase relative to an equivalent IL-2 polypeptide without the unnatural amino acid modification. In some cases, the increase in IL-2Rα subunit recruitment is about 10%. In some cases, the increase in IL-2Rα subunit recruitment is about 20%. In some cases, the increase in IL-2Rα subunit recruitment is about 40%. In some cases, the increase in IL-2Rα subunit recruitment is about 50%. In some cases, the increase in IL-2Rα subunit recruitment is about 60%. In some cases, the increase in IL-2Rα subunit recruitment is about 70%. In some cases, the increase in IL-2Rα subunit recruitment is about 80%. In some cases, the increase in IL-2Rα subunit recruitment is about 90%. In some cases, the increase in IL-2Rα subunit recruitment is about 99%. In some cases, the increase in IL-2Rα subunit recruitment is greater than 99%. In some cases, the increase in IL-2Rα subunit recruitment is about 100%. In some instances, the IL-2 conjugate further has a decrease in recruitment of an IL-2Rβ subunit and/or IL-2Rγ subunit.

In some embodiments, the increase in IL-2Rα subunit recruitment is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1,000-fold, or more relative to an equivalent IL-2 polypeptide without the unnatural amino acid modification (e.g., a wild-type IL-2 polypeptide). In some cases, the increase in IL-2Rα subunit recruitment is about 1-fold. In some cases, the increase in IL-2Rα subunit recruitment is about 2-fold. In some cases, the increase in IL-2Rα subunit recruitment is about 4-fold. In some cases, the increase in IL-2Rα subunit recruitment is about 5-fold. In some cases, the increase in IL-2Rα subunit recruitment is about 6-fold. In some cases, the increase in IL-2Rα subunit recruitment is about 8-fold. In some cases, the increase in IL-2Rα subunit recruitment is about 10-fold. In some cases, the increase in IL-2Rα subunit recruitment is about 30-fold. In some cases, the increase in IL-2Rα subunit recruitment is about 50-fold. In some cases, the increase in IL-2Rα subunit recruitment is about 100-fold. In some cases, the increase in IL-2Rα subunit recruitment is about 300-fold. In some cases, the increase in IL-2Rα subunit recruitment is about 500-fold. In some cases, the increase in IL-2Rα subunit recruitment is about 1000-fold. In some cases, the increase in IL-2Rα subunit recruitment is more than 1,000-fold. In some instances, the IL-2 conjugate further has a decrease in recruitment of an IL-2Rβ subunit and/or IL-2Rγ subunit.

In some embodiments, an IL-2 polypeptide described herein has a decrease in receptor signaling potency to IL-2Rβγ. In some instances, the decrease in receptor signaling potency is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1000-fold, or more to IL-2Rβγ relative to a wild-type IL-2 polypeptide. In some cases, the decrease in receptor signaling potency is about 2-fold. In some cases, the decrease in receptor signaling potency is about 5-fold. In some cases, the decrease in receptor signaling potency is about 10-fold. In some cases, the decrease in receptor signaling potency is about 20-fold. In some cases, the decrease in receptor signaling potency is about 30-fold. In some cases, the decrease in receptor signaling potency is about 40-fold. In some cases, the decrease in receptor signaling potency is about 50-fold. In some cases, the decrease in receptor signaling potency is about 100-fold. In some cases, the decrease in receptor signaling potency is about 200-fold. In some cases, the decrease in receptor signaling potency is about 300-fold. In some cases, the decrease in receptor signaling potency is about 400-fold. In some cases, the decrease in receptor signaling potency is about 500-fold. In some cases, the decrease in receptor signaling potency is about 1000-fold.

In some instances, the receptor signaling potency is measured by an EC50 value. In some cases, the decrease in receptor signaling potency is an increase in EC50. In some instances, the increase in EC50 is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1000-fold, or more relative to a wild-type IL-2 polypeptide.

In some instances, the receptor signaling potency is measured by an ED50 value. In some cases, the decrease in receptor signaling potency is an increase in ED50. In some instances, the increase in ED50 is about 1-fold, 2-fold, 3-fold, 4-fold, 5-fold, 6-fold, 7-fold, 8-fold, 9-fold, 10-fold, 30-fold, 50-fold, 100-fold, 200-fold, 300-fold, 400-fold, 500-fold, 1000-fold, or more relative to a wild-type IL-2 polypeptide.

In some embodiments, an IL-2 polypeptide described herein has an expanded therapeutic window compared to a therapeutic window of a wild-type IL-2 polypeptide. In some instances, the expanded therapeutic window is due to a decrease in binding between the IL-2 polypeptide and interleukin 2 receptor βγ (IL-2Rβγ), a decrease in receptor signaling potency to IL-2Rβγ, a decrease in recruitment of an IL-2Rγ subunit to the IL-2/IL-2Rβ complex, or an increase in recruitment of an IL-2Rα subunit to the IL-2 polypeptide. In some instances, the IL-2 polypeptide does not have an impaired activation of interleukin 2 αβγ receptor (IL-2Rαβγ).

In some embodiments, the modified IL-2 polypeptide exhibits a first receptor signaling potency to an IL-2βγ signaling complex and a second receptor signaling potency to an IL-2αβγ signaling complex, and wherein a difference between the first receptor signaling potency and the second receptor signaling potency is at least 1-fold. In some instances, the difference is at least 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 1000-fold, or more. In some instances, the first receptor signaling potency is less than the second receptor signaling potency. In some instances, the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, 1000-fold, or lower than the second receptor signaling potency. In some cases, the modified IL-2 polypeptide has a lower receptor signaling potency to an IL-2βγ signaling complex than a second receptor signaling potency to an IL-2αβγ signaling complex. In some cases, the first receptor signaling potency of the modified IL-2 polypeptide is at least 1-fold lower than a receptor signaling potency of the wild-type IL-2 polypeptide. In some cases, the first receptor signaling potency of the modified IL-2 polypeptide is at least 2-fold, 3-fold, 4-fold, 5-fold, 10-fold, 20-fold, 50-fold, 100-fold, 200-fold, or 500-fold lower than a receptor signaling potency of the wild-type IL-2 polypeptide. In some cases, the first receptor signaling potency and the second receptor signaling potency are both lower that the respective potencies of the wild-type IL-2 polypeptide, but the first receptor signaling potency is lower than the second receptor signaling potency. In some cases, the difference between the first receptor signaling potency and the second receptor signaling potency increases the therapeutic window for the modified IL-2 polypeptide.

In some instances, the conjugating moiety impairs or blocks the receptor signaling potency of IL-2 with IL-2Rβγ, or reduces recruitment of the IL-2Rγ subunit to the IL-2/IL-2Rβ complex.

In some instances, the modified IL-2 polypeptide with the decrease in receptor signaling potency to IL-2Rβγ is capable of expanding CD4+ T regulatory (Treg) cells.

In some embodiments, CD4+ Treg cell proliferation by the modified IL-2/IL-2Rαβγ complex is equivalent or greater to that of a wild-type IL-2 polypeptide.

In some embodiments, the IL-2/IL-2Rαβγ complex induces proliferation of the CD4+ Treg cells to a population that is sufficient to modulate a disease course in an animal model.

In some embodiments, described herein is an interleukin 2 αβγ receptor (IL-2Rαβγ) binding protein, wherein the receptor signaling potency for an interleukin 2 βγ receptor (IL-2Rβγ) of said binding protein is less than that of wild-type human IL-2 (hIL-2), and wherein said binding protein comprises at least one unnatural amino acid. In some cases, said binding protein is a modified IL-2 polypeptide or a functionally active fragment thereof, wherein the modified IL-2 polypeptide comprises at least one unnatural amino acid.

In some embodiments, described herein is an interleukin 2 αβγ receptor (IL-2Rαβγ) binding protein, wherein a recruitment of an IL-2Rγ subunit to an IL-2/IL-2Rβ complex by said binding protein is less than that of wild-type human IL-2 (hIL-2), and wherein said binding protein comprises at least one unnatural amino acid. In some cases, said binding protein is a modified IL-2 polypeptide or a functionally active fragment thereof, wherein the modified IL-2 polypeptide comprises at least one unnatural amino acid.

In some embodiments, described herein is an interleukin 2 αβγ receptor (IL-2Rαβγ) binding protein, wherein the binding affinity for an interleukin 2 βγ receptor (IL-2Rβγ) of said binding protein is less than that of wild-type human IL-2 (ML-2), and wherein said binding protein comprises at least one unnatural amino acid. In such cases, said binding protein is a modified IL-2 polypeptide or a functionally active fragment thereof, wherein the modified IL-2 polypeptide comprises at least one unnatural amino acid.

In some embodiments, described herein is an IL-2/IL-2Rαβγ complex comprising a modified IL-2 polypeptide comprising an unnatural amino acid and an IL-2Rαβγ, wherein the modified IL-2 polypeptide has a reduced receptor signaling potency toward IL-2Rβγ, and wherein the reduced receptor signaling potency is compared to a binding affinity between a wild-type IL-2 polypeptide and IL-2Rβγ. In some cases, the modified IL-2 polypeptide further comprises a conjugating moiety covalently attached to the unnatural amino acid.

In some embodiments, described herein is an IL-2/IL-2Rαβγ complex comprising a modified IL-2 polypeptide comprising an unnatural amino acid and an IL-2Rαβγ, wherein a recruitment of an IL-2Rγ subunit to an IL-2/IL-2Rβ complex by said modified IL-2 polypeptide is less than that of a wild-type IL-2 polypeptide. In some cases, the modified IL-2 polypeptide further comprises a conjugating moiety covalently attached to the unnatural amino acid.

In some embodiments, described herein is an IL-2/IL-2Rαβγ complex comprising a modified IL-2 polypeptide comprising an unnatural amino acid and an IL-2Rαβγ, wherein the modified IL-2 polypeptide has a reduced binding affinity toward IL-2Rβγ, and wherein the reduced binding affinity is compared to a binding affinity between a wild-type IL-2 polypeptide and IL-2Rβγ. In some embodiments, described herein is an IL-2/IL-2Rαβγ complex comprising a modified IL-2 polypeptide comprising an unnatural amino acid and an IL-2Rαβγ, wherein a recruitment of an IL-2Rγ subunit to an IL-2/IL-2Rβ complex by said modified IL-2 polypeptide is less than that of a wild-type IL-2 polypeptide. In some instances, the modified IL-2 polypeptide further comprises a conjugating moiety covalently attached to the unnatural amino acid.

In some embodiments, described herein is a CD4+ Treg cell activator that selectively expands CD4+ Treg cells in a cell population, wherein said activator comprises a modified IL-2 polypeptide comprising at least one unnatural amino acid. In some instances, said activator expands CD8+ effector T cell and/or Natural Killer cells by less than 20%, 15%, 10%, 5%, 1%, or 0.1% in the CD3+ cell population when said activator is in contact with said CD3+ cell population, relative to an expansion of CD8+ effector T cell and/or Natural Killer cells in the CD3+ cell population contacted by a wild-type IL-2 polypeptide. In some instances, said cell population is an in vivo cell population. In some instances, said cell population is an in vitro cell population. In some instances, said cell population is an ex vivo cell population.

In some embodiments, the modified IL-2 polypeptide comprising a mutation at residue K8 corresponding to a position 8 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at resident H15 corresponding to a position 15 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue L18 corresponding to a position 18 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue D19 corresponding to a position 19 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue M22 corresponding to a position 22 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue N25 corresponding to a position 25 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue N87 corresponding to a position 87 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue E99 corresponding to a position 99 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue N118 corresponding to a position 118 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue T122 corresponding to a position 122 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue Q125 corresponding to a position 125 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue S126 corresponding to a position 126 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue T130 corresponding to a position 130 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue D108 and N87 corresponding to positions 108 and 87 of SEQ ID NO: 3, respectively, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

In some embodiments, the modified IL-2 polypeptide comprising a mutation at residue V91 corresponding to a position 91 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, nor has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα.

Cytokines Conjugate Precursors

Described herein are cytokine conjugate precursors, comprising a mutant cytokine (such as IL-2), wherein one or more amino acids have been mutated from the wild type amino acid. Such precursors are often used with the methods described herein for the treatment of diseases or conditions. In some embodiments, a cytokine precursor is not conjugated. Such mutations variously comprise additions, deletions, or substitutions. In some embodiments, the mutation comprises substitution to a different natural amino acid. In some instances, the mutant cytokine comprises a mutation at amino acid position P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, 188, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, and T132, in which the numbering of the amino acid residues corresponds to SEQ ID NO: 3. In some instances, the amino acid position is selected from K8, H15, L18, D19, M22, N25, N87, V90, I91, L93, E94, K96, G97, S98, E99, D108 in the N87R variant, N118, T122, S124, Q125, S126, S129, and T130. In some instances, the amino acid position is selected from K8, H15, L18, D19, M22, N25, N87, V90, E99, D108 in the N87R variant, N118, T122, S124, and T130. In some instances, the amino acid position is selected from K8, H15, L18, D19, M22, N25, N87, V90, and E99. In some instances, the amino acid position is selected from K8, H15, L18, D19, M22, N25, N87, V90, and E99. In some instances, the amino acid position is selected from M22, N25, N87, V90, E99, D108 in the N87R variant, and N118. In some instances, the amino acid position is selected from P1, T2, S3, S4, S5, T6, K7, K8, Q10, L11, E14, H15, L17, L18, D19, Q21, M22, N25, G26, N28, N29, and Y30. In some instances, the amino acid position is selected from E14, H15, L17, and L18. In some instances, the amino acid position is selected from S3, S4, S5, T6, K7, K8, Q10. In some instances, the amino acid position is selected from D19, M22, N25, and N87. In some cases, the amino acid position is at K8. In some cases, the amino acid position is at H15. In some cases, the amino acid position is at L18. In some cases, the amino acid position is at D19. In some cases, the amino acid position is at M22. In some cases, the amino acid position is at N25. In some cases, the amino acid position is at N87. In some cases, the amino acid position is at E99. In some cases, the amino acid position is at N118. In some cases, the amino acid position is at T122. In some cases, the amino acid position is at Q125. In some cases, the amino acid position is at 5126. In some cases, the amino acid position is at T130. In some cases, the amino acid position is at N87 and D108. In some cases, the amino acid position is at V90. In some cases, the amino acid position is at D108. In some embodiments, a cytokine mutant comprises a conjugation moiety, wherein the conjugation moiety is attached to a mutated site in the mutant cytokine.

Cytokine mutants described herein often comprise one or more mutations to natural amino acids. In some embodiments, a cytokine mutant comprises SEQ ID NO: 3, and at least one mutation. In some embodiments, the cytokine mutant comprises SEQ ID NO: 3 and an H15K mutation. In some embodiments, the cytokine mutant comprises SEQ ID NO: 3 and an H15C mutation. In some embodiments, the cytokine mutant comprises SEQ ID NO: 3 and an H15A mutation. In some embodiments, the cytokine mutant comprises SEQ ID NO: 3 and an H15I mutation. In some embodiments, the cytokine mutant comprises SEQ ID NO: 3 and an H15L mutation. In some embodiments, the cytokine mutant comprises SEQ ID NO: 3 and an H15Y mutation. In some embodiments, the cytokine mutant comprises SEQ ID NO: 3 and an H15W mutation. In some embodiments, the cytokine mutant comprises SEQ ID NO: 3 and an H15N mutation. In some embodiments, the cytokine mutant comprises SEQ ID NO: 3 and an H15R mutation. In some embodiments, the cytokine mutant comprises SEQ ID NO: 3 and an H15D mutation. In some embodiments, the cytokine mutant comprises SEQ ID NO: 3 and an H15Q mutation. In some embodiments, the cytokine mutant comprises SEQ ID NO: 3 and an H15G mutation. In some embodiments, the cytokine mutant comprises SEQ ID NO: 3 and an H15H mutation. In some embodiments, the cytokine mutant comprises SEQ ID NO: 3 and an H15M mutation. In some embodiments, the cytokine mutant comprises SEQ ID NO: 3 and an H15F mutation. In some embodiments, the cytokine mutant comprises SEQ ID NO: 3 and an H15P mutation. In some embodiments, the cytokine mutant comprises SEQ ID NO: 3 and an H15S mutation. In some embodiments, the cytokine mutant comprises SEQ ID NO: 3 and an H15T mutation. In some embodiments, the cytokine mutant comprises SEQ ID NO: 3 and an H15V mutation.

Cytokine mutants described herein often comprise one or more mutations to natural amino acids. In some embodiments, a cytokine mutant comprises SEQ ID NO: 3, and at least one mutation. In some embodiments, the cytokine mutant comprises SEQ ID NO: 3 and an N87K mutation. In some embodiments, the cytokine mutant comprises SEQ ID NO: 3 and an N87C mutation. In some embodiments, the cytokine mutant comprises SEQ ID NO: 3 and an N87A mutation. In some embodiments, the cytokine mutant comprises SEQ ID NO: 3 and an N87I mutation. In some embodiments, the cytokine mutant comprises SEQ ID NO: 3 and an N87L mutation. In some embodiments, the cytokine mutant comprises SEQ ID NO: 3 and an N87Y mutation. In some embodiments, the cytokine mutant comprises SEQ ID NO: 3 and an N87W mutation. In some embodiments, the cytokine mutant comprises SEQ ID NO: 3 and an N87N mutation. In some embodiments, the cytokine mutant comprises SEQ ID NO: 3 and an N87R mutation. In some embodiments, the cytokine mutant comprises SEQ ID NO: 3 and an N87D mutation. In some embodiments, the cytokine mutant comprises SEQ ID NO: 3 and an N87Q mutation. In some embodiments, the cytokine mutant comprises SEQ ID NO: 3 and an N87G mutation. In some embodiments, the cytokine mutant comprises SEQ ID NO: 3 and an N87H mutation. In some embodiments, the cytokine mutant comprises SEQ ID NO: 3 and an N87M mutation. In some embodiments, the cytokine mutant comprises SEQ ID NO: 3 and an N87F mutation. In some embodiments, the cytokine mutant comprises SEQ ID NO: 3 and an N87P mutation. In some embodiments, the cytokine mutant comprises SEQ ID NO: 3 and an N87S mutation. In some embodiments, the cytokine mutant comprises SEQ ID NO: 3 and an N87T mutation. In some embodiments, the cytokine mutant comprises SEQ ID NO: 3 and an N87V mutation.

Cytokine mutants described herein often comprise one or more mutations to natural amino acids. In some embodiments, a cytokine mutant comprises SEQ ID NO: 3, and at least one mutation. In some embodiments, the cytokine mutant comprises SEQ ID NO: 3 and an Q125K mutation. In some embodiments, the cytokine mutant comprises SEQ ID NO: 3 and an Q125C mutation. In some embodiments, the cytokine mutant comprises SEQ ID NO: 3 and an Q125A mutation. In some embodiments, the cytokine mutant comprises SEQ ID NO: 3 and an Q125I mutation. In some embodiments, the cytokine mutant comprises SEQ ID NO: 3 and an Q125L mutation. In some embodiments, the cytokine mutant comprises SEQ ID NO: 3 and an Q125Y mutation. In some embodiments, the cytokine mutant comprises SEQ ID NO: 3 and an Q125W mutation. In some embodiments, the cytokine mutant comprises SEQ ID NO: 3 and an Q125N mutation. In some embodiments, the cytokine mutant comprises SEQ ID NO: 3 and an Q125R mutation. In some embodiments, the cytokine mutant comprises SEQ ID NO: 3 and an Q125D mutation. In some embodiments, the cytokine mutant comprises SEQ ID NO: 3 and an Q125Q mutation. In some embodiments, the cytokine mutant comprises SEQ ID NO: 3 and an Q125G mutation. In some embodiments, the cytokine mutant comprises SEQ ID NO: 3 and an Q125H mutation. In some embodiments, the cytokine mutant comprises SEQ ID NO: 3 and an Q125M mutation. In some embodiments, the cytokine mutant comprises SEQ ID NO: 3 and an Q125F mutation. In some embodiments, the cytokine mutant comprises SEQ ID NO: 3 and an Q125P mutation. In some embodiments, the cytokine mutant comprises SEQ ID NO: 3 and an Q125S mutation. In some embodiments, the cytokine mutant comprises SEQ ID NO: 3 and an Q125T mutation. In some embodiments, the cytokine mutant comprises SEQ ID NO: 3 and an Q125V mutation.

Cytokine mutants described herein often comprise one or more mutations to natural amino acids. In some embodiments, a cytokine mutant comprises SEQ ID NO: 3, and at least one mutation. In some embodiments, the cytokine mutant comprises SEQ ID NO: 3 and an L18K mutation. In some embodiments, the cytokine mutant comprises SEQ ID NO: 3 and an L18C mutation. In some embodiments, the cytokine mutant comprises SEQ ID NO: 3 and an L18A mutation. In some embodiments, the cytokine mutant comprises SEQ ID NO: 3 and an L18I mutation. In some embodiments, the cytokine mutant comprises SEQ ID NO: 3 and an L18L mutation. In some embodiments, the cytokine mutant comprises SEQ ID NO: 3 and an L18Y mutation. In some embodiments, the cytokine mutant comprises SEQ ID NO: 3 and an L18W mutation. In some embodiments, the cytokine mutant comprises SEQ ID NO: 3 and an L18N mutation. In some embodiments, the cytokine mutant comprises SEQ ID NO: 3 and an L18R mutation. In some embodiments, the cytokine mutant comprises SEQ ID NO: 3 and an L18D mutation. In some embodiments, the cytokine mutant comprises SEQ ID NO: 3 and an L18Q mutation. In some embodiments, the cytokine mutant comprises SEQ ID NO: 3 and an L18G mutation. In some embodiments, the cytokine mutant comprises SEQ ID NO: 3 and an L18H mutation. In some embodiments, the cytokine mutant comprises SEQ ID NO: 3 and an L18M mutation. In some embodiments, the cytokine mutant comprises SEQ ID NO: 3 and an L18F mutation. In some embodiments, the cytokine mutant comprises SEQ ID NO: 3 and an L18P mutation. In some embodiments, the cytokine mutant comprises SEQ ID NO: 3 and an L18S mutation. In some embodiments, the cytokine mutant comprises SEQ ID NO: 3 and an L18T mutation. In some embodiments, the cytokine mutant comprises SEQ ID NO: 3 and an L18V mutation.

Protein or Peptide Fusions

In some embodiments, a cytokine conjugate described herein comprises a cytokine (e.g., IL-2, or other cytokine) that is fused to a peptide or protein (fusion). In some embodiments, the peptide or protein is an antibody or antibody fragment. In some embodiments, a cytokine conjugate described herein comprises a cytokine (e.g., IL-2, or other cytokine) that is fused to an antibody, or its binding fragments thereof. In some embodiments, a cytokine described herein is fused to multiple proteins or peptides. In some embodiments, a cytokine conjugate comprises a cytokine fusion to a protein or peptide, and at least one conjugating moiety. In some instances, an antibody or its binding fragments thereof comprise a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. Such fusion proteins in some instances are generated directly through translation. In some embodiments, fusions are generated using chemical or other enzymatic ligation method. In some embodiments, a cytokine conjugate comprises a fused peptide or protein is attached by a linker. In some embodiments, the linker is a peptide. In some embodiments, a cytokine conjugate comprises an N-terminal peptide or protein fusion. In some embodiments, a cytokine conjugate comprises a C-terminal peptide or protein fusion. In some cases, the cytokine fused to the peptide or protein is further conjugated to one or more conjugation moieties described below.

In some instances, the cytokine conjugate comprises a fusion to an scFv, bis-scFv, (scFv)$_2$, dsFv, or sdAb fusion. In some cases, the fusion comprises a scFv. In some cases, the cytokine conjugate comprises a fusion to bis-scFv. In some cases, the cytokine conjugate comprises a fusion to (scFv)$_2$. In some cases, the cytokine conjugate comprises a fusion to dsFv. In some cases, the cytokine conjugate comprises a fusion to sdAb. In some cases, the cytokine fused to the scFv, bis-scFv, (scFv)$_2$, dsFv, or sdAb is further conjugated to one or more conjugation moieties described below.

In some instances, the cytokine conjugate comprises a fusion to an Fc portion of an antibody, e.g., of IgG, IgA, IgM, IgE, or IgD. In some instances, the cytokine conjugate comprises a fusion to an Fc portion of IgG (e.g., $IgG_1$, $IgG_3$, or $IgG_4$). In some cases, the cytokine fused to the Fc portion is further conjugated to one or more conjugation moieties described below.

In some cases, a cytokine (e.g., an interleukin, IFN, or TNF) polypeptide is fused to an antibody, or its binding fragments thereof. In some cases, the cytokine polypeptide is fused to a humanized antibody or binding fragment thereof, murine antibody or binding fragment thereof, chimeric antibody or binding fragment thereof, monoclonal antibody or binding fragment thereof, monovalent Fab', divalent $Fab_2$, $F(ab)'_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the cytokine polypeptide is fused to an Fc portion of an antibody. In additional cases, the cytokine polypeptide is fused to an Fc portion of IgG (e.g., $IgG_1$, $IgG_3$, or $IgG_4$). In some cases, the cytokine fused to the antibody, or its binding fragments thereof is further conjugated to one or more conjugation moieties described below.

In some cases, an IL-2 polypeptide is fused to an antibody, or its binding fragments thereof. In some cases, the IL-2 polypeptide is fused to a humanized antibody or binding fragment thereof, murine antibody or binding fragment thereof, chimeric antibody or binding fragment thereof, monoclonal antibody or binding fragment thereof, monovalent Fab', divalent $Fab_2$, $F(ab)'_3$ fragments, single-chain variable fragment (scFv), bis-scFv, $(scFv)_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the IL-2 polypeptide is fused to an Fc portion of an antibody. In additional cases, the IL-2 polypeptide is fused to an Fc portion of IgG (e.g., $IgG_1$, $IgG_3$, or $IgG_4$). In some cases, the IL-2 polypeptide fused to the antibody, or its binding fragments thereof is further conjugated to one or more conjugation moieties described below.

Natural and Unnatural Amino Acids

In some embodiments, an amino acid residue described herein (e.g., within a cytokine such as IL-2) is mutated to lysine, cysteine, histidine, arginine, aspartic acid, glutamic acid, serine, threonine, or tyrosine prior to binding to (or reacting with) a conjugating moiety. For example, the side chain of lysine, cysteine, histidine, arginine, aspartic acid, glutamic acid, serine, threonine, or tyrosine may bind to a conjugating moiety described herein. In some instances, the amino acid residue is mutated to cysteine, lysine, or histidine. In some cases, the amino acid residue is mutated to cysteine. In some cases, the amino acid residue is mutated to lysine. In some cases, the amino acid residue is mutated to histidine. In some cases, the amino acid residue is mutated to tyrosine. In some cases, the amino acid residue is mutated to tryptophan. In some embodiments, an unnatural amino acid is not conjugated with a conjugating moiety. In some embodiments, a cytokine described herein comprises an unnatural amino acid, wherein the cytokine is conjugated to the protein, wherein the point of attachment is not the unnatural amino acid.

In some embodiments, an amino acid residue described herein (e.g., within a cytokine such as IL-2) is mutated to an unnatural amino acid prior to binding to a conjugating moiety. In some cases, the mutation to an unnatural amino acid prevents or minimizes a self-antigen response of the immune system. As used herein, the term "unnatural amino acid" or "non-canonical amino acid" refers to an amino acid other than the 20 amino acids that occur naturally in protein. Non-limiting examples of unnatural amino acids include: p-acetyl-L-phenylalanine, p-iodo-L-phenylalanine, p-methoxyphenylalanine, O-methyl-L-tyrosine, p-propargyloxyphenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, o-azido-L-phenylalanine, m-azido-L-phenylalanine, p-azido-L-phenylalanine, p-acyl-L-phenylalanine, p-benzoyl-L-phenylalanine, p-Boronophenylalanine, O-propargyltyrosine, L-phosphoserine, phosphonoserine, phosphonotyrosine, p-bromophenylalanine, selenocysteine, p-amino-L-phenylalanine, isopropyl-L-phenylalanine, N6-(2-azidoethoxy)-carbonyl-L-lysine (AzK; the chemical structure of which is shown as compound 90 in FIG. 3C), an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynyl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an a-hydroxy containing acid; an amino thio acid; an a, a disubstituted amino acid; a β-amino acid; a cyclic amino acid other than proline or histidine, and an aromatic amino acid other than phenylalanine, tyrosine or tryptophan.

In some embodiments, the unnatural amino acid comprises a selective reactive group, or a reactive group for site-selective labeling of a target polypeptide. In some instances, the chemistry is a biorthogonal reaction (e.g., biocompatible and selective reactions). In some cases, the chemistry is a Cu(I)-catalyzed or "copper-free" alkyne-azide triazole-forming reaction, the Staudinger ligation, inverse-electron-demand Diels-Alder (IEDDA) reaction, "photoclick" chemistry, or a metal-mediated process such as olefin metathesis and Suzuki-Miyaura or Sonogashira cross-coupling.

In some embodiments, the unnatural amino acid comprises a photoreactive group, which crosslinks, upon irradiation with, e.g., UV.

In some embodiments, the unnatural amino acid comprises a photo-caged amino acid.

In some instances, the unnatural amino acid is a para-substituted, meta-substituted, or an ortho-substituted amino acid derivative.

In some instances, the unnatural amino acid comprises p-acetyl-L-phenylalanine, o-azidomethyl-L-phenylalanine, m-azidomethyl-L-phenylalanine, p-azidomethyl-L-phenylalanine (pAMF), p-iodo-L-phenylalanine, O-methyl-L-tyrosine, p-methoxyphenylalanine, p-propargyloxyphenylalanine, o-propargyl-phenylalanine, m-propargyl-phenylalanine, p-propargyl-phenylalanine, L-3-(2-naphthyl)alanine, 3-methyl-phenylalanine, O-4-allyl-L-tyrosine, 4-propyl-L-tyrosine, tri-O-acetyl-GlcNAcp-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-bromophenylalanine, p-amino-L-phenylalanine, or isopropyl-L-phenylalanine.

In some cases, the unnatural amino acid is 3-aminotyrosine, 3-nitrotyrosine, 3,4-dihydroxyphenylalanine, or 3-iodotyrosine.

In some cases, the unnatural amino acid is phenylselenocysteine.

In some instances, the unnatural amino acid is a benzophenone, ketone, iodide, methoxy, acetyl, benzoyl, or azide containing phenylalanine derivative.

In some instances, the unnatural amino acid is a benzophenone, ketone, iodide, methoxy, acetyl, benzoyl, or azide containing lysine derivative.

In some instances, the unnatural amino acid comprises an aromatic side chain.

In some instances, the unnatural amino acid does not comprise an aromatic side chain.

In some instances, the unnatural amino acid comprises an azido group.

In some instances, the unnatural amino acid comprises a Michael-acceptor group. In some instances, Michael-acceptor groups comprise an unsaturated moiety capable of forming a covalent bond through a 1,2-addition reaction. In some instances, Michael-acceptor groups comprise electron-deficient alkenes or alkynes. In some instances, Michael-acceptor groups include but are not limited to alpha,beta unsaturated: ketones, aldehydes, sulfoxides, sulfones, nitriles, imines, or aromatics.

In some instances, the unnatural amino acid is dehydroalanine.

In some instances, the unnatural amino acid comprises an aldehyde or ketone group.

In some instances, the unnatural amino acid is a lysine derivative comprising an aldehyde or ketone group.

In some instances, the unnatural amino acid is a lysine derivative comprising one or more O, N, Se, or S atoms at the beta, gamma, or delta position. In some instances, the unnatural amino acid is a lysine derivative comprising O, N, Se, or S atoms at the gamma position.

In some instances, the unnatural amino acid is a lysine derivative wherein the epsilon N atom is replaced with an oxygen atom.

In some instances, the unnatural amino acid is a lysine derivative that is not naturally-occurring post-translationally modified lysine.

In some instances, the unnatural amino acid is an amino acid comprising a side chain, wherein the sixth atom from the alpha position comprises a carbonyl group. In some instances, the unnatural amino acid is an amino acid comprising a side chain, wherein the sixth atom from the alpha position comprises a carbonyl group, and the fifth atom from the alpha position is a nitrogen. In some instances, the unnatural amino acid is an amino acid comprising a side chain, wherein the seventh atom from the alpha position is an oxygen atom.

In some instances, the unnatural amino acid is a serine derivative comprising selenium. In some instances, the unnatural amino acid is selenoserine (2-amino-3-hydroselenopropanoic acid). In some instances, the unnatural amino acid is 2-amino-3-((2-((3-(benzyloxy)-3-oxopropyl)amino)ethyl)selanyl)propanoic acid. In some instances, the unnatural amino acid is 2-amino-3-(phenylselanyl)propanoic acid. In some instances, the unnatural amino acid comprises selenium, wherein oxidation of the selenium results in the formation of an unnatural amino acid comprising an alkene.

In some instances, the unnatural amino acid comprises a cyclooctynyl group.

In some instances, the unnatural amino acid comprises a transcyclooctenyl group.

In some instances, the unnatural amino acid comprises a norbornenyl group.

In some instances, the unnatural amino acid comprises a cyclopropenyl group.

In some instances, the unnatural amino acid comprises a diazirine group.

In some instances, the unnatural amino acid comprises a tetrazine group.

In some instances, the unnatural amino acid is a lysine derivative, wherein the side-chain nitrogen is carbamylated. In some instances, the unnatural amino acid is a lysine derivative, wherein the side-chain nitrogen is acylated. In some instances, the unnatural amino acid is 2-amino-6-{[(tert-butoxy)carbonyl]amino}hexanoic acid. In some instances, the unnatural amino acid is 2-amino-6-{[(tert-butoxy)carbonyl]amino}hexanoic acid. In some instances, the unnatural amino acid is N6-Boc-N6-methyllysine. In some instances, the unnatural amino acid is N6-acetyllysine. In some instances, the unnatural amino acid is pyrrolysine. In some instances, the unnatural amino acid is N6-trifluoroacetyllysine. In some instances, the unnatural amino acid is 2-amino-6-{[(benzyloxy)carbonyl]amino}hexanoic acid. In some instances, the unnatural amino acid is 2-amino-6-{[(p-iodobenzyloxy)carbonyl]amino}hexanoic acid. In some instances, the unnatural amino acid is 2-amino-6-{[(p-nitrobenzyloxy)carbonyl]amino}hexanoic acid. In some instances, the unnatural amino acid is N6-prolyllysine. In some instances, the unnatural amino acid is 2-amino-6-{[(cyclopentyloxy)carbonyl]amino}hexanoic acid. In some instances, the unnatural amino acid is N6-(cyclopentanecarbonyl)lysine. In some instances, the unnatural amino acid is N6-(tetrahydrofuran-2-carbonyl)lysine. In some instances, the unnatural amino acid is N6-(3-ethynyltetrahydrofuran-2-carbonyl)lysine. In some instances, the unnatural amino acid is N6-((prop-2-yn-1-yloxy)carbonyl)lysine. In some instances, the unnatural amino acid is 2-amino-6-{[(2-azidocyclopentyloxy)carbonyl]amino}hexanoic acid. In some instances, the unnatural amino acid is N6-(2-azidoethoxy)-carbonyl-lysine. In some instances, the unnatural amino acid is 2-amino-6-{[(2-nitrobenzyloxy)carbonyl]amino}hexanoic acid. In some instances, the unnatural amino acid is 2-amino-6-{[(2-cyclooctynyloxy)carbonyl]amino}hexanoic acid. In some instances, the unnatural amino acid is N6-(2-aminobut-3-ynoyl)lysine. In some instances, the unnatural amino acid is 2-amino-6-((2-aminobut-3-ynoyl)oxy)hexanoic acid. In some instances, the unnatural amino acid is N6-(allyloxycarbonyl)lysine. In some instances, the unnatural amino acid is N6-(butenyl-4-oxycarbonyl)lysine. In some instances, the unnatural amino acid is N6-(pentenyl-5-oxycarbonyl)lysine. In some instances, the unnatural amino acid is N6-((but-3-yn-1-yloxy)carbonyl)-lysine. In some instances, the unnatural amino acid is N6-((pent-4-yn-1-yloxy)carbonyl)-lysine. In some instances, the unnatural amino acid is N6-(thiazolidine-4-carbonyl)lysine. In some instances, the unnatural amino acid is 2-amino-8-oxononanoic acid. In some instances, the unnatural amino acid is 2-amino-8-oxooctanoic acid. In some instances, the unnatural amino acid is N6-(2-oxoacetyl)lysine.

In some instances, the unnatural amino acid is N6-propionyllysine. In some instances, the unnatural amino acid is N6-butyryllysine, In some instances, the unnatural amino acid is N6-(but-2-enoyl)lysine. In some instances, the unnatural amino acid is N6-((bicyclo[2.2.1]hept-5-en-2-yloxy)carbonyl)lysine. In some instances, the unnatural amino acid is N6-((spiro[2.3]hex-1-en-5-ylmethoxy)carbonyl)lysine. In some instances, the unnatural amino acid is N6-(((4-(1-(trifluoromethyl)cycloprop-2-en-1-yl)benzyl)oxy)carbonyl)lysine. In some instances, the unnatural amino acid is N6-((bicyclo[2.2.1]hept-5-en-2-ylmethoxy)carbonyl)lysine. In some instances, the unnatural amino acid is cysteinyllysine. In some instances, the unnatural amino acid is N6-((1-(6-nitrobenzo[d][1,3]dioxol-5-yl)ethoxy)carbonyl)lysine. In some instances, the unnatural amino acid is N6-((2-(3-methyl-3H-diazirin-3-yl)ethoxy)carbonyl)lysine. In some instances, the unnatural amino acid is N6-((3-(3-methyl-3H-diazirin-3-yl)propoxy)carbonyl)lysine. In some instances, the unnatural amino acid is N6-((meta nitrobenyloxy)N6-methylcarbonyl)lysine. In some instances, the unnatural amino acid is N6-((bicyclo[6.1.0]non-4-yn-9-ylmethoxy)carbonyl)-lysine. In some instances, the unnatural amino acid is N6-((cyclohept-3-en-1-yloxy)carbonyl)-L-lysine.

In some instances, the unnatural amino acid is 2-amino-3-(((((benzyloxy)carbonyl)amino)methyl)selanyl)propanoic acid.

In some embodiments, the unnatural amino acid is incorporated into the cytokine (e.g., the IL polypeptide) by a repurposed amber, opal, or ochre stop codon.

In some embodiments, the unnatural amino acid is incorporated into the cytokine (e.g., the IL polypeptide) by a 4-base codon.

In some embodiments, the unnatural amino acid is incorporated into the cytokine (e.g., the IL polypeptide) by a repurposed rare sense codon.

In some embodiments, the unnatural amino acid is incorporated into the cytokine (e.g., the IL polypeptide) by a synthetic codon comprising an unnatural nucleic acid.

In some instances, the unnatural amino acid is incorporated into the cytokine by an orthogonal, modified synthetase/tRNA pair. Such orthogonal pairs comprise an unnatural synthetase that is capable of charging the unnatural tRNA with the unnatural amino acid, while minimizing charging of a) other endogenous amino acids onto the unnatural tRNA and b) unnatural amino acids onto other endogenous tRNAs. Such orthogonal pairs comprise tRNAs that are capable of being charged by the unnatural synthetase, while avoiding being charged with a) other endogenous amino acids by endogenous synthetases. In some embodiments, such pairs are identified from various organisms, such as bacteria, yeast, Archaea, or human sources. In some embodiments, an orthogonal synthetase/tRNA pair comprises components from a single organism. In some embodiments, an orthogonal synthetase/tRNA pair comprises components from two different organisms. In some embodiments, an orthogonal synthetase/tRNA pair comprising components that prior to modification, promote translation of two different amino acids. In some embodiments, an orthogonal synthetase is a modified alanine synthetase. In some embodiments, an orthogonal synthetase is a modified arginine synthetase. In some embodiments, an orthogonal synthetase is a modified asparagine synthetase. In some embodiments, an orthogonal synthetase is a modified aspartic acid synthetase. In some embodiments, an orthogonal synthetase is a modified cysteine synthetase. In some embodiments, an orthogonal synthetase is a modified glutamine synthetase. In some embodiments, an orthogonal synthetase is a modified glutamic acid synthetase. In some embodiments, an orthogonal synthetase is a modified alanine glycine. In some embodiments, an orthogonal synthetase is a modified histidine synthetase. In some embodiments, an orthogonal synthetase is a modified leucine synthetase. In some embodiments, an orthogonal synthetase is a modified isoleucine synthetase. In some embodiments, an orthogonal synthetase is a modified lysine synthetase. In some embodiments, an orthogonal synthetase is a modified methionine synthetase. In some embodiments, an orthogonal synthetase is a modified phenylalanine synthetase. In some embodiments, an orthogonal synthetase is a modified proline synthetase. In some embodiments, an orthogonal synthetase is a modified serine synthetase. In some embodiments, an orthogonal synthetase is a modified threonine synthetase. In some embodiments, an orthogonal synthetase is a modified tryptophan synthetase. In some embodiments, an orthogonal synthetase is a modified tyrosine synthetase. In some embodiments, an orthogonal synthetase is a modified valine synthetase. In some embodiments, an orthogonal synthetase is a modified phosphoserine synthetase. In some embodiments, an orthogonal tRNA is a modified alanine tRNA. In some embodiments, an orthogonal tRNA is a modified arginine tRNA. In some embodiments, an orthogonal tRNA is a modified asparagine tRNA. In some embodiments, an orthogonal tRNA is a modified aspartic acid tRNA. In some embodiments, an orthogonal tRNA is a modified cysteine tRNA. In some embodiments, an orthogonal tRNA is a modified glutamine tRNA. In some embodiments, an orthogonal tRNA is a modified glutamic acid tRNA. In some embodiments, an orthogonal tRNA is a modified alanine glycine. In some embodiments, an orthogonal tRNA is a modified histidine tRNA. In some embodiments, an orthogonal tRNA is a modified leucine tRNA. In some embodiments, an orthogonal tRNA is a modified isoleucine tRNA. In some embodiments, an orthogonal tRNA is a modified lysine tRNA. In some embodiments, an orthogonal tRNA is a modified methionine tRNA. In some embodiments, an orthogonal tRNA is a modified phenylalanine tRNA. In some embodiments, an orthogonal tRNA is a modified proline tRNA. In some embodiments, an orthogonal tRNA is a modified serine tRNA. In some embodiments, an orthogonal tRNA is a modified threonine tRNA. In some embodiments, an orthogonal tRNA is a modified tryptophan tRNA. In some embodiments, an orthogonal tRNA is a modified tyrosine tRNA. In some embodiments, an orthogonal tRNA is a modified valine tRNA. In some embodiments, an orthogonal tRNA is a modified phosphoserine tRNA.

In some embodiments, the unnatural amino acid is incorporated into the cytokine (e.g., the IL polypeptide) by an aminoacyl (aaRS or RS)-tRNA synthetase-tRNA pair. Exemplary aaRS-tRNA pairs include, but are not limited to, *Methanococcus jannaschii* (Mj-Tyr) aaRS/tRNA pairs, *E. coli* TyRS (Ec-Tyr)/*B. stearothennophilus* tRNA$_{CUA}$ pairs, *E. coli* LeuRS (Ec-Leu)/*B. stearothermophilus* tRNA$_{CUA}$ pairs, and pyrrolysyl-tRNA pairs. In some instances, the unnatural amino acid is incorporated into the cytokine (e.g., the IL polypeptide) by a Mj-TyrRS/tRNA pair. Exemplary UAAs that can be incorporated by a Mj-TyrRS/tRNA pair include, but are not limited to, para-substituted phenylalanine derivatives such as p-aminophenylalanine and p-methoxyphenylalanine; meta-substituted tyrosine derivatives such as 3-aminotyrosine, 3-nitrotyrosine, 3,4-dihydroxyphenylalanine, and 3-iodotyrosine; phenylselenocysteine; p-boronophenylalanine; and o-nitrobenzyltyrosine.

In some instances, the unnatural amino acid is incorporated into the cytokine (e.g., the IL polypeptide) by a Ec-Tyr/tRNA$_{CUA}$ or a Ec-Leu/tRNA$_{CUA}$ pair. Exemplary UAAs that can be incorporated by a Ec-Tyr/tRNA$_{CUA}$ or a Ec-Leu/tRNA$_{CUA}$ pair include, but are not limited to, phenylalanine derivatives containing benzophenone, ketone, iodide, or azide substituents; O-propargyltyrosine; a-aminocaprylic acid, O-methyl tyrosine, O-nitrobenzyl cysteine; and 3-(naphthalene-2-ylamino)-2-amino-propanoic acid.

In some instances, the unnatural amino acid is incorporated into the cytokine (e.g., the IL polypeptide) by a pyrrolysyl-tRNA pair. In some cases, the PylRS is obtained from an archaebacterial, e.g., from a methanogenic archaebacterial. In some cases, the PylRS is obtained from *Methanosarcina barkeri, Methanosarcina mazei,* or *Methanosarcina acetivorans*. Exemplary UAAs that can be incorporated by a pyrrolysyl-tRNA pair include, but are not limited to, amide and carbamate substituted lysines such as 2-amino-6-((R)-tetrahydrofuran-2-carboxamido)hexanoic acid, N-ε-D-prolyl-L-lysine, and N-ε-cyclopentyloxycarbonyl-L-lysine; N-ε-Acryloyl-L-lysine; N-ε-[(1-(6-nitrobenzo[d][1,3]dioxol-5-yl)ethoxy)carbonyl]-L-lysine; and N-ε-(1-methylcyclopro-2-enecarboxamido)lysine. In some embodiments, the IL-2 conjugates disclosed herein may be prepared by use of *M. mazei* Pyl tRNA which is selectively charged with a non-natural amino acid such as N6-(2-azidoethoxy)-carbonyl-L-lysine (AzK) by the *M. barkeri* pyrrolysyl-tRNA synthetase (Mb PylRS). Other methods are known to those of ordinary skill in the art, such as those disclosed in Zhang et al., Nature 2017, 551(7682): 644-647.

In some instances, an unnatural amino acid is incorporated into a cytokine described herein (e.g., the IL polypeptide) by a synthetase disclosed in U.S. Pat. Nos. 9,988,619 and 9,938,516. Exemplary UAAs that can be incorporated by such synthetases include para-methylazido-L-phenylalanine, aralkyl, heterocyclyl, heteroaralkyl unnatural amino acids, and others. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water-soluble moiety. In some embodiments, such synthetases are expressed and used to incorporate UAAs into cytokines in-vivo. In some embodiments, such synthetases are used to incorporate UAAs into cytokines using a cell-free translation system.

In some instances, an unnatural amino acid is incorporated into a cytokine described herein (e.g., the IL polypeptide) by a naturally occurring synthetase. In some embodiments, an unnatural amino acid is incorporated into a cytokine by an organism that is auxotrophic for one or more amino acids. In some embodiments, synthetases corresponding to the auxotrophic amino acid are capable of charging the corresponding tRNA with an unnatural amino acid. In some embodiments, the unnatural amino acid is selenocysteine, or a derivative thereof. In some embodiments, the unnatural amino acid is selenomethionine, or a derivative thereof. In some embodiments, the unnatural amino acid is an aromatic amino acid, wherein the aromatic amino acid comprises an aryl halide, such as an iodide. In embodiments, the unnatural amino acid is structurally similar to the auxotrophic amino acid.

In some instances, the unnatural amino acid comprises an unnatural amino acid illustrated in FIG. 1.

Figure 2A:
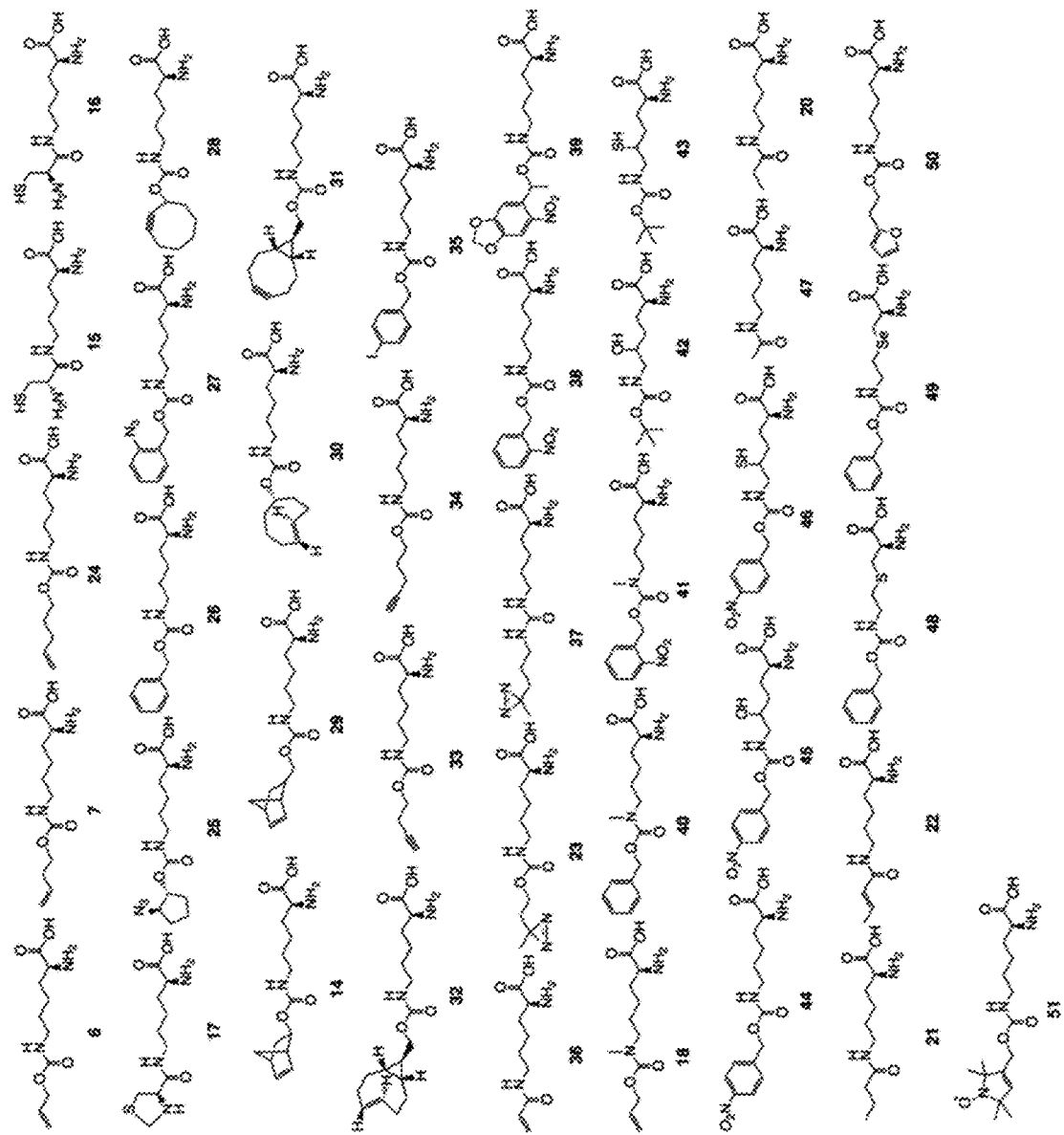
FIGS. 2A-FIG. 2B illustrate exemplary unnatural amino acids.
Figure 2B:
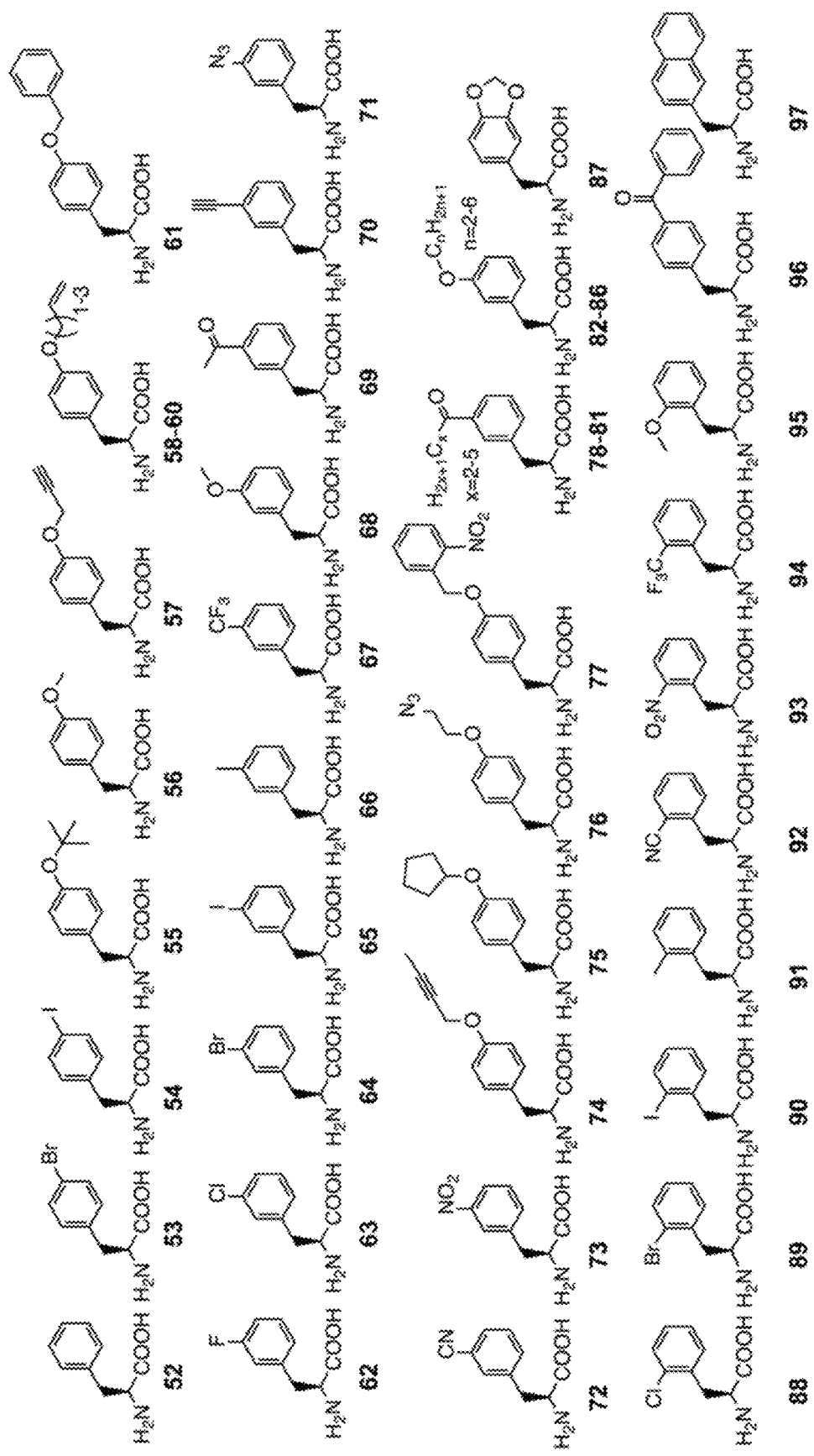

In some instances, the unnatural amino acid comprises a lysine or phenylalanine derivative or analogue. In some instances, the unnatural amino acid comprises a lysine derivative or a lysine analogue. In some instances, the unnatural amino acid comprises a pyrrolysine (Pyl). In some instances, the unnatural amino acid comprises a phenylalanine derivative or a phenylalanine analogue. In some instances, the unnatural amino acid is an unnatural amino acid described in Wan, et al., "Pyrrolysyl-tRNA synthetase: an ordinary enzyme but an outstanding genetic code expansion tool," Biochim Biophys Acta 1844(6): 1059-4070 (2014). In some instances, the unnatural amino acid comprises an unnatural amino acid illustrated in FIG. 2 (e.g., FIG. 2A and FIG. 2B).

In some embodiments, the unnatural amino acid comprises an unnatural amino acid illustrated in FIG. 3A-FIG. 3D (adopted from Table 1 of Dumas et al., *Chemical Science* 2015, 6, 50-69).

In some embodiments, an unnatural amino acid incorporated into a cytokine described herein (e.g., the IL polypeptide) is disclosed in U.S. Pat. Nos. 9,840,493; 9,682,934; US 2017/0260137; U.S. Pat. No. 9,938,516; or US 2018/0086734. Exemplary UAAs that can be incorporated by such synthetases include para-methylazido-L-phenylalanine, aralkyl, heterocyclyl, and heteroaralkyl, and lysine derivative unnatural amino acids. In some embodiments, such UAAs comprise pyridyl, pyrazinyl, pyrazolyl, triazolyl, oxazolyl, thiazolyl, thiophenyl, or other heterocycle. Such amino acids in some embodiments comprise azides, tetrazines, or other chemical group capable of conjugation to a coupling partner, such as a water-soluble moiety. In some embodiments, a UAA comprises an azide attached to an aromatic moiety via an alkyl linker. In some embodiments, an alkyl linker is a $C_1$-$C_{10}$ linker. In some embodiments, a UAA comprises a tetrazine attached to an aromatic moiety via an alkyl linker. In some embodiments, a UAA comprises a tetrazine attached to an aromatic moiety via an amino group. In some embodiments, a UAA comprises a tetrazine attached to an aromatic moiety via an alkylamino group. In some embodiments, a UAA comprises an azide attached to the terminal nitrogen (e.g., N6 of a lysine derivative, or N5, N4, or N3 of a derivative comprising a shorter alkyl side chain) of an amino acid side chain via an alkyl chain. In some embodiments, a UAA comprises a tetrazine attached to the terminal nitrogen of an amino acid side chain via an alkyl chain. In some embodiments, a UAA comprises an azide or tetrazine attached to an amide via an alkyl linker. In some embodiments, the UAA is an azide or tetrazine-containing carbamate or amide of 3-aminoalanine, serine, lysine, or derivative thereof. In some embodiments, such UAAs are incorporated into cytokines in-vivo. In some embodiments, such UAAs are incorporated into cytokines in a cell-free system.

Conjugating Moieties

In certain embodiments, disclosed herein are conjugating moieties that are bound to one or more cytokines (e.g., interleukins, IFNs, or TNFs) described supra. In some instances, the conjugating moiety is a molecule that perturbs the interaction of a cytokine with its receptor. In some instances, the conjugating moiety is any molecule that when bond to the cytokine, enables the cytokine conjugate to modulate an immune response. In some instances, the conjugating moiety is bound to the cytokine through a covalent bond. In some instances, a cytokine described herein is attached to a conjugating moiety with a triazole group. In some instances, a cytokine described herein is attached to a conjugating moiety with a dihydropyridazine or pyridazine group. In some instances, the conjugating moiety comprises a water-soluble polymer. In other instances, the conjugating moiety comprises a protein or a binding fragment thereof. In additional instances, the conjugating moiety comprises a peptide. In additional instances, the conjugating moiety comprises a nucleic acid. In additional instances, the conjugating moiety comprises a small molecule. In additional instances, the conjugating moiety comprises a bioconjugate (e.g., a TLR agonist such as a TLR1, TLR2, TLR3, TLR4, TLR5, TLR6, TLR7, TLR8, or TLR9 agonist; or a synthetic ligand such as Pam3Cys, CFA, MALP2, Pam2Cys, FSL-1, Hib-OMPC, Poly I:C, poly A:U, AGP, MPL A, RC-529, MDF2β, CFA, or Flagellin). In some cases, the conjugating moiety increases serum half-life, and/or improves stability. In some cases, the conjugating moiety reduces cytokine interaction with one or more cytokine receptor domains or subunits. In additional cases, the conjugating moiety blocks cytokine interaction with one or more cytokine domains or subunits with its cognate receptor(s). In some embodiments, cytokine conjugates described herein comprise multiple conjugating moieties. In some embodiments, a conjugating moiety is attached to an unnatural or natural amino acid in the cytokine peptide. In some embodiments, a cytokine conjugate comprises a conjugating moiety attached to a natural amino acid. In some embodiments, a cytokine conjugate is attached to an unnatural amino acid in the cytokine peptide. In some embodiments, a conjugating moiety is attached to the N or C terminal amino acid of the cytokine peptide. Various combinations sites are disclosed herein, for example, a first conjugating moiety is attached to an unnatural or natural amino acid in the cytokine peptide, and a second conjugating moiety is attached to the N or C terminal amino acid of the cytokine peptide. In some embodiments, a single conjugating moiety is attached to multiple residues of the cytokine peptide (e.g. a staple). In some embodiments, a conjugating moiety is attached to both the N and C terminal amino acids of the cytokine peptide.

Water-Soluble Polymers

In some embodiments, a conjugating moiety descried herein is a water-soluble polymer. In some instances, the water-soluble polymer is a nonpeptidic, nontoxic, and biocompatible. As used herein, a substance is considered biocompatible if the beneficial effects associated with use of the substance alone or with another substance (e.g., an active agent such as a cytokine moiety) in connection with living tissues (e.g., administration to a patient) outweighs any deleterious effects as evaluated by a clinician, e.g., a physician, a toxicologist, or a clinical development specialist. In some instances, a water-soluble polymer is further non-immunogenic. In some instances, a substance is considered non-immunogenic if the intended use of the substance in vivo does not produce an undesired immune response (e.g., the formation of antibodies) or, if an immune response is produced, that such a response is not deemed clinically significant or important as evaluated by a clinician, e.g., a physician, a toxicologist, or a clinical development specialist.

In some instances, the water-soluble polymer is characterized as having from about 2 to about 300 termini. Exemplary water soluble polymers include, but are not limited to, poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(a-hydroxy acid), poly(vinyl alcohol) (PVA), polyacrylamide (PAAm), poly(N-(2-hydroxypropyl) methacrylamide) (PHPMA), polydimethylacrylamide (PDAAm), polyphosphazene, polyoxazolines ("POZ") (which are described in WO 2008/106186), poly(N-acryloylmorpholine), and combinations of any of the foregoing.

In some cases, the water-soluble polymer is not limited to a particular structure. In some cases, the water-soluble polymer is linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the water-soluble polymer can be organized in any number of different repeat patterns and can be selected from the group consisting of homopolymer, alternating copolymer, random copolymer, block copolymer, alternating tripolymer, random tripolymer, and block tripolymer.

In some instances, the water-soluble polymer is represented by a length of repeating polymeric units, for example, a number n of polyethylene glycol units. In some instances, the water-soluble polymer has the structure:

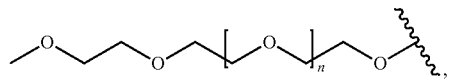

wherein the wavy line indicates attachment to a linker, reactive group, or unnatural amino acid, and n is 1-5000. In some instances, the water-soluble polymer has the structure:

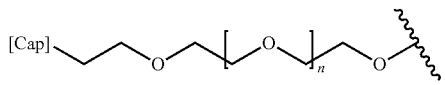

wherein the wavy line indicates attachment to a linker, reactive group, or unnatural amino acid, "Cap" indicates a capping group (for example, such as —OCH$_3$, —O(C$_1$-C$_6$ alkyl), -SMe, —S(C$_1$-C$_6$ alkyl), —CO$_2$H, —CO$_2$(C$_1$-C$_6$ alkyl), —CONH$_2$, —CONH(C$_1$-C$_6$ alkyl), —CON(C$_1$-C$_6$ alkyl)$_2$, —NH$_2$, —SH, or OH) and n is 1-5000. In some embodiments, n is 100-2000, 200-1000, 300-750, 400-600, 450-550, 400-2000, 750-3000, or 100-750. In some embodiments, n is about 100, 200, 300, 400, 500, 600, 700, 800, 900, or about 1000. In some embodiments, n is at least 100, 200, 300, 400, 500, 600, 700, 800, 900, or at least 1000. In some embodiments, n is no more than 100, 200, 300, 400, 500, 600, 700, 800, 900, or no more than 1000. In some embodiments, the n is represented as an average length of the water-soluble polymer.

In some embodiments, the weight-average molecular weight of the water-soluble polymer in the IL-2 conjugate is from about 100 Daltons to about 150,000 Daltons. Exemplary ranges include, for example, weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total molecular weight of any of the foregoing can also be used. In one or more embodiments, the conjugate will not have any PEG moieties attached, either directly or indirectly, with a PEG having a weight average molecular weight of less than about 6,000 Daltons.

PEGS will typically comprise a number of $(OCH_2CH_2)$ monomers [or $(CH_2CH_2O)$ monomers, depending on how the PEG is defined]. As used herein, the number of repeating units is identified by the subscript "n" in "$(OCH_2CH_2)n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

In some instances, the water-soluble polymer is an end-capped polymer, that is, a polymer having at least one terminus capped with a relatively inert group, such as a lower $C_{1-6}$ alkoxy group, or a hydroxyl group. When the polymer is PEG, for example, a methoxy-PEG (commonly referred to as mPEG) may be used, which is a linear form of PEG wherein one terminus of the polymer is a methoxy ($-OCH_3$) group, while the other terminus is a hydroxyl or other functional group that can be optionally chemically modified.

In some embodiments, the PEG group comprising the IL-2 conjugates disclosed herein is a linear or branched PEG group. In some embodiments, the PEG group is a linear PEG group. In some embodiments, the PEG group is a branched PEG group. In some embodiments, the PEG group is a methoxy PEG group. In some embodiments, the PEG group is a linear or branched methoxy PEG group. In some embodiments, the PEG group is a linear methoxy PEG group. In some embodiments, the PEG group is a branched methoxy PEG group. In some embodiments, the PEG group is a linear or branched PEG group having an average molecular weight of from about 100 Daltons to about 150,000 Daltons. Exemplary ranges include, for example, weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons. Exemplary weight-average molecular weights for the PEG group include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 90,000 Daltons, about 95,000 Daltons, and about 100,000 Daltons. In some embodiments, the PEG group is a linear PEG group having an average molecular weight as disclosed above. In some embodiments, the PEG group is a branched PEG group having an average molecular weight as disclosed above. In some embodiments, the PEG group comprising the IL-2 conjugates disclosed herein is a linear or branched PEG group having a defined molecular weight ±10%, or 15% or 20% or 25%. For example, included within the scope of the present disclosure are IL-2 conjugates comprising a PEG group having a molecular weight of 30,000 Da±3000 Da, or 30,000 Da±4,500 Da, or 30,000 Da±6,000 Da.

In some embodiments, the PEG group comprising the IL-2 conjugates disclosed herein is a linear or branched PEG group having an average molecular weight of from about 5,000 Daltons to about 60,000 Daltons. In some embodiments, the PEG group is a linear or branched PEG group having an average molecular weight of about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 90,000 Daltons, about 95,000 Daltons, and about 100,000 Daltons. In some embodiments, the PEG group is a linear or branched PEG group having an average molecular weight of about 5,000 Daltons, about 10,000 Daltons, about 20,000 Daltons, about 30,000 Daltons, about 50,000 Daltons, or about 60,000 Daltons. In some embodiments, the PEG group is a linear or branched PEG group having an average molecular weight of about 5,000 Daltons, about 30,000 Daltons, about 50,000 Daltons, or about 60,000 Daltons. In some embodiments, the PEG group is a linear PEG group having an average molecular of about 5,000 Daltons, about 10,000 Daltons, about 20,000 Daltons, about 30,000 Daltons, about 50,000 Daltons, or about 60,000 Daltons. In some embodiments, the PEG group is a branched PEG group having an average molecular weight of about 5,000 Daltons, about 10,000 Daltons, about 20,000 Daltons, about 30,000 Daltons, about 50,000 Daltons, or about 60,000 Daltons.

In some embodiments, the PEG group comprising the IL-2 conjugates disclosed herein is a linear methoxy PEG group having an average molecular weight of from about 5,000 Daltons to about 60,000 Daltons. In some embodiments, the PEG group is a linear methoxy PEG group having an average molecular weight of about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 90,000 Daltons, about 95,000 Daltons, and about 100,000 Daltons. In some embodiments, the PEG group is a linear methoxy PEG group having an average molecular weight of about 5,000 Daltons, about 10,000 Daltons, about 20,000 Daltons, about 30,000 Daltons, about 50,000 Daltons, or about 60,000 Daltons. In some embodiments, the PEG group is a linear methoxy PEG group having an average molecular weight of about 5,000 Daltons, about 30,000 Daltons, about 50,000 Daltons, or about 60,000 Daltons. In some embodiments, the PEG group is a linear methoxy PEG group having an average molecular of about 5,000 Daltons, about 10,000 Daltons, about 20,000 Daltons, about 30,000 Daltons, about 50,000 Daltons, or about 60,000 Daltons. In some embodiments, the PEG group is a linear methoxy PEG group having an average molecular of about 5,000 Daltons. In some embodiments, the PEG group is a linear methoxy PEG group having an average molecular of about 10,000 Daltons. In some embodiments, the PEG group is a linear methoxy PEG group having an average molecular of about 20,000 Daltons. In some embodiments, the PEG group is a linear methoxy PEG group having an average molecular of about 30,000 Daltons. In some embodiments, the PEG group is a linear methoxy PEG group having an average molecular of about 50,000 Daltons. In some embodiments, the PEG group is a linear methoxy PEG group having an average molecular of about 60,000 Daltons. In some embodiments, the PEG group comprising the IL-2 conjugates disclosed herein is a linear methoxy PEG group having a defined molecular weight ±10%, or 15% or 20% or 25%. For example, included within the scope of the present disclosure are IL-2 conjugates comprising a linear methoxy PEG group having a molecular weight of 30,000 Da±3000 Da, or 30,000 Da±4,500 Da, or 30,000 Da±6,000 Da.

In some embodiments, the PEG group comprising the IL-2 conjugates disclosed herein is a branched methoxy PEG group having an average molecular weight of from about 5,000 Daltons to about 60,000 Daltons. In some embodiments, the PEG group is a branched methoxy PEG group having an average molecular weight of about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, about 75,000 Daltons, about 80,000 Daltons, about 90,000 Daltons, about 95,000 Daltons, and about 100,000 Daltons. In some embodiments, the PEG group is a branched methoxy PEG group having an average molecular weight of about 5,000 Daltons, about 10,000 Daltons, about 20,000 Daltons, about 30,000 Daltons, about 50,000 Daltons, or about 60,000 Daltons. In some embodiments, the PEG group is a branched methoxy PEG group having an average molecular weight of about 5,000 Daltons, about 30,000 Daltons, about 50,000 Daltons, or about 60,000 Daltons. In some embodiments, the PEG group is a branched methoxy PEG group having an average molecular of about 5,000 Daltons, about 10,000 Daltons, about 20,000 Daltons, about 30,000 Daltons, about 50,000 Daltons, or about 60,000 Daltons. In some embodiments, the PEG group is a branched methoxy PEG group having an average molecular of about 5,000 Daltons, about 10,000 Daltons, about 20,000 Daltons, about 30,000 Daltons, about 50,000 Daltons, or about 60,000 Daltons. In some embodiments, the PEG group is a branched methoxy PEG group having an average molecular of about 5,000 Daltons. In some embodiments, the PEG group is a branched methoxy PEG group having an average molecular of about 10,000 Daltons. In some embodiments, the PEG group is a branched methoxy PEG group having an average molecular of about 20,000 Daltons. In some embodiments, the PEG group is a branched methoxy PEG group having an average molecular of about 30,000 Daltons. In some embodiments, the PEG group is a branched methoxy PEG group having an average molecular of about 50,000 Daltons. In some embodiments, the PEG group is a branched methoxy PEG group having an average molecular of about 60,000 Daltons. In some embodiments, the PEG group comprising the IL-2 conjugates disclosed herein is a branched methoxy PEG group having a defined molecular weight ±10%, or 15% or 20% or 25%. For example, included within the scope of the present disclosure are IL-2 conjugates comprising a branched methoxy PEG group having a molecular weight of 30,000 Da±3000 Da, or 30,000 Da±4,500 Da, or 30,000 Da±6,000 Da.

In some embodiments, exemplary water-soluble polymers include, but are not limited to, linear or branched discrete PEG (dPEG) from Quanta Biodesign, Ltd; linear, branched, or forked PEGS from Nektar Therapeutics; and Y-shaped PEG derivatives from JenKem Technology.

In some embodiments, a cytokine (e.g., an interleukin, IFN, or TNF) polypeptide described herein is conjugated to a water-soluble polymer selected from poly(alkylene glycols) such as polyethylene glycol ("PEG"), poly(propylene glycol) ("PPG"), copolymers of ethylene glycol and propylene glycol and the like, poly(oxyethylated polyol), poly (olefinic alcohol), poly(vinylpyrrolidone), poly(hydroxyalkylmethacrylamide), poly(hydroxyalkylmethacrylate), poly (saccharides), poly(a-hydroxy acid), poly(vinyl alcohol) (PVA), polyacrylamide (PAAm), polydimethylacrylamide (PDAAm), poly(N-(2-hydroxypropyl) methacrylamide) (PHPMA), polyphosphazene, polyoxazolines ("POZ"), poly (N-acryloylmorpholine), and a combination thereof. In some instances, the cytokine polypeptide is conjugated to PEG (e.g., PEGylated). In some instances, the cytokine polypeptide is conjugated to PPG. In some instances, the cytokine polypeptide is conjugated to POZ. In some instances, the cytokine polypeptide is conjugated to PVP.

In some embodiments, an IL-2 polypeptide described herein is conjugated to a water-soluble polymer selected from poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly($\alpha$-hydroxy acid), poly(vinyl alcohol) (PVA), polyacrylamide (PAAm), polydimethylacrylamide (PDAAm), poly(N-(2-hydroxypropyl) methacrylamide) (PHPMA), polyphosphazene, polyoxazolines ("POZ"), poly(N-acryloylmorpholine), and a combination thereof. In some instances, the IL-2 polypeptide is conjugated to PEG (e.g., PEGylated). In some instances, the IL-2 polypeptide is conjugated to PPG. In some instances, the IL-2 polypeptide is conjugated to POZ. In some instances, the IL-2 polypeptide is conjugated to PVP.

In some instances, a water-soluble polymer comprises a polyglycerol (PG). In some cases, the polyglycerol is a hyperbranched PG (HPG) (e.g., as described by Imran, et al. "Influence of architecture of high molecular weight linear and branched polyglycerols on their biocompatibility and biodistribution," *Biomaterials* 33:9135-9147 (2012)). In other cases, the polyglycerol is a linear PG (LPG). In additional cases, the polyglycerol is a midfunctional PG, a linear-block-hyperbranched PG (e.g., as described by Wurm et. Al., "Squaric acid mediated synthesis and biological activity of a library of linear and hyperbranched poly(glycerol)-protein conjugates," *Biomacromolecules* 13:1161-1171 (2012)), or a side-chain functional PG (e.g., as described by Li, et. al., "Synthesis of linear polyether polyol derivatives as new materials for bioconjugation," Bioconjugate Chem. 20:780-789 (2009).

In some instances, a cytokine (e.g., an interleukin, IFN, or TNF) polypeptide described herein is conjugated to a PG, e.g., a HPG, a LPG, a midfunctional PG, a linear-block-hyperbranched PG, or a side-chain functional PG. In some instances, the cytokine is an IL-2 polypeptide. In some cases, the IL-2 polypeptide is conjugated to a PG, a midfunctional PG, a linear-block-hyperbranched PG.

In some embodiments, a water-soluble polymer is a degradable synthetic PEG alternative. Exemplary degradable synthetic PEG alternatives include, but are not limited to, poly[oligo(ethylene glycol)methyl methacrylate] (POEGMA); backbone modified PEG derivatives generated by polymerization of telechelic, or di-end-functionalized PEG-based macromonomers; PEG derivatives comprising comonomers comprising degradable linkage such as poly[(ethylene oxide)-co-(methylene ethylene oxide)][P(EO-co-MEO)], cyclic ketene acetals such as 5,6-benzo-2-methylene-1,3-dioxepane (BMDO), 2-methylene-1,3-dioxepane (MDO), and 2-methylene-4-phenyl-1,3-dioxolane (MPDL) copolymerized with OEGMA; or poly-(c-caprolactone)-graft-poly(ethylene oxide) (PCL-g-PEO).

In some instances, a cytokine (e.g., an interleukin, IFN, or TNF) polypeptide described herein is conjugated to a degradable synthetic PEG alternative, such as for example, POEGM; backbone modified PEG derivatives generated by polymerization of telechelic, or di-end-functionalized PEG-based macromonomers; P(EO-co-MEO); cyclic ketene acetals such as BMDO, MDO, and MPDL copolymerized with OEGMA; or PCL-g-PEO. In some instances, the cytokine is an IL-2 polypeptide. In some cases, the IL-2 polypeptide is conjugated to a degradable synthetic PEG alternative, such as for example, POEGM; backbone modified PEG derivatives generated by polymerization of telechelic, or di-end-functionalized PEG-based macromonomers; P(EO-co-MEO); cyclic ketene acetals such as BMDO, MDO, and MPDL copolymerized with OEGMA; or PCL-g-PEO.

In some embodiments, a water-soluble polymer comprises a poly(zwitterions). Exemplary poly(zwitterions) include, but are not limited to, poly(sulfobetaine methacrylate) (PSBMA), poly(carboxybetaine methacrylate) (PCBMA), and poly(2-methyacryloyloxyethyl phosphorylcholine) (PMPC). In some instances, a cytokine (e.g., an interleukin, IFN, or TNF) polypeptide described herein is conjugated to a poly(zwitterion) such as PSBMA, PCBMA, or PMPC. In some cases, the cytokine is an IL-2 polypeptide. In some cases, the IL-2 polypeptide is conjugated to a poly(zwitterion) such as PSBMA, PCBMA, or PMPC.

In some embodiments, a water-soluble polymer comprises a polycarbonate. Exemplary polycarbones include, but are not limited to, pentafluorophenyl 5-methyl-2-oxo-1,3-dioxane-5-carboxylate (MTC-OC$_6$F$_5$). In some instances, a cytokine (e.g., an interleukin, IFN, or TNF) polypeptide described herein is conjugated to a polycarbonate such as MTC-OC$_6$F$_5$. In some cases, the cytokine is an IL-2 polypeptide. In some cases, the IL-2 polypeptide is conjugated to a polycarbonate such as MTC-OC$_6$F$_5$.

In some embodiments, a water-soluble polymer comprises a polymer hybrid, such as for example, a polycarbonate/PEG polymer hybrid, a peptide/protein-polymer conjugate, or a hydroxyl containing and/or zwitterionic derivatized polymer (e.g., a hydroxyl containing and/or zwitterionic derivatized PEG polymer). In some instances, a cytokine (e.g., an interleukin, IFN, or TNF) polypeptide described herein is conjugated to a polymer hybrid such as a polycarbonate/PEG polymer hybrid, a peptide/protein-polymer conjugate, or a hydroxyl containing and/or zwitterionic derivatized polymer (e.g., a hydroxyl containing and/or zwitterionic derivatized PEG polymer). In some cases, the cytokine is an IL-2 polypeptide. In some cases, the IL-2 polypeptide is conjugated to a polymer hybrid such as a polycarbonate/PEG polymer hybrid, a peptide/protein-polymer conjugate, or a hydroxyl containing and/or zwitterionic derivatized polymer (e.g., a hydroxyl containing and/or zwitterionic derivatized PEG polymer).

In some instances, a water-soluble polymer comprises a polysaccharide. Exemplary polysaccharides include, but are not limited to, dextran, polysialic acid (PSA), hyaluronic acid (HA), amylose, heparin, heparan sulfate (HS), dextrin, or hydroxyethyl-starch (HES). In some cases, a cytokine (e.g., an interleukin, IFN, or TNF) polypeptide is conjugated to a polysaccharide. In some cases, an IL-2 polypeptide is conjugated to dextran. In some cases, an IL-2 polypeptide is conjugated to PSA. In some cases, an IL-2 polypeptide is conjugated to HA. In some cases, an IL-2 polypeptide is conjugated to amylose. In some cases, an IL-2 polypeptide is conjugated to heparin. In some cases, an IL-2 polypeptide is conjugated to HS. In some cases, an IL-2 polypeptide is conjugated to dextrin. In some cases, an IL-2 polypeptide is conjugated to HES.

In some cases, a water-soluble polymer comprises a glycan. Exemplary classes of glycans include N-linked glycans, O-linked glycans, glycolipids, O-GlcNAc, and glycosaminoglycans. In some cases, a cytokine (e.g., an interleukin, IFN, or TNF) polypeptide is conjugated to a glycan.

In some cases, an IL-2 polypeptide is conjugated to N-linked glycans. In some cases, an IL-2 polypeptide is conjugated to O-linked glycans. In some cases, an IL-2 polypeptide is conjugated to glycolipids. In some cases, an IL-2 polypeptide is conjugated to O-GlcNAc. In some cases, an IL-2 polypeptide is conjugated to glycosaminoglycans.

In some embodiments, a water-soluble polymer comprises a polyoxazoline polymer. A polyoxazoline polymer is a linear synthetic polymer, and similar to PEG, comprises a low polydispersity. In some instances, a polyoxazoline polymer is a polydispersed polyoxazoline polymer, characterized with an average molecule weight. In some cases, the average molecule weight of a polyoxazoline polymer includes, for example, 1000, 1500, 2000, 2500, 3000, 3500, 4000, 4500, 5000, 5500, 6000, 6500, 7000, 7500, 8000, 10,000, 12,000, 20,000, 35,000, 40,000, 50,000, 60,000, 100,000, 200,000, 300,000, 400,000, or 500,000 Da. In some instances, a polyoxazoline polymer comprises poly(2-methyl 2-oxazoline) (PMOZ), poly(2-ethyl 2-oxazoline) (PEOZ), or poly (2-propyl 2-oxazoline) (PPOZ). In some cases, a cytokine (e.g., an interleukin, IFN, or TNF) polypeptide is conjugated to a polyoxazoline polymer. In some cases, an IL-2 polypeptide is conjugated to a polyoxazoline polymer. In some cases, an IL-2 polypeptide is conjugated to PMOZ. In some cases, an IL-2 polypeptide is conjugated to PEOZ. In some cases, an IL-2 polypeptide is conjugated to PPOZ.

In some instances, a water-soluble polymer comprises a polyacrylic acid polymer. In some cases, a cytokine (e.g., an interleukin, IFN, or TNF) polypeptide is conjugated to a polyacrylic acid polymer. In some cases, an IL-2 polypeptide is conjugated to a polyacrylic acid polymer.

In some instances, a water-soluble polymer comprises polyamine. Polyamine is an organic polymer comprising two or more primary amino groups. In some embodiments, a polyamine includes a branched polyamine, a linear polyamine, or cyclic polyamine. In some cases, a polyamine is a low-molecular-weight linear polyamine. Exemplary polyamines include putrescine, cadaverine, spermidine, spermine, ethylene diamine, 1,3-diaminopropane, hexamethylenediamine, tetraethylmethylenediamine, and piperazine. In some cases, a cytokine (e.g., an interleukin, IFN, or TNF) polypeptide is conjugated to a polyamine. In some cases, an IL-2 polypeptide is conjugated to polyamine. In some cases, an IL-2 polypeptide is conjugated to putrescine, cadaverine, spermidine, spermine, ethylene diamine, 1,3-diaminopropane, hexamethylenediamine, tetraethylmethylenediamine, or piperazine.

In some instances, a water-soluble polymer is described in U.S. Pat. Nos. 7,744,861, 8,273,833, and 7,803,777. In some instances, a cytokine (e.g., an interleukin, IFN, or TNF) polypeptide is conjugated to a linker described in U.S. Pat. Nos. 7,744,861, 8,273,833, or 7,803,777. In some cases, an IL-2 polypeptide is conjugated to a linker described in U.S. Pat. Nos. 7,744,861, 8,273,833, or 7,803,777.

Lipids

In some embodiments, a conjugating moiety descried herein is a lipid. In some instances, the lipid is a fatty acid. In some cases, the fatty acid is a saturated fatty acid. In other cases, the fatty acid is an unsaturated fatty acid. Exemplary fatty acids include, but are not limited to, fatty acids comprising from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some cases, the lipid binds to one or more serum proteins, thereby increasing serum stability and/or serum half-life.

In some embodiments, the lipid is conjugated to IL-2. In some instances, the lipid is a fatty acid, e.g., a saturated fatty acid or an unsaturated fatty acid. In some cases, the fatty acid is from about 6 to about 26 carbon atoms, from about 6 to about 24 carbon atoms, from about 6 to about 22 carbon atoms, from about 6 to about 20 carbon atoms, from about 6 to about 18 carbon atoms, from about 20 to about 26 carbon atoms, from about 12 to about 26 carbon atoms, from about 12 to about 24 carbon atoms, from about 12 to about 22 carbon atoms, from about 12 to about 20 carbon atoms, or from about 12 to about 18 carbon atoms. In some cases, the fatty acid comprises about 6, 7, 8, 9, 10, 11, 12, 13, 14, 15, 16, 17, 18, 19, 20, 21, 22, 23, 24, 25, or 26 carbon atoms in length. In some cases, the fatty acid comprises caproic acid (hexanoic acid), enanthic acid (heptanoic acid), caprylic acid (octanoic acid), pelargonic acid (nonanoic acid), capric acid (decanoic acid), undecylic acid (undecanoic acid), lauric acid (dodecanoic acid), tridecylic acid (tridecanoic acid), myristic acid (tetradecanoic acid), pentadecylic acid (pentadecanoic acid), palmitic acid (hexadecanoic acid), margaric acid (heptadecanoic acid), stearic acid (octadecanoic acid), nonadecylic acid (nonadecanoic acid), arachidic acid (eicosanoic acid), heneicosylic acid (heneicosanoic acid), behenic acid (docosanoic acid), tricosylic acid (tricosanoic acid), lignoceric acid (tetracosanoic acid), pentacosylic acid (pentacosanoic acid), or cerotic acid (hexacosanoic acid).

In some embodiments, the IL-2 lipid conjugate enhances serum stability and/or serum half-life.

Proteins

In some embodiments, a conjugating moiety descried herein is a protein or a binding fragment thereof. Exemplary proteins include albumin, transferrin, or transthyretin. In some instances, the protein or a binding fragment thereof comprises an antibody, or its binding fragments thereof. In some cases, a cytokine conjugate comprises a protein or a binding fragment thereof. In some cases, an IL-2 conjugate comprising a protein or a binding fragment thereof has an increased serum half-life, and/or stability. In some cases, an IL-2 conjugate comprising a protein or a binding fragment thereof has a reduced IL-2 interaction with one or more IL-2R subunits. In additional cases, the protein or a binding fragment thereof blocks IL-2 interaction with one or more IL-2R subunits.

In some embodiments, the conjugating moiety is albumin. Albumin is a family of water-soluble globular proteins. It is commonly found in blood plasma, comprising about 55-60% of all plasma proteins. Human serum albumin (HSA) is a 585 amino acid polypeptide in which the tertiary structure is divided into three domains, domain I (amino acid residues 1-195), domain II (amino acid residues 196-383), and domain III (amino acid residues 384-585). Each domain further comprises a binding site, which can interact either reversibly or irreversibly with endogenous ligands such as long- and medium-chain fatty acids, bilirubin, or hemin, or exogenous compounds such as heterocyclic or aromatic compounds.

In some cases, a cytokine (e.g., an interleukin, IFN, or TNF) polypeptide is conjugated to albumin. In some cases, the cytokine polypeptide is conjugated to human serum albumin (HSA). In additional cases, the cytokine polypeptide is conjugated to a functional fragment of albumin.

In some instances, an IL-2 polypeptide is conjugated to albumin. In some cases, the IL-2 polypeptide is conjugated to human serum albumin (HSA). In additional cases, the IL-2 polypeptide is conjugated to a functional fragment of albumin.

In some embodiments, the conjugating moiety is transferrin. Transferrin is a 679 amino acid polypeptide that is about 80 kDa in size and comprises two Fe' binding sites with one at the N-terminal domain and the other at the C-terminal domain. In some instances, human transferrin has a half-life of about 7-12 days.

In some instances, a cytokine (e.g., an interleukin, IFN, or TNF) polypeptide is conjugated to transferrin. In some cases, the cytokine polypeptide is conjugated to human transferrin. In additional cases, the cytokine polypeptide is conjugated to a functional fragment of transferrin.

In some instances, an IL-2 polypeptide is conjugated to transferrin. In some cases, the IL-2 polypeptide is conjugated to human transferrin. In additional cases, the IL-2 polypeptide is conjugated to a functional fragment of transferrin.

In some embodiments, the conjugating moiety is transthyretin (TTR). Transthyretin is a transport protein located in the serum and cerebrospinal fluid which transports the thyroid hormone thyroxine (T4) and retinol-binding protein bound to retinol.

In some instances, a cytokine (e.g., an interleukin, IFN, or TNF) polypeptide is conjugated to transthyretin (via one of its termini or via an internal hinge region). In some cases, the cytokine polypeptide is conjugated to a functional fragment of transthyretin.

In some instances, an IL-2 polypeptide is conjugated to transthyretin (via one of its termini or via an internal hinge region). In some cases, the IL-2 polypeptide is conjugated to a functional fragment of transthyretin.

In some embodiments, the conjugating moiety is an antibody, or its binding fragments thereof. In some instances, an antibody or its binding fragments thereof comprise a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof.

In some instances, the conjugating moiety comprises a scFv, bis-scFv, (scFv)$_2$, dsFv, or sdAb. In some cases, the conjugating moiety comprises a scFv. In some cases, the conjugating moiety comprises a bis-scFv. In some cases, the conjugating moiety comprises a (scFv)$_2$. In some cases, the conjugating moiety comprises a dsFv. In some cases, the conjugating moiety comprises a sdAb.

In some instances, the conjugating moiety comprises an Fc portion of an antibody, e.g., of IgG, IgA, IgM, IgE, or IgD. In some instances, the moiety comprises an Fc portion of IgG (e.g., IgG$_1$, IgG$_3$, or IgG$_4$).

In some cases, a cytokine (e.g., an interleukin, IFN, or TNF) polypeptide is conjugated to an antibody, or its binding fragments thereof. In some cases, the cytokine polypeptide is conjugated to a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the cytokine polypeptide is conjugated to an Fc portion of an antibody. In additional cases, the cytokine polypeptide is conjugated to an Fc portion of IgG (e.g., IgG$_1$, IgG$_3$, or IgG$_4$).

In some cases, an IL-2 polypeptide is conjugated to an antibody, or its binding fragments thereof. In some cases, the IL-2 polypeptide is conjugated to a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In additional cases, the IL-2 polypeptide is conjugated to an Fc portion of an antibody. In additional cases, the IL-2 polypeptide is conjugated to an Fc portion of IgG (e.g., IgG$_1$, IgG$_3$, or IgG$_4$).

In some embodiments, an IL-2 polypeptide is conjugated to a water-soluble polymer (e.g., PEG) and an antibody or binding fragment thereof. In some cases, the antibody or binding fragments thereof comprises a humanized antibody or binding fragment thereof, murine antibody or binding fragment thereof, chimeric antibody or binding fragment thereof, monoclonal antibody or binding fragment thereof, monovalent Fab', divalent Fab$_2$, F(ab)'$_3$ fragments, single-chain variable fragment (scFv), bis-scFv, (scFv)$_2$, diabody, minibody, nanobody, triabody, tetrabody, humabody, disulfide stabilized Fv protein (dsFv), single-domain antibody (sdAb), Ig NAR, camelid antibody or binding fragment thereof, bispecific antibody or biding fragment thereof, or a chemically modified derivative thereof. In some cases, the antibody or binding fragments thereof comprises a scFv, bis-scFv, (scFv)$_2$, dsFv, or sdAb. In some cases, the antibody or binding fragments thereof comprises a scFv. In some cases, the antibody or binding fragment thereof guides the IL-2 conjugate to a target cell of interest and the water-soluble polymer enhances stability and/or serum half-life.

In some instances, one or more IL-2 polypeptide—water-soluble polymer (e.g., PEG) conjugates are further bound to an antibody or binding fragments thereof. In some instances, the ratio of the IL-2 conjugate to the antibody is about 1:1, 2:1, 3:1, 4:1, 5:1, 6:1, 7:1, 8:1, 9:1, 10:1, 11:1, or 12:1. In some cases, the ratio of the IL-2 conjugate to the antibody is about 1:1. In other cases, the ratio of the IL-2 conjugate to the antibody is about 2:1, 3:1, or 4:1. In additional cases, the ratio of the IL-2 conjugate to the antibody is about 6:1 or higher.

In some embodiments, the one or more IL-2 polypeptide—water-soluble polymer (e.g., PEG) conjugates are directly bound to the antibody or binding fragments thereof. In other instances, the IL-2 conjugate is indirectly bound to the antibody or binding fragments thereof with a linker. Exemplary linkers include homobifunctional linkers, heterobifunctional linkers, maleimide-based linkers, zero-trace linkers, self-immolative linkers, spacers, and the like.

In some embodiments, the antibody or binding fragments thereof is bound either directly or indirectly to the IL-2 polypeptide portion of the IL-2 polypeptide—water-soluble polymer (e.g., PEG) conjugate. In such cases, the conjugation site of the antibody to the IL-2 polypeptide is at a site that will not impede binding of the IL-2 polypeptide with the IL-2Rβγ. In additional cases, the conjugation site of the antibody to the IL-2 polypeptide is at a site that partially blocks binding of the IL-2 polypeptide with the IL-2Rβγ. In additional cases, the conjugation site of the antibody to the IL-2 polypeptide is at a site that will impede or further impede binding of the IL-2 polypeptide with the IL-2Rα. In other embodiments, the antibody or binding fragments thereof is bound either directly or indirectly to the water-soluble polymer portion of the IL-2 polypeptide—water-soluble polymer (e.g., PEG) conjugate.

Peptides

In some embodiments, a conjugating moiety descried herein is a peptide. In some instances, the peptide is a non-structured peptide. In some cases, a cytokine (e.g., an interleukin, IFN, or TNF) polypeptide is conjugated to a peptide. In some cases, the IL-2 conjugate comprising a peptide has an increased serum half-life, and/or stability. In some cases, the IL-2 conjugate comprising a peptide has a reduced IL-2 interaction with one or more IL-2R subunits. In additional cases, the peptide blocks IL-2 interaction with one or more IL-2R subunits.

In some instances, the conjugating moiety is a XTEN™ peptide (Amunix Operating Inc.) and the modification is referred to as XTENylation. XTENylation is the genetic fusion of a nucleic acid encoding a polypeptide of interest with a nucleic acid encoding a XTEN™ peptide (Amunix Operating Inc.), a long unstructured hydrophilic peptide comprising different percentage of six amino acids: Ala, Glu, Gly, Ser, and Thr. In some instances, a XTEN™ peptide is selected based on properties such as expression, genetic stability, solubility, aggregation resistance, enhanced half-life, increased potency, and/or increased in vitro activity in combination with a polypeptide of interest. In some cases, a cytokine (e.g., an interleukin, IFN, or TNF) polypeptide is conjugated to a XTEN peptide. In some cases, an IL-2 polypeptide is conjugated to a XTEN peptide.

In some instances, the conjugating moiety is a glycine-rich homoamino acid polymer (HAP) and the modification is referred to as HAPylation. HAPylation is the genetic fusion of a nucleic acid encoding a polypeptide of interest with a nucleic acid encoding a glycine-rich homoamino acid polymer (HAP). In some instances, the HAP polymer comprises a $(Gly_4Ser)_n$ repeat motif and sometimes are about 50, 100, 150, 200, 250, 300, or more residues in length. In some cases, a cytokine (e.g., an interleukin, IFN, or TNF) polypeptide is conjugated to HAP. In some cases, an IL-2 polypeptide is conjugated to HAP.

In some embodiments, the conjugating moiety is a PAS polypeptide and the modification is referred to as PASylation. PASylation is the genetic fusion of a nucleic acid encoding a polypeptide of interest with a nucleic acid encoding a PAS polypeptide. A PAS polypeptide is a hydrophilic uncharged polypeptide consisting of Pro, Ala and Ser residues. In some instances, the length of a PAS polypeptide is at least about 100, 200, 300, 400, 500, or 600 amino acids. In some cases, a cytokine (e.g., an interleukin, IFN, or TNF) polypeptide is conjugated to a PAS polypeptide. In some cases, an IL-2 polypeptide is conjugated to a PAS polypeptide.

In some embodiments, the conjugating moiety is an elastin-like polypeptide (ELP) and the modification is referred to as ELPylation. ELPylation is the genetic fusion of a nucleic acid encoding a polypeptide of interest with a nucleic acid encoding an elastin-like polypeptide (ELPs). An ELP comprises a VPGxG repeat motif in which x is any amino acid except proline. In some cases, a cytokine (e.g., an interleukin, IFN, or TNF) polypeptide is conjugated to ELP. In some cases, an IL-2 polypeptide is conjugated to ELP.

In some embodiments, the conjugating moiety is a CTP peptide. A CTP peptide comprises a 30 or 31 amino acid residue peptide (FQSSSS*KAPPPS*LPSPS*RLPGPS*DTPILPQ (SEQ ID NO: 248) or FQDSSSS*KAPPPS*LPSPS*RLPGPS*DTPILPQ (SEQ ID NO: 249)) in which the S* denotes 0-glycosylation sites (OPKO). In some instances, a CTP peptide is genetically fused to a cytokine polypeptide (e.g., an IL-2 polypeptide). In some cases, a cytokine polypeptide (e.g., an IL-2 polypeptide) is conjugated to a CTP peptide.

In some embodiments, a cytokine (e.g., an IL-2 polypeptide) is modified by glutamylation. Glutamylation (or polyglutamylation) is a reversible posttranslational modification of glutamate, in which the γ-carboxy group of glutamate forms a peptide-like bond with the amino group of a free glutamate in which the α-carboxy group extends into a polyglutamate chain.

In some embodiments, a cytokine (e.g., an IL-2 polypeptide) is modified by a gelatin-like protein (GLK) polymer. In some instances, the GLK polymer comprises multiple repeats of Gly-Xaa-Yaa wherein Xaa and Yaa primarily comprise proline and 4-hydroxyproline, respectively. In some cases, the GLK polymer further comprises amino acid residues Pro, Gly, Glu, Qln, Asn, Ser, and Lys. In some cases, the length of the GLK polymer is about 20, 30, 40, 50, 60, 70, 80, 90, 100, 110, 120, 150 residues or longer.

Additional Conjugating Moieties

In some instances, the conjugating moiety comprises an extracellular biomarker. In some instances, the extracellular biomarker is a tumor antigen. In some instances, exemplary extracellular biomarker comprises CD19, PSMA, B7-H3, B7-H6, CD70, CEA, CSPG4, EGFRvIII, EphA3, EpCAM, EGFR, ErbB2 (HER2), FAP, FRα, GD2, GD3, Lewis-Y, mesothelin, Muc1, Muc 16, ROR1, TAG72, VEGFR2, CD11, Gr-1, CD204, CD16, CD49b, CD3, CD4, CD8, and B220. In some instances, the conjugating moiety is bond or conjugated to the cytokine (e.g., IL-2). In some cases, the conjugating moiety is genetically fused, for example, at the N-terminus or the C-terminus, of the cytokine (e.g., IL-2).

In some instances, the conjugating moiety comprises a molecule from a post-translational modification. In some instances, examples of post-translational modification include myristoylation, palmitoylation, isoprenylation (or prenylation) (e.g., farnesylation or geranylgeranylation), glypiation, acylation (e.g., O-acylation, N-acylation, S-acylation), alkylation (e.g., additional of alkyl groups such as methyl or ethyl groups), amidation, glycosylation, hydroxylation, iodination, nucleotide addition, oxidation, phosphorylation, succinylation, sulfation, glycation, carbamylation, glutamylation, or deamidation. In some instances, the cytokine (e.g., IL-2) is modified by a post-translational modification such as myristoylation, palmitoylation, isoprenylation (or prenylation) (e.g., farnesylation or geranylgeranylation), glypiation, acylation (e.g., O-acylation, N-acylation, S-acylation), alkylation (e.g., additional of alkyl groups such as methyl or ethyl groups), amidation, glycosylation, hydroxylation, iodination, nucleotide addition, oxidation, phosphorylation, succinylation, sulfation, glycation, carbamylation, glutamylation, or deamidation.

Conjugation
Linkers

In some embodiments, useful functional reactive groups for conjugating or binding a conjugating moiety to a cytokine polypeptide (e.g., an IL-2 polypeptide) described herein include, for example, zero or higher-order linkers. In some instances, an unnatural amino acid incorporated into an interleukin described herein comprises a functional reactive group. In some instances, a linker comprises a functional reactive group that reacts with an unnatural amino acid incorporated into an interleukin described herein. In some instances, a conjugating moiety comprises a functional reactive group that reacts with an unnatural amino acid incorporated into an interleukin described herein. In some instances, a conjugating moiety comprises a functional reactive group that reacts with a linker (optionally pre-attached to a cytokine peptide) described herein. In some embodiments, a linker comprises a reactive group that reacts with a natural amino acid in a cytokine peptide described herein. In some cases, higher-order linkers comprise bifunctional linkers, such as homobifunctional linkers or heterobifunctional linkers. Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis(succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

In some embodiments, the bifunctional linker comprises a heterobifunctional linker. Exemplary heterobifunctional linker include, but are not limited to, amine-reactive and sulfhydryl cross-linkers such as N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino)hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sI-ACX), p-nitrophenyl iodoacetate (NPIA), carbonyl-reactive and sulfhydryl-reactive cross-linkers such as 4-(4-N-maleimidophenyl)butyric acid hydrazide (MPBH), 4-(N-maleimidomethyl)cyclohexane-1-carboxyl-hydrazide-8 ($M_2C_2H$), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), sulfhydryl-reactive and photoreactive cross-linkers such as 1-(ρ-Azidosalicylamido)-4-(iodoacetamido)butane (AsIB), N-[4-(ρ-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as p-azidobenzoyl hydrazide (ABH), carboxylate-reactive and photoreactive cross-linkers such as 4-(ρ-azidosalicylamido)butylamine (AsBA), and arginine-reactive and photoreactive cross-linkers such as ρ-azidophenyl glyoxal (APG).

In some instances, the reactive functional group comprises a nucleophilic group that is reactive to an electrophilic group present on a binding moiety (e.g., on a conjugating moiety or on IL-2). Exemplary electrophilic groups include carbonyl groups—such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide. In some embodiments, an unnatural amino acid incorporated into an interleukin described herein comprises an electrophilic group.

In some embodiments, the linker is a cleavable linker. In some embodiments, the cleavable linker is a dipeptide linker. In some embodiments, the dipeptide linker is valine-citrulline (Val-Cit), phenylalanine-lysine (Phe-Lys), valine-alanine (Val-Ala) and valine-lysine (Val-Lys). In some embodiments, the dipeptide linker is valine-citrulline.

In some embodiments, the linker is a peptide linker comprising, e.g., at least 2, 3, 4, 5, 6, 7, 8, 9, 10, 11, 12, 15, 20, 25, 30, 35, 40, 45, 50, or more amino acids. In some instances, the peptide linker comprises at most 2, 3, 4, 5, 6, 7, 8, 9, 10, 11, 12, 15, 20, 25, 30, 35, 40, 45, 50, or less amino acids. In additional cases, the peptide linker comprises about 2, 3, 4, 5, 6, 7, 8, 9, 10, 11, 12, 15, 20, 25, 30, 35, 40, 45, or 50 amino acids.

In some embodiments, the linker comprises a self-immolative linker moiety. In some embodiments, the self-immolative linker moiety comprises p-aminobenzyl alcohol (PAB), p-aminobenzyoxycarbonyl (PABC), or derivatives or analogs thereof. In some embodiments, the linker comprises a dipeptide linker moiety and a self-immolative linker moiety. In some embodiments, the self-immolative linker moiety is such as described in U.S. Pat. No. 9,089,614 and WIPO Application No. WO2015038426.

In some embodiments, the cleavable linker is glucuronide. In some embodiments, the cleavable linker is an acid-cleavable linker. In some embodiments, the acid-cleavable linker is hydrazine. In some embodiments, the cleavable linker is a reducible linker.

In some embodiments, the linker comprises a maleimide group. In some instances, the maleimide group is also referred to as a maleimide spacer. In some instances, the maleimide group further comprises a caproic acid, forming maleimidocaproyl (mc). In some cases, the linker comprises maleimidocaproyl (mc). In some cases, linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of thiosuccinimide ring hydrolysis, thereby eliminating maleimide from undergoing an elimination reaction through a retro-Michael reaction. In some instances, the self-stabilizing maleimide is a maleimide group described in Lyon, et al., "Self-hydrolyzing maleimides improve the stability and pharmacological properties of antibody-drug conjugates," *Nat. Biotechnol.* 32(10): 1059-1062 (2014). In some instances, the linker comprises a self-stabilizing maleimide. In some instances, the linker is a self-stabilizing maleimide.

Described herein are IL-2 conjugates having the structure of Formula (I):

Formula (I)

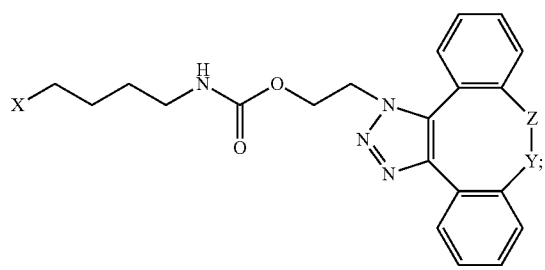

wherein:
Z is CH$_2$ and Y is

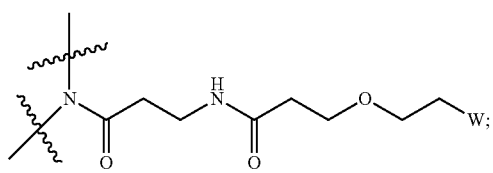

or
Y is CH$_2$ and Z is

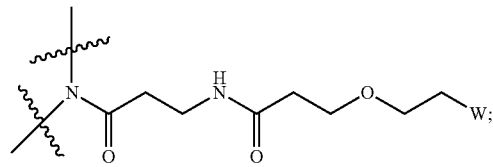

W is a PEG group having an average molecular weight selected from 5 kDa, 10 kDa, 15 kDa, 20 kDa, 25 kDa, 30 kDa, 35 kDa, 40 kDa, 45 kDa, and 50 kDa; and
X is an amino acid position of a recombinant human IL-2, wherein the amino acid position is in reference to the positions in SEQ ID NO: 1; or a pharmaceutically acceptable salt, solvate, or hydrate thereof. In some embodiments of an IL-2 conjugate of Formula (I), Z is CH$_2$ and Y is

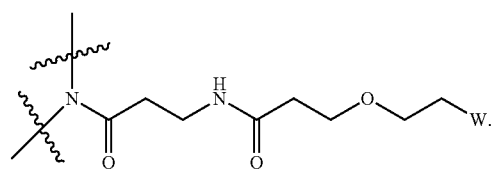

In some embodiments of an IL-2 conjugate of Formula (I), Y is CH$_2$ and Z is

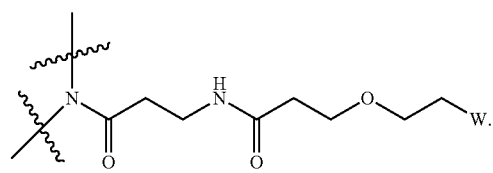

In some embodiments of an IL-2 conjugate of Formula (I), the PEG group has an average molecular weight selected from 5 kDa, 10 kDa, 30 kDa, 40 kDa, 45 kDa, 50 kDa, 55 kDa, and 60 kDa. In some embodiments of an IL-2 conjugate of Formula (I), the PEG group has an average molecular weight of 5 kDa. In some embodiments of an IL-2 conjugate of Formula (I), the PEG group has an average molecular weight of 10 kDa. In some embodiments of an IL-2 conjugate of Formula (I), the PEG group has an average molecular weight of 20 kDa. In some embodiments of an IL-2 conjugate of Formula (I), the PEG group has an average molecular weight of 30 kDa. In some embodiments of an IL-2 conjugate of Formula (I), the PEG group has an average molecular weight of 40 kDa. In some embodiments of an IL-2 conjugate of Formula (I), the PEG group has an average molecular weight of 50 kDa. In some embodiments of an IL-2 conjugate of Formula (I), the PEG group has an average molecular weight of 55 kDa. In some embodiments of an IL-2 conjugate of Formula (I), the PEG group has an average molecular weight of 60 kDa. In some embodiments of an IL-2 conjugate of Formula (I), X is K9. In some embodiments of an IL-2 conjugate of Formula (I), X is H16. In some embodiments of an IL-2 conjugate of Formula (I), X is L19. In some embodiments of an IL-2 conjugate of Formula (I), X is D20. In some embodiments of an IL-2 conjugate of Formula (I), X is M23. In some embodiments of an IL-2 conjugate of Formula (I), X is N26. In some embodiments of an IL-2 conjugate of Formula (I), X is T41. In some embodiments of an IL-2 conjugate of Formula (I), X is N88. In some embodiments of an IL-2 conjugate of Formula (I), X is E100. In some embodiments of an IL-2 conjugate of Formula (I), X is N119. In some embodiments of an IL-2 conjugate of Formula (I), X is T123. In some embodiments of an IL-2 conjugate of Formula (I), X is Q126. In some embodiments of an IL-2 conjugate of Formula (I), X is 5127. In some embodiments of an IL-2 conjugate of Formula (I), X is T131. In some embodiments of an IL-2 conjugate of Formula (I), X is 109 with variant N88R. In some embodiments of an IL-2 conjugate of Formula (I), X is V91. In some embodiments of an IL-2 conjugate of Formula (I), X is selected from K9, H16, L19, D20, M23, N26, N88, E100, N119, T123, Q126, S127, T131, D109, and V91. In some embodiments of an IL-2 conjugate of Formula (I), X is selected from K9, H16, M23, and Q126. In some embodiments an IL-2 conjugate of Formula (I) comprises the sequence of any one of SEQ ID NOs: 34-48. In some embodiments an IL-2 conjugate of Formula (I) comprises SEQ ID NOs.: 199-213. In some embodiments an IL-2 conjugate of Formula (I) comprises SEQ ID NOs.: 49-63. In some embodiments an IL-2 conjugate of Formula (I) comprises SEQ ID NOs.: 213-228. In some embodiments an IL-2 conjugate of Formula (I) comprises SEQ ID NOs.: 64-78. In some embodiments an IL-2 conjugate of Formula (I) comprises SEQ ID NOs.: 229-245. In some embodiments an IL-2 conjugate of Formula (I) comprises SEQ ID NOs.: 154-168. In some embodiments an IL-2 conjugate of Formula (I) comprises SEQ ID NOs.: 109-123. In some embodiments an IL-2 conjugate of Formula (I) comprises SEQ ID NOs.: 169-183. In some embodiments an IL-2 conjugate of Formula (I) comprises SEQ ID NOs.: 123-138. In some embodiments an IL-2 conjugate of Formula (I) comprises SEQ ID NOs.: 184-198. In some embodiments an IL-2 conjugate of Formula (I) comprises SEQ ID NOs.: 139-153. In some embodiments an IL-2 conjugate of Formula (I) comprises the sequence of SEQ ID NO: 3. In some embodiments an IL-2 conjugate of Formula (I) comprises the sequence of SEQ ID NO: 4. In some embodiments an IL-2 conjugate of Formula (I) comprises the sequence of SEQ ID NO: 5. In some embodiments an IL-2 conjugate of Formula (I) comprises the sequence of SEQ ID NO: 6. In some embodiments an IL-2 conjugate of Formula (I) comprises the sequence of SEQ ID NO: 7. In some embodiments an IL-2 conjugate of Formula (I) comprises the sequence of SEQ ID NO: 8. In some embodiments an IL-2 conjugate of Formula (I) comprises the sequence of SEQ ID NO: 9. In some embodiments an IL-2 conjugate of Formula (I) comprises the sequence of SEQ ID NO: 10. In some embodiments an IL-2 conjugate of Formula (I) comprises the sequence of SEQ ID NO: 11. In some embodiments an IL-2 conjugate of Formula (I) comprises the sequence of SEQ ID NO: 12. In some embodiments an IL-2 conjugate of Formula (I) comprises the sequence of SEQ ID NO: 13. In some embodiments an IL-2 conjugate of Formula (I) comprises the sequence of SEQ ID NO: 14. In some embodiments an IL-2 conjugate of Formula (I) comprises the sequence of SEQ ID NO: 15. In some embodiments an IL-2 conjugate of Formula (I) comprises the sequence of SEQ ID NO: 16. In some embodiments an IL-2 conjugate of Formula (I) comprises the sequence of SEQ ID NO: 17. In some embodiments an IL-2 conjugate of Formula (I) comprises the sequence of SEQ ID NO: 18. In some embodiments an IL-2 conjugate of Formula (I) comprises the sequence of SEQ ID NO: 19. In some embodiments an IL-2 conjugate of Formula (I) comprises the sequence of SEQ ID NO: 20. In some embodiments an IL-2 conjugate of Formula (I) comprises the sequence of SEQ ID NO: 21. In some embodiments an IL-2 conjugate of Formula (I) comprises the sequence of SEQ ID NO: 22. In some embodiments an IL-2 conjugate of Formula (I) comprises the sequence of SEQ ID NO: 23. In some embodiments an IL-2 conjugate of Formula (I) comprises the sequence of SEQ ID NO: 24. In some embodiments an IL-2 conjugate of Formula (I) comprises the sequence of SEQ ID NO: 25. In some embodiments an IL-2 conjugate of Formula (I) comprises the sequence of SEQ ID NO: 26. In some embodiments an IL-2 conjugate of Formula (I) comprises the sequence of SEQ ID NO: 27. In some embodiments an IL-2 conjugate of Formula (I) comprises the sequence of SEQ ID NO: 28. In some embodiments an IL-2 conjugate of Formula (I) comprises the sequence of SEQ ID NO: 29. In some embodiments an IL-2 conjugate of Formula (I) comprises the sequence of SEQ ID NO: 30. In some embodiments an IL-2 conjugate of Formula (I) comprises the sequence of SEQ ID NO: 31. In some embodiments an IL-2 conjugate of Formula (I) comprises the sequence of SEQ ID NO: 32. In some embodiments an IL-2 conjugate of Formula (I) comprises the sequence of SEQ ID NO: 33. In some embodiments an IL-2 conjugate of Formula (I) comprises the sequence of SEQ ID NO: 34. In some embodiments an IL-2 conjugate of Formula (I) comprises the sequence of SEQ ID NO: 35. In some embodiments an IL-2 conjugate of Formula (I) comprises the sequence of SEQ ID NO: 36. In some embodiments an IL-2 conjugate of Formula (I) comprises the sequence of SEQ ID NO: 37. In some embodiments an IL-2 conjugate of Formula (I) comprises the sequence of SEQ ID NO: 38. In some embodiments an IL-2 conjugate of Formula (I) comprises the sequence of SEQ ID NO: 39. In some embodiments an IL-2 conjugate of Formula (I) comprises the sequence of SEQ ID NO: 40. In some embodiments an IL-2 conjugate of Formula (I) comprises the sequence of SEQ ID NO: 41. In some embodiments an IL-2 conjugate of Formula (I) comprises the sequence of SEQ ID NO: 42. In some embodiments an IL-2 conjugate of Formula (I) comprises the sequence of SEQ ID NO: 43. In some embodiments an IL-2 conjugate of Formula (I) comprises the sequence of SEQ ID NO: 44. In some embodiments an IL-2 conjugate of Formula (I) comprises the sequence of SEQ ID NO: 45. In some embodiments an IL-2 conjugate of Formula (I) comprises the sequence of SEQ ID NO: 46. In some embodiments an IL-2 conjugate of Formula (I) comprises the sequence of SEQ ID NO: 47. In some embodiments an IL-2 conjugate of Formula (I) comprises the sequence of SEQ ID NO: 48. In some embodiments an IL-2 conjugate of Formula (I) comprises the sequence of SEQ ID NO: 49. In some embodiments an IL-2 conjugate of Formula (I) comprises the sequence of SEQ ID NO: 50. In some embodiments an IL-2 conjugate of Formula (I) comprises the sequence of SEQ ID NO: 51. In some embodiments an IL-2 conjugate of Formula (I) comprises the sequence of SEQ ID NO: 52. In some embodiments an IL-2 conjugate of Formula (I) comprises the sequence of SEQ ID NO: 53. In some embodiments an IL-2 conjugate of Formula (I) comprises the sequence of SEQ ID NO: 54. In some embodiments an IL-2 conjugate of Formula (I) comprises the sequence of SEQ ID NO: 55. In some embodiments an IL-2 conjugate of Formula (I) comprises the sequence of SEQ ID NO: 56. In some embodiments an IL-2 conjugate of Formula (I) comprises the sequence of SEQ ID NO: 57. In some embodiments an IL-2 conjugate of Formula (I) comprises the sequence of SEQ ID NO: 58. In some embodiments an IL-2 conjugate of Formula (I) comprises the sequence of SEQ ID NO: 59. In some embodiments an IL-2 conjugate of Formula (I) comprises the sequence of SEQ ID NO: 60. In some embodiments an IL-2 conjugate of Formula (I) comprises the sequence of SEQ ID NO: 61. In some embodiments an IL-2 conjugate of Formula (I) comprises the sequence of SEQ ID NO: 62. In some embodiments an IL-2 conjugate of Formula (I) comprises the sequence of SEQ ID NO: 63. In some embodiments an IL-2 conjugate of Formula (I) comprises the sequence of SEQ ID NO: 64. In some embodiments an IL-2 conjugate of Formula (I) comprises the sequence of SEQ ID NO: 65. In some embodiments an IL-2 conjugate of Formula (I) comprises the sequence of SEQ ID NO: 66. In some embodiments an IL-2 conjugate of Formula (I) comprises the sequence of SEQ ID NO: 67. In some embodiments an IL-2 conjugate of Formula (I) comprises the sequence of SEQ ID NO: 68. In some embodiments an IL-2 conjugate of Formula (I) comprises the sequence of SEQ ID NO: 69. In some embodiments an IL-2 conjugate of Formula (I) comprises the sequence of SEQ ID NO: 70. In some embodiments an IL-2 conjugate of Formula (I) comprises the sequence of SEQ ID NO: 71. In some embodiments an IL-2 conjugate of Formula (I) comprises the sequence of SEQ ID NO: 72. In some embodiments an IL-2 conjugate of Formula (I) comprises the sequence of SEQ ID NO: 73. In some embodiments an IL-2 conjugate of Formula (I) comprises the sequence of SEQ ID NO: 74. In some embodiments an IL-2 conjugate of Formula (I) comprises the sequence of SEQ ID NO: 75. In some embodiments an IL-2 conjugate of Formula (I) comprises the sequence of SEQ ID NO: 76. In some embodiments an IL-2 conjugate of Formula (I) comprises the sequence of SEQ ID NO: 77. In some embodiments an IL-2 conjugate of Formula (I) comprises the sequence of SEQ ID NO: 78. In some embodiments an IL-2 conjugate of Formula (I) comprises the sequence of SEQ ID NO: 79. In some embodiments an IL-2 conjugate of Formula (I) comprises the sequence of SEQ ID NO: 80. In some embodiments an IL-2 conjugate of Formula (I) comprises the sequence of SEQ ID NO: 81. In some embodiments an IL-2 conjugate of Formula (I) comprises the sequence of SEQ ID NO: 82. In some embodiments an IL-2 conjugate of Formula (I) comprises the sequence of SEQ ID NO: 83. In some embodiments an IL-2 conjugate of Formula (I) comprises the sequence of SEQ ID NO: 84. In some embodiments an IL-2 conjugate of Formula (I) comprises the sequence of SEQ ID NO: 85. In some embodiments an IL-2 conjugate of Formula (I) comprises the sequence of SEQ ID NO: 86. In some embodiments an IL-2 conjugate of Formula (I) comprises the sequence of SEQ ID NO: 87. In some embodiments an IL-2 conjugate of Formula (I) comprises the sequence of SEQ ID NO: 88. In some embodiments an IL-2 conjugate of Formula (I) comprises the sequence of SEQ ID NO: 89. In some embodiments an IL-2 conjugate of Formula (I) comprises the sequence of SEQ ID NO: 90. In some embodiments an IL-2 conjugate of Formula (I) comprises the sequence of SEQ ID NO: 91. In some embodiments an IL-2 conjugate of Formula (I) comprises the sequence of SEQ ID NO: 92. In some embodiments an IL-2 conjugate of Formula (I) comprises the sequence of SEQ ID NO: 93. In some embodiments an IL-2 conjugate of Formula (I) comprises the sequence of SEQ ID NO: 94. In some embodiments an IL-2 conjugate of Formula (I) comprises the sequence of SEQ ID NO: 95. In some embodiments an IL-2 conjugate of Formula (I) comprises the sequence of SEQ ID NO: 96. In some embodiments an IL-2 conjugate of Formula (I) comprises the sequence of SEQ ID NO: 97. In some embodiments an IL-2 conjugate of Formula (I) comprises the sequence of SEQ ID NO: 98. In some embodiments an IL-2 conjugate of Formula (I) comprises the sequence of SEQ ID NO: 99. In some embodiments an IL-2 conjugate of Formula (I) comprises the sequence of SEQ ID NO: 100. In some embodiments an IL-2 conjugate of Formula (I) comprises the sequence of SEQ ID NO: 101. In some embodiments an IL-2 conjugate of Formula (I) comprises the sequence of SEQ ID NO: 102. In some embodiments an IL-2 conjugate of Formula (I) comprises the sequence of SEQ ID NO: 103. In some embodiments an IL-2 conjugate of Formula (I) comprises the sequence of SEQ ID NO: 104. In some embodiments an IL-2 conjugate of Formula (I) comprises the sequence of SEQ ID NO: 105. In some embodiments an IL-2 conjugate of Formula (I) comprises the sequence of SEQ ID NO: 106. In some embodiments an IL-2 conjugate of Formula (I) comprises the sequence of SEQ ID NO: 107. In some embodiments an IL-2 conjugate of Formula (I) comprises the sequence of SEQ ID NO: 108. In some embodiments an IL-2 conjugate of Formula (I) comprises the sequence of SEQ ID NO: 109. In some embodiments an IL-2 conjugate of Formula (I) comprises the sequence of SEQ ID NO: 110. In some embodiments an IL-2 conjugate of Formula (I) comprises the sequence of SEQ ID NO: 111. In some embodiments an IL-2 conjugate of Formula (I) comprises the sequence of SEQ ID NO: 112. In some embodiments an IL-2 conjugate of Formula (I) comprises the sequence of SEQ ID NO: 113. In some embodiments an IL-2 conjugate of Formula (I) comprises the sequence of SEQ ID NO: 114. In some embodiments an IL-2 conjugate of Formula (I) comprises the sequence of SEQ ID NO: 115. In some embodiments an IL-2 conjugate of Formula (I) comprises the sequence of SEQ ID NO: 116. In some embodiments an IL-2 conjugate of Formula (I) comprises the sequence of SEQ ID NO: 117. In some embodiments an IL-2 conjugate of Formula (I) comprises the sequence of SEQ ID NO: 118. In some embodiments an IL-2 conjugate of Formula (I) comprises the sequence of SEQ ID NO: 119. In some embodiments an IL-2 conjugate of Formula (I) comprises the sequence of SEQ ID NO: 120. In some embodiments an IL-2 conjugate of Formula (I) comprises the sequence of SEQ ID NO: 121. In some embodiments an IL-2 conjugate of Formula (I) comprises the sequence of SEQ ID NO: 122. In some embodiments an IL-2 conjugate of Formula (I) comprises the sequence of SEQ ID NO: 123. In some embodiments an IL-2 conjugate of Formula (I) comprises the sequence of SEQ ID NO: 124. In some embodiments an IL-2 conjugate of Formula (I) comprises the sequence of SEQ ID NO: 125. In some embodiments an IL-2 conjugate of Formula (I) comprises the sequence of SEQ ID NO: 126. In some embodiments an IL-2 conjugate of Formula (I) comprises the sequence of SEQ ID NO: 127. In some embodiments an IL-2 conjugate of Formula (I) comprises the sequence of SEQ ID NO: 128. In some embodiments an IL-2 conjugate of Formula (I) comprises the sequence of SEQ ID NO: 129. In some embodiments an IL-2 conjugate of Formula (I) comprises the sequence of SEQ ID NO: 130. In some embodiments an IL-2 conjugate of Formula (I) comprises the sequence of SEQ ID NO: 131. In some embodiments an IL-2 conjugate of Formula (I) comprises the sequence of SEQ ID NO: 132. In some embodiments an IL-2 conjugate of Formula (I) comprises the sequence of SEQ ID NO: 133. In some embodiments an IL-2 conjugate of Formula (I) comprises the sequence of SEQ ID NO: 134. In some embodiments an IL-2 conjugate of Formula (I) comprises the sequence of SEQ ID NO: 135. In some embodiments an IL-2 conjugate of Formula (I) comprises the sequence of SEQ ID NO: 136. In some embodiments an IL-2 conjugate of Formula (I) comprises the sequence of SEQ ID NO: 137. In some embodiments an IL-2 conjugate of Formula (I) comprises the sequence of SEQ ID NO: 138. In some embodiments an IL-2 conjugate of Formula (I) comprises the sequence of SEQ ID NO: 139. In some embodiments an IL-2 conjugate of Formula (I) comprises the sequence of SEQ ID NO: 140. In some embodiments an IL-2 conjugate of Formula (I) comprises the sequence of SEQ ID NO: 141. In some embodiments an IL-2 conjugate of Formula (I) comprises the sequence of SEQ ID NO: 142. In some embodiments an IL-2 conjugate of Formula (I) comprises the sequence of SEQ ID NO: 143. In some embodiments an IL-2 conjugate of Formula (I) comprises the sequence of SEQ ID NO: 144. In some embodiments an IL-2 conjugate of Formula (I) comprises the sequence of SEQ ID NO: 145. In some embodiments an IL-2 conjugate of Formula (I) comprises the sequence of SEQ ID NO: 146. In some embodiments an IL-2 conjugate of Formula (I) comprises the sequence of SEQ ID NO: 147. In some embodiments an IL-2 conjugate of Formula (I) comprises the sequence of SEQ ID NO: 148. In some embodiments an IL-2 conjugate of Formula (I) comprises the sequence of SEQ ID NO: 149. In some embodiments an IL-2 conjugate of Formula (I) comprises the sequence of SEQ ID NO: 150. In some embodiments an IL-2 conjugate of Formula (I) comprises the sequence of SEQ ID NO: 151. In some embodiments an IL-2 conjugate of Formula (I) comprises the sequence of SEQ ID NO: 152. In some embodiments an IL-2 conjugate of Formula (I) comprises the sequence of SEQ ID NO: 153. In some embodiments an IL-2 conjugate of Formula (I) comprises the sequence of SEQ ID NO: 154. In some embodiments an IL-2 conjugate of Formula (I) comprises the sequence of SEQ ID NO: 155. In some embodiments an IL-2 conjugate of Formula (I) comprises the sequence of SEQ ID NO: 156. In some embodiments an IL-2 conjugate of Formula (I) comprises the sequence of SEQ ID NO: 157. In some embodiments an IL-2 conjugate of Formula (I) comprises the sequence of SEQ ID NO: 158. In some embodiments an IL-2 conjugate of Formula (I) comprises the sequence of SEQ ID NO: 159. In some embodiments an IL-2 conjugate of Formula (I) comprises the sequence of SEQ ID NO: 160. In some embodiments an IL-2 conjugate of Formula (I) comprises the sequence of SEQ ID NO: 161. In some embodiments an IL-2 conjugate of Formula (I) comprises the sequence of SEQ ID NO: 162. In some embodiments an IL-2 conjugate of Formula (I) comprises the sequence of SEQ ID NO: 163. In some embodiments an IL-2 conjugate of Formula (I) comprises the sequence of SEQ ID NO: 164. In some embodiments an IL-2 conjugate of Formula (I) comprises the sequence of SEQ ID NO: 165. In some embodiments an IL-2 conjugate of Formula (I) comprises the sequence of SEQ ID NO: 166. In some embodiments an IL-2 conjugate of Formula (I) comprises the sequence of SEQ ID NO: 167. In some embodiments an IL-2 conjugate of Formula (I) comprises the sequence of SEQ ID NO: 168. In some embodiments an IL-2 conjugate of Formula (I) comprises the sequence of SEQ ID NO: 169. In some embodiments an IL-2 conjugate of Formula (I) comprises the sequence of SEQ ID NO: 170. In some embodiments an IL-2 conjugate of Formula (I) comprises the sequence of SEQ ID NO: 171. In some embodiments an IL-2 conjugate of Formula (I) comprises the sequence of SEQ ID NO: 172. In some embodiments an IL-2 conjugate of Formula (I) comprises the sequence of SEQ ID NO: 173. In some embodiments an IL-2 conjugate of Formula (I) comprises the sequence of SEQ ID NO: 174. In some embodiments an IL-2 conjugate of Formula (I) comprises the sequence of SEQ ID NO: 175. In some embodiments an IL-2 conjugate of Formula (I) comprises the sequence of SEQ ID NO: 176. In some embodiments an IL-2 conjugate of Formula (I) comprises the sequence of SEQ ID NO: 177. In some embodiments an IL-2 conjugate of Formula (I) comprises the sequence of SEQ ID NO: 178. In some embodiments an IL-2 conjugate of Formula (I) comprises the sequence of SEQ ID NO: 179. In some embodiments an IL-2 conjugate of Formula (I) comprises the sequence of SEQ ID NO: 180. In some embodiments an IL-2 conjugate of Formula (I) comprises the sequence of SEQ ID NO: 181. In some embodiments an IL-2 conjugate of Formula (I) comprises the sequence of SEQ ID NO: 182. In some embodiments an IL-2 conjugate of Formula (I) comprises the sequence of SEQ ID NO: 183. In some embodiments an IL-2 conjugate of Formula (I) comprises the sequence of SEQ ID NO: 184. In some embodiments an IL-2 conjugate of Formula (I) comprises the sequence of SEQ ID NO: 185. In some embodiments an IL-2 conjugate of Formula (I) comprises the sequence of SEQ ID NO: 186. In some embodiments an IL-2 conjugate of Formula (I) comprises the sequence of SEQ ID NO: 187. In some embodiments an IL-2 conjugate of Formula (I) comprises the sequence of SEQ ID NO: 188. In some embodiments an IL-2 conjugate of Formula (I) comprises the sequence of SEQ ID NO: 189. In some embodiments an IL-2 conjugate of Formula (I) comprises the sequence of SEQ ID NO: 190. In some embodiments an IL-2 conjugate of Formula (I) comprises the sequence of SEQ ID NO: 191. In some embodiments an IL-2 conjugate of Formula (I) comprises the sequence of SEQ ID NO: 192. In some embodiments an IL-2 conjugate of Formula (I) comprises the sequence of SEQ ID NO: 193. In some embodiments an IL-2 conjugate of Formula (I) comprises the sequence of SEQ ID NO: 194. In some embodiments an IL-2 conjugate of Formula (I) comprises the sequence of SEQ ID NO: 195. In some embodiments an IL-2 conjugate of Formula (I) comprises the sequence of SEQ ID NO: 196. In some embodiments an IL-2 conjugate of Formula (I) comprises the sequence of SEQ ID NO: 197. In some embodiments an IL-2 conjugate of Formula (I) comprises the sequence of SEQ ID NO: 198. In some embodiments an IL-2 conjugate of Formula (I) comprises the sequence of SEQ ID NO: 199. In some embodiments an IL-2 conjugate of Formula (I) comprises the sequence of SEQ ID NO: 190. In some embodiments an IL-2 conjugate of Formula (I) comprises the sequence of SEQ ID NO: 191. In some embodiments an IL-2 conjugate of Formula (I) comprises the sequence of SEQ ID NO: 192. In some embodiments an IL-2 conjugate of Formula (I) comprises the sequence of SEQ ID NO: 193. In some embodiments an IL-2 conjugate of Formula (I) comprises the sequence of SEQ ID NO: 194. In some embodiments an IL-2 conjugate of Formula (I) comprises the sequence of SEQ ID NO: 195. In some embodiments an IL-2 conjugate of Formula (I) comprises the sequence of SEQ ID NO: 196. In some embodiments an IL-2 conjugate of Formula (I) comprises the sequence of SEQ ID NO: 197. In some embodiments an IL-2 conjugate of Formula (I) comprises the sequence of SEQ ID NO: 198. In some embodiments an IL-2 conjugate of Formula (I) comprises the sequence of SEQ ID NO: 199. In some embodiments an IL-2 conjugate of Formula (I) comprises the sequence of SEQ ID NO: 200. In some embodiments an IL-2 conjugate of Formula (I) comprises the sequence of SEQ ID NO: 201. In some embodiments an IL-2 conjugate of Formula (I) comprises the sequence of SEQ ID NO: 202. In some embodiments an IL-2 conjugate of Formula (I) comprises the sequence of SEQ ID NO: 203. In some embodiments an IL-2 conjugate of Formula (I) comprises the sequence of SEQ ID NO: 204. In some embodiments an IL-2 conjugate of Formula (I) comprises the sequence of SEQ ID NO: 205. In some embodiments an IL-2 conjugate of Formula (I) comprises the sequence of SEQ ID NO: 206. In some embodiments an IL-2 conjugate of Formula (I) comprises the sequence of SEQ ID NO: 207. In some embodiments an IL-2 conjugate of Formula (I) comprises the sequence of SEQ ID NO: 208. In some embodiments an IL-2 conjugate of Formula (I) comprises the sequence of SEQ ID NO: 209. In some embodiments an IL-2 conjugate of Formula (I) comprises the sequence of SEQ ID NO: 210. In some embodiments an IL-2 conjugate of Formula (I) comprises the sequence of SEQ ID NO: 211. In some embodiments an IL-2 conjugate of Formula (I) comprises the sequence of SEQ ID NO: 212. In some embodiments an IL-2 conjugate of Formula (I) comprises the sequence of SEQ ID NO: 213. In some embodiments an IL-2 conjugate of Formula (I) comprises the sequence of SEQ ID NO: 214. In some embodiments an IL-2 conjugate of Formula (I) comprises the sequence of SEQ ID NO: 215. In some embodiments an IL-2 conjugate of Formula (I) comprises the sequence of SEQ ID NO: 216. In some embodiments an IL-2 conjugate of Formula (I) comprises the sequence of SEQ ID NO: 217. In some embodiments an IL-2 conjugate of Formula (I) comprises the sequence of SEQ ID NO: 218. In some embodiments an IL-2 conjugate of Formula (I) comprises the sequence of SEQ ID NO: 219. In some embodiments an IL-2 conjugate of Formula (I) comprises the sequence of SEQ ID NO: 210. In some embodiments an IL-2 conjugate of Formula (I) comprises the sequence of SEQ ID NO: 211. In some embodiments an IL-2 conjugate of Formula (I) comprises the sequence of SEQ ID NO: 212. In some embodiments an IL-2 conjugate of Formula (I) comprises the sequence of SEQ ID NO: 213. In some embodiments an IL-2 conjugate of Formula (I) comprises the sequence of SEQ ID NO: 214. In some embodiments an IL-2 conjugate of Formula (I) comprises the sequence of SEQ ID NO: 215. In some embodiments an IL-2 conjugate of Formula (I) comprises the sequence of SEQ ID NO: 216. In some embodiments an IL-2 conjugate of Formula (I) comprises the sequence of SEQ ID NO: 217. In some embodiments an IL-2 conjugate of Formula (I) comprises the sequence of SEQ ID NO: 218. In some embodiments an IL-2 conjugate of Formula (I) comprises the sequence of SEQ ID NO: 219. In some embodiments an IL-2 conjugate of Formula (I) comprises the sequence of SEQ ID NO: 220. In some embodiments an IL-2 conjugate of Formula (I) comprises the sequence of SEQ ID NO: 221. In some embodiments an IL-2 conjugate of Formula (I) comprises the sequence of SEQ ID NO: 222. In some embodiments an IL-2 conjugate of Formula (I) comprises the sequence of SEQ ID NO: 223. In some embodiments an IL-2 conjugate of Formula (I) comprises the sequence of SEQ ID NO: 224. In some embodiments an IL-2 conjugate of Formula (I) comprises the sequence of SEQ ID NO: 225. In some embodiments an IL-2 conjugate of Formula (I) comprises the sequence of SEQ ID NO: 226. In some embodiments an IL-2 conjugate of Formula (I) comprises the sequence of SEQ ID NO: 227. In some embodiments an IL-2 conjugate of Formula (I) comprises the sequence of SEQ ID NO: 228. In some embodiments an IL-2 conjugate of Formula (I) comprises the sequence of SEQ ID NO: 229. In some embodiments an IL-2 conjugate of Formula (I) comprises the sequence of SEQ ID NO: 230. In some embodiments an IL-2 conjugate of Formula (I) comprises the sequence of SEQ ID NO: 231. In some embodiments an IL-2 conjugate of Formula (I) comprises the sequence of SEQ ID NO: 232. In some embodiments an IL-2 conjugate of Formula (I) comprises the sequence of SEQ ID NO: 233. In some embodiments an IL-2 conjugate of Formula (I) comprises the sequence of SEQ ID NO: 234. In some embodiments an IL-2 conjugate of Formula (I) comprises the sequence of SEQ ID NO: 235. In some embodiments an IL-2 conjugate of Formula (I) comprises the sequence of SEQ ID NO: 236. In some embodiments an IL-2 conjugate of Formula (I) comprises the sequence of SEQ ID NO: 237. In some embodiments an IL-2 conjugate of Formula (I) comprises the sequence of SEQ ID NO: 238. In some embodiments an IL-2 conjugate of Formula (I) comprises the sequence of SEQ ID NO: 239. In some embodiments an IL-2 conjugate of Formula (I) comprises the sequence of SEQ ID NO: 240. In some embodiments an IL-2 conjugate of Formula (I) comprises the sequence of SEQ ID NO: 241. In some embodiments an IL-2 conjugate of Formula (I) comprises the sequence of SEQ ID NO: 242. In some embodiments an IL-2 conjugate of Formula (I) comprises the sequence of SEQ ID NO: 243. In some embodiments an IL-2 conjugate of Formula (I) comprises the sequence of SEQ ID NO: 244. In some embodiments an IL-2 conjugate of Formula (I) comprises the sequence of SEQ ID NO: 245.

Described herein are IL-2 conjugates having the structure of Formula (II):

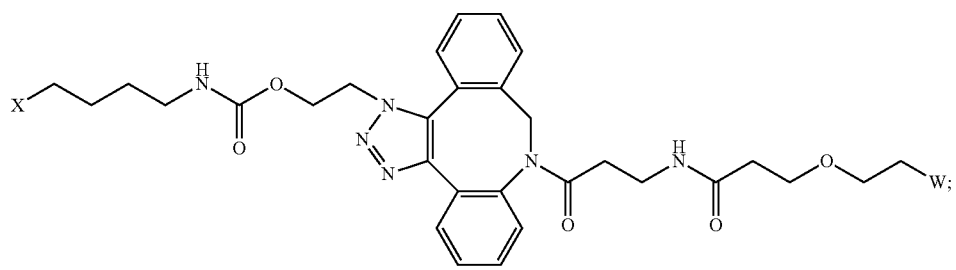

Formula (II)

wherein W is a PEG group having an average molecular weight selected from 5 kDa, 10 kDa, 15 kDa, 20 kDa, 25 kDa, 30 kDa, 35 kDa, 40 kDa, 45 kDa, and 50 kDa; and X is an amino acid position having the structure:

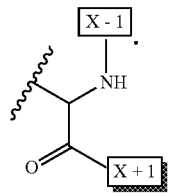

of a recombinant human IL-2 selected from K9, H16, L19, D20, M23, N26, N88, E100, N119, T123, Q126, S127, T131, D109, and V91, wherein the amino acid position corresponds to the positions in SEQ ID NO: 1.

Described herein are IL-2 conjugates having the structure of Formula (III):

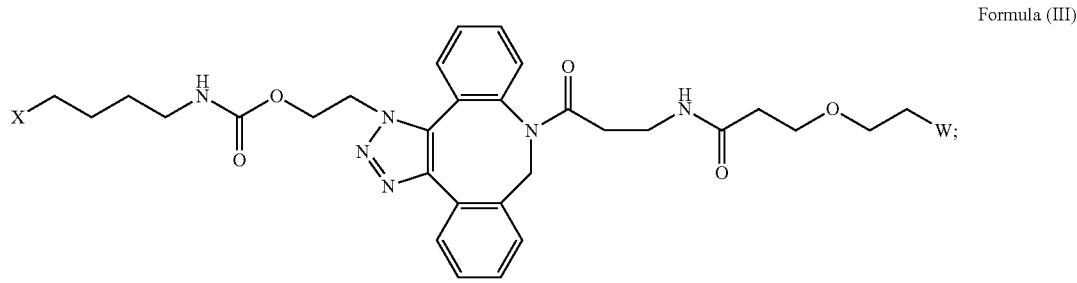

Formula (III)

wherein W is a PEG group having an average molecular weight selected from 5 kDa, 10 kDa, 15 kDa, 20 kDa, 25 kDa, 30 kDa, 35 kDa, 40 kDa, 45 kDa, and 50 kDa; and X is an amino acid position having the structure

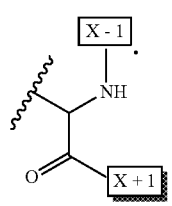

of a recombinant human IL-2 selected from K9, H16, L19, D20, M23, N26, N88, E100, N119, T123, Q126, S127, T131, D109, and V91, wherein the amino acid corresponds to the positions in SEQ ID NO: 1. In some embodiments of an IL-2 conjugate of Formula (II) or Formula (III), X is the K9 position of a recombinant human IL-2. In some embodiments of an IL-2 conjugate of Formula (II) or Formula (III), the PEG group has an average molecular weight of 50 kDa and X is the K9 position of a recombinant human IL-2. In some embodiments of an IL-2 conjugate of Formula (II) or Formula (III), X is the H16 position of a recombinant human IL-2. In some embodiments of an IL-2 conjugate of Formula (II) or Formula (III), the PEG group has an average molecular weight of 50 kDa and X is the H16 position of a recombinant human IL-2. In some embodiments of an IL-2 conjugate of Formula (II) or Formula (III), X is the L19 position of a recombinant human IL-2. In some embodiments of an IL-2 conjugate of Formula (II) or Formula (III), the PEG group has an average molecular weight of 50 kDa and X is the L19 position of a recombinant human IL-2. In some embodiments of an IL-2 conjugate of Formula (II) or Formula (III), X is the D20 position of a recombinant human IL-2. In some embodiments of an IL-2 conjugate of Formula (II) or Formula (III), the PEG group has an average molecular weight of 50 kDa and X is the D20 position of a recombinant human IL-2. In some embodiments of an IL-2 conjugate of Formula (II) or Formula (III), X is the M23 position of a recombinant human IL-2. In some embodiments of an IL-2 conjugate of Formula (II) or Formula (III), the PEG group has an average molecular weight of 50 kDa and X is the M23 position of a recombinant human IL-2. In some embodiments of an IL-2 conjugate of Formula (II) or Formula (III), X is the N26 position of a recombinant human IL-2. In some embodiments of an IL-2 conjugate of Formula (II) or Formula (III), the PEG group has an average molecular weight of 50 kDa and X is the N26 position of a recombinant human IL-2. In some embodiments of an IL-2 conjugate of Formula (II) or Formula (III), X is the N88 position of a recombinant human IL-2. In some embodiments of an IL-2 conjugate of Formula (II) or Formula (III), the PEG group has an average molecular weight of 50 kDa and X is the N88 position of a recombinant human IL-2. In some embodiments of an IL-2 conjugate of Formula (II) or Formula (III), X is the E100 position of a recombinant human IL-2. In some embodiments of an IL-2 conjugate of Formula (II) or Formula (III), the PEG group has an average molecular weight of 50 kDa and X is the E100 position of a recombinant human IL-2. In some embodiments of an IL-2 conjugate of Formula (II) or Formula (III), X is the N119 position of a recombinant human IL-2. In some embodiments of an IL-2 conjugate of Formula (II) or Formula (III), the PEG group has an average molecular weight of 50 kDa and X is the N119 position of a recombinant human IL-2. In some embodiments of an IL-2 conjugate of Formula (II) or Formula (III), X is the T123 position of a recombinant human IL-2. In some embodiments of an IL-2 conjugate of Formula (II) or Formula (III), the PEG group has an average molecular weight of 50 kDa and X is the T123 position of a recombinant human IL-2. In some embodiments of an IL-2 conjugate of Formula (II) or Formula (III), X is the Q126 position of a recombinant human IL-2. In some embodiments of an IL-2 conjugate of Formula (II) or Formula (III), the PEG group has an average molecular weight of 50 kDa and X is the Q126 position of a recombinant human IL-2. In some embodiments of an IL-2 conjugate of Formula (II) or Formula (III), X is the S127 position of a recombinant human IL-2. In some embodiments of an IL-2 conjugate of Formula (II) or Formula (III), the PEG group has an average molecular weight of 50 kDa and X is the S127 position of a recombinant human IL-2. In some embodiments of an IL-2 conjugate of Formula (II) or Formula (III), X is the T131 position of a recombinant human IL-2. In some embodiments of an IL-2 conjugate of Formula (II) or Formula (III), the PEG group has an average molecular weight of 50 kDa and X is the T131 position of a recombinant human IL-2. In some embodiments of an IL-2 conjugate of Formula (II) or Formula (III), X is the D109 position of a recombinant human IL-2. In some embodiments of an IL-2 conjugate of Formula (II) or Formula (III), the PEG group has an average molecular weight of 50 kDa and X is the D109 position of a recombinant human IL-2. In some embodiments of an IL-2 conjugate of Formula (II) or Formula (III), X is the V91 position of a recombinant human IL-2. In some embodiments of an IL-2 conjugate of Formula (II) or Formula (III), the PEG group has an average molecular weight of 50 kDa and X is the V91 position of a recombinant human IL-2.

In some embodiments of an IL-2 conjugate of Formula (II) or Formula (III), the PEG group has an average molecular weight of 10 kDa and X is the K9 position of a recombinant human IL-2. In some embodiments of an IL-2 conjugate of Formula (II) or Formula (III), the PEG group has an average molecular weight of 10 kDa and X is the H16 position of a recombinant human IL-2. In some embodiments of an IL-2 conjugate of Formula (II) or Formula (III), the PEG group has an average molecular weight of 10 kDa and X is the L19 position of a recombinant human IL-2. In some embodiments of an IL-2 conjugate of Formula (II) or Formula (III), the PEG group has an average molecular weight of 10 kDa and X is the D20 position of a recombinant human IL-2. In some embodiments of an IL-2 conjugate of Formula (II) or Formula (III), the PEG group has an average molecular weight of 10 kDa and X is the M23 position of a recombinant human IL-2. In some embodiments of an IL-2 conjugate of Formula (II) or Formula (III), the PEG group has an average molecular weight of 10 kDa and X is the N26 position of a recombinant human IL-2. In some embodiments of an IL-2 conjugate of Formula (II) or Formula (III), the PEG group has an average molecular weight of 10 kDa and X is the N88 position of a recombinant human IL-2. In some embodiments of an IL-2 conjugate of Formula (II) or Formula (III), the PEG group has an average molecular weight of 10 kDa and X is the E100 position of a recombinant human IL-2. In some embodiments of an IL-2 conjugate of Formula (II) or Formula (III), the PEG group has an average molecular weight of 10 kDa and X is the N119 position of a recombinant human IL-2. In some embodiments of an IL-2 conjugate of Formula (II) or Formula (III), the PEG group has an average molecular weight of 10 kDa and X is the T123 position of a recombinant human IL-2. In some embodiments of an IL-2 conjugate of Formula (II) or Formula (III), the PEG group has an average molecular weight of 10 kDa and X is the Q126 position of a recombinant human IL-2. In some embodiments of an IL-2 conjugate of Formula (II) or Formula (III), the PEG group has an average molecular weight of 10 kDa and X is the S127 position of a recombinant human IL-2. In some embodiments of an IL-2 conjugate of Formula (II) or Formula (III), the PEG group has an average molecular weight of 10 kDa and X is the T131 position of a recombinant human IL-2. In some embodiments of an IL-2 conjugate of Formula (II) or Formula (III), the PEG group has an average molecular weight of 10 kDa and X is the D109 position of a recombinant human IL-2. In some embodiments of an IL-2 conjugate of Formula (II) or Formula (III), the PEG group has an average molecular weight of 10 kDa and X is the V91 position of a recombinant human IL-2. In some embodiments of an IL-2 conjugate of Formula (II) or Formula (III), the PEG group has an average molecular weight of 30 kDa and X is the K9 position of a recombinant human IL-2. In some embodiments of an IL-2 conjugate of Formula (II) or Formula (III), the PEG group has an average molecular weight of 30 kDa and X is the H16 position of a recombinant human IL-2. In some embodiments of an IL-2 conjugate of Formula (II) or Formula (III), the PEG group has an average molecular weight of 30 kDa and X is the L19 position of a recombinant human IL-2. In some embodiments of an IL-2 conjugate of Formula (II) or Formula (III), the PEG group has an average molecular weight of 30 kDa and X is the D20 position of a recombinant human IL-2. In some embodiments of an IL-2 conjugate of Formula (II) or Formula (III), the PEG group has an average molecular weight of 30 kDa and X is the M23 position of a recombinant human IL-2. In some embodiments of an IL-2 conjugate of Formula (II) or Formula (III), the PEG group has an average molecular weight of 30 kDa and X is the N26 position of a recombinant human IL-2. In some embodiments of an IL-2 conjugate of Formula (II) or Formula (III), the PEG group has an average molecular weight of 30 kDa and X is the N88 position of a recombinant human IL-2. In some embodiments of an IL-2 conjugate of Formula (II) or Formula (III), the PEG group has an average molecular weight of 30 kDa and X is the E100 position of a recombinant human IL-2. In some embodiments of an IL-2 conjugate of Formula (II) or Formula (III), the PEG group has an average molecular weight of 30 kDa and X is the N119 position of a recombinant human IL-2. In some embodiments of an IL-2 conjugate of Formula (II) or Formula (III), the PEG group has an average molecular weight of 30 kDa and X is the T123 position of a recombinant human IL-2. In some embodiments of an IL-2 conjugate of Formula (II) or Formula (III), the PEG group has an average molecular weight of 30 kDa and X is the Q126 position of a recombinant human IL-2. In some embodiments of an IL-2 conjugate of Formula (II) or Formula (III), the PEG group has an average molecular weight of 30 kDa and X is the 5127 position of a recombinant human IL-2. In some embodiments of an IL-2 conjugate of Formula (II) or Formula (III), the PEG group has an average molecular weight of 30 kDa and X is the T131 position of a recombinant human IL-2. In some embodiments of an IL-2 conjugate of Formula (II) or Formula (III), the PEG group has an average molecular weight of 30 kDa and X is the D109 position of a recombinant human IL-2. In some embodiments of an IL-2 conjugate of Formula (II) or Formula (III), the PEG group has an average molecular weight of 30 kDa and X is the V91 position of a recombinant human IL-2.

In some embodiments an IL-2 conjugate of Formula (II) or Formula (III) comprises the sequence of any one of SEQ NOs: 34-48. In some embodiments an IL-2 conjugate of Formula (II) or Formula (III) comprises the sequence of any one of SEQ NOs: 199-213. In some embodiments an IL-2 conjugate of Formula (II) or Formula (III) comprises the sequence of any one of SEQ NOs: 49-63. In some embodiments an IL-2 conjugate of Formula (II) or Formula (III) comprises the sequence of any one of SEQ NOs: 214-228. In some embodiments an IL-2 conjugate of Formula (II) or Formula (III) comprises the sequence of any one of SEQ NOs: 64-78. In some embodiments an IL-2 conjugate of Formula (II) or Formula (III) comprises the sequence of any one of SEQ NOs: 229-245. In some embodiments an IL-2 conjugate of Formula (II) or Formula (III) comprises the sequence of any one of SEQ NOs: 154-168. In some embodiments an IL-2 conjugate of Formula (II) or Formula (III) comprises the sequence of any one of SEQ NOs: 109-123. In some embodiments an IL-2 conjugate of Formula (II) or Formula (III) comprises the sequence of any one of SEQ NOs: 169-183. In some embodiments an IL-2 conjugate of Formula (II) or Formula (III) comprises the sequence of any one of SEQ NOs: 124-138. In some embodiments an IL-2 conjugate of Formula (II) or Formula (III) comprises the sequence of any one of SEQ NOs: 184-198. In some embodiments an IL-2 conjugate of Formula (II) or Formula (III) comprises the sequence of any one of SEQ NOs: 139-153. In some embodiments an IL-2 conjugate of Formula (II) or Formula (III) comprises the sequence of SEQ ID NO: 3. In some embodiments an IL-2 conjugate of Formula (II) or Formula (III) comprises the sequence of SEQ ID NO: 4. In some embodiments an IL-2 conjugate of Formula (II) or Formula (III) comprises the sequence of SEQ ID NO: 5. In some embodiments an IL-2 conjugate of Formula (II) or Formula (III) comprises the sequence of SEQ ID NO: 6. In some embodiments an IL-2 conjugate of Formula (II) or Formula (III) comprises the sequence of SEQ ID NO: 7. In some embodiments an IL-2 conjugate of Formula (II) or Formula (III) comprises the sequence of SEQ ID NO: 8. In some embodiments an IL-2 conjugate of Formula (II) or Formula (III) comprises the sequence of SEQ ID NO: 9. In some embodiments an IL-2 conjugate of Formula (II) or Formula (III) comprises the sequence of SEQ ID NO: 10. In some embodiments an IL-2 conjugate of Formula (II) or Formula (III) comprises the sequence of SEQ ID NO: 11. In some embodiments an IL-2 conjugate of Formula (II) or Formula (III) comprises the sequence of SEQ ID NO: 12. In some embodiments an IL-2 conjugate of Formula (II) or Formula (III) comprises the sequence of SEQ ID NO: 13. In some embodiments an IL-2 conjugate of Formula (II) or Formula (III) comprises the sequence of SEQ ID NO: 14. In some embodiments an IL-2 conjugate of Formula (II) or Formula (III) comprises the sequence of SEQ ID NO: 15. In some embodiments an IL-2 conjugate of Formula (II) or Formula (III) comprises the sequence of SEQ ID NO: 16. In some embodiments an IL-2 conjugate of Formula (II) or Formula (III) comprises the sequence of SEQ ID NO: 17. In some embodiments an IL-2 conjugate of Formula (II) or Formula (III) comprises the sequence of SEQ ID NO: 18. In some embodiments an IL-2 conjugate of Formula (II) or Formula (III) comprises the sequence of SEQ ID NO: 19. In some embodiments an IL-2 conjugate of Formula (II) or Formula (III) comprises the sequence of SEQ ID NO: 20. In some embodiments an IL-2 conjugate of Formula (II) or Formula (III) comprises the sequence of SEQ ID NO: 21. In some embodiments an IL-2 conjugate of Formula (II) or Formula (III) comprises the sequence of SEQ ID NO: 22. In some embodiments an IL-2 conjugate of Formula (II) or Formula (III) comprises the sequence of SEQ ID NO: 23. In some embodiments an IL-2 conjugate of Formula (II) or Formula (III) comprises the sequence of SEQ ID NO: 24. In some embodiments an IL-2 conjugate of Formula (II) or Formula (III) comprises the sequence of SEQ ID NO: 25. In some embodiments an IL-2 conjugate of Formula (II) or Formula (III) comprises the sequence of SEQ ID NO: 26. In some embodiments an IL-2 conjugate of Formula (II) or Formula (III) comprises the sequence of SEQ ID NO: 27. In some embodiments an IL-2 conjugate of Formula (II) or Formula (III) comprises the sequence of SEQ ID NO: 28. In some embodiments an IL-2 conjugate of Formula (II) or Formula (III) comprises the sequence of SEQ ID NO: 29. In some embodiments an IL-2 conjugate of Formula (II) or Formula (III) comprises the sequence of SEQ ID NO: 70. In some embodiments an IL-2 conjugate of Formula (II) or Formula (III) comprises the sequence of SEQ ID NO: 71. In some embodiments an IL-2 conjugate of Formula (II) or Formula (III) comprises the sequence of SEQ ID NO: 72. In some embodiments an IL-2 conjugate of Formula (II) or Formula (III) comprises the sequence of SEQ ID NO: 73. In some embodiments an IL-2 conjugate of Formula (II) or Formula (III) comprises the sequence of SEQ ID NO: 74. In some embodiments an IL-2 conjugate of Formula (II) or Formula (III) comprises the sequence of SEQ ID NO: 75. In some embodiments an IL-2 conjugate of Formula (II) or Formula (III) comprises the sequence of SEQ ID NO: 76. In some embodiments an IL-2 conjugate of Formula (II) or Formula (III) comprises the sequence of SEQ ID NO: 77. In some embodiments an IL-2 conjugate of Formula (II) or Formula (III) comprises the sequence of SEQ ID NO: 78. In some embodiments an IL-2 conjugate of Formula (II) or Formula (III) comprises the sequence of SEQ ID NO: 79. In some embodiments an IL-2 conjugate of Formula (II) or Formula (III) comprises the sequence of SEQ ID NO: 80. In some embodiments an IL-2 conjugate of Formula (II) or Formula (III) comprises the sequence of SEQ ID NO: 81. In some embodiments an IL-2 conjugate of Formula (II) or Formula (III) comprises the sequence of SEQ ID NO: 82. In some embodiments an IL-2 conjugate of Formula (II) or Formula (III) comprises the sequence of SEQ ID NO: 83. In some embodiments an IL-2 conjugate of Formula (II) or Formula (III) comprises the sequence of SEQ ID NO: 84. In some embodiments an IL-2 conjugate of Formula (II) or Formula (III) comprises the sequence of SEQ ID NO: 85. In some embodiments an IL-2 conjugate of Formula (II) or Formula (III) comprises the sequence of SEQ ID NO: 86. In some embodiments an IL-2 conjugate of Formula (II) or Formula (III) comprises the sequence of SEQ ID NO: 87. In some embodiments an IL-2 conjugate of Formula (II) or Formula (III) comprises the sequence of SEQ ID NO: 88. In some embodiments an IL-2 conjugate of Formula (II) or Formula (III) comprises the sequence of SEQ ID NO: 89. In some embodiments an IL-2 conjugate of Formula (II) or Formula (III) comprises the sequence of SEQ ID NO: 90. In some embodiments an IL-2 conjugate of Formula (II) or Formula (III) comprises the sequence of SEQ ID NO: 91. In some embodiments an IL-2 conjugate of Formula (II) or Formula (III) comprises the sequence of SEQ ID NO: 92. In some embodiments an IL-2 conjugate of Formula (II) or Formula (III) comprises the sequence of SEQ ID NO: 93. In some embodiments an IL-2 conjugate of Formula (II) or Formula (III) comprises the sequence of SEQ ID NO: 94. In some embodiments an IL-2 conjugate of Formula (II) or Formula (III) comprises the sequence of SEQ ID NO: 95. In some embodiments an IL-2 conjugate of Formula (II) or Formula (III) comprises the sequence of SEQ ID NO: 96. In some embodiments an IL-2 conjugate of Formula (II) or Formula (III) comprises the sequence of SEQ ID NO: 97. In some embodiments an IL-2 conjugate of Formula (II) or Formula (III) comprises the sequence of SEQ ID NO: 98. In some embodiments an IL-2 conjugate of Formula (II) or Formula (III) comprises the sequence of SEQ ID NO: 99. In some embodiments an IL-2 conjugate of Formula (II) or Formula (III) comprises the sequence of SEQ ID NO: 100. In some embodiments an IL-2 conjugate of Formula (II) or Formula (III) comprises the sequence of SEQ ID NO: 101. In some embodiments an IL-2 conjugate of Formula (II) or Formula (III) comprises the sequence of SEQ ID NO: 102. In some embodiments an IL-2 conjugate of Formula (II) or Formula (III) comprises the sequence of SEQ ID NO: 103. In some embodiments an IL-2 conjugate of Formula (II) or Formula (III) comprises the sequence of SEQ ID NO: 104. In some embodiments an IL-2 conjugate of Formula (II) or Formula (III) comprises the sequence of SEQ ID NO: 105. In some embodiments an IL-2 conjugate of Formula (II) or Formula (III) comprises the sequence of SEQ ID NO: 106. In some embodiments an IL-2 conjugate of Formula (II) or Formula (III) comprises the sequence of SEQ ID NO: 107. In some embodiments an IL-2 conjugate of Formula (II) or Formula (III) comprises the sequence of SEQ ID NO: 108. In some embodiments an IL-2 conjugate of Formula (II) or Formula (III) comprises the sequence of SEQ ID NO: 109. In some embodiments an IL-2 conjugate of Formula (II) or Formula (III) comprises the sequence of SEQ ID NO: 110. In some embodiments an IL-2 conjugate of Formula (II) or Formula (III) comprises the sequence of SEQ ID NO: 111. In some embodiments an IL-2 conjugate of Formula (II) or Formula (III) comprises the sequence of SEQ ID NO: 112. In some embodiments an IL-2 conjugate of Formula (II) or Formula (III) comprises the sequence of SEQ ID NO: 113. In some embodiments an IL-2 conjugate of Formula (II) or Formula (III) comprises the sequence of SEQ ID NO: 114. In some embodiments an IL-2 conjugate of Formula (II) or Formula (III) comprises the sequence of SEQ ID NO: 115. In some embodiments an IL-2 conjugate of Formula (II) or Formula (III) comprises the sequence of SEQ ID NO: 116. In some embodiments an IL-2 conjugate of Formula (II) or Formula (III) comprises the sequence of SEQ ID NO: 117. In some embodiments an IL-2 conjugate of Formula (II) or Formula (III) comprises the sequence of SEQ ID NO: 118. In some embodiments an IL-2 conjugate of Formula (II) or Formula (III) comprises the sequence of SEQ ID NO: 119. In some embodiments an IL-2 conjugate of Formula (II) or Formula (III) comprises the sequence of SEQ ID NO: 120. In some embodiments an IL-2 conjugate of Formula (II) or Formula (III) comprises the sequence of SEQ ID NO: 121. In some embodiments an IL-2 conjugate of Formula (II) or Formula (III) comprises the sequence of SEQ ID NO: 122. In some embodiments an IL-2 conjugate of Formula (II) or Formula (III) comprises the sequence of SEQ ID NO: 123. In some embodiments an IL-2 conjugate of Formula (II) or Formula (III) comprises the sequence of SEQ ID NO: 124. In some embodiments an IL-2 conjugate of Formula (II) or Formula (III) comprises the sequence of SEQ ID NO: 125. In some embodiments an IL-2 conjugate of Formula (II) or Formula (III) comprises the sequence of SEQ ID NO: 126. In some embodiments an IL-2 conjugate of Formula (II) or Formula (III) comprises the sequence of SEQ ID NO: 127. In some embodiments an IL-2 conjugate of Formula (II) or Formula (III) comprises the sequence of SEQ ID NO: 128. In some embodiments an IL-2 conjugate of Formula (II) or Formula (III) comprises the sequence of SEQ ID NO: 129. In some embodiments an IL-2 conjugate of Formula (II) or Formula (III) comprises the sequence of SEQ ID NO: 130. In some embodiments an IL-2 conjugate of Formula (II) or Formula (III) comprises the sequence of SEQ ID NO: 131. In some embodiments an IL-2 conjugate of Formula (II) or Formula (III) comprises the sequence of SEQ ID NO: 132. In some embodiments an IL-2 conjugate of Formula (II) or Formula (III) comprises the sequence of SEQ ID NO: 133. In some embodiments an IL-2 conjugate of Formula (II) or Formula (III) comprises the sequence of SEQ ID NO: 134. In some embodiments an IL-2 conjugate of Formula (II) or Formula (III) comprises the sequence of SEQ ID NO: 135. In some embodiments an IL-2 conjugate of Formula (II) or Formula (III) comprises the sequence of SEQ ID NO: 136. In some embodiments an IL-2 conjugate of Formula (II) or Formula (III) comprises the sequence of SEQ ID NO: 137. In some embodiments an IL-2 conjugate of Formula (II) or Formula (III) comprises the sequence of SEQ ID NO: 138. In some embodiments an IL-2 conjugate of Formula (II) or Formula (III) comprises the sequence of SEQ ID NO: 139. In some embodiments an IL-2 conjugate of Formula (II) or Formula (III) comprises the sequence of SEQ ID NO: 140. In some embodiments an IL-2 conjugate of Formula (II) or Formula (III) comprises the sequence of SEQ ID NO: 141. In some embodiments an IL-2 conjugate of Formula (II) or Formula (III) comprises the sequence of SEQ ID NO: 142. In some embodiments an IL-2 conjugate of Formula (II) or Formula (III) comprises the sequence of SEQ ID NO: 143. In some embodiments an IL-2 conjugate of Formula (II) or Formula (III) comprises the sequence of SEQ ID NO: 144. In some embodiments an IL-2 conjugate of Formula (II) or Formula (III) comprises the sequence of SEQ ID NO: 145. In some embodiments an IL-2 conjugate of Formula (II) or Formula (III) comprises the sequence of SEQ ID NO: 146. In some embodiments an IL-2 conjugate of Formula (II) or Formula (III) comprises the sequence of SEQ ID NO: 147. In some embodiments an IL-2 conjugate of Formula (II) or Formula (III) comprises the sequence of SEQ ID NO: 148. In some embodiments an IL-2 conjugate of Formula (II) or Formula (III) comprises the sequence of SEQ ID NO: 149. In some embodiments an IL-2 conjugate of Formula (II) or Formula (III) comprises the sequence of SEQ ID NO: 150. In some embodiments an IL-2 conjugate of Formula (II) or Formula (III) comprises the sequence of SEQ ID NO: 151. In some embodiments an IL-2 conjugate of Formula (II) or Formula (III) comprises the sequence of SEQ ID NO: 152. In some embodiments an IL-2 conjugate of Formula (II) or Formula (III) comprises the sequence of SEQ ID NO: 153. In some embodiments an IL-2 conjugate of Formula (II) or Formula (III) comprises the sequence of SEQ ID NO: 154. In some embodiments an IL-2 conjugate of Formula (II) or Formula (III) comprises the sequence of SEQ ID NO: 155. In some embodiments an IL-2 conjugate of Formula (II) or Formula (III) comprises the sequence of SEQ ID NO: 156. In some embodiments an IL-2 conjugate of Formula (II) or Formula (III) comprises the sequence of SEQ ID NO: 157. In some embodiments an IL-2 conjugate of Formula (II) or Formula (III) comprises the sequence of SEQ ID NO: 158. In some embodiments an IL-2 conjugate of Formula (II) or Formula (III) comprises the sequence of SEQ ID NO: 159. In some embodiments an IL-2 conjugate of Formula (II) or Formula (III) comprises the sequence of SEQ ID NO: 160. In some embodiments an IL-2 conjugate of Formula (II) or Formula (III) comprises the sequence of SEQ ID NO: 161. In some embodiments an IL-2 conjugate of Formula (II) or Formula (III) comprises the sequence of SEQ ID NO: 162. In some embodiments an IL-2 conjugate of Formula (II) or Formula (III) comprises the sequence of SEQ ID NO: 163. In some embodiments an IL-2 conjugate of Formula (II) or Formula (III) comprises the sequence of SEQ ID NO: 164. In some embodiments an IL-2 conjugate of Formula (II) or Formula (III) comprises the sequence of SEQ ID NO: 165. In some embodiments an IL-2 conjugate of Formula (II) or Formula (III) comprises the sequence of SEQ ID NO: 166. In some embodiments an IL-2 conjugate of Formula (II) or Formula (III) comprises the sequence of SEQ ID NO: 167. In some embodiments an IL-2 conjugate of Formula (II) or Formula (III) comprises the sequence of SEQ ID NO: 168. In some embodiments an IL-2 conjugate of Formula (II) or Formula (III) comprises the sequence of SEQ ID NO: 169. In some embodiments an IL-2 conjugate of Formula (II) or Formula (III) comprises the sequence of SEQ ID NO: 170. In some embodiments an IL-2 conjugate of Formula (II) or Formula (III) comprises the sequence of SEQ ID NO: 171. In some embodiments an IL-2 conjugate of Formula (II) or Formula (III) comprises the sequence of SEQ ID NO: 172. In some embodiments an IL-2 conjugate of Formula (II) or Formula (III) comprises the sequence of SEQ ID NO: 173. In some embodiments an IL-2 conjugate of Formula (II) or Formula (III) comprises the sequence of SEQ ID NO: 174. In some embodiments an IL-2 conjugate of Formula (II) or Formula (III) comprises the sequence of SEQ ID NO: 175. In some embodiments an IL-2 conjugate of Formula (II) or Formula (III) comprises the sequence of SEQ ID NO: 176. In some embodiments an IL-2 conjugate of Formula (II) or Formula (III) comprises the sequence of SEQ ID NO: 177. In some embodiments an IL-2 conjugate of Formula (II) or Formula (III) comprises the sequence of SEQ ID NO: 178. In some embodiments an IL-2 conjugate of Formula (II) or Formula (III) comprises the sequence of SEQ ID NO: 179. In some embodiments an IL-2 conjugate of Formula (II) or Formula (III) comprises the sequence of SEQ ID NO: 180. In some embodiments an IL-2 conjugate of Formula (II) or Formula (III) comprises the sequence of SEQ ID NO: 181. In some embodiments an IL-2 conjugate of Formula (II) or Formula (III) comprises the sequence of SEQ ID NO: 182. In some embodiments an IL-2 conjugate of Formula (II) or Formula (III) comprises the sequence of SEQ ID NO: 183. In some embodiments an IL-2 conjugate of Formula (II) or Formula (III) comprises the sequence of SEQ ID NO: 184. In some embodiments an IL-2 conjugate of Formula (II) or Formula (III) comprises the sequence of SEQ ID NO: 185. In some embodiments an IL-2 conjugate of Formula (II) or Formula (III) comprises the sequence of SEQ ID NO: 186. In some embodiments an IL-2 conjugate of Formula (II) or Formula (III) comprises the sequence of SEQ ID NO: 187. In some embodiments an IL-2 conjugate of Formula (II) or Formula (III) comprises the sequence of SEQ ID NO: 188. In some embodiments an IL-2 conjugate of Formula (II) or Formula (III) comprises the sequence of SEQ ID NO: 189. In some embodiments an IL-2 conjugate of Formula (II) or Formula (III) comprises the sequence of SEQ ID NO: 190. In some embodiments an IL-2 conjugate of Formula (II) or Formula (III) comprises the sequence of SEQ ID NO: 191. In some embodiments an IL-2 conjugate of Formula (II) or Formula (III) comprises the sequence of SEQ ID NO: 192. In some embodiments an IL-2 conjugate of Formula (II) or Formula (III) comprises the sequence of SEQ ID NO: 193. In some embodiments an IL-2 conjugate of Formula (II) or Formula (III) comprises the sequence of SEQ ID NO: 194. In some embodiments an IL-2 conjugate of Formula (II) or Formula (III) comprises the sequence of SEQ ID NO: 195. In some embodiments an IL-2 conjugate of Formula (II) or Formula (III) comprises the sequence of SEQ ID NO: 196. In some embodiments an IL-2 conjugate of Formula (II) or Formula (III) comprises the sequence of SEQ ID NO: 197. In some embodiments an IL-2 conjugate of Formula (II) or Formula (III) comprises the sequence of SEQ ID NO: 198. In some embodiments an IL-2 conjugate of Formula (II) or Formula (III) comprises the sequence of SEQ ID NO: 199. In some embodiments an IL-2 conjugate of Formula (II) or Formula (III) comprises the sequence of SEQ ID NO: 200. In some embodiments an IL-2 conjugate of Formula (II) or Formula (III) comprises the sequence of SEQ ID NO: 201. In some embodiments an IL-2 conjugate of Formula (II) or Formula (III) comprises the sequence of SEQ ID NO: 202. In some embodiments an IL-2 conjugate of Formula (II) or Formula (III) comprises the sequence of SEQ ID NO: 203. In some embodiments an IL-2 conjugate of Formula (II) or Formula (III) comprises the sequence of SEQ ID NO: 204. In some embodiments an IL-2 conjugate of Formula (II) or Formula (III) comprises the sequence of SEQ ID NO: 205. In some embodiments an IL-2 conjugate of Formula (II) or Formula (III) comprises the sequence of SEQ ID NO: 206. In some embodiments an IL-2 conjugate of Formula (II) or Formula (III) comprises the sequence of SEQ ID NO: 207. In some embodiments an IL-2 conjugate of Formula (II) or Formula (III) comprises the sequence of SEQ ID NO: 208. In some embodiments an IL-2 conjugate of Formula (II) or Formula (III) comprises the sequence of SEQ ID NO: 209. In some embodiments an IL-2 conjugate of Formula (II) or Formula (III) comprises the sequence of SEQ ID NO: 210. In some embodiments an IL-2 conjugate of Formula (II) or Formula (III) comprises the sequence of SEQ ID NO: 211. In some embodiments an IL-2 conjugate of Formula (II) or Formula (III) comprises the sequence of SEQ ID NO: 212. In some embodiments an IL-2 conjugate of Formula (II) or Formula (III) comprises the sequence of SEQ ID NO: 213. In some embodiments an IL-2 conjugate of Formula (II) or Formula (III) comprises the sequence of SEQ ID NO: 214. In some embodiments an IL-2 conjugate of Formula (II) or Formula (III) comprises the sequence of SEQ ID NO: 215. In some embodiments an IL-2 conjugate of Formula (II) or Formula (III) comprises the sequence of SEQ ID NO: 216. In some embodiments an IL-2 conjugate of Formula (II) or Formula (III) comprises the sequence of SEQ ID NO: 217. In some embodiments an IL-2 conjugate of Formula (II) or Formula (III) comprises the sequence of SEQ ID NO: 218. In some embodiments an IL-2 conjugate of Formula (II) or Formula (III) comprises the sequence of SEQ ID NO: 219. In some embodiments an IL-2 conjugate of Formula (II) or Formula (III) comprises the sequence of SEQ ID NO: 220. In some embodiments an IL-2 conjugate of Formula (II) or Formula (III) comprises the sequence of SEQ ID NO: 221. In some embodiments an IL-2 conjugate of Formula (II) or Formula (III) comprises the sequence of SEQ ID NO: 222. In some embodiments an IL-2 conjugate of Formula (II) or Formula (III) comprises the sequence of SEQ ID NO: 223. In some embodiments an IL-2 conjugate of Formula (II) or Formula (III) comprises the sequence of SEQ ID NO: 224. In some embodiments an IL-2 conjugate of Formula (II) or Formula (III) comprises the sequence of SEQ ID NO: 225. In some embodiments an IL-2 conjugate of Formula (II) or Formula (III) comprises the sequence of SEQ ID NO: 226. In some embodiments an IL-2 conjugate of Formula (II) or Formula (III) comprises the sequence of SEQ ID NO: 227. In some embodiments an IL-2 conjugate of Formula (II) or Formula (III) comprises the sequence of SEQ ID NO: 228. In some embodiments an IL-2 conjugate of Formula (II) or Formula (III) comprises the sequence of SEQ ID NO: 229. In some embodiments an IL-2 conjugate of Formula (II) or Formula (III) comprises the sequence of SEQ ID NO: 230. In some embodiments an IL-2 conjugate of Formula (II) or Formula (III) comprises the sequence of SEQ ID NO: 231. In some embodiments an IL-2 conjugate of Formula (II) or Formula (III) comprises the sequence of SEQ ID NO: 232. In some embodiments an IL-2 conjugate of Formula (II) or Formula (III) comprises the sequence of SEQ ID NO: 233. In some embodiments an IL-2 conjugate of Formula (II) or Formula (III) comprises the sequence of SEQ ID NO: 234. In some embodiments an IL-2 conjugate of Formula (II) or Formula (III) comprises the sequence of SEQ ID NO: 235. In some embodiments an IL-2 conjugate of Formula (II) or Formula (III) comprises the sequence of SEQ ID NO: 236. In some embodiments an IL-2 conjugate of Formula (II) or Formula (III) comprises the sequence of SEQ ID NO: 237. In some embodiments an IL-2 conjugate of Formula (II) or Formula (III) comprises the sequence of SEQ ID NO: 238. In some embodiments an IL-2 conjugate of Formula (II) or Formula (III) comprises the sequence of SEQ ID NO: 239. In some embodiments an IL-2 conjugate of Formula (II) or Formula (III) comprises the sequence of SEQ ID NO: 240. In some embodiments an IL-2 conjugate of Formula (II) or Formula (III) comprises the sequence of SEQ ID NO: 241. In some embodiments an IL-2 conjugate of Formula (II) or Formula (III) comprises the sequence of SEQ ID NO: 242. In some embodiments an IL-2 conjugate of Formula (II) or Formula (III) comprises the sequence of SEQ ID NO: 243. In some embodiments an IL-2 conjugate of Formula (II) or Formula (III) comprises the sequence of SEQ ID NO: 244. In some embodiments an IL-2 conjugate of Formula (II) or Formula (III) comprises the sequence of SEQ ID NO: 245.

Described herein are pharmaceutical compositions of Formula (I), Formula (II), or Formula (III). In some embodiments, a pharmaceutical compositions of Formula (I), Formula (II), or Formula (III) comprises a sequence comprising any one of SEQ ID NOS: 3-29 and 70-84. In some embodiments, a pharmaceutical compositions of Formula (I), Formula (II), or Formula (III) comprises a sequence comprising any one of SEQ ID NO: 3. In some embodiments, a pharmaceutical compositions of Formula (I), Formula (II), or Formula (III) comprises a sequence comprising any one of SEQ ID NO: 4.

Described herein are IL-2 conjugates having the structure of Formula (IV):

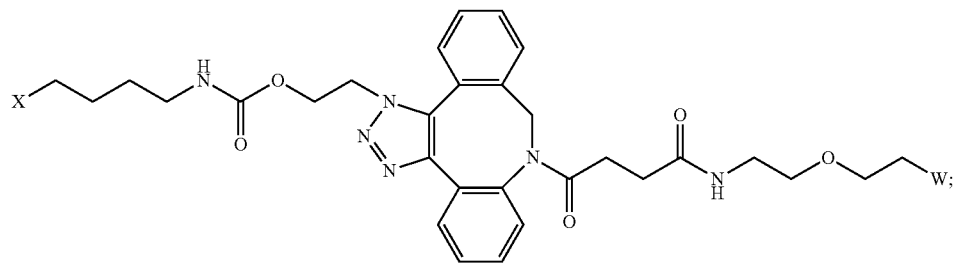

Formula (IV)

wherein W is a PEG group having an average molecular weight selected from 5 kDa, 10 kDa, and 30 kDa; and X is an amino acid position having the structure:

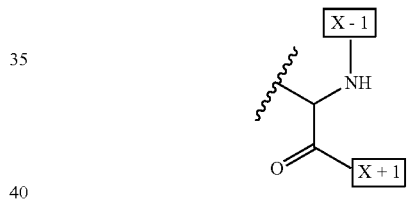

of a recombinant human IL-2 selected from K9, H16, L19, D20, M23, N26, N88, E100, N119, T123, Q126, S127, T131, D109, and V91, wherein the amino acid position corresponds to the positions in SEQ ID NO: 1.

Described herein are IL-2 conjugates having the structure of Formula (V):

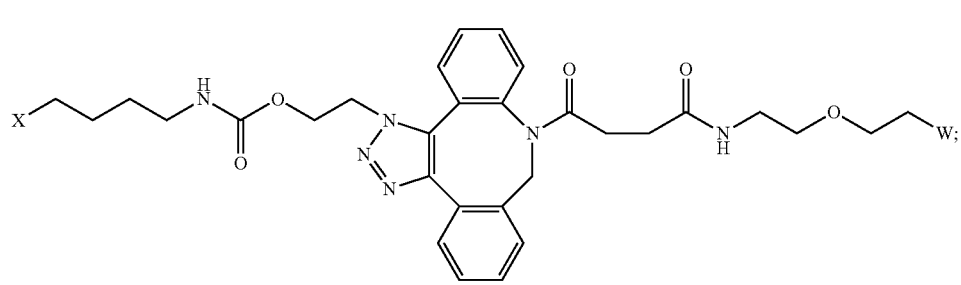

Formula (V)

wherein W is a PEG group having an average molecular weight selected from 5 kDa, 10 kDa, and 30 kDa; and X is an amino acid position having the structure

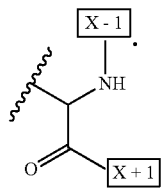

of a recombinant human IL-2 selected from K9, H16, L19, D20, M23, N26, N88, E100, N119, T123, Q126, S127, T131, D109, and V91, wherein the amino acid corresponds to the positions in SEQ ID NO: 1. In some embodiments of an IL-2 conjugate of Formula (IV) or Formula (V), X is the K9 position of a recombinant human IL-2. In some embodiments of an IL-2 conjugate of Formula (IV) or Formula (V), the PEG group has an average molecular weight of 50 kDa and X is the K9 position of a recombinant human IL-2. In some embodiments of an IL-2 conjugate of Formula (IV) or Formula (V), X is the H16 position of a recombinant human IL-2. In some embodiments of an IL-2 conjugate of Formula (IV) or Formula (V), the PEG group has an average molecular weight of 50 kDa and X is the H16 position of a recombinant human IL-2. In some embodiments of an IL-2 conjugate of Formula (IV) or Formula (V), X is the L19 position of a recombinant human IL-2. In some embodiments of an IL-2 conjugate of Formula (IV) or Formula (V), the PEG group has an average molecular weight of 50 kDa and X is the L19 position of a recombinant human IL-2. In some embodiments of an IL-2 conjugate of Formula (IV) or Formula (V), X is the D20 position of a recombinant human IL-2. In some embodiments of an IL-2 conjugate of Formula (IV) or Formula (V), the PEG group has an average molecular weight of 50 kDa and X is the D20 position of a recombinant human IL-2. In some embodiments of an IL-2 conjugate of Formula (IV) or Formula (V), X is the M23 position of a recombinant human IL-2. In some embodiments of an IL-2 conjugate of Formula (IV) or Formula (V), the PEG group has an average molecular weight of 50 kDa and X is the M23 position of a recombinant human IL-2. In some embodiments of an IL-2 conjugate of Formula (IV) or Formula (V), X is the N26 position of a recombinant human IL-2. In some embodiments of an IL-2 conjugate of Formula (IV) or Formula (V), the PEG group has an average molecular weight of 50 kDa and X is the N26 position of a recombinant human IL-2. In some embodiments of an IL-2 conjugate of Formula (IV) or Formula (V), X is the N88 position of a recombinant human IL-2. In some embodiments of an IL-2 conjugate of Formula (IV) or Formula (V), the PEG group has an average molecular weight of 50 kDa and X is the N88 position of a recombinant human IL-2. In some embodiments of an IL-2 conjugate of Formula (IV) or Formula (V), X is the E100 position of a recombinant human IL-2. In some embodiments of an IL-2 conjugate of Formula (IV) or Formula (V), the PEG group has an average molecular weight of 50 kDa and X is the E100 position of a recombinant human IL-2. In some embodiments of an IL-2 conjugate of Formula (IV) or Formula (V), X is the N119 position of a recombinant human IL-2. In some embodiments of an IL-2 conjugate of Formula (IV) or Formula (V), the PEG group has an average molecular weight of 50 kDa and X is the N119 position of a recombinant human IL-2. In some embodiments of an IL-2 conjugate of Formula (IV) or Formula (V), X is the T123 position of a recombinant human IL-2. In some embodiments of an IL-2 conjugate of Formula (IV) or Formula (V), the PEG group has an average molecular weight of 50 kDa and X is the T123 position of a recombinant human IL-2. In some embodiments of an IL-2 conjugate of Formula (IV) or Formula (V), X is the Q126 position of a recombinant human IL-2. In some embodiments of an IL-2 conjugate of Formula (IV) or Formula (V), the PEG group has an average molecular weight of 50 kDa and X is the Q126 position of a recombinant human IL-2. In some embodiments of an IL-2 conjugate of Formula (IV) or Formula (V), X is the S127 position of a recombinant human IL-2. In some embodiments of an IL-2 conjugate of Formula (IV) or Formula (V), the PEG group has an average molecular weight of 50 kDa and X is the S127 position of a recombinant human IL-2. In some embodiments of an IL-2 conjugate of Formula (IV) or Formula (V), X is the T131 position of a recombinant human IL-2. In some embodiments of an IL-2 conjugate of Formula (IV) or Formula (V), the PEG group has an average molecular weight of 50 kDa and X is the T131 position of a recombinant human IL-2. In some embodiments of an IL-2 conjugate of Formula (IV) or Formula (V), X is the D109 position of a recombinant human IL-2. In some embodiments of an IL-2 conjugate of Formula (IV) or Formula (V), the PEG group has an average molecular weight of 50 kDa and X is the D109 position of a recombinant human IL-2. In some embodiments of an IL-2 conjugate of Formula (IV) or Formula (V), X is the V91 position of a recombinant human IL-2. In some embodiments of an IL-2 conjugate of Formula (IV) or Formula (V), the PEG group has an average molecular weight of 50 kDa and X is the V91 position of a recombinant human IL-2.

In some embodiments of an IL-2 conjugate of Formula (IV) or Formula (V), the PEG group has an average molecular weight of 10 kDa and X is the K9 position of a recombinant human IL-2. In some embodiments of an IL-2 conjugate of Formula (IV) or Formula (V), the PEG group has an average molecular weight of 10 kDa and X is the H16 position of a recombinant human IL-2. In some embodiments of an IL-2 conjugate of Formula (IV) or Formula (V), the PEG group has an average molecular weight of 10 kDa and X is the L19 position of a recombinant human IL-2. In some embodiments of an IL-2 conjugate of Formula (IV) or Formula (V), the PEG group has an average molecular weight of 10 kDa and X is the D20 position of a recombinant human IL-2. In some embodiments of an IL-2 conjugate of Formula (IV) or Formula (V), the PEG group has an average molecular weight of 10 kDa and X is the M23 position of a recombinant human IL-2. In some embodiments of an IL-2 conjugate of Formula (IV) or Formula (V), the PEG group has an average molecular weight of 10 kDa and X is the N26 position of a recombinant human IL-2. In some embodiments of an IL-2 conjugate of Formula (IV) or Formula (V), the PEG group has an average molecular weight of 10 kDa and X is the N88 position of a recombinant human IL-2. In some embodiments of an IL-2 conjugate of Formula (IV) or Formula (V), the PEG group has an average molecular weight of 10 kDa and X is the E100 position of a recombinant human IL-2. In some embodiments of an IL-2 conjugate of Formula (IV) or Formula (V), the PEG group has an average molecular weight of 10 kDa and X is the N119 position of a recombinant human IL-2. In some embodiments of an IL-2 conjugate of Formula (IV) or Formula (V), the PEG group has an average molecular weight of 10 kDa and X is the T123 position of a recombinant human IL-2. In some embodiments of an IL-2 conjugate of Formula (IV) or Formula (V), the PEG group has an average molecular weight of 10 kDa and X is the Q126 position of a recombinant human IL-2. In some embodiments of an IL-2 conjugate of Formula (IV) or Formula (V), the PEG group has an average molecular weight of 10 kDa and X is the S127 position of a recombinant human IL-2. In some embodiments of an IL-2 conjugate of Formula (IV) or Formula (V), the PEG group has an average molecular weight of 10 kDa and X is the T131 position of a recombinant human IL-2. In some embodiments of an IL-2 conjugate of Formula (IV) or Formula (V), the PEG group has an average molecular weight of 10 kDa and X is the D109 position of a recombinant human IL-2. In some embodiments of an IL-2 conjugate of Formula (IV) or Formula (V), the PEG group has an average molecular weight of 10 kDa and X is the V91 position of a recombinant human IL-2. In some embodiments of an IL-2 conjugate of Formula (IV) or Formula (V), the PEG group has an average molecular weight of 30 kDa and X is the K9 position of a recombinant human IL-2. In some embodiments of an IL-2 conjugate of Formula (IV) or Formula (V), the PEG group has an average molecular weight of 30 kDa and X is the H16 position of a recombinant human IL-2. In some embodiments of an IL-2 conjugate of Formula (IV) or Formula (V), the PEG group has an average molecular weight of 30 kDa and X is the L19 position of a recombinant human IL-2. In some embodiments of an IL-2 conjugate of Formula (IV) or Formula (V), the PEG group has an average molecular weight of 30 kDa and X is the D20 position of a recombinant human IL-2. In some embodiments of an IL-2 conjugate of Formula (IV) or Formula (V), the PEG group has an average molecular weight of 30 kDa and X is the M23 position of a recombinant human IL-2. In some embodiments of an IL-2 conjugate of Formula (IV) or Formula (V), the PEG group has an average molecular weight of 30 kDa and X is the N26 position of a recombinant human IL-2. In some embodiments of an IL-2 conjugate of Formula (IV) or Formula (V), the PEG group has an average molecular weight of 30 kDa and X is the N88 position of a recombinant human IL-2. In some embodiments of an IL-2 conjugate of Formula (IV) or Formula (V), the PEG group has an average molecular weight of 30 kDa and X is the E100 position of a recombinant human IL-2. In some embodiments of an IL-2 conjugate of Formula (IV) or Formula (V), the PEG group has an average molecular weight of 30 kDa and X is the N119 position of a recombinant human IL-2. In some embodiments of an IL-2 conjugate of Formula (IV) or Formula (V), the PEG group has an average molecular weight of 30 kDa and X is the T123 position of a recombinant human IL-2. In some embodiments of an IL-2 conjugate of Formula (IV) or Formula (V), the PEG group has an average molecular weight of 30 kDa and X is the Q126 position of a recombinant human IL-2. In some embodiments of an IL-2 conjugate of Formula (IV) or Formula (V), the PEG group has an average molecular weight of 30 kDa and X is the S127 position of a recombinant human IL-2. In some embodiments of an IL-2 conjugate of Formula (IV) or Formula (V), the PEG group has an average molecular weight of 30 kDa and X is the T131 position of a recombinant human IL-2. In some embodiments of an IL-2 conjugate of Formula (IV) or Formula (V), the PEG group has an average molecular weight of 30 kDa and X is the D109 position of a recombinant human IL-2. In some embodiments of an IL-2 conjugate of Formula (IV) or Formula (V), the PEG group has an average molecular weight of 30 kDa and X is the V91 position of a recombinant human IL-2.

In some embodiments an IL-2 conjugate of Formula (IV) or Formula (V) comprises the sequence of any one of SEQ NOs: 34-48. In some embodiments an IL-2 conjugate of Formula (IV) or Formula (V) comprises the sequence of any one of SEQ NOs: 199-213. In some embodiments an IL-2 conjugate of Formula (IV) or Formula (V) comprises the sequence of any one of SEQ NOs: 49-63. In some embodiments an IL-2 conjugate of Formula (IV) or Formula (V) comprises the sequence of any one of SEQ NOs: 214-228. In some embodiments an IL-2 conjugate of Formula (IV) or Formula (V) comprises the sequence of any one of SEQ NOs: 64-78. In some embodiments an IL-2 conjugate of Formula (IV) or Formula (V) comprises the sequence of any one of SEQ NOs: 229-245. In some embodiments an IL-2 conjugate of Formula (IV) or Formula (V) comprises the sequence of any one of SEQ NOs: 154-168. In some embodiments an IL-2 conjugate of Formula (IV) or Formula (V) comprises the sequence of any one of SEQ NOs: 109-123. In some embodiments an IL-2 conjugate of Formula (IV) or Formula (V) comprises the sequence of any one of SEQ NOs: 169-183. In some embodiments an IL-2 conjugate of Formula (IV) or Formula (V) comprises the sequence of any one of SEQ NOs: 124-138. In some embodiments an IL-2 conjugate of Formula (IV) or Formula (V) comprises the sequence of any one of SEQ NOs: 184-198. In some embodiments an IL-2 conjugate of Formula (IV) or Formula (V) comprises the sequence of any one of SEQ NOs: 139-153. In some embodiments an IL-2 conjugate of Formula (IV) or Formula (V) comprises the sequence of SEQ ID NO: 3. In some embodiments an IL-2 conjugate of Formula (IV) or Formula (V) comprises the sequence of SEQ ID NO: 4. In some embodiments an IL-2 conjugate of Formula (IV) or Formula (V) comprises the sequence of SEQ ID NO: 5. In some embodiments an IL-2 conjugate of Formula (IV) or Formula (V) comprises the sequence of SEQ ID NO: 6. In some embodiments an IL-2 conjugate of Formula (IV) or Formula (V) comprises the sequence of SEQ ID NO: 7. In some embodiments an IL-2 conjugate of Formula (IV) or Formula (V) comprises the sequence of SEQ ID NO: 8. In some embodiments an IL-2 conjugate of Formula (IV) or Formula (V) comprises the sequence of SEQ ID NO: 9. In some embodiments an IL-2 conjugate of Formula (IV) or Formula (V) comprises the sequence of SEQ ID NO: 10. In some embodiments an IL-2 conjugate of Formula (IV) or Formula (V) comprises the sequence of SEQ ID NO: 11. In some embodiments an IL-2 conjugate of Formula (IV) or Formula (V) comprises the sequence of SEQ ID NO: 12. In some embodiments an IL-2 conjugate of Formula (IV) or Formula (V) comprises the sequence of SEQ ID NO: 13. In some embodiments an IL-2 conjugate of Formula (IV) or Formula (V) comprises the sequence of SEQ ID NO: 14. In some embodiments an IL-2 conjugate of Formula (IV) or Formula (V) comprises the sequence of SEQ ID NO: 15. In some embodiments an IL-2 conjugate of Formula (IV) or Formula (V) comprises the sequence of SEQ ID NO: 16. In some embodiments an IL-2 conjugate of Formula (IV) or Formula (V) comprises the sequence of SEQ ID NO: 17. In some embodiments an IL-2 conjugate of Formula (IV) or Formula (V) comprises the sequence of SEQ ID NO: 18. In some embodiments an IL-2 conjugate of Formula (IV) or Formula (V) comprises the sequence of SEQ ID NO: 19. In some embodiments an IL-2 conjugate of Formula (IV) or Formula (V) comprises the sequence of SEQ ID NO: 20. In some embodiments an IL-2 conjugate of Formula (IV) or Formula (V) comprises the sequence of SEQ ID NO: 21. In some embodiments an IL-2 conjugate of Formula (IV) or Formula (V) comprises the sequence of SEQ ID NO: 22. In some embodiments an IL-2 conjugate of Formula (IV) or Formula (V) comprises the sequence of SEQ ID NO: 23. In some embodiments an IL-2 conjugate of Formula (IV) or Formula (V) comprises the sequence of SEQ ID NO: 24. In some embodiments an IL-2 conjugate of Formula (IV) or Formula (V) comprises the sequence of SEQ ID NO: 25. In some embodiments an IL-2 conjugate of Formula (IV) or Formula (V) comprises the sequence of SEQ ID NO: 26. In some embodiments an IL-2 conjugate of Formula (IV) or Formula (V) comprises the sequence of SEQ ID NO: 27. In some embodiments an IL-2 conjugate of Formula (IV) or Formula (V) comprises the sequence of SEQ ID NO: 28. In some embodiments an IL-2 conjugate of Formula (IV) or Formula (V) comprises the sequence of SEQ ID NO: 29. In some embodiments an IL-2 conjugate of Formula (IV) or Formula (V) comprises the sequence of SEQ ID NO: 70. In some embodiments an IL-2 conjugate of Formula (IV) or Formula (V) comprises the sequence of SEQ ID NO: 71. In some embodiments an IL-2 conjugate of Formula (IV) or Formula (V) comprises the sequence of SEQ ID NO: 72. In some embodiments an IL-2 conjugate of Formula (IV) or Formula (V) comprises the sequence of SEQ ID NO: 73. In some embodiments an IL-2 conjugate of Formula (IV) or Formula (V) comprises the sequence of SEQ ID NO: 74. In some embodiments an IL-2 conjugate of Formula (IV) or Formula (V) comprises the sequence of SEQ ID NO: 75. In some embodiments an IL-2 conjugate of Formula (IV) or Formula (V) comprises the sequence of SEQ ID NO: 76. In some embodiments an IL-2 conjugate of Formula (IV) or Formula (V) comprises the sequence of SEQ ID NO: 77. In some embodiments an IL-2 conjugate of Formula (IV) or Formula (V) comprises the sequence of SEQ ID NO: 78. In some embodiments an IL-2 conjugate of Formula (IV) or Formula (V) comprises the sequence of SEQ ID NO: 79. In some embodiments an IL-2 conjugate of Formula (IV) or Formula (V) comprises the sequence of SEQ ID NO: 80. In some embodiments an IL-2 conjugate of Formula (IV) or Formula (V) comprises the sequence of SEQ ID NO: 81. In some embodiments an IL-2 conjugate of Formula (IV) or Formula (V) comprises the sequence of SEQ ID NO: 82. In some embodiments an IL-2 conjugate of Formula (IV) or Formula (V) comprises the sequence of SEQ ID NO: 83. In some embodiments an IL-2 conjugate of Formula (IV) or Formula (V) comprises the sequence of SEQ ID NO: 84. In some embodiments an IL-2 conjugate of Formula (IV) or Formula (V) comprises the sequence of SEQ ID NO: 85. In some embodiments an IL-2 conjugate of Formula (IV) or Formula (V) comprises the sequence of SEQ ID NO: 86. In some embodiments an IL-2 conjugate of Formula (IV) or Formula (V) comprises the sequence of SEQ ID NO: 87. In some embodiments an IL-2 conjugate of Formula (IV) or Formula (V) comprises the sequence of SEQ ID NO: 88. In some embodiments an IL-2 conjugate of Formula (IV) or Formula (V) comprises the sequence of SEQ ID NO: 89. In some embodiments an IL-2 conjugate of Formula (IV) or Formula (V) comprises the sequence of SEQ ID NO: 90. In some embodiments an IL-2 conjugate of Formula (IV) or Formula (V) comprises the sequence of SEQ ID NO: 91. In some embodiments an IL-2 conjugate of Formula (IV) or Formula (V) comprises the sequence of SEQ ID NO: 92. In some embodiments an IL-2 conjugate of Formula (IV) or Formula (V) comprises the sequence of SEQ ID NO: 93. In some embodiments an IL-2 conjugate of Formula (IV) or Formula (V) comprises the sequence of SEQ ID NO: 94. In some embodiments an IL-2 conjugate of Formula (IV) or Formula (V) comprises the sequence of SEQ ID NO: 95. In some embodiments an IL-2 conjugate of Formula (IV) or Formula (V) comprises the sequence of SEQ ID NO: 96. In some embodiments an IL-2 conjugate of Formula (IV) or Formula (V) comprises the sequence of SEQ ID NO: 97. In some embodiments an IL-2 conjugate of Formula (IV) or Formula (V) comprises the sequence of SEQ ID NO: 98. In some embodiments an IL-2 conjugate of Formula (IV) or Formula (V) comprises the sequence of SEQ ID NO: 99. In some embodiments an IL-2 conjugate of Formula (IV) or Formula (V) comprises the sequence of SEQ ID NO: 100. In some embodiments an IL-2 conjugate of Formula (IV) or Formula (V) comprises the sequence of SEQ ID NO: 101. In some embodiments an IL-2 conjugate of Formula (IV) or Formula (V) comprises the sequence of SEQ ID NO: 102. In some embodiments an IL-2 conjugate of Formula (IV) or Formula (V) comprises the sequence of SEQ ID NO: 103. In some embodiments an IL-2 conjugate of Formula (IV) or Formula (V) comprises the sequence of SEQ ID NO: 104. In some embodiments an IL-2 conjugate of Formula (IV) or Formula (V) comprises the sequence of SEQ ID NO: 105. In some embodiments an IL-2 conjugate of Formula (IV) or Formula (V) comprises the sequence of SEQ ID NO: 106. In some embodiments an IL-2 conjugate of Formula (IV) or Formula (V) comprises the sequence of SEQ ID NO: 107. In some embodiments an IL-2 conjugate of Formula (IV) or Formula (V) comprises the sequence of SEQ ID NO: 108. In some embodiments an IL-2 conjugate of Formula (IV) or Formula (V) comprises the sequence of SEQ ID NO: 109. In some embodiments an IL-2 conjugate of Formula (IV) or Formula (V) comprises the sequence of SEQ ID NO: 110. In some embodiments an IL-2 conjugate of Formula (IV) or Formula (V) comprises the sequence of SEQ ID NO: 111. In some embodiments an IL-2 conjugate of Formula (IV) or Formula (V) comprises the sequence of SEQ ID NO: 112. In some embodiments an IL-2 conjugate of Formula (IV) or Formula (V) comprises the sequence of SEQ ID NO: 113. In some embodiments an IL-2 conjugate of Formula (IV) or Formula (V) comprises the sequence of SEQ ID NO: 114. In some embodiments an IL-2 conjugate of Formula (IV) or Formula (V) comprises the sequence of SEQ ID NO: 115. In some embodiments an IL-2 conjugate of Formula (IV) or Formula (V) comprises the sequence of SEQ ID NO: 116. In some embodiments an IL-2 conjugate of Formula (IV) or Formula (V) comprises the sequence of SEQ ID NO: 117. In some embodiments an IL-2 conjugate of Formula (IV) or Formula (V) comprises the sequence of SEQ ID NO: 118. In some embodiments an IL-2 conjugate of Formula (IV) or Formula (V) comprises the sequence of SEQ ID NO: 119. In some embodiments an IL-2 conjugate of Formula (IV) or Formula (V) comprises the sequence of SEQ ID NO: 120. In some embodiments an IL-2 conjugate of Formula (IV) or Formula (V) comprises the sequence of SEQ ID NO: 121. In some embodiments an IL-2 conjugate of Formula (IV) or Formula (V) comprises the sequence of SEQ ID NO: 122. In some embodiments an IL-2 conjugate of Formula (IV) or Formula (V) comprises the sequence of SEQ ID NO: 123. In some embodiments an IL-2 conjugate of Formula (IV) or Formula (V) comprises the sequence of SEQ ID NO: 124. In some embodiments an IL-2 conjugate of Formula (IV) or Formula (V) comprises the sequence of SEQ ID NO: 125. In some embodiments an IL-2 conjugate of Formula (IV) or Formula (V) comprises the sequence of SEQ ID NO: 126. In some embodiments an IL-2 conjugate of Formula (IV) or Formula (V) comprises the sequence of SEQ ID NO: 127. In some embodiments an IL-2 conjugate of Formula (IV) or Formula (V) comprises the sequence of SEQ ID NO: 128. In some embodiments an IL-2 conjugate of Formula (IV) or Formula (V) comprises the sequence of SEQ ID NO: 129. In some embodiments an IL-2 conjugate of Formula (IV) or Formula (V) comprises the sequence of SEQ ID NO: 130. In some embodiments an IL-2 conjugate of Formula (IV) or Formula (V) comprises the sequence of SEQ ID NO: 131. In some embodiments an IL-2 conjugate of Formula (IV) or Formula (V) comprises the sequence of SEQ ID NO: 132. In some embodiments an IL-2 conjugate of Formula (IV) or Formula (V) comprises the sequence of SEQ ID NO: 133. In some embodiments an IL-2 conjugate of Formula (IV) or Formula (V) comprises the sequence of SEQ ID NO: 134. In some embodiments an IL-2 conjugate of Formula (IV) or Formula (V) comprises the sequence of SEQ ID NO: 135. In some embodiments an IL-2 conjugate of Formula (IV) or Formula (V) comprises the sequence of SEQ ID NO: 136. In some embodiments an IL-2 conjugate of Formula (IV) or Formula (V) comprises the sequence of SEQ ID NO: 137. In some embodiments an IL-2 conjugate of Formula (IV) or Formula (V) comprises the sequence of SEQ ID NO: 138. In some embodiments an IL-2 conjugate of Formula (IV) or Formula (V) comprises the sequence of SEQ ID NO: 139. In some embodiments an IL-2 conjugate of Formula (IV) or Formula (V) comprises the sequence of SEQ ID NO: 140. In some embodiments an IL-2 conjugate of Formula (IV) or Formula (V) comprises the sequence of SEQ ID NO: 141. In some embodiments an IL-2 conjugate of Formula (IV) or Formula (V) comprises the sequence of SEQ ID NO: 142. In some embodiments an IL-2 conjugate of Formula (IV) or Formula (V) comprises the sequence of SEQ ID NO: 143. In some embodiments an IL-2 conjugate of Formula (IV) or Formula (V) comprises the sequence of SEQ ID NO: 144. In some embodiments an IL-2 conjugate of Formula (IV) or Formula (V) comprises the sequence of SEQ ID NO: 145. In some embodiments an IL-2 conjugate of Formula (IV) or Formula (V) comprises the sequence of SEQ ID NO: 146. In some embodiments an IL-2 conjugate of Formula (IV) or Formula (V) comprises the sequence of SEQ ID NO: 147. In some embodiments an IL-2 conjugate of Formula (IV) or Formula (V) comprises the sequence of SEQ ID NO: 148. In some embodiments an IL-2 conjugate of Formula (IV) or Formula (V) comprises the sequence of SEQ ID NO: 149. In some embodiments an IL-2 conjugate of Formula (IV) or Formula (V) comprises the sequence of SEQ ID NO: 150. In some embodiments an IL-2 conjugate of Formula (IV) or Formula (V) comprises the sequence of SEQ ID NO: 151. In some embodiments an IL-2 conjugate of Formula (IV) or Formula (V) comprises the sequence of SEQ ID NO: 152. In some embodiments an IL-2 conjugate of Formula (IV) or Formula (V) comprises the sequence of SEQ ID NO: 153. In some embodiments an IL-2 conjugate of Formula (IV) or Formula (V) comprises the sequence of SEQ ID NO: 154. In some embodiments an IL-2 conjugate of Formula (IV) or Formula (V) comprises the sequence of SEQ ID NO: 155. In some embodiments an IL-2 conjugate of Formula (IV) or Formula (V) comprises the sequence of SEQ ID NO: 156. In some embodiments an IL-2 conjugate of Formula (IV) or Formula (V) comprises the sequence of SEQ ID NO: 157. In some embodiments an IL-2 conjugate of Formula (IV) or Formula (V) comprises the sequence of SEQ ID NO: 158. In some embodiments an IL-2 conjugate of Formula (IV) or Formula (V) comprises the sequence of SEQ ID NO: 159. In some embodiments an IL-2 conjugate of Formula (IV) or Formula (V) comprises the sequence of SEQ ID NO: 160. In some embodiments an IL-2 conjugate of Formula (IV) or Formula (V) comprises the sequence of SEQ ID NO: 161. In some embodiments an IL-2 conjugate of Formula (IV) or Formula (V) comprises the sequence of SEQ ID NO: 162. In some embodiments an IL-2 conjugate of Formula (IV) or Formula (V) comprises the sequence of SEQ ID NO: 163. In some embodiments an IL-2 conjugate of Formula (IV) or Formula (V) comprises the sequence of SEQ ID NO: 164. In some embodiments an IL-2 conjugate of Formula (IV) or Formula (V) comprises the sequence of SEQ ID NO: 165. In some embodiments an IL-2 conjugate of Formula (IV) or Formula (V) comprises the sequence of SEQ ID NO: 166. In some embodiments an IL-2 conjugate of Formula (IV) or Formula (V) comprises the sequence of SEQ ID NO: 167. In some embodiments an IL-2 conjugate of Formula (IV) or Formula (V) comprises the sequence of SEQ ID NO: 168. In some embodiments an IL-2 conjugate of Formula (IV) or Formula (V) comprises the sequence of SEQ ID NO: 169. In some embodiments an IL-2 conjugate of Formula (IV) or Formula (V) comprises the sequence of SEQ ID NO: 170. In some embodiments an IL-2 conjugate of Formula (IV) or Formula (V) comprises the sequence of SEQ ID NO: 171. In some embodiments an IL-2 conjugate of Formula (IV) or Formula (V) comprises the sequence of SEQ ID NO: 172. In some embodiments an IL-2 conjugate of Formula (IV) or Formula (V) comprises the sequence of SEQ ID NO: 173. In some embodiments an IL-2 conjugate of Formula (IV) or Formula (V) comprises the sequence of SEQ ID NO: 174. In some embodiments an IL-2 conjugate of Formula (IV) or Formula (V) comprises the sequence of SEQ ID NO: 175. In some embodiments an IL-2 conjugate of Formula (IV) or Formula (V) comprises the sequence of SEQ ID NO: 176. In some embodiments an IL-2 conjugate of Formula (IV) or Formula (V) comprises the sequence of SEQ ID NO: 177. In some embodiments an IL-2 conjugate of Formula (IV) or Formula (V) comprises the sequence of SEQ ID NO: 178. In some embodiments an IL-2 conjugate of Formula (IV) or Formula (V) comprises the sequence of SEQ ID NO: 179. In some embodiments an IL-2 conjugate of Formula (IV) or Formula (V) comprises the sequence of SEQ ID NO: 180. In some embodiments an IL-2 conjugate of Formula (IV) or Formula (V) comprises the sequence of SEQ ID NO: 181. In some embodiments an IL-2 conjugate of Formula (IV) or Formula (V) comprises the sequence of SEQ ID NO: 182. In some embodiments an IL-2 conjugate of Formula (IV) or Formula (V) comprises the sequence of SEQ ID NO: 183. In some embodiments an IL-2 conjugate of Formula (IV) or Formula (V) comprises the sequence of SEQ ID NO: 184. In some embodiments an IL-2 conjugate of Formula (IV) or Formula (V) comprises the sequence of SEQ ID NO: 185. In some embodiments an IL-2 conjugate of Formula (IV) or Formula (V) comprises the sequence of SEQ ID NO: 186. In some embodiments an IL-2 conjugate of Formula (IV) or Formula (V) comprises the sequence of SEQ ID NO: 187. In some embodiments an IL-2 conjugate of Formula (IV) or Formula (V) comprises the sequence of SEQ ID NO: 188. In some embodiments an IL-2 conjugate of Formula (IV) or Formula (V) comprises the sequence of SEQ ID NO: 189. In some embodiments an IL-2 conjugate of Formula (IV) or Formula (V) comprises the sequence of SEQ ID NO: 190. In some embodiments an IL-2 conjugate of Formula (IV) or Formula (V) comprises the sequence of SEQ ID NO: 191. In some embodiments an IL-2 conjugate of Formula (IV) or Formula (V) comprises the sequence of SEQ ID NO: 192. In some embodiments an IL-2 conjugate of Formula (IV) or Formula (V) comprises the sequence of SEQ ID NO: 193. In some embodiments an IL-2 conjugate of Formula (IV) or Formula (V) comprises the sequence of SEQ ID NO: 194. In some embodiments an IL-2 conjugate of Formula (IV) or Formula (V) comprises the sequence of SEQ ID NO: 195. In some embodiments an IL-2 conjugate of Formula (IV) or Formula (V) comprises the sequence of SEQ ID NO: 196. In some embodiments an IL-2 conjugate of Formula (IV) or Formula (V) comprises the sequence of SEQ ID NO: 197. In some embodiments an IL-2 conjugate of Formula (IV) or Formula (V) comprises the sequence of SEQ ID NO: 198. In some embodiments an IL-2 conjugate of Formula (IV) or Formula (V) comprises the sequence of SEQ ID NO: 199. In some embodiments an IL-2 conjugate of Formula (IV) or Formula (V) comprises the sequence of SEQ ID NO: 200. In some embodiments an IL-2 conjugate of Formula (IV) or Formula (V) comprises the sequence of SEQ ID NO: 201. In some embodiments an IL-2 conjugate of Formula (IV) or Formula (V) comprises the sequence of SEQ ID NO: 202. In some embodiments an IL-2 conjugate of Formula (IV) or Formula (V) comprises the sequence of SEQ ID NO: 203. In some embodiments an IL-2 conjugate of Formula (IV) or Formula (V) comprises the sequence of SEQ ID NO: 204. In some embodiments an IL-2 conjugate of Formula (IV) or Formula (V) comprises the sequence of SEQ ID NO: 205. In some embodiments an IL-2 conjugate of Formula (IV) or Formula (V) comprises the sequence of SEQ ID NO: 206. In some embodiments an IL-2 conjugate of Formula (IV) or Formula (V) comprises the sequence of SEQ ID NO: 207. In some embodiments an IL-2 conjugate of Formula (IV) or Formula (V) comprises the sequence of SEQ ID NO: 208. In some embodiments an IL-2 conjugate of Formula (IV) or Formula (V) comprises the sequence of SEQ ID NO: 209. In some embodiments an IL-2 conjugate of Formula (IV) or Formula (V) comprises the sequence of SEQ ID NO: 210. In some embodiments an IL-2 conjugate of Formula (IV) or Formula (V) comprises the sequence of SEQ ID NO: 211. In some embodiments an IL-2 conjugate of Formula (IV) or Formula (V) comprises the sequence of SEQ ID NO: 212. In some embodiments an IL-2 conjugate of Formula (IV) or Formula (V) comprises the sequence of SEQ ID NO: 213. In some embodiments an IL-2 conjugate of Formula (IV) or Formula (V) comprises the sequence of SEQ ID NO: 214. In some embodiments an IL-2 conjugate of Formula (IV) or Formula (V) comprises the sequence of SEQ ID NO: 215. In some embodiments an IL-2 conjugate of Formula (IV) or Formula (V) comprises the sequence of SEQ ID NO: 216. In some embodiments an IL-2 conjugate of Formula (IV) or Formula (V) comprises the sequence of SEQ ID NO: 217. In some embodiments an IL-2 conjugate of Formula (IV) or Formula (V) comprises the sequence of SEQ ID NO: 218. In some embodiments an IL-2 conjugate of Formula (IV) or Formula (V) comprises the sequence of SEQ ID NO: 219. In some embodiments an IL-2 conjugate of Formula (IV) or Formula (V) comprises the sequence of SEQ ID NO: 220. In some embodiments an IL-2 conjugate of Formula (IV) or Formula (V) comprises the sequence of SEQ ID NO: 221. In some embodiments an IL-2 conjugate of Formula (IV) or Formula (V) comprises the sequence of SEQ ID NO: 222. In some embodiments an IL-2 conjugate of Formula (IV) or Formula (V) comprises the sequence of SEQ ID NO: 223. In some embodiments an IL-2 conjugate of Formula (IV) or Formula (V) comprises the sequence of SEQ ID NO: 224. In some embodiments an IL-2 conjugate of Formula (IV) or Formula (V) comprises the sequence of SEQ ID NO: 225. In some embodiments an IL-2 conjugate of Formula (IV) or Formula (V) comprises the sequence of SEQ ID NO: 226. In some embodiments an IL-2 conjugate of Formula (IV) or Formula (V) comprises the sequence of SEQ ID NO: 227. In some embodiments an IL-2 conjugate of Formula (IV) or Formula (V) comprises the sequence of SEQ ID NO: 228. In some embodiments an IL-2 conjugate of Formula (IV) or Formula (V) comprises the sequence of SEQ ID NO: 229. In some embodiments an IL-2 conjugate of Formula (IV) or Formula (V) comprises the sequence of SEQ ID NO: 230. In some embodiments an IL-2 conjugate of Formula (IV) or Formula (V) comprises the sequence of SEQ ID NO: 231. In some embodiments an IL-2 conjugate of Formula (IV) or Formula (V) comprises the sequence of SEQ ID NO: 232. In some embodiments an IL-2 conjugate of Formula (IV) or Formula (V) comprises the sequence of SEQ ID NO: 233. In some embodiments an IL-2 conjugate of Formula (IV) or Formula (V) comprises the sequence of SEQ ID NO: 234. In some embodiments an IL-2 conjugate of Formula (IV) or Formula (V) comprises the sequence of SEQ ID NO: 235. In some embodiments an IL-2 conjugate of Formula (IV) or Formula (V) comprises the sequence of SEQ ID NO: 236. In some embodiments an IL-2 conjugate of Formula (IV) or Formula (V) comprises the sequence of SEQ ID NO: 237. In some embodiments an IL-2 conjugate of Formula (IV) or Formula (V) comprises the sequence of SEQ ID NO: 238. In some embodiments an IL-2 conjugate of Formula (IV) or Formula (V) comprises the sequence of SEQ ID NO: 239. In some embodiments an IL-2 conjugate of Formula (IV) or Formula (V) comprises the sequence of SEQ ID NO: 240. In some embodiments an IL-2 conjugate of Formula (IV) or Formula (V) comprises the sequence of SEQ ID NO: 241. In some embodiments an IL-2 conjugate of Formula (IV) or Formula (V) comprises the sequence of SEQ ID NO: 242. In some embodiments an IL-2 conjugate of Formula (IV) or Formula (V) comprises the sequence of SEQ ID NO: 243. In some embodiments an IL-2 conjugate of Formula (IV) or Formula (V) comprises the sequence of SEQ ID NO: 244.

Described herein are pharmaceutical compositions of Formula (I), Formula (IV), or Formula (V). In some embodiments, a pharmaceutical compositions of Formula (I), Formula (IV), or Formula (V) comprises a sequence comprising any one of SEQ ID NOS: 3, 4, and 5-244. In some embodiments, a pharmaceutical compositions of Formula (I), Formula (IV), or Formula (V) comprises a sequence comprising any one of SEQ ID NO: 3. Described herein are pharmaceutical compositions of Formula (I), Formula (VI), or Formula (VII). In some embodiments, a pharmaceutical compositions of Formula (I), Formula (VI), or Formula (VII) comprises a sequence comprising any one of SEQ ID NOS: 3, 4, and 5-244. In some embodiments, a pharmaceutical compositions of Formula (I), Formula (VI), or Formula (VII) comprises a sequence comprising any one of SEQ ID NO: 3. Described herein are pharmaceutical compositions of Formula (I), Formula (VIII), or Formula (IX). In some embodiments, a pharmaceutical compositions of Formula (I), Formula (VIII), or Formula (IX) comprises a sequence comprising any one of SEQ ID NOS: 3, 4, and 5-244. In some embodiments, a pharmaceutical compositions of Formula (I), Formula (VIII), or Formula (IX) comprises a sequence comprising any one of SEQ ID NO: 3. Described herein are pharmaceutical compositions of Formula (I), Formula (X), or Formula (XI). In some embodiments, a pharmaceutical compositions of Formula (I), Formula (X), or Formula (XI) comprises a sequence comprising any one of SEQ ID NOS: 3, 4, and 5-244. In some embodiments, a pharmaceutical compositions of Formula (I), Formula (X), or Formula (XI) comprises a sequence comprising any one of SEQ ID NO: 3. Described herein are pharmaceutical compositions of Formula (XII), Formula (XIII), or Formula (V). In some embodiments, a pharmaceutical compositions of Formula (I), Formula (XII), or Formula (XIII) comprises a sequence comprising any one of SEQ ID NOS: 3, 4, and 5-244. In some embodiments, a pharmaceutical compositions of Formula (I), Formula (XII), or Formula (XIII) comprises a sequence comprising any one of SEQ ID NO: 3.

In some embodiments described herein, a conjugation reaction described herein comprises an inverse-electron demand cycloaddition reaction comprising a diene and a dienophile. In some embodiments, the diene comprises a tetrazine. In some embodiments, the dienophile comprises an alkene. In some embodiments, the dienophile comprises an alkyne. In some embodiments, the alkyne is a strained alkyne. In some embodiments, the alkene is a strained diene. In some embodiments, the alkyne is a trans-cyclooctyne. In some embodiments, the alkyne is a cyclooctene. In some embodiments, the alkene is a cyclopropene. In some embodiments, the alkene is a fluorocyclopropene. In some embodiments, a conjugation reaction described herein results in the formation of a cytokine peptide attached to a linker or conjugation moiety via a 6-membered ring heterocycle comprising two nitrogen atoms in the ring.

In some embodiments described herein, a conjugation reaction described herein comprises an olefin metathesis reaction. In some embodiments, a conjugation reaction described herein comprises reaction of an alkene and an alkyne with a ruthenium catalyst. In some embodiments, a conjugation reaction described herein comprises reaction of two alkenes with a ruthenium catalyst. In some embodiments, a conjugation reaction described herein comprises reaction of two alkynes with a ruthenium catalyst. In some embodiments, a conjugation reaction described herein comprises reaction of an alkene or alkyne with a ruthenium catalyst and an amino acid comprising an allyl group. In some embodiments, a conjugation reaction described herein comprises reaction of an alkene or alkyne with a ruthenium catalyst and an amino acid comprising an allyl sulfide or selenide. In some embodiments, a ruthenium catalyst is Hoveda-Grubbs $2^{nd}$ generation catalyst. In some embodiments, an olefin metathesis reaction comprises reaction of one or more strained alkenes or alkynes.

In some embodiments described herein, a conjugation reaction described herein comprises a cross-coupling reaction. In some embodiments, cross-coupling reactions comprise transition metal catalysts, such as iridium, gold, ruthenium, rhodium, palladium, nickel, platinum, or other transition metal catalyst and one or more ligands. In some embodiments, transition metal catalysts are water-soluble. In some embodiments described herein, a conjugation reaction described herein comprises a Suzuki-Miyaura cross-coupling reaction. In some embodiments described herein, a conjugation reaction described herein comprises reaction of an aryl halide (or triflate, or tosylate), an aryl or alkenyl boronic acid, and a palladium catalyst. In some embodiments described herein, a conjugation reaction described herein comprises a Sonogashira cross-coupling reaction. In some embodiments described herein, a conjugation reaction described herein comprises reaction of an aryl halide (or triflate, or tosylate), an alkyne, and a palladium catalyst. In some embodiments, cross-coupling reactions result in attachment of a linker or conjugating moiety to a cytokine peptide via a carbon-carbon bond.

In some embodiments described herein, a conjugation reaction described herein comprises a deprotection or "uncaging" reaction of a reactive group prior to conjugation. In some embodiments, a conjugation reaction described herein comprises uncaging of a reactive group with light, followed by a conjugation reaction. In some embodiments, a reactive group is protected with an aralkyl moiety comprising one or more nitro groups. In some embodiments, uncaging of a reactive group results in a free amine, sulfide, or other reactive group. In some embodiments, a conjugation reaction described herein comprises uncaging of a reactive group with a transition metal catalyst, followed by a conjugation reaction. In some embodiments, the transition metal catalyst comprises palladium and one or more ligands. In some embodiments, a reactive group is protected with an allyl moiety. In some embodiments, a reactive group is protected with an allylic carbamate. In some embodiments, a reactive group is protected with a propargylic moiety. In some embodiments, a reactive group is protected with a propargyl carbamate. In some embodiments, a reactive group is protected with a dienophile, wherein exposure to a diene (such as a tetrazine) results in deprotection of the reactive group.

In some embodiments described herein, a conjugation reaction described herein comprises a ligand-directed reaction, wherein a ligand (optionally) attached to a reactive group) facilitates the site of conjugation between the reactive group and the cytokine peptide. In some embodiments, the ligand is cleaved during or after reaction of the cytokine peptide with the reactive group. In some embodiments, the conjugation site of the cytokine peptide is a natural amino acid. In some embodiments, the conjugation site of the cytokine peptide is a lysine, cysteine, or serine. In some embodiments, the conjugation site of the cytokine peptide is an unnatural amino acid described herein. In some embodiments the reactive group comprises a leaving group, such as an electron-poor aryl or heteroaryl group. In some embodiments the reactive group comprises a leaving group, such as an electron-poor alkyl group that is displaced by the cytokine peptide. In some embodiments, a conjugation reaction described herein comprises reaction of a radical trapping agent with a radical species. In some embodiments, a conjugation reaction described herein comprises an oxidative radical addition reaction. In some embodiments, a radical trapping agent is an arylamine. In some embodiments, a radical species is a tyrosyl radical. In some embodiments, radical species are generated by a ruthenium catalyst (such as [Ru(bpy)$_3$]) and light.

Enzymatic reactions are optionally used for conjugation reactions described herein. Exemplary enzymatic conjugations include SortA-mediated conjugation, a TGs-mediated conjugation, or an FGE-mediated conjugation. In some embodiments, a conjugation reaction described herein comprises native protein ligation (NPL) of a terminal 1-amino-2-thio group with a thioester to form an amide bond.

Various conjugation reactions are described herein for reacting a linker or conjugating moiety with a cytokine peptide, wherein the reaction occurs with a natural ("canonical") amino acid in the cytokine peptide. In some embodiments, the natural amino acid is found at a conjugation position is found in a wild type sequence, or alternatively the position has been mutated. In some embodiments, a conjugation reaction comprises formation of a disulfide bond at a cysteine residue. In some embodiments, a conjugation reaction comprises a 1,4 Michael addition reaction of a cysteine or lysine. In some embodiments, a conjugation reaction comprises a cyanobenzothiazole ligation of a cysteine. In some embodiments, a conjugation reaction comprises cross-linking with an acetone moiety, such as 1,3-dichloro-2-propionone. In some embodiments, a conjugation reaction comprises a 1,4 Michael addition to a dehydroalanine, formed by reaction of cysteine with O-mesitylenesulfonyl-hydroxylamine. In some embodiments a conjugation reaction comprises reaction of a tyrosine with a triazolinedione (TAD), or TAD derivative. In some embodiments a conjugation reaction comprises reaction of a tryptophan with a rhodium carbenoid.

Methods of Use

Autoimmune Disease or Disorder

In some embodiments, also described herein is a method of treating an autoimmune disease or disorder in a subject in need thereof, which comprises administering to the subject a therapeutically effective amount of a cytokine conjugate (e.g., IL-2 conjugate) described herein. In some instances, the IL-2 conjugate comprises an isolated and purified IL-2 polypeptide and a conjugating moiety, wherein the IL-2 conjugate has a decreased affinity to IL-2 receptor β (IL-2Rβ) subunit, IL-2 receptor γ (IL-2Rγ) subunit, or a combination thereof, relative to a wild-type IL-2 polypeptide. In some instances, the IL-2 conjugate comprises an isolated and purified IL-2 polypeptide; and a conjugating moiety that binds to the isolated and purified IL-2 polypeptide at an amino acid residue selected from A1, P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, I92, L94, E95, K97, G98, S99, E100, T101, T102, F103, M104, C105, E106, Y107, A108, D109, E110, T111, A112, T113, E116, N119, R120, T123, A125, Q126, S127, S130, T131, L132, and T133, wherein the numbering of the amino acid residues corresponds to SEQ ID NO: 1. In some instances, the amino acid residue is selected from K8, K9, Q11, L12, E15, H16, L18, L19, D20, Q22, M23, N26, R81, D84, S87, N88, V91, I92, L94, E95, E116, N119, R120, T123, A125, Q126, S127, S130, T131, L132, and T133. In some instances, the amino acid residue is selected from K8, K9, L12, E15, H16, L19, D20, Q22, M23, N26, D84, N88, E95, and Q126. In some instances, the amino acid residue is selected from K7, K8, Q10, L11, E14, H15, L17, L18, D19, Q21, M22, N25, R80, D83, S86, N87, V90, I91, L93, E94, E115, N118, R119, T122, A124, Q125, S126, S129, T130, L131, and T132. In some instances, the amino acid residue is selected from K8, K9, L12, E15, H16, L19, D20, Q22, M23, N26, D84, N88, E95, and Q126, wherein the numbering of the amino acid residues corresponds to SEQ ID NO: 3. In some cases, the IL-2 conjugate interacts with an IL-2Rαβγ complex but with a reduced affinity toward the IL-2Rβ and IL-2Rγ subunits, or will decrease the recruitment of the IL-2R γ subunit to the IL-2/IL-2Rβ complex. In some cases, the modified IL-2 polypeptide maintains the binding affinity toward IL-2Rα relative to a wild-type IL-2 polypeptide. In such cases, the IL-2/IL-2Rαβγ complex stimulates or enhances expansion of CD4+ Treg cells. In additional cases, the modified IL-2 polypeptide increases the dose required for activation of the Teff and/or NK cells via the IL-2Rβγ complex, thereby expanding the dose ranges for activation of Treg cells via the IL-2Rαβγ complex (or expanding the therapeutic window of the IL-2 for activation of Treg cells via the IL-2Rαβγ complex). In some embodiments, described herein is a method of treating an autoimmune disease or disorder in a subject in need thereof, which comprises administering to the subject a therapeutically effective amount of a cytokine conjugate (e.g., an IL-2 conjugate) described Table 1. In some embodiments, described herein is a method of treating an autoimmune disease or disorder in a subject in need thereof, which comprises administering to the subject a therapeutically effective amount of a cytokine conjugate of Formula (I) comprising the sequence of any one of SEQ ID NOs: 34-48. In some embodiments, described herein is a method of treating an autoimmune disease or disorder in a subject in need thereof, which comprises administering to the subject a therapeutically effective amount of a cytokine conjugate of Formula (I) comprising any one of SEQ ID NOs.: 199-213. In some embodiments, described herein is a method of treating an autoimmune disease or disorder in a subject in need thereof, which comprises administering to the subject a therapeutically effective amount of a cytokine conjugate of Formula (I) comprising any one of SEQ ID NOs.: 49-63. In some embodiments, described herein is a method of treating an autoimmune disease or disorder in a subject in need thereof, which comprises administering to the subject a therapeutically effective amount of a cytokine conjugate of Formula (I) comprising any one of SEQ ID NOs.: 213-228. In some embodiments, described herein is a method of treating an autoimmune disease or disorder in a subject in need thereof, which comprises administering to the subject a therapeutically effective amount of a cytokine conjugate of Formula (I) comprising any one of SEQ ID NOs.: 64-78. In some embodiments, described herein is a method of treating an autoimmune disease or disorder in a subject in need thereof, which comprises administering to the subject a therapeutically effective amount of a cytokine conjugate of Formula (I) comprising any one of SEQ ID NOs.: 229-243. In some embodiments, described herein is a method of treating an autoimmune disease or disorder in a subject in need thereof, which comprises administering to the subject a therapeutically effective amount of a cytokine conjugate of Formula (I) comprising any one of SEQ ID NOs.: 154-168. In some embodiments, described herein is a method of treating an autoimmune disease or disorder in a subject in need thereof, which comprises administering to the subject a therapeutically effective amount of a cytokine conjugate of Formula (I) comprising any one of SEQ ID NOs.: 109-123. In some embodiments, described herein is a method of treating an autoimmune disease or disorder in a subject in need thereof, which comprises administering to the subject a therapeutically effective amount of a cytokine conjugate of Formula (I) comprising any one of SEQ ID NOs.: 169-183. In some embodiments, described herein is a method of treating an autoimmune disease or disorder in a subject in need thereof, which comprises administering to the subject a therapeutically effective amount of a cytokine conjugate of Formula (I) comprising any one of SEQ ID NOs.: 123-138. In some embodiments, described herein is a method of treating an autoimmune disease or disorder in a subject in need thereof, which comprises administering to the subject a therapeutically effective amount of a cytokine conjugate of Formula (I) comprising any one of SEQ ID NOs.: 184-198. In some embodiments, described herein is a method of treating an autoimmune disease or disorder in a subject in need thereof, which comprises administering to the subject a therapeutically effective amount of a cytokine conjugate of Formula (I) comprising any one of SEQ ID NOs.: 139-153.

In some instances, the autoimmune disease or disorder comprises alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis nodosa, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis.

In some cases, a cytokine (e.g., interleukin, IFN, or TNF) conjugate is administered to a subject having alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis nodosa, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis.

In some cases, an IL-2 conjugate is administered to a subject having alopecia areata, autoimmune hemolytic anemia, autoimmune hepatitis, dermatomyositis, type 1 diabetes, juvenile idiopathic arthritis, glomerulonephritis, Graves' disease, Guillain-Barré syndrome, idiopathic thrombocytepenic purpura, myasthenia gravis, multiple sclerosis, pemphigus/pemphigoid, pernicious anemia, polyarteritis nodosa, polymyositis, primary biliary cirrhosis, psoriasis, rheumatoid arthritis, scleroderma, Sjögren's syndrome, systemic lupus erythematosus, thyroiditis, uveitis, vitiligo, or Wegener's granulomatosis. In some cases, the IL-2 conjugate is administered to a subject having type 1 diabetes. In some cases, the IL-2 conjugate is administered to a subject having Graves' disease. In some cases, the IL-2 conjugate is administered to a subject having multiple sclerosis. In some cases, the IL-2 conjugate is administered to a subject having psoriasis. In some cases, the IL-2 conjugate is administered to a subject having rheumatoid arthritis. In some cases, the IL-2 conjugate is administered to a subject having Sjögren's syndrome. In some cases, the IL-2 conjugate is administered to a subject having systemic lupus erythematosus. In some cases, the IL-2 conjugate is administered to a subject having uveitis. In some cases, the IL-2 conjugate is administered to a subject having Wegener's granulomatosis.

In some cases, a cytokine conjugate (e.g., an IL-2 conjugate) is administered to a subject for the treatment of a Graft-versus-Host disease (GVHD).

In some embodiments, a cytokine conjugate (e.g., an IL-2 conjugate) of the disclosure is administered to a subject for the treatment of transplant rejection.

In some embodiments, a cytokine conjugate (e.g., an IL-2 conjugate) of the disclosure is administered to a subject for the treatment of contact sensitivity.

Delayed-type hypersensitivity (DTH), also called Type IV hypersensitivity, is an inflammatory reaction mediated by antigen-specific effector T-lymphocytes. The inflammatory reaction is characterized by local skin swelling, erythema, induration, and cellular infiltration. DTH can be actively induced by immunization with antigens, such as bovine serum albumin (BSA), keyhole limpet hemocyanin (KLH), or ovalbumin (OVA). Adoptive transfer of antigen-specific T lymphocytes could also be used to elicit a DTH response. DTH provides a way to assess the effect of compounds in an animal model of a chronic immune response and/or chronic inflammation. DTH can also be used to measure an agent's effect on suppression of a subject's acute response to an antigen. Development of a DTH response is accomplished in two separate phases: an initial sensitizing phase and an elicitation phase. The initial sensitizing phase occurs when subjects are exposed to a specific antigen. The latter phase can be initiated, for example, 5-12 days after sensitization, whereby the previously sensitized subjects are challenged by, for example, subcutaneous footpad injection or intradermal ear injection of the same antigen.

A cytokine conjugate (e.g., IL-2 conjugate) described herein may be adminstered to a subject having an autoimmune condition modeled by, represented by, and/or characterized by a DTH reaction. Accordingly, in some embodiments, described herein is a method of alleviating or eliminating an autoimmune condition modeled by, represented by, and/or characterized by a DTH reaction in a subject in need thereof, which comprises administering to the subject a therapeutically effective amount of a cytokine conjugate (e.g., IL-2 conjugate) described herein. In some embodiments, described herein is a method of alleviating or eliminating DTH in a subject in need thereof, which comprises administering to the subject a therapeutically effective amount of a cytokine conjugate (e.g., IL-2 conjugate) described herein. In some embodiments, the subject in need thereof is administered a therapeutically effective amount of the cytokine conjugate (e.g., IL-2 conjugate) to prevent or reduce development of a DTH reaction or to prevent or reduce development a condition (and/or symptoms of a condition) modeled by, represented by, and/or characterized by a DTH reaction.

In some embodiments, an additional therapeutic agent is further administered to the subject. In some cases, the additional therapeutic agent is administered simultaneously with a cytokine conjugate (e.g., IL-2 conjugate). In other cases, the additional therapeutic agent and the cytokine conjugate (e.g., IL-2 conjugate) are administered sequentially, e.g., the cytokine conjugate (e.g., IL-2 conjugate) is administered prior to the additional therapeutic agent or that the cytokine conjugate (e.g., IL-2 conjugate) is administered after administration of the additional therapeutic agent.

Exemplary additional therapeutic agents for the treatment of an autoimmune disease or disorder include, but are not limited to, corticosteroids such as prednisone, budesonide, or prednisolone; calcineurin inhibitors such as cyclosporine or tacrolimus; mTOR inhibitors such as sirolimus or everolimus; IMDH inhibitors such as azathioprine, leflunomide, or mycophenolate; biologics such as abatacept, adalimumab, anakinra, certolizumab, etanercept, golimumab, infliximab, ixekizumab, natalizumab, rituximab, secukinumab, tocilizumab, ustekinumab, or vedolizumab; and monoclonal antibodies such as basiliximab, daclizumab, or muromonab.

In some cases, a cytokine conjugate (e.g., IL-2 conjugate) is administered with an additional therapeutic agent selected from a corticosteroid such as prednisone, budesonide, or prednisolone; a calcineurin inhibitor such as cyclosporine or tacrolimus; an mTOR inhibitor such as sirolimus or everolimus; an IMDH inhibitor such as azathioprine, leflunomide, or mycophenolate; a biologics such as abatacept, adalimumab, anakinra, certolizumab, etanercept, golimumab, infliximab, ixekizumab, natalizumab, rituximab, secukinumab, tocilizumab, ustekinumab, or vedolizumab; and a monoclonal antibody such as basiliximab, daclizumab, or muromonab.

Additional Therapeutic Agents

In some embodiments, an additional therapeutic agent is further administered to the subject. In some cases, the additional therapeutic agent is administered simultaneously with a cytokine conjugate (e.g., an IL-2 conjugate). In other cases, the additional therapeutic agent and the IL-2 conjugate are administered sequentially, e.g., the cytokine conjugate (e.g., IL-2 conjugate) is administered prior to the additional therapeutic agent or that the cytokine conjugate (e.g., IL-2 conjugate) is administered after administration of the additional therapeutic agent.

In some cases, the additional therapeutic agent comprises a chemotherapeutic agent, an immunotherapeutic agent, a targeted therapy, radiation therapy, or a combination thereof. Illustrative additional therapeutic agents include, but are not limited to NSAIDS ((1) salicylic acid derivatives: acetyl-salicylic acid (aspirin), diflunisal and sulfasalazine; (2) para-aminophenol derivatives: acetaminophen; (3) fenamates: mefenamic acid, meclofenamate, flufenamic acid; (4) propionic acid derivatives: ibuprofen, naproxen, fenoprofen, ketoprofen, flurbiprofen, oxaprozin; and (5) enolic acid (oxicam) derivatives: piroxicam, tenoxicam); COX-2 inhibitors (celecoxib, rofecoxib, valdecoxib, lumiracoxib, parecoxib, and etoricoxib); glucocorticoids prednisone/prednisolone, methylprednisolone, and the fluorinated glucocorticoids such as dexamethasone and betamethason), cDMARDs (Conventional Disease-Modifying Anti-Rheumatic Drugs: Methotrexate; Leflunomide; gold compounds, sulfasalazine, azathioprine, cyclophosphamide, antimalarials, d-penicillamine, cyclosporine); anti-TNFs (Infliximab, Etanercept, Adalimumab, Golimumab, Certolizumab Pegol).

In some cases, a cytokine conjugate (e.g., IL-2 conjugate) is administered with an additional therapeutic agent selected from a corticosteroid such as prednisone, methylprednisolone, or dexamethasone.

In some instances, a cytokine conjugate (e.g., IL-2 conjugate) described herein is administered with an immune checkpoint inhibitor. Exemplary checkpoint inhibitors include:

PD-L1 inhibitors such as Genentech's MPDL3280A (RG7446), Anti-mouse PD-L1 antibody Clone 10F.9G2 (Cat #BE0101) from BioXcell, anti-PD-L1 monoclonal antibody MDX-1105 (BMS-936559) and BMS-935559 from Bristol-Meyer's Squibb, MSB0010718C, mouse anti-PD-L1 Clone 29E.2A3, AstraZeneca's MEDI4736, atezolizumab (also known as Tecentriq®), bavelizumab (also known as Imfinzi®), and avelumab (also known as Bavencio®);

PD-L2 inhibitors such as GlaxoSmithKline's AMP-224 (Amplimmune), and rHIgM12B7;

PD-1 inhibitors such as anti-mouse PD-1 antibody Clone J43 (Cat #BE0033-2) from BioXcell, anti-mouse PD-1 antibody Clone RMP1-14 (Cat #BE0146) from BioXcell, mouse anti-PD-1 antibody Clone EH12, Merck's MK-3475 anti-mouse PD-1 antibody (Keytruda, pembrolizumab, lambrolizumab), AnaptysBio's anti-PD-1 antibody known as ANB011, antibody MDX-1 106 (ONO-4538), Bristol-Myers Squibb's human IgG4 monoclonal antibody nivolumab (Opdivo®, BMS-936558, MDX1106), AstraZeneca's AMP-514 and AMP-224, and Pidilizumab (CT-011) from CureTech Ltd;

CTLA-4 inhibitors such as Bristol Meyers Squibb's anti-CTLA-4 antibody ipilimumab (also known as Yervoy®, MDX-010, BMS-734016 and MDX-101), anti-CTLA4 antibody clone 9H10 from Millipore, Pfizer's tremelimumab (CP-675,206, ticilimumab), and anti-CTLA4 antibody clone BNI3 from Abcam;

LAG3 inhibitors such as anti-Lag-3 antibody clone eBioC9B7W (C9B7W) from eBioscience, anti-Lag3 antibody LS-B2237 from LifeSpan Biosciences, IMP321 (ImmuFact) from Immutep, anti-Lag3 antibody BMS-986016, and the LAG-3 chimeric antibody A9H12;

B7-H3 inhibitors such as MGA271;

KIR inhibitors such as Lirilumab (IPH2101);

CD137 inhibitors such as urelumab (BMS-663513, Bristol-Myers Squibb), PF-05082566 (anti-4-1BB, PF-2566, Pfizer), or XmAb-5592 (Xencor);

PS inhibitors such as Bavituximab;

and inhibitors such as an antibody or fragments (e.g., a monoclonal antibody, a human, humanized, or chimeric antibody) thereof, RNAi molecules, or small molecules to TIM3, CD52, CD30, CD20, CD33, CD27, OX40, GITR, ICOS, BTLA (CD272), CD160, 2B4, LAIR1, TIGHT, LIGHT, DR3, CD226, CD2, or SLAM.

In some instances, the cytokine conjugate (e.g., IL-2 conjugate) is administered in combination with pembrolizumab, nivolumab, tremelimumab, or ipilimumab.

In some instances, a cytokine conjugate (e.g., IL-2 conjugate) described herein is administered with an antibody such as alemtuzumab, trastuzumab, ibritumomab tiuxetan, brentuximab vedotin, ado-trastuzumab emtansine, or blinatumomab.

In some instances, a cytokine conjugate (e.g., IL-2 conjugate) is administered with an additional therapeutic agent selected from a receptor agonist. In some instances, the receptor agonist comprises a Toll-like receptor (TLR) ligand. In some cases, the TLR ligand comprises TLR1, TLR2, TLR3, TLR4, TLR5, TLR6, TLR7, TLR8, or TLR9. In some cases, the TLR ligand comprises a synthetic ligand such as, for example, Pam3Cys, CFA, MALP2, Pam2Cys, FSL-1, Hib-OMPC, Poly I:C, poly A:U, AGP, MPL A, RC-529, MDF2$\beta$, CFA, or Flagellin. In some cases, the cytokine conjugate (e.g., IL-2 conjugate) is administered with one or more TLR agonists selected from TLR1, TLR2, TLR3, TLR4, TLR5, TLR6, TLR7, TLR8, and TLR9. In some cases, the cytokine conjugate (e.g., IL-2 conjugate) is administered with one or more TLR agonists selected from Pam3Cys, CFA, MALP2, Pam2Cys, FSL-1, Hib-OMPC, Poly I:C, poly A:U, AGP, MPL A, RC-529, MDF2$\beta$, CFA, and Flagellin.

In some embodiments, a cytokine conjugate (e.g., IL-2 conjugate) is used for an ex vivo activation and/or expansion of an autologous and/or allogenic T cell transfer. In such cases, the cytokine conjugate (e.g., IL-2 conjugate) is used to activate and/or expand a sample comprising autologous and/or allogenic T cells and the cytokine conjugate (e.g., IL-2 conjugate) is optionally removed from the sample prior to administering the sample to a subject in need thereof.

In some embodiments, a cytokine conjugate (e.g., IL-2 conjugate) is administered in combination with surgery.

Development of Adoptive Cell Therapies

Disclosed herein, in some embodiments, are methods of generating an adoptive cell therapy composition useful for the treatment of a disease or condition described herein (e.g., proliferative disease or condition, pathogenic infection, and/or autoimmune disease or condition) in a subject in need thereof, comprising: a) providing immune cells obtained from a subject in need thereof; b) contacting the immune cells to with a modified IL-2 polypeptide, an IL-2 conjugate, an IL-2R$\beta\gamma$ binding protein, or an activator of the immune cell, wherein the immune cell comprises a CD4+ helper cell, a CD8+ effector naïve and memory cell, a CD8+ cytotoxic T cell, a suppressor T Cell, a Natural Killer (NK) cell, or a Natural killer T (NKT) cell. In some embodiments, the immune cell is engineered to additionally express a chimeric antigen receptor (CAR). In some instances, the modified IL-2 polypeptide, the IL-2 conjugate, the IL-2R$\beta\gamma$ binding protein, or the activator of the immune cell comprises the articles of manufacture disclosed herein. In some instances, the methods of generating the adoptive cell therapy are performed using the kits disclosed herein. In some embodiments, the subject is treated with the adoptive cell therapy, by administering a therapeutically effective amount of the adoptive cell therapy. In some instances, the subject is diagnosed with the disease or condition. In some instances, the adoptive cell therapy is effective to treat the disease or condition in the subject. In some instances, the disease or condition comprises an autoimmune disease. In some embodiments, the IL-2 conjugate is a conjugate of any one of SEQ ID NOS. 5-244.

In some instances, the molecular weight of the PEG is effective to improve the manufacturing process of the IL-2 polypeptide or the IL-2 conjugate as a reagent for adoptive cell therapies. In some embodiments, the molecular weight of the PEG improves the solubility of the IL-2 polypeptide or IL-2 conjugate. In some instances, the molecular weight of the PEG improves the purification process of manufacturing the adoptive cell therapy. In some instances, the molecular weight of the PEG improves the stability of the IL-2 polypeptide or the IL-2 conjugate.

Disclosed herein, in some embodiments, are methods of treating an autoimmune disease or disorder in a subject in need thereof, which comprises administering to the subject an adoptive cell therapy described herein. In some instances, the adoptive cell therapy is developed using the methods described herein. In some instances, the adoptive cell therapy is administered to the subject in addition to the cytokine conjugate (e.g., IL-2 conjugate) described herein. In some instances, the cytokine conjugate is administered before the adoptive cell therapy. In some instances, the cytokine conjugate is administered after the adoptive cell therapy. In some instances, the adoptive cell therapy is effective to expand a population of immune cells in the subject (e.g., CD4+ helper cell, CD8+ effector naïve and memory cell, NK cell, and/or NKT cell populations, Treg cell population).

Conjugation Chemistry

Various conjugation reactions are used to conjugate linkers, conjugation moieties, and unnatural amino acids incorporated into cytokine peptides described herein. Such conjugation reactions are often compatible with aqueous conditions, such as "bioorthogonal" reactions. In some embodiments, conjugation reactions are mediated by chemical reagents such as catalysts, light, or reactive chemical groups found on linkers, conjugation moieties, or unnatural amino acids. In some embodiments, conjugation reactions are mediated by enzymes. In some embodiments, a conjugation reaction used herein is described in Gong, Y., Pan, L. Tett. Lett. 2015, 56, 2123. In some embodiments, a conjugation reaction used herein is described in Chen, X.; Wu. Y-W. Org. Biomol. Chem. 2016, 14, 5417.

In some embodiments described herein, a conjugation reaction described herein comprises a 1,3-dipolar cycloaddition reaction. In some embodiments, the 1,3-dipolar cycloaddition reaction comprises reaction of an azide and a phosphine ("Click" reaction). In some embodiments, the conjugation reaction is catalyzed by copper. In some embodiments, a conjugation reaction described herein results in cytokine peptide comprising a linker or conjugation moiety attached via a triazole. In some embodiments, a conjugation reaction described herein comprises reaction of an azide with a strained olefin. In some embodiments, a conjugation reaction described herein comprises reaction of an azide with a strained alkyne. In some embodiments, a conjugation reaction described herein comprises reaction of an azide with a cycloalkyne, for example DBCO.

In some embodiments described herein, a conjugation reaction described herein comprises:

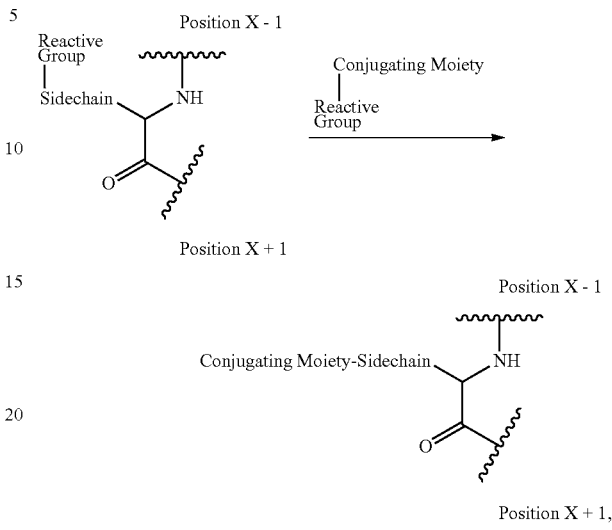

wherein X is the position in the IL-2 conjugate comprising an unnatural amino acid, such as in any one of SEQ ID NOS: 5 to 19 and 79 to 93. In some embodiments, the conjugating moiety comprises water soluble polymer. In some embodiments, a reactive group comprises an alkyne or azide. In some embodiments described herein, a conjugation reaction described herein comprises:

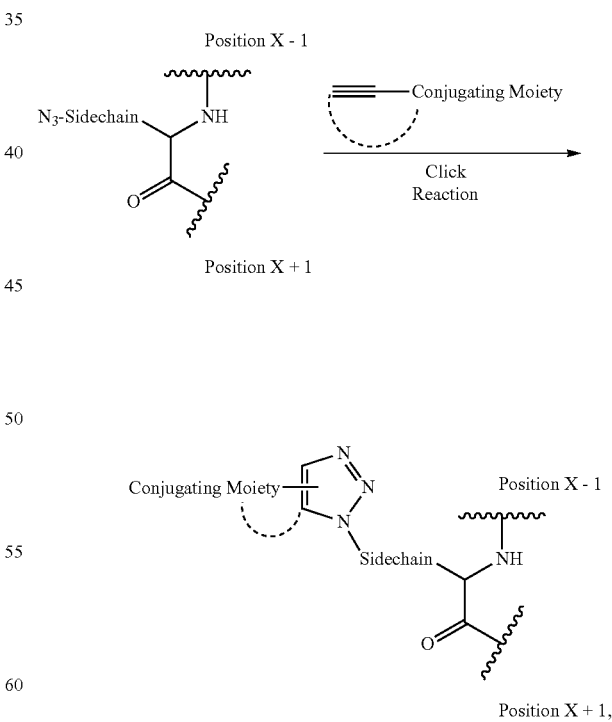

wherein X is the position in the IL-2 conjugate comprising an unnatural amino acid, such as in any one of SEQ ID NOS: 5 to 19 and 79 to 93. In some embodiments described herein, a conjugation reaction described herein comprises:

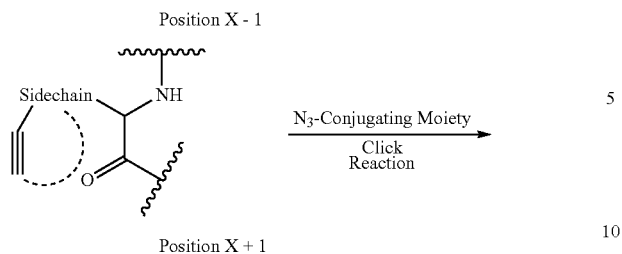
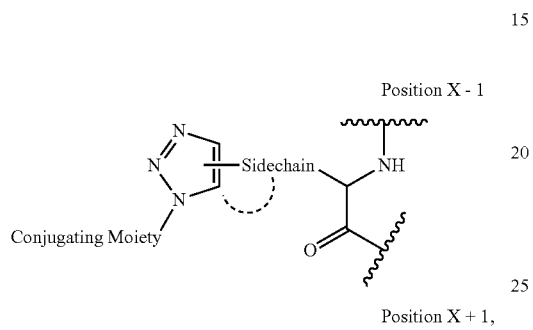
wherein X is the position in the IL-2 conjugate comprising an unnatural amino acid, such as in any one of SEQ ID NOS: 5 to 19 and 79 to 93. In some embodiments described herein, a conjugation reaction described herein comprises:
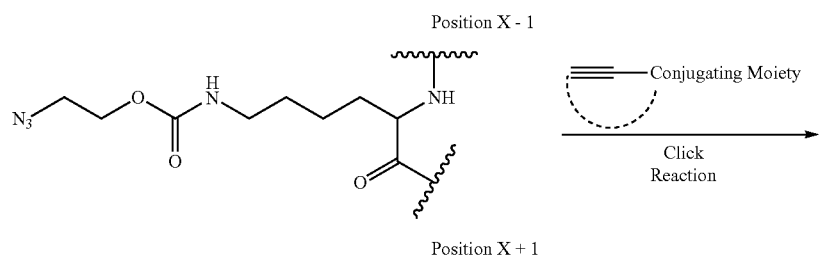
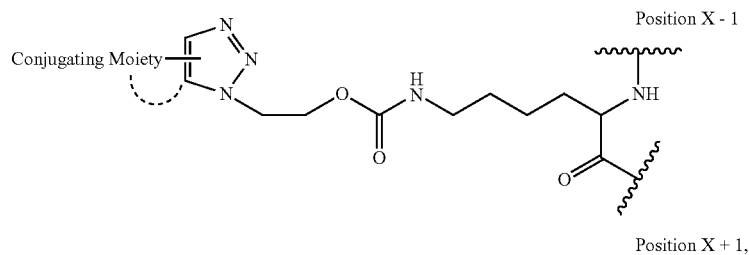

wherein X is the position in the IL-2 conjugate comprising an unnatural amino acid, such as in any one of SEQ ID NOS: 5 to 19 and 79 to 93.

In some embodiments described herein, a conjugation reaction described herein comprises are cycloaddition reaction between an azide moiety, such as that contained in a protein containing an amino acid residue derived from N6-((2-azidoethoxy)-carbonyl)-L-lysine (AzK), and a strained cycloalkyne, such as that derived from DBCO, which is a chemical moiety comprising a dibenzocyclooctyne group. PEG groups comprising a DBCO moiety are commercially available or may be prepared by methods known to those of ordinary skill in the art.

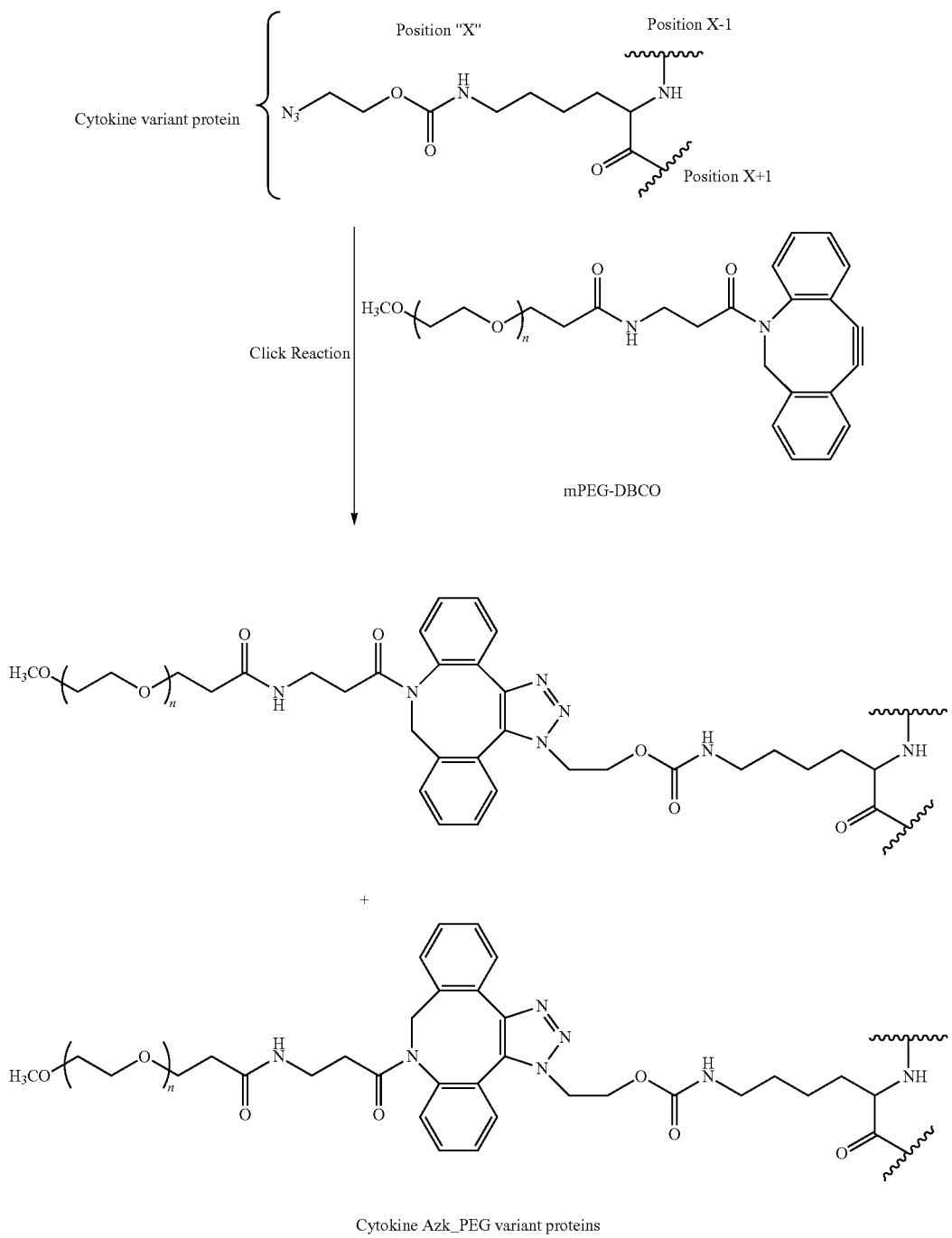

Cytokine Azk_PEG variant proteins

Cytokine Azk_PEG variant proteins

Conjugation reactions such as a click reaction described herein may generate a single regioisomer, or a mixture of regioisomers. In some instances the ratio of regioisomers is about 1:1. In some instances the ratio of regioisomers is about 2:1. In some instances the ratio of regioisomers is about 1.5:1. In some instances the ratio of regioisomers is about 1.2:1. In some instances the ratio of regioisomers is about 1.1:1. In some instances the ratio of regioisomers is greater than 1:1.

Cytokine Polypeptide Production

In some instances, the IL-2 conjugates described herein, either containing a natural amino acid mutation or an unnatural amino acid mutation, are generated recombinantly or are synthesized chemically. In some instances, IL-2 conjugates described herein are generated recombinantly, for example, either by a host cell system, or in a cell-free system.

In some instances, IL-2 conjugates are generated recombinantly through a host cell system. In some cases, the host cell is a eukaryotic cell (e.g., mammalian cell, insect cells, yeast cells or plant cell) or a prokaryotic cell (e.g., gram-positive bacterium or a gram-negative bacterium). In some cases, a eukaryotic host cell is a mammalian host cell. In some cases, a mammalian host cell is a stable cell line, or a cell line that has incorporated a genetic material of interest into its own genome and has the capability to express the product of the genetic material after many generations of cell division. In other cases, a mammalian host cell is a transient cell line, or a cell line that has not incorporated a genetic material of interest into its own genome and does not have the capability to express the product of the genetic material after many generations of cell division.

Exemplary mammalian host cells include 293T cell line, 293A cell line, 293FT cell line, 293F cells, 293 H cells, A549 cells, MDCK cells, CHO DG44 cells, CHO-S cells, CHO-Kl cells, Expi293F™ cells, Flp-In™ T-REx™ 293 cell line, Flp-In™-293 cell line, Flp-In™-3T3 cell line, Flp-In™-BHK cell line, Flp-In™-CHO cell line, Flp-In™-CV-1 cell line, Flp-In™-Jurkat cell line, FreeStyle™ 293-F cells, FreeStyle™ CHO-S cells, GripTite™ 293 MSR cell line, GS-CHO cell line, HepaRG™ cells, T-REx™ Jurkat cell line, Per.C6 cells, T-REx™-293 cell line, T-REx™-CHO cell line, and T-REx™-HeLa cell line.

In some embodiments, a eukaryotic host cell is an insect host cell. Exemplary insect host cell include *Drosophila* S2 cells, Sf9 cells, Sf21 cells, High Five™ cells, and expresSF+® cells.

In some embodiments, a eukaryotic host cell is a yeast host cell. Exemplary yeast host cells include *Pichia pastoris* yeast strains such as GS115, KM71H, SMD1168, SMD1168H, and X-33, and *Saccharomyces cerevisiae* yeast strain such as INVSc1.

In some embodiments, a eukaryotic host cell is a plant host cell. In some instances, the plant cells comprise a cell from algae. Exemplary plant cell lines include strains from *Chlamydomonas reinhardtii* 137c, or *Synechococcus elongatus* PPC 7942.

In some embodiments, a host cell is a prokaryotic host cell. Exemplary prokaryotic host cells include BL21, Mach1™, DH10B™, TOP10, DH5a, DH10Bac™, OmniMax™, MegaX™, DH12S™, INV110, TOP10F™, INVαF, TOP10/P3, ccdB Survival, PIR1, PIR2, Stbl2™, Stbl3™, or Stbl4™.

In some instances, suitable polynucleic acid molecules or vectors for the production of an IL-2 polypeptide described herein include any suitable vectors derived from either a eukaryotic or prokaryotic source. Exemplary polynucleic acid molecules or vectors include vectors from bacteria (e.g., *E. coli*), insects, yeast (e.g., *Pichia pastoris*), algae, or mammalian source. Bacterial vectors include, for example, pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Insect vectors include, for example, pFastBacl, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

Yeast vectors include, for example, Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 *Pichia* vector, pFLD1 *Pichi pastoris* vector, pGAPZA, B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector.

Algae vectors include, for example, pChlamy-4 vector or MCS vector.

Mammalian vectors include, for example, transient expression vectors or stable expression vectors. Exemplary mammalian transient expression vectors include p3xFLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3xFLAG-CMV 7.1, pFLAG-CMV 20, p3xFLAG-Myc-CMV 24, pCMV-FLAG-MAT1, pCMV-FLAG-MAT2, pBICEP-CMV 3, or pBICEP-CMV 4. Exemplary mammalian stable expression vectors include pFLAG-CMV 3, p3xFLAG-CMV 9, p3xFLAG-CMV 13, pFLAG-Myc-CMV 21, p3xFLAG-Myc-CMV 25, pFLAG-CMV 4, p3xFLAG-CMV 10, p3xFLAG-CMV 14, pFLAG-Myc-CMV 22, p3xFLAG-Myc-CMV 26, pBICEP-CMV 1, or pBICEP-CMV 2.

In some instances, a cell-free system is used for the production of a cytokine (e.g., IL-2) polypeptide described herein. In some cases, a cell-free system comprises a mixture of cytoplasmic and/or nuclear components from a cell and is suitable for in vitro nucleic acid synthesis. In some instances, a cell-free system utilizes prokaryotic cell components. In other instances, a cell-free system utilizes eukaryotic cell components. Nucleic acid synthesis is obtained in a cell-free system based on, for example, *Drosophila* cell, *Xenopus* egg, Archaea, or HeLa cells. Exemplary cell-free systems include *E. coli* S30 Extract system, *E. coli* T7 S30 system, or PURExpress®, XpressCF, and XpressCF+.

Cell-free translation systems variously comprise components such as plasmids, mRNA, DNA, tRNAs, synthetases, release factors, ribosomes, chaperone proteins, translation initiation and elongation factors, natural and/or unnatural amino acids, and/or other components used for protein expression. Such components are optionally modified to improve yields, increase synthesis rate, increase protein product fidelity, or incorporate unnatural amino acids. In some embodiments, cytokines described herein are synthesized using cell-free translation systems described in U.S. Pat. No. 8,778,631; US 2017/0283469; US 2018/0051065; US 2014/0315245; or U.S. Pat. No. 8,778,631. In some embodiments, cell-free translation systems comprise modified release factors, or even removal of one or more release factors from the system. In some embodiments, cell-free translation systems comprise a reduced protease concentration. In some embodiments, cell-free translation systems comprise modified tRNAs with re-assigned codons used to code for unnatural amino acids. In some embodiments, the synthetases described herein for the incorporation of unnatural amino acids are used in cell-free translation systems. In some embodiments, tRNAs are pre-loaded with unnatural amino acids using enzymatic or chemical methods before being added to a cell-free translation system. In some embodiments, components for a cell-free translation system are obtained from modified organisms, such as modified bacteria, yeast, or other organism.

In some embodiments, a cytokine (e.g., IL-2) polypeptide is generated as a circularly permuted form, either via an expression host system or through a cell-free system.

Production of Cytokine Polypeptide Comprising an Unnatural Amino Acid

An orthogonal or expanded genetic code can be used in the present disclosure, in which one or more specific codons present in the nucleic acid sequence of a cytokine (e.g., IL-2) polypeptide are allocated to encode the unnatural amino acid so that it can be genetically incorporated into the cytokine (e.g., IL-2) by using an orthogonal tRNA synthetase/tRNA pair. The orthogonal tRNA synthetase/tRNA pair is capable of charging a tRNA with an unnatural amino acid and is capable of incorporating that unnatural amino acid into the polypeptide chain in response to the codon.

In some instances, the codon is the codon amber, ochre, opal or a quadruplet codon. In some cases, the codon corresponds to the orthogonal tRNA which will be used to carry the unnatural amino acid. In some cases, the codon is amber. In other cases, the codon is an orthogonal codon.

In some instances, the codon is a quadruplet codon, which can be decoded by an orthogonal ribosome ribo-Q1. In some cases, the quadruplet codon is as illustrated in Neumann, et al., "Encoding multiple unnatural amino acids via evolution of a quadruplet-decoding ribosome," Nature, 464(7287): 441-444 (2010).

In some instances, a codon used in the present disclosure is a recoded codon, e.g., a synonymous codon or a rare codon that is replaced with alternative codon. In some cases, the recoded codon is as described in Napolitano, et al., "Emergent rules for codon choice elucidated by editing rare arginine codons in Escherichia coli," PNAS, 113(38): E5588-5597 (2016). In some cases, the recoded codon is as described in Ostrov et al., "Design, synthesis, and testing toward a 57-codon genome," Science 353(6301): 819-822 (2016).

In some instances, unnatural nucleic acids are utilized leading to incorporation of one or more unnatural amino acids into the cytokine (e.g., IL-2). Exemplary unnatural nucleic acids include, but are not limited to, uracil-5-yl, hypoxanthin-9-yl (I), 2-aminoadenin-9-yl, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Certain unnatural nucleic acids, such as 5-substituted pyrimidines, 6-azapyrimidines and N-2 substituted purines, N-6 substituted purines, O-6 substituted purines, 2-aminopropyladenine, 5-propynyluracil, 5-propynylcytosine, 5-methylcytosine, those that increase the stability of duplex formation, universal nucleic acids, hydrophobic nucleic acids, promiscuous nucleic acids, size-expanded nucleic acids, fluorinated nucleic acids, 5-substituted pyrimidines, 6-azapyrimidines and N-2, N-6 and 0-6 substituted purines, including 2-aminopropyladenine, 5-propynyluracil and 5-propynylcytosine. 5-methylcytosine (5-me-C), 5-hydroxymethyl cytosine, xanthine, hypoxanthine, 2-aminoadenine, 6-methyl, other alkyl derivatives of adenine and guanine, 2-propyl and other alkyl derivatives of adenine and guanine, 2-thiouracil, 2-thiothymine and 2-thiocytosine, 5-halouracil, 5-halocytosine, 5-propynyl (—C≡C—CH$_3$) uracil, 5-propynyl cytosine, other alkynyl derivatives of pyrimidine nucleic acids, 6-azo uracil, 6-azo cytosine, 6-azo thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl, other 5-substituted uracils and cytosines, 7-methylguanine, 7-methyladenine, 2-F-adenine, 2-amino-adenine, 8-azaguanine, 8-azaadenine, 7-deazaguanine, 7-deazaadenine, 3-deazaguanine, 3-deazaadenine, tricyclic pyrimidines, phenoxazine cytidine ([5,4-b][1,4]benzoxazin-2(3H)-one), phenothiazine cytidine (1H-pyrimido[5,4-b][1,4]benzothiazin-2(3H)-one), G-clamps, phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one), those in which the purine or pyrimidine base is replaced with other heterocycles, 7-deaza-adenine, 7-deazaguanosine, 2-aminopyridine, 2-pyridone, azacytosine, 5-bromocytosine, bromouracil, 5-chlorocytosine, chlorinated cytosine, cyclocytosine, cytosine arabinoside, 5-fluorocytosine, fluoropyrimidine, fluorouracil, 5,6-dihydrocytosine, 5-iodocytosine, hydroxyurea, iodouracil, 5-nitrocytosine, 5-bromouracil, 5-chlorouracil, 5-fluorouracil, and 5-iodouracil, 2-amino-adenine, 6-thio-guanine, 2-thio-thymine, 4-thio-thymine, 5-propynyl-uracil, 4-thiouracil, N4-ethylcytosine, 7-deazaguanine, 7-deaza-8-azaguanine, 5-hydroxycytosine, 2'-deoxyuridine, 2-amino-2'-deoxyadenosine, and those described in U.S. Pat. Nos. 3,687,808; 4,845,205; 4,910,300; 4,948,882; 5,093,232; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096; WO 99/62923; Kandimalla et al., (2001) Bioorg. Med. Chem. 9:807-813; The Concise Encyclopedia of Polymer Science and Engineering, Kroschwitz, J. I., Ed., John Wiley & Sons, 1990, 858-859; Englisch et al., Angewandte Chemie, International Edition, 1991, 30, 613; and Sanghvi, Chapter 15, Antisense Research and Applications, Crooke and Lebleu Eds., CRC Press, 1993, 273-288. Additional base modifications can be found, for example, in U.S. Pat. No. 3,687,808; Englisch et al., Angewandte Chemie, International Edition, 1991, 30, 613; and Sanghvi, Chapter 15, Antisense Research and Applications, pages 289-302, Crooke and Lebleu ed., CRC Press, 1993.

Unnatural nucleic acids comprising various heterocyclic bases and various sugar moieties (and sugar analogs) are available in the art, and the nucleic acids in some cases include one or several heterocyclic bases other than the principal five base components of naturally-occurring nucleic acids. For example, the heterocyclic base includes, in some cases, uracil-5-yl, cytosin-5-yl, adenin-7-yl, adenin-8-yl, guanin-7-yl, guanin-8-yl, 4-aminopyrrolo [2.3-d] pyrimidin-5-yl, 2-amino-4-oxopyrolo [2, 3-d] pyrimidin-5-yl, 2-amino-4-oxopyrrolo [2.3-d] pyrimidin-3-yl groups, where the purines are attached to the sugar moiety of the nucleic acid via the 9-position, the pyrimidines via the 1-position, the pyrrolopyrimidines via the 7-position and the pyrazolopyrimidines via the 1-position.

In some embodiments, nucleotide analogs are also modified at the phosphate moiety. Modified phosphate moieties include, but are not limited to, those with modification at the linkage between two nucleotides and contains, for example, a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides are through a 3'-5' linkage or a 2'-5' linkage, and the linkage contains inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

In some embodiments, unnatural nucleic acids include 2',3'-dideoxy-2',3'-didehydro-nucleosides (PCT/US2002/006460), 5'-substituted DNA and RNA derivatives (PCT/US2011/033961; Saha et al., J. Org Chem., 1995, 60, 788-789; Wang et al., Bioorganic & Medicinal Chemistry Letters, 1999, 9, 885-890; and Mikhailov et al., Nucleosides & Nucleotides, 1991, 10(1-3), 339-343; Leonid et al., 1995, 14(3-5), 901-905; and Eppacher et al., Helvetica Chimica Acta, 2004, 87, 3004-3020; PCT/JP2000/004720; PCT/JP2003/002342; PCT/JP2004/013216; PCT/JP2005/020435; PCT/JP2006/315479; PCT/JP2006/324484; PCT/JP2009/056718; PCT/JP2010/067560), or 5'-substituted monomers made as the monophosphate with modified bases (Wang et al., Nucleosides Nucleotides & Nucleic Acids, 2004, 23 (1 & 2), 317-337).

In some embodiments, unnatural nucleic acids include modifications at the 5'-position and the 2'-position of the sugar ring (PCT/US94/02993), such as 5'-CH$_2$-substituted 2'-O-protected nucleosides (Wu et al., Helvetica Chimica Acta, 2000, 83, 1127-1143 and Wu et al., Bioconjugate Chem. 1999, 10, 921-924). In some cases, unnatural nucleic acids include amide linked nucleoside dimers have been prepared for incorporation into oligonucleotides wherein the 3' linked nucleoside in the dimer (5' to 3') comprises a 2'-OCH$_3$ and a 5'-(S)—CH$_3$ (Mesmaeker et al., Synlett, 1997, 1287-1290). Unnatural nucleic acids can include 2'-substituted 5'-CH$_2$ (or O) modified nucleosides (PCT/US92/01020). Unnatural nucleic acids can include 5'-methylenephosphonate DNA and RNA monomers, and dimers (Bohringer et al., Tet. Lett., 1993, 34, 2723-2726; Collingwood et al., Synlett, 1995, 7, 703-705; and Hutter et al., Helvetica Chimica Acta, 2002, 85, 2777-2806). Unnatural nucleic acids can include 5'-phosphonate monomers having a 2'-substitution (US2006/0074035) and other modified 5'-phosphonate monomers (WO1997/35869). Unnatural nucleic acids can include 5'-modified methylenephosphonate monomers (EP614907 and EP629633). Unnatural nucleic acids can include analogs of 5' or 6'-phosphonate ribonucleosides comprising a hydroxyl group at the 5' and/or 6'-position (Chen et al., Phosphorus, Sulfur and Silicon, 2002, 777, 1783-1786; Jung et al., Bioorg. Med. Chem., 2000, 8, 2501-2509; Gallier et al., Eur. J. Org. Chem., 2007, 925-933; and Hampton et al., J. Med. Chem., 1976, 19(8), 1029-1033). Unnatural nucleic acids can include 5'-phosphonate deoxyribonucleoside monomers and dimers having a 5'-phosphate group (Nawrot et al., Oligonucleotides, 2006, 16(1), 68-82). Unnatural nucleic acids can include nucleosides having a 6'-phosphonate group wherein the 5' or/and 6'-position is unsubstituted or substituted with a thio-tert-butyl group (SC(CH$_3$)$_3$) (and analogs thereof); a methyleneamino group (CH$_2$NH$_2$) (and analogs thereof) or a cyano group (CN) (and analogs thereof) (Fairhurst et al., Synlett, 2001, 4, 467-472; Kappler et al., J. Med. Chem., 1986, 29, 1030-1038; Kappler et al., J. Med. Chem., 1982, 25, 1179-1184; Vrudhula et al., J. Med. Chem., 1987, 30, 888-894; Hampton et al., J. Med. Chem., 1976, 19, 1371-1377; Geze et al., J. Am. Chem. Soc, 1983, 105(26), 7638-7640; and Hampton et al., J. Am. Chem. Soc, 1973, 95(13), 4404-4414).

In some embodiments, unnatural nucleic acids also include modifications of the sugar moiety. In some cases, nucleic acids contain one or more nucleosides wherein the sugar group has been modified. Such sugar modified nucleosides may impart enhanced nuclease stability, increased binding affinity, or some other beneficial biological property. In certain embodiments, nucleic acids comprise a chemically modified ribofuranose ring moiety. Examples of chemically modified ribofuranose rings include, without limitation, addition of substituent groups (including 5' and/or 2' substituent groups; bridging of two ring atoms to form bicyclic nucleic acids (BNA); replacement of the ribosyl ring oxygen atom with S, N(R), or C(R$_1$)(R$_2$) (R═H, C$_1$-C$_{12}$ alkyl or a protecting group); and combinations thereof. Examples of chemically modified sugars can be found in WO2008/101157, US2005/0130923, and WO2007/134181.

In some instances, a modified nucleic acid comprises modified sugars or sugar analogs. Thus, in addition to ribose and deoxyribose, the sugar moiety can be pentose, deoxypentose, hexose, deoxyhexose, glucose, arabinose, xylose, lyxose, or a sugar "analog" cyclopentyl group. The sugar can be in a pyranosyl or furanosyl form. The sugar moiety may be the furanoside of ribose, deoxyribose, arabinose or 2'-O-alkylribose, and the sugar can be attached to the respective heterocyclic bases either in [alpha] or [beta] anomeric configuration. Sugar modifications include, but are not limited to, 2'-alkoxy-RNA analogs, 2'-amino-RNA analogs, 2'-fluoro-DNA, and 2'-alkoxy- or amino-RNA/DNA chimeras. For example, a sugar modification may include 2'-O-methyl-uridine or 2'-O-methyl-cytidine. Sugar modifications include 2'-O-alkyl-substituted deoxyribonucleosides and 2'-O-ethyleneglycol like ribonucleosides. The preparation of these sugars or sugar analogs and the respective "nucleosides" wherein such sugars or analogs are attached to a heterocyclic base (nucleic acid base) is known. Sugar modifications may also be made and combined with other modifications.

Modifications to the sugar moiety include natural modifications of the ribose and deoxy ribose as well as unnatural modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$, alkyl or C$_2$ to C$_{10}$ alkenyl and alkynyl. 2' sugar modifications also include but are not limited to —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$ONH$_2$, and —O(CH$_2$)$_n$ON[(CH$_2$)$_n$ CH$_3$)]$_2$, where n and m are from 1 to about 10.

Other modifications at the 2' position include but are not limited to: C$_1$ to C$_{10}$ lower alkyl, substituted lower alkyl, alkaryl, aralkyl, O-alkaryl, O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of the 5' terminal nucleotide. Modified sugars also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures and which detail and describe a range of base modifications, such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,700,920, each of which is herein incorporated by reference in its entirety.

Examples of nucleic acids having modified sugar moieties include, without limitation, nucleic acids comprising 5'-vinyl, 5'-methyl (R or S), 4'-S, 2'-F, 2'-OCH$_3$, and 2'-O(CH$_2$)$_2$OCH$_3$ substituent groups. The substituent at the 2' position can also be selected from allyl, amino, azido, thio, O-allyl, O—(C$_1$-C$_{10}$ alkyl), OCF$_3$, O(CH$_2$)$_2$SCH$_3$, O(CH$_2$)$_2$—O—N(R$_m$)(R$_n$), and O—CH$_2$—C(=O)—N(R$_m$)(R$_n$), where each R$_m$ and R$_n$ is, independently, H or substituted or unsubstituted C$_1$-C$_{10}$ alkyl.

In certain embodiments, nucleic acids described herein include one or more bicyclic nucleic acids. In certain such embodiments, the bicyclic nucleic acid comprises a bridge between the 4' and the 2' ribosyl ring atoms. In certain embodiments, nucleic acids provided herein include one or more bicyclic nucleic acids wherein the bridge comprises a 4' to 2' bicyclic nucleic acid. Examples of such 4' to 2' bicyclic nucleic acids include, but are not limited to, one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2', and analogs thereof (see, U.S. Pat. No. 7,399,845); 4'-C(CH$_3$)(CH$_3$)—O-2' and analogs thereof, (see WO2009/006478, WO2008/150729, US2004/0171570, U.S. Pat. No. 7,427,672, Chattopadhyaya et al., J. Org. Chem., 209, 74, 118-134, and WO2008/154401). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invens. Drugs, 2001, 2, 558-561; Braasch et al., Chem. Biol, 2001, 8, 1-7; Oram et al., Curr. Opinion Mol. Ther., 2001, 3, 239-243; U.S. Pat. Nos. 4,849,513; 5,015,733; 5,118,800; 5,118,802; 7,053,207; 6,268,490; 6,770,748; 6,794,499; 7,034,133; 6,525,191; 6,670,461; and 7,399,845; International Publication Nos. WO2004/106356, WO1994/14226, WO2005/021570, WO2007/090071, and WO2007/134181; U.S. Patent Publication Nos. US2004/0171570, US2007/0287831, and US2008/0039618; U.S. Provisional Application Nos. 60/989,574, 61/026,995, 61/026,998, 61/056,564, 61/086,231, 61/097,787, and 61/099,844; and International Applications Nos. PCT/US2008/064591, PCT US2008/066154, PCT US2008/068922, and PCT/DK98/00393.

In certain embodiments, nucleic acids comprise linked nucleic acids. Nucleic acids can be linked together using any inter nucleic acid linkage. The two main classes of inter nucleic acid linking groups are defined by the presence or absence of a phosphorus atom. Representative phosphorus containing inter nucleic acid linkages include, but are not limited to, phosphodiesters, phosphotriesters, methylphosphonates, phosphoramidate, and phosphorothioates (P=S). Representative non-phosphorus containing inter nucleic acid linking groups include, but not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N*-dimethylhydrazine (—CH$_2$—N(CH$_3$)—N(CH$_3$)). In certain embodiments, inter nucleic acids linkages having a chiral atom can be prepared as a racemic mixture, as separate enantiomers, e.g., alkylphosphonates and phosphorothioates. Unnatural nucleic acids can contain a single modification. Unnatural nucleic acids can contain multiple modifications within one of the moieties or between different moieties.

Backbone phosphate modifications to nucleic acid include, but are not limited to, methyl phosphonate, phosphorothioate, phosphoramidate (bridging or non-bridging), phosphotriester, phosphorodithioate, phosphodithioate, and boranophosphate, and may be used in any combination. Other non-phosphate linkages may also be used.

In some embodiments, backbone modifications (e.g., methylphosphonate, phosphorothioate, phosphoroamidate and phosphorodithioate internucleotide linkages) can confer immunomodulatory activity on the modified nucleic acid and/or enhance their stability in vivo.

In some instances, a phosphorous derivative (or modified phosphate group) is attached to the sugar or sugar analog moiety in and can be a monophosphate, diphosphate, triphosphate, alkylphosphonate, phosphorothioate, phosphorodithioate, phosphoramidate or the like. Exemplary polynucleotides containing modified phosphate linkages or non-phosphate linkages can be found in Peyrottes et al., 1996, Nucleic Acids Res. 24: 1841-1848; Chaturvedi et al., 1996, Nucleic Acids Res. 24:2318-2323; and Schultz et al., (1996) Nucleic Acids Res. 24:2966-2973; Matteucci, 1997, "Oligonucleotide Analogs: an Overview" in Oligonucleotides as Therapeutic Agents, (Chadwick and Cardew, ed.) John Wiley and Sons, New York, NY; Zon, 1993, "Oligonucleoside Phosphorothioates" in Protocols for Oligonucleotides and Analogs, Synthesis and Properties, Humana Press, pp. 165-190; Miller et al., 1971, JACS 93:6657-6665; Jager et al., 1988, Biochem. 27:7247-7246; Nelson et al., 1997, JOC 62:7278-7287; U.S. Pat. No. 5,453,496; and Micklefield, 2001, Curr. Med. Chem. 8: 1157-1179.

In some cases, backbone modification comprises replacing the phosphodiester linkage with an alternative moiety such as an anionic, neutral or cationic group. Examples of such modifications include: anionic internucleoside linkage; N3' to P5' phosphoramidate modification; boranophosphate DNA; prooligonucleotides; neutral internucleoside linkages such as methylphosphonates; amide linked DNA; methylene (methylimino) linkages; formacetal and thioformacetal linkages; backbones containing sulfonyl groups; morpholino oligos; peptide nucleic acids (PNA); and positively charged deoxyribonucleic guanidine (DNG) oligos (Micklefield, 2001, Current Medicinal Chemistry 8: 1157-1179). A modified nucleic acid may comprise a chimeric or mixed backbone comprising one or more modifications, e.g. a combination of phosphate linkages such as a combination of phosphodiester and phosphorothioate linkages.

Substitutes for the phosphate include, for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439. It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. See also Nielsen et al., Science, 1991, 254, 1497-1500. It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. KY. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EM5OJ, 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium l-di-O-hexadecyl-rac-glycero-S-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochem. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937). Numerous United States patents teach the preparation of such conjugates and include, but are not limited to U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some cases, the unnatural nucleic acids further form unnatural base pairs. Exemplary unnatural nucleotides capable of forming an unnatural DNA or RNA base pair (UBP) under conditions in vivo includes, but is not limited to, TPT3, dTPT3, 5SICS, d5SICS, NaM, dNaM, CNMO, dCNMO, and combinations thereof. Other examples of unnatural nucleotides capable of forming unnatural UBPs that may be used to prepare the IL-2 conjugates disclosed herein may be found in Dien et al., J Am Chem Soc., 2018, 140:16115-16123; Feldman et al., J Am Chem Soc, 2017, 139:11427-11433; Ledbetter et al., J Am Chem Soc., 2018, 140:758-765; Dhami et al., Nucleic Acids Res. 2014, 42:10235-10244; Malyshev et al., Nature, 2014, 509:385-388; Betz et al., J Am Chem Soc., 2013, 135:18637-18643; Lavergne et al., J Am Chem Soc. 2013, 135:5408-5419; and Malyshev et al. Proc Natl Acad Sci USA, 2012, 109:12005-12010. In some embodiments, unnatural nucleotides include:

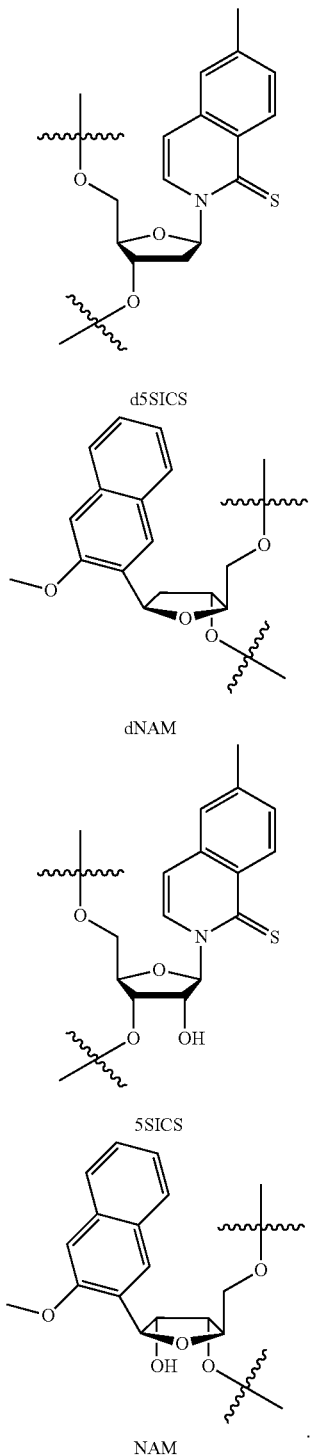

In some embodiments, the unnatural nucleotides that may be used to prepare the IL-2 conjugates disclosed herein may be derived from a compound of the formula

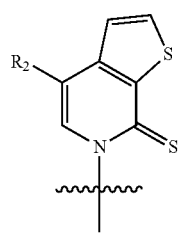

wherein R₂ is selected from the group consisting of hydrogen, alkyl, alkenyl, alkynyl, methoxy, methanethiol, methaneseleno, halogen, cyano, and azido; and the wavy line indicates a bond to a ribosyl or 2'-deoxyribosyl, wherein the 5'-hydroxy group of the ribosyl or 2'-deoxyribosyl moiety is in free form, or is optionally bonded to a monophosphate, a diphosphate, or a triphosphate group.

In some embodiments, the unnatural nucleotides that may be used to prepare the IL-2 conjugates disclosed herein may be derived from

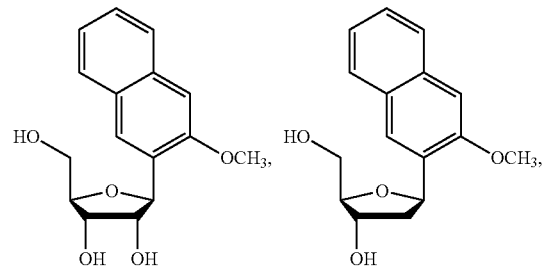

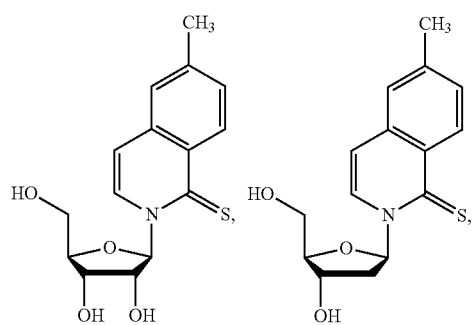

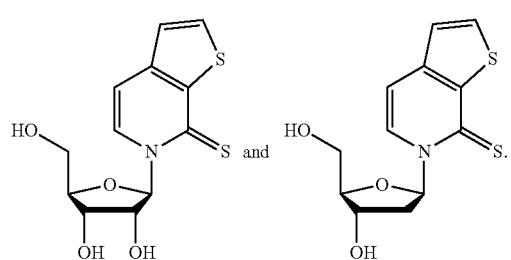

In some embodiments, the unnatural nucleotides that may be used to prepare the IL-2 conjugates disclosed herein include

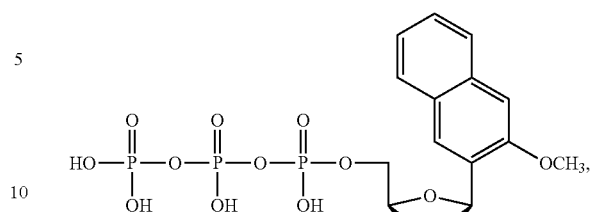

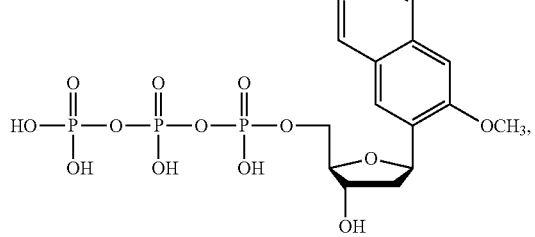

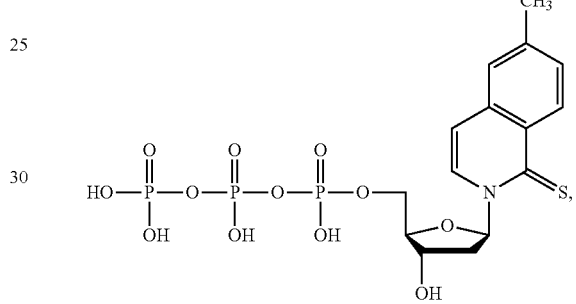

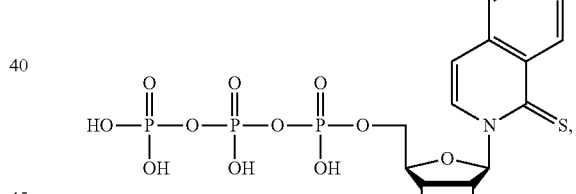

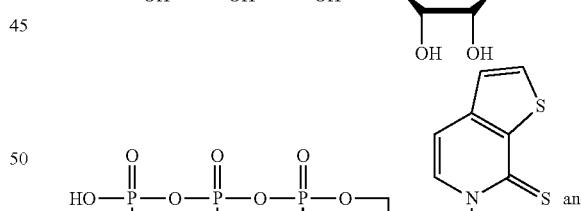

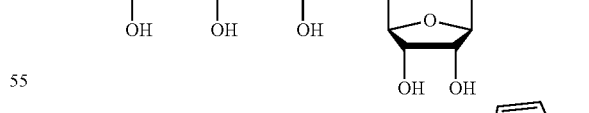

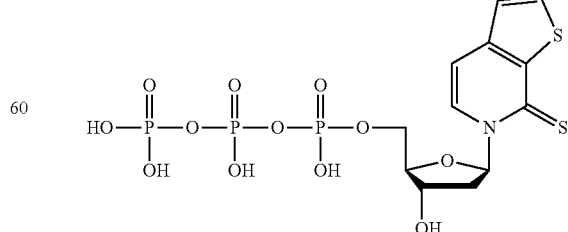

or salts thereof.

In some embodiments, an unnatural base pair generate an unnatural amino acid described in Dumas et al., "Designing logical codon reassignment—Expanding the chemistry in biology," *Chemical Science*, 6: 50-69 (2015).

In some embodiments, the unnatural amino acid is incorporated into the cytokine (e.g., the IL polypeptide) by a synthetic codon comprising an unnatural nucleic acid. In some instances, the unnatural amino acid is incorporated into the cytokine by an orthogonal, modified synthetase/tRNA pair. Such orthogonal pairs comprise an unnatural synthetase that is capable of charging the unnatural tRNA with the unnatural amino acid, while minimizing charging of a) other endogenous amino acids onto the unnatural tRNA and b) unnatural amino acids onto other endogenous tRNAs. Such orthogonal pairs comprise tRNAs that are capable of being charged by the unnatural synthetase, while avoiding being charged with a) other endogenous amino acids by endogenous synthetases. In some embodiments, such pairs are identified from various organisms, such as bacteria, yeast, Archaea, or human sources. In some embodiments, an orthogonal synthetase/tRNA pair comprises components from a single organism. In some embodiments, an orthogonal synthetase/tRNA pair comprises components from two different organisms. In some embodiments, an orthogonal synthetase/tRNA pair comprising components that prior to modification, promote translation of two different amino acids. In some embodiments, an orthogonal synthetase is a modified alanine synthetase. In some embodiments, an orthogonal synthetase is a modified arginine synthetase. In some embodiments, an orthogonal synthetase is a modified asparagine synthetase. In some embodiments, an orthogonal synthetase is a modified aspartic acid synthetase. In some embodiments, an orthogonal synthetase is a modified cysteine synthetase. In some embodiments, an orthogonal synthetase is a modified glutamine synthetase. In some embodiments, an orthogonal synthetase is a modified glutamic acid synthetase. In some embodiments, an orthogonal synthetase is a modified alanine glycine. In some embodiments, an orthogonal synthetase is a modified histidine synthetase. In some embodiments, an orthogonal synthetase is a modified leucine synthetase. In some embodiments, an orthogonal synthetase is a modified isoleucine synthetase. In some embodiments, an orthogonal synthetase is a modified lysine synthetase. In some embodiments, an orthogonal synthetase is a modified methionine synthetase. In some embodiments, an orthogonal synthetase is a modified phenylalanine synthetase. In some embodiments, an orthogonal synthetase is a modified proline synthetase. In some embodiments, an orthogonal synthetase is a modified serine synthetase. In some embodiments, an orthogonal synthetase is a modified threonine synthetase. In some embodiments, an orthogonal synthetase is a modified tryptophan synthetase. In some embodiments, an orthogonal synthetase is a modified tyrosine synthetase. In some embodiments, an orthogonal synthetase is a modified valine synthetase. In some embodiments, an orthogonal synthetase is a modified phosphoserine synthetase. In some embodiments, an orthogonal tRNA is a modified alanine tRNA. In some embodiments, an orthogonal tRNA is a modified arginine tRNA. In some embodiments, an orthogonal tRNA is a modified asparagine tRNA. In some embodiments, an orthogonal tRNA is a modified aspartic acid tRNA. In some embodiments, an orthogonal tRNA is a modified cysteine tRNA. In some embodiments, an orthogonal tRNA is a modified glutamine tRNA. In some embodiments, an orthogonal tRNA is a modified glutamic acid tRNA. In some embodiments, an orthogonal tRNA is a modified alanine glycine. In some embodiments, an orthogonal tRNA is a modified histidine tRNA. In some embodiments, an orthogonal tRNA is a modified leucine tRNA. In some embodiments, an orthogonal tRNA is a modified isoleucine tRNA. In some embodiments, an orthogonal tRNA is a modified lysine tRNA. In some embodiments, an orthogonal tRNA is a modified methionine tRNA. In some embodiments, an orthogonal tRNA is a modified phenylalanine tRNA. In some embodiments, an orthogonal tRNA is a modified proline tRNA. In some embodiments, an orthogonal tRNA is a modified serine tRNA. In some embodiments, an orthogonal tRNA is a modified threonine tRNA. In some embodiments, an orthogonal tRNA is a modified tryptophan tRNA. In some embodiments, an orthogonal tRNA is a modified tyrosine tRNA. In some embodiments, an orthogonal tRNA is a modified valine tRNA. In some embodiments, an orthogonal tRNA is a modified phosphoserine tRNA.

In some embodiments, the unnatural amino acid is incorporated into the cytokine (e.g., the IL polypeptide) by an aminoacyl (aaRS or RS)-tRNA synthetase-tRNA pair. Exemplary aaRS-tRNA pairs include, but are not limited to, *Methanococcus jannaschii* (Mj-Tyr) aaRS/tRNA pairs, *E. coli* TyrRS (Ec-Tyr)/*B. stearothennophilus* tRNA$_{CUA}$ pairs, *E. coli* LeuRS (Ec-Leu)/*B. stearothermophilus* tRNA$_{CUA}$ pairs, and pyrrolysyl-tRNA pairs. In some instances, the unnatural amino acid is incorporated into the cytokine (e.g., the IL polypeptide) by a Mj-TyrRS/tRNA pair. Exemplary UAAs that can be incorporated by a Mj-TyrRS/tRNA pair include, but are not limited to, para-substituted phenylalanine derivatives such as p-aminophenylalanine and p-methoxyphenylalanine; meta-substituted tyrosine derivatives such as 3-aminotyrosine, 3-nitrotyrosine, 3,4-dihydroxyphenylalanine, and 3-iodotyrosine; phenylselenocysteine; p-boronophenylalanine; and o-nitrobenzyltyrosine.

In some instances, the unnatural amino acid is incorporated into the cytokine (e.g., the IL polypeptide) by a Ec-Tyr/tRNA$_{CUA}$ or a Ec-Leu/tRNA$_{CUA}$ pair. Exemplary UAAs that can be incorporated by a Ec-Tyr/tRNA$_{CUA}$ or a Ec-Leu/tRNA$_{CUA}$ pair include, but are not limited to, phenylalanine derivatives containing benzophenone, ketone, iodide, or azide substituents; 0-propargyltyrosine; a-aminocaprylic acid, O-methyl tyrosine, 0-nitrobenzyl cysteine; and 3-(naphthalene-2-ylamino)-2-amino-propanoic acid.

In some instances, the unnatural amino acid is incorporated into the cytokine (e.g., the IL polypeptide) by a pyrrolysyl-tRNA pair. In some cases, the PylRS is obtained from an archaebacterial, e.g., from a methanogenic archaebacterial. In some cases, the PylRS is obtained from *Methanosarcina barkeri*, *Methanosarcina mazei*, or *Methanosarcina acetivorans*. Exemplary UAAs that can be incorporated by a pyrrolysyl-tRNA pair include, but are not limited to, amide and carbamate substituted lysines such as 2-amino-6-((R)-tetrahydrofuran-2-carboxamido)hexanoic acid, N-ε-D-prolyl-L-lysine, and N-ε-cyclopentyloxycarbonyl-L-lysine; N-ε-Acryloyl-L-lysine; N-ε-[(1-(6-nitrobenzo[d][1,3]dioxol-5-yl)ethoxy)carbonyl]-L-lysine; and N-ε-(1-methylcyclopro-2-enecarboxamido)lysine. In some embodiments, the IL-2 conjugates disclosed herein may be prepared by use of *M. mazei* tRNA which is selectively charged with a non-natural amino acid such as N6-((2-azidoethoxy)-carbonyl)-L-lysine (AzK) by the *M. barkeri* pyrrolysyl-tRNA synthetase (Mb PylRS). Other methods are known to those of ordinary skill in the art, such as those disclosed in Zhang et al., Nature 2017, 551(7682): 644-647.

In some instances, an unnatural amino acid is incorporated into a cytokine described herein (e.g., the IL polypeptide) by a synthetase disclosed in U.S. Pat. Nos. 9,988,619 and 9,938,516.

The host cell into which the constructs or vectors disclosed herein are introduced is cultured or maintained in a suitable medium such that the tRNA, the tRNA synthetase and the protein of interest are produced. The medium also comprises the unnatural amino acid(s) such that the protein of interest incorporates the unnatural amino acid(s). In some embodiments, a nucleoside triphosphate transporter (NTT) from bacteria, plant, or algae is also present in the host cell. In some embodiments, the IL-2 conjugates disclosed herein are prepared by use of a host cell that expresses a NTT. In some embodiments, the nucleotide nucleoside triphosphate transporter used in the host cell may be selected from TpNTT1, TpNTT2, TpNTT3, TpNTT4, TpNTT5, TpNTT6, TpNTT7, TpNTT8 (*T. pseudonana*), PtNTT1, PtNTT2, PtNTT3, PtNTT4, PtNTT5, PtNTT6 (*P. tricornutum*), GsNTT (*Galdieria sulphuraria*), AtNTT1, AtNTT2 (*Arabidopsis thaliana*), CtNTT1, CtNTT2 (*Chlamydia trachomatis*), PamNTT1, PamNTT2 (*Protochlamydia amoebophila*), CcNTT (*Caedibacter caryophilus*), RpNTT1 (*Rickettsia prowazekii*). In some embodiments, the NTT is selected from PtNTT1, PtNTT2, PtNTT3, PtNTT4, PtNTT5, and PtNTT6. In some embodiments, the NTT is PtNTT1. In some embodiments, the NTT is PtNTT2. In some embodiments, the NTT is PtNTT3. In some embodiments, the NTT is PtNTT4. In some embodiments, the NTT is PtNTT5. In some embodiments, the NTT is PtNTT6. Other NTTs that may be used are disclosed in Zhang et al., *Nature* 2017,551 (7682): 644-647; Malyshev et al. *Nature* 2014 (509(7500), 385-388; and Zhang et al. Proc Natl Acad Sci USA, 2017, 114:1317-1322.

The orthogonal tRNA synthetase/tRNA pair charges a tRNA with an unnatural amino acid and incorporates the unnatural amino acid into the polypeptide chain in response to the codon. Exemplary aaRS-tRNA pairs include, but are not limited to, *Methanococcus jannaschii* (Mj-Tyr) aaRS/tRNA pairs, *E. coli* TyrRS (Ec-Tyr)/*B. stearothermophilus* tRNA$_{CUA}$ pairs, *E. coli* LeuRS (Ec-Leu)/*B. stearothermophilus* tRNA$_{CUA}$ pairs, and pyrrolysyl-tRNA pairs. Other aaRS-tRNA pairs that may be used according to the present disclosure include those derived from *M. mazei* those described in Feldman et al., J Am Chem Soc., 2018 140: 1447-1454; and Zhang et al. Proc Natl Acad Sci USA, 2017, 114:1317-1322.

In some embodiments are provided methods of preparing the IL-2 conjugates disclosed herein in a cellular system that expresses a NTT and a tRNA synthetase. In some embodiments described herein, the NTT is selected from PtNTT1, PtNTT2, PtNTT3, PtNTT4, PtNTT5, and PtNTT6, and the tRNA synthetase is selected from *Methanococcus jannaschii*, *E. coli* TyrRS (Ec-Tyr)/*B. stearothermophilus*, and *M. mazei*. In some embodiments, the NTT is PtNTT1 and the tRNA synthetase is derived from *Methanococcus jannaschii*, *E. coli* TyrRS (Ec-Tyr)/*B. stearothermophilus*, or *M. mazei*. In some embodiments, the NTT is PtNTT2 and the tRNA synthetase is derived from *Methanococcus jannaschii*, *E. coli* TyrRS (Ec-Tyr)/*B. stearothermophilus*, or *M. mazei*. In some embodiments, the NTT is PtNTT3 and the tRNA synthetase is derived from *Methanococcus jannaschii*, *E. coli* TyrRS (Ec-Tyr)/*B. stearothermophilus*, or *M. mazei*. In some embodiments, the NTT is PtNTT3 and the tRNA synthetase is derived from *Methanococcus jannaschii*, *E. coli* TyrRS (Ec-Tyr)/*B. stearothermophilus*, or *M. mazei*. In some embodiments, the NTT is PtNTT4 and the tRNA synthetase is derived from *Methanococcus jannaschii*, *E. coli* TyrRS (Ec-Tyr)/*B. stearothermophilus*, or *M. mazei*. In some embodiments, the NTT is PtNTT5 and the tRNA synthetase is derived from *Methanococcus jannaschii*, *E. coli* TyrRS (Ec-Tyr)/*B. stearothennophilus*, or *M. mazei*. In some embodiments, the NTT is PtNTT6 and the tRNA synthetase is derived from *Methanococcus jannaschii*, *E. coli* TyrRS (Ec-Tyr)/*B. stearothermophilus*, or *M. mazei*.

In some embodiments, the IL-2 conjugates disclosed herein may be prepared in a cell, such as *E. coli*, comprising (a) nucleoside triphosphate transporter PtNTT2 (including a truncated variant in which the first 65 amino acid residues of the full-length protein are deleted), (b) a plasmid comprising a double-stranded oligonucleotide that encodes an IL-2 variant having a desired amino acid sequence and that contains a unnatural base pair comprising a first unnatural nucleotide and a second unnatural nucleotide to provide a codon at the desired position at which an unnatural amino acid, such as N6-((2-azidoethoxy)-carbonyl)-L-lysine (AzK), will be incorporated, (c) a plasmid encoding a tRNA derived from *M. mazei* and which comprises an unnatural nucleotide to provide a recognized anticodon (to the codon of the IL-2 variant) in place of its native sequence, and (d) a plasmid encoding a *M. barkeri* derived pyrrolysyl-tRNA synthetase (Mb PylRS), which may be the same plasmid that encodes the tRNA or a different plasmid. In some embodiments, the cell is further supplemented with deoxyribo triphosphates comprising one or more unnatural bases. In some embodiments, the cell is further supplemented with ribo triphosphates comprising one or more unnatural bases. In some embodiments, the cells is further supplemented with one or more unnatural amino acids, such as N6-((2-azidoethoxy)-carbonyl)-L-lysine (AzK). In some embodiments, the double-stranded oligonucleotide that encodes the amino acid sequence of the desired IL-2 variant contains a codon AXC at, for example, position 9, 16, 19, 20, 23, 26, 88, 91, 100, 109, 119, 123, 126, 127, or 131 of the sequence that encodes the protein having SEQ ID NO: 4 (IL-2_C125S), or at position 8, 15, 18, 19, 22, 25, 87, 90, 99, 108, 118, 122, 125, 126, or 130 of the sequence that encodes the protein having SEQ ID NO: 3 (aldesleukin), wherein X is an unnatural nucleotide. In some embodiments, the cell further comprises a plasmid, which may be the protein expression plasmid or another plasmid, that encodes an orthogonal tRNA gene from *M. mazei* that comprises an AXC-matching anticodon GYT in place of its native sequence, wherein Y is an unnatural nucleotide that is complementary and may be the same or different as the unnatural nucleotide in the codon. In some embodiments, the unnatural nucleotide in the codon is different than and complimentary to the unnatural nucleotide in the anti-codon. In some embodiments, the unnatural nucleotide in the codon is the same as the unnatural nucleotide in the anti-codon. In some embodiments, the first unnatural nucleotide and second unnatural nucleotide of the unnatural base pair in the double-stranded oligonucleotide may be derived from

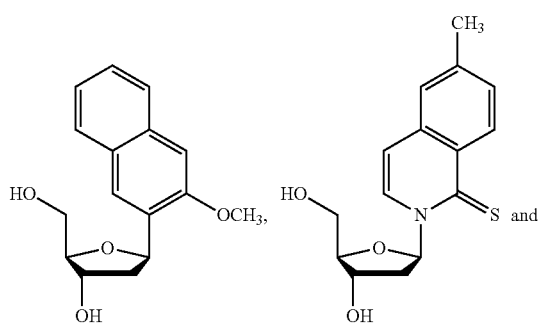

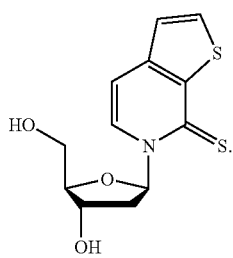

In some embodiments, the first unnatural nucleotide and second unnatural nucleotide of the unnatural base pair in the double-stranded oligonucleotide may be derived from

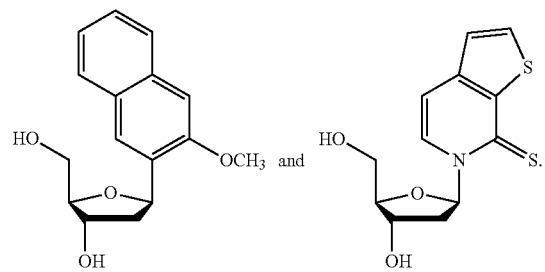

In some embodiments, the triphosphates of the first and second unnatural nucleotides include,

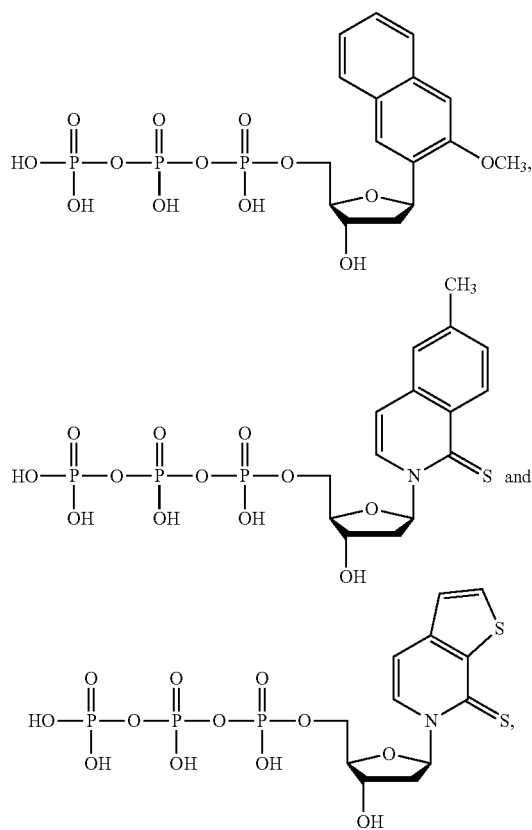

or salts thereof. In some embodiments, the triphosphates of the first and second unnatural nucleotides include,

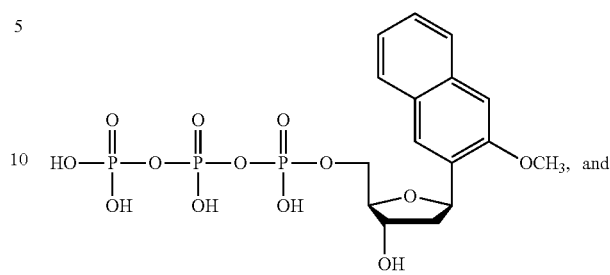

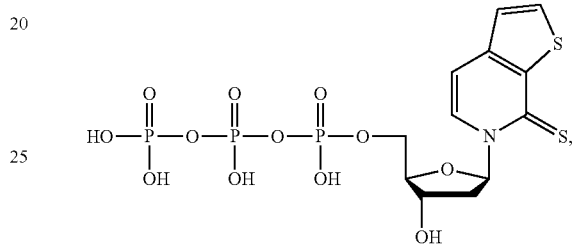

or salts thereof. In some embodiments, the mRNA derived the double-stranded oligonucleotide comprising a first unnatural nucleotide and a second unnatural nucleotide may comprise a codon comprising an unnatural nucleotide derived from

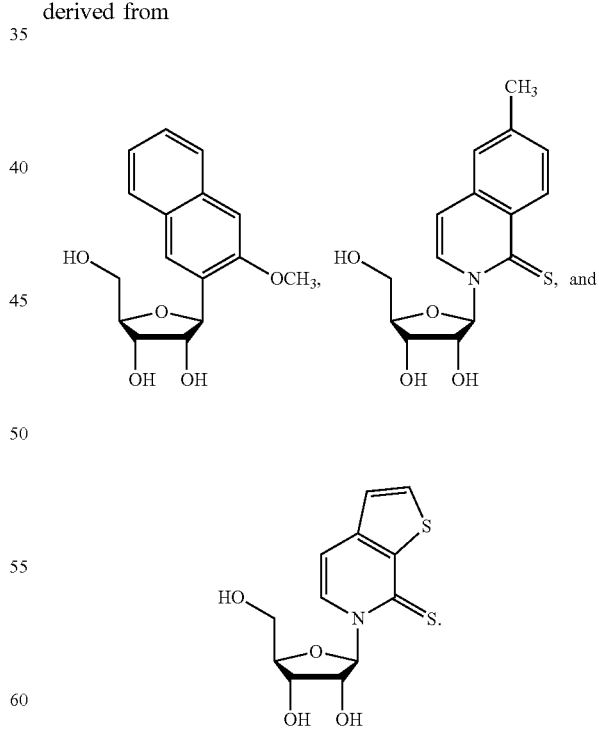

In some embodiments, the *M. mazei* tRNA may comprise an anti-codon comprising an unnatural nucleotide that recognizes the codon comprising the unnatural nucleotide of the mRNA. The anti-codon in the *M. mazei* tRNA may comprise an unnatural nucleotide derived from

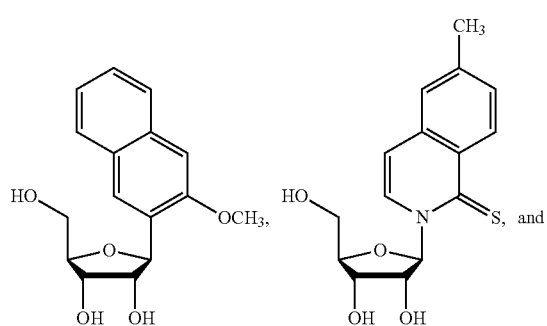

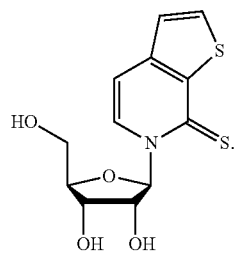

In some embodiments, the mRNA comprises an unnatural nucleotide derived from

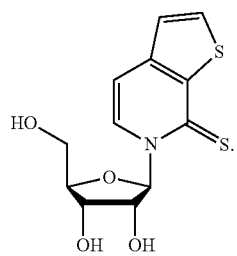

In some embodiments, the mRNA comprises an unnatural nucleotide derived from

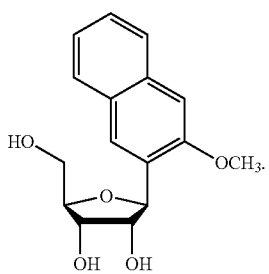

In some embodiments, the tRNA comprises an unnatural nucleotide derived from

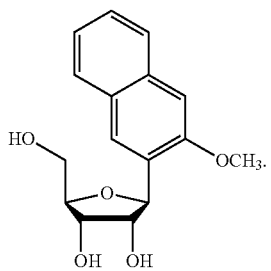

In some embodiments, the mRNA comprises an unnatural nucleotide derived from

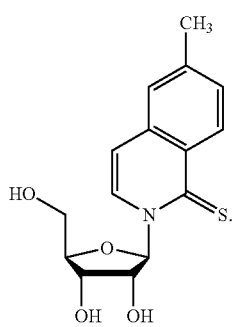

In some embodiments, the tRNA comprises an unnatural nucleotide derived from

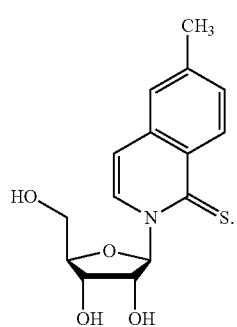

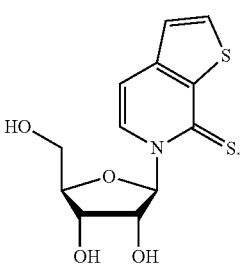

In some embodiments, the tRNA comprises an unnatural nucleotide derived from

In some embodiments, the mRNA comprises an unnatural nucleotide derived from

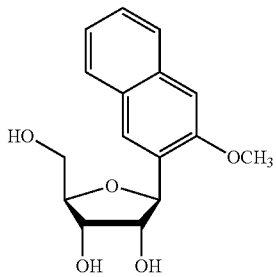

and the tRNA comprises an unnatural nucleotide derived from

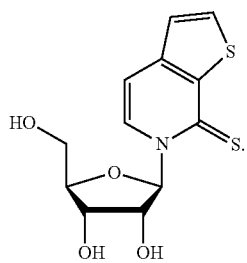

In some embodiments, the mRNA comprises an unnatural nucleotide derived from

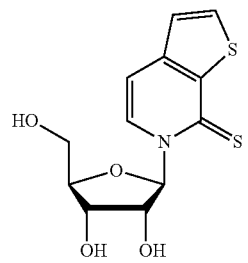

and the tRNA comprises an unnatural nucleotide derived from

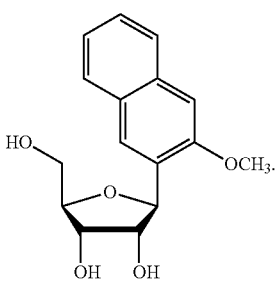

The host cell is cultured in a medium containing appropriate nutrients, and is supplemented with (a) the triphosphates of the deoxyribo nucleosides comprising one or more unnatural bases that are necessary for replication of the plasmid(s) encoding the cytokine gene harboring the codon, (b) the triphosphates of the ribo nucleosides comprising one or more unnatural bases necessary for transcription of (i) the mRNA corresponding to the coding sequence of the cytokine and containing the codon comprising one or more unnatural bases, and (ii) the tRNA containing the anticodon comprising one or more unnatural bases, and (c) the unnatural amino acid(s) to be incorporated in to the polypeptide sequence of the cytokine of interest. The host cells are then maintained under conditions which permit expression of the protein of interest.

The resulting protein comprising the one or more unnatural amino acids, Azk for example, that is expressed may be purified by methods known to those of ordinary skill in the art and may then be allowed to react with an alkyne, such as DBCO comprising a PEG chain having a desired average molecular weight as disclosed herein, under conditions known to those of ordinary skill in the art, to afford the IL-2 conjugates disclosed herein. Other methods are known to those of ordinary skill in the art, such as those disclosed in Zhang et al., Nature 2017, 551(7682): 644-647; WO 2015157555; WO 2015021432; WO 2016115168; WO 2017106767; WO 2017223528; WO 2019014262; WO 2019014267; WO 2019028419; and WO2019/028425.

Alternatively, a cytokine (e.g., IL-2) polypeptide comprising an unnatural amino acid(s) is prepared by introducing the nucleic acid constructs described herein comprising the tRNA and aminoacyl tRNA synthetase and comprising a nucleic acid sequence of interest with one or more in-frame orthogonal (stop) codons into a host cell. The host cell is cultured in a medium containing appropriate nutrients, is supplemented with (a) the triphosphates of the deoxyribo nucleosides comprising one or more unnatural bases required for replication of the plasmid(s) encoding the cytokine gene harboring the new codon and anticodon, (b) the triphosphates of the ribo nucleosides required for transcription of the mRNA corresponding to (i) the cytokine sequence containing the codon, and (ii) the orthogonal tRNA containing the anticodon, and (c) the unnatural amino acid(s). The host cells are then maintained under conditions which permit expression of the protein of interest. The unnatural amino acid(s) is incorporated into the polypeptide chain in response to the unnatural codon. For example, one or more unnatural amino acids are incorporated into the cytokine (e.g., IL-2) polypeptide. Alternatively, two or more unnatural amino acids may be incorporated into the cytokine (e.g., IL-2) polypeptide at two or more sites in the protein.

Once the cytokine (e.g., IL-2) polypeptide incorporating the unnatural amino acid(s) has been produced in the host cell it can be extracted therefrom by a variety of techniques known in the art, including enzymatic, chemical and/or osmotic lysis and physical disruption. The cytokine (e.g., IL-2) polypeptide can be purified by standard techniques known in the art such as preparative ion exchange chromatography, hydrophobic chromatography, affinity chromatography, or any other suitable technique known to those of ordinary skill in the art.

Suitable host cells may include bacterial cells (e.g., *E. coli*, BL21(DE3)), but most suitably host cells are eukaryotic cells, for example insect cells (e.g. *Drosophila* such as *Drosophila melanogaster*), yeast cells, nematodes (e.g. *C. elegans*), mice (e.g. *Mus musculus*), or mammalian cells (such as Chinese hamster ovary cells (CHO) or COS cells, human 293T cells, HeLa cells, NIH 3T3 cells, and mouse erythroleukemia (MEL) cells) or human cells or other eukaryotic cells. Other suitable host cells are known to those skilled in the art. Suitably, the host cell is a mammalian cell—such as a human cell or an insect cell. In some embodiments, the suitable host cells comprise *E. coli*.

Other suitable host cells which may be used generally in the embodiments of the invention are those mentioned in the examples section. Vector DNA can be introduced into host cells via conventional transformation or transfection techniques. As used herein, the terms "transformation" and "transfection" are intended to refer to a variety of well-recognized techniques for introducing a foreign nucleic acid molecule (e.g., DNA) into a host cell, including calcium phosphate or calcium chloride co-precipitation, DEAE-dextran-mediated transfection, lipofection, or electroporation. Suitable methods for transforming or transfecting host cells are well known in the art.

When creating cell lines, it is generally preferred that stable cell lines are prepared. For stable transfection of mammalian cells for example, it is known that, depending upon the expression vector and transfection technique used, only a small fraction of cells may integrate the foreign DNA into their genome. In order to identify and select these integrants, a gene that encodes a selectable marker (for example, for resistance to antibiotics) is generally introduced into the host cells along with the gene of interest. Preferred selectable markers include those that confer resistance to drugs, such as G418, hygromycin, or methotrexate. Nucleic acid molecules encoding a selectable marker can be introduced into a host cell on the same vector or can be introduced on a separate vector. Cells stably transfected with the introduced nucleic acid molecule can be identified by drug selection (for example, cells that have incorporated the selectable marker gene will survive, while the other cells die).

In one embodiment, the constructs described herein are integrated into the genome of the host cell. An advantage of stable integration is that the uniformity between individual cells or clones is achieved. Another advantage is that selection of the best producers may be carried out. Accordingly, it is desirable to create stable cell lines. In another embodiment, the constructs described herein are transfected into a host cell. An advantage of transfecting the constructs into the host cell is that protein yields may be maximized. In one aspect, there is described a cell comprising the nucleic acid construct or the vector described herein.

Pharmaceutical Compositions and Formulations

In some embodiments, the pharmaceutical composition and formulations described herein are administered to a subject by multiple administration routes, including but not limited to, parenteral, oral, buccal, rectal, sublingual, or transdermal administration routes. In some cases, parenteral administration comprises intravenous, subcutaneous, intramuscular, intracerebral, intranasal, intra-arterial, intra-articular, intradermal, intravitreal, intraosseous infusion, intraperitoneal, or intrathecal administration. In some instances, the pharmaceutical composition is formulated for local administration. In other instances, the pharmaceutical composition is formulated for systemic administration. In some embodiments, the pharmaceutical composition and formulations described herein are administered to a subject by intravenous, subcutaneous, and intramuscular administration. In some embodiments, the pharmaceutical composition and formulations described herein are administered to a subject by intravenous administration. In some embodiments, the pharmaceutical composition and formulations described herein are administered to a subject by administration. In some embodiments, the pharmaceutical composition and formulations described herein are administered to a subject by intramuscular administration.

In some embodiments, the pharmaceutical formulations include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations (e.g., nanoparticle formulations), and mixed immediate and controlled release formulations.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995), Hoover, John E., *Remington's Pharmaceutical Sciences*, Mack Publishing Co., Easton, Pennsylvania 1975, Liberman, H. A. and Lachman, L., Eds., *Pharmaceutical Dosage Forms*, Marcel Decker, New York, N.Y., 1980, and *Pharmaceutical Dosage Forms and* Drug Delivery Systems, Seventh Ed. (Lippincott Williams & Wilkins 1999).

In some cases, the pharmaceutical composition is formulated as an immunoliposome, which comprises a plurality of IL-2 conjugates bound either directly or indirectly to lipid bilayer of liposomes. Exemplary lipids include, but are not limited to, fatty acids; phospholipids; sterols such as cholesterols; sphingolipids such as sphingomyelin; glycosphingolipids such as gangliosides, globocides, and cerebrosides; surfactant amines such as stearyl, oleyl, and linoleyl amines. In some instances, the lipid comprises a cationic lipid. In some instances, the lipid comprises a phospholipid. Exemplary phospholipids include, but are not limited to, phosphatidic acid ("PA"), phosphatidylcholine ("PC"), phosphatidylglycerol ("PG"), phophatidylethanolamine ("PE"), phophatidylinositol ("PI"), and phosphatidylserine ("PS"), sphingomyelin (including brain sphingomyelin), lecithin, lysolecithin, lysophosphatidylethanolamine, cerebrosides, diarachidoylphosphatidylcholine ("DAPC"), didecanoyl-L-alpha-phosphatidylcholine ("DDPC"), dielaidoylphosphatidylcholine ("DEPC"), dilauroylphosphatidylcholine ("DLPC"), dilinoleoylphosphatidylcholine, dimyristoylphosphatidylcholine ("DMPC"), dioleoylphosphatidylcholine ("DOPC"), dipalmitoylphosphatidylcholine ("DPPC"), distearoylphosphatidylcholine ("DSPC"), 1-palmitoyl-2-oleoyl-phosphatidylcholine ("POPC"), diarachidoylphosphatidylglycerol ("DAPG"), didecanoyl-L-alpha-phosphatidylglycerol ("DDPG"), dielaidoylphosphatidylglycerol ("DEPG"), dilauroylphosphatidylglycerol ("DLPG"), dilinoleoylphosphatidylglycerol, dimyristoylphosphatidylglycerol ("DMPG"), dioleoylphosphatidylglycerol ("DOPG"), dipalmitoylphosphatidylglycerol ("DPPG"), distearoylphosphatidylglycerol ("DSPG"), 1-palmitoyl-2-oleoyl-phosphatidylglycerol ("POPG"), diarachidoylphosphatidylethanolamine ("DAPE"), didecanoyl-L-alpha-phosphatidylethanolamine ("DDPE"), dielaidoylphosphatidylethanolamine ("DEPE"), dilauroylphosphatidylethanolamine ("DLPE"), dilinoleoylphosphatidylethanolamine, dimyristoylphosphatidylethanolamine ("DMPE"), dioleoylphosphatidylethanolamine ("DOPE"), dipalmitoylphosphatidylethanolamine ("DPPE"), distearoylphosphatidylethanolamine ("DSPE"), 1-palmitoyl-2-oleoyl-phosphatidylethanolamine ("POPE"), diarachidoylphosphatidylinositol ("DAPI"), didecanoyl-L-alpha-phosphatidylinositol ("DDPI"), dielaidoylphosphatidylinositol ("DEPT"), dilauroylphosphatidylinositol ("DLPI"), dilinoleoylphosphatidylinositol, dimyristoylphosphatidylinositol ("DMPI"), dioleoylphosphatidylinositol ("DOPI"), dipalmitoylphosphatidylinositol ("DPPI"), distearoylphosphatidylinositol ("DSPI"), 1-palmitoyl-2-oleoyl-phosphatidylinositol ("POPI"), diarachidoylphosphatidylserine ("DAPS"), didecanoyl-L-alpha-phosphatidylserine ("DDPS"), dielaidoylphosphatidylserine ("DEPS"), dilauroylphosphatidylserine ("DLPS"), dilinoleoylphosphatidylserine, dimyristoylphosphatidylserine ("DMPS"), dioleoylphosphatidylserine ("DOPS"), dipalmitoylphosphatidylserine ("DPPS"), distearoylphosphatidylserine ("DSPS"), 1-palmitoyl-2-oleoyl-phosphatidylserine ("POPS"), diarachidoyl sphingomyelin, didecanoyl sphingomyelin, dielaidoyl sphingomyelin, dilauroyl sphingomyelin, dilinoleoyl sphingomyelin, dimyristoyl sphingomyelin, sphingomyelin, dioleoyl sphingomyelin, dipalmitoyl sphingomyelin, distearoyl sphingomyelin, and 1-palmitoyl-2-oleoyl-sphingomyelin.

In some instances, the pharmaceutical formulations further include pH adjusting agents or buffering agents which include acids such as acetic, boric, citric, lactic, phosphoric and hydrochloric acids, bases such as sodium hydroxide, sodium phosphate, sodium borate, sodium citrate, sodium acetate, sodium lactate and tris-hydroxymethylaminomethane, and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions, suitable salts include sodium chloride, potassium chloride, sodium thiosulfate, sodium bisulfite and ammonium sulfate.

In some embodiments, the pharmaceutical formulations include, but are not limited to, sugars like trehalose, sucrose, mannitol, maltose, glucose, or salts like potassium phosphate, sodium citrate, ammonium sulfate and/or other agents such as heparin to increase the solubility and in vivo stability of polypeptides.

In some instances, the pharmaceutical formulations further include diluent which are used to stabilize compounds because they can provide a more stable environment. Salts dissolved in buffered solutions (which also can provide pH control or maintenance) are utilized as diluents in the art, including, but not limited to a phosphate buffered saline solution. In certain instances, diluents increase bulk of the composition to facilitate compression or create sufficient bulk for homogenous blend for capsule filling. Such compounds can include e.g., lactose, starch, mannitol, sorbitol, dextrose, microcrystalline cellulose such as Avicel®, dibasic calcium phosphate, dicalcium phosphate dihydrate, tricalcium phosphate, calcium phosphate, anhydrous lactose, spray-dried lactose, pregelatinized starch, compressible sugar, such as Di-Pac® (Amstar), mannitol, hydroxypropylmethylcellulose, hydroxypropylmethylcellulose acetate stearate, sucrose-based diluents, confectioner's sugar, monobasic calcium sulfate monohydrate, calcium sulfate dihydrate, calcium lactate trihydrate, dextrates, hydrolyzed cereal solids, amylose, powdered cellulose, calcium carbonate, glycine, kaolin, mannitol, sodium chloride, inositol, bentonite, and the like. In some embodiments, the IL-2 conjugates disclosed herein may be used in pharmaceutical formulations comprising histidine, sorbitol, and polysorbate 80, or any combination that affords a stable formulation and can be administered to subjects in need thereof. In one embodiment, the IL-2 conjugates disclosed herein may be presented as a finished drug product in a suitable container, such as a vial, as follows: IL-2 conjugate (about 2 mg to about 10 mg); L-histidine (about 0.5 mg to about 2 mg); L-histidine hydrochloride (about 1 mg to about 2 mg); sorbitol (about 20 mg to about 80 mg); and polysorbate 80 (about 0.1 mg to about 0.2 mg); with a sufficient quantity of water for injection to provide a liquid formulation suitable for use in the disclosed methods.

In some cases, the pharmaceutical formulations include disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In some instances, the pharmaceutical formulations include filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil® starch such as corn starch, silicone oil, a surfactant, and the like.

Plasticizers include compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. Plasticizers can also function as dispersing agents or wetting agents.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like. Exemplary stabilizers include L-arginine hydrochloride, tromethamine, albumin (human), citric acid, benzyl alcohol, phenol, disodium biphosphate dehydrate, propylene glycol, metacresol or m-cresol, zinc acetate, polysorbate-20 or Tween® 20, or trometamol.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil, and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Therapeutic Regimens

In some embodiments, the pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does improve, upon the doctor's discretion the administration of the composition is given continuously, alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

In some embodiments, an effective amount of the IL-2 conjugate is administered to a subject in need thereof once per week, once every two weeks, once every three weeks, once every 4 weeks, once every 5 weeks, once every 6 weeks, once every 7 weeks, once every 8 weeks, once every 9 weeks, once every 10 weeks, once every 11 weeks, once every 12 weeks, once every 13 weeks, once every 14 weeks, once every 15 weeks, once every 16 weeks, once every 17 weeks, once every 18 weeks, once every 19 weeks, once every 20 weeks, once every 21 weeks, once every 22 weeks, once every 23 weeks, once every 24 weeks, once every 25 weeks, once every 26 weeks, once every 27 weeks, or once every 28 weeks. In some embodiments, an effective amount of the IL-2 conjugate is administered to a subject in need thereof once per week. In some embodiments, an effective amount of the IL-2 conjugate is administered to a subject in need thereof once every two weeks. In some embodiments, an effective amount of the IL-2 conjugate is administered to a subject in need thereof once every three weeks. In some embodiments, an effective amount of the IL-2 conjugate is administered to a subject in need thereof once every 4 weeks. In some embodiments, an effective amount of the IL-2 conjugate is administered to a subject in need thereof once every 5 weeks. In some embodiments, an effective amount of the IL-2 conjugate is administered to a subject in need thereof once every 6 weeks. In some embodiments, an effective amount of the IL-2 conjugate is administered to a subject in need thereof once every 7 weeks. In some embodiments, an effective amount of the IL-2 conjugate is administered to a subject in need thereof once every 8 weeks. In some embodiments, an effective amount of the IL-2 conjugate is administered to a subject in need thereof once every 9 weeks. In some embodiments, an effective amount of the IL-2 conjugate is administered to a subject in need thereof once every 10 weeks. In some embodiments, an effective amount of the IL-2 conjugate is administered to a subject in need thereof once every 11 weeks. In some embodiments, an effective amount of the IL-2 conjugate is administered to a subject in need thereof once every 12 weeks. In some embodiments, an effective amount of the IL-2 conjugate is administered to a subject in need thereof once every 13 weeks. In some embodiments, an effective amount of the IL-2 conjugate is administered to a subject in need thereof once every 14 weeks. In some embodiments, an effective amount of the IL-2 conjugate is administered to a subject in need thereof once every 15 weeks. In some embodiments, an effective amount of the IL-2 conjugate is administered to a subject in need thereof once every 16 weeks. In some embodiments, an effective amount of the IL-2 conjugate is administered to a subject in need thereof once every 17 weeks. In some embodiments, an effective amount of the IL-2 conjugate is administered to a subject in need thereof once every 18 weeks. In some embodiments, an effective amount of the IL-2 conjugate is administered to a subject in need thereof once every 19 weeks. In some embodiments, an effective amount of the IL-2 conjugate is administered to a subject in need thereof once every 20 weeks. In some embodiments, an effective amount of the IL-2 conjugate is administered to a subject in need thereof once every 21 weeks. In some embodiments, an effective amount of the IL-2 conjugate is administered to a subject in need thereof once every 22 weeks. In some embodiments, an effective amount of the IL-2 conjugate is administered to a subject in need thereof once every 23 weeks. In some embodiments, an effective amount of the IL-2 conjugate is administered to a subject in need thereof once every 24 weeks.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

In some embodiments, the methods include the dosing of an IL-2 conjugate to a subject in need thereof at a dose in the range from 1 µg of the IL-2 conjugate per kg of the subject's body weight to about 200 µg of the IL-2 conjugate per kg of the subject's body weight, or from about 2 µg of the IL-2 conjugate per kg of the subject's body weight to about 200 µg of the IL-2 conjugate per kg of the subject's body weight, or from about 4 µg of the IL-2 conjugate per kg of the subject's body weight to about 200 µg of the IL-2 conjugate per kg of the subject's body weight, or from about 6 µg of the IL-2 conjugate per kg of the subject's body weight to about 200 µg of the IL-2 conjugate per kg of the subject's body weight, or from about 8 µg of the IL-2 conjugate per kg of the subject's body weight to about 200 µg of the IL-2 conjugate per kg of the subject's body weight, or from about 10 µg of the IL-2 conjugate per kg of the subject's body weight to about 200 µg of the IL-2 conjugate per kg of the subject's body weight, or from about 12 µg of the IL-2 conjugate per kg of the subject's body weight to about 200 µg of the IL-2 conjugate per kg of the subject's body weight, or from about 14 µg of the IL-2 conjugate per kg of the subject's body weight to about 200 µg of the IL-2 conjugate per kg of the subject's body weight, or from about 16 µg of the IL-2 conjugate per kg of the subject's body weight to about 200 µg of the IL-2 conjugate per kg of the subject's body weight, or from about 18 µg of the IL-2 conjugate per kg of the subject's body weight to about 200 µg of the IL-2 conjugate per kg of the subject's body weight, or from about 20 µg of the IL-2 conjugate per kg of the subject's body weight to about 200 µg of the IL-2 conjugate per kg of the subject's body weight, or from about 22 µg of the IL-2 conjugate per kg of the subject's body weight to about 200 µg of the IL-2 conjugate per kg of the subject's body weight, or from about 24 µg of the IL-2 conjugate per kg of the subject's body weight to about 200 µg of the IL-2 conjugate per kg of the subject's body weight, or from about 26 µg of the IL-2 conjugate per kg of the subject's body weight to about 200 µg of the IL-2 conjugate per kg of the subject's body weight, or from about 28 µg of the IL-2 conjugate per kg of the subject's body weight to about 200 µg of the IL-2 conjugate per kg of the subject's body weight, or from about 32 µg of the IL-2 conjugate per kg of the subject's body weight to about 200 µg of the IL-2 conjugate per kg of the subject's body weight, or from about 34 µg of the IL-2 conjugate per kg of the subject's body weight to about 200 µg of the IL-2 conjugate per kg of the subject's body weight, or from about 36 µg of the IL-2 conjugate per kg of the subject's body weight to about 200 µg of the IL-2 conjugate per kg of the subject's body weight, or from about 40 µg of the IL-2 conjugate per kg of the subject's body weight to about 200 µg of the IL-2 conjugate per kg of the subject's body weight, or from about 45 µg of the IL-2 conjugate per kg of the subject's body weight to about 200 µg of the IL-2 conjugate per kg of the subject's body weight, or from about 50 µg of the IL-2 conjugate per kg of the subject's body weight to about 200 µg of the IL-2 conjugate per kg of the subject's body weight, or from about 55 µg of the IL-2 conjugate per kg of the subject's body weight to about 200 µg of the IL-2 conjugate per kg of the subject's body weight, or from about 60 µg of the IL-2 conjugate per kg of the subject's body weight to about 200 µg of the IL-2 conjugate per kg of the subject's body weight, or from about 65 µg of the IL-2 conjugate per kg of the subject's body weight to about 200 µg of the IL-2 conjugate per kg of the subject's body weight, or from about 70 µg of the IL-2 conjugate per kg of the subject's body weight to about 200 µg of the IL-2 conjugate per kg of the subject's body weight, or from about 75 µg of the IL-2 conjugate per kg of the subject's body weight to about 200 µg of the IL-2 conjugate per kg of the subject's body weight, or from about 80 µg of the IL-2 conjugate per kg of the subject's body weight to about 200 µg of the IL-2 conjugate per kg of the subject's body weight, or from about 85 µg of the IL-2 conjugate per kg of the subject's body weight to about 200 µg of the IL-2 conjugate per kg of the subject's body weight, or from about 90 µg of the IL-2 conjugate per kg of the subject's body weight to about 200 µg of the IL-2 conjugate per kg of the subject's body weight, or from about 95 µg of the IL-2 conjugate per kg of the subject's body weight to about 200 µg of the IL-2 conjugate per kg of the subject's body weight, or from about 100 µg of the IL-2 conjugate per kg of the subject's body weight to about 200 µg of the IL-2 conjugate per kg of the subject's body weight, or from about 110 µg of the IL-2 conjugate per kg of the subject's body weight to about 200 µg of the IL-2 conjugate per kg of the subject's body weight, or from about 120 µg of the IL-2 conjugate per kg of the subject's body weight to about 200 µg of the IL-2 conjugate per kg of the subject's body weight, or from about 130 µg of the IL-2 conjugate per kg of the subject's body weight to about 200 µg of the IL-2 conjugate per kg of the subject's body weight, or from about 140 µg of the IL-2 conjugate per kg of the subject's body weight to about 200 µg of the IL-2 conjugate per kg of the subject's body weight, or from about 150 µg of the IL-2 conjugate per kg of the subject's body weight to about 200 µg of the IL-2 conjugate per kg of the subject's body weight, or from about 160 µg of the IL-2 conjugate per kg of the subject's body weight to about 200 µg of the IL-2 conjugate per kg of the subject's body weight, or from about 170 µg of the IL-2 conjugate per kg of the subject's body weight to about 200 µg of the IL-2 conjugate per kg of the subject's body weight, or from about 180 µg of the IL-2 conjugate per kg of the subject's body weight to about 200 µg of the IL-2 conjugate per kg of the subject's body weight, or from about 190 µg of the IL-2 conjugate per kg of the subject's body weight to about 200 µg of the IL-2 conjugate per kg of the subject's body weight. The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner. In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

In some embodiments, the methods include the dosing of an IL-2 conjugate to a subject in need thereof at a dose of about 1 µg of the IL-2 conjugate per kg of the subject's body weight, or about 2 µg of the IL-2 conjugate per kg of the subject's body weight, about 4 µg of the IL-2 conjugate per kg of the subject's body weight, about 6 µg of the IL-2 conjugate per kg of the subject's body weight, about 8 µg of the IL-2 conjugate per kg of the subject's body weight, about 10 µg of the IL-2 conjugate per kg of the subject's body weight, about 12 µg of the IL-2 conjugate per kg of the subject's body weight, about 14 µg of the IL-2 conjugate per kg of the subject's body weight, about 16 µg of the IL-2 conjugate per kg of the subject's body weight, about 18 µg of the IL-2 conjugate per kg of the subject's body weight, about 20 µg of the IL-2 conjugate per kg of the subject's body weight, about 22 µg of the IL-2 conjugate per kg of the subject's body weight, about 24 µg of the IL-2 conjugate per kg of the subject's body weight, about 26 µg of the IL-2 conjugate per kg of the subject's body weight, about 28 µg of the IL-2 conjugate per kg of the subject's body weight, about 30 µg of the IL-2 conjugate per kg of the subject's body weight, about 32 µg of the IL-2 conjugate per kg of the subject's body weight, about 34 µg of the IL-2 conjugate per kg of the subject's body weight, about 36 µg of the IL-2 conjugate per kg of the subject's body weight, about 38 µg of the IL-2 conjugate per kg of the subject's body weight, about 40 µg of the IL-2 conjugate per kg of the subject's body weight, about 42 µg of the IL-2 conjugate per kg of the subject's body weight, about 44 µg of the IL-2 conjugate per kg of the subject's body weight, about 46 µg of the IL-2 conjugate per kg of the subject's body weight, about 48 µg of the IL-2 conjugate per kg of the subject's body weight, about 50 µg of the IL-2 conjugate per kg of the subject's body weight, about 55 µg of the IL-2 conjugate per kg of the subject's body weight, about 60 µg of the IL-2 conjugate per kg of the subject's body weight, about 65 µg of the IL-2 conjugate per kg of the subject's body weight, about 70 µg of the IL-2 conjugate per kg of the subject's body weight, about 75 µg of the IL-2 conjugate per kg of the subject's body weight, about 80 µg of the IL-2 conjugate per kg of the subject's body weight, about 85 µg of the IL-2 conjugate per kg of the subject's body weight, about 90 µg of the IL-2 conjugate per kg of the subject's body weight, about 95 µg of the IL-2 conjugate per kg of the subject's body weight, about 100 µg of the IL-2 conjugate per kg of the subject's body weight, about 110 µg of the IL-2 conjugate per kg of the subject's body weight, about 120 µg of the IL-2 conjugate per kg of the subject's body weight, about 130 µg of the IL-2 conjugate per kg of the subject's body weight, about 140 µg of the IL-2 conjugate per kg of the subject's body weight, about 150 µg of the IL-2 conjugate per kg of the subject's body weight, about 160 µg of the IL-2 conjugate per kg of the subject's body weight, about 170 µg of the IL-2 conjugate per kg of the subject's body weight, about 180 µg of the IL-2 conjugate per kg of the subject's body weight, about 190 µg of the IL-2 conjugate per kg of the subject's body weight, or about 200 µg of the IL-2 conjugate per kg of the subject's body weight. The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner. In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

The foregoing ranges are merely suggestive, as the number of variables in regard to an individual treatment regime is large, and considerable excursions from these recommended values are not uncommon. Such dosages are altered depending on a number of variables, not limited to the activity of the compound used, the disease or condition to be treated, the mode of administration, the requirements of the individual subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein, in certain embodiments, are kits and articles of manufacture for use with one or more methods and compositions described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

In some embodiments, the kits comprise articles of manufacture that are useful for developing adoptive cell therapies. In some embodiments, kits comprise one or more of the cytokine (e.g., IL-2) polypeptides or cytokine (e.g., IL-2) conjugates disclosed herein, and optionally one or more pharmaceutical excipients described herein to facilitate the delivery of cytokine (e.g., IL-2) polypeptides or cytokine (e.g., IL-2) conjugates. Such kits might optionally include one or more accessory components comprising inducers of T cell receptor signaling or modulation (e.g., checkpoint antibodies, CD3/CD28 antibodies, major histocompatibility complexes (MHC), and the like), or alternative cytokines or cytokine receptor agonists. Such kits further optionally include an identifying description or label or instructions relating to its use in the methods described herein. In some embodiments, kits comprise one or more polynucleic acid sequences encoding the IL-2 conjugates disclosed herein, an activator of a CD4+ helper cell, CD8+ effector naïve and memory cell, Natural Killer (NK) cell, or Natural killer T (NKT) cell and/or a pharmaceutical composition thereof.

Proliferative and Infectious Disease Kits and Articles of Manufacture

Disclosed herein, in some embodiments are kits comprising an isolated and modified interleukin 2 (IL-2) polypeptide comprising at least one unnatural amino acid at a position on the polypeptide that reduces binding between the modified IL-2 polypeptide and interleukin 2 receptor α (IL-2Rα) but retains significant binding with interleukin 2 βγ receptor (IL-2Rβγ) signaling complex to form an IL-2/IL-2Rβγ complex, wherein the reduced binding to IL-2Rα is compared to binding between a wild-type IL-2 polypeptide and IL-2Rα. In some embodiments, the reduction in binding to IL-2Rα comprises a decrease in binding affinity of about 30%, 40%, 50%, 60%, 70%, 80%, 90%, 95%, 99%, or 100% relative to a wild-type IL-2 polypeptide. In some embodiments, the reduction in binding to IL-2Rα comprises a decrease of 3-fold, 4-fold, 5-fold, 6-fold, 7-fold, 8-fold, 9-fold, 10-fold, or more relative to a wild-type IL-2 polypeptide.

Disclosed herein, in some embodiments are kits comprising isolated and modified interleukin 2 (IL-2) polypeptide comprising at least one unnatural amino acid, wherein the isolated and modified IL-2 polypeptide exhibits a first receptor signaling potency to an IL-2βγ signaling complex and a second receptor signaling potency to an IL-2αβγ signaling complex, and wherein a difference between the first receptor signaling potency and the second receptor signaling potency is less than 10-fold. In some embodiments, the difference in receptor signaling potency is less than 5-fold, less than 4-fold, less than 3-fold, less than 2-fold, or less than 1-fold.

Disclosed herein, in some embodiments, are kits comprising a polynucleotide sequence encoding a modified interleukin 2 (IL-2) polypeptide comprising at least one unnatural amino acid at a position on the polypeptide that reduces binding between the modified IL-2 polypeptide and interleukin 2 receptor α (IL-2Rα) but retains significant binding with interleukin 2 βγ receptor (IL-2Rβγ) signaling complex to form an IL-2/IL-2Rβγ complex, wherein the reduced binding to IL-2Rα is compared to binding between a wild-type IL-2 polypeptide and IL-2Rα.

Disclosed herein, in some embodiments, are kits comprising a polynucleotide sequence encoding a modified interleukin 2 (IL-2) polypeptide comprising at least one unnatural amino acid, wherein the isolated and modified IL-2 polypeptide exhibits a first receptor signaling potency to an IL-2βγ signaling complex and a second receptor signaling potency to an IL-2αβγ signaling complex, and wherein a difference between the first receptor signaling potency and the second receptor signaling potency is less than 10-fold. In some embodiments, the difference in receptor signaling potency is less than 5-fold, less than 4-fold, less than 3-fold, less than 2-fold, or less than 1-fold.

Autoimmune Kits and Articles of Manufacture

Disclosed herein, in some embodiments are kits comprising an isolated and modified interleukin 2 (IL-2) polypeptide comprising at least one unnatural amino acid at a position on the polypeptide reduces receptor signaling potency to interleukin 2 receptor βγ (IL-2Rβγ) or reduces a recruitment of an IL-2Rγ subunit to the IL-2/IL-2Rβ complex, but retains significant activation of interleukin 2 αβγ receptor (IL-2Rαβγ), wherein the reduced receptor signaling potency is compared to the receptor signaling potency between a wild-type IL-2 polypeptide and IL-2Rβγ, and wherein the recruitment is compared to a recruitment of an IL-2Rγ subunit by a wild-type IL-2 polypeptide.

Disclosed herein, in some embodiments are kits comprising an isolated and modified interleukin 2 (IL-2) polypeptide comprising at least one unnatural amino acid at a position on the polypeptide increases a recruitment of an IL-2Rα subunit to the IL-2 polypeptide leading to activation of interleukin 2 αβγ receptor (IL-2Rαβγ), wherein the increase in recruitment is compared to a recruitment of an IL-2Rα subunit by a wild-type IL-2 polypeptide.

In some embodiments, the modified IL-2 polypeptide with the decrease in receptor signaling potency to IL-2Rβγ is capable of expanding CD4+ T regulatory (Treg) cells. In some embodiments, the conjugating moiety impairs or blocks the receptor signaling potency of IL-2 with IL-2Rβγ, or reduces recruitment of the IL-2Rγ subunit to the IL-2/IL-2Rβ complex. In some embodiments, CD4+ Treg cell proliferation by the modified IL-2/IL-2Rαβγ complex is equivalent or greater to that of a wild-type IL-2 polypeptide. In some embodiments, the modified IL-2/IL-2Rαβγ complex induces proliferation of the CD4+ Treg cells to a population that is sufficient to modulate a disease course in an animal model. In some embodiments, the modified IL-2 polypeptide exhibits a first receptor signaling potency to IL-2Rβγ and a second receptor signaling potency to IL-2Rαβγ, wherein the first receptor signaling potency is at least 1-fold, 2-fold, 3-fold, 4-fold, 5-fold, 6-fold, 7-fold, 8-fold, 9-fold, 10-fold, 20-fold, 30-fold, 50-fold, 100-fold, 500-fold, 1000-fold, or lower than the second receptor signaling potency. In some embodiments, the first receptor signaling potency of the modified IL-2 polypeptide is lower than a receptor signaling potency of the wild-type IL-2 polypeptide to IL-2Rβγ. In some embodiments, the second receptor signaling potency of the modified IL-2 polypeptide is lower than a receptor signaling potency of the wild-type IL-2 polypeptide to IL-2Rαβγ. In some embodiments, the modified IL-2 polypeptide further provides an increase in a recruitment of an IL-2Rα subunit to the IL-2 polypeptide leading to activation of interleukin 2 αβγ receptor (IL-2Rαβγ), wherein the increase in recruitment is compared to a recruitment of an IL-2Rα subunit by a wild-type IL-2 polypeptide. In some embodiments, the modified IL-2 polypeptide further provides a decrease in a recruitment of an IL-2Rγ subunit to the IL-2/IL-2Rβ complex, wherein the reduced recruitment is compared to a recruitment of an IL-2Rβ subunit and/or IL-2Rγ subunit by a wild-type IL-2 polypeptide.

In some embodiments, the position of the at least one unnatural amino acid is selected from A1, P2, T3, S4, S5, S6, T7, K8, K9, Q11, L12, E15, H16, L18, L19, D20, Q22, M23, N26, G27, N29, N30, Y31, K32, K35, T37, M46, K47, K48, A50, T51, E52, K53, H55, Q57, E60, E67, N71, Q74, S75, K76, N77, F78, H79, R81, P82, R83, D84, S87, N88, N89, V91, I92, L94, E95, K97, G98, S99, E100, T101, T102, F103, M104, C105, E106, Y107, A108, D109, E110, T111, A112, T113, E116, N119, R120, T123, A125, Q126, S127, S130, T131, L132, and T133, wherein the numbering of the amino acid residues corresponds to SEQ ID NO: 1. In some embodiments, the position of the at least one unnatural amino acid is selected from K8, K9, Q11, L12, E15, H16, L18, L19, D20, Q22, M23, N26, R81, D84, S87, N88, V91, I92, L94, E95, E116, N119, R120, T123, A125, Q126, S127, S130, T131, L132, and T133, wherein the numbering of the amino acid residues corresponds to SEQ ID NO: 1. In some embodiments, the position of the at least one unnatural amino acid is selected from A1, P2, T3, S4, S5, S6, T7, G27, N29, N30, Y31, K32, K35, T37, M46, K47, K48, A50, T51, E52, K53, H55, Q57, E60, E67, N71, Q74, S75, K76, N77, F78, H79, P82, R83, N89, K97, G98, S99, E100, T101, T102, F103, M104, C105, E106, Y107, A108, D109, E110, T111, A112, and T113, wherein the numbering of the amino acid residues corresponds to SEQ ID NO: 1. In some embodiments, the position of the at least one unnatural amino acid is selected from K8, K9, L12, E15, H16, L19, D20, Q22, M23, N26, D84, N88, E95, and Q126, wherein the numbering of the amino acid residues corresponds to SEQ ID NO: 1. In some embodiments, the position of the at least one unnatural amino acid is selected from K8, K9, and H16, wherein the numbering of the amino acid residues corresponds to SEQ ID NO: 1. In some embodiments, the position of the at least one unnatural amino acid is selected from Q22, N26, N88, and Q126, wherein the numbering of the amino acid residues corresponds to SEQ ID NO: 1. In some embodiments, the position of the at least one unnatural amino acid is selected from E15, D20, D84, and E95, wherein the numbering of the amino acid residues corresponds to SEQ ID NO: 1. In some embodiments, the position of the at least one unnatural amino acid is selected from L12, L19, and M23, wherein the numbering of the amino acid residues corresponds to SEQ ID NO: 1. In some embodiments, the position of the at least one unnatural amino acid is selected from Q22 and N26, wherein the numbering of the amino acid residues corresponds to SEQ ID NO: 1.

Kits and Articles of Manufacture Generally

In some embodiments, the at least one unnatural amino acid: is a lysine analogue; comprises an aromatic side chain; comprises an azido group; comprises an alkyne group; or comprises an aldehyde or ketone group. In some embodiments, the at least one unnatural amino acid does not comprise an aromatic side chain. In some embodiments, the at least one unnatural amino acid comprises N6-(2-azidoethoxy)-carbonyl-L-lysine (AzK; the chemical structure of which is shown as compound 90 in FIG. 3C), N6-(propargyloxy)-carbonyl)-L-lysine (PraK; the chemical structure of which is shown as compound 112 in FIG. 3C), BCN-L-lysine, norbornene lysine, TCO-lysine, methyltetrazine lysine, allyloxycarbonyllysine, 2-amino-8-oxononanoic acid, 2-amino-8-oxooctanoic acid, p-acetyl-L-phenylalanine, p-azidomethyl-L-phenylalanine (pAMF), p-iodo-L-phenylalanine, m-acetylphenylalanine, 2-amino-8-oxononanoic acid, p-propargyloxyphenylalanine, p-propargyl-phenylalanine, 3-methyl-phenylalanine, L-Dopa, fluorinated phenylalanine, isopropyl-L-phenylalanine, p-azido-L-phenylalanine, p-acyl-L-phenylalanine, p-benzoyl-L-phenylalanine, p-bromophenylalanine, p-amino-L-phenylalanine, isopropyl-L-phenylalanine, O-allyltyrosine, O-methyl-L-tyrosine, O-4-allyl-L-tyrosine, 4-propyl-L-tyrosine, phosphonotyrosine, tri-O-acetyl-GlcNAcp-serine, L-phosphoserine, phosphonoserine, L-3-(2-naphthyl)alanine, 2-amino-3-((2-((3-(benzyloxy)-3-oxopropyl)amino)ethyl)selanyl)propanoic acid, 2-amino-3-(phenylselanyl)propanoic, or selenocysteine. In some embodiments, the at least one unnatural amino acid comprises N6-(2-azidoethoxy)-carbonyl-L-lysine (AzK; the chemical structure of which is shown as compound 90 in FIG. 3C) or N6-(propargyloxy)-carbonyl)-L-lysine (PraK; the chemical structure of which is shown as compound 112 in FIG. 3C). In some embodiments, the at least one unnatural amino acid comprises N6-(2-azidoethoxy)-carbonyl-L-lysine (AzK; the chemical structure of which is shown as compound 90 in FIG. 3C). In some embodiments, the at least one unnatural amino acid comprises N6-(propargyloxy)-carbonyl)-L-lysine (PraK; the chemical structure of which is shown as compound 112 in FIG. 3C).

In some embodiments, the at least one unnatural amino acid comprises an alkyne that is allowed to react with a conjugating moiety that comprises a water-soluble polymer comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule In some embodiments, the modified IL-2 polypeptide comprises a conjugating moiety. In some embodiments, the conjugating moiety comprises a water-soluble polymer, a lipid, a protein, and/or a peptide. In some embodiments, the water-soluble polymer comprises polyethylene glycol (PEG), poly(propylene glycol) (PPG), copolymers of ethylene glycol and propylene glycol, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazolines (POZ), poly(N-acryloylmorpholine), or a combination thereof. In some embodiments, the water-soluble polymer comprises a PEG molecule.

In some embodiments, the molecular weight of the PEG determines, at least in part, the in vivo plasma half-life of the modified IL-2 polypeptide. In some instances, the conjugating moiety comprises a PEG molecule that corresponds with a longer in vivo plasma half-life of the modified IL-2 polypeptide, as compared to the in vivo plasma half-life of a PEG that is smaller than the conjugating moiety. In some instances, the conjugating moiety comprises a PEG molecule that corresponds with a shorter in vivo plasma half-life of the modified IL-2 polypeptide, as compared to the in vivo plasma half-life of a PEG that is larger than the conjugating moiety.

In some embodiments, the molecular weight of the PEG does not affect, or has minimal effect, on the receptor signaling potency to the IL-2βγ or IL-2αβγ signaling complexes. In some embodiments, the molecular weight of the PEG does not affect, or has minimal effect, on the desired reduced binding to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2/IL-2Rβγ complex, wherein the reduced binding to IL-2Rα is compared to binding between a wild-type IL-2 polypeptide and IL-2Rα.

In some embodiments, the PEG molecule is a linear PEG. In some embodiments, wherein the PEG molecule is a branched PEG. In some embodiments, the PEG comprises between about 2,000-50,000 Daltons (Da). In some embodiments, the PEG has a molecular weight comprising about 5,000 Da, 10,000 Da, 15,000 Da, 20,000 Da, 25,000 Da, 30,000 Da, 35,000 Da, 40,000 Da, 45,000 Da, or 50,000 Da. In some instances, the PEG is 5,000 Da. In some instances, the PEG is 10,000 Da. In some instances, the PEG is 15,000 Da. In some instances, the PEG is 20,000 Da. In some instances, the PEG is 25,000 Da. In some instances, the PEG is 30,000 Da. In some instances, the PEG is 35,000 Da. In some instances, the PEG is 40,000 Da. In some instances, the PEG is 45,000 Da. In some instances, the PEG is 50,000 Da.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include one or more movie IL-2 polypeptides comprising a A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, or T133 with residue positions corresponding with 2, 3, 4, 5, 6, 7, 8, 9, 11, 12, 15, 16, 18, 19, 20, 22, 23, 26, 27, 29, 30, 31, 32, 35, 37, 46, 47, 48, 50, 51, 52, 53, 55, 57, 60, 67, 71, 74, 75, 76, 77, 78, 79, 81, 82, 83, 84, 87, 88, 89, 91, 92, 94, 95, 97, 98, 99, 100, 101, 102, 103, 104, 105, 106, 107, 108, 109, 109 and 88, 110, 111, 112, 113, 116, 119, 120, 123, 125, 126, 127, 130, 131, 132, and 133 as set forth in SEQ ID NO: 1. In some embodiments, the modified IL-2 polypeptide comprising the T37 with residue positions correspond to the positions 9, 11, 12, 15, 16, 18, 19, 20, 22, 23, 26, 27, 29, 53, 55, 57, 60, 67, 71, 74, 75, 76, 99, 100, 101, 102, 10 116, 119, 120, 123, 125, 131, 132, and 133 as set forth in SEQ ID NO: 1, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue K8 corresponding to position 8 of SEQ ID NO: 3, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue H15 corresponding to position 15 of SEQ ID NO: 3, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue V90 corresponding to position 90 of SEQ ID NO: 3, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue D108 in the N87R variant corresponding to positions 108 and 87 of SEQ ID NO: 3, comprises a conjugating moiety comprising a PEG having a molecular weight of about 2,000-50,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue S124 corresponding to position 124 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα

In some embodiments, the modified IL-2 polypeptide comprising a mutation at residue S129 corresponding to position 129 of SEQ ID NO: 3, comprises a conjugating moiety comprising a PEG having a molecular weight of about 2,000-60,000 Da. In some embodiments, the molecular weight comprises 5,000 Da. In some embodiments, the molecular weight comprises 10,000 Da. In some embodiments, the molecular weight comprises 15,000 Da. In some embodiments, the molecular weight comprises 20,000 Da. In some embodiments, the molecular weight comprises 25,000 Da. In some embodiments, the molecular weight comprises 30,000 Da. In some embodiments, the molecular weight comprises 35,000 Da. In some embodiments, the molecular weight comprises 40,000 Da. In some embodiments, the molecular weight comprises 45,000 Da. In some embodiments, the molecular weight comprises 50,000 Da. In some embodiments, the molecular weight comprises 55,000 Da. In some embodiments, the molecular weight comprises 60,000 Da. In some embodiments, the molecular weight of the PEG determines, at least in part, the in vivo plasma half-life of the modified IL-2 polypeptide. In some instances, the PEG corresponds with a longer in vivo plasma half-life of the modified IL-2 polypeptide, as compared to the in vivo plasma half-life of a smaller PEG. In some instances, the PEG corresponds with a shorter in vivo plasma half-life of the modified IL-2 polypeptide, as compared to the in vivo plasma half-life of a larger PEG. In some embodiments, the molecular weight of the PEG does not affect, or has minimal effect, on the receptor signaling potency of the modified IL-2 polypeptide to the IL-2βγ or IL-2αβγ signaling complexes. In some embodiments, the molecular weight of the PEG does not affect, or has minimal effect, on the desired reduced binding of the modified IL-2 polypeptide to IL-2Rα or the maintained binding with IL-2Rβγ signaling complex, wherein the reduced binding to IL-2Rα is compared to binding between a wild-type IL-2 polypeptide and IL-2Rα. In some embodiments, the molecular weight of the PEG does not affect the formation of the modified IL-2polypeptide/IL-2Rβγ complex, wherein the reduced binding to IL-2Rα is compared to binding between a wild-type IL-2 polypeptide and IL-2Rα

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself, a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

In certain embodiments, the pharmaceutical compositions are presented in a pack or dispenser device which contains one or more unit dosage forms containing a compound provided herein. The pack, for example, contains metal or plastic foil, such as a blister pack. In one embodiment, the pack or dispenser device is accompanied by instructions for administration. In one embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for drugs, or the approved product insert. In one embodiment, compositions containing a compound provided herein formulated in a compatible pharmaceutical carrier are also prepared, placed in an appropriate container, and labeled for treatment of an indicated condition.

Certain Terminologies

Unless defined otherwise, all technical and scientific terms used herein have the same meaning as is commonly understood by one of skill in the art to which the claimed subject matter belongs. It is to be understood that the detailed description are exemplary and explanatory only and are not restrictive of any subject matter claimed. In this application, the use of the singular includes the plural unless specifically stated otherwise. It must be noted that, as used in the specification, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error, such as for example, within 15%, 10%, or 5%.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly or a hospice worker).

As used herein, the term "significant" or "significantly" in reference to binding affinity means a change in the binding affinity of the cytokine (e.g., IL-2 polypeptide) sufficient to impact binding of the cytokine (e.g., IL-2 polypeptide) to a target receptor. In some instances, the term refers to a change of at least 10%, 20%, 30%, 40%, 50%, 60%, 70%, 80%, 90%, 95%, or more. In some instances, the term means a change of at least 2-fold, 3-fold, 4-fold, 5-fold, 6-fold, 7-fold, 8-fold, 9-fold, 10-fold, 50-fold, 100-fold, 500-fold, 1000-fold, or more.

In some instances, the term "significant" or "significantly" in reference to activation of one or more cell populations via a cytokine signaling complex means a change sufficient to activate the cell population. In some cases, the change to activate the cell population is measured as a receptor signaling potency. In such cases, an EC50 value may be provided. In other cases, an ED50 value may be provided. In additional cases, a concentration or dosage of the cytokine may be provided.

As used herein, the term "potency" refers to the amount of a cytokine (e.g., IL-2 polypeptide) required to produce a target effect. In some instances, the term "potency" refers to the amount of cytokine (e.g., IL-2 polypeptide) required to activate a target cytokine receptor (e.g., IL-2 receptor). In other instances, the term "potency" refers to the amount of cytokine (e.g., IL-2 polypeptide) required to activate a target cell population. In some cases, potency is measured as ED50 (Effective Dose 50), or the dose required to produce 50% of a maximal effect. In other cases, potency is measured as EC50 (Effective Concentration 50), or the dose required to produce the target effect in 50% of the population.

As used herein, an "IL-2 conjugate" is an IL-2 polypeptide attached (such as through a linker) to a conjugating moiety, e.g., comprising a PEG group; the IL-2 conjugate may be but is not necessarily in the form of a pharmaceutically acceptable salt, solvate, or hydrate. As described in detail elsewhere herein, the IL-2 polypeptide may comprise an unnatural amino acid, which can serve as the site of attachment to the conjugating moiety.

Numbered Embodiments

The present disclosure includes the following non-limiting numbered embodiments:

Embodiment 1. An IL-2 conjugate comprising the amino acid sequence of SEQ ID NO: 3 in which at least one amino acid residue in the IL-2 conjugate is replaced by the structure of Formula (I):

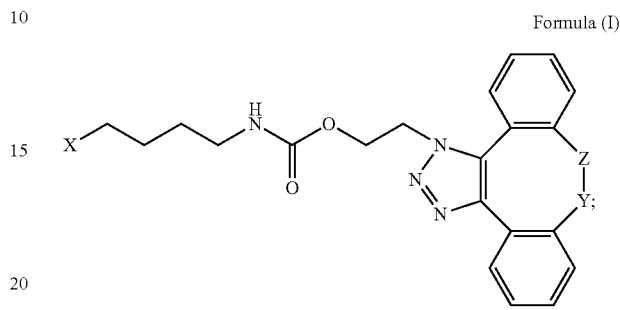

Formula (I)

wherein:

Z is CH$_2$ and Y is

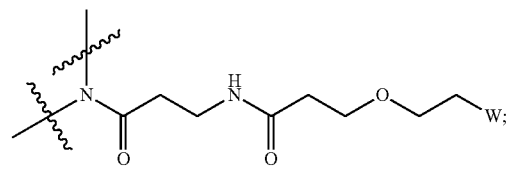

Y is CH$_2$ and Z is

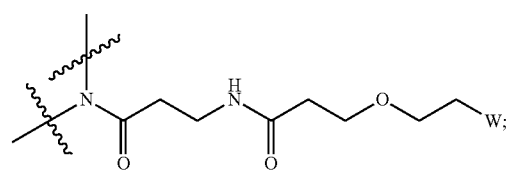

Z is CH$_2$ and Y is or

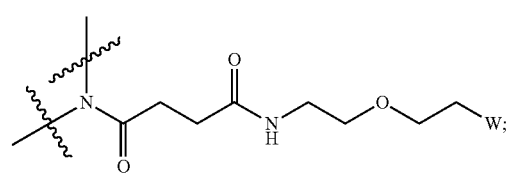

Y is CH$_2$ and Z is

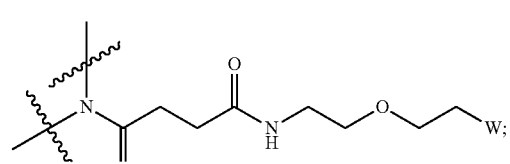

W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and X has the structure:

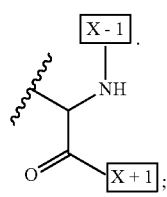

or a pharmaceutically acceptable salt, solvate, or hydrate thereof.

Embodiment 1.1. An IL-2 conjugate comprising the amino acid sequence of SEQ ID NO: 3 in which at least one amino acid residue in the IL-2 conjugate is replaced by the structure of Formula (I):

Formula (I)

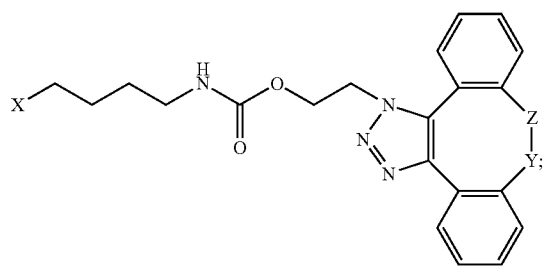

wherein:

Z is $CH_2$ and Y is

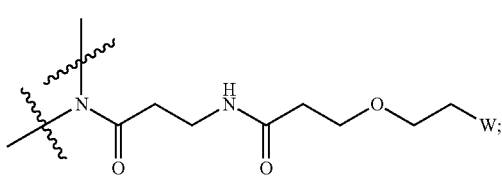

Y is $CH_2$ and Z is

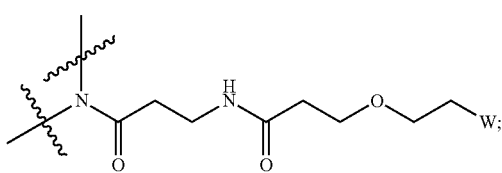

Z is $CH_2$ and Y is or

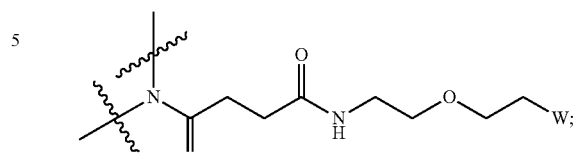

Y is $CH_2$ and Z is

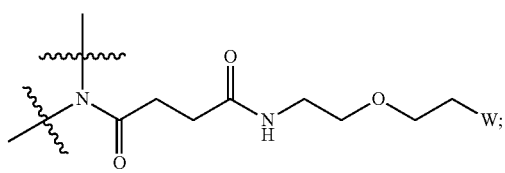

W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and X has the structure:

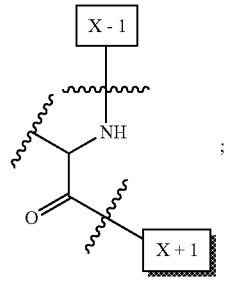

X−1 indicates the point of attachment to the preceding amino acid residue; and

X+1 indicates the point of attachment to the following amino acid residue.

Embodiment 2. An IL-2 conjugate comprising the amino acid sequence of SEQ ID NO: 4 in which at least one amino acid residue in the IL-2 conjugate is replaced by the structure of Formula (I):

Formula (I)

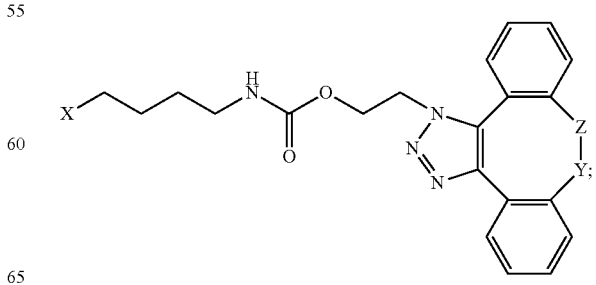

wherein:
Z is CH$_2$ and Y is

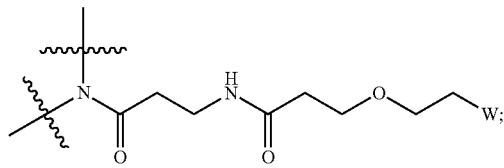

Y is CH$_2$ and Z is

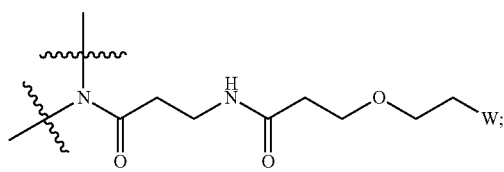

Z is CH$_2$ and Y is or

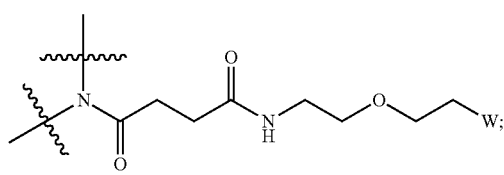

Y is CH$_2$ and Z is

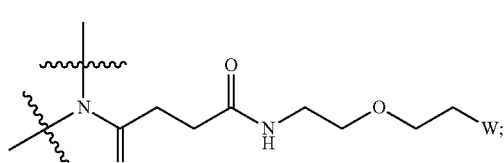

W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa;
X has the structure:

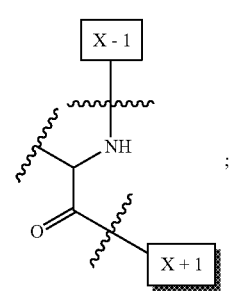

or a pharmaceutically acceptable salt, solvate, or hydrate thereof.

Embodiment 2.1. An IL-2 conjugate comprising the amino acid sequence of SEQ ID NO: 4 in which at least one amino acid residue in the IL-2 conjugate is replaced by the structure of Formula (I):

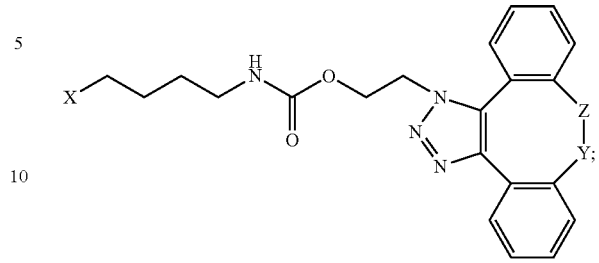

Formula (I)

wherein:
Z is CH$_2$ and Y is

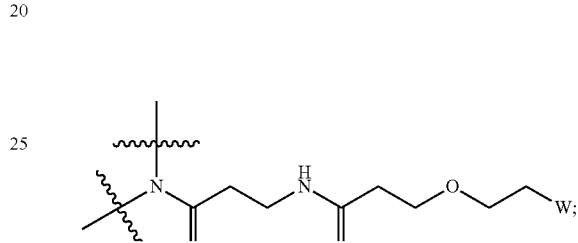

Y is CH$_2$ and Z is

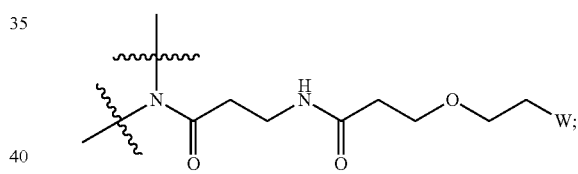

Z is CH$_2$ and Y is or

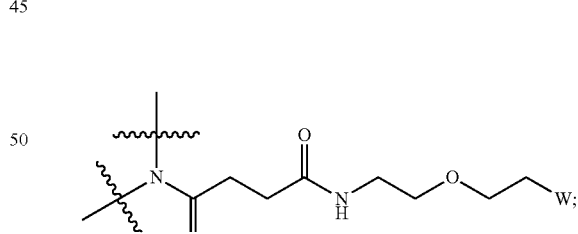

Y is CH$_2$ and Z is

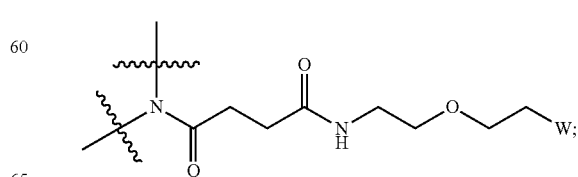

W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa;

X has the structure:

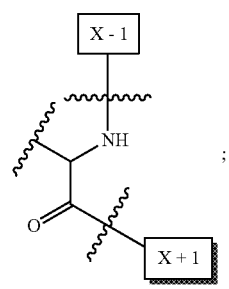

X−1 indicates the point of attachment to the preceding amino acid residue; and

X+1 indicates the point of attachment to the following amino acid residue.

Embodiment 3. The IL-2 conjugate of any one of embodiments 1-2.1 wherein Z is $CH_2$ and Y is

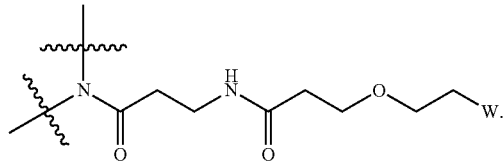

Embodiment 4. The IL-2 conjugate of any one of embodiments 1-2.1 wherein Y is $CH_2$ and Z is

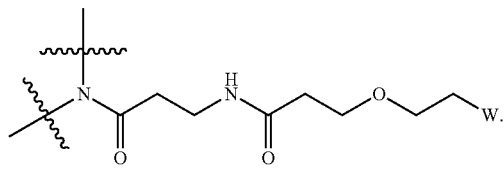

Embodiment 5. The IL-2 conjugate of any one of embodiments 1-2.1 wherein Z is $CH_2$ and Y is

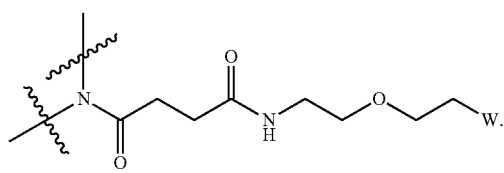

Embodiment 6. The IL-2 conjugate of any one of embodiments 1-2.1 wherein Z is $CH_2$ and Y is

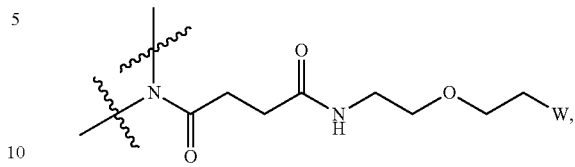

and W is a PEG group having an average molecular weight selected from 15 kDa, 20 kDa, 25 kDa, 30 kDa, 35 kDa, 40 kDa, 45 kDa, 50 kDa, 55 kDa, and 60 kDa.

Embodiment 7. The IL-2 conjugate of any one of embodiments 1-2.1 wherein Y is $CH_2$ and Z is

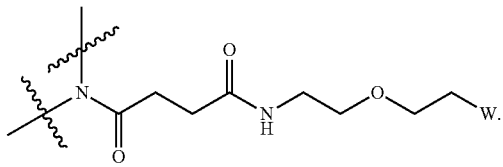

Embodiment 8. The IL-2 conjugate of any one of embodiments 1-2.1 wherein the PEG group has an average molecular weight selected from 5 kDa, 10 kDa, 20 kDa, 30 kDa, 40 kDa, or 50 kDa.

Embodiment 9. The IL-2 conjugate of any one of embodiments 1-1.1 wherein the PEG group has an average molecular weight of 50 kDa.

Embodiment 10. The IL-2 conjugate of any one of embodiments 1-1.1 wherein the PEG group has an average molecular weight of 30 kDa.

Embodiment 11. The IL-2 conjugate of any one of embodiments 1-1.1, wherein the position of the structure of Formula (I) in the amino acid sequence of the IL-2 conjugate is selected from P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, I88, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, and T132.

Embodiment 12. The IL-2 conjugate of embodiment 11, wherein the position of the structure of Formula (I) in the amino acid sequence of the IL-2 conjugate is selected from K8, H15, L18, D19, M22, N25, N87, V90, I91, L93, E94, K96, G97, S98, E99, D108 in the N87R variant, N118, T122, S124, Q125, S126, S129, and T130.

Embodiment 13. The IL-2 conjugate of embodiment 12, wherein the position of the structure of Formula (I) in the amino acid sequence of the IL-2 conjugate is selected from K8, H15, L18, D19, M22, N25, N87, V90, E99, D108 in the N87R variant, N118, T122, S124, and T130.

Embodiment 14. The IL-2 conjugate of embodiment 13, wherein the position of the structure of Formula (I) in the amino acid sequence of the IL-2 conjugate is K8.

Embodiment 15. The IL-2 conjugate of embodiment 13, wherein the position of the structure of Formula (I) in the amino acid sequence of the IL-2 conjugate is H15.

Embodiment 16. The IL-2 conjugate of embodiment 13, wherein the position of the structure of Formula (I) in the amino acid sequence of the IL-2 conjugate is L18.

Embodiment 17. The IL-2 conjugate of embodiment 13, wherein the position of the structure of Formula (I) in the amino acid sequence of the IL-2 conjugate is D19.

Embodiment 18. The IL-2 conjugate of embodiment 13, wherein the position of the structure of Formula (I) in the amino acid sequence of the IL-2 conjugate is M22.

Embodiment 19. The IL-2 conjugate of embodiment 13, wherein the position of the structure of Formula (I) in the amino acid sequence of the IL-2 conjugate is N25.

Embodiment 20. The IL-2 conjugate of embodiment 13, wherein the position of the structure of Formula (I) in the amino acid sequence of the IL-2 conjugate is N87.

Embodiment 21. The IL-2 conjugate of embodiment 13, wherein the position of the structure of Formula (I) in the amino acid sequence of the IL-2 conjugate is V90.

Embodiment 22. The IL-2 conjugate of embodiment 13, wherein the position of the structure of Formula (I) in the amino acid sequence of the IL-2 conjugate is E99.

Embodiment 23. The IL-2 conjugate of embodiment 13, wherein the position of the structure of Formula (I) in the amino acid sequence of the IL-2 conjugate is D108 in the N87R variant.

Embodiment 24. The IL-2 conjugate of embodiment 13, wherein the position of the structure of Formula (I) in the amino acid sequence of the IL-2 conjugate is N118.

Embodiment 25. The IL-2 conjugate of embodiment 13, wherein the position of the structure of Formula (I) in the amino acid sequence of the IL-2 conjugate is T122.

Embodiment 26. The IL-2 conjugate of embodiment 13, wherein the position of the structure of Formula (I) in the amino acid sequence of the IL-2 conjugate is S124.

Embodiment 27. The IL-2 conjugate of embodiment 13, wherein the position of the structure of Formula (I) in the amino acid sequence of the IL-2 conjugate is T130.

Embodiment 28. The IL-2 conjugate of embodiment 2, wherein the position of the structure of Formula (I) in the amino acid sequence of the IL-2 conjugate is selected from A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133.

Embodiment 29. The IL-2 conjugate of embodiment 28, wherein the position of the structure of Formula (I) in the amino acid sequence of the IL-2 conjugate is selected from K9, H16, L19, D20, M23, N26, N88, V91, I92, L94, E95, K97, G98, S99, E100, D109 in the N88R variant, N119, T123, S125, Q126, S127, S130, and T131, or a pharmaceutically acceptable salt, solvate, or hydrate thereof Embodiment 30. The IL-2 conjugate of embodiment 29, wherein the position of the structure of Formula (I) in the amino acid sequence of the IL-2 conjugate is selected from K9, H16, L19, D20, M23, N26, N88, V91, E100, D109 in the N88R variant, N119, T123, S125, and T131.

Embodiment 31. The IL-2 conjugate of embodiment 30, wherein the position of the structure of Formula (I) in the amino acid sequence of the IL-2 conjugate is K9.

Embodiment 32. The IL-2 conjugate of embodiment 30, wherein the position of the structure of Formula (I) in the amino acid sequence of the IL-2 conjugate is H16.

Embodiment 33. The IL-2 conjugate of embodiment 30, wherein the position of the structure of Formula (I) in the amino acid sequence of the IL-2 conjugate is L19.

Embodiment 34. The IL-2 conjugate of embodiment 30, wherein the position of the structure of Formula (I) in the amino acid sequence of the IL-2 conjugate is D20.

Embodiment 35. The IL-2 conjugate of embodiment 30, wherein the position of the structure of Formula (I) in the amino acid sequence of the IL-2 conjugate is M23.

Embodiment 36. The IL-2 conjugate of embodiment 30, wherein the position of the structure of Formula (I) in the amino acid sequence of the IL-2 conjugate is N26.

Embodiment 37. The IL-2 conjugate of embodiment 30, wherein the position of the structure of Formula (I) in the amino acid sequence of the IL-2 conjugate is N88.

Embodiment 38. The IL-2 conjugate of embodiment 30, wherein the position of the structure of Formula (I) in the amino acid sequence of the IL-2 conjugate is V91.

Embodiment 39. The IL-2 conjugate of embodiment 30, wherein the position of the structure of Formula (I) in the amino acid sequence of the IL-2 conjugate is E100.

Embodiment 40. The IL-2 conjugate of embodiment 30, wherein the position of the structure of Formula (I) in the amino acid sequence of the IL-2 conjugate is D109 in the N88R variant.

Embodiment 41. The IL-2 conjugate of embodiment 30, wherein the position of the structure of Formula (I) in the amino acid sequence of the IL-2 conjugate is N119.

Embodiment 42. The IL-2 conjugate of embodiment 30, wherein the position of the structure of Formula (I) in the amino acid sequence of the IL-2 conjugate is T123.

Embodiment 43. The IL-2 conjugate of embodiment 30, wherein the position of the structure of Formula (I) in the amino acid sequence of the IL-2 conjugate is 5125.

Embodiment 44. The IL-2 conjugate of embodiment 30, wherein the position of the structure of Formula (I) in the amino acid sequence of the IL-2 conjugate is and T131.

Embodiment 45. An IL-2 conjugate comprising the amino acid sequence of any one of SEQ ID NOS: 34-48, and 199-213, wherein [AzK_PEG] has the structure of Formula (II) or Formula (III), or a mixture of Formula (II) and Formula (III):

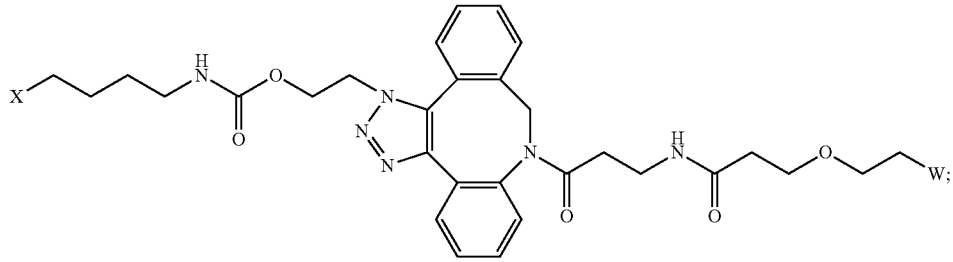

Formula (II)

-continued

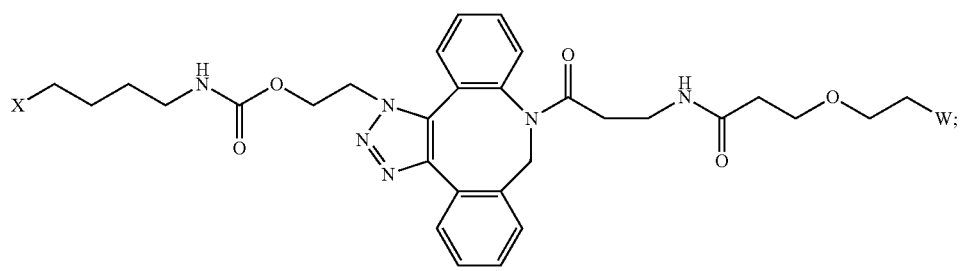
Formula (III)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and
X has the structure:

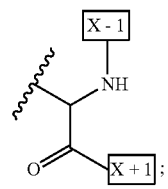 [SMILES: *C(NC)C(C)=O]

or a pharmaceutically acceptable salt, solvate, or hydrate thereof.

Embodiment 45.1 An IL-2 conjugate comprising the amino acid sequence of any one of SEQ ID NOS: 34-48, and 199-213, wherein [AzK_PEG] has the structure of Formula (II) or Formula (III), or a mixture of Formula (II) and Formula (III):

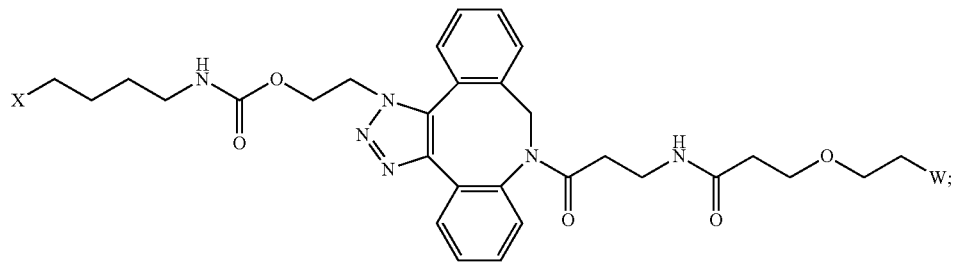
Formula (II)

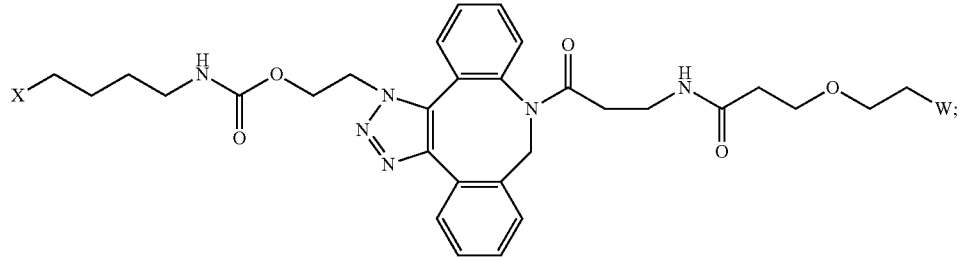
Formula (III)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and
X has the structure:

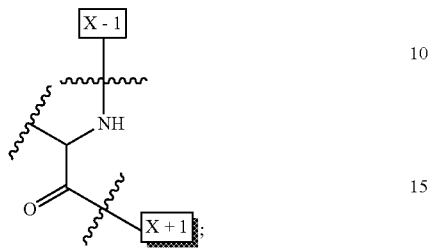

X−1 indicates the point of attachment to the preceding amino acid residue; and
X+1 indicates the point of attachment to the following amino acid residue.

Embodiment 46. The IL-2 conjugate of any one of embodiments 45-45.1, wherein the [AzK_PEG] is a mixture of Formula (II) and Formula (III), or a pharmaceutically acceptable salt, solvate, or hydrate thereof.

Embodiment 47. The IL-2 conjugate of any one of embodiments 45-45.1, wherein the [AzK_PEG] has the structure of formula (II):

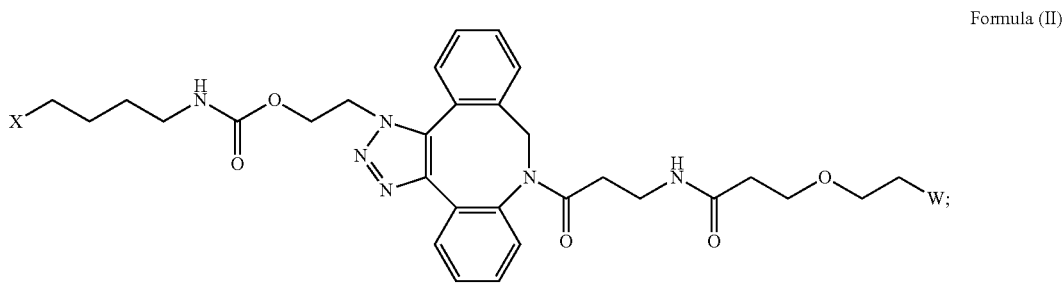

Formula (II)

or a pharmaceutically acceptable salt, solvate, or hydrate thereof.

Embodiment 48. The IL-2 conjugate of embodiment 47, wherein the IL-2 conjugate has the amino acid sequence of any one of SEQ ID NOS: 34-48.

Embodiment 49. The IL-2 conjugate of embodiment 47, wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa.

Embodiment 50. The IL-2 conjugate of embodiment 49, wherein W is a PEG group having an average molecular weight selected from 50 kDa and 30 kDa.

Embodiment 51. The IL-2 conjugate of embodiment 50, wherein W is a PEG group having an average molecular weight of 50 kDa, or a pharmaceutically acceptable salt, solvate, or hydrate thereof.

Embodiment 52. The IL-2 conjugate of embodiment 50, wherein W is a PEG group having an average molecular weight of 30 kDa, or a pharmaceutically acceptable salt, solvate, or hydrate thereof.

Embodiment 53. The IL-2 conjugate of embodiment 47, wherein the IL-2 conjugate has the amino acid sequence of any one of SEQ ID NOS: 199-213.

Embodiment 54. The IL-2 conjugate of embodiment 53, wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa.

Embodiment 55. The IL-2 conjugate of embodiment 54, wherein W is a PEG group having an average molecular weight selected from 50 kDa and 30 kDa.

Embodiment 56. The IL-2 conjugate of embodiment 55, wherein W is a PEG group having an average molecular weight of 50 kDa.

Embodiment 57. The IL-2 conjugate of embodiment 55, wherein W is a PEG group having an average molecular weight of 30 kDa.

Embodiment 58. The IL-2 conjugate of embodiment 45, wherein the IL-2 conjugate has the amino acid sequence of SEQ ID NO: 35 or 200.

Embodiment 59. The IL-2 conjugate of embodiment 58, wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa.

Embodiment 60. The IL-2 conjugate of embodiment 59, wherein W is a PEG group having an average molecular weight selected from 50 kDa and 30 kDa.
Embodiment 61. The IL-2 conjugate of embodiment 60, wherein W is a PEG group having an average molecular weight of 50 kDa.
Embodiment 62. The IL-2 conjugate of embodiment 60, wherein W is a PEG group having an average molecular weight of 30 kDa.
Embodiment 63. The IL-2 conjugate of embodiment 45, wherein the [AzK_PEG] has the structure of formula (III)

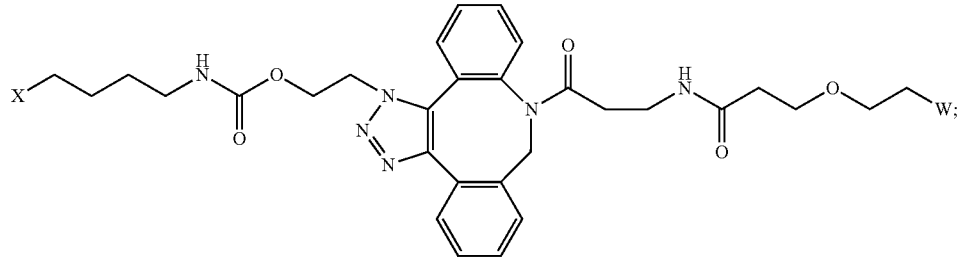

Formula (III)

or a pharmaceutically acceptable salt, solvate, or hydrate thereof.
Embodiment 64. The IL-2 conjugate of embodiment 63, wherein the IL-2 conjugate has the amino acid sequence of any one of SEQ ID NOS: 34-48.
Embodiment 65. The IL-2 conjugate of embodiment 64, wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa.
Embodiment 66. The IL-2 conjugate of embodiment 65, wherein W is a PEG group having an average molecular weight selected from 50 kDa and 30 kDa.
Embodiment 67. The IL-2 conjugate of embodiment 66, wherein W is a PEG group having an average molecular weight of 50 kDa.
Embodiment 68. The IL-2 conjugate of embodiment 66, wherein W is a PEG group having an average molecular weight of 30 kDa.
Embodiment 69. The IL-2 conjugate of embodiment 45, wherein the IL-2 conjugate has the amino acid sequence of any one of SEQ ID NOS: 199-213.
Embodiment 70. The IL-2 conjugate of embodiment 69, wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa.
Embodiment 71. The IL-2 conjugate of embodiment 70, wherein W is a PEG group having an average molecular weight selected from 50 kDa and 30 kDa.
Embodiment 72. The IL-2 conjugate of embodiment 71, wherein W is a PEG group having an average molecular weight of 50 kDa.
Embodiment 73. The IL-2 conjugate of embodiment 71, wherein W is a PEG group having an average molecular weight of 30 kDa.
Embodiment 74. The IL-2 conjugate according to any one of embodiments 1 to 73, wherein W is a linear or branched PEG group.
Embodiment 75. The IL-2 conjugate according to any one of embodiments 1 to 73, wherein W is a linear PEG group.
Embodiment 76. The IL-2 conjugate according to any one of embodiments 1 to 73, wherein W is a branched PEG group.
Embodiment 77. The IL-2 conjugate according to any one of embodiments 1 to 73, wherein W is a methoxy PEG group.
Embodiment 78. The IL-2 conjugate according to embodiment 77, wherein the methoxy PEG group is linear or branched.
Embodiment 79. The IL-2 conjugate according to embodiment 78, wherein the methoxy PEG group is linear.
Embodiment 80. The IL-2 conjugate according to embodiment 78, wherein the methoxy PEG group is branched.
Embodiment 81. An IL-2 conjugate comprising the amino acid sequence of any one of SEQ ID NOS: 49-63 and 214-228, wherein [AzK_PEG50 kDa] has the structure of Formula (II) or Formula (III), or a mixture of Formula (II) and Formula (III):

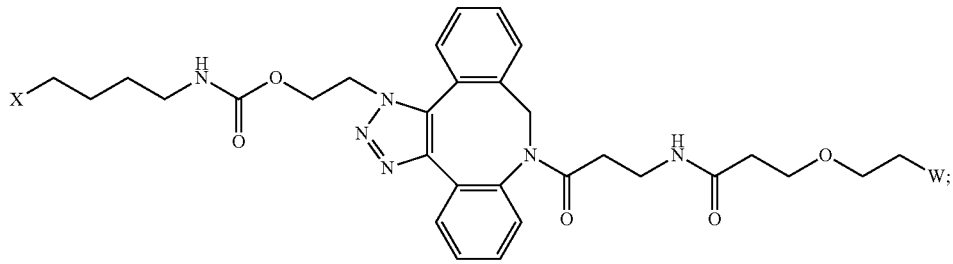

Formula (II)

-continued

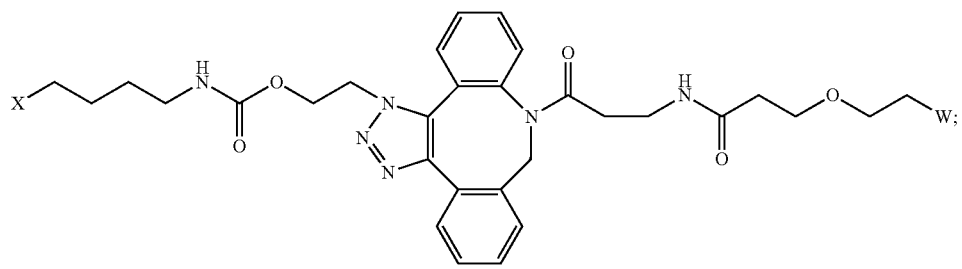
Formula (III)

wherein:
W is a PEG group having an average molecular weight of 50 kDa; and
X has the structure:

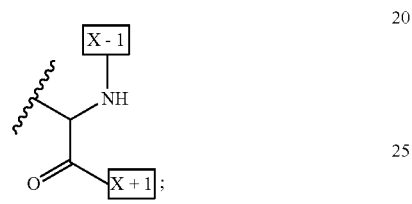

or a pharmaceutically acceptable salt, solvate, or hydrate thereof.

Embodiment 81.1. An IL-2 conjugate comprising the amino acid sequence of any one of SEQ ID NOS: 49-63 and 214-228, wherein [AzK_PEG50 kDa] has the structure of Formula (II) or Formula (III), or a mixture of Formula (II) and Formula (III):

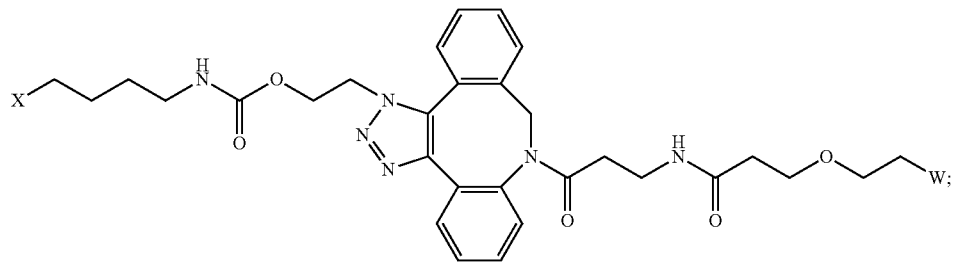
Formula (II)

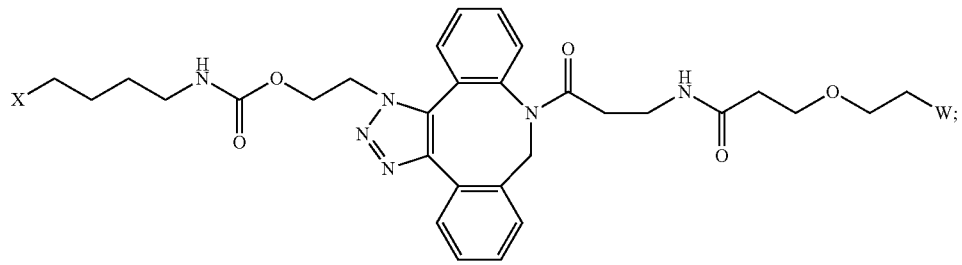
Formula (III)

wherein:
W is a PEG group having an average molecular weight of 50 kDa; and
X has the structure:

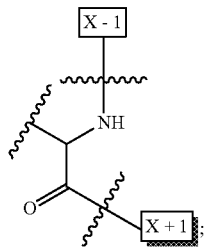

X−1 indicates the point of attachment to the preceding amino acid residue; and
X+1 indicates the point of attachment to the following amino acid residue.

Embodiment 82. The IL-2 conjugate of any one of embodiments 81-81.1, wherein the IL-2 conjugate has the amino acid sequence of any one of SEQ ID NOS: 49-63.

Embodiment 83. The IL-2 conjugate of any one of embodiments 81-81.1, wherein the IL-2 conjugate has the amino acid sequence of any one of SEQ ID NOS: 214-228.

Embodiment 84. The IL-2 conjugate of any one of embodiments 81-81.1, wherein the IL-2 conjugate has the amino acid sequence of SEQ ID NO: 50 or 215.

Embodiment 85. The IL-2 conjugate of any one of embodiments 81-81.1, wherein the [AzK_PEG50 kDa] has the structure of formula (II)

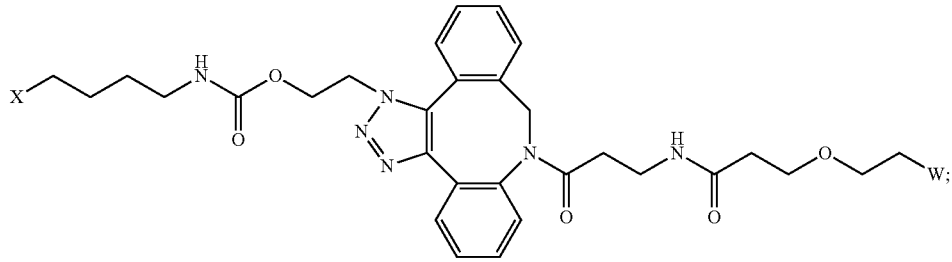

Formula (II)

or a pharmaceutically acceptable salt, solvate, or hydrate thereof.

Embodiment 86. The IL-2 conjugate of embodiment 85, wherein the IL-2 conjugate has the amino acid sequence of any one of SEQ ID NOS: 49-63.

Embodiment 87. The IL-2 conjugate of embodiment 85, wherein the IL-2 conjugate has the amino acid sequence of any one of SEQ ID NOS: 214-228.

Embodiment 88. The IL-2 conjugate of embodiment 85, wherein the IL-2 conjugate has the amino acid sequence of SEQ ID NO: 50 or 215.

Embodiment 89. The IL-2 conjugate of any one of embodiments 81-81.1, wherein the [AzK_PEG50 kDa] has the structure of formula (III)

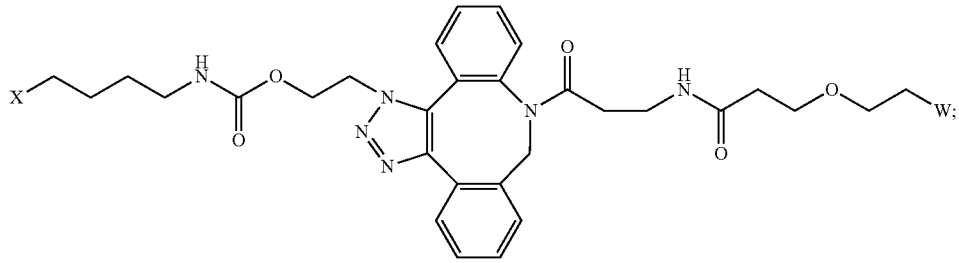

Formula (III)

or a pharmaceutically acceptable salt, solvate, or hydrate thereof.

Embodiment 90. The IL-2 conjugate of embodiment 89, wherein the IL-2 conjugate has the amino acid sequence of any one of SEQ ID NOS: 49-63.

Embodiment 91. The IL-2 conjugate of embodiment 89, wherein the IL-2 conjugate has the amino acid sequence of any one of SEQ ID NOS: 214-228.

Embodiment 92. The IL-2 conjugate of embodiment 89, wherein the IL-2 conjugate has the amino acid sequence of SEQ ID NO: 50 or 215.

Embodiment 93. An IL-2 conjugate comprising the amino acid sequence of any one of SEQ ID NOS: 64-78 and 229-243, wherein [AzK_PEG30 kDa] has the structure of Formula (II) or Formula (III), or is a mixture of the structures of Formula (II) and Formula (III):

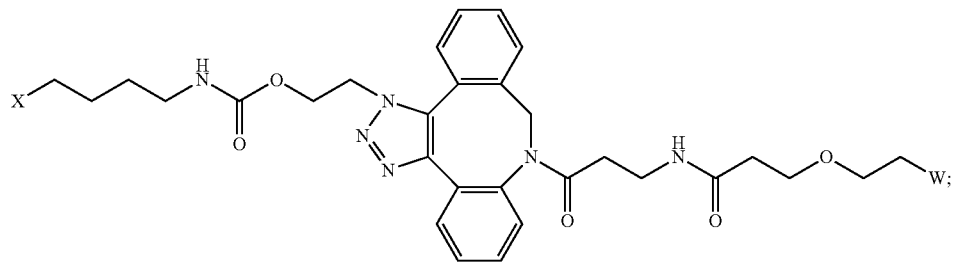

Formula (II)

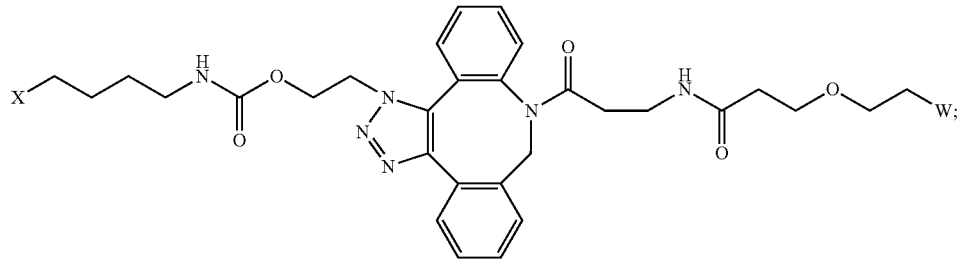

Formula (III)

wherein:
W is a PEG group having an average molecular weight of 30 kDa; and
X has the structure:

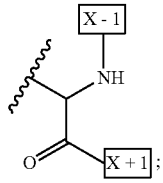 [SMILES: *C(NC)C(C)=O]

or a pharmaceutically acceptable salt, solvate, or hydrate thereof.

Embodiment 93.1. An IL-2 conjugate comprising the amino acid sequence of any one of SEQ ID NOS: 64-78 and 229-243, wherein [AzK_PEG30 kDa] has the structure of Formula (II) or Formula (III), or is a mixture of the structures of Formula (II) and Formula (III):

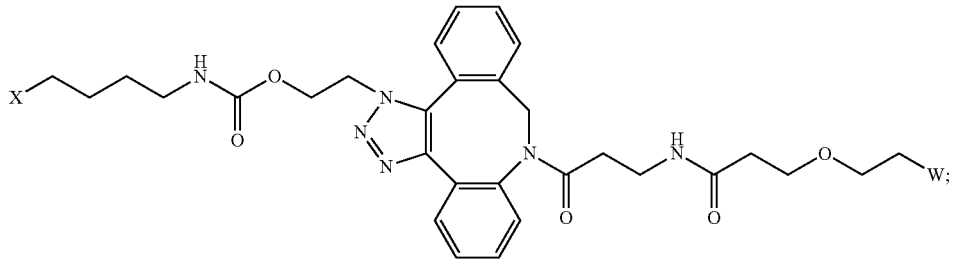

Formula (II)

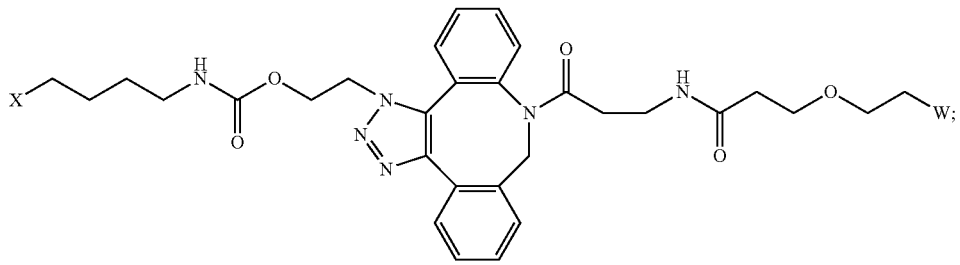

Formula (III)

wherein:
W is a PEG group having an average molecular weight of 30 kDa; and
X has the structure:

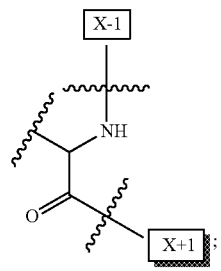

X–1 indicates the point of attachment to the preceding amino acid residue; and

X+1 indicates the point of attachment to the following amino acid residue.

Embodiment 94. The IL-2 conjugate of any one of embodiments 93-93.1, wherein the IL-2 conjugate has the amino acid sequence of any one of SEQ ID NOS: 64-78.

Embodiment 95. The IL-2 conjugate of any one of embodiments 93-93.1, wherein the IL-2 conjugate has the amino acid sequence of any one of SEQ ID NOS: 229-243.

Embodiment 96. The IL-2 conjugate of any one of embodiments 93-93.1, wherein the IL-2 conjugate has the amino acid sequence of SEQ ID NO: 65 or 230.

Embodiment 97. The IL-2 conjugate of any one of embodiments 93-93.1, wherein the [AzK_PEG30 kDa] has the structure of formula (II):

Formula (II)

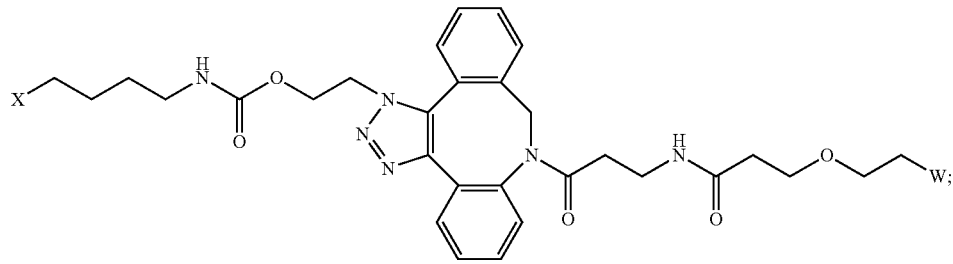

or a pharmaceutically acceptable salt, solvate, or hydrate thereof.

Embodiment 98. The IL-2 conjugate of embodiment 97, wherein the IL-2 conjugate has the amino acid sequence of any one of SEQ ID NOS: 64-78.

Embodiment 99. The IL-2 conjugate of embodiment 97, wherein the IL-2 conjugate has the amino acid sequence of any one of SEQ ID NOS: 229-243.

Embodiment 100. The IL-2 conjugate of embodiment 97, wherein the IL-2 conjugate has the amino acid sequence of SEQ ID NO: 65 or 230.

Embodiment 101. The IL-2 conjugate of any one of embodiments 93-93.1, wherein the [AzK_PEG30 kDa] has the structure of formula (III)

Formula (III)

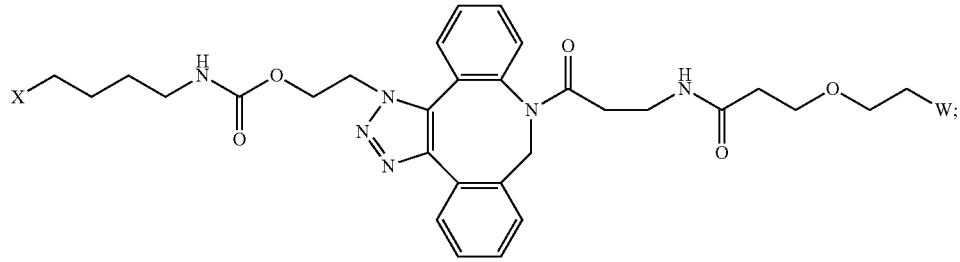

or a pharmaceutically acceptable salt, solvate, or hydrate thereof.

Embodiment 102. The IL-2 conjugate of embodiment 101, wherein the IL-2 conjugate has the amino acid sequence of any one of SEQ ID NOS: 64-78.

Embodiment 103. The IL-2 conjugate of embodiment 101, wherein the IL-2 conjugate has the amino acid sequence of any one of SEQ ID NOS: 229-243.

Embodiment 104. The IL-2 conjugate of embodiment 101, wherein the IL-2 conjugate has the amino acid sequence of SEQ ID NO: 65 or 230.

Embodiment 105. An IL-2 conjugate comprising the amino acid sequence of any one of SEQ ID NOS: 34-48 and 199-213, wherein [AzK_PEG] is a mixture of the structures of Formula (II) and Formula (III):

Formula (II)

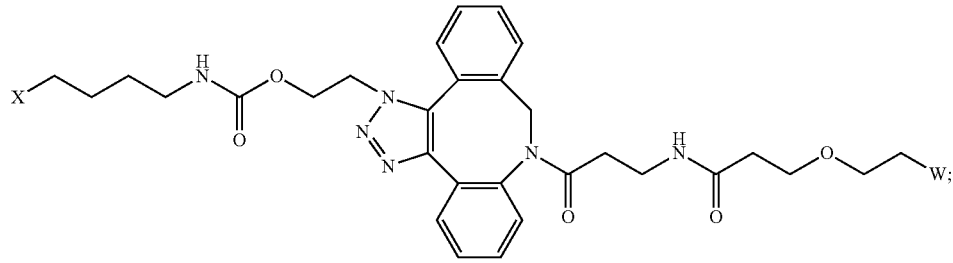

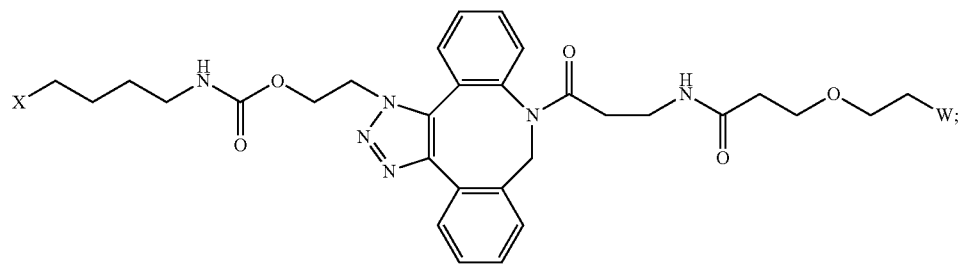

Formula (III)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and
X has the structure:

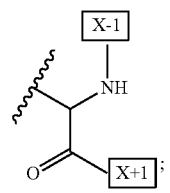

or a pharmaceutically acceptable salt, solvate, or hydrate thereof.

Embodiment 105.1. An IL-2 conjugate comprising the amino acid sequence of any one of SEQ ID NOS: 34-48 and 199-213, wherein [AzK_PEG] is a mixture of the structures of Formula (II) and Formula (III):

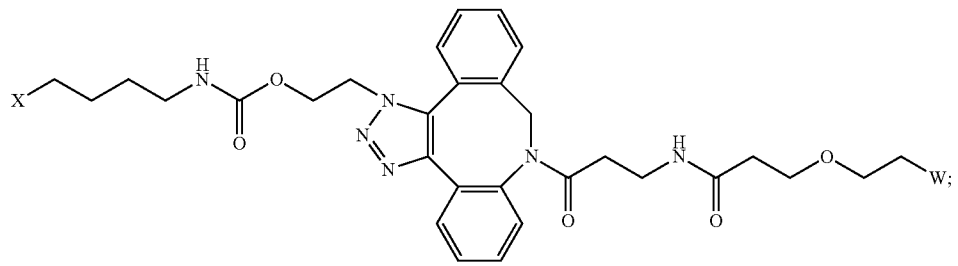

Formula (II)

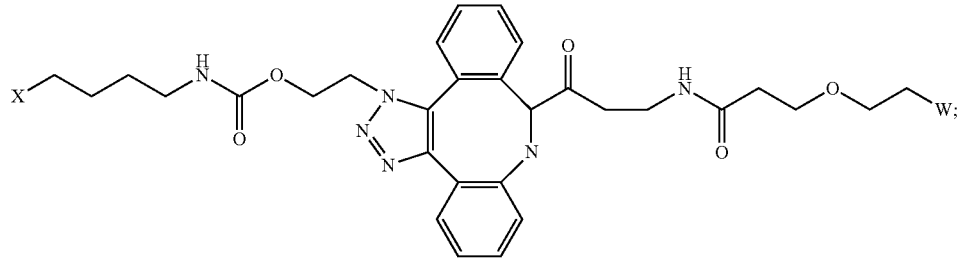

Formula (III)

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and X has the structure:

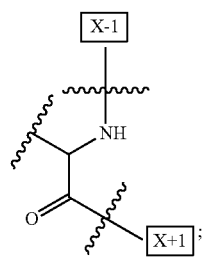

X−1 indicates the point of attachment to the preceding amino acid residue; and

X+1 indicates the point of attachment to the following amino acid residue.

Embodiment 106. The IL-2 conjugate according to any of embodiments 105-105.1, wherein the ratio of the amount of the structure of Formula (II) to the amount of the structure of Formula (III) comprising the total amount of [AzK_PEG] in the IL-2 conjugate is about 1:1.

Embodiment 107. The IL-2 conjugate according to any of embodiments 105-105.1, wherein the ratio of the amount of the structure of Formula (II) to the amount of the structure of Formula (III) comprising the total amount of [AzK_PEG] in the IL-2 conjugate is greater than 1:1.

Embodiment 108. The IL-2 conjugate according to any of embodiments 105-105.1, wherein the ratio of the amount of the structure of Formula (II) to the amount of the structure of Formula (III) comprising the total amount of [AzK_PEG] in the IL-2 conjugate is less than 1:1.

Embodiment 109. The IL-2 conjugate according to any one of embodiments 105 to 109, wherein W is a linear or branched PEG group.

Embodiment 110. The IL-2 conjugate according to any one of embodiments 105 to 109, wherein W is a linear PEG group.

Embodiment 111. The IL-2 conjugate according to any one of embodiments 105 to 109, wherein W is a branched PEG group.

Embodiment 112. The IL-2 conjugate according to any one of embodiments 105 to 109, wherein W is a methoxy PEG group.

Embodiment 113. The IL-2 conjugate according to embodiment 112, wherein the methoxy PEG group is linear or branched.

Embodiment 114. The IL-2 conjugate according to embodiment 113, wherein the methoxy PEG group is linear.

Embodiment 115. The IL-2 conjugate according to embodiment 113, wherein the methoxy PEG group is branched.

Embodiment 116. An IL-2 conjugate comprising the amino acid sequence of any one of SEQ ID NOS: 49-63 and 214-228, wherein [AzK_PEG50 kDa] is a mixture of the structures of Formula (II) and Formula (III):

Formula (II)

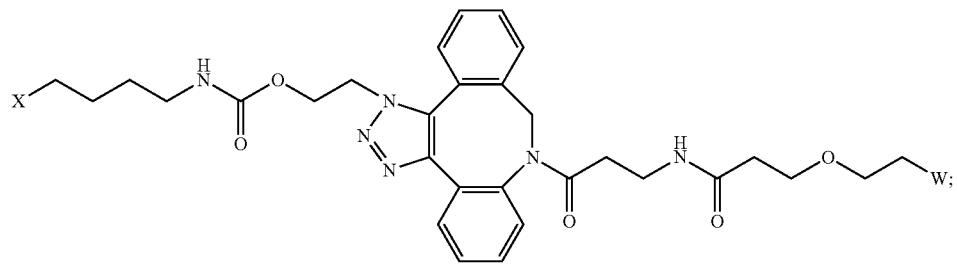

Formula (III)

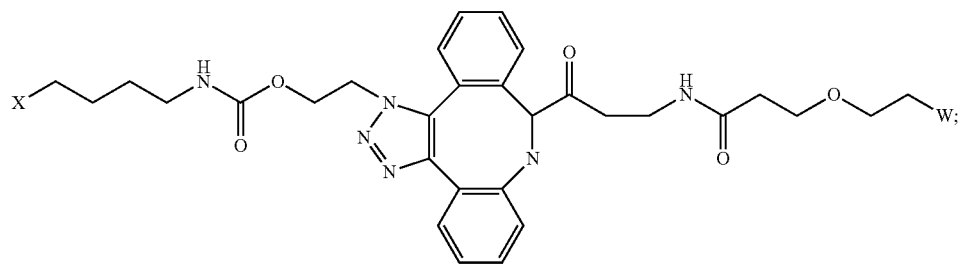

wherein:
W is a PEG group having an average molecular weight of 50 kDa; and
X has the structure:

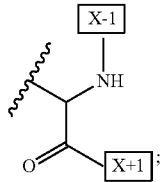

or a pharmaceutically acceptable salt, solvate, or hydrate thereof.

Embodiment 116.1. An IL-2 conjugate comprising the amino acid sequence of any one of SEQ ID NOS: 49-63 and 214-228, wherein [AzK_PEG50 kDa] is a mixture of the structures of Formula (II) and Formula (III):

Formula (II)

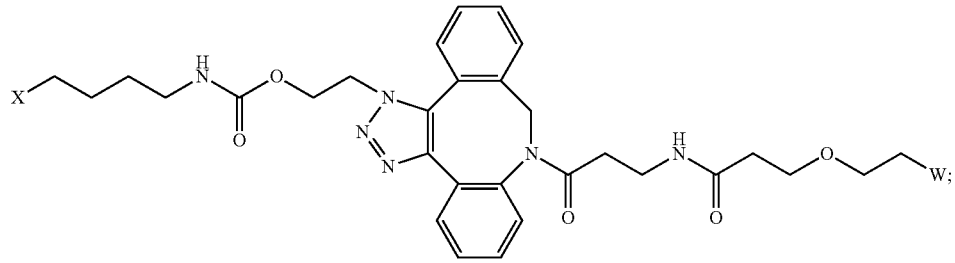

Formula (III)

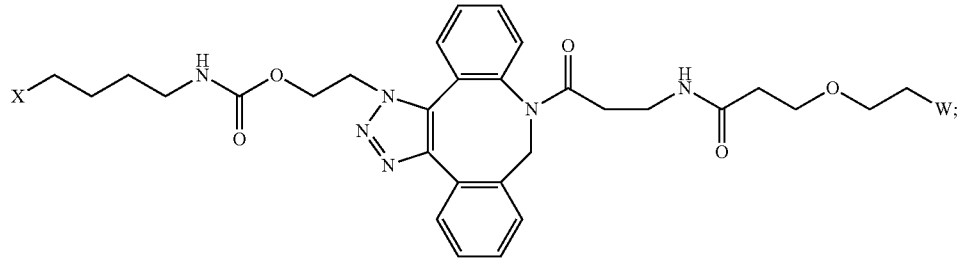

wherein:
W is a PEG group having an average molecular weight of 50 kDa; and
X has the structure:

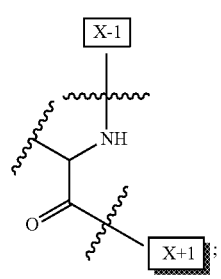

X-1 indicates the point of attachment to the preceding amino acid residue; and
X+1 indicates the point of attachment to the following amino acid residue.

Embodiment 117. The IL-2 conjugate according to any one of embodiments 116-116.1, wherein the ratio of the amount of the structure of Formula (II) to the amount of the structure of Formula (III) comprising the total amount of [AzK_PEG50 kDa] in the IL-2 conjugate is about 1:1.

Embodiment 118. The IL-2 conjugate according to any one of embodiments 116-116.1, wherein the ratio of the amount of the structure of Formula (II) to the amount of the structure of Formula (III) comprising the total amount of [AzK_PEG50 kDa] in the IL-2 conjugate is greater than 1:1.

Embodiment 119. The IL-2 conjugate according to any one of embodiments 116-116.1, wherein the ratio of the amount of the structure of Formula (II) to the amount of the structure of Formula (III) comprising the total amount of [AzK_PEG50 kDa] in the IL-2 conjugate is less than 1:1.

Embodiment 120. An IL-2 conjugate comprising the amino acid sequence of any one of SEQ ID NOS: 64-78 and 229-243, wherein [AzK_PEG30 kDa] is a mixture of the structures of Formula (II) and Formula (III):

Formula (II)

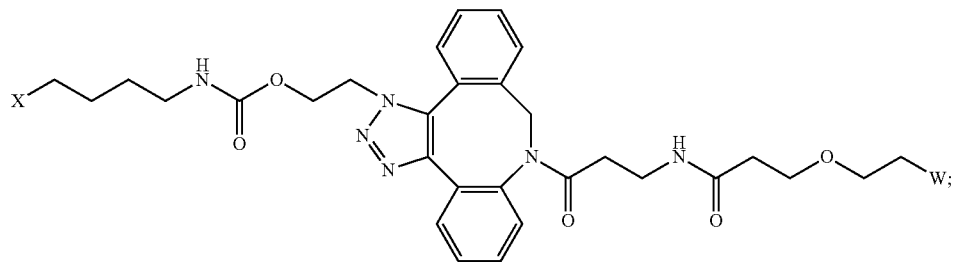

Formula (III)

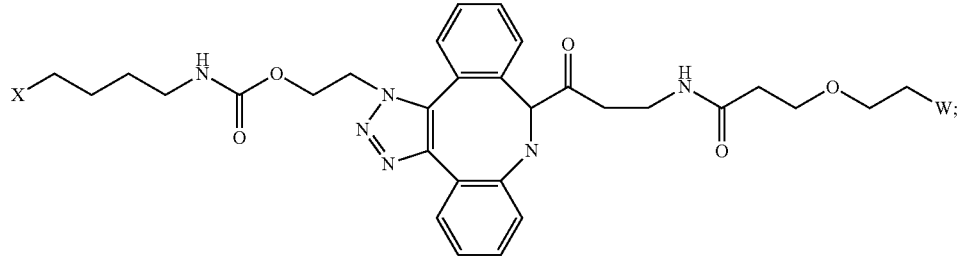

wherein:
W is a PEG group having an average molecular weight of 30 kDa; and
X has the structure:

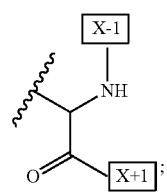

or a pharmaceutically acceptable salt, solvate, or hydrate thereof.

Embodiment 120.1. An IL-2 conjugate comprising the amino acid sequence of any one of SEQ ID NOS: 64-78 and 229-243, wherein [AzK_PEG30 kDa] is a mixture of the structures of Formula (II) and Formula (III):

Formula (II)

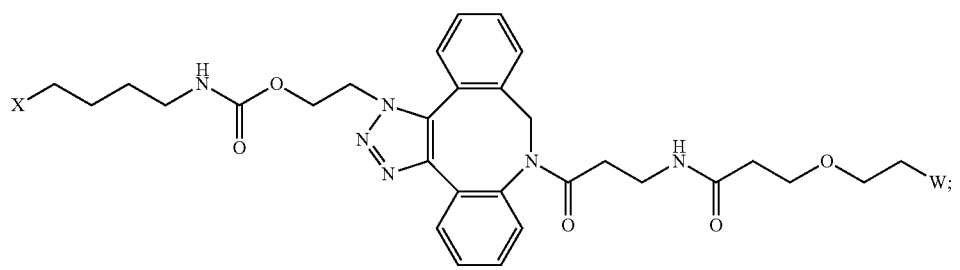

Formula (III)

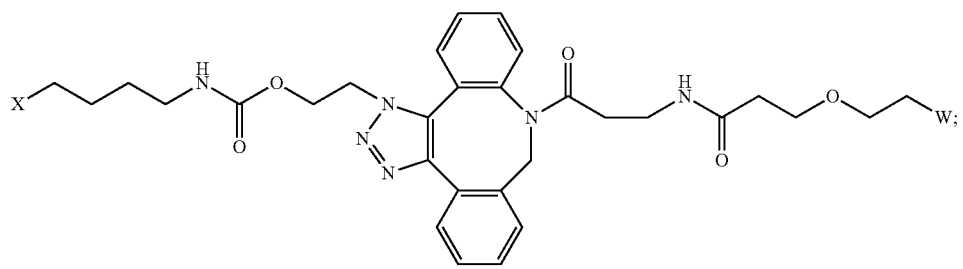

wherein:
W is a PEG group having an average molecular weight of 30 kDa; and
X has the structure:

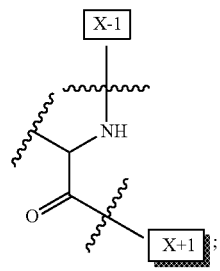

X−1 indicates the point of attachment to the preceding amino acid residue; and
X+1 indicates the point of attachment to the following amino acid residue.

Embodiment 121. The IL-2 conjugate according to any one of embodiments 120-120.1, wherein the ratio of the amount of the structure of Formula (II) to the amount of the structure of Formula (III) comprising the total amount of [AzK_PEG30 kDa] in the IL-2 conjugate is about 1:1.

Embodiment 122. The IL-2 conjugate according to any one of embodiments 120-120.1, wherein the ratio of the amount of the structure of Formula (II) to the amount of the structure of Formula (III) comprising the total amount of [AzK_PEG30 kDa] in the IL-2 conjugate is greater than 1:1.

Embodiment 123. The IL-2 conjugate according to any one of embodiments 120-120.1, wherein the ratio of the amount of the structure of Formula (II) to the amount of the structure of Formula (III) comprising the total amount of [AzK_PEG30 kDa] in the IL-2 conjugate is less than 1:1.

Embodiment 124. An IL-2 conjugate comprising the amino acid sequence of any one of SEQ ID NOS: 154-168 and 109-123, wherein [AzK_L1_PEG] has the structure of Formula (IV) or Formula (V), or a mixture of Formula (IV) and Formula (V):

Formula (IV)

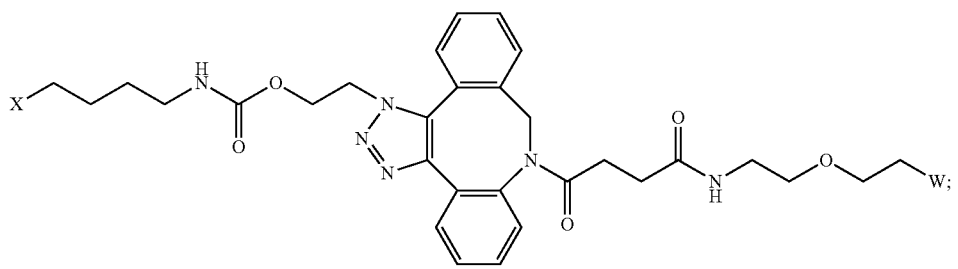

Formula (V)

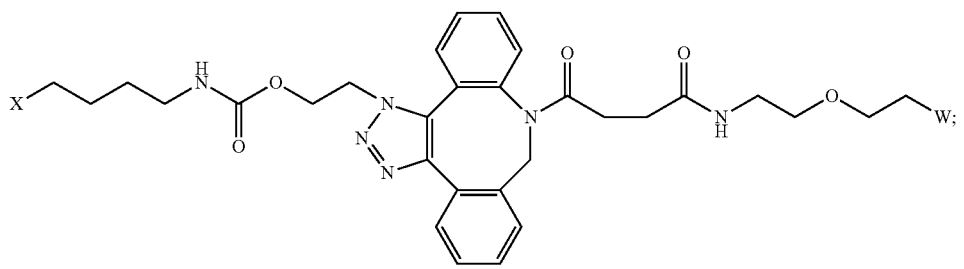

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and
X has the structure:

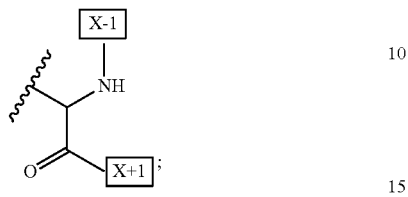

or a pharmaceutically acceptable salt, solvate, or hydrate thereof.

Embodiment 124.1. An IL-2 conjugate comprising the amino acid sequence of any one of SEQ ID NOS: 154-168 and 109-123, wherein [AzK_L1_PEG] has the structure of Formula (IV) or Formula (V), or a mixture of Formula (IV) and Formula (V):

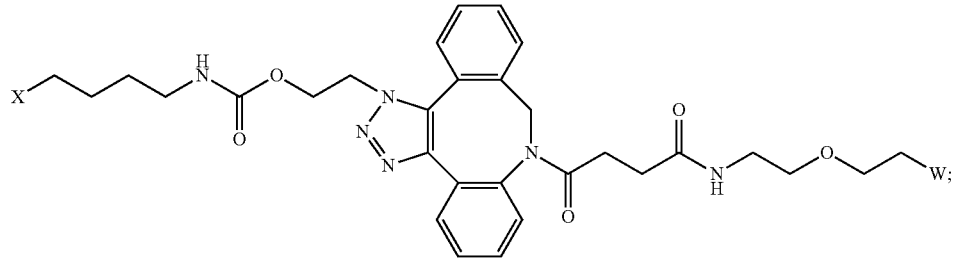

Formula (IV)

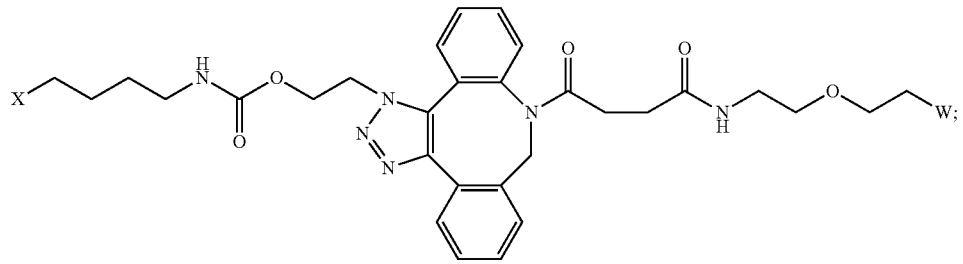

Formula (V)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and
X has the structure:

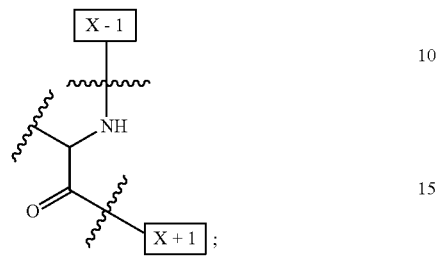

X−1 indicates the point of attachment to the preceding amino acid residue; and
X+1 indicates the point of attachment to the following amino acid residue.

Embodiment 125. The IL-2 conjugate of any one of embodiments 124-124.1, wherein the [AzK_L1_PEG] is a mixture of Formula (IV) and Formula (V), or a pharmaceutically acceptable salt, solvate, or hydrate thereof.

Embodiment 126. The IL-2 conjugate of any one of embodiments 124-124.1, wherein the [AzK_L1_PEG] has the structure of Formula (IV):

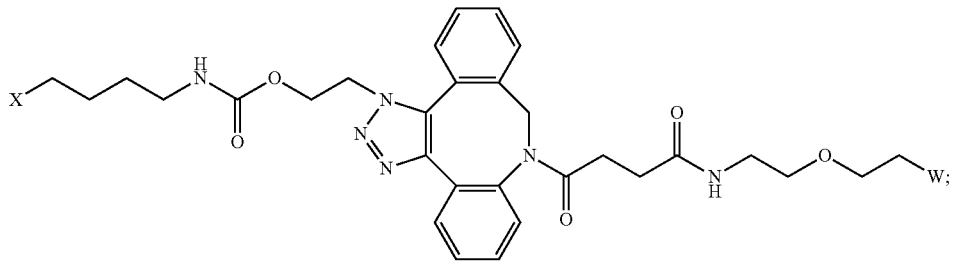

Formula (IV)

or a pharmaceutically acceptable salt, solvate, or hydrate thereof.

Embodiment 127. The IL-2 conjugate of embodiment 126, wherein the IL-2 conjugate has the amino acid sequence of any one of SEQ ID NOS: 109-123.

Embodiment 128. The IL-2 conjugate of embodiment 127, wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa.

Embodiment 129. The IL-2 conjugate of embodiment 128, wherein W is a PEG group having an average molecular weight selected from 50 kDa and 30 kDa.

Embodiment 130. The IL-2 conjugate of embodiment 129, wherein W is a PEG group having an average molecular weight of 50 kDa.

Embodiment 131. The IL-2 conjugate of embodiment 129, wherein W is a PEG group having an average molecular weight of 30 kDa.

Embodiment 132. The IL-2 conjugate of embodiment 126, wherein the IL-2 conjugate has the amino acid sequence of SEQ ID NO: 155 or 110.

Embodiment 133. The IL-2 conjugate of embodiment 132, wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa.

Embodiment 134. The IL-2 conjugate of embodiment 133, wherein W is a PEG group having an average molecular weight selected from 50 kDa and 30 kDa.

Embodiment 135. The IL-2 conjugate of embodiment 134, wherein W is a PEG group having an average molecular weight of 50 kDa.

Embodiment 136. The IL-2 conjugate of embodiment 134, wherein W is a PEG group having an average molecular weight of 30 kDa.

Embodiment 137. The IL-2 conjugate of any one of embodiments 124-124.1, wherein the [AzK_L1_PEG] has the structure of Formula (V)

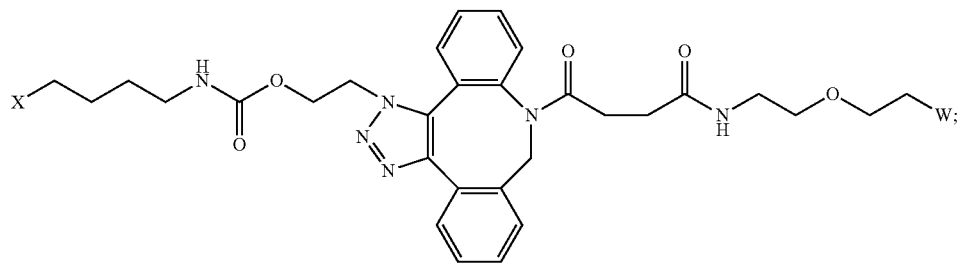

Formula (V)

or a pharmaceutically acceptable salt, solvate, or hydrate thereof.

Embodiment 138. The IL-2 conjugate of embodiment 137, wherein the IL-2 conjugate has the amino acid sequence of any one of SEQ ID NOS: 109-123.

Embodiment 139. The IL-2 conjugate of embodiment 138, wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa.

Embodiment 140. The IL-2 conjugate of embodiment 139, wherein W is a PEG group having an average molecular weight selected from 50 kDa and 30 kDa.

Embodiment 141. The IL-2 conjugate of embodiment 140, wherein W is a PEG group having an average molecular weight of 50 kDa.

Embodiment 142. The IL-2 conjugate of embodiment 140, wherein W is a PEG group having an average molecular weight of 30 kDa.

Embodiment 143. The IL-2 conjugate of embodiment 137, wherein the IL-2 conjugate has the amino acid sequence of SEQ ID NO: 155 or 110.

Embodiment 144. The IL-2 conjugate of embodiment 143, wherein W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, or 60 kDa.

Embodiment 145. The IL-2 conjugate of embodiment 144, wherein W is a PEG group having an average molecular weight selected from 50 kDa and 30 kDa.

Embodiment 146. The IL-2 conjugate of embodiment 145, wherein W is a PEG group having an average molecular weight of 50 kDa.

Embodiment 147. The IL-2 conjugate of embodiment 145, wherein W is a PEG group having an average molecular weight of 30 kDa.

Embodiment 148. The IL-2 conjugate according to any one of embodiments 124 to 147, wherein W is a linear or branched PEG group.

Embodiment 149. The IL-2 conjugate according to any one of embodiments 124 to 147, wherein W is a linear PEG group.

Embodiment 150. The IL-2 conjugate according to any one of embodiments 124 to 147, wherein W is a branched PEG group.

Embodiment 151. The IL-2 conjugate according to any one of embodiments 124 to 147, wherein W is a methoxy PEG group.

Embodiment 152. The IL-2 conjugate according to embodiment 151, wherein the methoxy PEG group is linear or branched.

Embodiment 153. The IL-2 conjugate according to embodiment 152, wherein the methoxy PEG group is linear.

Embodiment 154. The IL-2 conjugate according to embodiment 152, wherein the methoxy PEG group is branched.

Embodiment 155. An IL-2 conjugate comprising the amino acid sequence of any one of SEQ ID NOS: 169-183 and 124-138, wherein [AzK_L1_PEG50 kDa] has the structure of Formula (IV) or Formula (V), or a mixture of Formula (IV) and Formula (V):

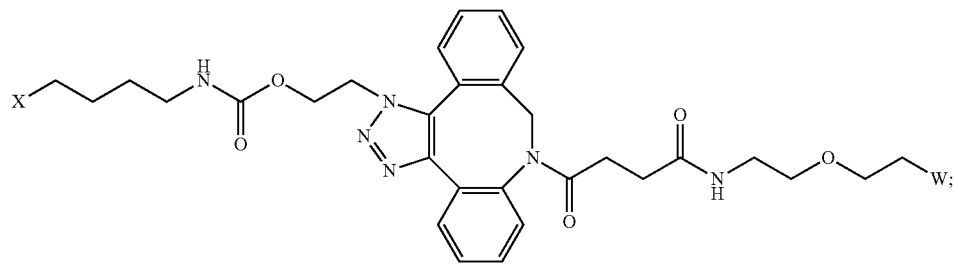

Formula (IV)

-continued

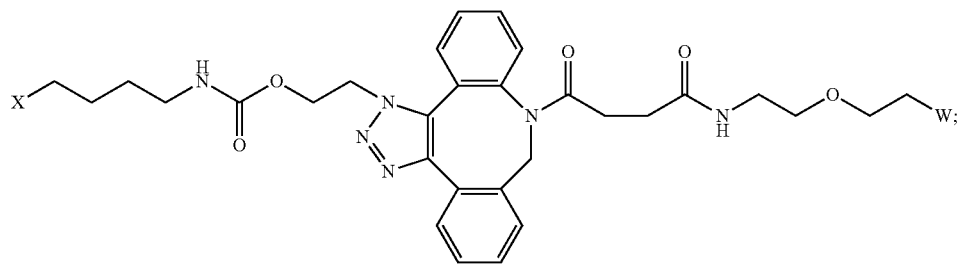

Formula (V)

wherein:
W is a PEG group having an average molecular weight of 50 kDa; and
X has the structure:

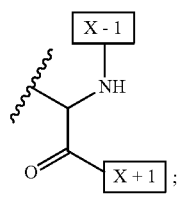 [SMILES: *C(NC)C(C)=O]

or a pharmaceutically acceptable salt, solvate, or hydrate thereof.

Embodiment 155.1. An IL-2 conjugate comprising the amino acid sequence of any one of SEQ ID NOS: 169-183 and 124-138, wherein [AzK_L1_PEG50 kDa] has the structure of Formula (IV) or Formula (V), or a mixture of Formula (IV) and Formula (V):

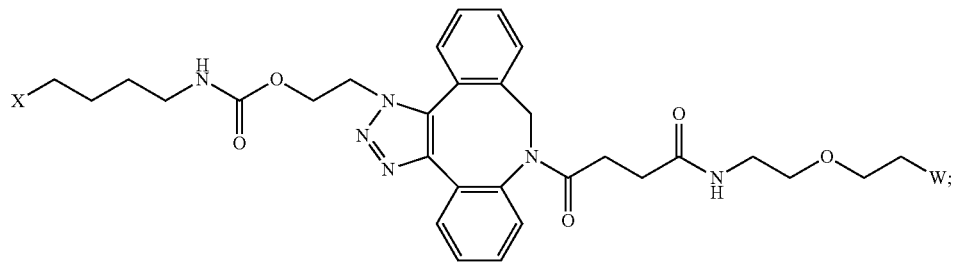

Formula (IV)

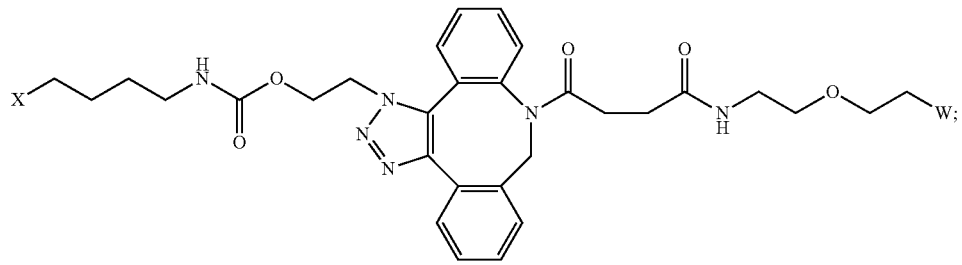

Formula (V)

wherein:
W is a PEG group having an average molecular weight of 50 kDa; and
X has the structure:

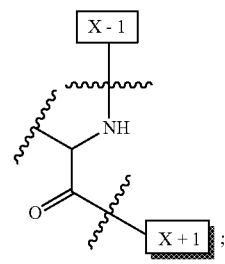

X−1 indicates the point of attachment to the preceding amino acid residue; and

X+1 indicates the point of attachment to the following amino acid residue.

Embodiment 156. The IL-2 conjugate of any one of embodiments 155-155.1, wherein the IL-2 conjugate has the amino acid sequence of any one of SEQ ID NOS: 169-183.

Embodiment 157. The IL-2 conjugate of any one of embodiments 155-155.1, wherein the IL-2 conjugate has the amino acid sequence of any one of SEQ ID NOS: 124-138.

Embodiment 158. The IL-2 conjugate of any one of embodiments 155-155.1, wherein the IL-2 conjugate has the amino acid sequence of SEQ ID NO: 170 or 125.

Embodiment 159. The IL-2 conjugate of any one of embodiments 155-155.1, wherein the [AzK_L1_PEG50 kDa] has the structure of Formula (IV)

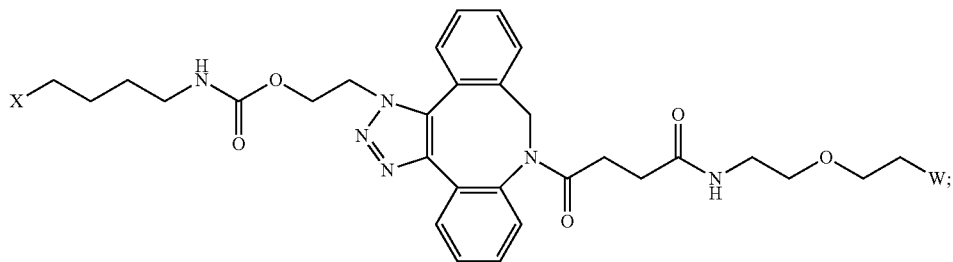

Formula (IV)

or a pharmaceutically acceptable salt, solvate, or hydrate thereof.

Embodiment 160. The IL-2 conjugate of embodiment 159, wherein the IL-2 conjugate has the amino acid sequence of any one of SEQ ID NOS: 169-183.

Embodiment 161. The IL-2 conjugate of embodiment 159, wherein the IL-2 conjugate has the amino acid sequence of any one of SEQ ID NOS: 124-138.

Embodiment 162. The IL-2 conjugate of embodiment 159, wherein the IL-2 conjugate has the amino acid sequence of SEQ ID NO: 170 or 125.

Embodiment 163. The IL-2 conjugate of any one of embodiments 155-155.1 wherein the [AzK_L1_PEG50 kDa] has the structure of Formula (V)

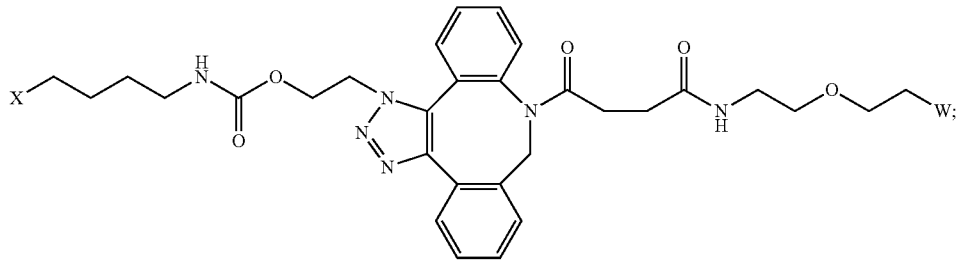

Formula (V)

or a pharmaceutically acceptable salt, solvate, or hydrate thereof.

Embodiment 164. The IL-2 conjugate of embodiment 163, wherein the IL-2 conjugate has the amino acid sequence of any one of SEQ ID NOS: 169-183.

Embodiment 165. The IL-2 conjugate of embodiment 163, wherein the IL-2 conjugate has the amino acid sequence of any one of SEQ ID NOS: 124-138.

Embodiment 166. The IL-2 conjugate of embodiment 163, wherein the IL-2 conjugate has the amino acid sequence of SEQ ID NO: 170 or 125.

Embodiment 167. An IL-2 conjugate comprising the amino acid sequence of any one of SEQ ID NOS: 184-198 and 139-153, wherein [AzK_L1_PEG30 kDa] has the structure of Formula (IV) or Formula (V), or is a mixture of the structures of Formula (IV) and Formula (V):

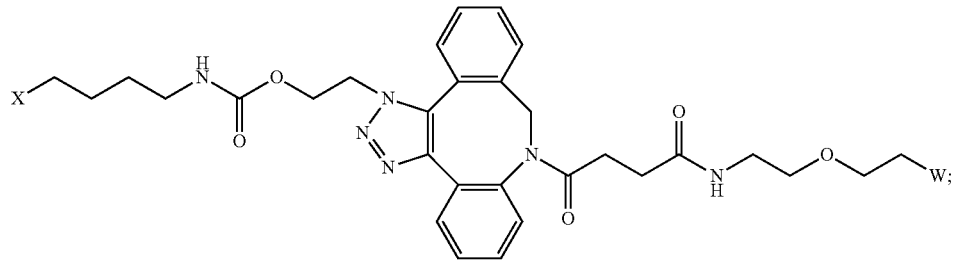

Formula (IV)

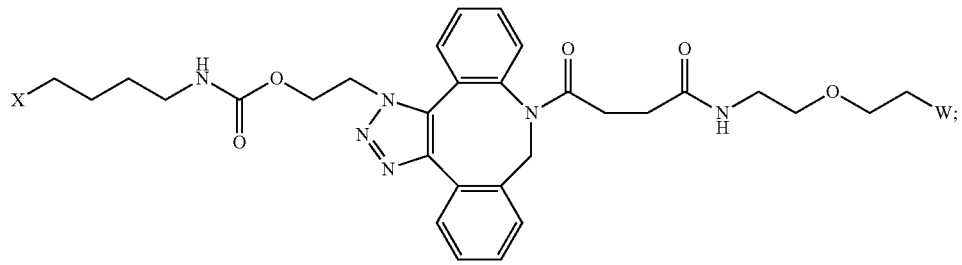

Formula (V)

wherein:
W is a PEG group having an average molecular weight of 30 kDa; and
X has the structure:

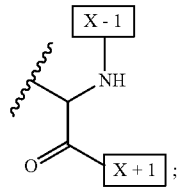 [SMILES: *C(NC)C(C)=O]

or a pharmaceutically acceptable salt, solvate, or hydrate thereof.

Embodiment 167.1. An IL-2 conjugate comprising the amino acid sequence of any one of SEQ ID NOS: 184-198 and 139-153, wherein [AzK_L1_PEG30 kDa] has the structure of Formula (IV) or Formula (V),
or is a mixture of the structures of Formula (IV) and Formula (V):

Formula (IV)

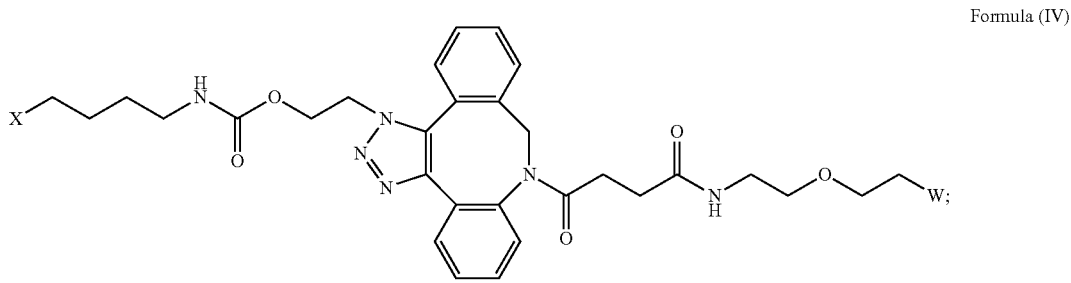

Formula (V)

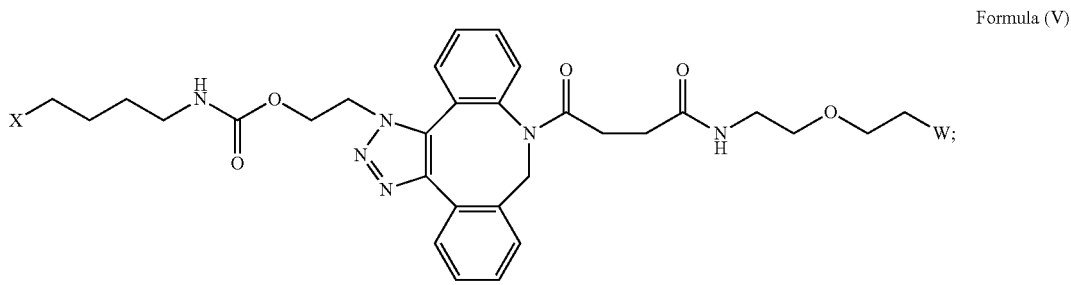

wherein:
W is a PEG group having an average molecular weight of 30 kDa; and
X has the structure:

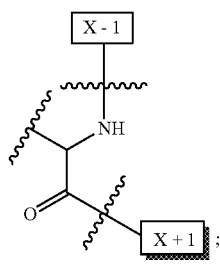

X–1 indicates the point of attachment to the preceding amino acid residue; and

X+1 indicates the point of attachment to the following amino acid residue.

Embodiment 168. The IL-2 conjugate of any one of embodiments 167-167.1, wherein the IL-2 conjugate has the amino acid sequence of any one of SEQ ID NOS: 184-198.

Embodiment 169. The IL-2 conjugate of any one of embodiments 167-167.1, wherein the IL-2 conjugate has the amino acid sequence of any one of SEQ ID NOS: 139-153.

Embodiment 170. The IL-2 conjugate of any one of embodiments 167-167.1, wherein the IL-2 conjugate has the amino acid sequence of SEQ ID NO: 185 or 140.

Embodiment 171. The IL-2 conjugate of any one of embodiments 167-167.1, wherein the [AzK_L1_PEG30 kDa] has the structure of Formula (IV):

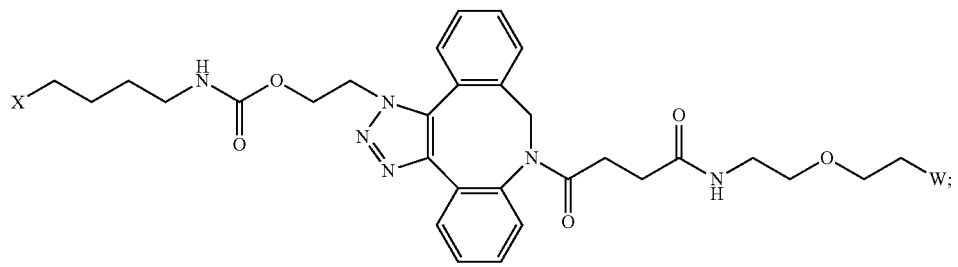

Formula (IV)

or a pharmaceutically acceptable salt, solvate, or hydrate thereof.

Embodiment 172. The IL-2 conjugate of embodiment 171, wherein the IL-2 conjugate has the amino acid sequence of any one of SEQ ID NOS: 184-198.

Embodiment 173. The IL-2 conjugate of embodiment 171, wherein the IL-2 conjugate has the amino acid sequence of any one of SEQ ID NOS: 139-153.

Embodiment 174. The IL-2 conjugate of embodiment 171, wherein the IL-2 conjugate has the amino acid sequence of SEQ ID NO: 185 or 140.

Embodiment 175. The IL-2 conjugate of any one of embodiments 167-167.1, wherein the [AzK_L1_PEG30 kDa] has the structure of Formula (V)

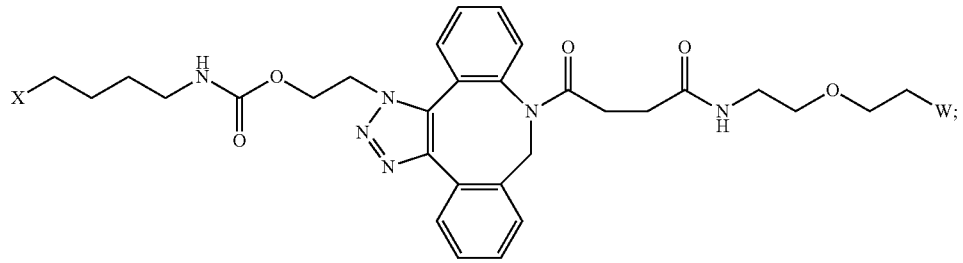

Formula (V)

or a pharmaceutically acceptable salt, solvate, or hydrate thereof.

Embodiment 176. The IL-2 conjugate of embodiment 175, wherein the IL-2 conjugate has the amino acid sequence of any one of SEQ ID NOS: 184-198.

Embodiment 177. The IL-2 conjugate of embodiment 175, wherein the IL-2 conjugate has the amino acid sequence of any one of SEQ ID NOS: 139-153.

Embodiment 178. The IL-2 conjugate of embodiment 175, wherein the IL-2 conjugate has the amino acid sequence of SEQ ID NO: 185 or 140.

Embodiment 179. An IL-2 conjugate comprising the amino acid sequence of any one of SEQ ID NOS: 154-168 and 109-123, wherein [Azk_L1 PEG] is a mixture of the structures of Formula (IV) and Formula (V):

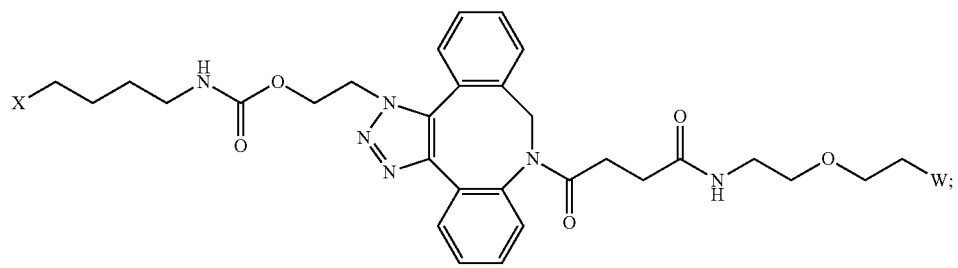

Formula (IV)

-continued

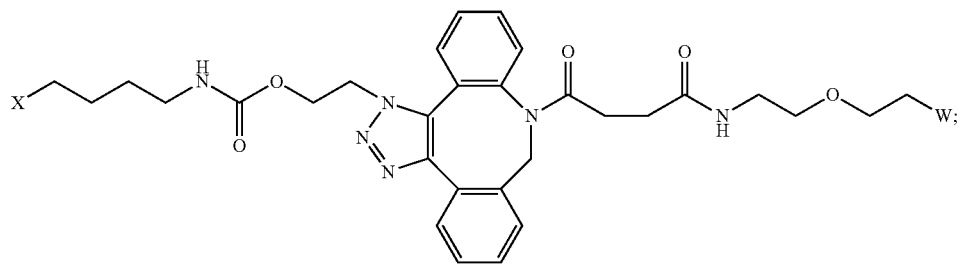
Formula (V)

wherein:
W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and
X has the structure:

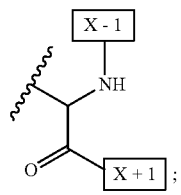 [SMILES: *C(NC)C(C)=O]

or a pharmaceutically acceptable salt, solvate, or hydrate thereof.

Embodiment 179.1. An IL-2 conjugate comprising the amino acid sequence of any one of SEQ ID NOS: 154-168 and 109-123, wherein [Azk_L1 PEG] is a mixture of the structures of Formula (IV) and Formula (V):

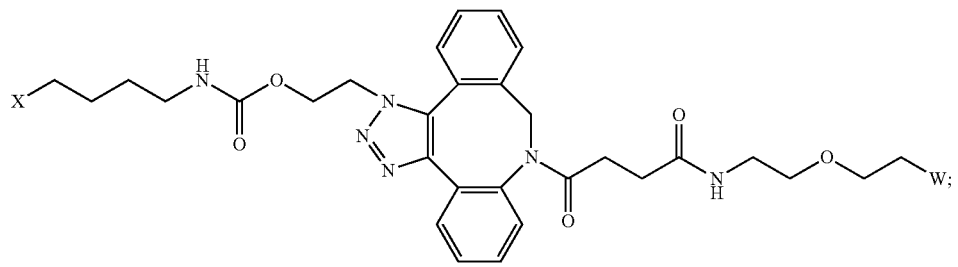
Formula (IV)

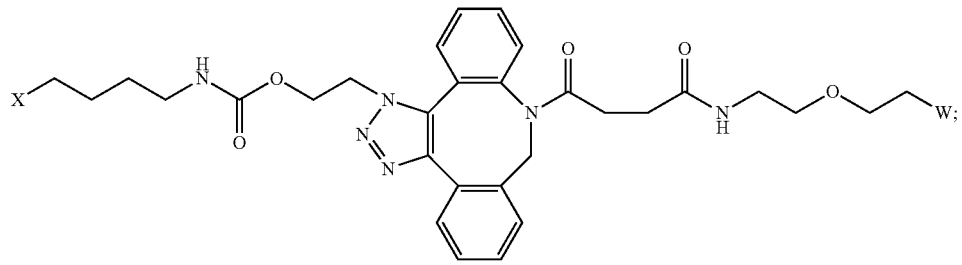
Formula (V)

wherein:

W is a PEG group having an average molecular weight selected from 5 kDa, 10 kDa, 15 kDa, 20 kDa, 25 kDa, 30 kDa, 35 kDa, 40 kDa, 45 kDa, 50 kDa, 55 kDa, and 60 kDa; and X has the structure:

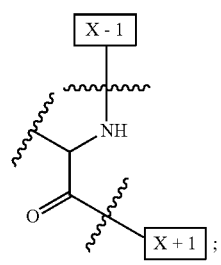 [SMILES: *NC(*)C(*)=O]

X−1 indicates the point of attachment to the preceding amino acid residue; and
X+1 indicates the point of attachment to the following amino acid residue.

Embodiment 180. The IL-2 conjugate according to any one of embodiments 179-179.1, wherein the ratio of the amount of the structure of Formula (IV) to the amount of the structure of Formula (V) comprising the total amount of [AzK_L1_PEG] in the IL-2 conjugate is about 1:1.

Embodiment 181. The IL-2 conjugate according to any one of embodiments 179-179.1, wherein the ratio of the amount of the structure of Formula (IV) to the amount of the structure of Formula (V) comprising the total amount of [AzK_L1_PEG] in the IL-2 conjugate is greater than 1:1.

Embodiment 182. The IL-2 conjugate according to any one of embodiments 179-179.1, wherein the ratio of the amount of the structure of Formula (IV) to the amount of the structure of Formula (V) comprising the total amount of [AzK_L1_PEG] in the IL-2 conjugate is less than 1:1.

Embodiment 183. The IL-2 conjugate according to any one of embodiments 179 to 182, wherein W is a linear or branched PEG group.

Embodiment 184. The IL-2 conjugate according to any one of embodiments 179 to 182, wherein W is a linear PEG group.

Embodiment 185. The IL-2 conjugate according to any one of embodiments 179 to 182, wherein W is a branched PEG group.

Embodiment 186. The IL-2 conjugate according to any one of embodiments 179 to 182, wherein W is a methoxy PEG group.

Embodiment 187. The IL-2 conjugate according to embodiment 186, wherein the methoxy PEG group is linear or branched.

Embodiment 188. The IL-2 conjugate according to embodiment 186, wherein the methoxy PEG group is linear.

Embodiment 189. The IL-2 conjugate according to embodiment 186, wherein the methoxy PEG group is branched.

Embodiment 190. An IL-2 conjugate comprising the amino acid sequence of any one of SEQ ID NOS: 169-183 and 124-138, wherein [AzK_L1_PEG50 kDa] is a mixture of the structures of Formula (IV) and Formula (V):

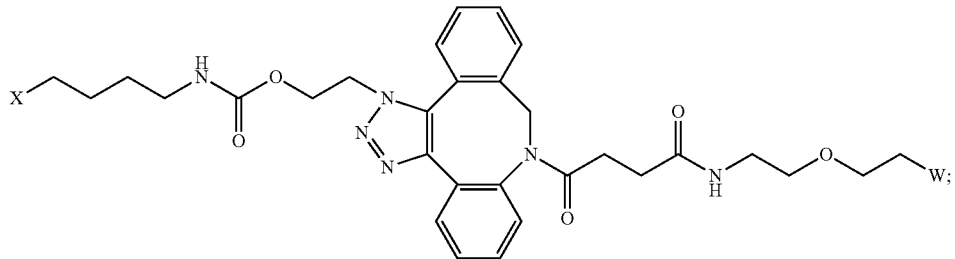

Formula (IV)

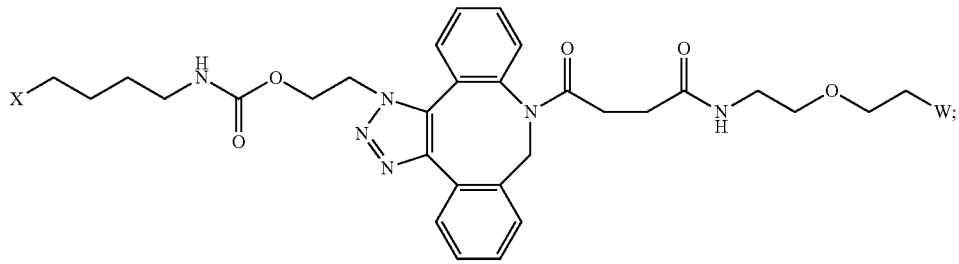

Formula (V)

wherein:
W is a PEG group having an average molecular weight of 50 kDa; and
X has the structure:
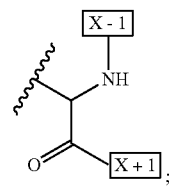
or a pharmaceutically acceptable salt, solvate, or hydrate thereof.
Embodiment 190.1. An IL-2 conjugate comprising the amino acid sequence of any one of SEQ ID NOS: 169-183 and 124-138, wherein [AzK_L1_PEG50 kDa] is a mixture of the structures of Formula (IV) and Formula (V):
Formula (IV)
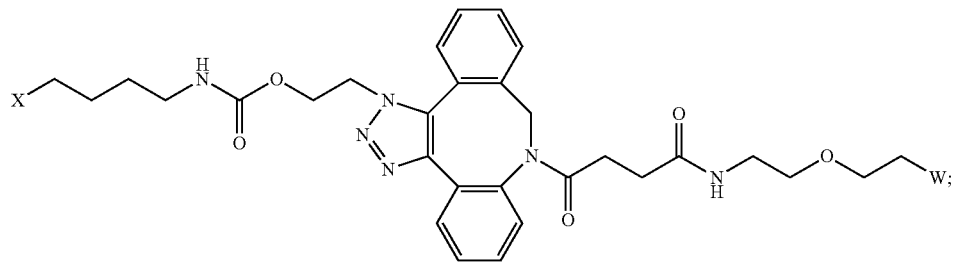
Formula (V)
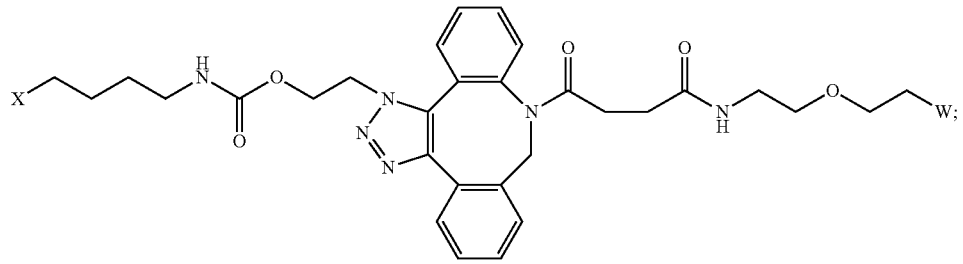

wherein:
W is a PEG group having an average molecular weight of 50 kDa; and
X has the structure:

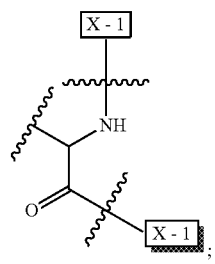

X−1 indicates the point of attachment to the preceding amino acid residue; and
X+1 indicates the point of attachment to the following amino acid residue.

Embodiment 191. The IL-2 conjugate according to any one of embodiments 190-190.1, wherein the ratio of the amount of the structure of Formula (IV) to the amount of the structure of Formula (V) comprising the total amount of [AzK_L1_PEG50 kDa] in the IL-2 conjugate is about 1:1.

Embodiment 192. The IL-2 conjugate according to any one of embodiments 190-190.1, wherein the ratio of the amount of the structure of Formula (IV) to the amount of the structure of Formula (V) comprising the total amount of [AzK_L1_PEG50 kDa] in the IL-2 conjugate is greater than 1:1.

Embodiment 193. The IL-2 conjugate according to any one of embodiments 190-190.1, wherein the ratio of the amount of the structure of Formula (IV) to the amount of the structure of Formula (V) comprising the total amount of [AzK_L1_PEG50 kDa] in the IL-2 conjugate is less than 1:1.

Embodiment 194. An IL-2 conjugate comprising the amino acid sequence of any one of SEQ ID NOS: 184-198 and 139-153, wherein [AzK_L1_PEG30 kDa] is a mixture of the structures of Formula (IV) and Formula (V):

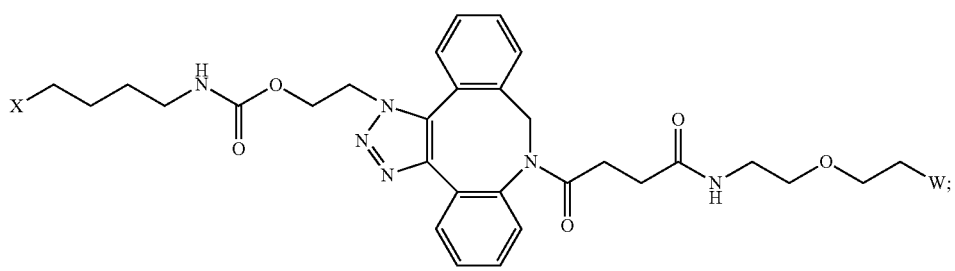

Formula (IV)

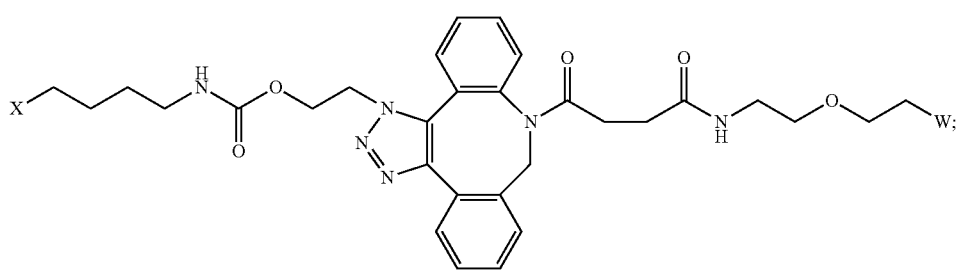

Formula (V)

wherein:

W is a PEG group having an average molecular weight of 30 kDa; and

X has the structure:

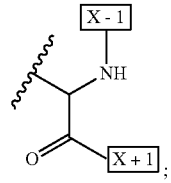

or a pharmaceutically acceptable salt, solvate, or hydrate thereof.

Embodiment 194.1. An IL-2 conjugate comprising the amino acid sequence of any one of SEQ ID NOS: 184-198 and 139-153, wherein [AzK_L1_PEG30 kDa] is a mixture of the structures of Formula (IV) and Formula (V):

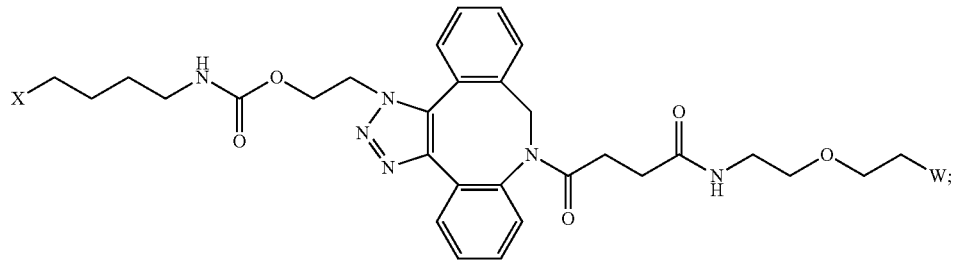

Formula (IV)

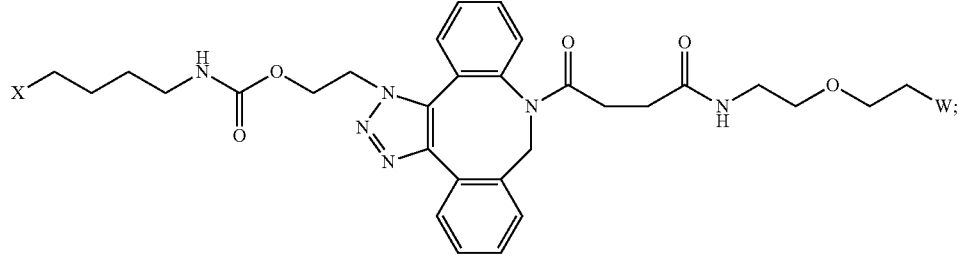

Formula (V)

wherein:

W is a PEG group having an average molecular weight of 30 kDa; and

X has the structure:

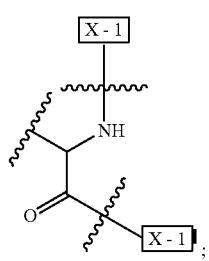

X−1 indicates the point of attachment to the preceding amino acid residue; and

X+1 indicates the point of attachment to the following amino acid residue.

Embodiment 195. The IL-2 conjugate according to any one of embodiments 194-194.1, wherein the ratio of the amount of the structure of Formula (IV) to the amount of the structure of Formula (V) comprising the total amount of [AzK_L1_PEG30 kDa] in the IL-2 conjugate is about 1:1.

Embodiment 196. The IL-2 conjugate according to any one of embodiments 194-194.1, wherein the ratio of the amount of the structure of Formula (IV) to the amount of the structure of Formula (V) comprising the total amount of [AzK_L1_PEG30 kDa] in the IL-2 conjugate is greater than 1:1.

Embodiment 197. The IL-2 conjugate according to any one of embodiments 194-194.1, wherein the ratio of the amount of the structure of Formula (IV) to the amount of the structure of Formula (V) comprising the total amount of [AzK_L1_PEG30 kDa] in the IL-2 conjugate is less than 1:1.

Embodiment 198. An IL-2 conjugate comprising the amino acid sequence of SEQ ID NO: 3 in which at least one amino acid residue in the IL-2 conjugate is replaced by the structure of Formula (VI) or (VII), or a mixture of (VI) and (VII):

Formula (VI)

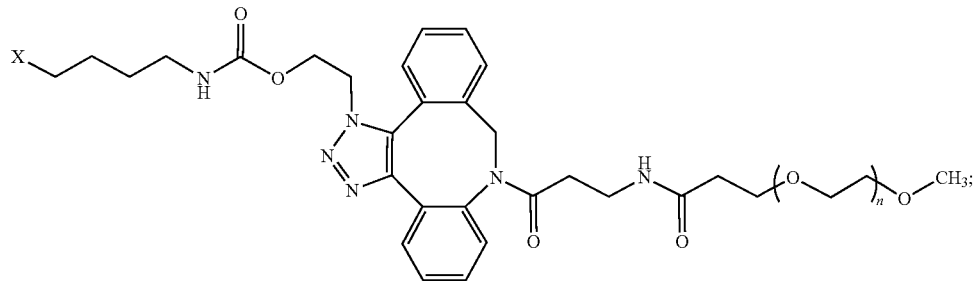

(VII)

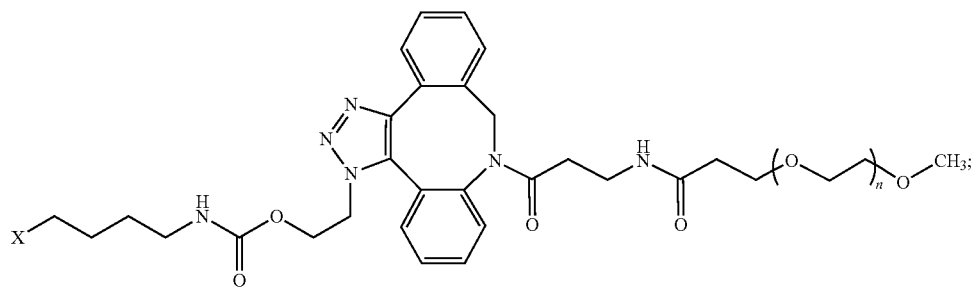

wherein:
n is an integer in the range from about 2 to about 5000; and
X has the structure:

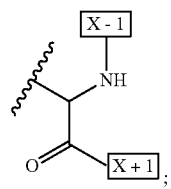

or a pharmaceutically acceptable salt, solvate, or hydrate thereof.

Embodiment 198.1. An IL-2 conjugate comprising the amino acid sequence of SEQ ID NO: 3 in which at least one amino acid residue in the IL-2 conjugate is replaced by the structure of Formula (VI) or (VII), or a mixture of (VI) and (VII):

Formula (VI)

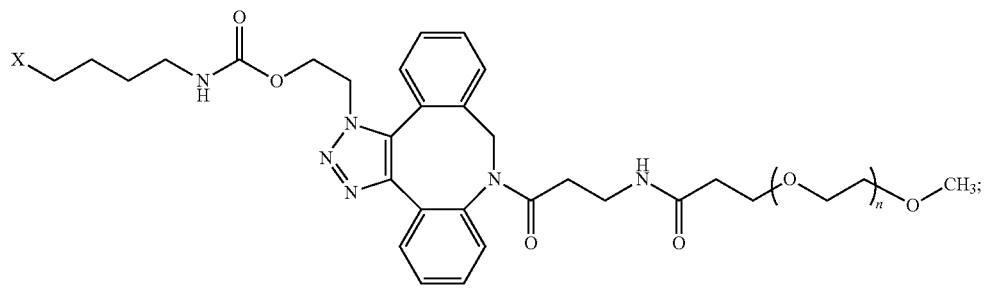

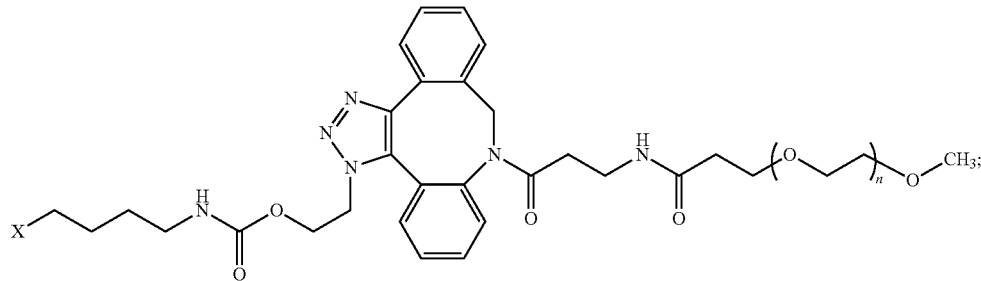

(VII)

wherein:
n is an integer in the range from about 2 to about 5000; and
X has the structure:

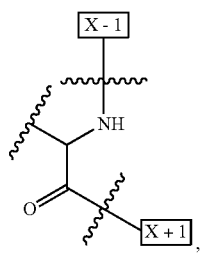

X−1 indicates the point of attachment to the preceding amino acid residue; and
X+1 indicates the point of attachment to the following amino acid residue.

Embodiment 199. The IL-2 conjugate of any one of embodiments 198-198.1, wherein the position of the structure of Formula (VI) or (VII), or a mixture of (VI) and (VII), in the amino acid sequence of the IL-2 conjugate is selected from P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, I88, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, and T132.

Embodiment 200. The IL-2 conjugate of embodiment 199, wherein the position of the structure of Formula (VI) or (VII), or a mixture of (VI) and (VII), in the amino acid sequence of the IL-2 conjugate is selected from K8, H15, L18, D19, M22, N25, N87, V90, I91, L93, E94, K96, G97, S98, E99, D108 in the N87R variant, N118, T122, S124, Q125, S126, S129, and T130.

Embodiment 201. The IL-2 conjugate of embodiment 200, wherein the position of the structure of Formula (VI) or (VII), or a mixture of (VI) and (VII), in the amino acid sequence of the IL-2 conjugate is selected from K8, H15, L18, D19, M22, N25, N87, V90, E99, D108 in the N87R variant, N118, T122, S124, and T130.

Embodiment 202. The IL-2 conjugate of embodiment 201, wherein the position of the structure of Formula (VI) or (VII), or a mixture of (VI) and (VII), in the amino acid sequence of the IL-2 conjugate is selected from in the amino acid sequence of the IL-2 conjugate is K8.

Embodiment 203. The IL-2 conjugate of embodiment 201, wherein the position of the structure of Formula (VI) or (VII), or a mixture of (VI) and (VII), in the amino acid sequence of the IL-2 conjugate is H15.

Embodiment 204. The IL-2 conjugate of embodiment 201, wherein the position of the structure of Formula (VI) or (VII), or a mixture of (VI) and (VII), in the amino acid sequence of the IL-2 conjugate is L18.

Embodiment 205. The IL-2 conjugate of embodiment 201, wherein the position of the structure of Formula (VI) or (VII), or a mixture of (VI) and (VII), in the amino acid sequence of the IL-2 conjugate is D19.

Embodiment 206. The IL-2 conjugate of embodiment 201, wherein the position of the structure of Formula (VI) or (VII), or a mixture of (VI) and (VII), in the amino acid sequence of the IL-2 conjugate is M22.

Embodiment 207. The IL-2 conjugate of embodiment 201, wherein the position of the structure of Formula (VI) or (VII), or a mixture of (VI) and (VII), in the amino acid sequence of the IL-2 conjugate is N25.

Embodiment 208. The IL-2 conjugate of embodiment 201, wherein the position of the structure of Formula (VI) or (VII), or a mixture of (VI) and (VII), in the amino acid sequence of the IL-2 conjugate is N87.

Embodiment 209. The IL-2 conjugate of embodiment 201, wherein the position of the structure of Formula (VI) or (VII), or a mixture of (VI) and (VII), in the amino acid sequence of the IL-2 conjugate is V90.

Embodiment 210. The IL-2 conjugate of embodiment 201, wherein the position of the structure of Formula (VI) or (VII), or a mixture of (VI) and (VII), in the amino acid sequence of the IL-2 conjugate is E99.

Embodiment 211. The IL-2 conjugate of embodiment 201, wherein the position of the structure of Formula (VI) or (VII), or a mixture of (VI) and (VII), in the amino acid sequence of the IL-2 conjugate is D108 in the N87R variant.

Embodiment 212. The IL-2 conjugate of embodiment 201, wherein the position of the structure of Formula (VI) or (VII), or a mixture of (VI) and (VII), in the amino acid sequence of the IL-2 conjugate is N118.

Embodiment 213. The IL-2 conjugate of embodiment 201, wherein the position of the structure of Formula (VI) or (VII), or a mixture of (VI) and (VII), in the amino acid sequence of the IL-2 conjugate is T122.

Embodiment 214. The IL-2 conjugate of embodiment 201, wherein the position of the structure of Formula (VI) or (VII), or a mixture of (VI) and (VII), in the amino acid sequence of the IL-2 conjugate is S124.

Embodiment 215. The IL-2 conjugate of embodiment 201, wherein the position of the structure of Formula (VI) or (VII), or a mixture of (VI) and (VII), in the amino acid sequence of the IL-2 conjugate is T130.

Embodiment 216. The IL-2 conjugate of any one of embodiments 198 to 215, wherein n is about 75 to about 1000.
Embodiment 217. The IL-2 conjugate of any one of embodiments 198 to 215, wherein n is about 100 to about 1000.
Embodiment 218. The IL-2 conjugate of any one of embodiments 198 to 215, wherein n is about 200 to about 5000.
Embodiment 219. The IL-2 conjugate of any one of embodiments 198 to 215, wherein n is about 500 to about 1000.
Embodiment 220. The IL-2 conjugate of any one of embodiments 198 to 215, wherein n is about 400 to about 800.
Embodiment 221. An IL-2 conjugate comprising the amino acid sequence of SEQ ID NO: 3 in which at least one amino acid residue in the IL-2 conjugate is replaced by the structure of Formula (VIII) or (IX), or a mixture of (VIII) and (IX):

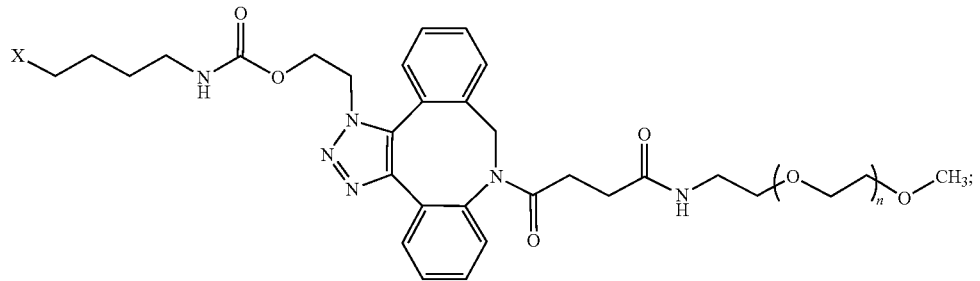

Formula (VIII)

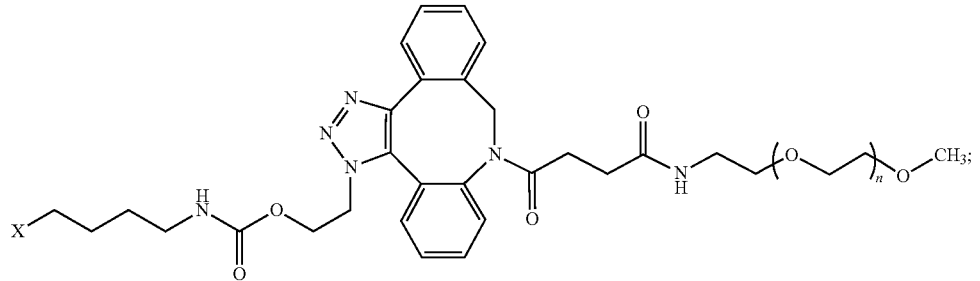

Formula (IX)

wherein:
n is an integer in the range from about 2 to about 5000; and
X has the structure:

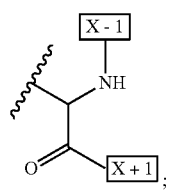

or a pharmaceutically acceptable salt, solvate, or hydrate thereof.

Embodiment 221.1. An IL-2 conjugate comprising the amino acid sequence of SEQ ID NO: 3 in which at least one amino acid residue in the IL-2 conjugate is replaced by the structure of Formula (VIII) or (IX), or a mixture of (VIII) and (IX):

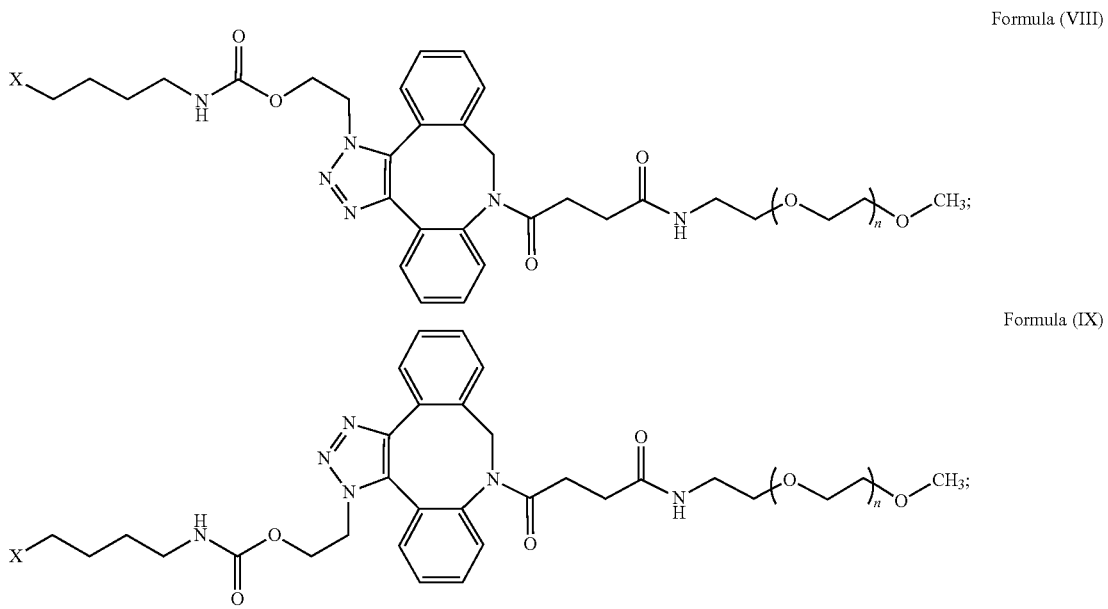

Formula (VIII)

Formula (IX)

wherein:
n is an integer in the range from about 2 to about 5000; and

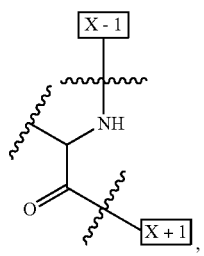

X has the structure:
X−1 indicates the point of attachment to the preceding amino acid residue; and
X+1 indicates the point of attachment to the following amino acid residue.

Embodiment 222. The IL-2 conjugate of any one of embodiments 221-221.1, wherein the position of the structure of Formula (VIII) or (IX), or a mixture of (VIII) and (IX), in the amino acid sequence of the IL-2 conjugate is selected from P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, I88, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, and T132.

Embodiment 223. The IL-2 conjugate of embodiment 222, wherein the position of the structure of Formula (VIII) or (IX), or a mixture of (VIII) and (IX), in the amino acid sequence of the IL-2 conjugate is selected from K8, H15, L18, D19, M22, N25, N87, V90, I91, L93, E94, K96, G97, S98, E99, D108 in the N87R variant, N118, T122, S124, Q125, S126, S129, and T130.

Embodiment 224. The IL-2 conjugate of embodiment 223, wherein the position of the structure of Formula (VIII) or (IX), or a mixture of (VIII) and (IX), in the amino acid sequence of the IL-2 conjugate is selected from K8, H15, L18, D19, M22, N25, N87, V90, E99, D108 in the N87R variant, N118, T122, S124, and T130.

Embodiment 225. The IL-2 conjugate of embodiment 224, wherein the position of the structure of Formula (VIII) or (IX), or a mixture of (VIII) and (IX), in the amino acid sequence of the IL-2 conjugate is K8.

Embodiment 226. The IL-2 conjugate of embodiment 224, wherein the position of the structure of Formula (VIII) or (IX), or a mixture of (VIII) and (IX), in the amino acid sequence of the IL-2 conjugate is H15.

Embodiment 227. The IL-2 conjugate of embodiment 224, wherein the position of the structure of Formula (VIII) or (IX), or a mixture of (VIII) and (IX), in the amino acid sequence of the IL-2 conjugate is L18.

Embodiment 228. The IL-2 conjugate of embodiment 224, wherein the position of the structure of Formula (VIII) or (IX), or a mixture of (VIII) and (IX), in the amino acid sequence of the IL-2 conjugate is D19.

Embodiment 229. The IL-2 conjugate of embodiment 224, wherein the position of the structure of Formula (VIII) or (IX), or a mixture of (VIII) and (IX), in the amino acid sequence of the IL-2 conjugate is M22.

Embodiment 230. The IL-2 conjugate of embodiment 224, wherein the position of the structure of Formula (VIII) or (IX), or a mixture of (VIII) and (IX), in the amino acid sequence of the IL-2 conjugate is N25.

Embodiment 231. The IL-2 conjugate of embodiment 224, wherein the position of the structure of Formula (VIII) or (IX), or a mixture of (VIII) and (IX), in the amino acid sequence of the IL-2 conjugate is N87.

Embodiment 232. The IL-2 conjugate of embodiment 224, wherein the position of the structure of Formula (VIII) or (IX), or a mixture of (VIII) and (IX), in the amino acid sequence of the IL-2 conjugate is V90.

Embodiment 233. The IL-2 conjugate of embodiment 224, wherein the position of the structure of Formula (VIII) or (IX), or a mixture of (VIII) and (IX), in the amino acid sequence of the IL-2 conjugate is E99.

Embodiment 234. The IL-2 conjugate of embodiment 224, wherein the position of the structure of Formula (VIII) or (IX), or a mixture of (VIII) and (IX), in the amino acid sequence of the IL-2 conjugate is D108 in the N87R variant.

Embodiment 235. The IL-2 conjugate of embodiment 224, wherein the position of the structure of Formula (VIII) or (IX), or a mixture of (VIII) and (IX), in the amino acid sequence of the IL-2 conjugate is N118.

Embodiment 236. The IL-2 conjugate of embodiment 224, wherein the position of the structure of Formula (VIII) or (IX), or a mixture of (VIII) and (IX), in the amino acid sequence of the IL-2 conjugate is T122.

Embodiment 237. The IL-2 conjugate of embodiment 224, wherein the position of the structure of Formula (VIII) or (IX), or a mixture of (VIII) and (IX), in the amino acid sequence of the IL-2 conjugate is S124.

Embodiment 238. The IL-2 conjugate of embodiment 224, wherein the position of the structure of Formula (VIII) or (IX), or a mixture of (VIII) and (IX), in the amino acid sequence of the IL-2 conjugate is T130.

Embodiment 239. The IL-2 conjugate of any one of embodiments 221 to 238, wherein n is about 75 to about 1000.

Embodiment 240. The IL-2 conjugate of any one of embodiments 221 to 238, wherein n is about 100 to about 1000.

Embodiment 241. The IL-2 conjugate of any one of embodiments 221 to 238, wherein n is about 200 to about 5000.

Embodiment 242. The IL-2 conjugate of any one of embodiments 221 to 238, wherein n is about 500 to about 1000.

Embodiment 243. The IL-2 conjugate of any one of embodiments 221 to 238, wherein n is about 400 to about 800.

Embodiment 244. An IL-2 conjugate comprising the amino acid sequence of SEQ ID NO: 3 in which at least one amino acid residue in the IL-2 conjugate is replaced by the structure of Formula (X) or (XI), or a mixture of (X) and (XI):

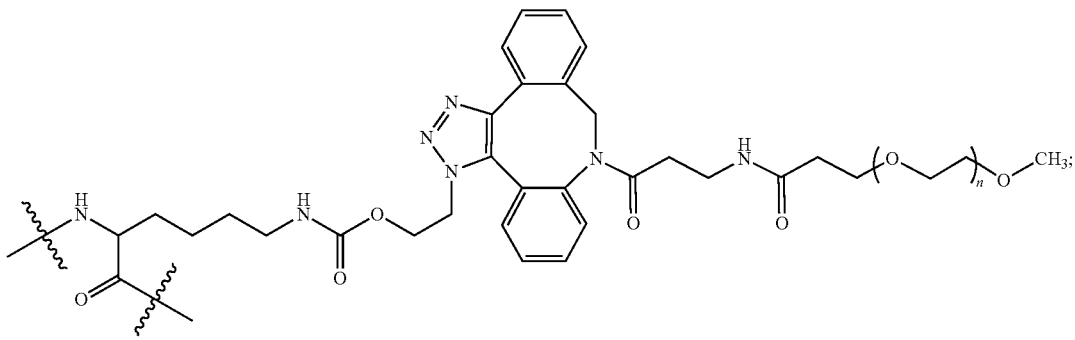

Formula (X)

-continued

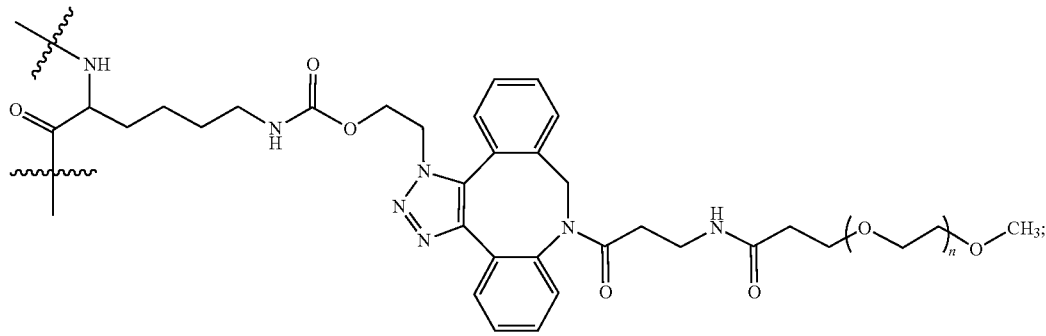

Formula (XI)

wherein:

n is an integer in the range from about 2 to about 5000; and the wavy lines indicate covalent bonds to amino acid residues within SEQ ID NO: 3 that are not replaced, or a pharmaceutically acceptable salt, solvate, or hydrate thereof.

Embodiment 245. The IL-2 conjugate of embodiment 244, wherein the position of the structure of Formula (X) or (XI), or a mixture of (X) and (XI), in the amino acid sequence of the IL-2 conjugate is selected from P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, I88, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, and T132, or a pharmaceutically acceptable salt, solvate, or hydrate thereof.

Embodiment 246. The IL-2 conjugate of embodiment 245, wherein the position of the structure of Formula (X) or (XI), or a mixture of (X) and (XI), in the amino acid sequence of the IL-2 conjugate is selected from K8, H15, L18, D19, M22, N25, N87, V90, I91, L93, E94, K96, G97, S98, E99, D108 in the N87R variant, N118, T122, S124, Q125, S126, S129, and T130, or a pharmaceutically acceptable salt, solvate, or hydrate thereof.

Embodiment 247. The IL-2 conjugate of embodiment 246, wherein the position of the structure of Formula (X) or (XI), or a mixture of (X) and (XI), in the amino acid sequence of the IL-2 conjugate is selected from K8, H15, L18, D19, M22, N25, N87, V90, E99, D108 in the N87R variant, N118, T122, S124, and T130, or a pharmaceutically acceptable salt, solvate, or hydrate thereof.

Embodiment 248. The IL-2 conjugate of embodiment 247, wherein the position of the structure of Formula (X) or (XI), or a mixture of (X) and (XI), in the amino acid sequence of the IL-2 conjugate is K8.

Embodiment 249. The IL-2 conjugate of embodiment 247, wherein the position of the structure of Formula (X) or (XI), or a mixture of (X) and (XI), in the amino acid sequence of the IL-2 conjugate is H15.

Embodiment 250. The IL-2 conjugate of embodiment 247, wherein the position of the structure of Formula (X) or (XI), or a mixture of (X) and (XI), in the amino acid sequence of the IL-2 conjugate is L18.

Embodiment 251. The IL-2 conjugate of embodiment 247, wherein the position of the structure of Formula (X) or (XI), or a mixture of (X) and (XI), in the amino acid sequence of the IL-2 conjugate is D19.

Embodiment 252. The IL-2 conjugate of embodiment 247, wherein the position of the structure of Formula (X) or (XI), or a mixture of (X) and (XI), in the amino acid sequence of the IL-2 conjugate is M22.

Embodiment 253. The IL-2 conjugate of embodiment 247, wherein the position of the structure of Formula (X) or (XI), or a mixture of (X) and (XI), in the amino acid sequence of the IL-2 conjugate is N25.

Embodiment 254. The IL-2 conjugate of embodiment 247, wherein the position of the structure of Formula (X) or (XI), or a mixture of (X) and (XI), in the amino acid sequence of the IL-2 conjugate is N87.

Embodiment 255. The IL-2 conjugate of embodiment 247, wherein the position of the structure of Formula (X) or (XI), or a mixture of (X) and (XI), in the amino acid sequence of the IL-2 conjugate is V90.

Embodiment 256. The IL-2 conjugate of embodiment 247, wherein the position of the structure of Formula (X) or (XI), or a mixture of (X) and (XI), in the amino acid sequence of the IL-2 conjugate is E99.

Embodiment 257. The IL-2 conjugate of embodiment 247, wherein the position of the structure of Formula (X) or (XI), or a mixture of (X) and (XI), in the amino acid sequence of the IL-2 conjugate is D108 in the N87R variant.

Embodiment 258. The IL-2 conjugate of embodiment 247, wherein the position of the structure of Formula (X) or (XI), or a mixture of (X) and (XI), in the amino acid sequence of the IL-2 conjugate is N118.

Embodiment 259. The IL-2 conjugate of embodiment 247, wherein the position of the structure of Formula (X) or (XI), or a mixture of (X) and (XI), in the amino acid sequence of the IL-2 conjugate is T122.

Embodiment 260. The IL-2 conjugate of embodiment 247, wherein the position of the structure of Formula (X) or (XI), or a mixture of (X) and (XI), in the amino acid sequence of the IL-2 conjugate ate is S124.

Embodiment 261. The IL-2 conjugate of embodiment 247, wherein the position of the structure of Formula (X) or (XI), or a mixture of (X) and (XI), in the amino acid sequence of the IL-2 conjugate is T130.

Embodiment 262. The IL-2 conjugate of any one of embodiments 244 to 261, wherein n is about 75 to about 1000.

Embodiment 263. The IL-2 conjugate of any one of embodiments 244 to 261, wherein n is about 100 to about 1000.

Embodiment 264. The IL-2 conjugate of any one of embodiments 244 to 261, wherein n is about 200 to about 5000.

Embodiment 265. The IL-2 conjugate of any one of embodiments 244 to 261, wherein n is about 500 to about 1000.

Embodiment 266. The IL-2 conjugate of any one of embodiments 244 to 261, wherein n is about 400 to about 800.

Embodiment 267. An IL-2 conjugate comprising the amino acid sequence of SEQ ID NO: 3 in which at least one amino acid residue in the IL-2 conjugate is replaced by the structure of Formula (XII) or (XIII), or a mixture of (XII) and (XIII):

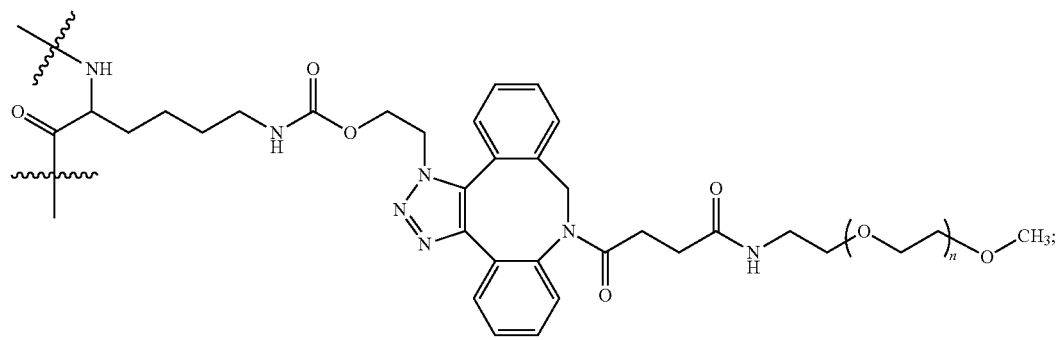

Formula (XII)

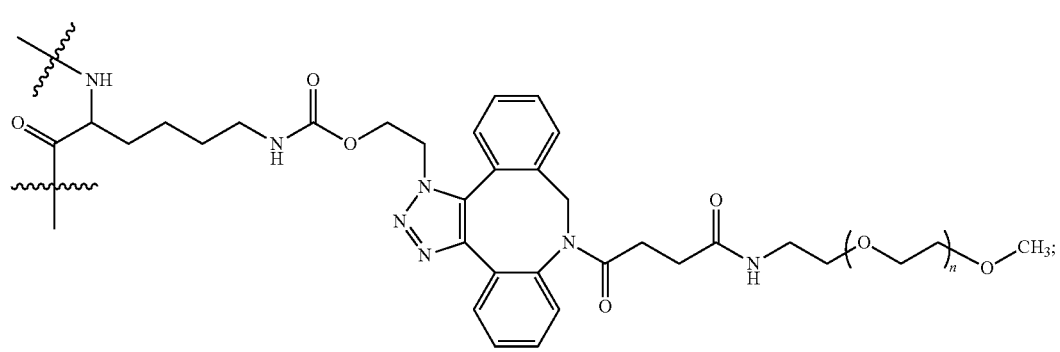

Formula (XIII)

wherein:
n is an integer in the range from about 2 to about 5000; and the wavy lines indicate covalent bonds to amino acid residues within SEQ ID NO: 3 that are not replaced, or a pharmaceutically acceptable salt, solvate, or hydrate thereof.

Embodiment 267.1. An IL-2 conjugate comprising the amino acid sequence of SEQ ID NO: 3 in which at least one amino acid residue in the IL-2 conjugate is replaced by the structure of Formula (XII) or (XIII), or a mixture of (XII) and (XIII):

Formula (XII)

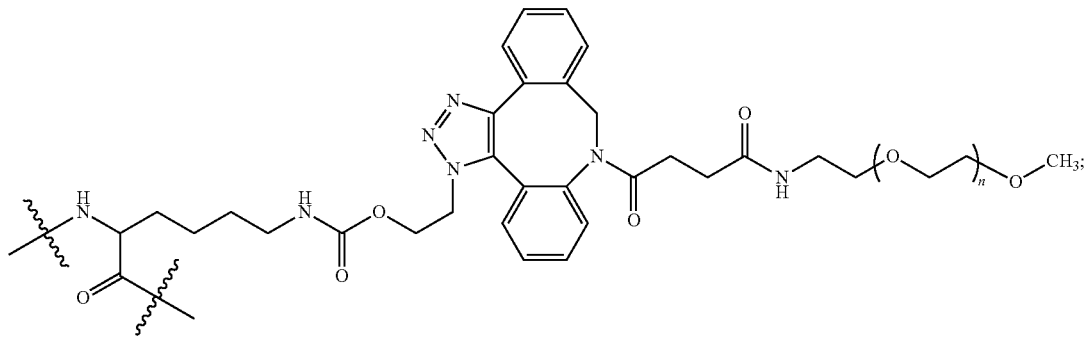

Formula (XIII)

wherein:
n is an integer in the range from about 2 to about 5000; and the wavy lines indicate covalent bonds to amino acid residues within SEQ ID NO: 3 that are not replaced.

Embodiment 268. The IL-2 conjugate of embodiment 267 or 267.1, wherein the position of the structure of Formula (XII) or (XIII), or a mixture of (XII) and (XIII), in the amino acid sequence of the IL-2 conjugate is selected from P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, I88, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, and T132, or a pharmaceutically acceptable salt, solvate, or hydrate thereof.

Embodiment 269. The IL-2 conjugate of embodiment 268, wherein the position of the structure of Formula (XII) or (XIII), or a mixture of (XII) and (XIII), in the amino acid sequence of the IL-2 conjugate is selected from K8, H15, L18, D19, M22, N25, N87, V90, I91, L93, E94, K96, G97, S98, E99, D108 in the N87R variant, N118, T122, S124, Q125, S126, S129, and T130 thereof.

Embodiment 270. The IL-2 conjugate of embodiment 269, wherein the position of the structure of Formula (XII) or (XIII), or a mixture of (XII) and (XIII), in the amino acid sequence of the IL-2 conjugate is selected from K8, H15, L18, D19, M22, N25, N87, V90, E99, D108 in the N87R variant, N118, T122, S124, and T130.

Embodiment 271. The IL-2 conjugate of embodiment 270, wherein the position of the structure of Formula (XII) or (XIII), or a mixture of (XII) and (XIII), in the amino acid sequence of the IL-2 conjugate is K8.

Embodiment 272. The IL-2 conjugate of embodiment 270, wherein the position of the structure of Formula (XII) or (XIII), or a mixture of (XII) and (XIII), in the amino acid sequence of the IL-2 conjugate is H15.

Embodiment 273. The IL-2 conjugate of embodiment 270, wherein the position of the structure of Formula (XII) or (XIII), or a mixture of (XII) and (XIII), in the amino acid sequence of the IL-2 conjugate is L18.

Embodiment 274. The IL-2 conjugate of embodiment 270, wherein the position of the structure of Formula (XII) or (XIII), or a mixture of (XII) and (XIII), in the amino acid sequence of the IL-2 conjugate is D19.

Embodiment 275. The IL-2 conjugate of embodiment 270, wherein the position of the structure of Formula (XII) or (XIII), or a mixture of (XII) and (XIII), in the amino acid sequence of the IL-2 conjugate is M22.

Embodiment 276. The IL-2 conjugate of embodiment 270, wherein the position of the structure of Formula (XII) or (XIII), or a mixture of (XII) and (XIII), in the amino acid sequence of the IL-2 conjugate is N25.

Embodiment 277. The IL-2 conjugate of embodiment 270, wherein the position of the structure of Formula (XII) or (XIII), or a mixture of (XII) and (XIII), in the amino acid sequence of the IL-2 conjugate is N87.

Embodiment 278. The IL-2 conjugate of embodiment 270, wherein the position of the structure of Formula (XII) or (XIII), or a mixture of (XII) and (XIII), in the amino acid sequence of the IL-2 conjugate is V90.

Embodiment 279. The IL-2 conjugate of embodiment 270, wherein the position of the structure of Formula (XII) or (XIII), or a mixture of (XII) and (XIII), in the amino acid sequence of the IL-2 conjugate is E99.

Embodiment 280. The IL-2 conjugate of embodiment 270, wherein the position of the structure of Formula (XII) or (XIII), or a mixture of (XII) and (XIII), in the amino acid sequence of the IL-2 conjugate is D108 in the N87R variant.

Embodiment 281. The IL-2 conjugate of embodiment 270, wherein the position of the structure of Formula (XII) or (XIII), or a mixture of (XII) and (XIII), in the amino acid sequence of the IL-2 conjugate is N118.

Embodiment 282. The IL-2 conjugate of embodiment 270, wherein the position of the structure of Formula (XII) or (XIII), or a mixture of (XII) and (XIII), in the amino acid sequence of the IL-2 conjugate is T122.

Embodiment 283. The IL-2 conjugate of embodiment 270, wherein the position of the structure of Formula (XII) or (XIII), or a mixture of (XII) and (XIII), in the amino acid sequence of the IL-2 conjugate is S124.

Embodiment 284. The IL-2 conjugate of embodiment 270, wherein the position of the structure of Formula (XII) or (XIII), or a mixture of (XII) and (XIII), in the amino acid sequence of the IL-2 conjugate is T130.

Embodiment 285. The IL-2 conjugate of any one of embodiments 267 to 284, wherein n is about 75 to about 1000.

Embodiment 286. The IL-2 conjugate of any one of embodiments 267 to 284, wherein n is about 100 to about 1000.

Embodiment 287. The IL-2 conjugate of any one of embodiments 267 to 284, wherein n is about 200 to about 5000.

Embodiment 288. The IL-2 conjugate of any one of embodiments 267 to 284, wherein n is about 500 to about 1000.

Embodiment 289. The IL-2 conjugate of any one of embodiments 267 to 284, wherein n is about 400 to about 800.

Embodiment 290. An IL-2 conjugate comprising the amino acid sequence of SEQ ID NO: 4 in which at least one amino acid residue in the IL-2 conjugate is replaced by the structure of Formula (VI) or (VII), or a mixture of (VI) and (VII):

Formula (VI)

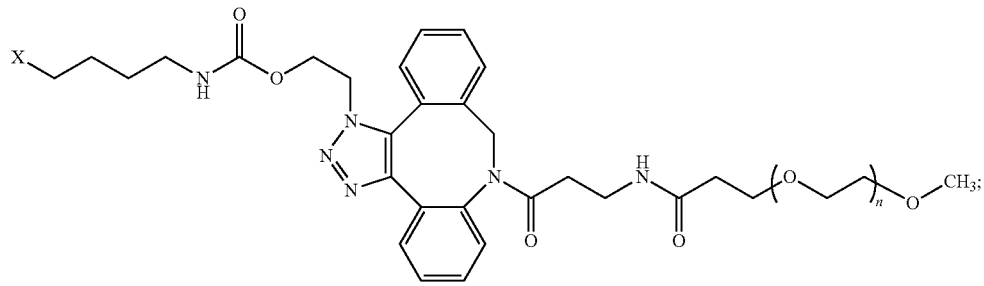

(VII)

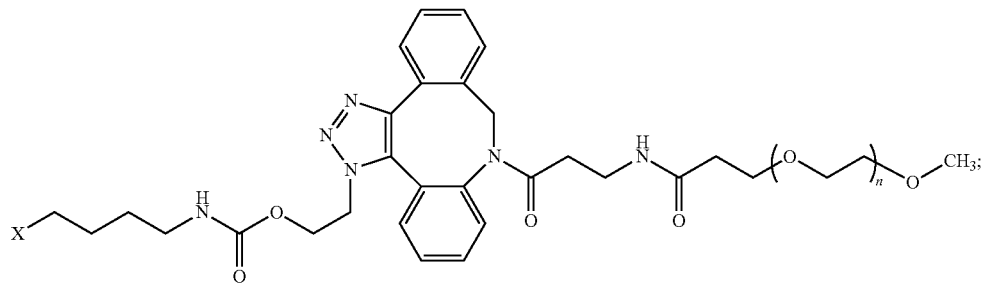

wherein:
n is an integer in the range from about 2 to about 5000; and
X has the structure:

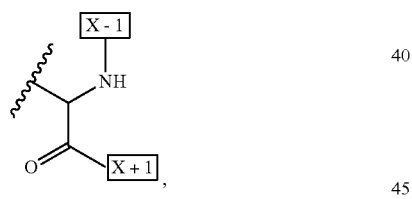

or a pharmaceutically acceptable salt, solvate, or hydrate thereof.

Embodiment 290.1. An IL-2 conjugate comprising the amino acid sequence of SEQ ID NO: 4 in which at least one amino acid residue in the IL-2 conjugate is replaced by the structure of Formula (VI) or (VII), or a mixture of (VI) and (VII):

Formula (VI)

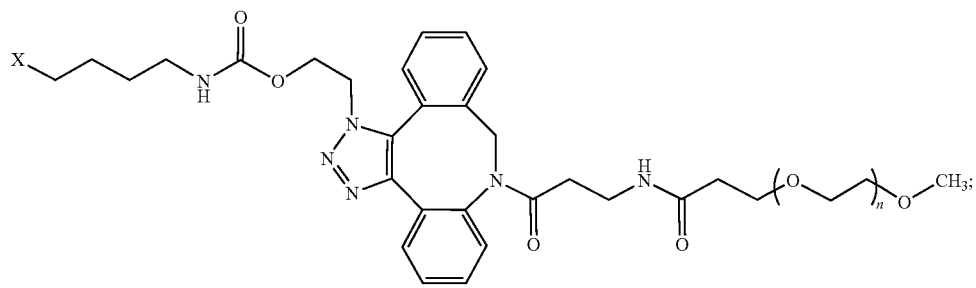

-continued (VII)

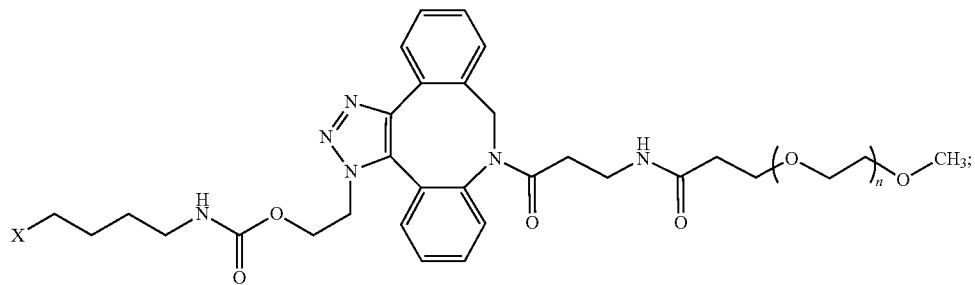

wherein:
n is an integer in the range from about 2 to about 5000; and
X has the structure:

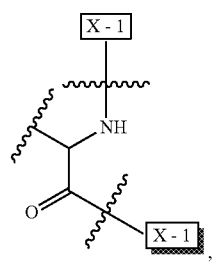

X−1 indicates the point of attachment to the preceding amino acid residue; and
X+1 indicates the point of attachment to the following amino acid residue.

Embodiment 291. The IL-2 conjugate of any one of embodiments 290-290.1, wherein the position of the structure of Formula (VI) or (VII), or a mixture of (VI) and (VII), in the amino acid sequence of the IL-2 conjugate is selected from A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133x.

Embodiment 292. The IL-2 conjugate of embodiment 291, wherein the position of the structure of Formula (VI) or (VII), or a mixture of (VI) and (VII), in the amino acid sequence of the IL-2 conjugate is selected from K9, H16, L19, D20, M23, N26, N88, V91, I92, L94, E95, K97, G98, S99, E100, D109 in the N88R variant, N119, T123, S125, Q126, S127, S130, and T131.

Embodiment 293. The IL-2 conjugate of embodiment 292, wherein the position of the structure of Formula (VI) or (VII), or a mixture of (VI) and (VII), in the amino acid sequence of the IL-2 conjugate is selected from K9, H16, L19, D20, M23, N26, N88, V91, E100, D109 in the N88R variant, N119, T123, S125, and T131.

Embodiment 294. The IL-2 conjugate of embodiment 293, wherein the position of the structure of Formula (VI) or (VII), or a mixture of (VI) and (VII), in the amino acid sequence of the IL-2 conjugate is K9.

Embodiment 295. The IL-2 conjugate of embodiment 293, wherein the position of the structure of Formula (VI) or (VII), or a mixture of (VI) and (VII), in the amino acid sequence of the IL-2 conjugate is H16.

Embodiment 296. The IL-2 conjugate of embodiment 293, wherein the position of the structure of Formula (VI) or (VII), or a mixture of (VI) and (VII), in the amino acid sequence of the IL-2 conjugate is L19.

Embodiment 297. The IL-2 conjugate of embodiment 293, wherein the position of the structure of Formula (VI) or (VII), or a mixture of (VI) and (VII), in the amino acid sequence of the IL-2 conjugate is D20.

Embodiment 298. The IL-2 conjugate of embodiment 293, wherein the position of the structure of Formula (VI) or (VII), or a mixture of (VI) and (VII), in the amino acid sequence of the IL-2 conjugate is M23.

Embodiment 299. The IL-2 conjugate of embodiment 293, wherein the position of the structure of Formula (VI) or (VII), or a mixture of (VI) and (VII), in the amino acid sequence of the IL-2 conjugate is N26.

Embodiment 300. The IL-2 conjugate of embodiment 293, wherein the position of the structure of Formula (VI) or (VII), or a mixture of (VI) and (VII), in the amino acid sequence of the IL-2 conjugate is N88.

Embodiment 301. The IL-2 conjugate of embodiment 293, wherein the position of the structure of Formula (VI) or (VII), or a mixture of (VI) and (VII), in the amino acid sequence of the IL-2 conjugate is V91.

Embodiment 302. The IL-2 conjugate of embodiment 293, wherein the position of the structure of Formula (VI) or (VII), or a mixture of (VI) and (VII), in the amino acid sequence of the IL-2 conjugate is E100.

Embodiment 303. The IL-2 conjugate of embodiment 293, wherein the position of the structure of Formula (VI) or (VII), or a mixture of (VI) and (VII), in the amino acid sequence of the IL-2 conjugate is D109 in the N88R variant.

Embodiment 304. The IL-2 conjugate of embodiment 293, wherein the position of the structure of Formula (VI) or (VII), or a mixture of (VI) and (VII), in the amino acid sequence of the IL-2 conjugate is N119.

Embodiment 305. The IL-2 conjugate of embodiment 293, wherein the position of the structure of Formula (VI) or (VII), or a mixture of (VI) and (VII), in the amino acid sequence of the IL-2 conjugate is T123.

Embodiment 306. The IL-2 conjugate of embodiment 293, wherein the position of the structure of Formula (VI) or (VII), or a mixture of (VI) and (VII), in the amino acid sequence of the IL-2 conjugate is S125.

Embodiment 307. The IL-2 conjugate of embodiment 293, wherein the position of the structure of Formula (VI) or (VII), or a mixture of (VI) and (VII), in the amino acid sequence of the IL-2 conjugate is T131.

Embodiment 308. The IL-2 conjugate of any one of embodiments 290 to 307, wherein n is about 75 to about 1000.

Embodiment 309. The IL-2 conjugate of any one of embodiments 290 to 307, wherein n is about 100 to about 1000.
Embodiment 310. The IL-2 conjugate of any one of embodiments 290 to 307, wherein n is about 200 to about 5000.
Embodiment 311. The IL-2 conjugate of any one of embodiments 290 to 307, wherein n is about 500 to about 1000.
Embodiment 312. The IL-2 conjugate of any one of embodiments 290 to 307, wherein n is about 400 to about 800.
Embodiment 313. An IL-2 conjugate comprising the amino acid sequence of SEQ ID NO: 4 in which at least one amino acid residue in the IL-2 conjugate is replaced by the structure of Formula (VIII) or (IX), or a mixture of (VIII) and (IX):

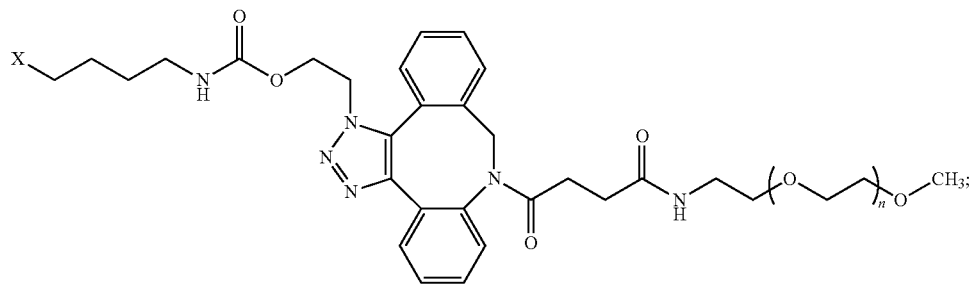

Formula (VIII)

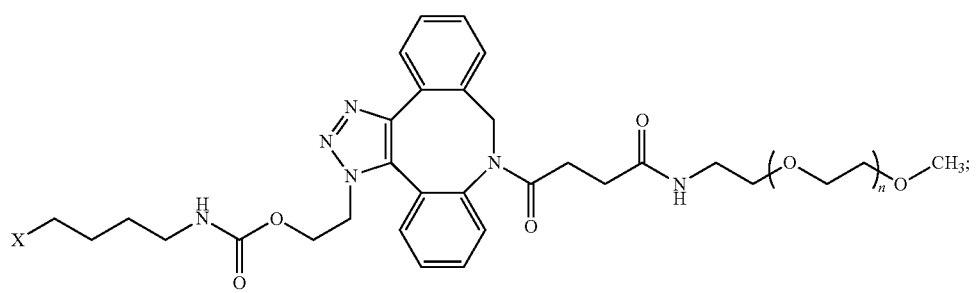

Formula (IX)

wherein:
n is an integer in the range from about 2 to about 5000; and
X has the structure:

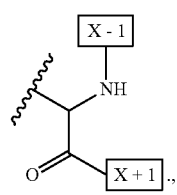

or a pharmaceutically acceptable salt, solvate, or hydrate thereof.

Embodiment 313.1. An IL-2 conjugate comprising the amino acid sequence of SEQ ID NO: 4 in which at least one amino acid residue in the IL-2 conjugate is replaced by the structure of Formula (VIII) or (IX), or a mixture of (VIII) and (IX):

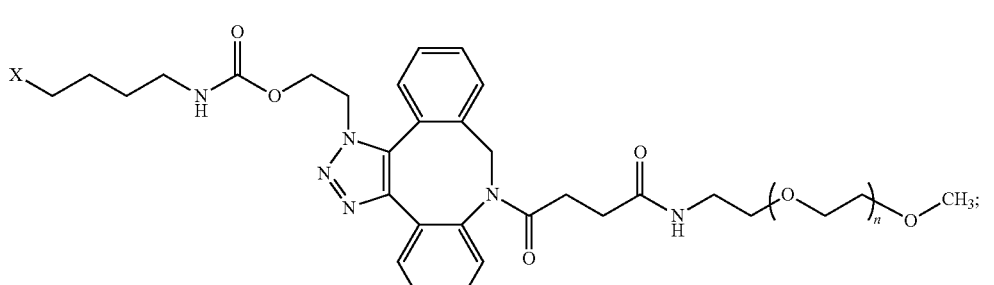

Formula (VIII)

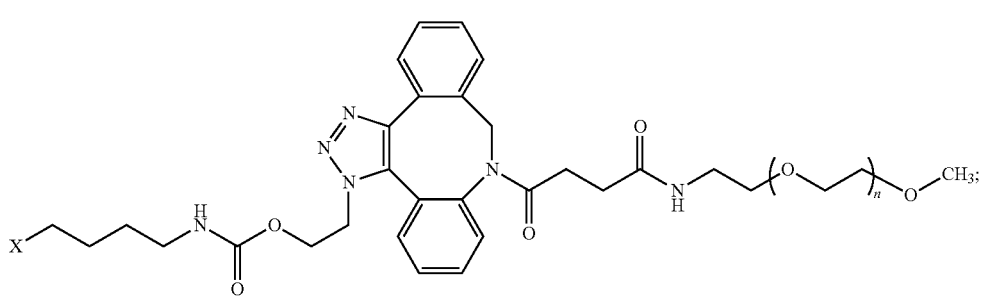

Formula (IX)

wherein:
n is an integer in the range from about 2 to about 5000; and
X has the structure:

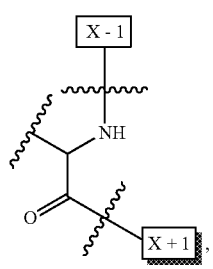

X-1 indicates the point of attachment to the preceding amino acid residue; and
X+1 indicates the point of attachment to the following amino acid residue.

Embodiment 314. The IL-2 conjugate of any one of embodiments 313-313.1, wherein the position of the structure of Formula (VIII) or (IX), or a mixture of (VIII) and (IX), in the amino acid sequence of the IL-2 conjugate is selected from A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133.

Embodiment 315. The IL-2 conjugate of embodiment 314, wherein the position of the structure of Formula (VIII) or (IX), or a mixture of (VIII) and (IX), in the amino acid sequence of the IL-2 conjugate is selected from K9, H16, L19, D20, M23, N26, N88, V91, I92, L94, E95, K97, G98, S99, E100, D109 in the N88R variant, N119, T123, S125, Q126, S127, S130, and T131.

Embodiment 316. The IL-2 conjugate of embodiment 315, wherein the position of the structure of Formula (VIII) or (IX), or a mixture of (VIII) and (IX), in the amino acid sequence of the IL-2 conjugate is selected from K9, H16, L19, D20, M23, N26, N88, V91, E100, D109 in the N88R variant, N119, T123, S125, and T131.

Embodiment 317. The IL-2 conjugate of embodiment 316, wherein the position of the structure of Formula (VIII) or (IX), or a mixture of (VIII) and (IX), in the amino acid sequence of the IL-2 conjugate is K9.

Embodiment 318. The IL-2 conjugate of embodiment 316, wherein the position of the structure of Formula (VIII) or (IX), or a mixture of (VIII) and (IX), in the amino acid sequence of the IL-2 conjugate is H16.

Embodiment 319. The IL-2 conjugate of embodiment 316, wherein the position of the structure of Formula (VIII) or (IX), or a mixture of (VIII) and (IX), in the amino acid sequence of the IL-2 conjugate is L19.

Embodiment 320. The IL-2 conjugate of embodiment 316, wherein the position of the structure of Formula (VIII) or (IX), or a mixture of (VIII) and (IX), in the amino acid sequence of the IL-2 conjugate is D20.

Embodiment 321. The IL-2 conjugate of embodiment 316, wherein the position of the structure of Formula (VIII) or (IX), or a mixture of (VIII) and (IX), in the amino acid sequence of the IL-2 conjugate is M23.

Embodiment 322. The IL-2 conjugate of embodiment 316, wherein the position of the structure of Formula (VIII) or (IX), or a mixture of (VIII) and (IX), in the amino acid sequence of the IL-2 conjugate is N26.

Embodiment 323. The IL-2 conjugate of embodiment 316, wherein the position of the structure of Formula (VIII) or (IX), or a mixture of (VIII) and (IX), in the amino acid sequence of the IL-2 conjugate is N88.

Embodiment 324. The IL-2 conjugate of embodiment 316, wherein the position of the structure of Formula (VIII) or (IX), or a mixture of (VIII) and (IX), in the amino acid sequence of the IL-2 conjugate is V91.

Embodiment 325. The IL-2 conjugate of embodiment 316, wherein the position of the structure of Formula (VIII) or (IX), or a mixture of (VIII) and (IX), in the amino acid sequence of the IL-2 conjugate is E100.

Embodiment 326. The IL-2 conjugate of embodiment 316, wherein the position of the structure of Formula (VIII) or (IX), or a mixture of (VIII) and (IX), in the amino acid sequence of the IL-2 conjugate is D109 in the N88R variant.

Embodiment 327. The IL-2 conjugate of embodiment 316, wherein the position of the structure of Formula (VIII) or (IX), or a mixture of (VIII) and (IX), in the amino acid sequence of the IL-2 conjugate is N119.

Embodiment 328. The IL-2 conjugate of embodiment 316, wherein the position of the structure of Formula (VIII) or (IX), or a mixture of (VIII) and (IX), in the amino acid sequence of the IL-2 conjugate is T123.

Embodiment 329. The IL-2 conjugate of embodiment 316, wherein the position of the structure of Formula (VIII) or (IX), or a mixture of (VIII) and (IX), in the amino acid sequence of the IL-2 conjugate is S125.

Embodiment 330. The IL-2 conjugate of embodiment 316, wherein the position of the structure of Formula (VIII) or (IX), or a mixture of (VIII) and (IX), in the amino acid sequence of the IL-2 conjugate is T131.

Embodiment 331. The IL-2 conjugate of any one of embodiments 313 to 330, wherein n is about 75 to about 1000.

Embodiment 332. The IL-2 conjugate of any one of embodiments 313 to 330, wherein n is about 100 to about 1000.

Embodiment 333. The IL-2 conjugate of any one of embodiments 313 to 330, wherein n is about 200 to about 5000.

Embodiment 334. The IL-2 conjugate of any one of embodiments 313 to 330, wherein n is about 500 to about 1000.

Embodiment 335. The IL-2 conjugate of any one of embodiments 313 to 330, wherein n is about 400 to about 800.

Embodiment 336. An IL-2 conjugate comprising the amino acid sequence of SEQ ID NO: 4 in which at least one amino acid residue in the IL-2 conjugate is replaced by the structure of Formula (X) or (XI), or a mixture of (X) and (XI):

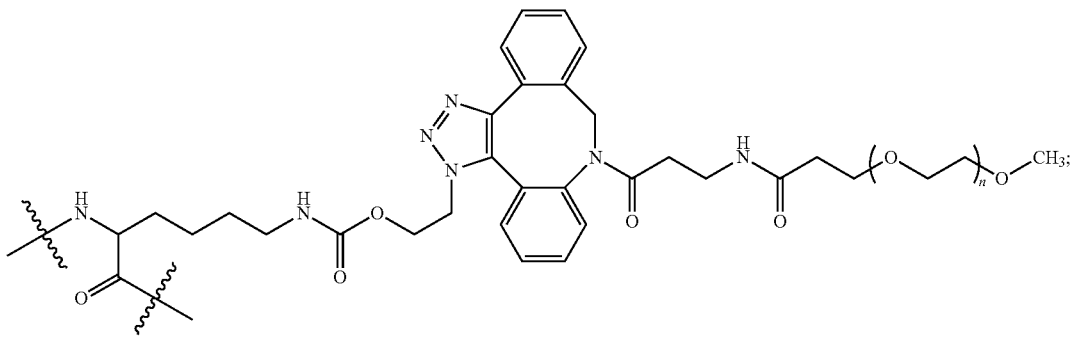

Formula (X)

Formula (XI)

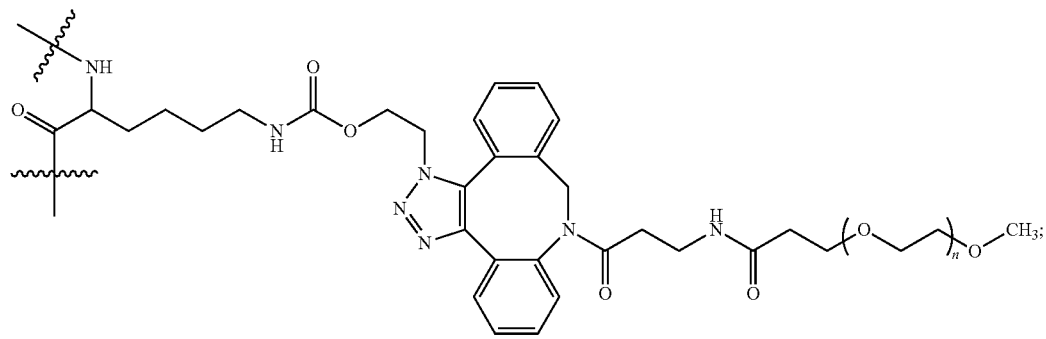

wherein:
n is an integer in the range from about 2 to about 5000; and the wavy lines indicate covalent bonds to amino acid residues within SEQ ID NO: 4 that are not replaced, or a pharmaceutically acceptable salt, solvate, or hydrate thereof.
Embodiment 336.1. An IL-2 conjugate comprising the amino acid sequence of SEQ ID NO: 4 in which at least one amino acid residue in the IL-2 conjugate is replaced by the structure of Formula (X) or (XI), or a mixture of (X) and (XI):

Formula (X)

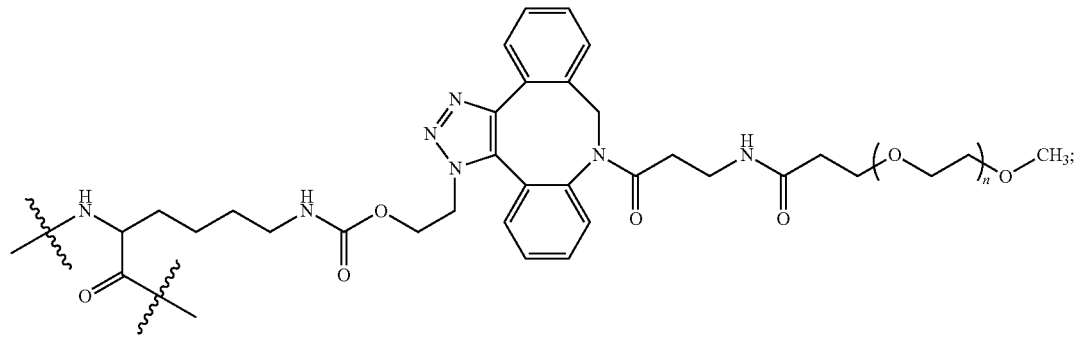

Formula (XI)

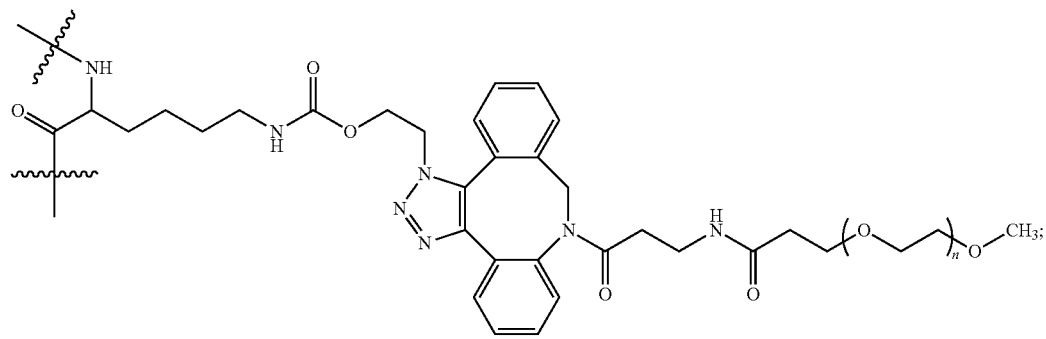

wherein:
n is an integer in the range from about 2 to about 5000; and the wavy lines indicate covalent bonds to amino acid residues within SEQ ID NO: 4 that are not replaced.
Embodiment 337. The IL-2 conjugate of embodiment 336 or 336.1, wherein the position of the structure of Formula (X) or (XI), or a mixture of (X) and (XI), in the amino acid sequence of the IL-2 conjugate is selected from A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133.
Embodiment 338. The IL-2 conjugate of embodiment 337, wherein the position of the structure of Formula (X) or (XI), or a mixture of (X) and (XI), in the amino acid sequence of the IL-2 conjugate is selected from K9, H16, L19, D20, M23, N26, N88, V91, I92, L94, E95, K97, G98, S99, E100, D109 in the N88R variant, N119, T123, S125, Q126, S127, S130, and T131.

Embodiment 339. The IL-2 conjugate of embodiment 338, wherein the position of the structure of Formula (X) or (XI), or a mixture of (X) and (XI), in the amino acid sequence of the IL-2 conjugate is selected from K9, H16, L19, D20, M23, N26, N88, V91, E100, D109 in the N88R variant, N119, T123, S125, and T131.

Embodiment 340. The IL-2 conjugate of embodiment 339, wherein the position of the structure of Formula (X) or (XI), or a mixture of (X) and (XI), in the amino acid sequence of the IL-2 conjugate is K9.

Embodiment 341. The IL-2 conjugate of embodiment 339, wherein the position of the structure of Formula (X) or (XI), or a mixture of (X) and (XI), in the amino acid sequence of the IL-2 conjugate is H16.

Embodiment 342. The IL-2 conjugate of embodiment 339, wherein the position of the structure of Formula (X) or (XI), or a mixture of (X) and (XI), in the amino acid sequence of the IL-2 conjugate is L19.

Embodiment 343. The IL-2 conjugate of embodiment 339, wherein the position of the structure of Formula (X) or (XI), or a mixture of (X) and (XI), in the amino acid sequence of the IL-2 conjugate is D20.

Embodiment 344. The IL-2 conjugate of embodiment 339, wherein the position of the structure of Formula (X) or (XI), or a mixture of (X) and (XI), in the amino acid sequence of the IL-2 conjugate is M23.

Embodiment 345. The IL-2 conjugate of embodiment 339, wherein the position of the structure of Formula (X) or (XI), or a mixture of (X) and (XI), in the amino acid sequence of the IL-2 conjugate is N26.

Embodiment 346. The IL-2 conjugate of embodiment 339, wherein the position of the structure of Formula (X) or (XI), or a mixture of (X) and (XI), in the amino acid sequence of the IL-2 conjugate is N88.

Embodiment 347. The IL-2 conjugate of embodiment 339, wherein the position of the structure of Formula (X) or (XI), or a mixture of (X) and (XI), in the amino acid sequence of the IL-2 conjugate is V91.

Embodiment 348. The IL-2 conjugate of embodiment 339, wherein the position of the structure of Formula (X) or (XI), or a mixture of (X) and (XI), in the amino acid sequence of the IL-2 conjugate is E100.

Embodiment 349. The IL-2 conjugate of embodiment 339, wherein the position of the structure of Formula (X) or (XI), or a mixture of (X) and (XI), in the amino acid sequence of the IL-2 conjugate is D109 in the N88R variant.

Embodiment 350. The IL-2 conjugate of embodiment 339, wherein the position of the structure of Formula (X) or (XI), or a mixture of (X) and (XI), in the amino acid sequence of the IL-2 conjugate is N119.

Embodiment 351. The IL-2 conjugate of embodiment 339, wherein the position of the structure of Formula (X) or (XI), or a mixture of (X) and (XI), in the amino acid sequence of the IL-2 conjugate is T123.

Embodiment 352. The IL-2 conjugate of embodiment 339, wherein the position of the structure of Formula (X) or (XI), or a mixture of (X) and (XI), in the amino acid sequence of the IL-2 conjugate is S125.

Embodiment 353. The IL-2 conjugate of embodiment 339, wherein the position of the structure of Formula (X) or (XI), or a mixture of (X) and (XI), in the amino acid sequence of the IL-2 conjugate is T131.

Embodiment 354. The IL-2 conjugate of any one of embodiments 336 to 353, wherein n is about 75 to about 1000.

Embodiment 355. The IL-2 conjugate of any one of embodiments 336 to 353, wherein n is about 100 to about 1000.

Embodiment 356. The IL-2 conjugate of any one of embodiments 336 to 353, wherein n is about 200 to about 5000.

Embodiment 357. The IL-2 conjugate of any one of embodiments 336 to 353, wherein n is about 500 to about 1000.

Embodiment 358. The IL-2 conjugate of any one of embodiments 336 to 353, wherein n is about 400 to about 800.

Embodiment 359. An IL-2 conjugate comprising the amino acid sequence of SEQ ID NO: 4 in which at least one amino acid residue in the IL-2 conjugate is replaced by the structure of Formula (XII) or (XIII), or a mixture of (XII) and (XIII):

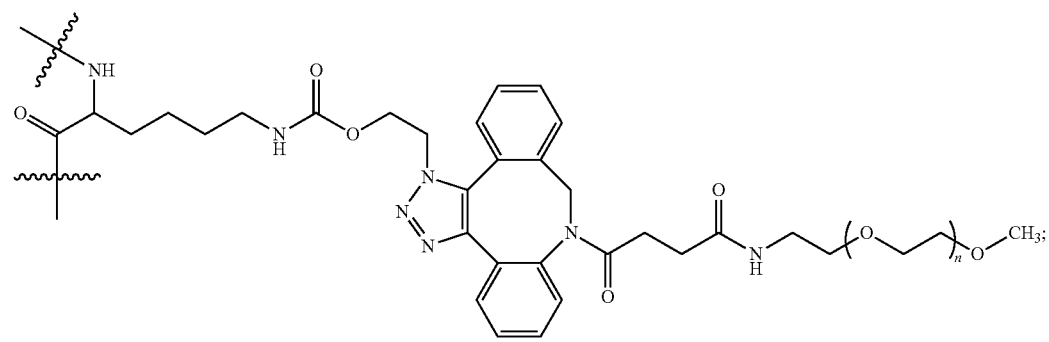

Formula (XII)

-continued

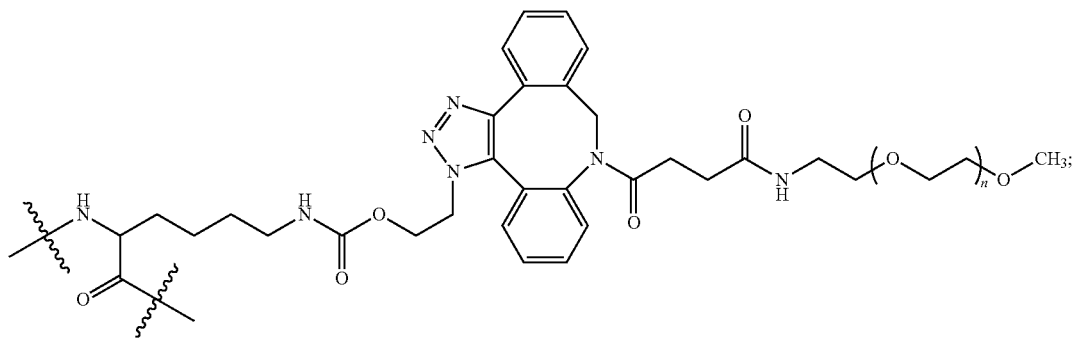

Formula (XIII)

wherein:
n is an integer in the range from about 2 to about 5000; and the wavy lines indicate covalent bonds to amino acid residues within SEQ ID NO: 4 that are not replaced, or a pharmaceutically acceptable salt, solvate, or hydrate thereof.

Embodiment 359.1. An IL-2 conjugate comprising the amino acid sequence of SEQ ID NO: 4 in which at least one amino acid residue in the IL-2 conjugate is replaced by the structure of Formula (XII) or (XIII), or a mixture of (XII) and (XIII):

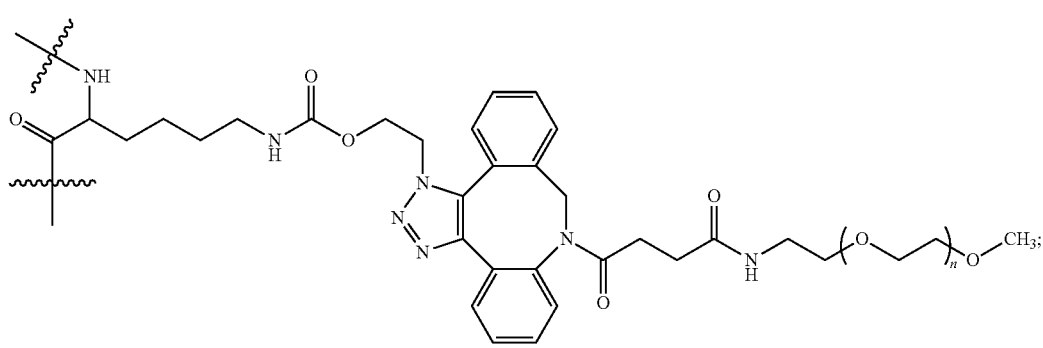

Formula (XII)

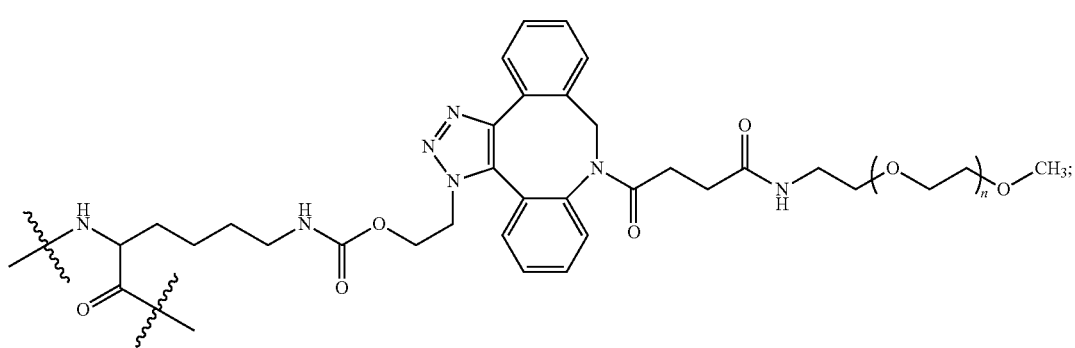

Formula (XIII)

wherein:
n is an integer in the range from about 2 to about 5000; and the wavy lines indicate covalent bonds to amino acid residues within SEQ ID NO: 4 that are not replaced.

Embodiment 360. The IL-2 conjugate of embodiment 359 or 359.1, wherein the position of the structure of Formula (XII) or (XIII), or a mixture of (XII) and (XIII), in the amino acid sequence of the IL-2 conjugate is selected from A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, and T133.

Embodiment 361. The IL-2 conjugate of embodiment 360, wherein the position of the structure of Formula (XII) or (XIII), or a mixture of (XII) and (XIII), in the amino acid sequence of the IL-2 conjugate is selected from K9, H16, L19, D20, M23, N26, N88, V91, I92, L94, E95, K97, G98, S99, E100, D109 in the N88R variant, N119, T123, S125, Q126, S127, S130, and T131.

Embodiment 362. The IL-2 conjugate of embodiment 361, wherein the position of the structure of Formula (XII) or (XIII), or a mixture of (XII) and (XIII), in the amino acid sequence of the IL-2 conjugate is selected from K9, H16, L19, D20, M23, N26, N88, V91, E100, D109 in the N88R variant, N119, T123, S125, and T131.

Embodiment 363. The IL-2 conjugate of embodiment 362, wherein the position of the structure of Formula (XII) or (XIII), or a mixture of (XII) and (XIII), in the amino acid sequence of the IL-2 conjugate is K9.

Embodiment 364. The IL-2 conjugate of embodiment 362, wherein the position of the structure of Formula (XII) or (XIII), or a mixture of (XII) and (XIII), in the amino acid sequence of the IL-2 conjugate is H16.

Embodiment 365. The IL-2 conjugate of embodiment 362, wherein the position of the structure of Formula (XII) or (XIII), or a mixture of (XII) and (XIII), in the amino acid sequence of the IL-2 conjugate is L19.

Embodiment 366. The IL-2 conjugate of embodiment 362, wherein the position of the structure of Formula (XII) or (XIII), or a mixture of (XII) and (XIII), in the amino acid sequence of the IL-2 conjugate is D20.

Embodiment 367. The IL-2 conjugate of embodiment 362, wherein the position of the structure of Formula (XII) or (XIII), or a mixture of (XII) and (XIII), in the amino acid sequence of the IL-2 conjugate is M23.

Embodiment 368. The IL-2 conjugate of embodiment 362, wherein the position of the structure of Formula (XII) or (XIII), or a mixture of (XII) and (XIII), in the amino acid sequence of the IL-2 conjugate is N26.

Embodiment 369. The IL-2 conjugate of embodiment 362, wherein the position of the structure of Formula (XII) or (XIII), or a mixture of (XII) and (XIII), in the amino acid sequence of the IL-2 conjugate is N88.

Embodiment 370. The IL-2 conjugate of embodiment 362, wherein the position of the structure of Formula (XII) or (XIII), or a mixture of (XII) and (XIII), in the amino acid sequence of the IL-2 conjugate is V91.

Embodiment 371. The IL-2 conjugate of embodiment 362, wherein the position of the structure of Formula (XII) or (XIII), or a mixture of (XII) and (XIII), in the amino acid sequence of the IL-2 conjugate is E100.

Embodiment 372. The IL-2 conjugate of embodiment 362, wherein the position of the structure of Formula (XII) or (XIII), or a mixture of (XII) and (XIII), in the amino acid sequence of the IL-2 conjugate is D109 in the N88R variant.

Embodiment 373. The IL-2 conjugate of embodiment 362, wherein the position of the structure of Formula (XII) or (XIII), or a mixture of (XII) and (XIII), in the amino acid sequence of the IL-2 conjugate is N119.

Embodiment 374. The IL-2 conjugate of embodiment 362, wherein the position of the structure of Formula (XII) or (XIII), or a mixture of (XII) and (XIII), in the amino acid sequence of the IL-2 conjugate is T123.

Embodiment 375. The IL-2 conjugate of embodiment 362, wherein the position of the structure of Formula (XII) or (XIII), or a mixture of (XII) and (XIII), in the amino acid sequence of the IL-2 conjugate is S125.

Embodiment 376. The IL-2 conjugate of embodiment 362, wherein the position of the structure of Formula (XII) or (XIII), or a mixture of (XII) and (XIII), in the amino acid sequence of the IL-2 conjugate is T131.

Embodiment 377. The IL-2 conjugate of any one of embodiments 359 to 376, wherein n is about 75 to about 1000.

Embodiment 378. The IL-2 conjugate of any one of embodiments 359 to 376, wherein n is about 100 to about 1000.

Embodiment 379. The IL-2 conjugate of any one of embodiments 359 to 376, wherein n is about 200 to about 5000.

Embodiment 380. The IL-2 conjugate of any one of embodiments 359 to 376, wherein n is about 500 to about 1000.

Embodiment 381. The IL-2 conjugate of any one of embodiments 359 to 376, wherein n is about 400 to about 800.

Embodiment 382. A method of treating an autoimmune disease in a subject, comprising administering to a subject in need thereof a therapeutically effective amount of an IL-2 conjugate according to any one of embodiments 1 to 381.

Embodiment 383. The method of embodiment 382, wherein the autoimmune disease is selected from the group consisting of graft versus host disease (GVHD), atopic dermatitis, Crohn's disease, alopecia areata, autoimmune hemolytic anemia, autoimmune hepatitis, dermatomyositis, type 1 diabetes, juvenile/pediatric type 1 diabetes, juvenile idiopathic arthritis, glomerulonephritis, Graves' disease, Guillain-Barré syndrome, idiopathic thrombocytopenic purpura, myasthenia gravis, multiple sclerosis, pemphigus/pemphigoid, pernicious anemia, polyarteritis nodosa, polymyositis, primary biliary cholangitis, primary biliary cirrhosis, nonalcoholic steatohepatitis (NASH), psoriasis, rheumatoid arthritis, scleroderma, CREST syndrome, Sjögren's syndrome, systemic lupus erythematosus, thyroiditis, uveitis, vitiligo, Wegener's granulomatosis, Addison's disease (adrenal insufficiency), Hashimoto thyroiditis, autoimmune hepatitis, infertility, ANCA-associated vasculitis, psoriatic arthritis, Celiac disease, ulcerative colitis, lichen sclerosus, and Behcet's disease.

Embodiment 384. The method of embodiment 383, wherein the autoimmune disease is selected from the group consisting of graft versus host disease (GVHD), atopic dermatitis, Crohn's disease, type 1 diabetes, multiple sclerosis, rheumatoid arthritis, myasthenia gravis, primary biliary cirrhosis, nonalcoholic steatohepatitis (NASH), glomerulonephritis, idiopathic thrombocytopenic purpura, systemic lupus erythematosus, scleroderma, CREST syndrome, psoriasis, Celiac disease, ulcerative colitis, pemphigus, psoriatic arthritis, and infertility.

Embodiment 385. The method of embodiment 384, wherein the autoimmune disease is graft versus host disease (GVHD).

Embodiment 386. The method of embodiment 384, wherein the autoimmune disease is atopic dermatitis.

Embodiment 387. The method of embodiment 384, wherein the autoimmune disease is Crohn's disease.

Embodiment 388. The method of embodiment 384, wherein the autoimmune disease is type 1 diabetes.

Embodiment 389. The method of embodiment 384, wherein the autoimmune disease is multiple sclerosis.

Embodiment 390. The method of embodiment 384, wherein the autoimmune disease is rheumatoid arthritis.

Embodiment 391. The method of embodiment 384, wherein the autoimmune disease is myasthenia gravis.

Embodiment 392. The method of embodiment 384, wherein the autoimmune disease is primary biliary cholangitis or primary biliary cirrhosis.

Embodiment 393. The method of embodiment 384, wherein the autoimmune disease is nonalcoholic steatohepatitis (NASH).

Embodiment 394. The method of embodiment 384, wherein the autoimmune disease is glomerulonephritis.

Embodiment 395. The method of embodiment 384, wherein the autoimmune disease is idiopathic thrombocytopenic purpura.
Embodiment 396. The method of embodiment 384, wherein the autoimmune disease is systemic lupus erythematosus.
Embodiment 397. The method of embodiment 384, wherein the autoimmune disease is scleroderma.
Embodiment 398. The method of embodiment 384, wherein the autoimmune disease is CREST syndrome.
Embodiment 399. The method of embodiment 384, wherein the autoimmune disease is infertility.
Embodiment 400. The method of any one of embodiments 382 to 399, wherein the IL-2 conjugate is administered to the subject in need thereof once per week, once every two weeks, once every three weeks, once every 4 weeks, once every 5 weeks, once every 6 weeks, once every 7 weeks, or once every 8 weeks.
Embodiment 401. The method of embodiment 400, wherein the IL-2 conjugate is administered to the subject in need thereof once per week, once every two weeks, once every three weeks, or once every 4 weeks.
Embodiment 402. The method of embodiment 401, wherein the IL-2 conjugate is administered to the subject in need thereof once per week.
Embodiment 403. The method of embodiment 401, wherein the IL-2 conjugate is administered to the subject in need thereof once every two weeks.
Embodiment 404. The method of embodiment 401, wherein the IL-2 conjugate is administered to the subject in need thereof once every three weeks.
Embodiment 405. The method of embodiment 401, wherein the IL-2 conjugate is administered to the subject in need thereof once every four weeks.
Embodiment 406. The method of any one of embodiments 382 to 405, wherein the subject in need thereof is determined to exhibit an increased concentration of rheumatoid factor in the blood of the subject prior to administration to the subject of the therapeutically effective amount of the IL-2 conjugate.
Embodiment 407. The method of embodiment 406, wherein the increased concentration of rheumatoid factor in the blood of the subject is about 14 IU/mL or higher, or about 15 IU/mL or higher.
Embodiment 408. The method of embodiment 407, wherein the increased concentration of rheumatoid factor in the blood of the subject is about 14 IU/mL or higher.
Embodiment 409. The method of embodiment 407, wherein the increased concentration of rheumatoid factor in the blood of the subject is about 15 IU/mL or higher.
Embodiment 410. A method of treating rheumatoid arthritis in a subject in need thereof, comprising:
(a) determining the concentration of rheumatoid factor in the blood of the subject; and
(b) administering to the subject in need thereof a therapeutically effective amount of an IL-2 conjugate according to any one of embodiments 1 to 381 if the concentration of rheumatoid factor in the blood of the subject is greater than about 14 IU/mL.
Embodiment 411. The method of embodiment 410, wherein a therapeutically effective amount of the IL-2 conjugate is administered to the subject in need thereof if the concentration of rheumatoid factor in the blood of the subject is greater than about 15 IU/mL.
Embodiment 412. A method of treating rheumatoid arthritis in a subject in need thereof, comprising administering to the subject in need thereof a therapeutically effective amount of an IL-2 conjugate according to any one of embodiments 1 to 381 if the concentration of rheumatoid factor in the blood of the subject is determined to be greater than about 14 IU/mL.
Embodiment 413. A method of treating rheumatoid arthritis in a subject in need thereof, comprising administering to the subject in need thereof a therapeutically effective amount of an IL-2 conjugate according to any one of embodiments 1 to 381 if the concentration of rheumatoid factor in the blood of the subject is determined to be greater than about 15 IU/mL.
Embodiment 414. The method of any one of embodiments 382 to 405, wherein the subject in need thereof is determined to exhibit an abnormal erythrocyte sedimentation rate (ESR) test prior to administration to the subject of the therapeutically effective amount of the IL-2 conjugate.
Embodiment 414.1. The method of any one of embodiments 382 to 405, wherein the subject in need thereof is determined to exhibit an abnormal erythrocyte sedimentation rate (ESR) test, optionally using the Westergren rate method or the Wintrobe rate method, prior to administration to the subject of the therapeutically effective amount of the IL-2 conjugate.
Embodiment 415. The method of any one of embodiments 414-414.1, wherein the subject is determined to exhibit an abnormal erythrocyte sedimentation rate (ESR) test using the Westergren rate method prior to administration to the subject of the therapeutically effective amount of the IL-2 conjugate.
Embodiment 416. The method of any one of embodiments 414-414.1, wherein the subject is determined to exhibit an abnormal erythrocyte sedimentation rate (ESR) test using the Wintrobe rate method prior to administration to the subject of the therapeutically effective amount of the IL-2 conjugate.
Embodiment 417. The method of any one of embodiments 414 to 416, wherein the subject is a woman under age 50 and exhibits a Westergren rate greater than about 20 mm/hr.
Embodiment 418. The method of any one of embodiments 414 to 416, wherein the subject is a woman greater than age 50 and exhibits a Westergren rate greater than about 30 mm/hr.
Embodiment 419. The method of any one of embodiments 414 to 416, wherein the subject is a man under age 50 and exhibits a Westergren rate greater than about 15 mm/hr.
Embodiment 420. The method of any one of embodiments 414 to 416, wherein the subject is a man greater than age 50 and exhibits a Westergren rate greater than about 20 mm/hr.
Embodiment 421. The method of any one of embodiments 414 to 416, wherein the subject is a child and exhibits a Westergren rate greater than about 10 mm/hr.
Embodiment 422. A method of treating an autoimmune disease in a subject in need thereof, comprising:
(a) determining the erythrocyte sedimentation rate (ESR) in the subject; and
(b) administering to the subject in need thereof a therapeutically effective amount of an IL-2 conjugate according to any one of embodiments 1 to 381 if the ESR is determined to be abnormal.
Embodiment 423. The method of embodiment 422, wherein the subject is determined to exhibit an abnormal erythrocyte sedimentation rate (ESR) test using the Wintrobe rate method
Embodiment 424. The method of embodiment 422, wherein the subject is determined to exhibit an abnormal erythrocyte sedimentation rate (ESR) test using the Westergren rate method.
Embodiment 425. The method of embodiment 424, wherein the subject is a woman under age 50 and exhibits a Westergren rate greater than about 20 mm/hr.

Embodiment 426. The method of embodiment 424, wherein the subject is a woman greater than age 50 and exhibits a Westergren rate greater than about 30 mm/hr.
Embodiment 427. The method of embodiment 424, wherein the subject is a man under age 50 and exhibits a Westergren rate greater than about 15 mm/hr.
Embodiment 428. The method of embodiment 424, wherein the subject is a man greater than age 50 and exhibits a Westergren rate greater than 20 mm/hr.
Embodiment 429. The method of embodiment 424, wherein the subject is a child and exhibits a Westergren rate greater than about 10 mm/hr.
Embodiment 430. The method of any one of embodiments 382 to 405, wherein the subject in need thereof is determined to exhibit an increased concentration of C-reactive protein (CRP) in the blood of the subject prior to administration to the subject the therapeutically effective amount of the IL-2 conjugate.
Embodiment 431. The method of embodiment 430, wherein the subject in need thereof is determined to exhibit a concentration of C-reactive protein (CRP) in the blood greater than 10 mg/L prior to administration to the subject the therapeutically effective amount of the IL-2 conjugate.
Embodiment 432. A method of treating an autoimmune disease in a subject in need thereof, comprising:
(a) determining the concentration of C-reactive protein (CRP) in the blood of the subject; and
(b) administering to the subject in need thereof a therapeutically effective amount of an IL-2 conjugate according to any one of embodiments 1 to 381 if the concentration of C-reactive protein (CRP) in the blood of the subject is determined to be abnormal.
Embodiment 433. The method of embodiment 68, wherein the subject in need thereof is determined to exhibit a concentration of C-reactive protein (CRP) in the blood greater than 10 mg/L prior to administration to the subject of the therapeutically effective amount of the IL-2 conjugate.
Embodiment 434. A method of treating rheumatoid arthritis in a subject in need thereof, comprising:
(a) determining the concentration of anti-cyclic citrullinated peptide (anti-CCP) in the blood of the subject; and
(b) administering to the subject in need thereof a therapeutically effective amount of an IL-2 conjugate according to any one of embodiments 1 to 381 if the concentration of rheumatoid factor in the subject is determined to be abnormal.
Embodiment 435. The method of embodiment 434, wherein a therapeutically effective amount of the IL-2 conjugate is administered to the subject in need thereof if the concentration of anti-cyclic citrullinated peptide (anti-CCP) in the blood of the subject is determined to be greater than about 20 Iu/mL.
Embodiment 436. A method of treating rheumatoid arthritis in a subject in need thereof, comprising administering to the subject in need thereof a therapeutically effective amount of an IL-2 conjugate according to any one of embodiments 1 to 381 if the concentration of anti-cyclic citrullinated peptide (anti-CCP) in the blood of the subject is determined to be abnormal.
Embodiment 437. A method of treating rheumatoid arthritis in a subject in need thereof, comprising administering to the subject in need thereof a therapeutically effective amount of an IL-2 conjugate according to any one of embodiments 1 to 381 if the concentration of anti-cyclic citrullinated peptide (anti-CCP) in the blood of the subject is determined to be greater than about 20 Iu/mL.
Embodiment 438. The method of embodiment 384, wherein the autoimmune disease is psoriasis.
Embodiment 439. The method of embodiment 384, wherein the autoimmune disease is Celiac disease.
Embodiment 440. The method of embodiment 384, wherein the autoimmune disease is ulcerative colitis.
Embodiment 441. The method of embodiment 384, wherein the autoimmune disease is pemphigus.
Embodiment 442. The IL-2 conjugate of any one of embodiments 93-93.1, wherein the IL-2 conjugate has the amino acid sequence of SEQ ID NO: 64.
Embodiment 443. The IL-2 conjugate of any one of embodiments 93-93.1, wherein the IL-2 conjugate has the amino acid sequence of SEQ ID NO: 65.
Embodiment 444. The IL-2 conjugate of any one of embodiments 93-93.1, wherein the IL-2 conjugate has the amino acid sequence of SEQ ID NO: 66.
Embodiment 445. The IL-2 conjugate of any one of embodiments 93-93.1, wherein the IL-2 conjugate has the amino acid sequence of SEQ ID NO: 67.
Embodiment 446. The IL-2 conjugate of any one of embodiments 93-93.1, wherein the IL-2 conjugate has the amino acid sequence of SEQ ID NO: 68.
Embodiment 447. The IL-2 conjugate of any one of embodiments 93-93.1, wherein the IL-2 conjugate has the amino acid sequence of SEQ ID NO: 69.
Embodiment 448. The IL-2 conjugate of any one of embodiments 93-93.1, wherein the IL-2 conjugate has the amino acid sequence of SEQ ID NO: 70.
Embodiment 449. The IL-2 conjugate of any one of embodiments 93-93.1, wherein the IL-2 conjugate has the amino acid sequence of SEQ ID NO: 71.
Embodiment 450. The IL-2 conjugate of any one of embodiments 93-93.1, wherein the IL-2 conjugate has the amino acid sequence of SEQ ID NO: 72.
Embodiment 451. The IL-2 conjugate of any one of embodiments 93-93.1, wherein the IL-2 conjugate has the amino acid sequence of SEQ ID NO: 73.
Embodiment 452. The IL-2 conjugate any one of embodiments 93-93.1, wherein the IL-2 conjugate has the amino acid sequence of SEQ ID NO: 74.
Embodiment 453. The IL-2 conjugate of any one of embodiments 93-93.1, wherein the IL-2 conjugate has the amino acid sequence of SEQ ID NO: 75.
Embodiment 454. The IL-2 conjugate of any one of embodiments 93-93.1, wherein the IL-2 conjugate has the amino acid sequence of SEQ ID NO: 76.
Embodiment 455. The IL-2 conjugate of any one of embodiments 93-93.1, wherein the IL-2 conjugate has the amino acid sequence of SEQ ID NO: 77.
Embodiment 456. The IL-2 conjugate of any one of embodiments 155-155.1, wherein the IL-2 conjugate has the amino acid sequence of SEQ ID NO: 170.
Embodiment 457. The IL-2 conjugate of any one of embodiments 167-167.1, wherein the IL-2 conjugate has the amino acid sequence of SEQ ID NO: 185.
Embodiment 458. The IL-2 conjugate of any one of embodiments 167-167.1, wherein the IL-2 conjugate has the amino acid sequence of SEQ ID NO: 190.
Embodiment 459. The IL-2 conjugate of any one of embodiments 167-167.1, wherein the IL-2 conjugate has the amino acid sequence of SEQ ID NO: 197.
Embodiment 460. A method of making an IL-2 conjugate, comprising:
reacting an IL-2 polypeptide comprising an unnatural amino acid of formula

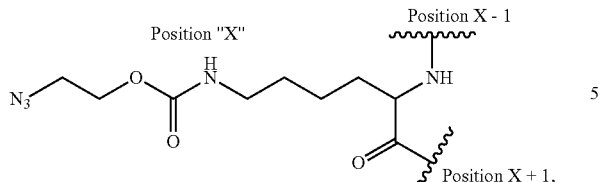

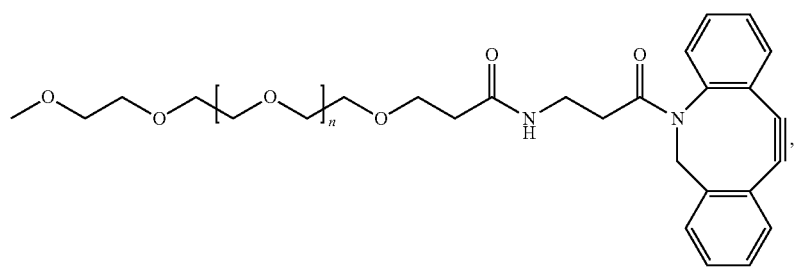

mPEG-DBCO wherein the IL-2 polypeptide comprises the amino acid sequence of SEQ ID NO: 3 or 4 in which at least one amino acid residue in the IL-2 polypeptide is replaced by the unnatural amino acid, Position X−1 indicates the point of attachment to the preceding amino acid residue, Position X+1 indicates the point of attachment to the following amino acid residue, and Position X indicates the position of the amino acid for which the unnatural amino acid substitutes,
with an mPEG-DBCO of formula wherein n is such that the mPEG-DBCO comprises a PEG having a molecular weight of about 5 kDa, 10 kDa, 15 kDa, 20 kDa, 25 kDa, 30 kDa, 35 kDa, 40 kDa, 45 kDa, or 50 kDa, thereby producing the IL-2 conjugate.

Embodiment 461. The method of embodiment 460, wherein Position X is P1, T2, S3, S4, S5, T6, K7, K8, Q10, L11, E14, H15, L17, L18, D19, Q21, M22, N25, G26, N28, N29, Y30, K31, K34, T36, M45, P46, K47, A49, T50, E51, L52, K53, H54, Q56, E59, E66, N70, Q73, S74, K75, N76, F77, H78, R80, P81, R82, D83, S86, N87, I88, V90, I91, L93, E94, K96, G97, S98, E99, T100, T101, F102, M103, C104, E105, Y106, A107, D108, D108 in the N87R variant, E109, T110, A111, T112, E115, N118, R119, T122, F123, S124, Q125, S126, S129, T130, L131, or T132, in reference to the amino acid positions within SEQ ID NO: 3.

Embodiment 462. The method of embodiment 460, wherein Position X is A1, P2, T3, S4, S5, S6, T7, K8, K9, Q11, L12, E15, H16, L18, L19, D20, Q22, M23, N26, G27, N29, N30, Y31, K32, K35, T37, M46, P47, K48, A50, T51, E52, L53, H55, Q57, E60, E67, N71, Q74, S75, K76, N77, F78, H79, R81, P82, R83, D84, S87, N88, I89, V91, I92, L94, E95, K97, G98, S99, E100, T101, T102, F103, M104, C105, E106, Y107, A108, D109, D109 in the N88R variant, E110, T111, A112, T113, E116, N119, R120, T123, S125, Q126, S127, S130, T131, L132, or T133, in reference to the amino acid positions within SEQ ID NO: 4.

Embodiment 463. The method of any one of embodiments 460-462, wherein the IL-2 polypeptide comprises the amino acid sequence of SEQ ID NO: 3 or 4 in which at least one amino acid residue in the IL-2 polypeptide is replaced by the unnatural amino acid.

Embodiment 464. The method of any one of embodiments 460-463, wherein the PEG has a molecular weight of about 30 kDa.

Embodiment 465. The method of any one of embodiments 460-463, wherein the PEG has a molecular weight of about 50 kDa.

Embodiment 466. The method of embodiments 460, wherein the IL-2 conjugate is the IL-2 conjugate of any one of embodiments 1-381 or 442-459.

EXAMPLES

These examples are provided for illustrative purposes only and not to limit the scope of the claims provided herein.

Each of the compounds disclosed in Example 1 utilized SEQ ID NO: 4 and the [AzK_PEG] moiety, wherein the position of the substituted amino acid in the IL-2 conjugate is in reference to the positions in SEQ ID NO: 4.

For example, the compound labelled "K9_30 kDa" in Table 3, was prepared using methods similar to those disclosed in Example 1, wherein a protein was first prepared having SEQ ID NO: 4 in which the proline at position 9 was replaced by AzK. The AzK-containing protein was then allowed to react under click chemistry conditions with DBCO comprising a methoxy, linear PEG group having an average molecular weight of 30 kDa to afford a product having SEQ ID NO: 20 comprising Formula (II), Formula (III), or a mixture of Formula (II) and (III), wherein W is a methoxy, linear PEG group having an average molecular weight of 30 kDa.

In another example, the compound labelled "H16_30 kDa" in Table 3 was prepared by first preparing a protein having SEQ ID NO: 4 in which the proline at position 16 was replaced by AzK. The AzK-containing protein was then allowed to react under click chemistry conditions with DBCO comprising a methoxy, linear PEG group having an average molecular weight of 30 kDa to afford a product having SEQ ID NO: 21 comprising Formula (II), Formula (III), or a mixture of Formula (II) and (III), wherein W is a methoxy, linear PEG group having an average molecular weight of 30 kDa.

In another example, the compound labelled "N26_30 kDa" in Table 3 was prepared by first preparing a protein having SEQ ID NO: 4 in the glutamic acid at position 26 was replaced by AzK. The AzK-containing protein was then allowed to react under click chemistry conditions with DBCO comprising a methoxy, linear PEG group having an average molecular weight of 30 kDa to afford a product having SEQ ID NO: 25 comprising Formula (II), Formula (III), or a mixture of Formula (II) and (III), wherein W is a methoxy, linear PEG group having an average molecular weight of 30 kDa.

An exemplary detailed procedure for preparing IL-2 compounds used herein is as follows. The IL-2 conjugates are expressed as inclusion bodies in *E. coli* using methods disclosed herein wherein expression plasmids encoding the protein with the desired amino acid sequence are prepared that contain (a) an unnatural base pair comprising a first unnatural nucleotide and a second unnatural nucleotide to provide a codon at the desired position at which an unnatural amino acid N6-((2-azidoethoxy)-carbonyl)-L-lysine (AzK) is incorporated and a matching anticodon in a tRNA, (b) a plasmid encoding a tRNA derived from *M. mazei* Pyl and which comprises an unnatural nucleotide to provide a matching anticodon in place of its native sequence, (c) a plasmid encoding a *M. barkeri* derived pyrrolysyl-tRNA synthetase (Mb PylRS), and (d) N6-((2-azidoethoxy)-carbonyl)-L-lysine (AzK). The double-stranded oligonucleotide that encodes the amino acid sequence of the desired IL-2 variant contain a codon AXC at, for example, position 1, 2, 3, 4, 5, 6, 7, 8, 10, 11, 14, 15, 17, 18, 19, 21, 22, 25, 26, 28, 29, 30, 31, 34, 36, 45, 46, 47, 49, 50, 51, 52, 53, 54, 56, 59, 66, 70, 73, 74, 75, 76, 77, 78, 80, 81, 82, 83, 86, 87, 88, 90, 91, 93, 94, 96, 97, 98, 99, 100, 101, 102, 103, 104, 105, 106, 107, 108, 108 in the N87R variant, 109, 110, 111, 112, 115, 118, 119, 122, 123, 124, 125, 126, 129, 130, 131, or 132 of the sequence that encodes the protein having SEQ ID NO: 3, or at position 2, 3, 4, 5, 6, 7, 8, 9, 11, 12, 15, 16, 18, 19, 20, 22, 23, 26, 27, 29, 30, 31, 32, 35, 37, 46, 47, 48, 50, 51, 52, 53, 55, 57, 60, 67, 71, 74, 75, 76, 77, 78, 79, 81, 82, 83, 84, 87, 88, 89, 91, 92, 94, 95, 97, 98, 99, 100, 101, 102, 103, 104, 105, 106, 107, 108, 109, 109 in the N88R variant, 110, 111, 112, 113, 116, 119, 120, 123, 125, 126, 127, 130, 131, 132, or 133 of the sequence that encodes the protein having SEQ ID NO: 4, wherein X is an unnatural nucleotide as disclosed herein. In some embodiments, the cell further comprises a plasmid, which may be the protein expression plasmid or another plasmid, that encodes an orthogonal tRNA gene from *M. mazei* that comprises an AXC-matching anticodon GYT in place of its native sequence, wherein Y is an unnatural nucleotide as disclosed herein and that may be the same or different as the unnatural nucleotide in the codon. X and Y are selected from unnatural nucleotides dTPT3, dNaM and dCNMO as disclosed herein. The expressed protein is purified and re-folded using standard procedures before site-specifically pegylating the AzK-containing IL-2 product using DBCO-mediated copper-free click chemistry to attach stable, covalent mPEG moieties to the AzK (see Scheme 1 below).

Example 1

Ex-Vivo Immune Response Profiling of Exemplary IL-2 Compounds in Primary Human Leukocyte Reduction System (LRS)-Derived PBMC Samples To determine how the differential receptor specificity of exemplary IL-2 compounds affects activation of primary immune cell subpopulations, concentration-response profiling of lymphocyte activation in human LRS-derived peripheral blood mononuclear cell (PBMC) samples were performed using multi-color flow cytometry. Conjugates of Table 3 were synthesized by modification of SEQ ID NO. 1.

Exemplary IL-2 conjugates were subjected to functional analysis are shown in Table 3. The IL-2 conjugates were expressed as inclusion bodies in *E. coli*, purified and re-folded using standard procedures before site-specifically pegylating the IL-2 product using DBCO-mediated copper-free click chemistry to attach stable, covalent mPEG moieties to the AzK (Scheme 1).

Scheme 1.

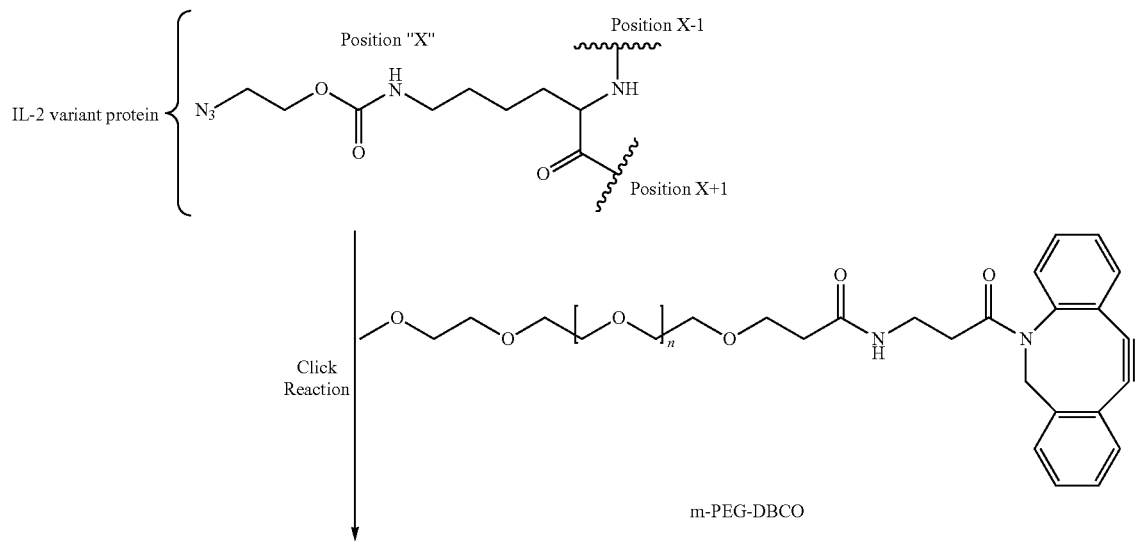

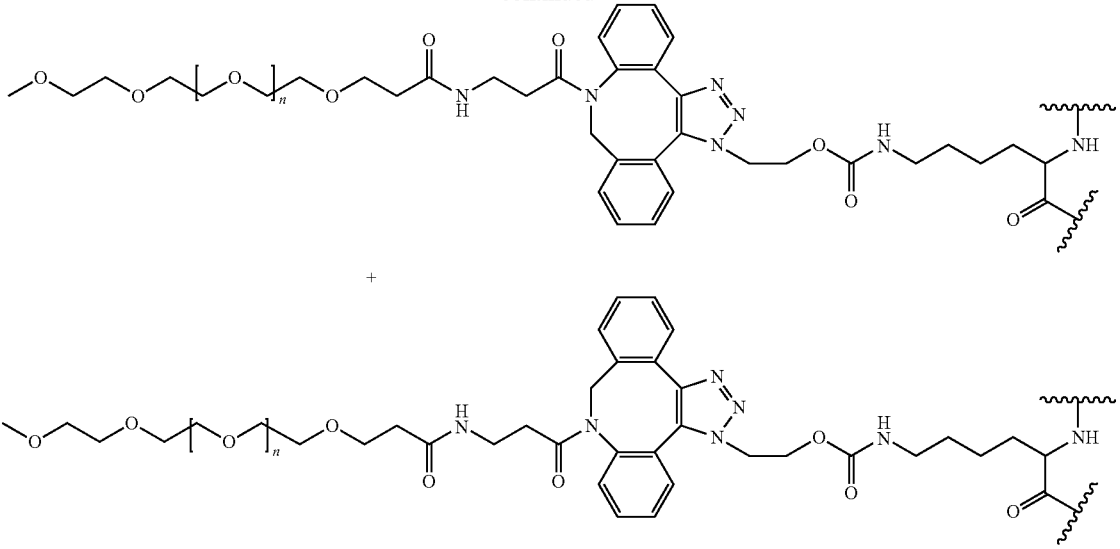

IL-2 AzK_PEG variant proteins

Exemplary synthesis of AzK_PEG interleukin variants (wherein n indicates the number of repeating PEG units). Regioisomers formed from the click reaction are shown.

These studies were performed at PrimityBio LLC (Fremont, CA). Primary lymphocytes derived from human LRS samples were treated with dilutions series of exemplary IL-2 compounds and quantified based on pSTAT5 signaling in each lymphocyte cell type using the panel shown in Table 2.

TABLE 2

Key indicating cell populations

| Marker | Cell population |
|---|---|
| CD3 | T cells |
| CD4 | Th cells |
| CD8 | T effector cells |
| CD45RA | Naive T cells |
| CD56 | NK cells |
| CD14/19 | Monocyte/B cells |
| CD25 | Tregs or experienced T cell |
| CD127 | Not Treg |

TABLE 2-continued

Key indicating cell populations

| Marker | Cell population |
|---|---|
| CD62L | Memory T vs effector memory T cell |
| pSTAT5 (Y694) | Activation marker |

Flow cytometry data were analyzed for activation of different T and NK cell subsets in concentration-response mode, reading pSTAT5 accumulation after treatment with an exemplary IL-2 variant K9_30 kDa.

Figure 4A:
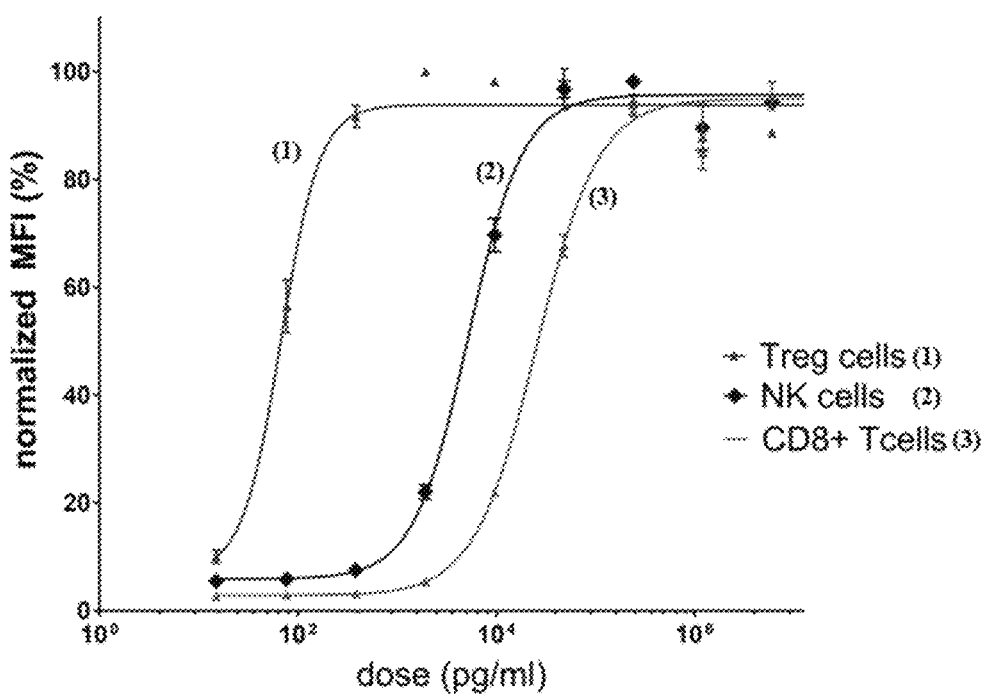
FIGS. 4A-FIG. 4B show the dose response curves of an exemplary IL-2 variant for pSTAT5 signaling in human LRS primary cell (FIG. 4A) and proliferation response in mouse CTLL-2 populations (FIG. 4B).
Figure 4B:
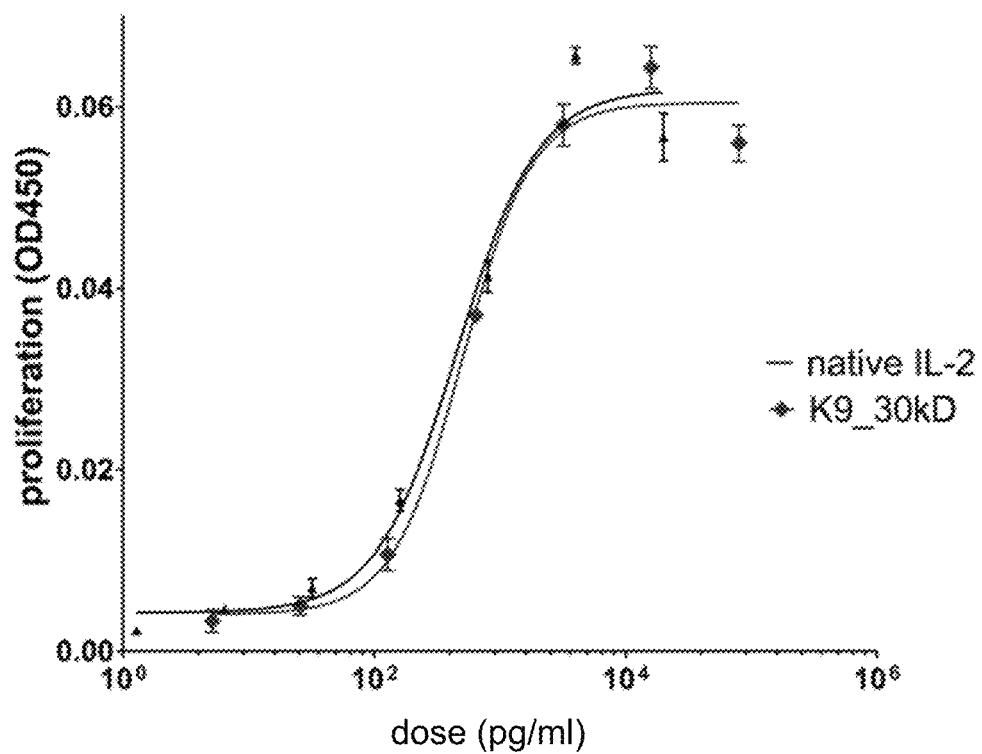

FIG. 4A-FIG. 4B show the dose response curves for pSTAT5 signaling in human LRS primary cell (FIG. 4A) and proliferation response in mouse CTLL-2 populations (FIG. 4B).

Table 3 shows the dose response EC50 for pSTAT5 signaling (EC50) in human LRS samples or CTLL-2 proliferation treated with indicated IL-2 variant.

TABLE 3

Dose response EC50 for pSTAT5 signaling (EC50) in human LRS samples or CTLL-2 proliferation treated with indicated IL-2 variant

| Compound | NK cells | CD8+ Tcells | Treg cells | CD8+/Treg ratio | Fold increase in Treg EC50 vs native IL-2 | CTLL-2 proliferation |
|---|---|---|---|---|---|---|
| native IL-2 | 4586 | 31024 | 75 | 414 | 1 | 455.8 |
| K9_30kDa | 169578 | 1100679 | 2217 | 496 | 30 | 504 |
| H16_30kDa | 2545257 | 12070108 | 34976 | 345 | 466 | 80755 |
| L19_30kDa | 6756768 | 22436430 | 93205 | 241 | 1243 | 3510 |
| D20_30kDa | 2643930 | 9505217 | 1129455 | 8 | 15059 | 689939 |
| M23_30kDa | 143620 | 539824 | 1030 | 524 | 14 | 1102 |
| N26_30kDa | 258531 | 1188859 | 2459 | 483 | 33 | 2594 |
| N88_30kDa | 3298113 | 11111537 | 323201 | 34 | 4309 | 66606 |
| E100_30kDa | 35088 | 195823 | 483 | 405 | 6 | 1676 |
| N119_30kDa | 34010 | 143380 | 535 | 268 | 11 | 1215 |
| T123_30kDa | 33396 | 152928 | 269 | 569 | 6 | 255 |
| Q126_30kDa | 3676807 | 19722480 | 29454 | 670 | 393 | 3584 |
| S127_30kDa | 20210 | 92190 | 150 | 615 | 3 | 123 |
| T131_30kDa | 24207 | 132922 | 258 | 515 | 3 | 641 |
| N88R/D109_30kDa | 2780819 | 12503386 | 175805 | 71 | 3663 | 59577 |

TABLE 3-continued

Dose response EC50 for pSTAT5 signaling (EC50) in human LRS samples or CTLL-2 proliferation treated with indicated IL-2 variant

| Compound | NK cells | CD8+ Tcells | Treg cells | CD8+/Treg ratio | Fold increase in Treg EC50 vs native IL-2 | CTLL-2 proliferation |
|---|---|---|---|---|---|---|
| V91K | 20537 | 102255 | 142 | 720 | 3 | 99.5 |
| N88R | 2312847 | 15025734 | 11082 | 1356 | 148 | 363 |

The EC50 values (pg/ml) were calculated from dose response curves generated from the MFI plots.
*Treg potency change compared to native IL-2 (wild-type IL-2) run in each individual experiment.

Example 2

Design of PEG-IL-2 Conjugates that Preferentially Reduce Signaling on the IL-2 Receptor Beta Gamma Versus the IL-2 R Alpha Beta Gamma Complex To identify sites for PEGylation of the polypeptide of SEQ ID NO. 3 or 4, structural data of the IL-2/heterotrimeric receptor signaling complex (PDB: 2ERJ, [Stauber 2006]) were used to guide design of the IL-2 conjugates. The resulting IL-2 conjugates were prepared as described herein. The proteins comprising the unnatural amino acid N6-((2-azidoethoxy)-carbonyl)-L-lysine (AzK) were expressed as inclusion bodies in *E. coli*, purified and re-folded using procedures known to those of ordinary skill in the art. The proteins comprising AzK were then allowed to react with a DBCO-containing reagent comprising the desired PEG group (e.g., a PEG group having a size selected from 5 kDa, 10 kDa, 15 kDa, 20 kDa, 25 kDa, 30 kDa, 35 kDa, 40 kDa, 45 kDa, 50 kDa, 55 kDa, and 60 kDa) to afford the desired IL-2 conjugate.

Example 3

Design and Screening of PEG-IL-2 Conjugates that Preferentially Reduce Signaling on the IL-2 Receptor Beta Gamma Versus the IL-2 R Alpha Beta Gamma Complex Various IL-2 conjugates having SEQ ID NO: 4 in which an amino acid residue at an indicated position was replaced with a structure of Formula (II), Formula (III), or a mixture of Formula (II) and (III) having the indicated PEG size were screened for functional activity at Discoverx (Fremont CA) using the PathHunter IL-2 Cytokine Receptor assay. For example, the compounds labelled "D20_30" in this example is the compound having SEQ ID NO: 4 in which the structure of Formula (II), Formula (III), or a mixture of Formula (II) and (III) was substituted at the D20 residue (SEQ ID NO: 67) with a PEG group having a molecular weight of 30 kDa. Similarly, the following compounds were tested in this Example:

TABLE 4(a)

| Compound | Structure |
|---|---|
| H16_30 | SEQ ID NO: 4 in which the structure of Formula (II), Formula (III), or a mixture of Formula (II) and (III) was substituted at the H16 residue (SEQ ID NO: 65) with a linear, mPEG group having a molecular weight of 30 kDa |
| D20_30 | SEQ ID NO: 4 in which the structure of Formula (II), Formula (III), or a mixture of Formula (II) and (III) was substituted at the D20 residue (SEQ ID NO: 67) with a linear mPEG group having a molecular weight of 30 kDa |
| N88_30 | SEQ ID NO: 4 in which the structure of Formula (II), Formula (III), or a mixture of Formula (II) and (III) was substituted at the N88 residue (SEQ ID NO: 70) with a linear mPEG group having a molecular weight of 30 kDa |
| L12_30 | SEQ ID NO: 4 in which the structure of Formula (II), Formula (III), or a mixture of Formula (II) and (III) was substituted at the L12 residue (SEQ ID NO: 244) with a linear mPEG group having a molecular weight of 30 kDa |
| E15_30 | SEQ ID NO: 4 in which the structure of Formula (II), Formula (III), or a mixture of Formula (II) and (III) was substituted at the E15 residue (SEQ ID NO: 245) with a linear mPEG group having a molecular weight of 30 kDa |

The assay used a recombinant human U2OS cell line that expresses the IL-2 receptor beta (IL-2Rbeta) and gamma (IL-2Rgamma) subunits, each fused to half of a split reporter enzyme. A second cell line was engineered to express the IL-2Ralpha subunit. Parallel testing with these two cell lines allowed assessment of variant activation of the IL-2 receptor alpha beta gamma as well as the basal beta gamma complex. IL-2 agonist activity on the IL-2 beta gamma receptor complex stimulates receptor dimerization and reporter beta-galactosidase reconstitution that results in a chemiluminescent signal. The assay was run in agonist mode to determine the potency ($EC_{50}$) of each IL-2 conjugate that was tested and the dose-response curve profiles between IL2Ralpha positive and negative cell types for each IL-2 conjugate tested was determined.

Methodology for Discoverx IL-2 Receptor Beta Gamma and Alpha Beta Gamma Agonist Assay PathHunter cell lines were expanded from freezer stocks according to standard procedures. Cells were seeded in a total volume of 20 µL into white walled, 384-well microplates and incubated for the appropriate time prior to testing. For agonist determination, cells were incubated with the IL-2 conjugate to be tested to induce response. Intermediate dilution of sample stocks was performed to generate 5× sample in assay buffer. About 5 µL of 5× sample was added to cells and incubated at 37° C. for a period of from 6 hours to 16 hours depending on the assay. Vehicle concentration was 1%. The assay signal was generated through a single addition of 12.5 or 15 µL (50% v/v) of PathHunter Detection reagent cocktail for agonist and antagonist assays respectively, followed by incubation at room temperature for one hour. For some assays, activity was detected using a high sensitivity detection reagent (PathHunter Flash Kit) to improve assay performance. In these assays, an equal volume of detection reagent (25 µL or 30 µL) was added to the wells, followed incubation at room temperature for one hour. Microplates were read following signal generation with a PerkinElmer Envision instrument for chemiluminescent signal detection.

Figure 5A:
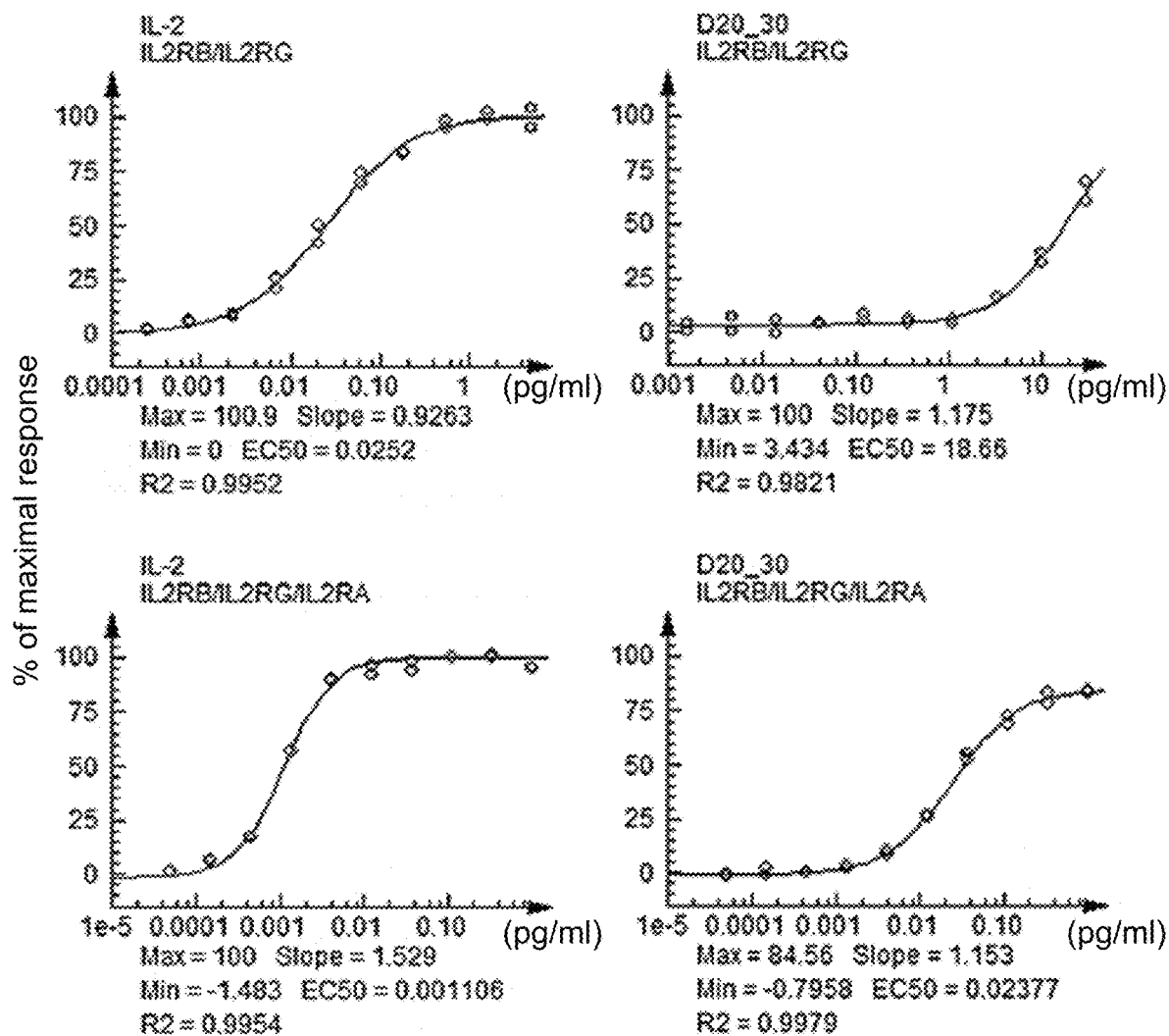
FIGS. 5A-FIG. 5C show plots from a screen for functional activity of IL-2 conjugates at Discoverx (Fremont CA) using the PathHunter IL-2 Cytokine Receptor assay from Example 3.
Figure 5B:
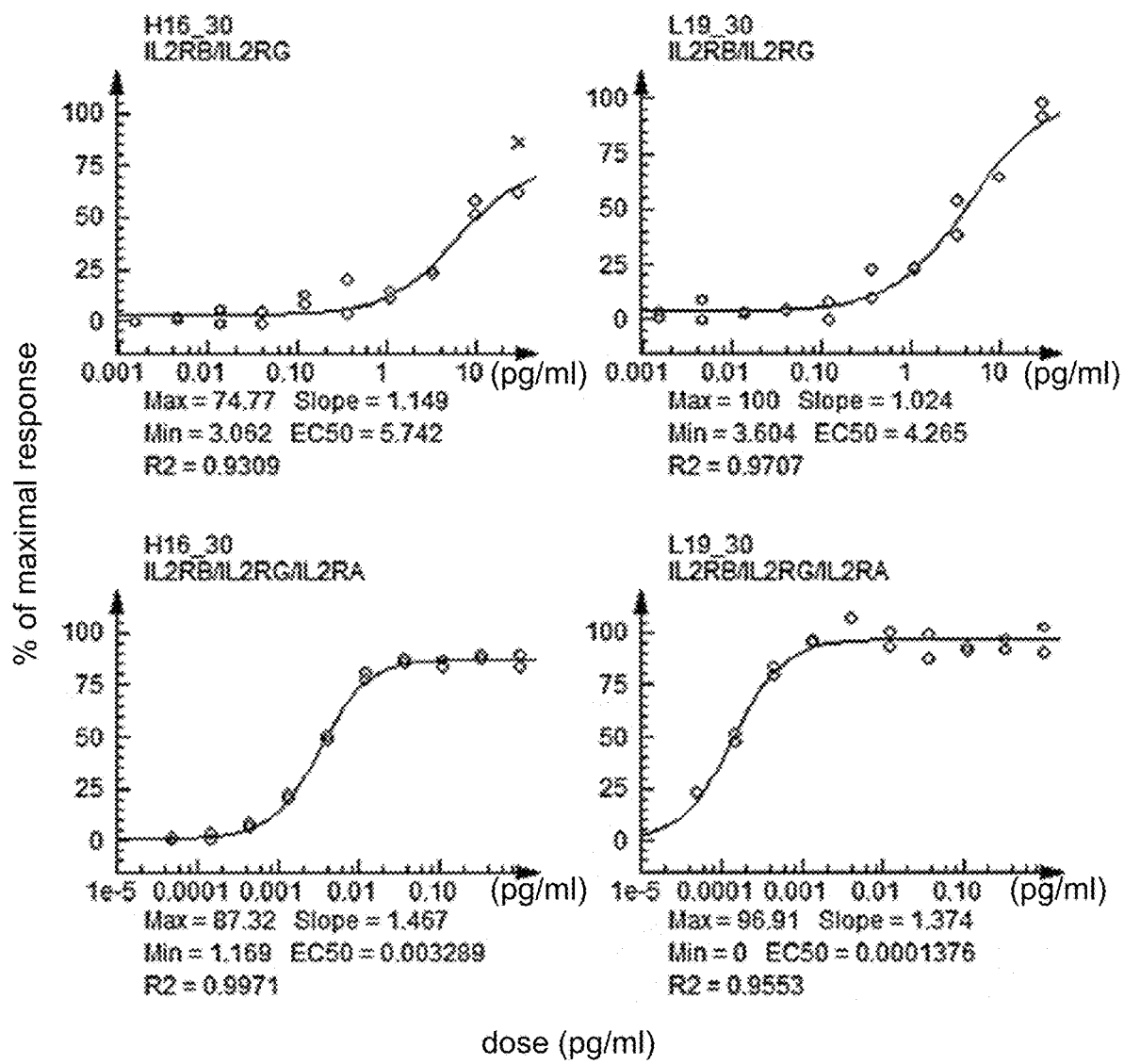
Figure 5C:
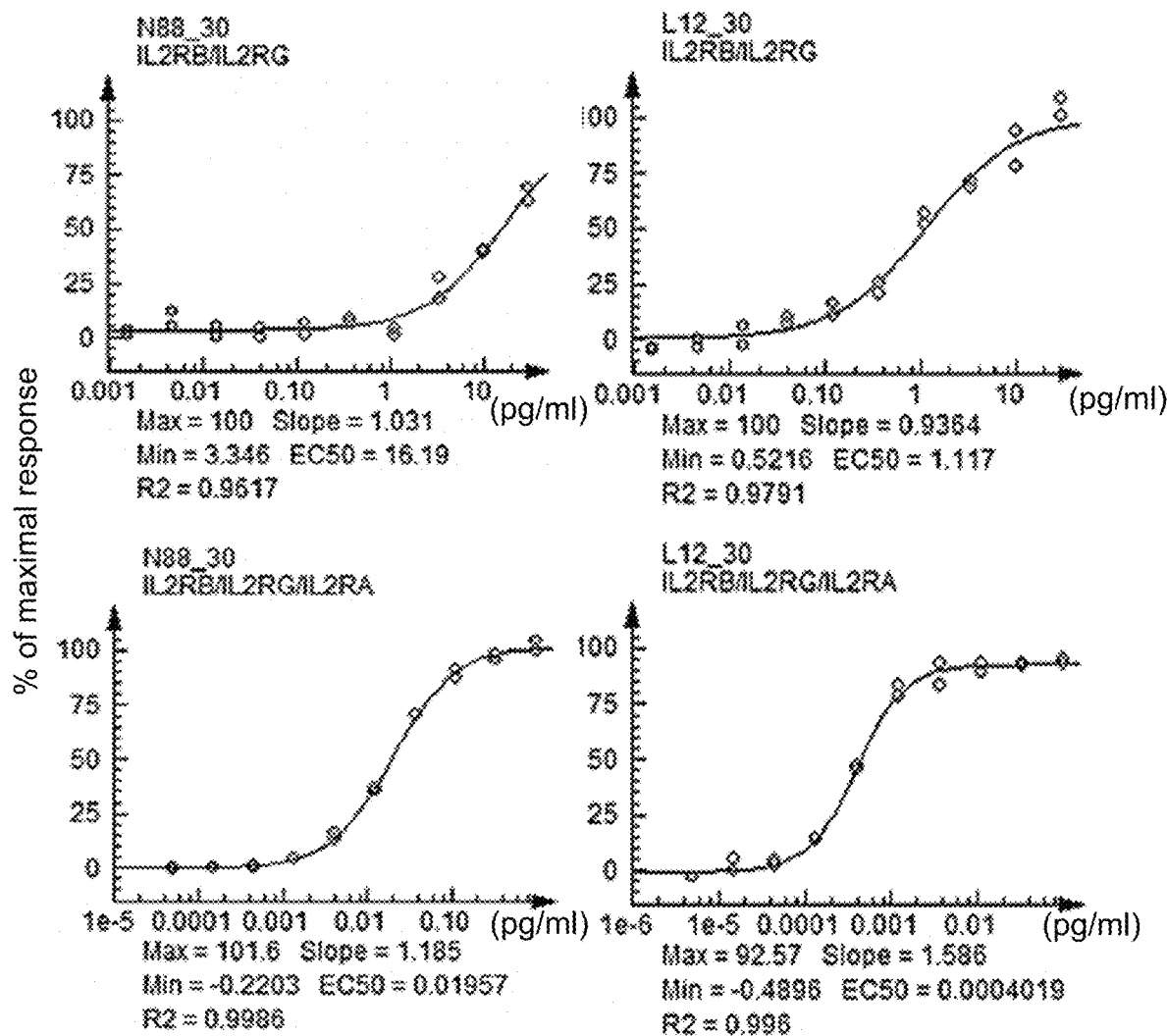

Compound activity was analyzed using CBIS data analysis suite software (ChemInnovation, CA). The percentage activity was calculated using the following formula: % Activity=100%×(mean RLU of test sample−mean RLU of vehicle control)/(mean MAX RLU control ligand−mean RLU of vehicle control). The compound activity is shown in FIGS. 5A, 5B, and 5C.

Potency ($EC_{50}$) data for IL-2 receptor agonism in cell-based screen for IL-2 conjugates are shown in the table below. $EC_{50}$ values are reported in nanograms of IL-2 conjugate per mL. Note, to facilitate comparison of the PEGylated and non-PEGylated compounds, the reported mass value corresponds to the mass of the IL-2 polypeptide in each IL-2 conjugate and does not include the mass of the mPEG or linker components.

TABLE 4(b)

| IL-2 Conjugate | Alpha beta gamma $EC_{50}$ (ng/mL) | Beta gamma $EC_{50}$ (ng/mL) |
| --- | --- | --- |
| Native IL-2 | 2.6 | 56 |
| K9 | <0.5 | 531 |
| L12 | 0.6 | 1375 |
| E15 | 0.1 | 187 |
| N88 | 19.6 | 16190 |
| M23 | 0.1 | 367 |
| H16 | 3.3 | 5742 |
| L19 | 0.14 | 4265 |
| D20 | 24 | 18660 |
| E100 | 1.4 | 454 |

Example 4

Screening of IL-2 Conjugates in Mice

To characterize the pharmacokinetic and pharmacodynamic effects of each IL-2 conjugate in mice, each conjugate described in Table 5(a) was administered as a single subcutaneous injection into naïve C57/BL6 mice at approximately 0.9 mg/kg (note—the dose was determined by measuring the mass of the polypeptide protein and did not include the mass of the polyethylene glycol or linker moieties). Samples were collected via terminal bleeding as indicated in Table 5(a), collected at the indicated times, and subjected to PK analysis using ELISA and flow cytometry to quantitate signaling, activation, and proliferation of individual lymphocyte populations. All of the compounds used in this study, except N88_30 kD, have the SEQ ID NO: 4 in which the amino acid at the indicated position was substituted with the structure of Formula (II), Formula (III), or a mixture of Formula (II) and (III) was substituted at the indicated amino acid residue comprising a linear, mPEG group having a molecular weight of 30 kDa. For the N88_30 kD variant, the compound had sequence SEQ ID NO: 4 in which the amino acid at the indicated position was substituted with the structure of Formula (IV), Formula (V), or a mixture of Formula (IV) and (V) was substituted at the indicated amino acid residue comprising a linear, mPEG group having a molecular weight of 30 kDa.

TABLE 5(a)

Mouse PK/PD study details

| IL-2 Conjugate | Dose (mg/kg) | Dose Route | Collection time point (Days) | Collection |
| --- | --- | --- | --- | --- |
| vehicle | 0 | subcutaneous | 0, 1, 2, 3, 4, 5, 6, 7, 8 | Terminal bleed |
| K9_30 kD | 0.9 | subcutaneous | 0, 1, 2, 3, 4, 5, 6, 7, 8 | Terminal bleed |
| L19_30 kD | 0.9 | subcutaneous | 0, 1, 2, 3, 4, 5, 6, 7, 8 | Terminal bleed |
| Q126_30 kD | 0.4 | subcutaneous | 0, 1, 2, 3, 4, 5, 6, 7, 8 | Terminal bleed |
| E100_30 kD | 0.9 | subcutaneous | 0, 1, 2, 3, 4, 5, 6, 7, 8 | Terminal bleed |
| N88R/ D109_30 kD | 0.9 | subcutaneous | 0, 1, 2, 3, 4, 5, 6, 7, 8 | Terminal bleed |
| T123_30 kD | 0.8 | subcutaneous | 0, 1, 2, 3, 4, 5, 6, 7, 8 | Terminal bleed |
| N88_30 kD | 0.9 | subcutaneous | 0, 1, 2, 3, 4, 5, 6, 7, 8 | Terminal bleed |
| H16_30 kD | 0.9 | subcutaneous | 0, 1, 2, 3, 4, 5, 6, 7, 8 | Terminal bleed |

Figure 6:
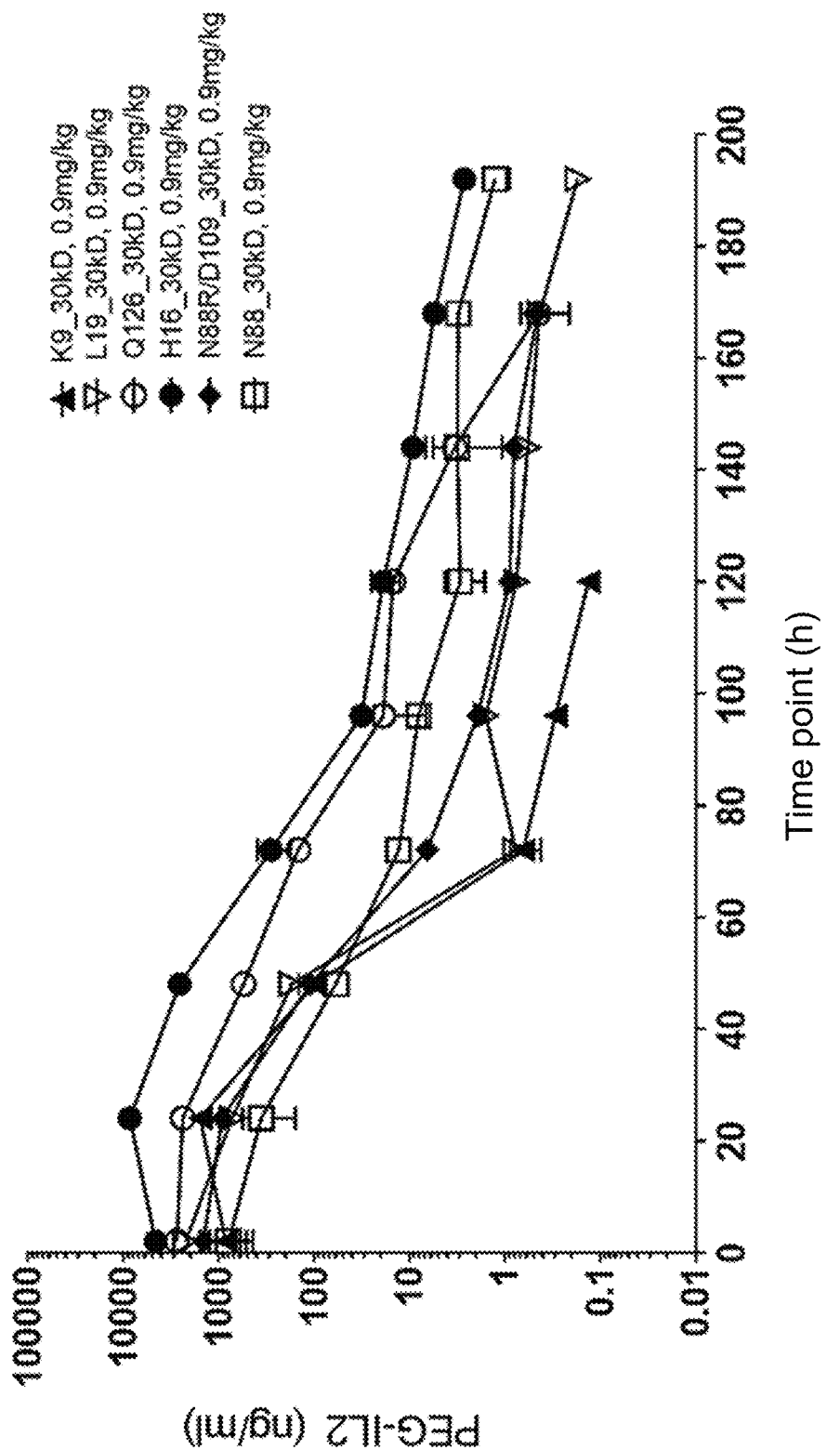
FIG. 6 shows the plasma concentration profiles of IL-2 conjugates K9_30 kD, L19_30 kD, N88R/D109_30 kD, H16_30 kD, Q126_30 kD, and N88_30 kD (all dosed at 0.9 mg/kg) following dosing in C57/BL6 mice from Example 4.

Bioanalysis of plasma samples was performed using a commercially available human IL-2 ELISA assay (Abcam, Cambridge, UK). Concentrations of each IL-2 conjugate dosed and the internal standard in samples derived from plasma were determined following the manufacturer's instructions, and each time point was measured under conditions within the linear range of the standard measurement. The plasma concentration profiles of IL-2 conjugates K9_30 kD, L19_30 kD, N88R/D109_30 kD, H16_30 kD, Q126_30 kD, and N88_30 kD (all dosed at 0.9 mg/kg) are plotted in FIG. 6.

To characterize the pharmacodynamic effects of IL-2 conjugates in mice, each conjugate was dosed as a single subcutaneous injection into naïve C57/B16 mice at a dose of approximately 0.9 mg/kg (note—the dose was determined by measuring the mass of the polypeptide protein and did not include the mass of the polyethylene glycol or linker moieties). Samples were collected via terminal bleeding as indicated in Table 5(b). Compound formulation, dosing, and sample collection were carried out at Crown Bio (La Jolla, CA). Pharmacodynamic analysis using flow cytometry was carried out by PrimityBio (Fremont, CA) and this analysis was used to quantitate signaling, activation, and proliferation of individual lymphocyte populations.

TABLE 5(b)

Marker panel for flow cytometry study of IL-2 conjugates in C57/BL6 mice
Flow cytometry marker panel

| |
| --- |
| CD3 |
| CD4 |
| CD8 |
| CD44 |
| CD25 |
| FoxP3 |
| NK1.1 |
| STAT5 |
| Ki-67 |
| ICOS |
| Helios |

Figure 7:
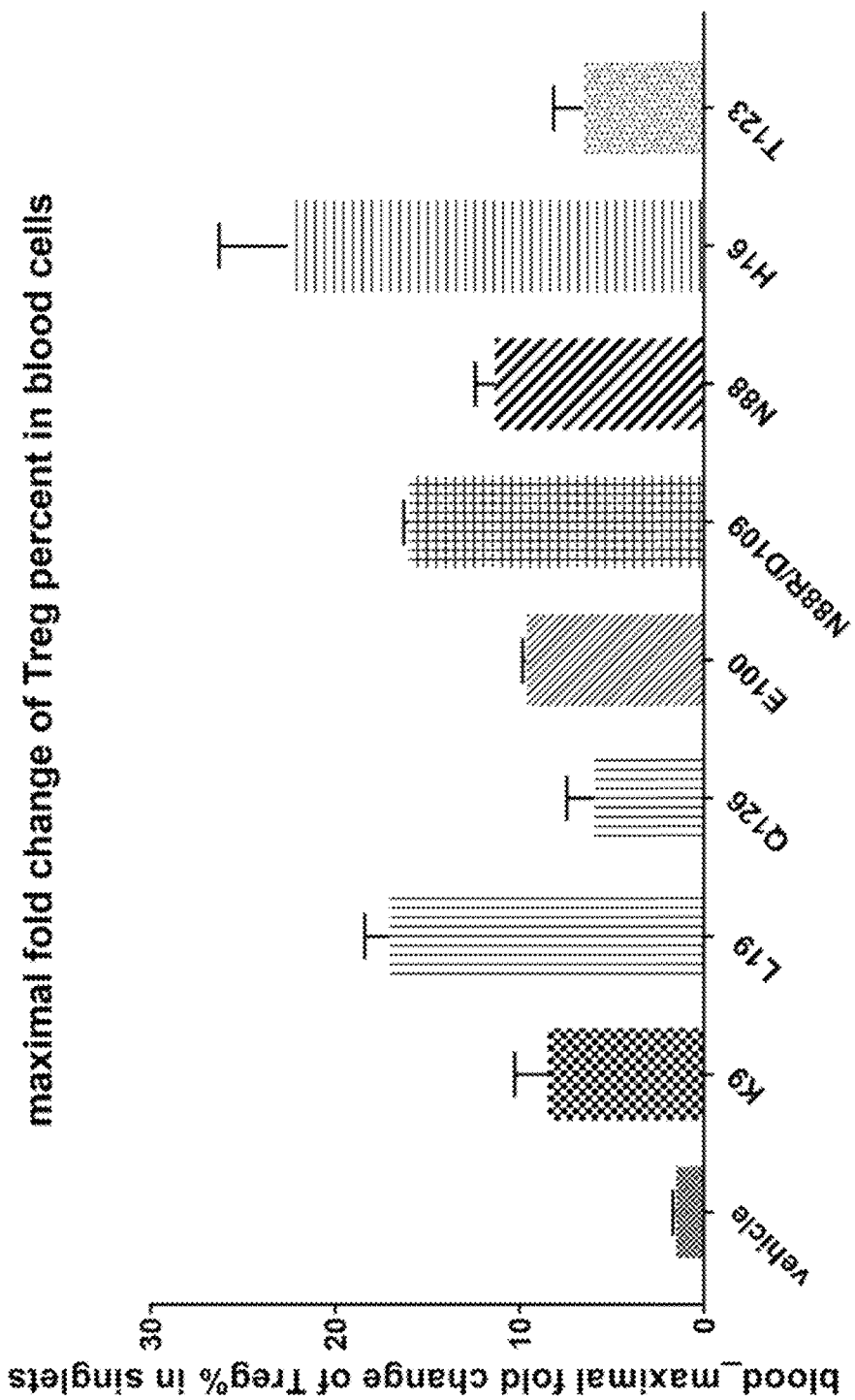
FIG. 7 shows the mean fold change of Treg (% in singlets) following the dosing of IL-2 conjugates in C57/BL6 mice from Example 4.

The cells were first gated on singlets using FSC-A by FSC-HOUR to exclude any aggregates or doublets. Within this gate the cells are gated on mid to high forward scatter (FSC-A) and side scatter (SSC-A) to exclude the red blood cells and debris. The T cells are then gated as the CD3+ population. The T cells are then divided into CD4+ T cells and CD8+ T cells. The Tregs are then gated from the CD4+ T cells as the CD25+ FoxP3+ population. The NK cells are identified from the CD3 negative population as the NK1.1 positive population. Statistics and plotting for derivation of $EC_{50}$ values The Median Fluorescence Intensity (MFI) for each of the cell population, donor, and the IL-2 conjugate dosed was calculated from the signal in the channel detecting phosphorylated STAT5 using CellEngine software. The statistics were analyzed using Spotfire. Within Spotfire, the data was plotted on a log scale for the doses of IL-2 conjugate and a linear scale for the MFI readings. These data were fit using a 4-parameter logistic regression equation. The $EC_{50}$ was calculated as the inflection point of the curve. For each IL-2 conjugate tested, Treg (CD3+CD4+CD25 high FoxP3+) cells were quantitated in singlets (total lymphocytes observed). The mean fold change of Treg (% in singlets) from three independent animals is plotted for each IL-2 conjugate, represented as the maximum percentage of Treg in singlets/percentage of Treg in singlets in pre-dosed samples. Each bars represent the standard error of the indicated mean. Results showing the maximal fold-change in Treg percentage in singlets from subcutaneous dose of IL-2 conjugates in mice are shown in FIG. 7.

Figure 8:
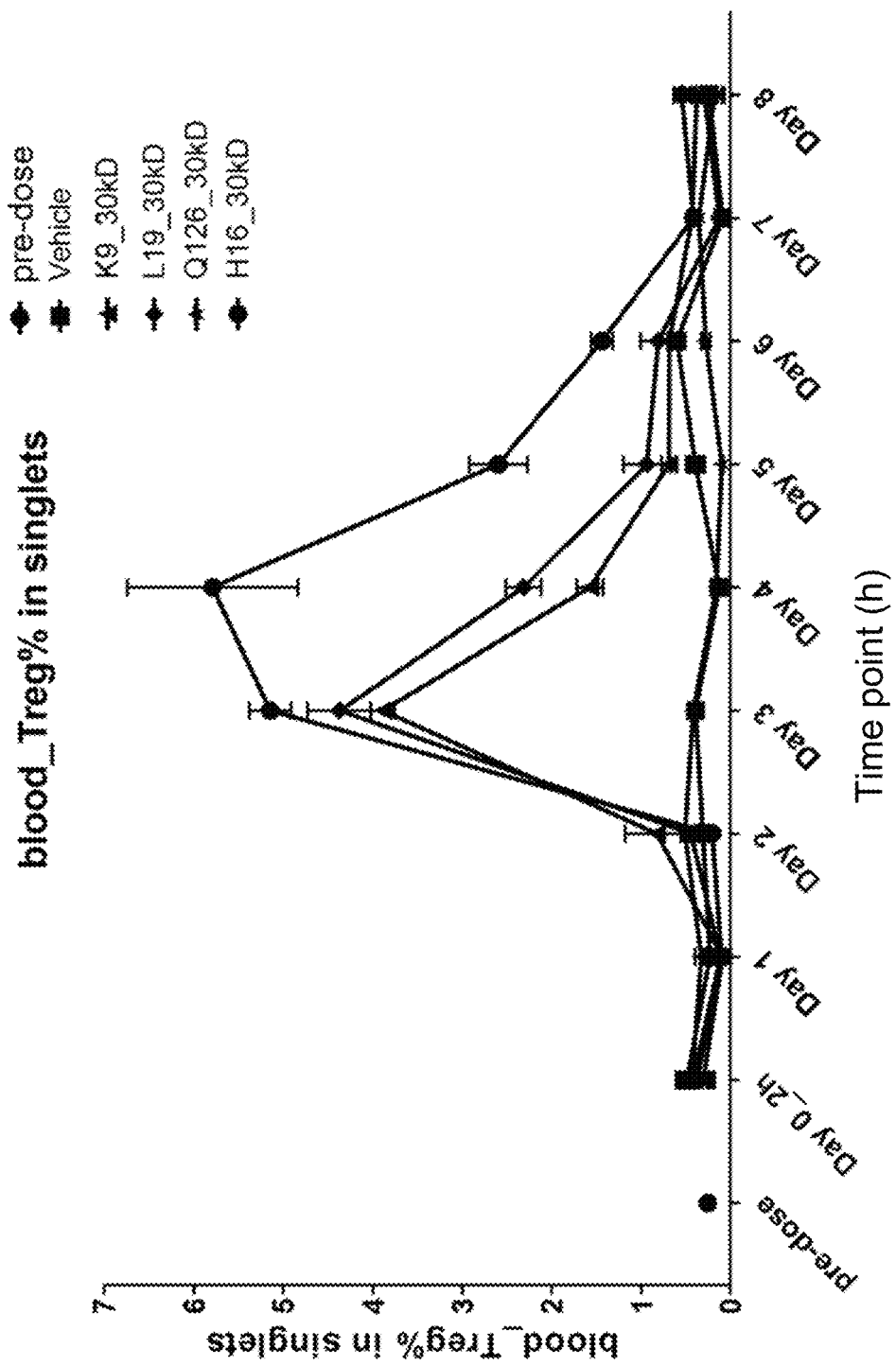
FIG. 8 shows the proportion of the Treg (CD3+ CD4+ CD25+ FoxP3+) cell population within the total cell population (singlets) of IL-2 conjugates in C57/BL6 mice from Example 4.

Treg percentage in singlets versus time after single subcutaneous dose of IL-2 conjugates in C57/BL6 mice were determined. For each IL-2 conjugate, the samples were subjected to flow cytometry to identify and quantitate the proportion of the Treg (CD3+ CD4+ CD25+ FoxP3+) cell population within the total cell population (singlets). Shown are data for IL-2 K9_30 kD, L19_30 kD, Q126_30 kD, and H16_30 kD in FIG. 8.

Figure 9A:
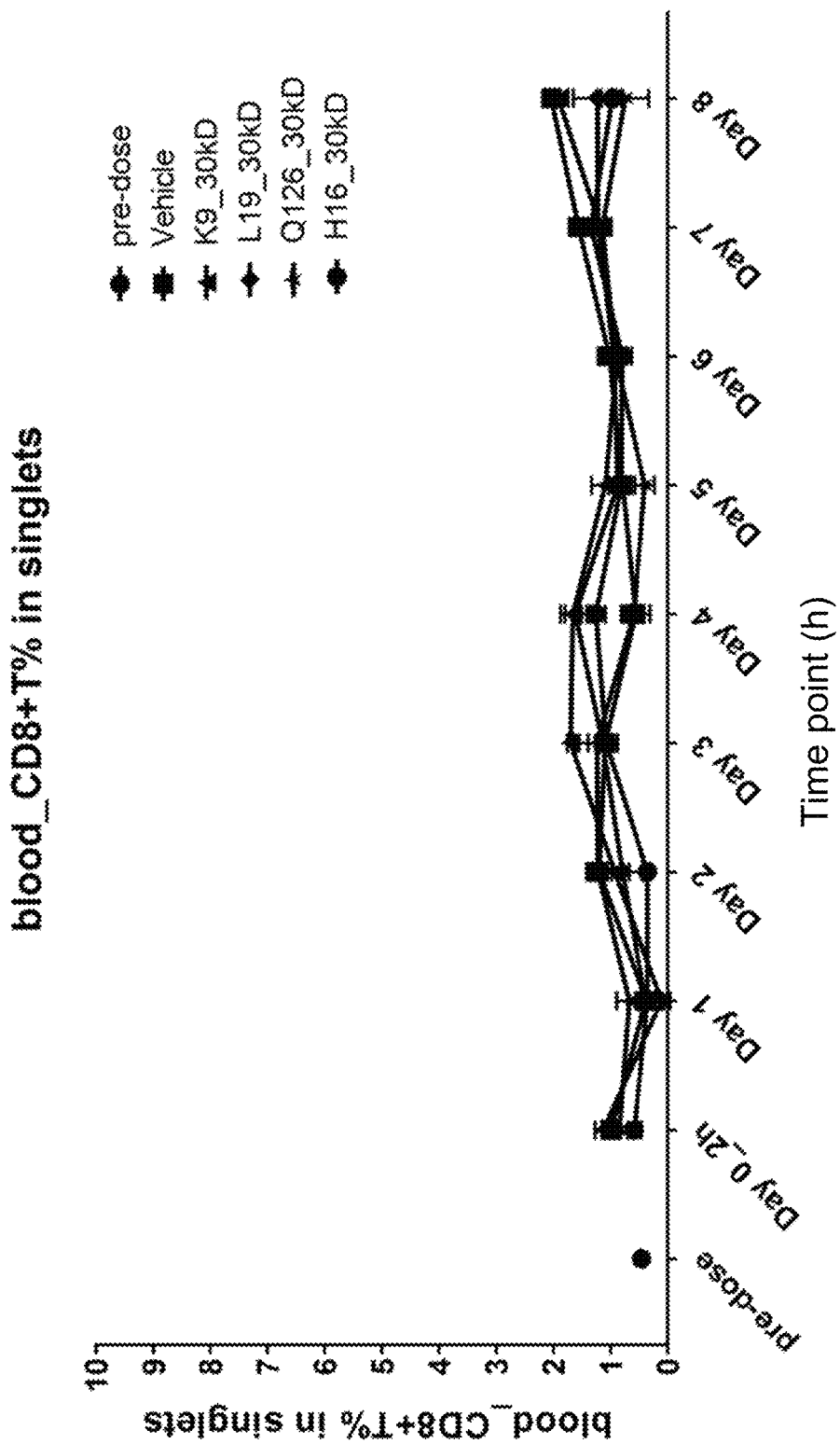
FIG. 9A shows the proportion of the CD8+ T cell population (CD3+ CD4− CD8+) within the total cell population (singlets) following a single dose of IL-2 conjugates K9_30 kD, L19_30 kD, Q126_30 kD, and H16_30 kD in C57/BL6 mice from Example 4.

FIG. 9A shows the proportion of the CD8+ T cell population (CD3+ CD4− CD8+) within the total cell population (singlets) in C57/BL6 mice for the K9_30 kD, L19_30 kD, Q126_30 kD, and H16_30 kD IL-2 conjugates. Each point represents the mean of three independent animals, error bars represent the standard error of the mean.

Figure 9B:
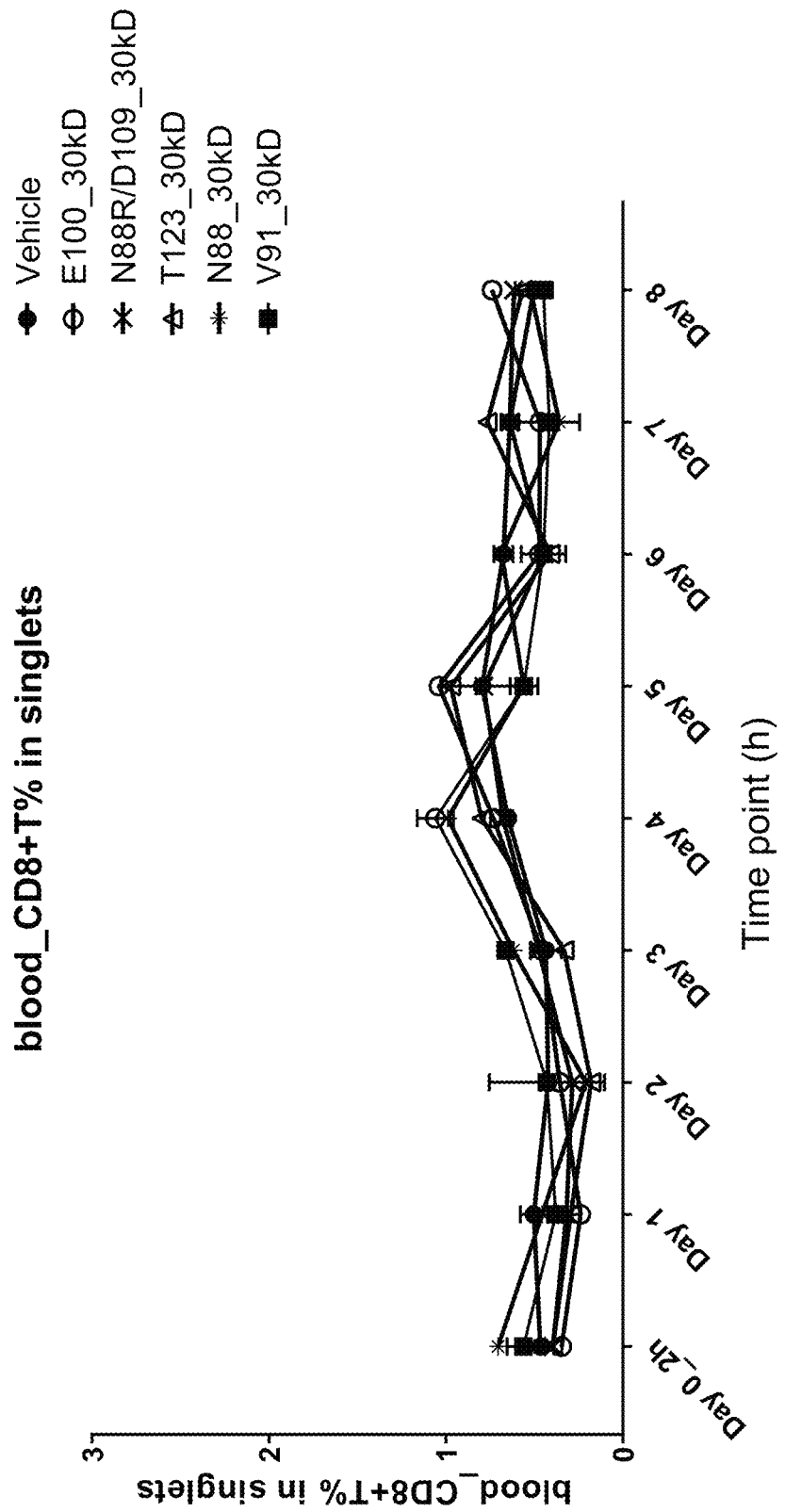
FIG. 9B shows the proportion of the CD8+ T cell (CD3+ CD4− CD8+) population within the total cell population (singlets) following a single dose of IL-2 conjugates E100_30 kD, N88R/D109_30 kD, T123_30 kD, N88_30 kD, and V91_30 kD in C57/BL6 mice from Example 4.

FIG. 9B shows the CD8+ T cell (CD3+ CD4− CD8+) population within the total cell population (singlets) for IL-2 conjugates E100_30 kD, N88R/D109_30 kD, T123_30 kD, N88_30 kD, and V91_30 kD conjugates in $C_{57}$/BL6 mice. Each point represents the mean of three independent animals, error bars represent the standard error of the mean.

Example 5

Pharmacokinetic Analysis of IL-2 Conjugates after Subcutaneous Dosing in Cynomolgus Monkey The following compounds shown in Table 6 were used in Example 5:

TABLE 6

| Compound | Structure |
| --- | --- |
| H16_30 kD | SEQ ID NO: 4 in which the structure of Formula (II), Formula (III), or a mixture of Formula (II) and (III) was substituted at the H16 residue (SEQ ID NO: 65) with a PEG group having a molecular weight of 30 kDa |
| N88_30 kD | SEQ ID NO: 4 in which the structure of Formula (IV), Formula (V), or a mixture of Formula (IV) and (V) was substituted at the N88 residue (SEQ ID NO: 190) with a PEG group having a molecular weight of 30 kDa |

TABLE 6-continued

| Compound | Structure |
| --- | --- |
| L19_30 kD | SEQ ID NO: 4 in which the structure of Formula (II), Formula (III), or a mixture of Formula (II) and (III) was substituted at the L19 residue (SEQ ID NO: 66) with a PEG group having a molecular weight of 30 kDa |
| N88R/D109_30 kD | SEQ ID NO: 4 in which N88 is substituted with R and the structure of Formula (IV), Formula (V), or a mixture of Formula (IV) and (V) was substituted at the D109 residue (SEQ ID NO: 197) with a PEG group having a molecular weight of 30 kDa |

Figure 10:
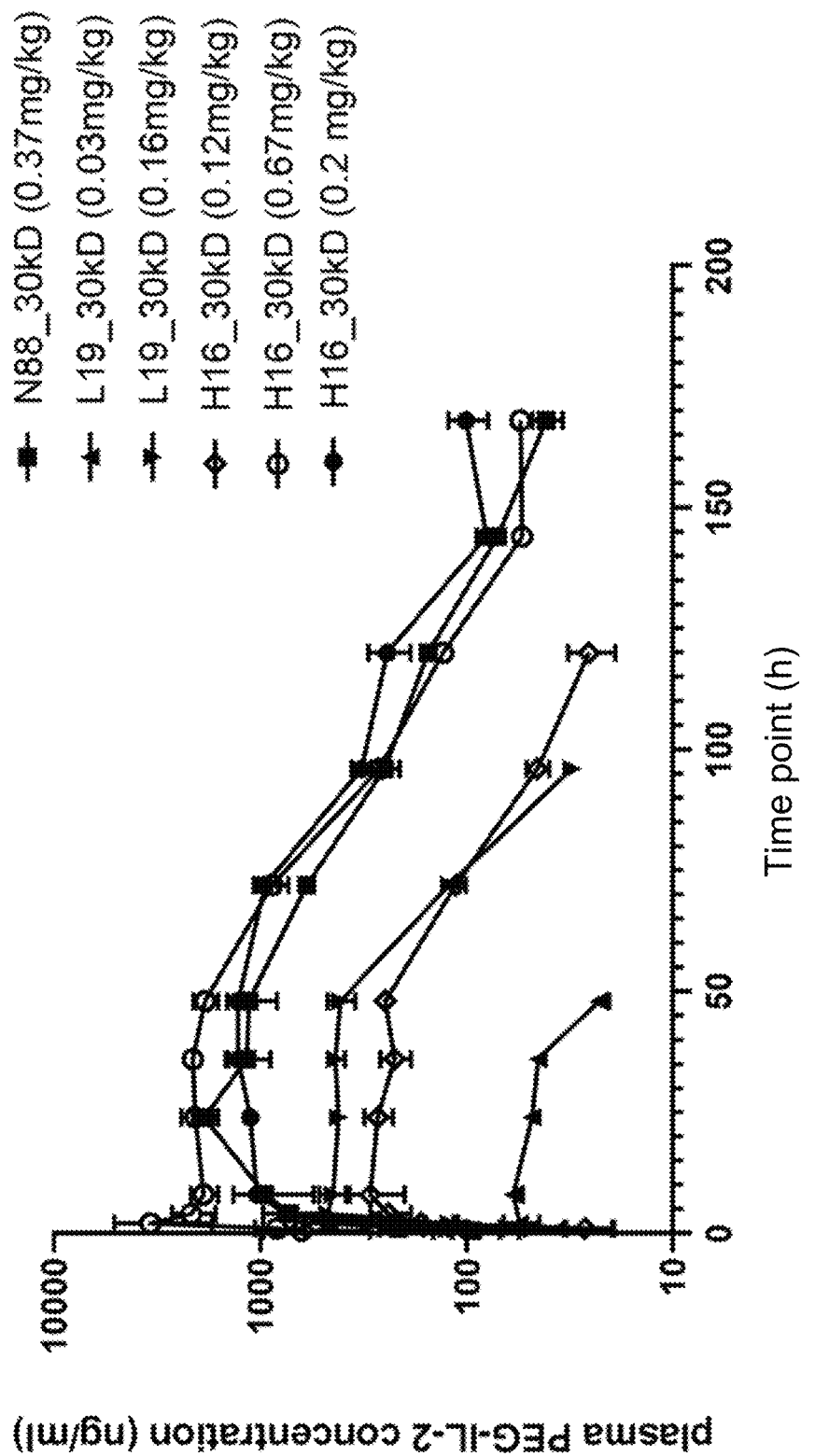
FIG. 10 shows the plasma concentration profiles of IL-2 conjugates following dosing in Cynomolgus monkey from Example 5.

L19_30 kD, H16_30 kD, and N88_30 kD were dosed subcutaneously into three male Cynomolgus monkeys at doses of 0.37 mg/kg N88_30 kD, 0.03 mg/kg L19_30 kD, 0.16 mg/kg L19_30 kD, 0.12 mg/kg H16_30 kD, 0.67 mg/kg H16_30 kD, and 0.2 mg/kg H16_30 kD. The plasma concentration profiles of IL-2 conjugates L19_30 kD, H16_30 kD, and N88_30 kD are shown in FIG. 10.

Figure 11:
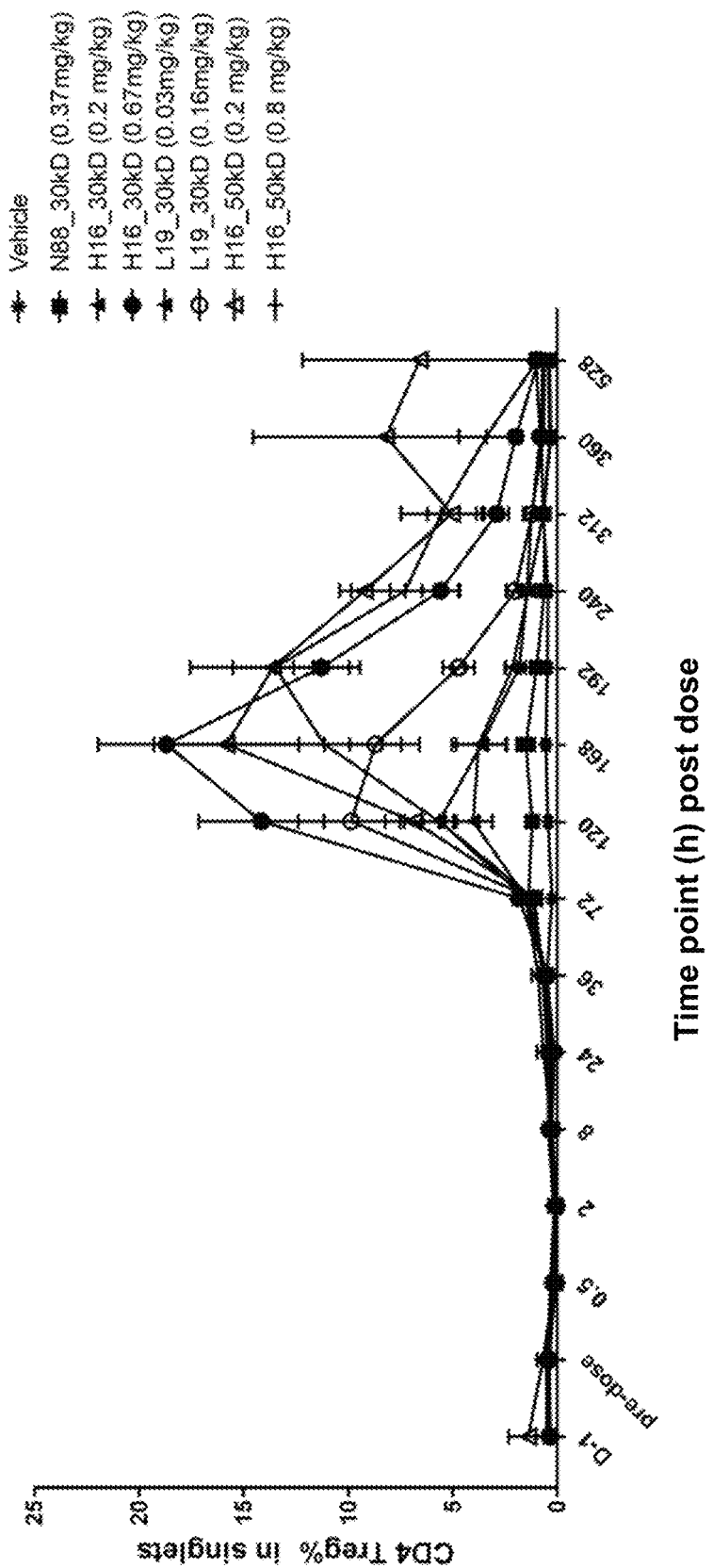
FIG. 11 shows the proportion of the Treg cell population within the total blood cell population (singlets) in Cynomolgus monkeys following dosing with IL-2 conjugates from Example 5.
Figure 12:
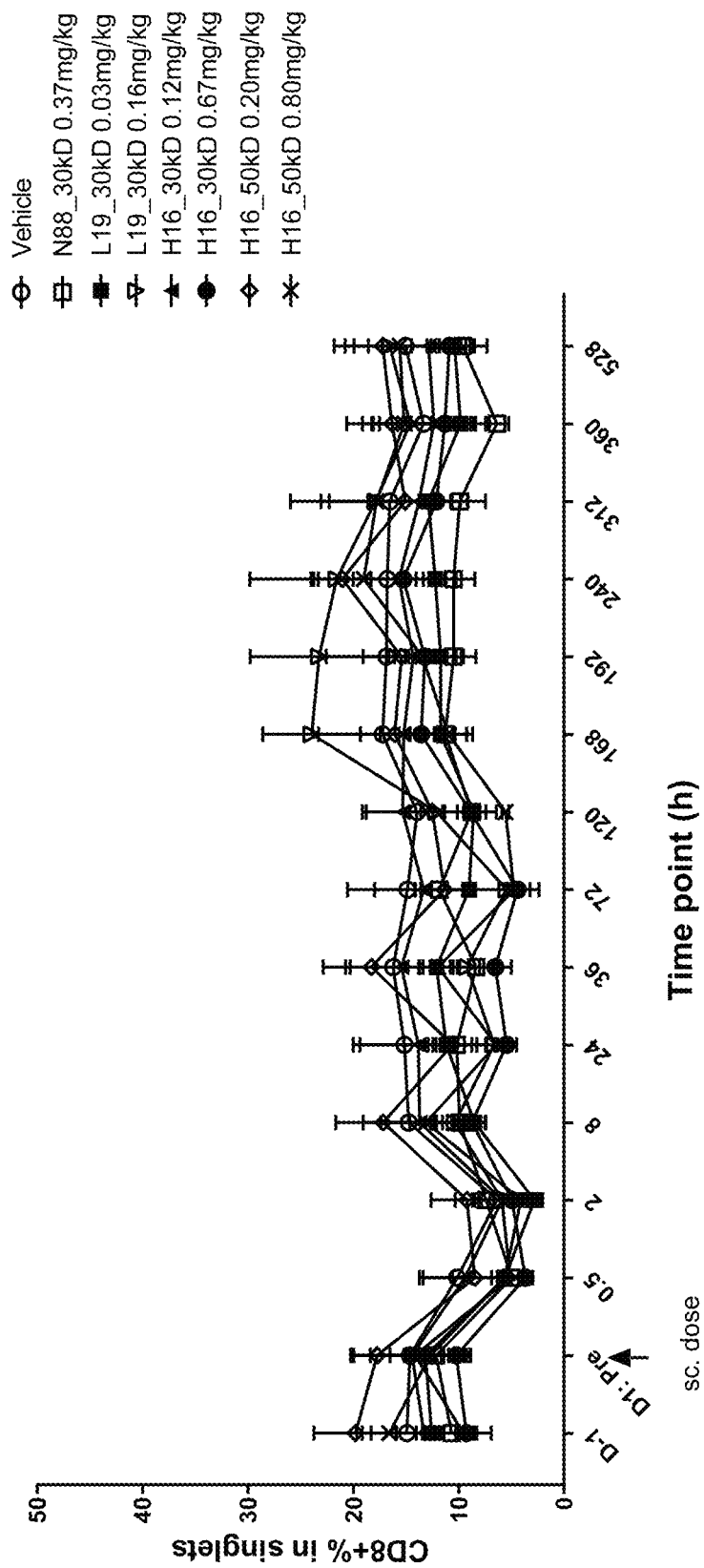
FIG. 12 shows the proportion of the CD8+ T cell population within the total blood cell population (singlets) in Cynomolgus monkeys following dosing with IL-2 conjugates from Example 5.

The IL-2 conjugates N88_30 kD, L19_30 kD, H16_30 kD, and H16_50 kD were dosed subcutaneously into three male Cynomolgus monkeys at doses of 0.37 mg/kg N88_30 kD, 0.2 mg/kg H16_30 kD, 0.67 mg/kg H16_30 kD, 0.03 mg/kg L19_30 kD, 0.16 mg/kg L19_30 kD, 0.2 mg/kg H16_50 kD, and 0.8 mg/kg H16_50 kD at Day 0. For each IL-2 conjugate, peripheral blood samples were collected at the indicated timepoints, and the samples were subjected to flow cytometry to identify and quantitate the proportion of the Treg cell population within the total blood cell population (singlets). Each point represents the mean of three independent animals, error bars represent the standard error of the mean. Bioanalysis of plasma samples was performed using a human IL-2 ELISA assay that captures the IL-2 conjugates to the surface using anti-IL-2 and detects the IL-2 conjugate via anti-PEG antibodies. Concentrations of each test article and the internal standard in samples derived from plasma were determined, and each time point was measured under conditions within the linear range of the standard measurement. The results showing the identity and quantity of the proportion of the Treg cell population within the total blood cell population (singlets) in Cynomolgus monkeys following dosing with IL-2 conjugates N88_30 kD, H16_30 kD, H16_50 kD, and L19_30 kD are shown in FIG. 11. The The IL-2 conjugates N88_30 kD, L19_30 kD, H16_30 kD, and H16_50 kD were dosed subcutaneously into three male Cynomolgus monkeys at doses of 0.37 mg/kg N88_30 kD, 0.03 mg/kg L19_30 kD, 0.16 mg/kg L19_30 kD, 0.12 mg/kg H16_30 kD, 0.67 mg/kg H16_30 kD, 0.2 mg/kg H16_50 kD, and 0.80 mg/kg H16_50 kD at Day 0. The results showing the identity and quantity of the proportion of the CD8+ T cell population within the total blood cell population (singlets) in Cynomolgus monkeys following dosing with IL-2 conjugates N88_30 kD, H16_30 kD, H16_50 kD, and L19_30 kD are shown in FIG. 12.

Example 6

Dosing of Cynomolgus Monkeys with IL-2 Conjugates

The IL-2 conjugates described in Table 7 below were dosed in Cynomolgus monkeys with 3 male animals in each dosing group (24 total animals). The animals were given a single subcutaneous dose of the indicated IL-2 conjugate at day 0. Each of the conjugates described below, except H16_30 kDa and H16_50 kDa, had SEQ ID NO: 4 in which the indicated amino acid position is substituted with the structure of Formula (II), Formula (III), or a mixture of Formula (II) and (III), and they contain a PEG chain of the indicated size. For example, the variant labeled "L19_30 kDa" has SEQ ID NO: 4 in which the amino acid at position L19 is replaced by the structure of Formula (II), Formula (III), or a mixture of Formula (II) and (III), and contains a 30 kDa, linear mPEG group. For the H16_30 kDa and H16_50 kDa variants, the compounds had SEQ ID NO: 4 in which the indicated amino acid position is substituted with the structure of Formula (IV), Formula (V), or a mixture of Formula (IV) and (IV), and a linear, mPEG group having a molecular weight of 30 kDa or 50 kDa, respectively.

TABLE 7

| Group | Test Article | Dose Level (mg/kg) |
| --- | --- | --- |
| 1 | Vehicle | NA |
| 2 | N88_30 kDa | 0.37 |
| 3 | L19_30 kDa | 0.03 |
| 4 | L19_30 kDa | 0.16 |
| 5 | H16_30 kDa | 0.12 |
| 6 | H16_30 kDa | 0.67 |
| 7 | H16_50 kDa | 0.2 |
| 8 | H16_50 kDa | 0.8 |

Blood samples were taken from each animal at the following time points: Samples for hematology: Day −1, Day 1 (Predose), 3, 6, 10, 15 and 22. Samples for pharmacokinetics and pharmacodynamics: (Predose), 0.5, 1, 2, 4, 8, 24, 36, 48, 72, 96, 120, 144, 168, and 240, 360, 528 (Day 22) hours post-dose. Cytokine sample collection and analysis: Day −1, and Day 1 (Predose), 8, 24, 72, 120 and 168, 360, and 528 (Day 22) hours post-dose.

The peak fold-change in white blood cell count (WBC), peak fold-change in lymphocyte count, and the day on which the peak lymphocyte counts were observed for each IL-2 conjugate are indicated in Table 8.

TABLE 8

| Group No. | IL-2 Conjugate | Dose Level (mg/kg) | Peak fold change of WBC | Peak fold change of lymphocytes | Date at the peak of lymphocytes |
| --- | --- | --- | --- | --- | --- |
| 1 | Vehicle | 0 | 1.04 | 1.05 | pre dose |
| 2 | N88_30 kDa | 0.37 | 1.05 | 1.19 | 6 days post |
| 3 | L19_30 kDa | 0.03 | 1.14 | 1.28 | 6 days post |
| 4 | L19_30 kDa | 0.16 | 2.49 | 3.21 | 6 days post |
| 5 | H16_30 kDa | 0.12 | 1.24 | 1.31 | 6 days post |
| 6 | H16_30 kDa | 0.67 | 2.3 | 2.76 | 6 days post |
| 7 | H16_50 kDa | 0.2 | 1.71 | 2.25 | 10 days post |
| 8 | H16_50 kDa | 0.8 | 2.9 | 3.38 | 10 days post |

Figure 13:
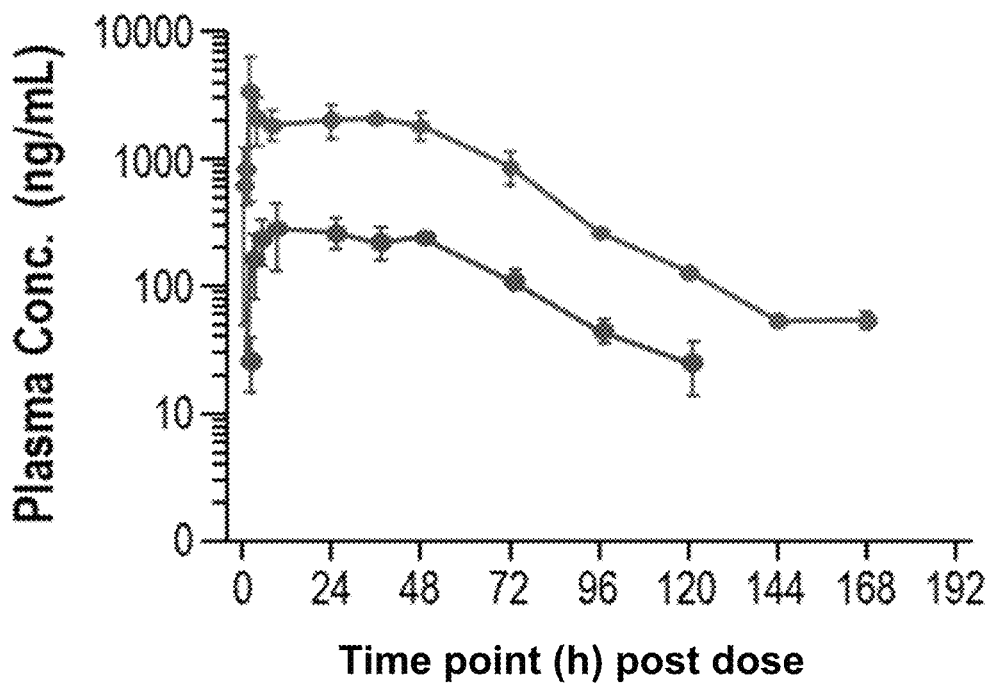
FIG. 13 shows the plots of plasma concentration versus time for the H16_30 kD variant in non-human primates at doses of 0.12 mg/kg and 0.67 mg/kg from Example 6, wherein the 0.12 mg/kg dose is shown as the lower trace, while the 0.67 mg/kg dose is shown as the upper trace.

The pharmacokinetic parameters for the H16_30 kD variant in non-human primates at doses of 0.12 mg/kg and 0.67 mg/kg are shown in Table 9 below and the plots of plasma concentration versus time of the H16_30 kD variant at a dose of 0.12 mg/kg and 0.67 mg/kg are shown in FIG. 13 (the 0.12 mg/kg dose is shown as the lower trace, while the 0.67 mg/kg dose is shown as the upper trace).

TABLE 9

| Dose of H16_30 kD variant | Mean $t_{1/2}$ (hours) | Mean AUC last (h*ng/mL) | Mean Cmax (ng/mL) |
| --- | --- | --- | --- |
| 0.12 mg/kg | 17.2 | 18,349 | 361 |
| 0.67 mg/kg | 18.0 | 71,940 | 1,358 |

Figure 14:
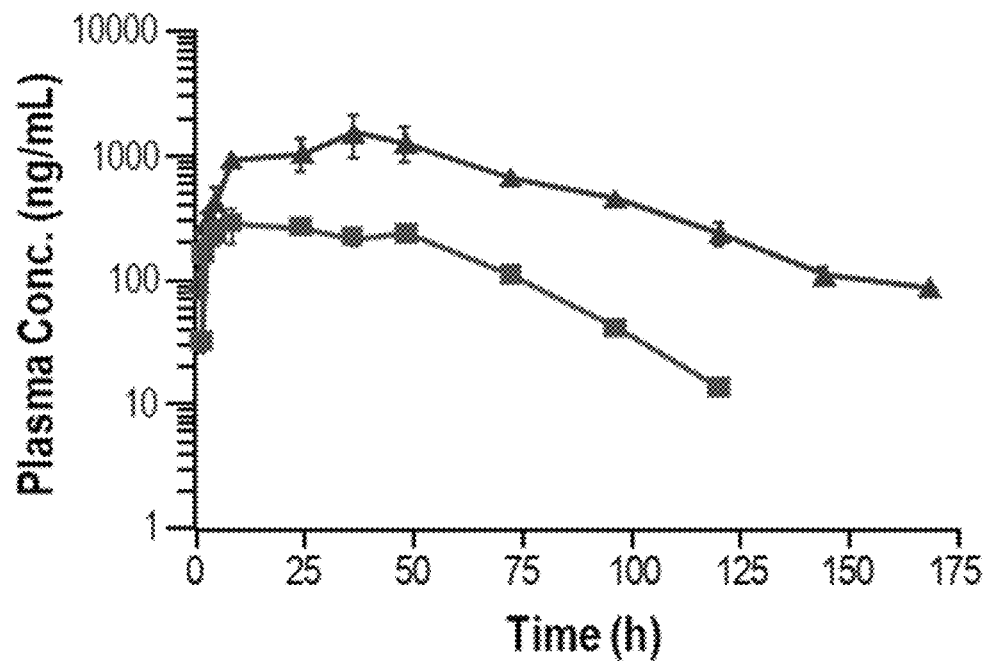
FIG. 14 shows the plots of plasma concentration versus time for the H16_30 kDa variant and the H16_50 kDa variant in non-human primates at a dose of 0.12 mg/kg, and the H16_50 kDa variant at a dose of 0.2 mg/kg from Example 6, wherein the trace for the 30 kDa variant is shown as the lower trace (squares) and the trace for the 50 kDa variant is shown as the upper trace (triangles).
Figure 15:
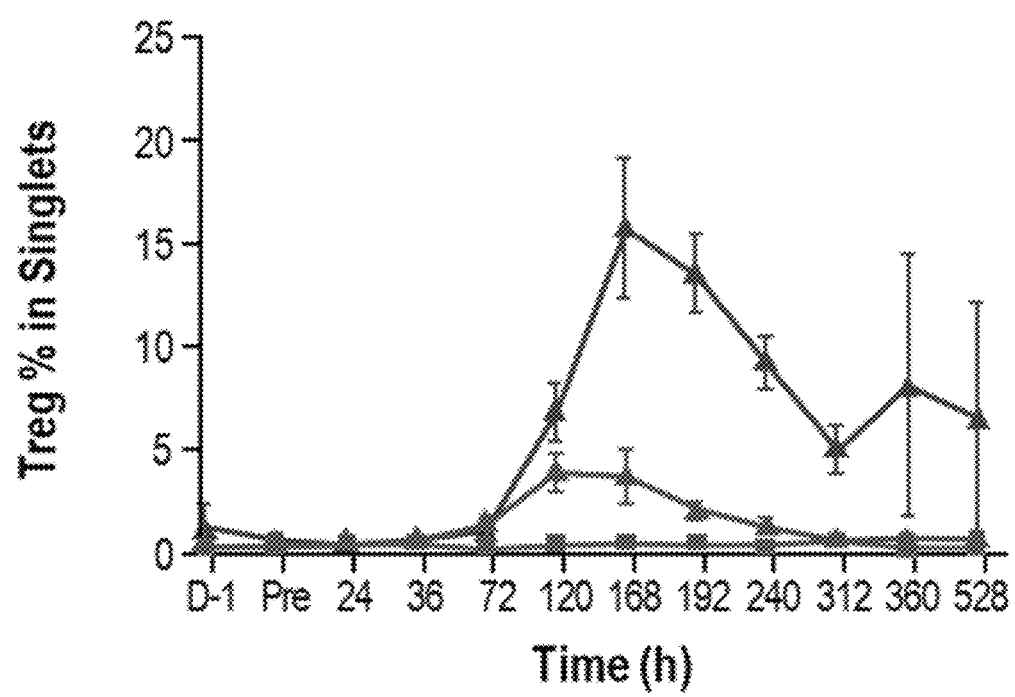
FIG. 15 shows plots of $T_{reg}$ percent in singles versus time post-dose in non-human primates from Example 6 for the H16_30 kDa variant at a dose of 0.12 mg/kg, and the H16_50 kDa variant at a dose of 0.2 mg/kg, wherein the trace for the vehicle is the lower trace (squares), the trace for the 30 kDa variant is shown in the middle trace, and the trace for the 50 kDa variant is shown in the upper trace.

The plots of plasma concentration of the H16_30 kDa variant at a dose of 0.12 mg/kg, and the H16_50 kDa variant at a dose of 0.2 mg/kg, are shown in FIG. 14, wherein the trace for the 30 kDa variant is shown as the lower trace (squares) and the trace for the 50 kDa variant is shown as the upper trace (triangles). The plot of $T_{reg}$ cells percentage in singlets versus time post-dose in the plasma of non-human primates for the H16_30 kDa variant at a dose of 0.12 mg/kg, and the H16_50 kDa variant at a dose of 0.2 mg/kg, are shown in FIG. 15, wherein the trace for the vehicle is the lower trace (squares), the trace for the 30 kDa variant is shown in the middle trace, and the trace for the 50 kDa variant is shown in the upper trace.

Example 7

Figure 16:
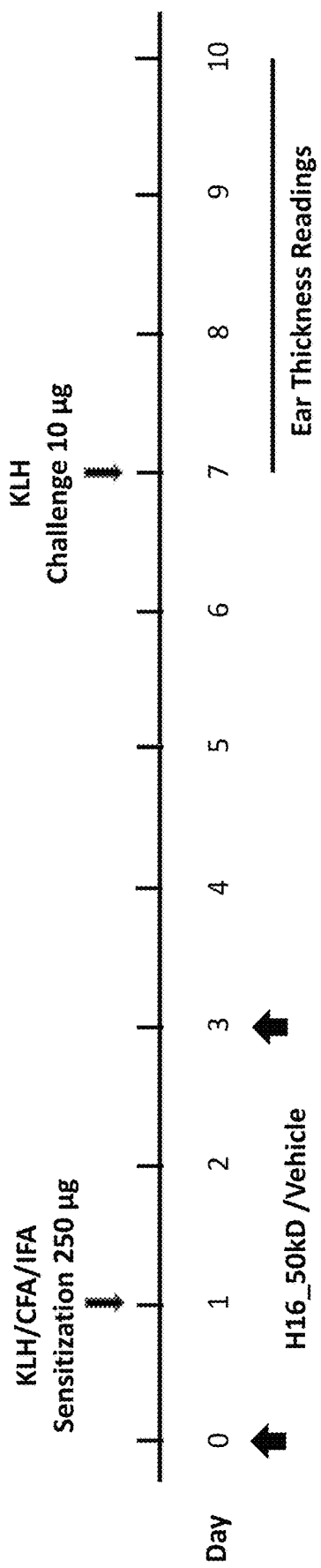
FIG. 16 shows the study design of Example 7 to assess the effects of H16_50 kD on delayed-type hypersensitivity (DTH) in C57BL/6 mice. DTH in mice was induced with keyhole limpet hemocyanin (KLH) (challenge at Day 7 following sensitization at Day 1 via subcutaneous injection) with dosing of H16_50 kD (Day 0 and 3), at a dose of 0.03 mg/kg, 0.1 mg/kg, and 0.3 mg/kg from Example 7.

To study the effects of the IL-2 conjugate (H16_50 kD) on delayed-type hypersensitivity (DTH) induced with keyhole limpet hemocyanin (KLH) in mice, DTH was induced in female $C_{57}BL/6$ mice by KLH sensitization at Day 1 and challenge at Day 7, and the mice were treated with H16_50 kD at Days 0 and 3. Details of the study plan are provided in Table 10 and also in FIG. 16.

TABLE 10

DTH study details

| Group | H16_50 kD Treatment | Dose Level (mg/kg) | Dose Volume (mL/kg) | Dosing route, frequency | N |
| --- | --- | --- | --- | --- | --- |
| 1 | KLH challenge only + Vehicle | 0 | 0 | SC, QD, Day 0 and 3 | 10 |
| 2 | KLH + Vehicle | 0 | 0 | SC, QD, Day 0 and 3 | 10 |
| 3 | KLH + Low Dose | 0.03 | 10 | SC, QD, Day 0 and 3 | 10 |
| 4 | KLH + Mid Dose | 0.1 | 10 | SC, QD, Day 0 and 3 | 10 |
| 5 | KLH + High Dose | 0.3 | 10 | SC, QD, Day 0 and 3 | 10 |
| 6 | KLH + Cyclosporine A (CsA) | 60 | 10 | PO, QD, Day 1-9 | 10 |

SC: subcutaneous injection;
QD: once a day

Hypersensitivity Induction: On Day 1, Groups 2 to 6 mice received intrascapular subcutaneous (SC) injection with a KLH/CFA/IFA emulsion (2.5 mg/mL) at a dose volume of 0.1 mL (KLH dose of 250 µg). On Day 7, all mice from Groups 1 to 6 received an intradermal (ID) injection of KLH (1 mg/mL PBS) in the right ear (or the left ear if needed) using a Hamilton syringe and dose volume 10 µL (KLH dose level 10 µg).

The KLH/CFA/IFA emulsion for sensitization was prepared as follows: KLH (Calbiochem; Cat. No. 374807) was prepared in PBS to achieve a 3× solution (7.5 mg/mL). Incomplete Freund's Adjuvant (IFA, Sigma) and Complete Freund's Adjuvant (CFA, Sigma) were placed in ice bath. The KLH solution was provided in a 50 mL conical tube; and an equivalent volume of CFA and IFA (1:1:1) were added to yield a final KLH/CFA/IFA emulsion at the required 1× concentrations of 2.5 mg/mL.

Administration of vehicle and H16_50 kD: Groups 1 to 5 mice were treated subcutaneously (SC in lumbar area) on Day 0 and Day 3. Group 6 mice received the positive control by gavage (PO) from Day 1-9. Administration of Cyclosporine A (CsA, Tokyo Chemical Industry) (0.5% methyl cellulose (400 cP) in ultrapure water) was done 2 hours prior to KLH injections on Day 1 and Day 7.

Assessment of ear thickness and blood immunotypes: An 8 mm punch (around the injection site) was taken from the injected ear (and contralateral from Group 1 animals) prior to KLH challenge (on Day 7) and then subsequently on Days 8, 9 and 10. The animals were slightly anesthetized by isoflurane inhalation at approximately 24 h, 48 h and 72 h post KLH challenge. Thickness of the ear flap was measured using an engineering micrometer.

Whole blood samples (150 µL) were collected from 5 mice per group for all groups on Day 0, Day 3, Day 7 alternatively via jugular venipuncture (2-3 hours before the H16_50 kD dosing and/or KLH injection) and terminally on Day 10. The blood samples were subjected to blood immunophenotying using flow cytometry analysis (CD45/CD3/CD4/CD25/FoxP3). The relative percentage of CD4+ T cells that are Treg cells (CD25+/FoxP3+) for all timepoints were determined. On Day 10 only, the absolute counts of CD4+ Tregs were determined using lymphocyte counts by the Sysmex system.

On Day 10, at the end of final assessment, all animals from Group 1-6 were anesthetized (with 1-5% isoflurane) and blood samples (~0.5-1 mL) were collected via abdominal aorta or by intracardiac puncture. Then, animals underwent exsanguination of the abdominal aorta and ear tissues were collected immediately thereafter (both ears from Group 1 and KLH injected ears for Group 2-6) for the ear thickness measurements.

Figure 17A:
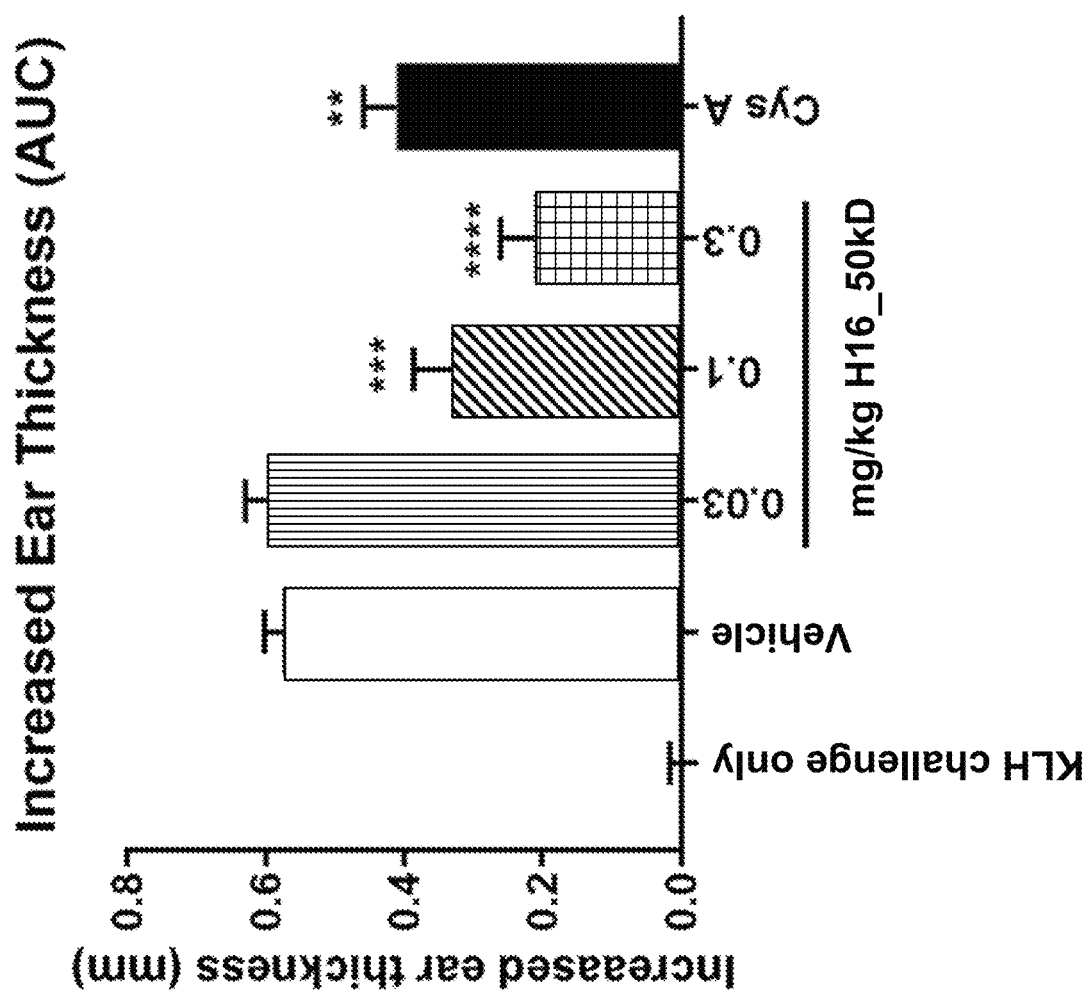
FIG. 17A-FIG. 17C show changes in ear thickness measurements and blood immunotypes of C57BL/6 mice from Example 7.
Figure 17B:
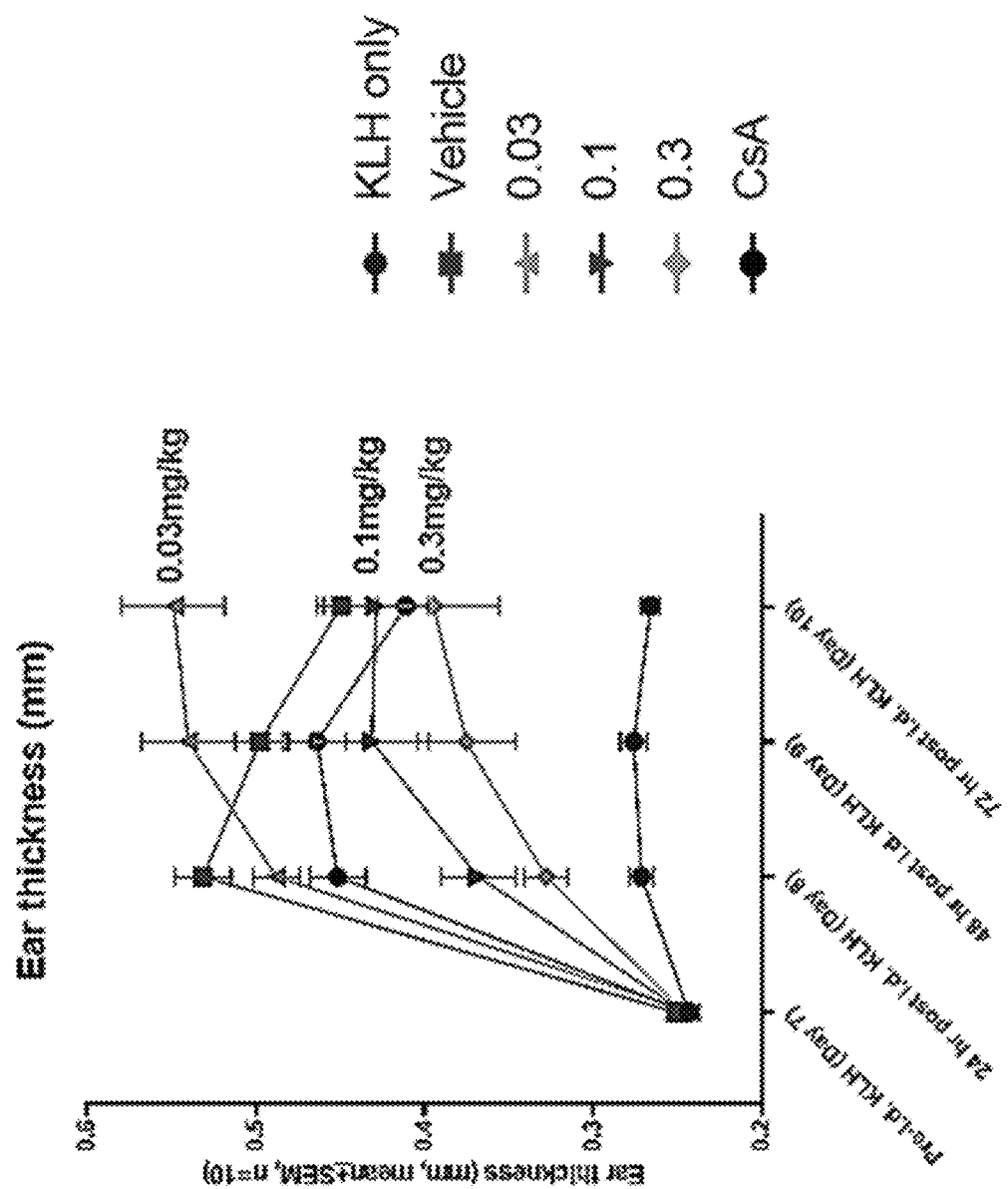
Figure 17C:
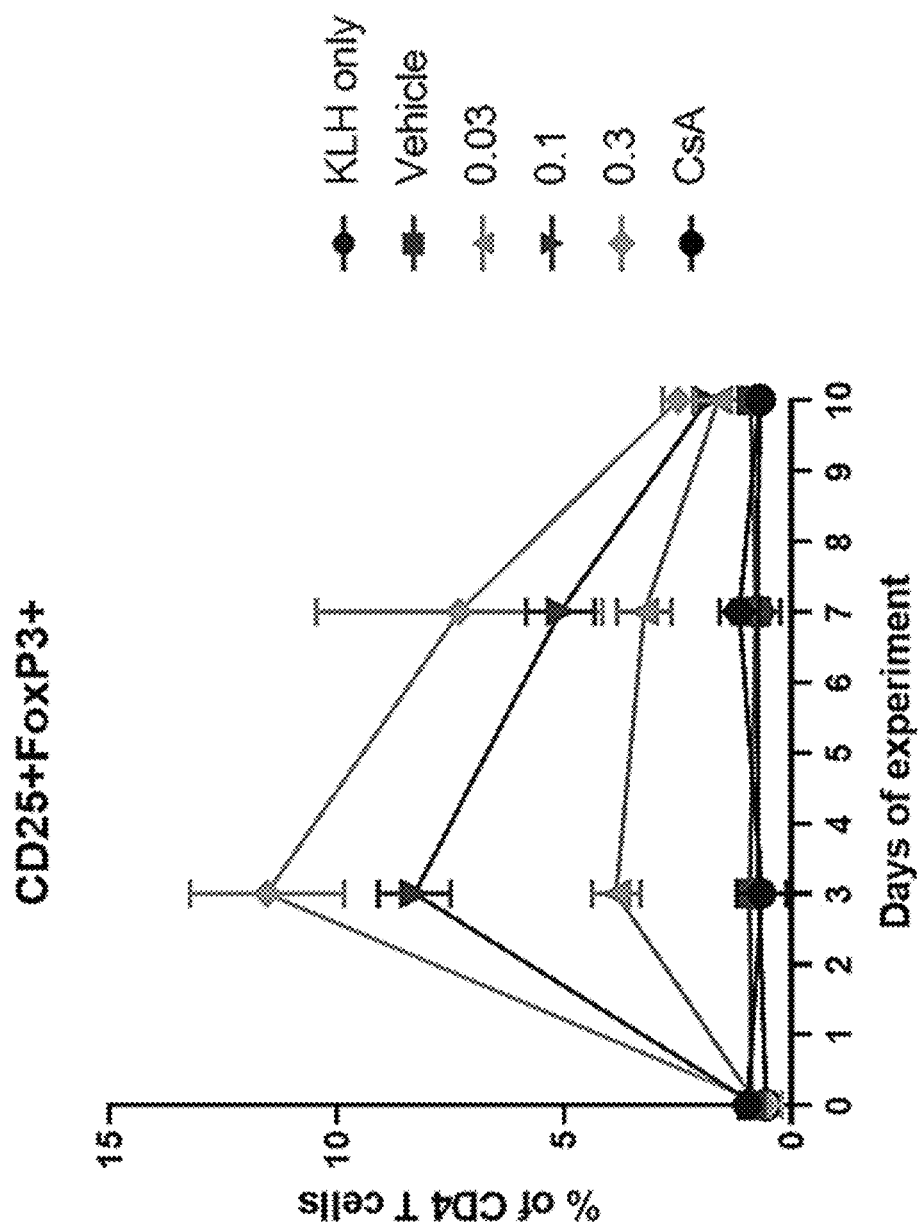

As shown in FIG. 17A-FIG. 17B, dosing with H16_50 kD at 0.1 mg/kg and 0.3 mg/kg reduced ear thicknesses as compared to the negative control (vehicle only), indicating reducing the delayed-type hypersensitivity. As shown in FIG. 17C, the relative percentage of CD4+ T cells within CD25+FoxP3+ cell population increased compared to the negative control (vehicle only) and the positive control (Cyclosporine A) by dosing with H16_50 kD at 0.03 mg/kg, 0.1 mg/kg and 0.3 mg/kg, respectively.

Figure 18A:
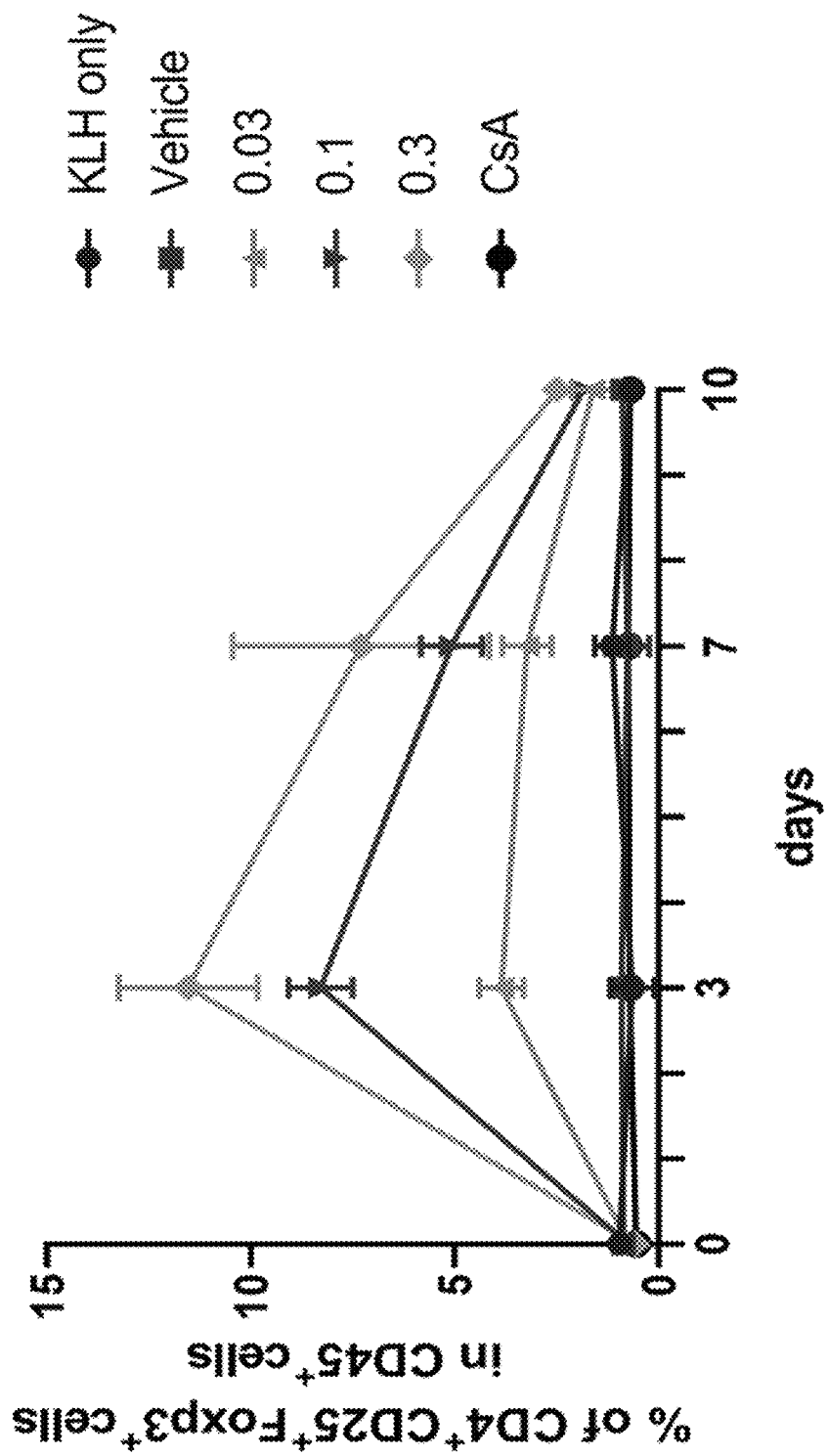
FIGS. 18A-FIG. 18C show changes over time in the relative percentage of CD4+ CD25+ FoxP3+ cells within CD45+ cell population (FIG. 18A), within TCRβ+ cell population (FIG. 18B), and within CD4+ cell population (FIG. 18C) in whole blood samples from the mice from Example 7.
Figure 18B:
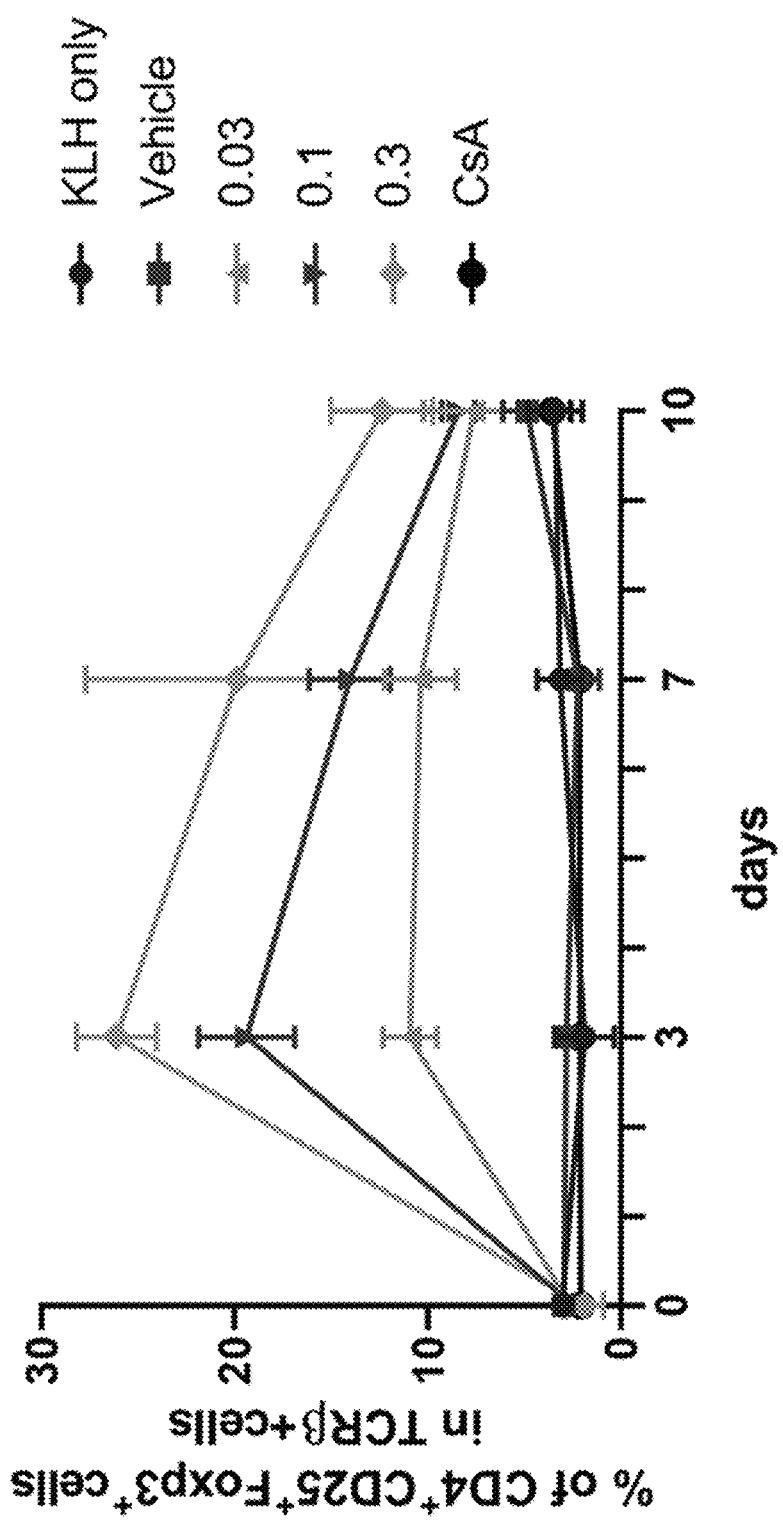
Figure 18C:
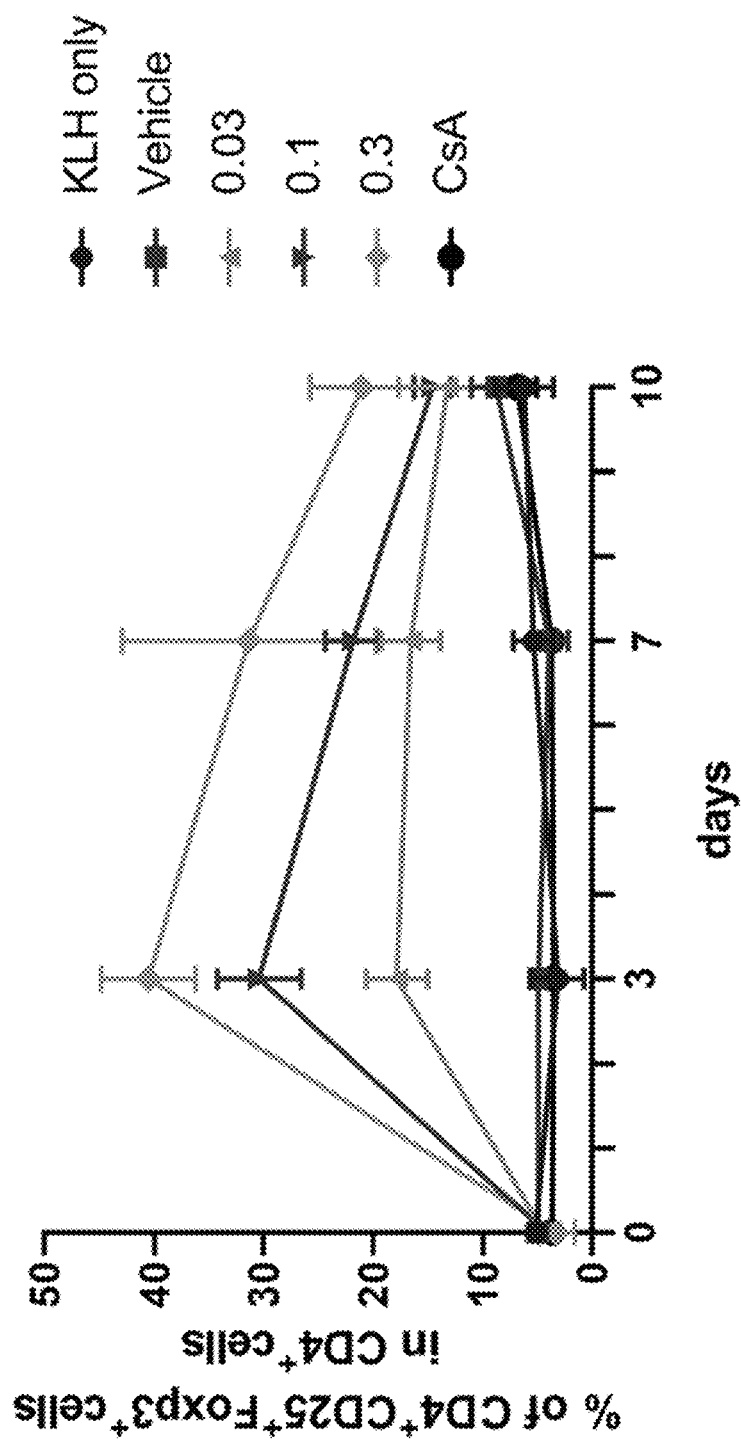
Figure 19:
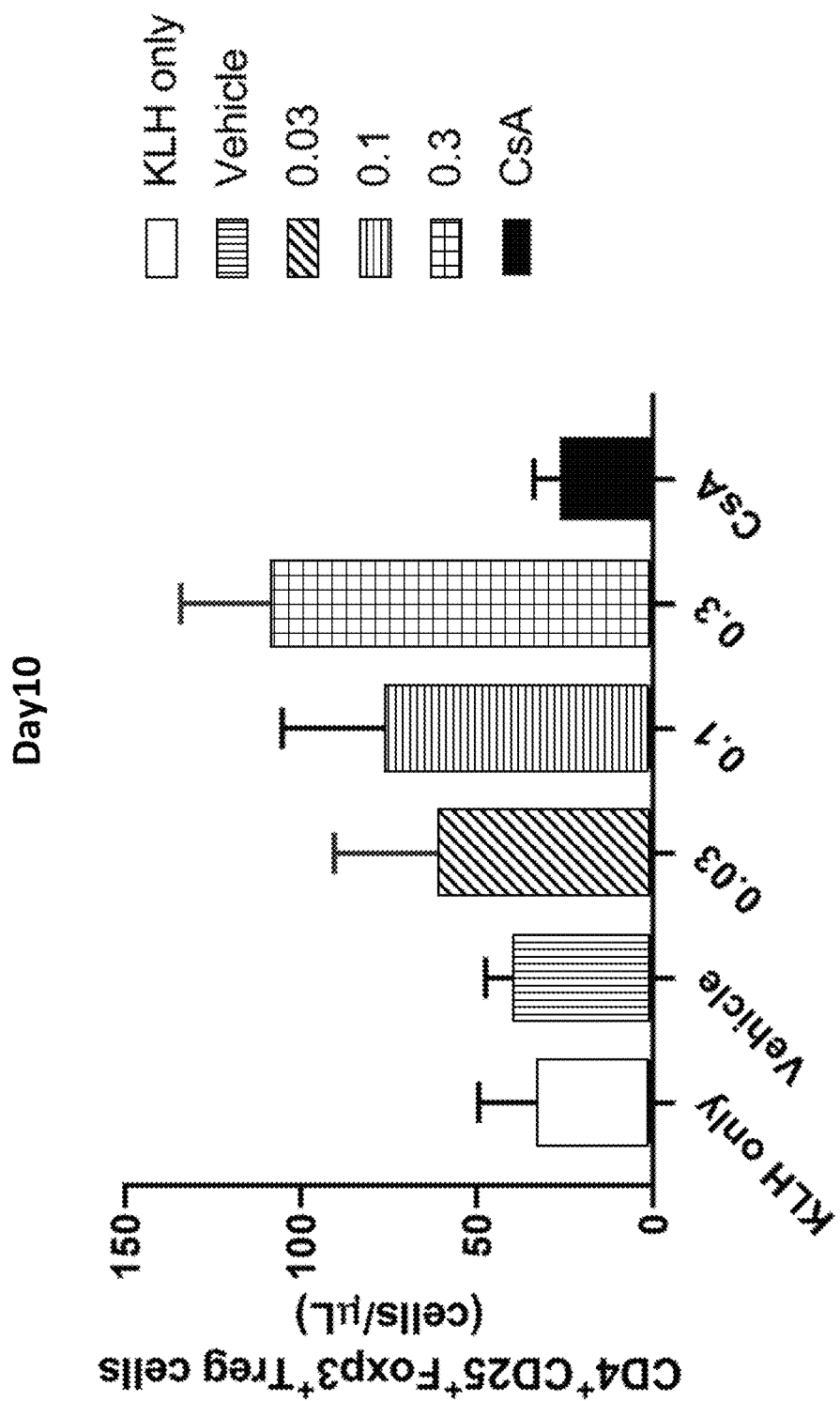
FIG. 19 shows the absolute counts of CD4+ CD25+ FoxP3+ cells on Day 10 in whole blood samples from the mice from Example 7.

As shown in FIGS. 18A-18C, the relative percentage of Treg (CD4+CD25+FoxP3+) cells within CD45+ cell population (FIG. 18A), within TCRβ+ cell population (FIG. 18B), and within CD4+ cell population (FIG. 18C) all increased compared to the negative control (vehicle only) and the positive control (Cyclosporine A) by dosing with H16_50 kD at 0.03 mg/kg, 0.1 mg/kg and 0.3 mg/kg, respectively. FIG. 19 also shows that at the end of Day 10, the absolute counts of Treg (CD4+CD25+FoxP3+) cells were higher in the mice following dosing with H16_50 kD at 0.03 mg/kg, 0.1 mg/kg and 0.3 mg/kg, respectively, as compared to the negative control (vehicle only) and the positive control (Cyclosporine A).

The above data demonstrate that administration of H16_50 kD showed therapeutic activity in a disease model (DTH) involving suppression of recall responses to a sensitizing agent by induced Tregs.

Example 8

To characterize the binding of the IL-2 conjugate H16_50 kD (the conjugate used in Example 7) and human IL2 ligand to human, mouse and cynomolgus forms of IL2 receptor Alpha and IL2 receptor Beta, Fc-tagged IL2 receptors were captured onto a Protein A coated sensor chip, and H16_50 kD and human IL2 ligand binding to the receptors was measured with a Biacore SPR biosensor system. A surface without receptor (Protein A only) was used to as a reference surface.

Capture of Fc-tagged receptors onto Protein A coated sensor chips: Protein A was coupled to a C1 sensor chip using standard amine coupling as described within the Biacore handbook. Each lyophilized Fc-receptor sample was dissolved up to 0.25 ug/ml then diluted 1/100 for capturing onto the Protein A surface. Capture times were varied to create different density surfaces from ~300 to 1000 RU for the kinetic studies. An additional experiment was run using high density surfaces for human and cynomolgus Beta receptor. These receptors were captured to ~8,000 and ~13,000 RU, respectively.

IL2 and H16_50 KD binding to human, mouse and cynomolgus alpha receptor surfaces: IL2 and H16_50 KD samples were tested for binding to the human, mouse and cynomolgus alpha receptor surfaces using a 2-fold concentration series from 0.7 to 200 nM. Response data were processed by subtracting the signals from a reference surface without receptor as well as an average of buffer injections using Scrubber-2 (Biologic Software Pty Ltd). Eight data sets for each test sample were globally fit to a 1:1 interaction model including a step for mass transport.

IL2 and H16_50 KD binding to human and cynomolgus beta receptor surfaces: IL2 and H16_50 KD samples were tested for binding to the human and cynomolgus beta receptor surfaces using a 2-fold concentration series from 16 nM to 4 uM. Response data were processed by subtracting the signals from a reference surface without receptor as well as an average of buffer injections. Four data sets for IL2 interacting with the human and cynomolgus beta receptor surfaces were globally fit to a 1:1 interaction model. No binding was observed for H16_50 KD to the human or cynomolgus beta receptor surfaces.

In order to determine if any interaction could be detected for H16_50 KD to the human and cynomolgus Beta receptor surfaces, addition binding studies were done using high density surfaces of each receptor. For these tests, H16_50 KD was assayed first using a 2-fold concentration series from 23 nM up to 12 uM. No specific interaction could be detected for H16_50 KD to either human or cynomolgus BetaR receptor even up to 12 uM in concentration. By contrast, a significant response or 900 RU and 1700 RU was observed for IL2 to both the human and cynomolgus Beta receptor surfaces, respectively. No binding of IL2 was observed to the reference surface.

Summary of Results: Overall, IL2 bound to the Alpha forms of human, mouse and cynomolgus receptor with similar affinities of ~10 nM, while H16_50 KD displayed an affinity for the Alpha receptors that was ~3 fold weaker at ~30 nM. IL2 bound to the human and cynomolgus Beta receptor with a similar affinity of ~300 nM. No significant binding of H16_50 KD could be detected to the Beta receptors. H16_50 KD appears to be a compound with significantly reduced or eliminated beta receptor affinity in that binding to IL2 Beta receptors was undetectable, even at high concentrations. Table 11 provides a summary of the binding constants.

TABLE 11

IL2 and H16_50 KD binding constants to receptors determined at 25° C.

| Surface | Sample | $k_a$ (M$^{-1}$s$^{-1}$) | $k_d$ (s$^{-1}$) | KD (nM) |
|---|---|---|---|---|
| hAlphaR | IL2 | 1.3(8)*e8 | 1.2(7) | 9.29(1)** |
| hAlphaR | H16_50 KD | 3.88(1)e6 | 0.1257(4) | 32.41(3) |
| mAlphaR | IL2 | 8.92(4)e6 | 0.0986(5) | 11.05(1) |
| mAlphaR | H16_50 KD | 1.400(3)e6 | 0.0748(2) | 53.42(7) |
| rAlphaR | IL2 | 6.4(2)e7 | 0.59(2) | 9.26(1) |
| rAlphaR | H16_50 KD | 2.870(7)e6 | 0.0751(2) | 26.16(3) |
| hBetaR | IL2 | 9.00(4)e5 | 0.2634(5) | 293(1) |
| hBetaR | H16_50 KD | NO BINDING DETECTED | | |
| rBetaR | IL2 | 8.51(2)e5 | 0.2415(4) | 283.8(5) |
| rBetaR | H16_50 KD | NO BINDING DETECTED | | |

NOTE:
Values in parentheses represent the standard deviation from a fit of 8 or 4 data sets reported for the last significant digit. For example, 1.3(8)e8 represents (1.3 ± 0.8)e8. The values for the association rate of IL2 to hAlphaR are very fast and therefore mass transport limited. This leads to a higher error. However, because the association and dissociation rates are highly correlated the ratio of the kinetic parameters for highly mass transport limited data still provides an accurate value for the equilibrium dissociation constant (KD).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An IL-2 conjugate comprising an IL-2 polypeptide having the amino acid sequence of SEQ ID NO: 3 or 4 in which at least one amino acid residue in the IL-2 polypeptide is replaced by the structure of Formula (I):

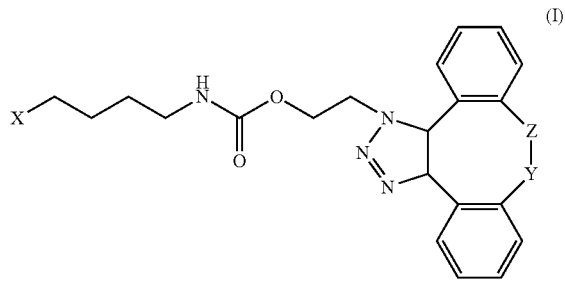

wherein:
Z is CH$_2$ and Y is

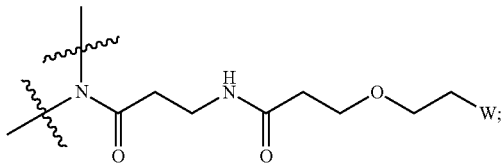

Y is CH$_2$ and Z is

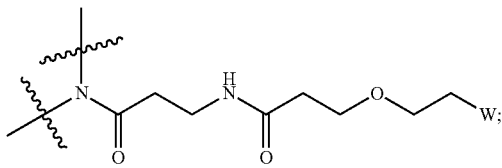

Z is CH$_2$ and Y is

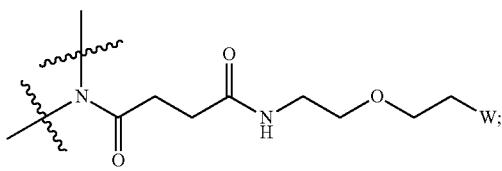

or
Y is CH$_2$ and Z is

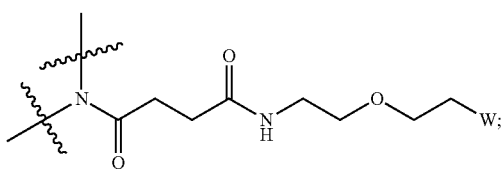

W is a PEG group having a molecular weight selected from about 5 kDa, 10 kDa, 15 kDa, 20 kDa, 25 kDa, 30 kDa, 35 kDa, 40 kDa, 45 kDa, 50 kDa, 55 kDa, and 60 kDa;

X has the structure:

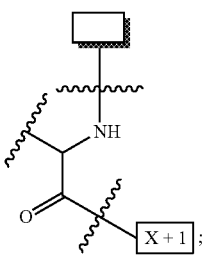

X−1 indicates the point of attachment to the preceding amino acid residue; and
X+1 indicates the point of attachment to the following amino acid residue;
wherein when the IL-2 conjugate comprises the amino acid sequence of SEQ ID NO: 3, the at least one amino acid residue replaced by the structure of Formula (I) is located in the IL-2 polypeptide at a position selected from P1, T2, S3, S4, S5, T6, K7, K8, Q10, L11, E14, H15, L17, L18, D19, Q21, M22, N25, G26, N28, N29, Y30, K31, M45, P46, K47, A49, T50, E51, L52, K53, H54, Q56, E66, Q73, S74, K75, N76, F77, H78, R80, P81, R82, D83, S86, N87, I88, V90, I91, L93, E94, K96, G97, S98, E99, T100, T101, F102, E105, A107, D108, E109, T110, A111, T112, E115, N118, R119, T122, F123, S124, Q125, S126, S129, T130, L131, and T132; or
wherein when the IL-2 conjugate comprises the amino acid sequence of SEQ ID NO: 4, the at least one amino acid replaced by the structure of Formula (I) is located in the IL-2 polypeptide at a position selected from A1, P2, T3, S4, S5, S6, T7, K8, K9, Q11, L12, E15, H16, L18, L19, D20, Q22, M23, N26, G27, N29, N30, Y31, K32, M46, P47, K48, A50, T51, E52, L53, H55, Q57, [E60,] E67, Q74, S75, K76, N77, F78, H79, R81, P82, R83, D84, S87, N88, I89, V91, I92, L94, E95, K97, G98, S99, E100, T101, T102, F103, E106, A108, D109, E110, T111, A112, T113, E116, N119, R120, T123, S125, Q126, S127, S130, T131, L132, and T133.

2. The IL-2 conjugate of claim 1, wherein Z is CH$_2$ and Y is

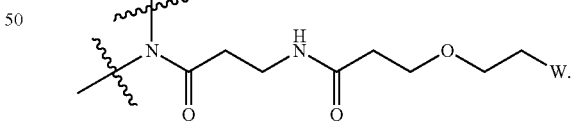

3. The IL-2 conjugate of claim 1, wherein Y is CH$_2$ and Z is

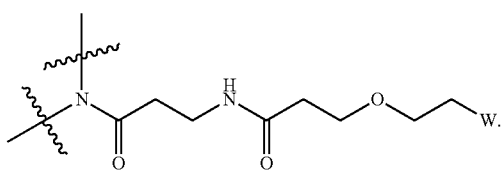

4. The IL-2 conjugate of claim 1, wherein Z is CH$_2$ and Y is

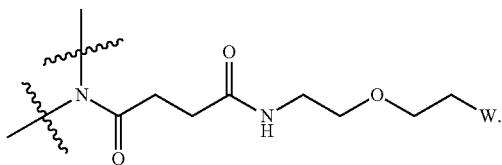

5. The IL-2 conjugate of claim 1, wherein Y is CH$_2$ and Z is

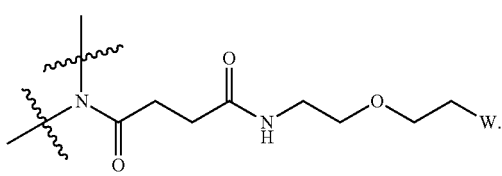

6. The IL-2 conjugate of claim 1, wherein the PEG group has a molecular weight selected from about 30 kDa, 40 kDa, 50 kDa, and 60 kDa.

7. The IL-2 conjugate of claim 6, wherein the PEG group has a molecular weight of about 50 kDa.

8. The IL-2 conjugate of claim 6, wherein the PEG group has a molecular weight of about 30 kDa.

9. The IL-2 conjugate of claim 1, wherein the IL-2 conjugate comprises the amino acid sequence of SEQ ID NO: 3 and the position is H15; or the IL-2 conjugate comprises the amino acid sequence of SEQ ID NO: 4 and the position is H16.

10. The IL-2 conjugate of claim 1, wherein the IL-2 conjugate comprises the amino acid sequence of SEQ ID NO: 3 and the position is L18; or the IL-2 conjugate comprises the amino acid sequence of SEQ ID NO: 4 and the position is L19.

11. The IL-2 conjugate of claim 1, wherein the IL-2 conjugate comprises the amino acid sequence of SEQ ID NO: 3 and the position is N87; or the IL-2 conjugate comprises the amino acid sequence of SEQ ID NO: 4 and the position is N88.

12. The IL-2 conjugate of claim 1, wherein the structure of Formula (I) has the structure of Formula (II) or Formula (III):

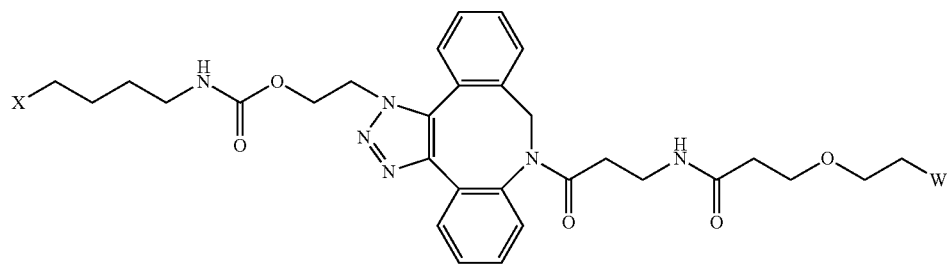

(II)

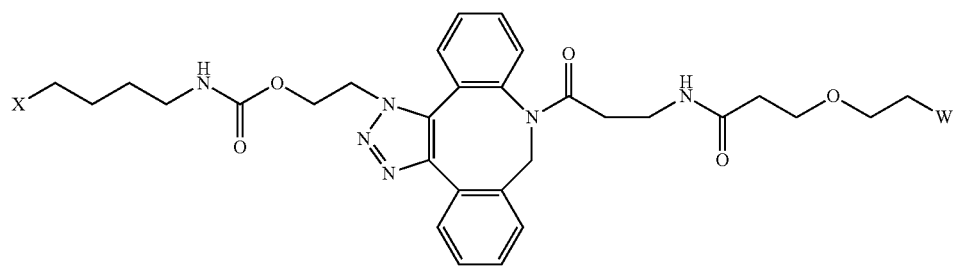

(III)

wherein:
W is a PEG group having a molecular weight selected from about 5 kDa, 10 kDa, 15 kDa, 20 kDa, 25 kDa, 30 kDa, 35 kDa, 40 kDa, 45 kDa, 50 kDa, 55 kDa, and 60 kDa;
X has the structure:

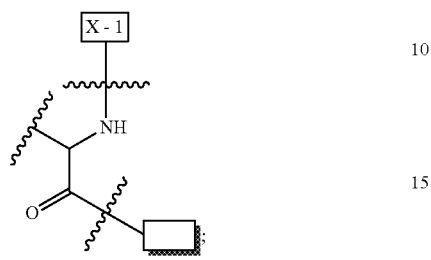

X−1 indicates the point of attachment to the preceding amino acid residue; and
X+1 indicates the point of attachment to the following amino acid residue.

13. The IL-2 conjugate of claim 12, wherein W is a PEG group having a molecular weight of about 50 kDa.

14. The IL-2 conjugate of claim 1, wherein the structure of Formula (I) has the structure of Formula (IV) or Formula (V):

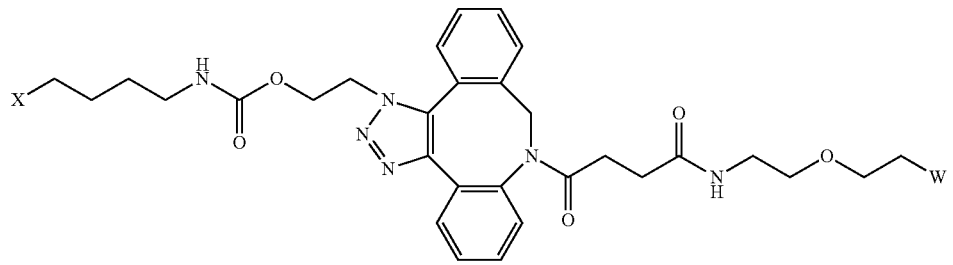

(IV)

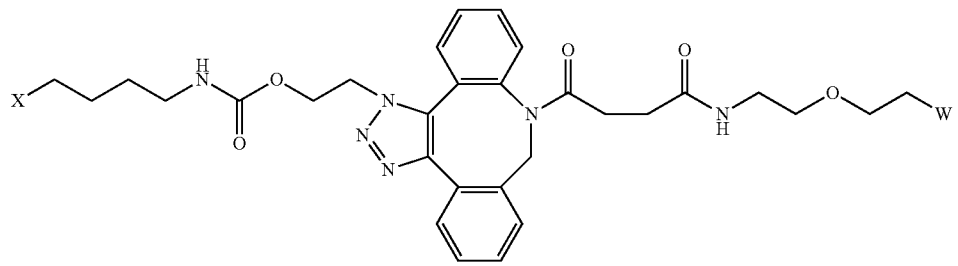

(V)

wherein:
W is a PEG group having a molecular weight selected from about 5 kDa, 10 kDa, 15 kDa, 20 kDa, 25 kDa, 30 kDa, 35 kDa, 40 kDa, 45 kDa, 50 kDa, 55 kDa, and 60 kDa;
X has the structure:

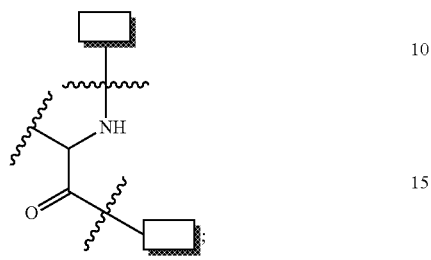

X−1 indicates the point of attachment to the preceding amino acid residue; and
X+1 indicates the point of attachment to the following amino acid residue.

15. The IL-2 conjugate of claim 14, wherein W is a PEG group having a molecular weight of about 50 kDa.

16. The IL-2 conjugate of claim 1, wherein the structure of Formula (I) has the structure of Formula (X) or Formula (XI):

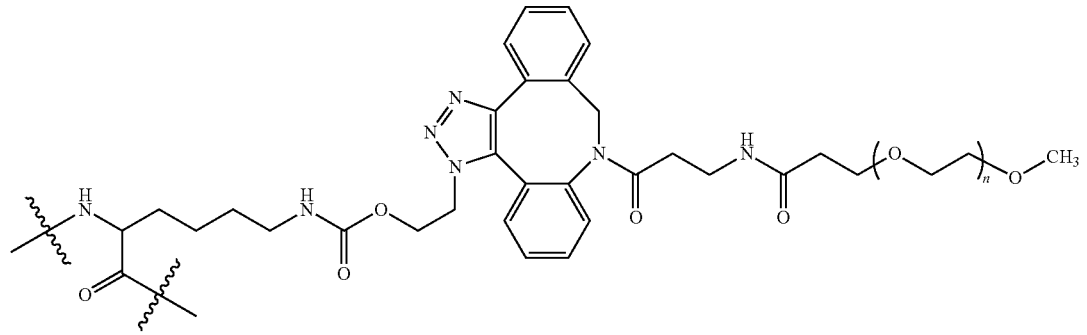

(X)

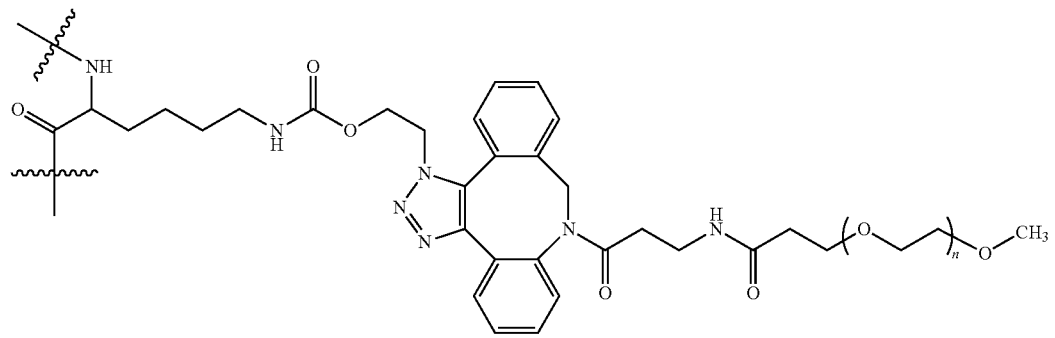

(XI)

wherein:
n is an integer such that a PEG group having the structure of —(OCH$_2$CH$_2$)$_n$—OCH$_3$ has a molecular weight selected from about 5 kDa, 10 kDa, 15 kDa, 20 kDa, 25 kDa, 30 kDa, 35 kDa, 40 kDa, 45 kDa, 50 kDa, 55 kDa, and 60 kDa; and
the wavy lines indicate covalent bonds to the first amino acid residue preceding the at least one amino acid residue and the first amino acid residue following the at least one amino acid residue, respectively, within SEQ ID NO: 3 or 4.

17. The IL-2 conjugate of claim 1, wherein the structure of Formula (I) has the structure of Formula (XII) or Formula (XIII):

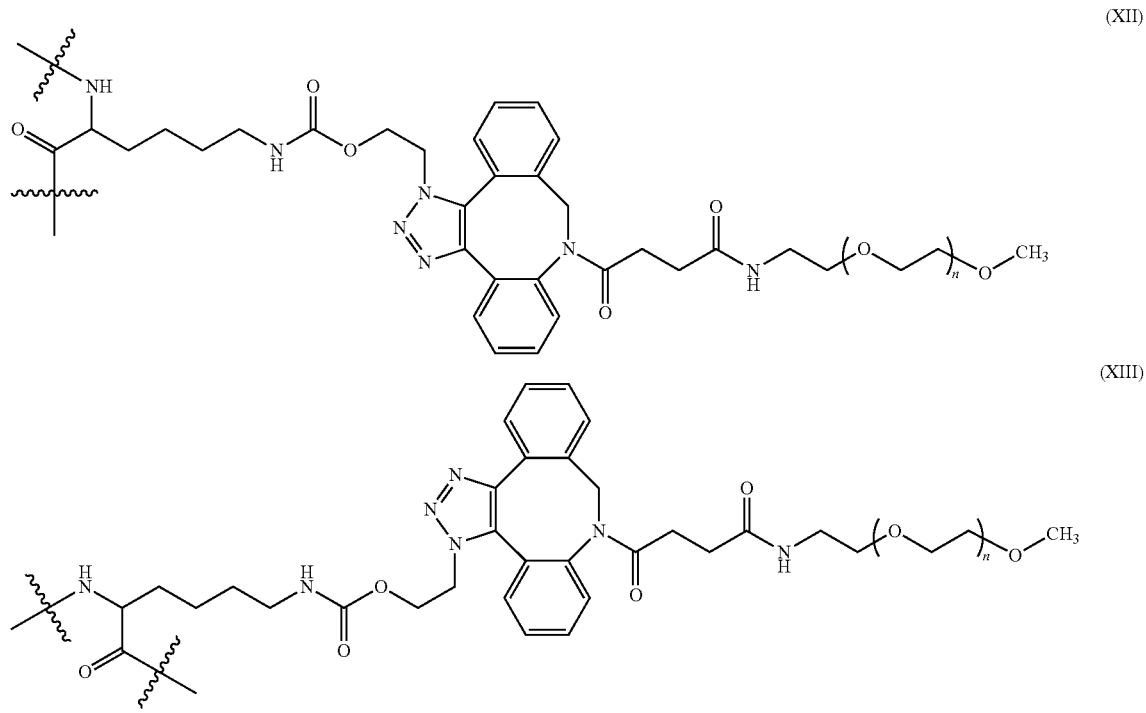

wherein:
n is an integer such that a PEG group having the structure of —(OCH$_2$CH$_2$)$_n$—OCH$_3$ has a molecular weight selected from about 5 kDa, 10 kDa, 15 kDa, 20 kDa, 25 kDa, 30 kDa, 35 kDa, 40 kDa, 45 kDa, 50 kDa, 55 kDa, and 60 kDa; and
the wavy lines indicate covalent bonds to the first amino acid residue preceding the at least one amino acid residue and the first amino acid residue following the at least one amino acid residue, respectively, within SEQ ID NO: 3 or 4.

18. A pharmaceutical composition comprising a mixture of the IL-2 conjugates of claim 12, wherein the mixture comprises (i) an IL-2 conjugate in which the structure of Formula (I) has the structure of Formula (II) and (ii) an IL-2 conjugate in which the structure of Formula (I) has the structure of Formula (III).

19. A pharmaceutical composition comprising a mixture of the IL-2 conjugates of claim 14, wherein the mixture comprises (i) an IL-2 conjugate in which the structure of Formula (I) has the structure of Formula (IV) and (ii) an IL-2 conjugate in which the structure of Formula (I) has the structure of Formula (V).

20. A pharmaceutical composition comprising a mixture of the IL-2 conjugates of claim 16, wherein the mixture comprises (i) an IL-2 conjugate in which the structure of Formula (I) has the structure of Formula (X) and (ii) an IL-2 conjugate in which the structure of Formula (I) has the structure of Formula (XI).

21. A pharmaceutical composition comprising a mixture of the IL-2 conjugates of claim 17, wherein the mixture comprises (i) an IL-2 conjugate in which the structure of Formula (I) has the structure of Formula (XII) and (ii) an IL-2 conjugate in which the structure of Formula (I) has the structure of Formula (XIII).

22. The IL-2 conjugate of claim 9, wherein: Z is CH$_2$ and Y is

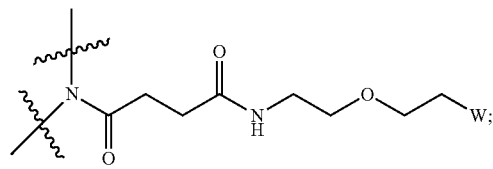

or

Y is CH$_2$ and Z is

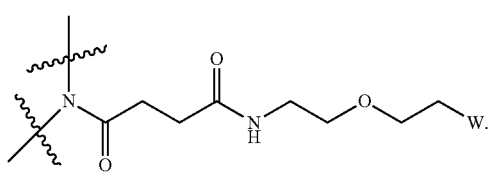

23. An IL-2 conjugate comprising an IL-2 polypeptide having the amino acid sequence of SEQ ID NO: 3 or 4 in which at least one amino acid residue in the IL-2 polypeptide is replaced by the structure of Formula (I):

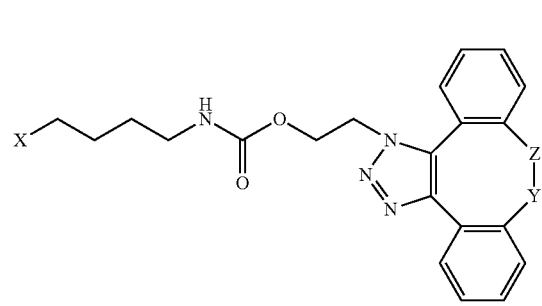

(I)

wherein:

Z is CH$_2$ and Y is

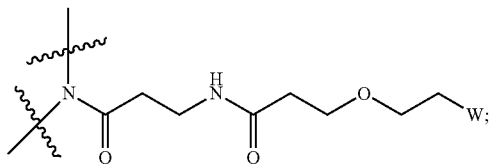

Y is CH$_2$ and Z is

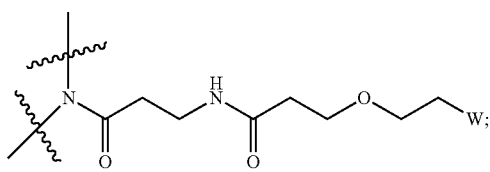

Z is CH$_2$ and Y is

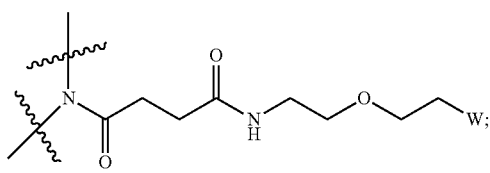

or

Y is CH$_2$ and Z is

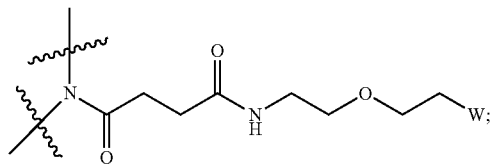

W is a PEG group having a molecular weight of about 50 kDa;

X has the structure:

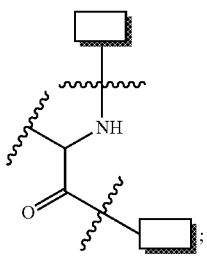

X−1 indicates the point of attachment to the preceding amino acid residue; and

X+1 indicates the point of attachment to the following amino acid residue;

wherein when the IL-2 conjugate comprises the amino acid sequence of SEQ ID NO: 3, the at least one amino acid residue replaced by the structure of Formula (I) is located in the IL-2 polypeptide at a position selected from K8, H15, L18, D19, N25, N87, E99, and N118; or wherein when the IL-2 conjugate comprises the amino acid sequence of SEQ ID NO: 4, the at least one amino acid replaced by the structure of Formula (I) is located in the IL-2 polypeptide at a position selected from K9, H16, L19, D20, N26, N88, E100, and N119.

24. The IL-2 conjugate of claim 23, wherein Z is CH$_2$ and Y is

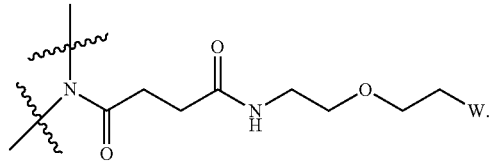

25. The IL-2 conjugate of claim 23, wherein Y is CH$_2$ and Z is

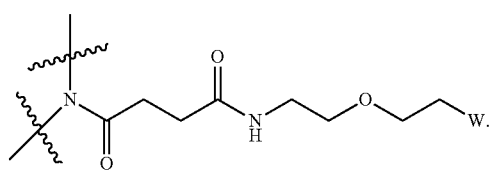

26. The IL-2 conjugate of claim 23, wherein the IL-2 conjugate comprises the amino acid sequence of SEQ ID NO: 3 and the position is H15; or the IL-2 conjugate comprises the amino acid sequence of SEQ ID NO: 4 and the position is H16.

27. The IL-2 conjugate of claim 23, wherein the IL-2 conjugate comprises the amino acid sequence of SEQ ID NO: 3 and the position is L18; or the IL-2 conjugate comprises the amino acid sequence of SEQ ID NO: 4 and the position is L19.

28. The IL-2 conjugate of claim 23, wherein the IL-2 conjugate comprises the amino acid sequence of SEQ ID NO: 3 and the position is N87; or the IL-2 conjugate comprises the amino acid sequence of SEQ ID NO: 4 and the position is N88.

29. The IL-2 conjugate of claim 23, wherein the structure of Formula (I) has the structure of Formula (IV) or Formula (V):

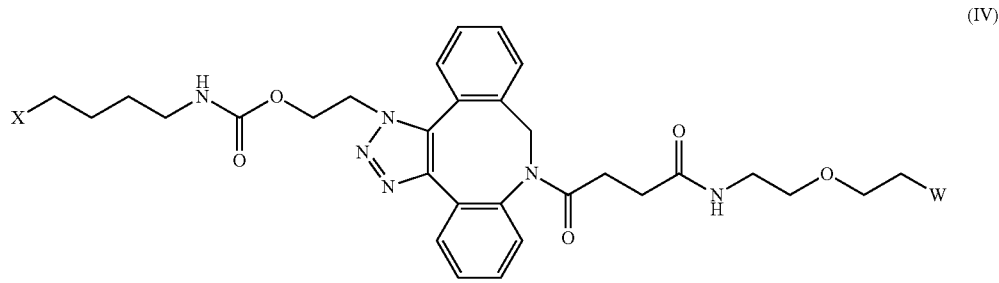

(IV)

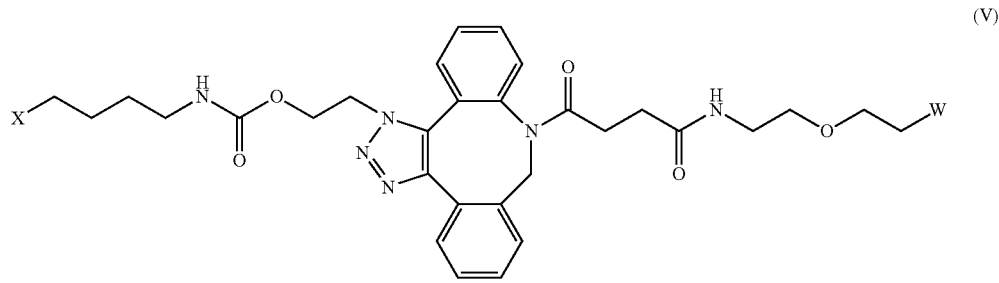

(V)

wherein:

W is a PEG group having a molecular weight of about 50 kDa;

X has the structure:

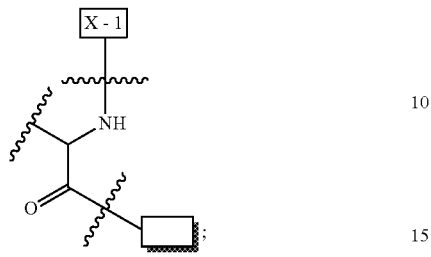

X−1 indicates the point of attachment to the preceding amino acid residue; and

X+1 indicates the point of attachment to the following amino acid residue.

30. The IL-2 conjugate of claim 23, wherein the structure of Formula (I) has the structure of Formula (XII) or Formula (XIII):

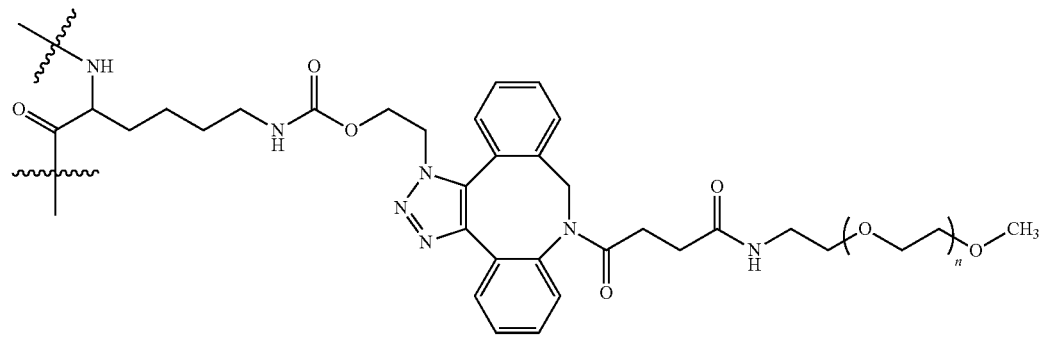

(XII)

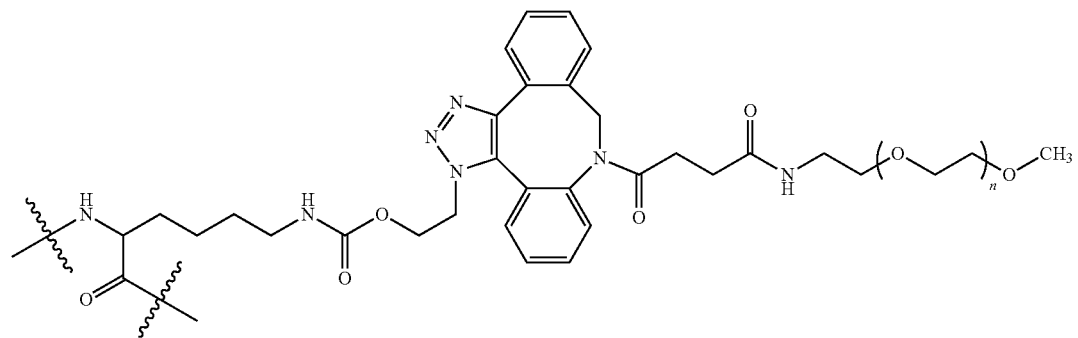

(XIII)

wherein:

n is an integer such that a PEG group having the structure of $-(OCH_2CH_2)_n-OCH_3$ has a molecular weight of about 50 kDa; and the wavy lines indicate covalent bonds to the first amino acid residue preceding the at least one amino acid residue and the first amino acid residue following the at least one amino acid residue, respectively, within SEQ ID NO: 3 or 4.

31. The IL-2 conjugate of claim 30, wherein the IL-2 conjugate comprises the amino acid sequence of SEQ ID NO: 3 and the position is H15; or the IL-2 conjugate comprises the amino acid sequence of SEQ ID NO: 4 and the position is H16.

32. The IL-2 conjugate of claim 31, wherein the IL-2 conjugate comprises the amino acid sequence of SEQ ID NO: 3 and the position is H15.

33. A pharmaceutical composition comprising a mixture of the IL-2 conjugates of claim 29, wherein the mixture comprises (i) an IL-2 conjugate in which the structure of Formula (I) has the structure of Formula (IV) and (ii) an IL-2 conjugate in which the structure of Formula (I) has the structure of Formula (V).

34. A pharmaceutical composition comprising a mixture of the IL-2 conjugates of claim 30, wherein the mixture comprises (i) an IL-2 conjugate in which the structure of Formula (I) has the structure of Formula (XII) and (ii) an IL-2 conjugate in which the structure of Formula (I) has the structure of Formula (XIII).

35. A pharmaceutical composition comprising a mixture of the IL-2 conjugates of claim 32, wherein the mixture comprises (i) an IL-2 conjugate in which the structure of Formula (I) has the structure of Formula (XII) and an (ii) IL-2 conjugate in which the structure of Formula (I) has the structure of Formula (XIII).

36. The IL-2 conjugate of claim 26, wherein:
Z is $CH_2$ and Y is

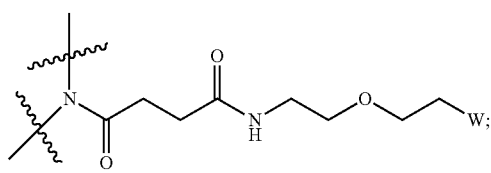

or
Y is $CH_2$ and Z is

37. An IL-2 conjugate consisting of the amino acid sequence of SEQ ID NO: 3 in which a modified amino acid of the structure of Formula (XII) or Formula (XIII) is present at position 15 of SEQ ID NO: 3 instead of histidine:

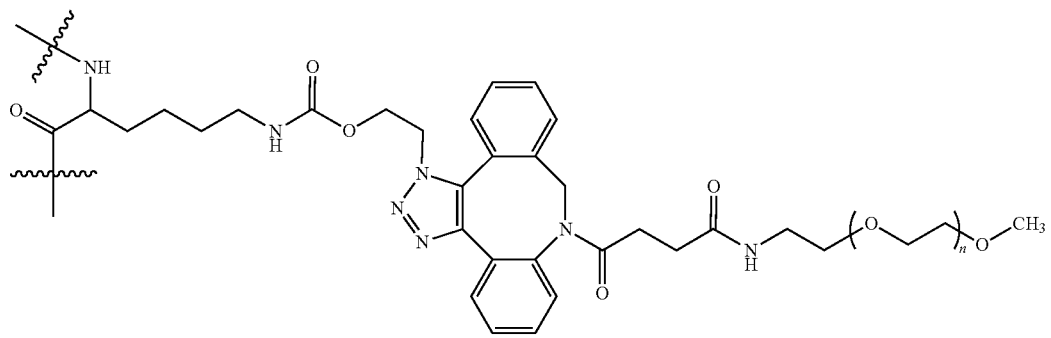

(XII)

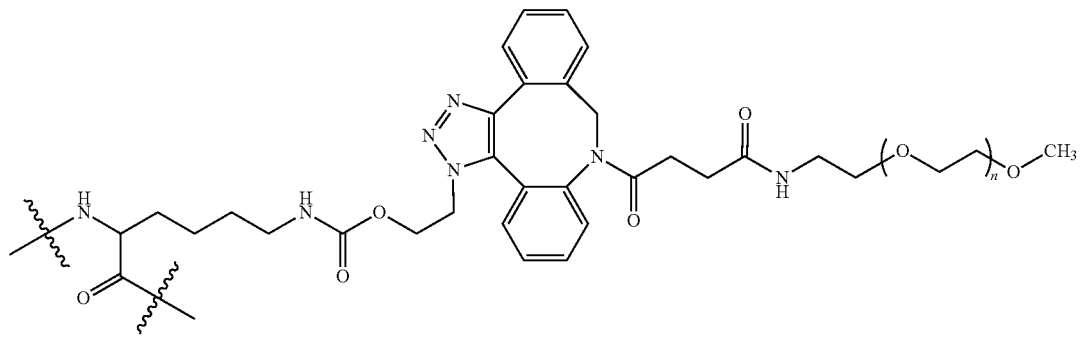

(XIII)

wherein:
n is an integer such that a PEG group having the structure of —(OCH$_2$CH$_2$)$_n$—OCH$_3$ has a molecular weight of about 50 kDa; and
the wavy lines indicate covalent bonds to an amino acid residue at position 14 and an amino acid residue at position 16, respectively, within SEQ ID NO: 3.

38. An IL-2 conjugate comprising an amino acid sequence that (i) is at least 97% identical to the amino acid sequence of SEQ ID NO: 80 and (ii) includes X at a position corresponding to position 15 of SEQ ID NO: 80, wherein X is N6-(2-azidoethoxy)-carbonyl-L-lysine (AzK) covalently attached via a conjugating moiety comprising a dibenzocyclooctyne group to a PEG group having a molecular weight of about 50 kDa.

39. The IL-2 conjugate of claim 38, wherein the AzK covalently attached via the conjugating moiety to the PEG group is collectively represented by the structure of Formula (XII) or Formula XIII):

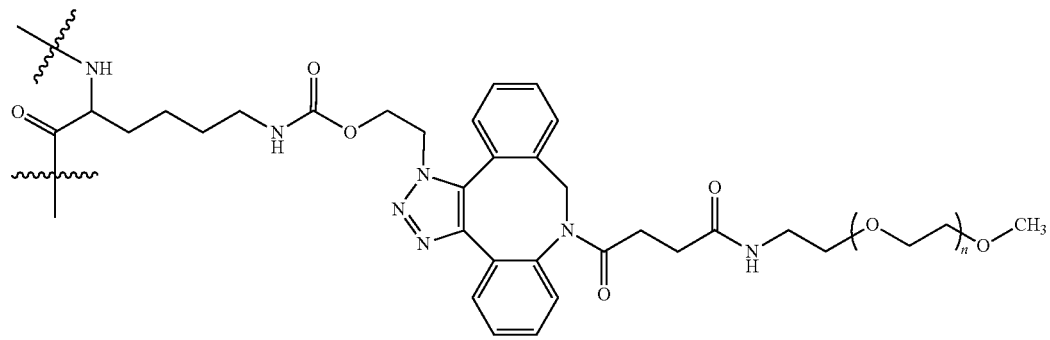

(XII)

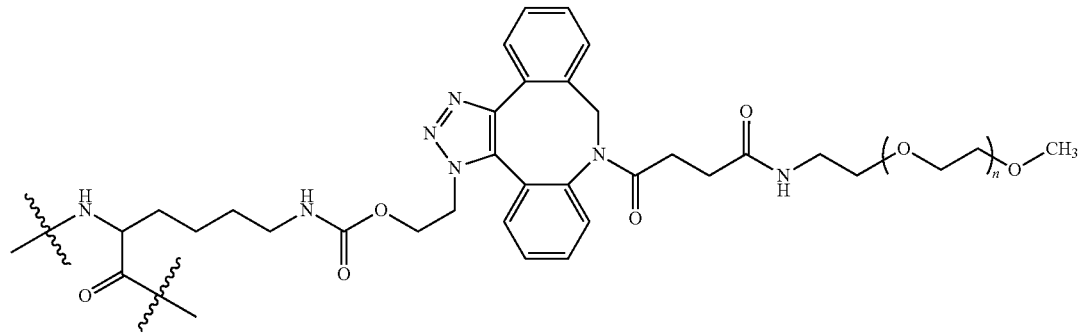

(XIII)

wherein:
n is an integer such that the PEG group having the structure of —(OCH$_2$CH$_2$)$_n$—OCH$_3$ has a molecular weight of about 50 kDa; and
the wavy lines indicate covalent bonds to the first amino acid residue preceding the X and the first amino acid residue following the X, respectively, within SEQ ID NO: 80.

40. An IL-2 conjugate comprising an amino acid sequence that (i) is at least 98% identical to the amino acid sequence of SEQ ID NO: 80 and (ii) includes X at a position corresponding to position 15 of SEQ ID NO: 80, wherein X is N6-(2-azidoethoxy)-carbonyl-L-lysine (AzK) covalently attached via a conjugating moiety comprising a dibenzocyclooctyne group to a PEG group having a molecular weight of about 50 kDa.

41. The IL-2 conjugate of claim 40, wherein the AzK covalently attached via the conjugating moiety to the PEG group is collectively represented by the structure of Formula (XII) or Formula (XIII):

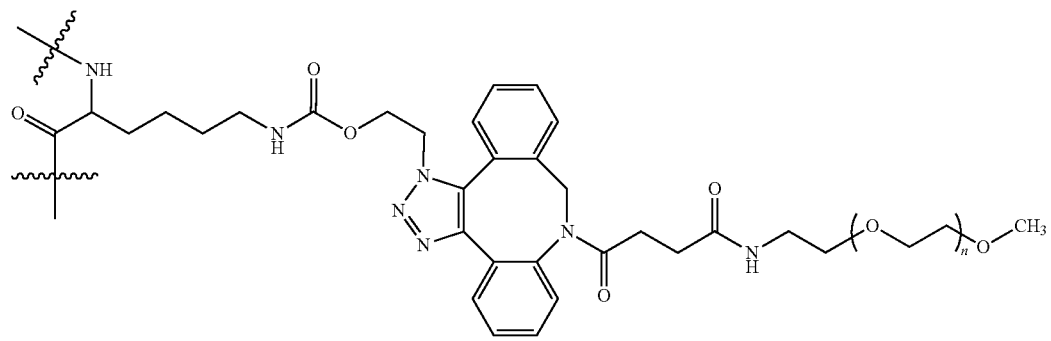

(XII)

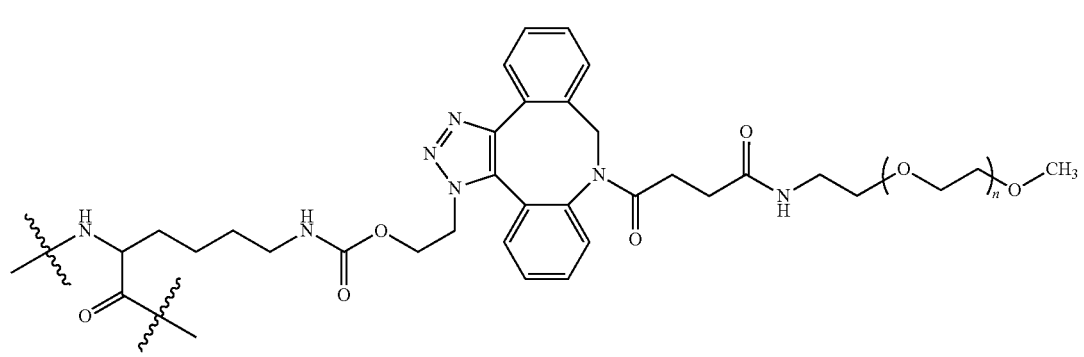

(XIII)

wherein:
n is an integer such that the PEG group having the structure of —(OCH$_2$CH$_2$)$_n$—OCH$_3$ has a molecular weight of about 50 kDa; and
the wavy lines indicate covalent bonds to the first amino acid residue preceding the X and the first amino acid residue following the X, respectively, within SEQ ID NO: 80.

42. An IL-2 conjugate comprising the amino acid sequence of SEQ ID NO: 80, wherein X in SEQ ID NO: 80 is N6-(2-azidoethoxy)-carbonyl-L-lysine (AzK) covalently attached via a conjugating moiety comprising a dibenzocyclooctyne group to a PEG group having a molecular weight of about 50 kDa.

43. The IL-2 conjugate of claim 42, wherein the AzK covalently attached via the conjugating moiety to the PEG group is collectively represented by the structure of Formula (XII) or Formula (XIII):

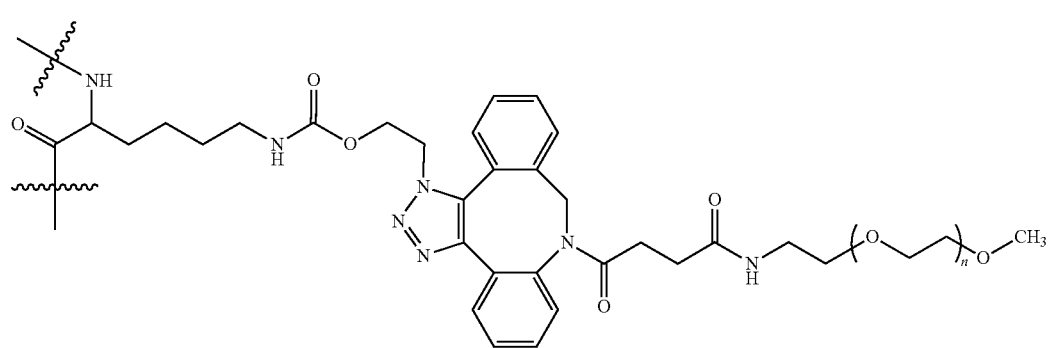

(XII)

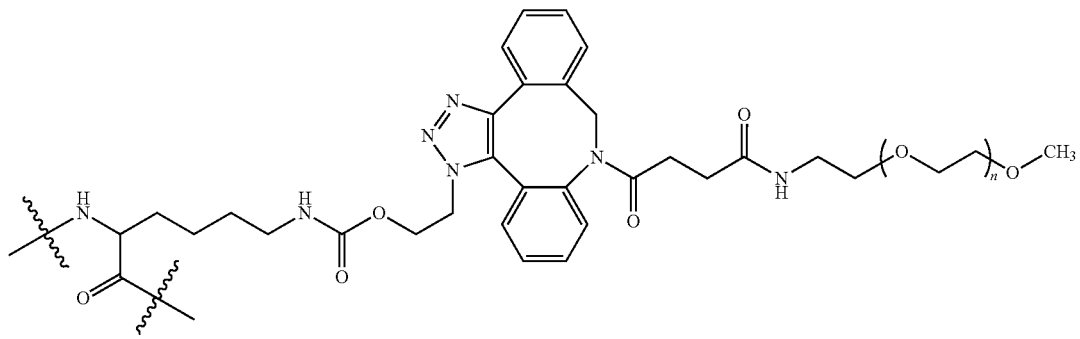

wherein:
n is an integer such that the PEG group having the structure of —(OCH$_2$CH$_2$)$_n$—OCH$_3$ has a molecular weight of about 50 kDa; and
the wavy lines indicate covalent bonds to the first amino acid residue preceding the X and the first amino acid residue following the X, respectively, within SEQ ID NO: 80.

44. A pharmaceutical composition comprising a mixture of IL-2 conjugates of claim 37, wherein the mixture comprises (i) an IL-2 conjugate comprising the structure of Formula (XII), and (ii) an IL-2 conjugate comprising the structure of Formula (XIII).

45. The pharmaceutical composition of claim 44, further comprising a diluent, a buffering agent, a stabilizer, a surfactant, or any combination thereof.

46. The pharmaceutical composition of claim 44, further comprising sorbitol.

47. The pharmaceutical composition of claim 44, further comprising polysorbate-20.

48. A dispenser device comprising the pharmaceutical composition of claim 44.

49. A syringe comprising the pharmaceutical composition of claim 44.

50. A vial comprising the pharmaceutical composition of claim 44.

51. A pharmaceutical composition comprising the IL-2 conjugate of claim 42.

52. A pharmaceutical composition comprising a mixture of IL-2 conjugates of claim 43, wherein the mixture comprises (i) an IL-2 conjugate comprising the structure of Formula (XII), and (ii) an IL-2 conjugate comprising the structure of Formula (XIII).

53. The IL-2 conjugate of claim 23, wherein the IL-2 conjugate comprises the amino acid sequence of SEQ ID NO: 3 and the position is K8; or the IL-2 conjugate comprises the amino acid sequence of SEQ ID NO: 4 and the position is K9.

54. The IL-2 conjugate of claim 23, wherein the IL-2 conjugate comprises the amino acid sequence of SEQ ID NO: 3 and the position is D19; or the IL-2 conjugate comprises the amino acid sequence of SEQ ID NO: 4 and the position is D20.

55. The IL-2 conjugate of claim 23, wherein the IL-2 conjugate comprises the amino acid sequence of SEQ ID NO: 3 and the position is N25; or the IL-2 conjugate comprises the amino acid sequence of SEQ ID NO: 4 and the position is N26.

56. The IL-2 conjugate of claim 23, wherein the IL-2 conjugate comprises the amino acid sequence of SEQ ID NO: 3 and the position is E99; or the IL-2 conjugate comprises the amino acid sequence of SEQ ID NO: 4 and the position is E100.

57. The IL-2 conjugate of claim 23, wherein the IL-2 conjugate comprises the amino acid sequence of SEQ ID NO: 3 and the position is N118; or the IL-2 conjugate comprises the amino acid sequence of SEQ ID NO: 4 and the position is N119.

* * * * *

```
                            SEQUENCE LISTING

<160> NUMBER OF SEQ ID NOS: 249

<210> SEQ ID NO 1
<211> LENGTH: 133
<212> TYPE: PRT
<213> ORGANISM: Homo sapiens
<220> FEATURE:
<221> NAME/KEY: misc_feature
<223> OTHER INFORMATION: IL-2 (homo sapiens) (mature form)

<400> SEQUENCE: 1

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Cys Gln Ser Ile
            115                 120                 125

Ile Ser Thr Leu Thr
    130

<210> SEQ ID NO 2
<211> LENGTH: 153
<212> TYPE: PRT
<213> ORGANISM: Homo sapiens
<220> FEATURE:
<221> NAME/KEY: misc_feature
<223> OTHER INFORMATION: IL-2 (homo sapiens) (precursor)

<400> SEQUENCE: 2

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
                20                  25                  30

Gln Leu Glu His Leu Leu Leu Asp Leu Gln Met Ile Leu Asn Gly Ile
            35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
                100                 105                 110
```

```
Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

<210> SEQ ID NO 3
<211> LENGTH: 132
<212> TYPE: PRT
<213> ORGANISM: Artificial Sequence
<220> FEATURE:
<223> OTHER INFORMATION: Synthetic: aldesleukin

<400> SEQUENCE: 3

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 4
<211> LENGTH: 133
<212> TYPE: PRT
<213> ORGANISM: Artificial Sequence
<220> FEATURE:
<223> OTHER INFORMATION: Synthetic: IL-2_C125S

<400> SEQUENCE: 4

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
```

-continued

```
                115                 120                 125
Ile Ser Thr Leu Thr
            130

<210> SEQ ID NO 5
<211> LENGTH: 133
<212> TYPE: PRT
<213> ORGANISM: Artificial Sequence
<220> FEATURE:
<223> OTHER INFORMATION: Synthetic: IL-2_K9X
<220> FEATURE:
<221> NAME/KEY: misc_feature
<222> LOCATION: (9)..(9)
<223> OTHER INFORMATION: Xaa is an unnatural amino acid

<400> SEQUENCE: 5

Ala Pro Thr Ser Ser Ser Thr Lys Xaa Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
            130

<210> SEQ ID NO 6
<211> LENGTH: 133
<212> TYPE: PRT
<213> ORGANISM: Artificial Sequence
<220> FEATURE:
<223> OTHER INFORMATION: Synthetic: IL-2_H16X
<220> FEATURE:
<221> NAME/KEY: misc_feature
<222> LOCATION: (16)..(16)
<223> OTHER INFORMATION: Xaa is an unnatural amino acid

<400> SEQUENCE: 6

Ala Pro Thr Ser Ser Ser Thr Lys Lys Thr Gln Leu Gln Leu Glu Xaa
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
```

-continued

```
                    100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 7
<211> LENGTH: 133
<212> TYPE: PRT
<213> ORGANISM: Artificial Sequence
<220> FEATURE:
<223> OTHER INFORMATION: Synthetic: IL-2_L19X
<220> FEATURE:
<221> NAME/KEY: misc_feature
<222> LOCATION: (19)..(19)
<223> OTHER INFORMATION: Xaa is an unnatural amino acid

<400> SEQUENCE: 7

Ala Pro Thr Ser Ser Ser Thr Lys Lys Thr Gln Leu Gln Leu Glu His
1               5                   10                  15

Leu Leu Xaa Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 8
<211> LENGTH: 133
<212> TYPE: PRT
<213> ORGANISM: Artificial Sequence
<220> FEATURE:
<223> OTHER INFORMATION: Synthetic: IL-2_D20X
<220> FEATURE:
<221> NAME/KEY: misc_feature
<222> LOCATION: (20)..(20)
<223> OTHER INFORMATION: Xaa is an unnatural amino acid

<400> SEQUENCE: 8

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
```

```
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 9
<211> LENGTH: 133
<212> TYPE: PRT
<213> ORGANISM: Artificial Sequence
<220> FEATURE:
<223> OTHER INFORMATION: Synthetic: IL-2_M23X
<220> FEATURE:
<221> NAME/KEY: misc_feature
<222> LOCATION: (23)..(23)
<223> OTHER INFORMATION: Xaa is an unnatural amino acid

<400> SEQUENCE: 9

Ala Pro Thr Ser Ser Ser Thr Lys Lys Thr Gln Leu Gln Leu Glu His
1               5                   10                  15

Leu Leu Leu Asp Leu Gln Xaa Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 10
<211> LENGTH: 133
<212> TYPE: PRT
<213> ORGANISM: Artificial Sequence
<220> FEATURE:
<223> OTHER INFORMATION: Synthetic: IL-2_N26X
<220> FEATURE:
<221> NAME/KEY: misc_feature
<222> LOCATION: (26)..(26)
<223> OTHER INFORMATION: Xaa is an unnatural amino acid

<400> SEQUENCE: 10

Ala Pro Thr Ser Ser Ser Thr Lys Lys Thr Gln Leu Gln Leu Glu His
1               5                   10                  15

Leu Leu Leu Asp Leu Gln Met Ile Leu Xaa Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
```

```
                65                  70                  75                  80
Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
            130

<210> SEQ ID NO 11
<211> LENGTH: 133
<212> TYPE: PRT
<213> ORGANISM: Artificial Sequence
<220> FEATURE:
<223> OTHER INFORMATION: Synthetic: IL-2_N88X
<220> FEATURE:
<221> NAME/KEY: misc_feature
<222> LOCATION: (88)..(88)
<223> OTHER INFORMATION: Xaa is an unnatural amino acid

<400> SEQUENCE: 11

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Xaa Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
            130

<210> SEQ ID NO 12
<211> LENGTH: 133
<212> TYPE: PRT
<213> ORGANISM: Artificial Sequence
<220> FEATURE:
<223> OTHER INFORMATION: Synthetic: IL-2_E100X
<220> FEATURE:
<221> NAME/KEY: misc_feature
<222> LOCATION: (100)..(100)
<223> OTHER INFORMATION: Xaa is an unnatural amino acid

<400> SEQUENCE: 12

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
```

```
                    50                  55                  60
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Xaa Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 13
<211> LENGTH: 133
<212> TYPE: PRT
<213> ORGANISM: Artificial Sequence
<220> FEATURE:
<223> OTHER INFORMATION: Synthetic: IL-2_N119X
<220> FEATURE:
<221> NAME/KEY: misc_feature
<222> LOCATION: (119)..(119)
<223> OTHER INFORMATION: Xaa is an unnatural amino acid

<400> SEQUENCE: 13

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Xaa Arg Trp Ile Thr Phe Ser Gln Ser Ile
            115                 120                 125

Ile Ser Thr Leu Thr
            130

<210> SEQ ID NO 14
<211> LENGTH: 133
<212> TYPE: PRT
<213> ORGANISM: Artificial Sequence
<220> FEATURE:
<223> OTHER INFORMATION: Synthetic: IL-2_T123X
<220> FEATURE:
<221> NAME/KEY: misc_feature
<222> LOCATION: (123)..(123)
<223> OTHER INFORMATION: Xaa is an unnatural amino acid

<400> SEQUENCE: 14

Ala Pro Thr Ser Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
```

```
                35                  40                  45
Lys Ala Thr Glu Leu Lys His Leu Gln Cys Leu Glu Glu Leu Lys
 50                  55                  60
Pro Leu Glu Glu Val Leu Asn Leu Ala Gln Ser Lys Asn Phe His Leu
 65                  70                  75                  80
Arg Pro Arg Asp Leu Ile Ser Asn Ile Asn Val Ile Val Leu Glu Leu
                 85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Xaa Phe Ser Gln Ser Ile
                115                 120                 125
Ile Ser Thr Leu Thr
                130

<210> SEQ ID NO 15
<211> LENGTH: 133
<212> TYPE: PRT
<213> ORGANISM: Artificial Sequence
<220> FEATURE:
<223> OTHER INFORMATION: Synthetic: IL-2_Q126X
<220> FEATURE:
<221> NAME/KEY: misc_feature
<222> LOCATION: (126)..(126)
<223> OTHER INFORMATION: Xaa is an unnatural amino acid

<400> SEQUENCE: 15

Ala Pro Thr Ser Ser Ser Thr Lys Lys Thr Gln Leu Gln Leu Glu His
 1               5                  10                  15
Leu Leu Leu Asp Leu Gln Met Ile Leu Asn Gly Ile Asn Asn Tyr Lys
                 20                  25                  30
Asn Pro Lys Leu Thr Arg Met Leu Thr Phe Lys Phe Tyr Met Pro Lys
                 35                  40                  45
Lys Ala Thr Glu Leu Lys His Leu Gln Cys Leu Glu Glu Leu Lys
 50                  55                  60
Pro Leu Glu Glu Val Leu Asn Leu Ala Gln Ser Lys Asn Phe His Leu
 65                  70                  75                  80
Arg Pro Arg Asp Leu Ile Ser Asn Ile Asn Val Ile Val Leu Glu Leu
                 85                  90                  95
Lys Gly Ser Glu Thr Thr Phe Met Cys Glu Tyr Ala Asp Glu Thr Ala
                100                 105                 110
Thr Ile Val Glu Phe Leu Asn Arg Trp Ile Thr Phe Ser Xaa Ser Ile
                115                 120                 125
Ile Ser Thr Leu Thr
                130

<210> SEQ ID NO 16
<211> LENGTH: 133
<212> TYPE: PRT
<213> ORGANISM: Artificial Sequence
<220> FEATURE:
<223> OTHER INFORMATION: Synthetic: IL-2_S127X
<220> FEATURE:
<221> NAME/KEY: misc_feature
<222> LOCATION: (127)..(127)
<223> OTHER INFORMATION: Xaa is an unnatural amino acid

<400> SEQUENCE: 16

Ala Pro Thr Ser Ser Ser Thr Lys Lys Thr Gln Leu Gln Leu Glu His
 1               5                  10                  15
Leu Leu Leu Asp Leu Gln Met Ile Leu Asn Gly Ile Asn Asn Tyr Lys
```

```
                    20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Xaa Ile
        115                 120                 125

Ile Ser Thr Leu Thr
        130

<210> SEQ ID NO 17
<211> LENGTH: 133
<212> TYPE: PRT
<213> ORGANISM: Artificial Sequence
<220> FEATURE:
<223> OTHER INFORMATION: Synthetic: IL-2_T131X
<220> FEATURE:
<221> NAME/KEY: misc_feature
<222> LOCATION: (131)..(131)
<223> OTHER INFORMATION: Xaa is an unnatural amino acid

<400> SEQUENCE: 17

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Xaa Leu Thr
        130

<210> SEQ ID NO 18
<211> LENGTH: 133
<212> TYPE: PRT
<213> ORGANISM: Artificial Sequence
<220> FEATURE:
<223> OTHER INFORMATION: Synthetic: IL-2_N88R_D109X
<220> FEATURE:
<221> NAME/KEY: misc_feature
<222> LOCATION: (109)..(109)
<223> OTHER INFORMATION: Xaa is an unnatural amino acid

<400> SEQUENCE: 18

Ala Pro Thr Ser Ser Ser Thr Lys Lys Thr Gln Leu Gln Leu Glu His
```

```
                1               5                  10                  15
            Leu Leu Leu Asp Leu Gln Met Ile Leu Asn Gly Ile Asn Asn Tyr Lys
                        20                  25                  30

Asn Pro Lys Leu Thr Arg Met Leu Thr Phe Lys Phe Tyr Met Pro Lys
                        35                  40                  45

Lys Ala Thr Glu Leu Lys His Leu Gln Cys Leu Glu Glu Glu Leu Lys
                        50                  55                  60

Pro Leu Glu Glu Val Leu Asn Leu Ala Gln Ser Lys Asn Phe His Leu
             65                  70                  75                  80

Arg Pro Arg Asp Leu Ile Ser Arg Ile Asn Val Ile Val Leu Glu Leu
                        85                  90                  95

Lys Gly Ser Glu Thr Thr Phe Met Cys Glu Tyr Ala Xaa Glu Thr Ala
                        100                 105                 110

Thr Ile Val Glu Phe Leu Asn Arg Trp Ile Thr Phe Ser Gln Ser Ile
                        115                 120                 125

Ile Ser Thr Leu Thr
                        130

<210> SEQ ID NO 19
<211> LENGTH: 133
<212> TYPE: PRT
<213> ORGANISM: Artificial Sequence
<220> FEATURE:
<223> OTHER INFORMATION: Synthetic: IL-2_V91X
<220> FEATURE:
<221> NAME/KEY: misc_feature
<222> LOCATION: (91)..(91)
<223> OTHER INFORMATION: Xaa is an unnatural amino acid

<400> SEQUENCE: 19

Ala Pro Thr Ser Ser Ser Thr Lys Lys Thr Gln Leu Gln Leu Glu His
             1               5                  10                  15

Leu Leu Leu Asp Leu Gln Met Ile Leu Asn Gly Ile Asn Asn Tyr Lys
                        20                  25                  30

Asn Pro Lys Leu Thr Arg Met Leu Thr Phe Lys Phe Tyr Met Pro Lys
                        35                  40                  45

Lys Ala Thr Glu Leu Lys His Leu Gln Cys Leu Glu Glu Glu Leu Lys
                        50                  55                  60

Pro Leu Glu Glu Val Leu Asn Leu Ala Gln Ser Lys Asn Phe His Leu
             65                  70                  75                  80

Arg Pro Arg Asp Leu Ile Ser Asn Ile Asn Xaa Ile Val Leu Glu Leu
                        85                  90                  95

Lys Gly Ser Glu Thr Thr Phe Met Cys Glu Tyr Ala Asp Glu Thr Ala
                        100                 105                 110

Thr Ile Val Glu Phe Leu Asn Arg Trp Ile Thr Phe Ser Gln Ser Ile
                        115                 120                 125

Ile Ser Thr Leu Thr
                        130

<210> SEQ ID NO 20
<211> LENGTH: 133
<212> TYPE: PRT
<213> ORGANISM: Artificial Sequence
<220> FEATURE:
<223> OTHER INFORMATION: Synthetic: IL-2_K9[AzK]
<220> FEATURE:
<221> NAME/KEY: misc_feature
<222> LOCATION: (9)..(9)
<223> OTHER INFORMATION: Xaa is [AzK]
```

<400> SEQUENCE: 20

```
Ala Pro Thr Ser Ser Ser Thr Lys Xaa Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130
```

<210> SEQ ID NO 21
<211> LENGTH: 133
<212> TYPE: PRT
<213> ORGANISM: Artificial Sequence
<220> FEATURE:
<223> OTHER INFORMATION: Synthetic: IL-2_H16[AzK]
<220> FEATURE:
<221> NAME/KEY: misc_feature
<222> LOCATION: (16)..(16)
<223> OTHER INFORMATION: Xaa is [AzK]

<400> SEQUENCE: 21

```
Ala Pro Thr Ser Ser Ser Thr Lys Lys Thr Gln Leu Gln Leu Glu Xaa
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130
```

<210> SEQ ID NO 22
<211> LENGTH: 133
<212> TYPE: PRT
<213> ORGANISM: Artificial Sequence
<220> FEATURE:
<223> OTHER INFORMATION: Synthetic: IL-2_L19[AzK]
<220> FEATURE:
<221> NAME/KEY: misc_feature

```
<222> LOCATION: (19)..(19)
<223> OTHER INFORMATION: Xaa is [AzK]

<400> SEQUENCE: 22

Ala Pro Thr Ser Ser Ser Thr Lys Lys Thr Gln Leu Gln Leu Glu His
1               5                   10                  15

Leu Leu Xaa Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 23
<211> LENGTH: 133
<212> TYPE: PRT
<213> ORGANISM: Artificial Sequence
<220> FEATURE:
<223> OTHER INFORMATION: Synthetic: IL-2_D20[AzK]
<220> FEATURE:
<221> NAME/KEY: misc_feature
<222> LOCATION: (20)..(20)
<223> OTHER INFORMATION: Xaa is [AzK]

<400> SEQUENCE: 23

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 24
<211> LENGTH: 133
<212> TYPE: PRT
<213> ORGANISM: Artificial Sequence
<220> FEATURE:
```

<223> OTHER INFORMATION: Synthetic: IL-2_M23[AzK]
<220> FEATURE:
<221> NAME/KEY: misc_feature
<222> LOCATION: (23)..(23)
<223> OTHER INFORMATION: Xaa is [AzK]

<400> SEQUENCE: 24

Ala Pro Thr Ser Ser Ser Thr Lys Lys Thr Gln Leu Gln Leu Glu His
1               5                   10                  15

Leu Leu Leu Asp Leu Gln Xaa Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 25
<211> LENGTH: 133
<212> TYPE: PRT
<213> ORGANISM: Artificial Sequence
<220> FEATURE:
<223> OTHER INFORMATION: Synthetic: IL-2_N26[AzK]
<220> FEATURE:
<221> NAME/KEY: misc_feature
<222> LOCATION: (26)..(26)
<223> OTHER INFORMATION: Xaa is [AzK]

<400> SEQUENCE: 25

Ala Pro Thr Ser Ser Ser Thr Lys Lys Thr Gln Leu Gln Leu Glu His
1               5                   10                  15

Leu Leu Leu Asp Leu Gln Met Ile Leu Xaa Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 26
<211> LENGTH: 133

```
<212> TYPE: PRT
<213> ORGANISM: Artificial Sequence
<220> FEATURE:
<223> OTHER INFORMATION: Synthetic: IL-2_N88[AzK]
<220> FEATURE:
<221> NAME/KEY: misc_feature
<222> LOCATION: (88)..(88)
<223> OTHER INFORMATION: Xaa is [AzK]

<400> SEQUENCE: 26

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Xaa Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 27
<211> LENGTH: 133
<212> TYPE: PRT
<213> ORGANISM: Artificial Sequence
<220> FEATURE:
<223> OTHER INFORMATION: Synthetic: IL-2_E100[AzK]
<220> FEATURE:
<221> NAME/KEY: misc_feature
<222> LOCATION: (100)..(100)
<223> OTHER INFORMATION: Xaa is [AzK]

<400> SEQUENCE: 27

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Xaa Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130
```

```
<210> SEQ ID NO 28
<211> LENGTH: 133
<212> TYPE: PRT
<213> ORGANISM: Artificial Sequence
<220> FEATURE:
<223> OTHER INFORMATION: Synthetic: IL-2_N119[AzK]
<220> FEATURE:
<221> NAME/KEY: misc_feature
<222> LOCATION: (119)..(119)
<223> OTHER INFORMATION: Xaa is [AzK]

<400> SEQUENCE: 28

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Xaa Arg Trp Ile Thr Phe Ser Gln Ser Ile
        115                 120                 125

Ile Ser Thr Leu Thr
        130

<210> SEQ ID NO 29
<211> LENGTH: 133
<212> TYPE: PRT
<213> ORGANISM: Artificial Sequence
<220> FEATURE:
<223> OTHER INFORMATION: Synthetic: IL-2_T123[AzK]
<220> FEATURE:
<221> NAME/KEY: misc_feature
<222> LOCATION: (123)..(123)
<223> OTHER INFORMATION: Xaa is [AzK]

<400> SEQUENCE: 29

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Xaa Phe Ser Gln Ser Ile
        115                 120                 125
```

```
Ile Ser Thr Leu Thr
    130
```

<210> SEQ ID NO 30
<211> LENGTH: 133
<212> TYPE: PRT
<213> ORGANISM: Artificial Sequence
<220> FEATURE:
<223> OTHER INFORMATION: Synthetic: IL-2_Q126[AzK]
<220> FEATURE:
<221> NAME/KEY: misc_feature
<222> LOCATION: (126)..(126)
<223> OTHER INFORMATION: Xaa is [AzK]

<400> SEQUENCE: 30

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Xaa Ser Ile
        115                 120                 125

Ile Ser Thr Leu Thr
    130
```

<210> SEQ ID NO 31
<211> LENGTH: 133
<212> TYPE: PRT
<213> ORGANISM: Artificial Sequence
<220> FEATURE:
<223> OTHER INFORMATION: Synthetic: IL-2_S127[AzK]
<220> FEATURE:
<221> NAME/KEY: misc_feature
<222> LOCATION: (127)..(127)
<223> OTHER INFORMATION: Xaa is [AzK]

<400> SEQUENCE: 31

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110
```

```
Thr Ile Val Glu Phe Leu Asn Arg Trp Ile Thr Phe Ser Gln Xaa Ile
            115                 120                 125

Ile Ser Thr Leu Thr
        130
```

<210> SEQ ID NO 32
<211> LENGTH: 133
<212> TYPE: PRT
<213> ORGANISM: Artificial Sequence
<220> FEATURE:
<223> OTHER INFORMATION: Synthetic: IL-2_T131[AzK]
<220> FEATURE:
<221> NAME/KEY: misc_feature
<222> LOCATION: (131)..(131)
<223> OTHER INFORMATION: Xaa is [AzK]

<400> SEQUENCE: 32

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Xaa Leu Thr
    130
```

<210> SEQ ID NO 33
<211> LENGTH: 133
<212> TYPE: PRT
<213> ORGANISM: Artificial Sequence
<220> FEATURE:
<223> OTHER INFORMATION: Synthetic: IL-2_N88R_D109[AzK]
<220> FEATURE:
<221> NAME/KEY: misc_feature
<222> LOCATION: (109)..(109)
<223> OTHER INFORMATION: Xaa is [AzK]

<400> SEQUENCE: 33

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95
```

-continued

```
Lys Gly Ser Glu Thr Thr Phe Met Cys Glu Tyr Ala Xaa Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 34
<211> LENGTH: 133
<212> TYPE: PRT
<213> ORGANISM: Artificial Sequence
<220> FEATURE:
<223> OTHER INFORMATION: Synthetic: IL-2_K9[AzK_PEG]
<220> FEATURE:
<221> NAME/KEY: misc_feature
<222> LOCATION: (9)..(9)
<223> OTHER INFORMATION: Xaa is [AzK_PEG]

<400> SEQUENCE: 34

Ala Pro Thr Ser Ser Ser Thr Lys Xaa Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 35
<211> LENGTH: 133
<212> TYPE: PRT
<213> ORGANISM: Artificial Sequence
<220> FEATURE:
<223> OTHER INFORMATION: Synthetic: IL-2_H16[AzK_PEG]
<220> FEATURE:
<221> NAME/KEY: misc_feature
<222> LOCATION: (16)..(16)
<223> OTHER INFORMATION: Xaa is [AzK_PEG]

<400> SEQUENCE: 35

Ala Pro Thr Ser Ser Ser Thr Lys Lys Thr Gln Leu Gln Leu Glu Xaa
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 36
<211> LENGTH: 133
<212> TYPE: PRT
<213> ORGANISM: Artificial Sequence
<220> FEATURE:
<223> OTHER INFORMATION: Synthetic: IL-2_L19[AzK_PEG]
<220> FEATURE:
<221> NAME/KEY: misc_feature
<222> LOCATION: (19)..(19)
<223> OTHER INFORMATION: Xaa is [AzK_PEG]

<400> SEQUENCE: 36

Ala Pro Thr Ser Ser Ser Thr Lys Lys Thr Gln Leu Gln Leu Glu His
1               5                   10                  15

Leu Leu Xaa Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 37
<211> LENGTH: 133
<212> TYPE: PRT
<213> ORGANISM: Artificial Sequence
<220> FEATURE:
<223> OTHER INFORMATION: Synthetic: IL-2_D20[AzK_PEG]
<220> FEATURE:
<221> NAME/KEY: misc_feature
<222> LOCATION: (20)..(20)
<223> OTHER INFORMATION: Xaa is [AzK_PEG]

<400> SEQUENCE: 37

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 38
<211> LENGTH: 133
<212> TYPE: PRT
<213> ORGANISM: Artificial Sequence
<220> FEATURE:
<223> OTHER INFORMATION: Synthetic: IL-2_M23[AzK_PEG]
<220> FEATURE:
<221> NAME/KEY: misc_feature
<222> LOCATION: (23)..(23)
<223> OTHER INFORMATION: Xaa is [AzK_PEG]

<400> SEQUENCE: 38

Ala Pro Thr Ser Ser Ser Thr Lys Lys Thr Gln Leu Gln Leu Glu His
1               5                   10                  15

Leu Leu Leu Asp Leu Gln Xaa Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 39
<211> LENGTH: 133
<212> TYPE: PRT
<213> ORGANISM: Artificial Sequence
<220> FEATURE:
<223> OTHER INFORMATION: Synthetic: IL-2_N26[AzK_PEG]
<220> FEATURE:
<221> NAME/KEY: misc_feature
<222> LOCATION: (26)..(26)
<223> OTHER INFORMATION: Xaa is [AzK_PEG]

<400> SEQUENCE: 39

Ala Pro Thr Ser Ser Ser Thr Lys Lys Thr Gln Leu Gln Leu Glu His
1               5                   10                  15

Leu Leu Leu Asp Leu Gln Met Ile Leu Xaa Gly Ile Asn Asn Tyr Lys
                20                  25                  30

Asn Pro Lys Leu Thr Arg Met Leu Thr Phe Lys Phe Tyr Met Pro Lys
            35                  40                  45
```

```
Lys Ala Thr Glu Leu Lys His Leu Gln Cys Leu Glu Glu Leu Lys
            50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
            130

<210> SEQ ID NO 40
<211> LENGTH: 133
<212> TYPE: PRT
<213> ORGANISM: Artificial Sequence
<220> FEATURE:
<223> OTHER INFORMATION: Synthetic: IL-2_N88[AzK_PEG]
<220> FEATURE:
<221> NAME/KEY: misc_feature
<222> LOCATION: (88)..(88)
<223> OTHER INFORMATION: Xaa is [AzK_PEG]

<400> SEQUENCE: 40

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Leu Lys
            50                  55                  60

Pro Leu Glu Glu Val Leu Asn Leu Ala Gln Ser Lys Asn Phe His Leu
 65                  70                  75                  80

Arg Pro Arg Asp Leu Ile Ser Xaa Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
            130

<210> SEQ ID NO 41
<211> LENGTH: 133
<212> TYPE: PRT
<213> ORGANISM: Artificial Sequence
<220> FEATURE:
<223> OTHER INFORMATION: Synthetic: IL-2_E100[AzK_PEG]
<220> FEATURE:
<221> NAME/KEY: misc_feature
<222> LOCATION: (100)..(100)
<223> OTHER INFORMATION: Xaa is [AzK_PEG]

<400> SEQUENCE: 41

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                20                  25                  30
```

```
Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Xaa Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130
```

```
<210> SEQ ID NO 42
<211> LENGTH: 133
<212> TYPE: PRT
<213> ORGANISM: Artificial Sequence
<220> FEATURE:
<223> OTHER INFORMATION: Synthetic: IL-2_N119[AzK_PEG]
<220> FEATURE:
<221> NAME/KEY: misc_feature
<222> LOCATION: (119)..(119)
<223> OTHER INFORMATION: Xaa is [AzK_PEG]

<400> SEQUENCE: 42

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Xaa Arg Trp Ile Thr Phe Ser Gln Ser Ile
            115                 120                 125

Ile Ser Thr Leu Thr
        130
```

```
<210> SEQ ID NO 43
<211> LENGTH: 133
<212> TYPE: PRT
<213> ORGANISM: Artificial Sequence
<220> FEATURE:
<223> OTHER INFORMATION: Synthetic: IL-2_T123[AzK_PEG]
<220> FEATURE:
<221> NAME/KEY: misc_feature
<222> LOCATION: (123)..(123)
<223> OTHER INFORMATION: Xaa is [AzK_PEG]

<400> SEQUENCE: 43

Ala Pro Thr Ser Ser Ser Thr Lys Lys Thr Gln Leu Gln Leu Glu His
 1               5                  10                  15
```

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Xaa Phe Ser Gln Ser Ile
            115                 120                 125

Ile Ser Thr Leu Thr
        130

<210> SEQ ID NO 44
<211> LENGTH: 133
<212> TYPE: PRT
<213> ORGANISM: Artificial Sequence
<220> FEATURE:
<223> OTHER INFORMATION: Synthetic: IL-2_Q126[AzK_PEG]
<220> FEATURE:
<221> NAME/KEY: misc_feature
<222> LOCATION: (126)..(126)
<223> OTHER INFORMATION: Xaa is [AzK_PEG]

<400> SEQUENCE: 44

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Xaa Ser Ile
            115                 120                 125

Ile Ser Thr Leu Thr
        130

<210> SEQ ID NO 45
<211> LENGTH: 133
<212> TYPE: PRT
<213> ORGANISM: Artificial Sequence
<220> FEATURE:
<223> OTHER INFORMATION: Synthetic: IL-2_S127[AzK_PEG]
<220> FEATURE:
<221> NAME/KEY: misc_feature
<222> LOCATION: (127)..(127)
<223> OTHER INFORMATION: Xaa is [AzK_PEG]

<400> SEQUENCE: 45

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Xaa Ile
                115                 120                 125

Ile Ser Thr Leu Thr
            130

<210> SEQ ID NO 46
<211> LENGTH: 133
<212> TYPE: PRT
<213> ORGANISM: Artificial Sequence
<220> FEATURE:
<223> OTHER INFORMATION: Synthetic: IL-2_T131[AzK_PEG]
<220> FEATURE:
<221> NAME/KEY: misc_feature
<222> LOCATION: (131)..(131)
<223> OTHER INFORMATION: Xaa is [AzK_PEG]

<400> SEQUENCE: 46

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Xaa Leu Thr
            130

<210> SEQ ID NO 47
<211> LENGTH: 133
<212> TYPE: PRT
<213> ORGANISM: Artificial Sequence
<220> FEATURE:
<223> OTHER INFORMATION: Synthetic: IL-2_N88R_D109[AzK_PEG]
<220> FEATURE:
<221> NAME/KEY: misc_feature
<222> LOCATION: (109)..(109)
<223> OTHER INFORMATION: Xaa is [AzK_PEG]

<400> SEQUENCE: 47

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Xaa Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 48
<211> LENGTH: 133
<212> TYPE: PRT
<213> ORGANISM: Artificial Sequence
<220> FEATURE:
<223> OTHER INFORMATION: Synthetic: IL-2_V91[AzK_PEG]
<220> FEATURE:
<221> NAME/KEY: misc_feature
<222> LOCATION: (91)..(91)
<223> OTHER INFORMATION: Xaa is [AzK_PEG]

<400> SEQUENCE: 48

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Xaa Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 49
<211> LENGTH: 133
<212> TYPE: PRT
<213> ORGANISM: Artificial Sequence
<220> FEATURE:
<223> OTHER INFORMATION: Synthetic: IL-2_K9[AzK_PEG50kDa]
<220> FEATURE:

```
<221> NAME/KEY: misc_feature
<222> LOCATION: (9)..(9)
<223> OTHER INFORMATION: Xaa is [AzK_PEG50kDa]

<400> SEQUENCE: 49
```

| Ala | Pro | Thr | Ser | Ser | Ser | Thr | Lys | Xaa | Thr | Gln | Leu | Gln | Leu | Glu | His |
|---|---|---|---|---|---|---|---|---|---|---|---|---|---|---|---|
| 1 |  |  |  | 5 |  |  |  |  | 10 |  |  |  |  | 15 |  |

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

```
<210> SEQ ID NO 50
<211> LENGTH: 133
<212> TYPE: PRT
<213> ORGANISM: Artificial Sequence
<220> FEATURE:
<223> OTHER INFORMATION: Synthetic: IL-2_H16[AzK_PEG50kDa]
<220> FEATURE:
<221> NAME/KEY: misc_feature
<222> LOCATION: (16)..(16)
<223> OTHER INFORMATION: Xaa is [AzK_PEG50kDa]

<400> SEQUENCE: 50
```

Ala Pro Thr Ser Ser Ser Thr Lys Lys Thr Gln Leu Gln Leu Glu Xaa
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

```
<210> SEQ ID NO 51
<211> LENGTH: 133
<212> TYPE: PRT
<213> ORGANISM: Artificial Sequence
```

```
<220> FEATURE:
<223> OTHER INFORMATION: Synthetic: IL-2_L19[AzK_PEG50kDa]
<220> FEATURE:
<221> NAME/KEY: misc_feature
<222> LOCATION: (19)..(19)
<223> OTHER INFORMATION: Xaa is [AzK_PEG50kDa]

<400> SEQUENCE: 51

Ala Pro Thr Ser Ser Ser Thr Lys Lys Thr Gln Leu Gln Leu Glu His
1               5                   10                  15

Leu Leu Xaa Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 52
<211> LENGTH: 133
<212> TYPE: PRT
<213> ORGANISM: Artificial Sequence
<220> FEATURE:
<223> OTHER INFORMATION: Synthetic: IL-2_D20[AzK_PEG50kDa]
<220> FEATURE:
<221> NAME/KEY: misc_feature
<222> LOCATION: (20)..(20)
<223> OTHER INFORMATION: Xaa is [AzK_PEG50kDa]

<400> SEQUENCE: 52

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 53
```

```
<211> LENGTH: 133
<212> TYPE: PRT
<213> ORGANISM: Artificial Sequence
<220> FEATURE:
<223> OTHER INFORMATION: Synthetic: IL-2_M23[AzK_PEG50kDa]
<220> FEATURE:
<221> NAME/KEY: misc_feature
<222> LOCATION: (23)..(23)
<223> OTHER INFORMATION: Xaa is [AzK_PEG50kDa]

<400> SEQUENCE: 53

Ala Pro Thr Ser Ser Ser Thr Lys Lys Thr Gln Leu Gln Leu Glu His
1               5                   10                  15

Leu Leu Leu Asp Leu Gln Xaa Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 54
<211> LENGTH: 133
<212> TYPE: PRT
<213> ORGANISM: Artificial Sequence
<220> FEATURE:
<223> OTHER INFORMATION: Synthetic: IL-2_N26[AzK_PEG50kDa]
<220> FEATURE:
<221> NAME/KEY: misc_feature
<222> LOCATION: (26)..(26)
<223> OTHER INFORMATION: Xaa is [AzK_PEG50kDa]

<400> SEQUENCE: 54

Ala Pro Thr Ser Ser Ser Thr Lys Lys Thr Gln Leu Gln Leu Glu His
1               5                   10                  15

Leu Leu Leu Asp Leu Gln Met Ile Leu Xaa Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130
```

```
<210> SEQ ID NO 55
<211> LENGTH: 133
<212> TYPE: PRT
<213> ORGANISM: Artificial Sequence
<220> FEATURE:
<223> OTHER INFORMATION: Synthetic: IL-2_N88[AzK_PEG50kDa]
<220> FEATURE:
<221> NAME/KEY: misc_feature
<222> LOCATION: (88)..(88)
<223> OTHER INFORMATION: Xaa is [AzK_PEG50kDa]

<400> SEQUENCE: 55
```

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Xaa Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

```
<210> SEQ ID NO 56
<211> LENGTH: 133
<212> TYPE: PRT
<213> ORGANISM: Artificial Sequence
<220> FEATURE:
<223> OTHER INFORMATION: Synthetic: IL-2_E100[AzK_PEG50kDa]
<220> FEATURE:
<221> NAME/KEY: misc_feature
<222> LOCATION: (100)..(100)
<223> OTHER INFORMATION: Xaa is [AzK_PEG50kDa]

<400> SEQUENCE: 56
```

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Xaa Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 57
<211> LENGTH: 133
<212> TYPE: PRT
<213> ORGANISM: Artificial Sequence
<220> FEATURE:
<223> OTHER INFORMATION: Synthetic: IL-2_N119[AzK_PEG50kDa]
<220> FEATURE:
<221> NAME/KEY: misc_feature
<222> LOCATION: (119)..(119)
<223> OTHER INFORMATION: Xaa is [AzK_PEG50kDa]

<400> SEQUENCE: 57

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Xaa Arg Trp Ile Thr Phe Ser Gln Ser Ile
        115                 120                 125

Ile Ser Thr Leu Thr
    130

<210> SEQ ID NO 58
<211> LENGTH: 133
<212> TYPE: PRT
<213> ORGANISM: Artificial Sequence
<220> FEATURE:
<223> OTHER INFORMATION: Synthetic: IL-2_T123[AzK_PEG50kDa]
<220> FEATURE:
<221> NAME/KEY: misc_feature
<222> LOCATION: (123)..(123)
<223> OTHER INFORMATION: Xaa is [AzK_PEG50kDa]

<400> SEQUENCE: 58

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

```
Thr Ile Val Glu Phe Leu Asn Arg Trp Ile Xaa Phe Ser Gln Ser Ile
        115                 120                 125

Ile Ser Thr Leu Thr
        130

<210> SEQ ID NO 59
<211> LENGTH: 133
<212> TYPE: PRT
<213> ORGANISM: Artificial Sequence
<220> FEATURE:
<223> OTHER INFORMATION: Synthetic: IL-2_Q126[AzK_PEG50kDa]
<220> FEATURE:
<221> NAME/KEY: misc_feature
<222> LOCATION: (126)..(126)
<223> OTHER INFORMATION: Xaa is [AzK_PEG50kDa]

<400> SEQUENCE: 59

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Xaa Ser Ile
        115                 120                 125

Ile Ser Thr Leu Thr
        130

<210> SEQ ID NO 60
<211> LENGTH: 133
<212> TYPE: PRT
<213> ORGANISM: Artificial Sequence
<220> FEATURE:
<223> OTHER INFORMATION: Synthetic: IL-2_S127[AzK_PEG50kDa]
<220> FEATURE:
<221> NAME/KEY: misc_feature
<222> LOCATION: (127)..(127)
<223> OTHER INFORMATION: Xaa is [AzK_PEG50kDa]

<400> SEQUENCE: 60

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95
```

-continued

```
Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Xaa Ile
        115                 120                 125

Ile Ser Thr Leu Thr
        130

<210> SEQ ID NO 61
<211> LENGTH: 133
<212> TYPE: PRT
<213> ORGANISM: Artificial Sequence
<220> FEATURE:
<223> OTHER INFORMATION: Synthetic: IL-2_T131[AzK_PEG50kDa]
<220> FEATURE:
<221> NAME/KEY: misc_feature
<222> LOCATION: (131)..(131)
<223> OTHER INFORMATION: Xaa is [AzK_PEG50kDa]

<400> SEQUENCE: 61

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Xaa Leu Thr
        130

<210> SEQ ID NO 62
<211> LENGTH: 133
<212> TYPE: PRT
<213> ORGANISM: Artificial Sequence
<220> FEATURE:
<223> OTHER INFORMATION: Synthetic: IL-2_N88R_D109[AzK_PEG50kDa]
<220> FEATURE:
<221> NAME/KEY: misc_feature
<222> LOCATION: (109)..(109)
<223> OTHER INFORMATION: Xaa is [AzK_PEG50kDa]

<400> SEQUENCE: 62

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80
```

```
Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Xaa Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 63
<211> LENGTH: 133
<212> TYPE: PRT
<213> ORGANISM: Artificial Sequence
<220> FEATURE:
<223> OTHER INFORMATION: Synthetic: IL-2_V91[AzK_PEG50kDa]
<220> FEATURE:
<221> NAME/KEY: misc_feature
<222> LOCATION: (91)..(91)
<223> OTHER INFORMATION: Xaa is [AzK_PEG50kDa]

<400> SEQUENCE: 63

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Xaa Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 64
<211> LENGTH: 133
<212> TYPE: PRT
<213> ORGANISM: Artificial Sequence
<220> FEATURE:
<223> OTHER INFORMATION: Synthetic: IL-2_K9[AzK_PEG30kDa]
<220> FEATURE:
<221> NAME/KEY: misc_feature
<222> LOCATION: (9)..(9)
<223> OTHER INFORMATION: Xaa is [AzK_PEG30kDa]

<400> SEQUENCE: 64

Ala Pro Thr Ser Ser Ser Thr Lys Xaa Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 65
<211> LENGTH: 133
<212> TYPE: PRT
<213> ORGANISM: Artificial Sequence
<220> FEATURE:
<223> OTHER INFORMATION: Synthetic: IL-2_H16[AzK_PEG30kDa]
<220> FEATURE:
<221> NAME/KEY: misc_feature
<222> LOCATION: (16)..(16)
<223> OTHER INFORMATION: Xaa is [AzK_PEG30kDa]

<400> SEQUENCE: 65

Ala Pro Thr Ser Ser Ser Thr Lys Lys Thr Gln Leu Gln Leu Glu Xaa
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 66
<211> LENGTH: 133
<212> TYPE: PRT
<213> ORGANISM: Artificial Sequence
<220> FEATURE:
<223> OTHER INFORMATION: Synthetic: IL-2_L19[AzK_PEG30kDa]
<220> FEATURE:
<221> NAME/KEY: misc_feature
<222> LOCATION: (19)..(19)
<223> OTHER INFORMATION: Xaa is [AzK_PEG30kDa]

<400> SEQUENCE: 66

Ala Pro Thr Ser Ser Ser Thr Lys Lys Thr Gln Leu Gln Leu Glu His
  1               5                  10                  15

Leu Leu Xaa Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45
```

```
Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 67
<211> LENGTH: 133
<212> TYPE: PRT
<213> ORGANISM: Artificial Sequence
<220> FEATURE:
<223> OTHER INFORMATION: Synthetic: IL-2_D20[AzK_PEG30kDa]
<220> FEATURE:
<221> NAME/KEY: misc_feature
<222> LOCATION: (20)..(20)
<223> OTHER INFORMATION: Xaa is [AzK_PEG30kDa]

<400> SEQUENCE: 67

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 68
<211> LENGTH: 133
<212> TYPE: PRT
<213> ORGANISM: Artificial Sequence
<220> FEATURE:
<223> OTHER INFORMATION: Synthetic: IL-2_M23[AzK_PEG30kDa]
<220> FEATURE:
<221> NAME/KEY: misc_feature
<222> LOCATION: (23)..(23)
<223> OTHER INFORMATION: Xaa is [AzK_PEG30kDa]

<400> SEQUENCE: 68

Ala Pro Thr Ser Ser Ser Thr Lys Lys Thr Gln Leu Gln Leu Glu His
1               5                   10                  15

Leu Leu Leu Asp Leu Gln Xaa Ile Leu Asn Gly Ile Asn Asn Tyr Lys
                20                  25                  30
```

-continued

```
Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 69
<211> LENGTH: 133
<212> TYPE: PRT
<213> ORGANISM: Artificial Sequence
<220> FEATURE:
<223> OTHER INFORMATION: Synthetic: IL-2_N26[AzK_PEG30kDa]
<220> FEATURE:
<221> NAME/KEY: misc_feature
<222> LOCATION: (26)..(26)
<223> OTHER INFORMATION: Xaa is [AzK_PEG30kDa]

<400> SEQUENCE: 69

Ala Pro Thr Ser Ser Ser Thr Lys Lys Thr Gln Leu Gln Leu Glu His
 1               5                  10                  15

Leu Leu Leu Asp Leu Gln Met Ile Leu Xaa Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 70
<211> LENGTH: 133
<212> TYPE: PRT
<213> ORGANISM: Artificial Sequence
<220> FEATURE:
<223> OTHER INFORMATION: Synthetic: IL-2_N88[AzK_PEG30kDa]
<220> FEATURE:
<221> NAME/KEY: misc_feature
<222> LOCATION: (88)..(88)
<223> OTHER INFORMATION: Xaa is [AzK_PEG30kDa]

<400> SEQUENCE: 70

Ala Pro Thr Ser Ser Ser Thr Lys Lys Thr Gln Leu Gln Leu Glu His
 1               5                  10                  15
```

```
Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Xaa Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 71
<211> LENGTH: 133
<212> TYPE: PRT
<213> ORGANISM: Artificial Sequence
<220> FEATURE:
<223> OTHER INFORMATION: Synthetic: IL-2_E100[AzK_PEG30kDa]
<220> FEATURE:
<221> NAME/KEY: misc_feature
<222> LOCATION: (100)..(100)
<223> OTHER INFORMATION: Xaa is [AzK_PEG30kDa]

<400> SEQUENCE: 71

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Xaa Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 72
<211> LENGTH: 133
<212> TYPE: PRT
<213> ORGANISM: Artificial Sequence
<220> FEATURE:
<223> OTHER INFORMATION: Synthetic: IL-2_N119[AzK_PEG30kDa]
<220> FEATURE:
<221> NAME/KEY: misc_feature
<222> LOCATION: (119)..(119)
<223> OTHER INFORMATION: Xaa is [AzK_PEG30kDa]

<400> SEQUENCE: 72
```

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Xaa Arg Trp Ile Thr Phe Ser Gln Ser Ile
        115                 120                 125

Ile Ser Thr Leu Thr
    130

<210> SEQ ID NO 73
<211> LENGTH: 133
<212> TYPE: PRT
<213> ORGANISM: Artificial Sequence
<220> FEATURE:
<223> OTHER INFORMATION: Synthetic: IL-2_T123[AzK_PEG30kDa]
<220> FEATURE:
<221> NAME/KEY: misc_feature
<222> LOCATION: (123)..(123)
<223> OTHER INFORMATION: Xaa is [AzK_PEG30kDa]

<400> SEQUENCE: 73

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Xaa Phe Ser Gln Ser Ile
        115                 120                 125

Ile Ser Thr Leu Thr
    130

<210> SEQ ID NO 74
<211> LENGTH: 133
<212> TYPE: PRT
<213> ORGANISM: Artificial Sequence
<220> FEATURE:
<223> OTHER INFORMATION: Synthetic: IL-2_Q126[AzK_PEG30kDa]
<220> FEATURE:
<221> NAME/KEY: misc_feature
<222> LOCATION: (126)..(126)
```

<223> OTHER INFORMATION: Xaa is [AzK_PEG30kDa]

<400> SEQUENCE: 74

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Xaa Ser Ile
        115                 120                 125

Ile Ser Thr Leu Thr
        130

<210> SEQ ID NO 75
<211> LENGTH: 133
<212> TYPE: PRT
<213> ORGANISM: Artificial Sequence
<220> FEATURE:
<223> OTHER INFORMATION: Synthetic: IL-2_S127[AzK_PEG30kDa]
<220> FEATURE:
<221> NAME/KEY: misc_feature
<222> LOCATION: (127)..(127)
<223> OTHER INFORMATION: Xaa is [AzK_PEG30kDa]

<400> SEQUENCE: 75

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Xaa Ile
        115                 120                 125

Ile Ser Thr Leu Thr
        130

<210> SEQ ID NO 76
<211> LENGTH: 133
<212> TYPE: PRT
<213> ORGANISM: Artificial Sequence
<220> FEATURE:
<223> OTHER INFORMATION: Synthetic: IL-2_T131[AzK_PEG30kDa]

```
<220> FEATURE:
<221> NAME/KEY: misc_feature
<222> LOCATION: (131)..(131)
<223> OTHER INFORMATION: Xaa is [AzK_PEG30kDa]

<400> SEQUENCE: 76

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Xaa Leu Thr
        130

<210> SEQ ID NO 77
<211> LENGTH: 133
<212> TYPE: PRT
<213> ORGANISM: Artificial Sequence
<220> FEATURE:
<223> OTHER INFORMATION: Synthetic: IL-2_N88R_D109[AzK_PEG30kDa]
<220> FEATURE:
<221> NAME/KEY: misc_feature
<222> LOCATION: (109)..(109)
<223> OTHER INFORMATION: Xaa is [AzK_PEG30kDa]

<400> SEQUENCE: 77

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Xaa Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 78
<211> LENGTH: 133
<212> TYPE: PRT
```

```
<213> ORGANISM: Artificial Sequence
<220> FEATURE:
<223> OTHER INFORMATION: Synthetic: IL-2_V91[AzK_PEG30kDa]
<220> FEATURE:
<221> NAME/KEY: misc_feature
<222> LOCATION: (91)..(91)
<223> OTHER INFORMATION: Xaa is [AzK_PEG30kDa]

<400> SEQUENCE: 78

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Xaa Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 79
<211> LENGTH: 132
<212> TYPE: PRT
<213> ORGANISM: Artificial Sequence
<220> FEATURE:
<223> OTHER INFORMATION: Synthetic: IL-2_K8X
<220> FEATURE:
<221> NAME/KEY: misc_feature
<222> LOCATION: (8)..(8)
<223> OTHER INFORMATION: Xaa is an unnatural amino acid

<400> SEQUENCE: 79

Pro Thr Ser Ser Ser Thr Lys Xaa Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 80
<211> LENGTH: 132
<212> TYPE: PRT
<213> ORGANISM: Artificial Sequence
<220> FEATURE:
<223> OTHER INFORMATION: Synthetic: IL-2_H15X
<220> FEATURE:
<221> NAME/KEY: misc_feature
<222> LOCATION: (15)..(15)
<223> OTHER INFORMATION: Xaa is an unnatural amino acid

<400> SEQUENCE: 80

Pro Thr Ser Ser Ser Thr Lys Lys Thr Gln Leu Gln Leu Glu Xaa Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 81
<211> LENGTH: 132
<212> TYPE: PRT
<213> ORGANISM: Artificial Sequence
<220> FEATURE:
<223> OTHER INFORMATION: Synthetic: IL-2_L18X
<220> FEATURE:
<221> NAME/KEY: misc_feature
<222> LOCATION: (18)..(18)
<223> OTHER INFORMATION: Xaa is an unnatural amino acid

<400> SEQUENCE: 81

Pro Thr Ser Ser Ser Thr Lys Lys Thr Gln Leu Gln Leu Glu His Leu
1               5                   10                  15

Leu Xaa Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr

<210> SEQ ID NO 82
<211> LENGTH: 132
<212> TYPE: PRT
<213> ORGANISM: Artificial Sequence
<220> FEATURE:
<223> OTHER INFORMATION: Synthetic: IL-2_D19X
<220> FEATURE:
<221> NAME/KEY: misc_feature
<222> LOCATION: (19)..(19)
<223> OTHER INFORMATION: Xaa is an unnatural amino acid

<400> SEQUENCE: 82

```
Pro Thr Ser Ser Ser Thr Lys Lys Thr Gln Leu Gln Leu Glu His Leu
1               5                   10                  15

Leu Leu Xaa Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 83
<211> LENGTH: 132
<212> TYPE: PRT
<213> ORGANISM: Artificial Sequence
<220> FEATURE:
<223> OTHER INFORMATION: Synthetic: IL-2_M22X
<220> FEATURE:
<221> NAME/KEY: misc_feature
<222> LOCATION: (22)..(22)
<223> OTHER INFORMATION: Xaa is an unnatural amino acid

<400> SEQUENCE: 83

```
Pro Thr Ser Ser Ser Thr Lys Lys Thr Gln Leu Gln Leu Glu His Leu
1               5                   10                  15

Leu Leu Asp Leu Gln Xaa Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
```

Ser Thr Leu Thr
    130

<210> SEQ ID NO 84
<211> LENGTH: 132
<212> TYPE: PRT
<213> ORGANISM: Artificial Sequence
<220> FEATURE:
<223> OTHER INFORMATION: Synthetic: IL-2_N25X
<220> FEATURE:
<221> NAME/KEY: misc_feature
<222> LOCATION: (25)..(25)
<223> OTHER INFORMATION: Xaa is an unnatural amino acid

<400> SEQUENCE: 84

Pro Thr Ser Ser Ser Thr Lys Lys Thr Gln Leu Gln Leu Glu His Leu
1               5                   10                  15

Leu Leu Asp Leu Gln Met Ile Leu Xaa Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 85
<211> LENGTH: 132
<212> TYPE: PRT
<213> ORGANISM: Artificial Sequence
<220> FEATURE:
<223> OTHER INFORMATION: Synthetic: IL-2_N87X
<220> FEATURE:
<221> NAME/KEY: misc_feature
<222> LOCATION: (87)..(87)
<223> OTHER INFORMATION: Xaa is an unnatural amino acid

<400> SEQUENCE: 85

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Xaa Ile Asn Val Ile Val Leu Glu Leu Lys
                85                  90                  95

Gly Ser Glu Thr Thr Phe Met Cys Glu Tyr Ala Asp Glu Thr Ala Thr

-continued

```
                    100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 86
<211> LENGTH: 132
<212> TYPE: PRT
<213> ORGANISM: Artificial Sequence
<220> FEATURE:
<223> OTHER INFORMATION: Synthetic: IL-2_E99X
<220> FEATURE:
<221> NAME/KEY: misc_feature
<222> LOCATION: (99)..(99)
<223> OTHER INFORMATION: Xaa is an unnatural amino acid

<400> SEQUENCE: 86

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Xaa Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                     120                 125

Ser Thr Leu Thr
    130

<210> SEQ ID NO 87
<211> LENGTH: 132
<212> TYPE: PRT
<213> ORGANISM: Artificial Sequence
<220> FEATURE:
<223> OTHER INFORMATION: Synthetic: IL-2_N118X
<220> FEATURE:
<221> NAME/KEY: misc_feature
<222> LOCATION: (118)..(118)
<223> OTHER INFORMATION: Xaa is an unnatural amino acid

<400> SEQUENCE: 87

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
```

```
                    85                  90                  95

Gly Ser Glu Thr Thr Phe Met Cys Glu Tyr Ala Asp Glu Thr Ala Thr
            100                 105                 110

Ile Val Glu Phe Leu Xaa Arg Trp Ile Thr Phe Ser Gln Ser Ile Ile
        115                 120                 125

Ser Thr Leu Thr
    130

<210> SEQ ID NO 88
<211> LENGTH: 132
<212> TYPE: PRT
<213> ORGANISM: Artificial Sequence
<220> FEATURE:
<223> OTHER INFORMATION: Synthetic: IL-2_T122X
<220> FEATURE:
<221> NAME/KEY: misc_feature
<222> LOCATION: (122)..(122)
<223> OTHER INFORMATION: Xaa is an unnatural amino acid

<400> SEQUENCE: 88

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Xaa Phe Ser Gln Ser Ile Ile
        115                 120                 125

Ser Thr Leu Thr
    130

<210> SEQ ID NO 89
<211> LENGTH: 132
<212> TYPE: PRT
<213> ORGANISM: Artificial Sequence
<220> FEATURE:
<223> OTHER INFORMATION: Synthetic: IL-2_Q125X
<220> FEATURE:
<221> NAME/KEY: misc_feature
<222> LOCATION: (125)..(125)
<223> OTHER INFORMATION: Xaa is an unnatural amino acid

<400> SEQUENCE: 89

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
```

```
                65                  70                  75                  80
Pro Arg Asp Leu Ile Ser Asn Ile Asn Val Ile Val Leu Glu Leu Lys
                    85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Xaa Ser Ile Ile
                115                 120                 125

Ser Thr Leu Thr
        130

<210> SEQ ID NO 90
<211> LENGTH: 132
<212> TYPE: PRT
<213> ORGANISM: Artificial Sequence
<220> FEATURE:
<223> OTHER INFORMATION: Synthetic: IL-2_S126X
<220> FEATURE:
<221> NAME/KEY: misc_feature
<222> LOCATION: (126)..(126)
<223> OTHER INFORMATION: Xaa is an unnatural amino acid

<400> SEQUENCE: 90

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                    85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Xaa Ile Ile
                115                 120                 125

Ser Thr Leu Thr
        130

<210> SEQ ID NO 91
<211> LENGTH: 132
<212> TYPE: PRT
<213> ORGANISM: Artificial Sequence
<220> FEATURE:
<223> OTHER INFORMATION: Synthetic: IL-2_T130X
<220> FEATURE:
<221> NAME/KEY: misc_feature
<222> LOCATION: (130)..(130)
<223> OTHER INFORMATION: Xaa is an unnatural amino acid

<400> SEQUENCE: 91

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
```

```
            50                  55                  60
Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Xaa Leu Thr
        130

<210> SEQ ID NO 92
<211> LENGTH: 132
<212> TYPE: PRT
<213> ORGANISM: Artificial Sequence
<220> FEATURE:
<223> OTHER INFORMATION: Synthetic: IL-2_N87R_D108X
<220> FEATURE:
<221> NAME/KEY: misc_feature
<222> LOCATION: (108)..(108)
<223> OTHER INFORMATION: Xaa is an unnatural amino acid

<400> SEQUENCE: 92

Pro Thr Ser Ser Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
                 20                  25                  30

Pro Lys Leu Thr Arg Met Leu Thr Phe Lys Phe Tyr Met Pro Lys Lys
                 35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Arg Ile Asn Val Ile Val Leu Glu Leu Lys
                 85                  90                  95

Gly Ser Glu Thr Thr Phe Met Cys Glu Tyr Ala Xaa Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
        130

<210> SEQ ID NO 93
<211> LENGTH: 132
<212> TYPE: PRT
<213> ORGANISM: Artificial Sequence
<220> FEATURE:
<223> OTHER INFORMATION: Synthetic: IL-2_V90X
<220> FEATURE:
<221> NAME/KEY: misc_feature
<222> LOCATION: (90)..(90)
<223> OTHER INFORMATION: Xaa is an unnatural amino acid

<400> SEQUENCE: 93

Pro Thr Ser Ser Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
                 20                  25                  30

Pro Lys Leu Thr Arg Met Leu Thr Phe Lys Phe Tyr Met Pro Lys Lys
```

Ala Thr Glu Leu Lys His Leu Gln Cys Leu Glu Glu Leu Lys Pro
          50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Xaa Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
    130

<210> SEQ ID NO 94
<211> LENGTH: 132
<212> TYPE: PRT
<213> ORGANISM: Artificial Sequence
<220> FEATURE:
<223> OTHER INFORMATION: Synthetic: IL-2_K8[AzK]
<220> FEATURE:
<221> NAME/KEY: misc_feature
<222> LOCATION: (8)..(8)
<223> OTHER INFORMATION: Xaa is [AzK]

<400> SEQUENCE: 94

Pro Thr Ser Ser Ser Thr Lys Xaa Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Leu Lys Pro
          50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
    130

<210> SEQ ID NO 95
<211> LENGTH: 132
<212> TYPE: PRT
<213> ORGANISM: Artificial Sequence
<220> FEATURE:
<223> OTHER INFORMATION: Synthetic: IL-2_H15[AzK]
<220> FEATURE:
<221> NAME/KEY: misc_feature
<222> LOCATION: (15)..(15)
<223> OTHER INFORMATION: Xaa is [AzK]

<400> SEQUENCE: 95

Pro Thr Ser Ser Ser Thr Lys Lys Thr Gln Leu Gln Leu Glu Xaa Leu
1               5                   10                  15

Leu Leu Asp Leu Gln Met Ile Leu Asn Gly Ile Asn Asn Tyr Lys Asn

```
                    20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 96
<211> LENGTH: 132
<212> TYPE: PRT
<213> ORGANISM: Artificial Sequence
<220> FEATURE:
<223> OTHER INFORMATION: Synthetic: IL-2_L18[AzK]
<220> FEATURE:
<221> NAME/KEY: misc_feature
<222> LOCATION: (18)..(18)
<223> OTHER INFORMATION: Xaa is [AzK]

<400> SEQUENCE: 96

Pro Thr Ser Ser Ser Thr Lys Lys Thr Gln Leu Gln Leu Glu His Leu
1               5                   10                  15

Leu Xaa Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 97
<211> LENGTH: 132
<212> TYPE: PRT
<213> ORGANISM: Artificial Sequence
<220> FEATURE:
<223> OTHER INFORMATION: Synthetic: IL-2_D19[AzK]
<220> FEATURE:
<221> NAME/KEY: misc_feature
<222> LOCATION: (19)..(19)
<223> OTHER INFORMATION: Xaa is [AzK]

<400> SEQUENCE: 97

Pro Thr Ser Ser Ser Thr Lys Lys Thr Gln Leu Gln Leu Glu His Leu
```

```
                1               5                  10                 15
            Leu Leu Xaa Leu Gln Met Ile Leu Asn Gly Ile Asn Asn Tyr Lys Asn
                        20                  25                 30

Pro Lys Leu Thr Arg Met Leu Thr Phe Lys Phe Tyr Met Pro Lys Lys
                        35                  40                 45

Ala Thr Glu Leu Lys His Leu Gln Cys Leu Glu Glu Leu Lys Pro
                50                  55                  60

Leu Glu Glu Val Leu Asn Leu Ala Gln Ser Lys Asn Phe His Leu Arg
             65                  70                  75                  80

Pro Arg Asp Leu Ile Ser Asn Ile Asn Val Ile Val Leu Glu Leu Lys
                        85                  90                 95

Gly Ser Glu Thr Thr Phe Met Cys Glu Tyr Ala Asp Glu Thr Ala Thr
                        100                 105                110

Ile Val Glu Phe Leu Asn Arg Trp Ile Thr Phe Ser Gln Ser Ile Ile
                        115                 120                125

Ser Thr Leu Thr
                    130
```

<210> SEQ ID NO 98
<211> LENGTH: 132
<212> TYPE: PRT
<213> ORGANISM: Artificial Sequence
<220> FEATURE:
<223> OTHER INFORMATION: Synthetic: IL-2_M22[AzK]
<220> FEATURE:
<221> NAME/KEY: misc_feature
<222> LOCATION: (22)..(22)
<223> OTHER INFORMATION: Xaa is [AzK]

<400> SEQUENCE: 98

```
            Pro Thr Ser Ser Ser Thr Lys Lys Thr Gln Leu Gln Leu Glu His Leu
             1               5                  10                 15

Leu Leu Asp Leu Gln Xaa Ile Leu Asn Gly Ile Asn Asn Tyr Lys Asn
                        20                  25                 30

Pro Lys Leu Thr Arg Met Leu Thr Phe Lys Phe Tyr Met Pro Lys Lys
                        35                  40                 45

Ala Thr Glu Leu Lys His Leu Gln Cys Leu Glu Glu Leu Lys Pro
                50                  55                  60

Leu Glu Glu Val Leu Asn Leu Ala Gln Ser Lys Asn Phe His Leu Arg
             65                  70                  75                  80

Pro Arg Asp Leu Ile Ser Asn Ile Asn Val Ile Val Leu Glu Leu Lys
                        85                  90                 95

Gly Ser Glu Thr Thr Phe Met Cys Glu Tyr Ala Asp Glu Thr Ala Thr
                        100                 105                110

Ile Val Glu Phe Leu Asn Arg Trp Ile Thr Phe Ser Gln Ser Ile Ile
                        115                 120                125

Ser Thr Leu Thr
                    130
```

<210> SEQ ID NO 99
<211> LENGTH: 132
<212> TYPE: PRT
<213> ORGANISM: Artificial Sequence
<220> FEATURE:
<223> OTHER INFORMATION: Synthetic: IL-2_N25[AzK]
<220> FEATURE:
<221> NAME/KEY: misc_feature
<222> LOCATION: (25)..(25)
<223> OTHER INFORMATION: Xaa is [AzK]

<400> SEQUENCE: 99

Pro Thr Ser Ser Thr Lys Lys Thr Gln Leu Gln Leu Glu His Leu
1               5                   10                  15

Leu Leu Asp Leu Gln Met Ile Leu Xaa Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 100
<211> LENGTH: 132
<212> TYPE: PRT
<213> ORGANISM: Artificial Sequence
<220> FEATURE:
<223> OTHER INFORMATION: Synthetic: IL-2_N87[AzK]
<220> FEATURE:
<221> NAME/KEY: misc_feature
<222> LOCATION: (87)..(87)
<223> OTHER INFORMATION: Xaa is [AzK]

<400> SEQUENCE: 100

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Xaa Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 101
<211> LENGTH: 132
<212> TYPE: PRT
<213> ORGANISM: Artificial Sequence
<220> FEATURE:
<223> OTHER INFORMATION: Synthetic: IL-2_E99 [AzK]
<220> FEATURE:
<221> NAME/KEY: misc_feature

```
<222> LOCATION: (99)..(99)
<223> OTHER INFORMATION: Xaa is [AzK]

<400> SEQUENCE: 101
```

| | | | | | | | | | | | | | | | |
|---|---|---|---|---|---|---|---|---|---|---|---|---|---|---|---|
| Pro | Thr | Ser | Ser | Thr | Lys | Lys | Thr | Gln | Leu | Gln | Leu | Glu | His | Leu |
| 1 | | | | 5 | | | | | 10 | | | | | 15 |

| | | | | | | | | | | | | | | | |
|---|---|---|---|---|---|---|---|---|---|---|---|---|---|---|---|
| Leu | Leu | Asp | Leu | Gln | Met | Ile | Leu | Asn | Gly | Ile | Asn | Asn | Tyr | Lys | Asn |
| | | | 20 | | | | | 25 | | | | | 30 | | |

| | | | | | | | | | | | | | | | |
|---|---|---|---|---|---|---|---|---|---|---|---|---|---|---|---|
| Pro | Lys | Leu | Thr | Arg | Met | Leu | Thr | Phe | Lys | Phe | Tyr | Met | Pro | Lys | Lys |
| | | 35 | | | | | 40 | | | | | 45 | | | |

| | | | | | | | | | | | | | | | |
|---|---|---|---|---|---|---|---|---|---|---|---|---|---|---|---|
| Ala | Thr | Glu | Leu | Lys | His | Leu | Gln | Cys | Leu | Glu | Glu | Glu | Leu | Lys | Pro |
| | 50 | | | | | 55 | | | | | 60 | | | | |

| | | | | | | | | | | | | | | | |
|---|---|---|---|---|---|---|---|---|---|---|---|---|---|---|---|
| Leu | Glu | Glu | Val | Leu | Asn | Leu | Ala | Gln | Ser | Lys | Asn | Phe | His | Leu | Arg |
| 65 | | | | | 70 | | | | | 75 | | | | | 80 |

| | | | | | | | | | | | | | | | |
|---|---|---|---|---|---|---|---|---|---|---|---|---|---|---|---|
| Pro | Arg | Asp | Leu | Ile | Ser | Asn | Ile | Asn | Val | Ile | Val | Leu | Glu | Leu | Lys |
| | | | | 85 | | | | | 90 | | | | | 95 | |

| | | | | | | | | | | | | | | | |
|---|---|---|---|---|---|---|---|---|---|---|---|---|---|---|---|
| Gly | Ser | Xaa | Thr | Thr | Phe | Met | Cys | Glu | Tyr | Ala | Asp | Glu | Thr | Ala | Thr |
| | | | 100 | | | | | 105 | | | | | 110 | | |

| | | | | | | | | | | | | | | | |
|---|---|---|---|---|---|---|---|---|---|---|---|---|---|---|---|
| Ile | Val | Glu | Phe | Leu | Asn | Arg | Trp | Ile | Thr | Phe | Ser | Gln | Ser | Ile | Ile |
| | | 115 | | | | | 120 | | | | | 125 | | | |

| | | | |
|---|---|---|---|
| Ser | Thr | Leu | Thr |
| | 130 | | |

```
<210> SEQ ID NO 102
<211> LENGTH: 132
<212> TYPE: PRT
<213> ORGANISM: Artificial Sequence
<220> FEATURE:
<223> OTHER INFORMATION: Synthetic: IL-2_N118[AzK]-1
<220> FEATURE:
<221> NAME/KEY: misc_feature
<222> LOCATION: (118)..(118)
<223> OTHER INFORMATION: Xaa is [AzK]

<400> SEQUENCE: 102
```

| | | | | | | | | | | | | | | | |
|---|---|---|---|---|---|---|---|---|---|---|---|---|---|---|---|
| Pro | Thr | Ser | Ser | Thr | Lys | Lys | Thr | Gln | Leu | Gln | Leu | Glu | His | Leu |
| 1 | | | | 5 | | | | | 10 | | | | | 15 |

| | | | | | | | | | | | | | | | |
|---|---|---|---|---|---|---|---|---|---|---|---|---|---|---|---|
| Leu | Leu | Asp | Leu | Gln | Met | Ile | Leu | Asn | Gly | Ile | Asn | Asn | Tyr | Lys | Asn |
| | | | 20 | | | | | 25 | | | | | 30 | | |

| | | | | | | | | | | | | | | | |
|---|---|---|---|---|---|---|---|---|---|---|---|---|---|---|---|
| Pro | Lys | Leu | Thr | Arg | Met | Leu | Thr | Phe | Lys | Phe | Tyr | Met | Pro | Lys | Lys |
| | | 35 | | | | | 40 | | | | | 45 | | | |

| | | | | | | | | | | | | | | | |
|---|---|---|---|---|---|---|---|---|---|---|---|---|---|---|---|
| Ala | Thr | Glu | Leu | Lys | His | Leu | Gln | Cys | Leu | Glu | Glu | Glu | Leu | Lys | Pro |
| | 50 | | | | | 55 | | | | | 60 | | | | |

| | | | | | | | | | | | | | | | |
|---|---|---|---|---|---|---|---|---|---|---|---|---|---|---|---|
| Leu | Glu | Glu | Val | Leu | Asn | Leu | Ala | Gln | Ser | Lys | Asn | Phe | His | Leu | Arg |
| 65 | | | | | 70 | | | | | 75 | | | | | 80 |

| | | | | | | | | | | | | | | | |
|---|---|---|---|---|---|---|---|---|---|---|---|---|---|---|---|
| Pro | Arg | Asp | Leu | Ile | Ser | Asn | Ile | Asn | Val | Ile | Val | Leu | Glu | Leu | Lys |
| | | | | 85 | | | | | 90 | | | | | 95 | |

| | | | | | | | | | | | | | | | |
|---|---|---|---|---|---|---|---|---|---|---|---|---|---|---|---|
| Gly | Ser | Glu | Thr | Thr | Phe | Met | Cys | Glu | Tyr | Ala | Asp | Glu | Thr | Ala | Thr |
| | | | 100 | | | | | 105 | | | | | 110 | | |

| | | | | | | | | | | | | | | | |
|---|---|---|---|---|---|---|---|---|---|---|---|---|---|---|---|
| Ile | Val | Glu | Phe | Leu | Xaa | Arg | Trp | Ile | Thr | Phe | Ser | Gln | Ser | Ile | Ile |
| | | 115 | | | | | 120 | | | | | 125 | | | |

| | | | |
|---|---|---|---|
| Ser | Thr | Leu | Thr |
| | 130 | | |

```
<210> SEQ ID NO 103
<211> LENGTH: 132
<212> TYPE: PRT
<213> ORGANISM: Artificial Sequence
<220> FEATURE:
```

<223> OTHER INFORMATION: Synthetic: IL-2_T122[AzK]-1
<220> FEATURE:
<221> NAME/KEY: misc_feature
<222> LOCATION: (122)..(122)
<223> OTHER INFORMATION: Xaa is [AzK]

<400> SEQUENCE: 103

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Xaa Phe Ser Gln Ser Ile Ile
        115                 120                 125

Ser Thr Leu Thr
    130

<210> SEQ ID NO 104
<211> LENGTH: 132
<212> TYPE: PRT
<213> ORGANISM: Artificial Sequence
<220> FEATURE:
<223> OTHER INFORMATION: Synthetic: IL-2_Q125[AzK]
<220> FEATURE:
<221> NAME/KEY: misc_feature
<222> LOCATION: (125)..(125)
<223> OTHER INFORMATION: Xaa is [AzK]

<400> SEQUENCE: 104

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Xaa Ser Ile Ile
        115                 120                 125

Ser Thr Leu Thr
    130

<210> SEQ ID NO 105
<211> LENGTH: 132

```
<212> TYPE: PRT
<213> ORGANISM: Artificial Sequence
<220> FEATURE:
<223> OTHER INFORMATION: Synthetic: IL-2_S126[AzK]
<220> FEATURE:
<221> NAME/KEY: misc_feature
<222> LOCATION: (126)..(126)
<223> OTHER INFORMATION: Xaa is [AzK]

<400> SEQUENCE: 105
```

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Xaa Ile Ile
                115                 120                 125

Ser Thr Leu Thr
    130

```
<210> SEQ ID NO 106
<211> LENGTH: 132
<212> TYPE: PRT
<213> ORGANISM: Artificial Sequence
<220> FEATURE:
<223> OTHER INFORMATION: Synthetic: IL-2_T130[AzK]
<220> FEATURE:
<221> NAME/KEY: misc_feature
<222> LOCATION: (130)..(130)
<223> OTHER INFORMATION: Xaa is [AzK]

<400> SEQUENCE: 106
```

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Xaa Leu Thr
    130

<210> SEQ ID NO 107
<211> LENGTH: 132
<212> TYPE: PRT
<213> ORGANISM: Artificial Sequence
<220> FEATURE:
<223> OTHER INFORMATION: Synthetic: IL-2_N87R_D108[AzK]
<220> FEATURE:
<221> NAME/KEY: misc_feature
<222> LOCATION: (108)..(108)
<223> OTHER INFORMATION: Xaa is [AzK]

<400> SEQUENCE: 107

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Arg Ile Asn Val Ile Val Leu Glu Leu Lys
                85                  90                  95

Gly Ser Glu Thr Thr Phe Met Cys Glu Tyr Ala Xaa Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 108
<211> LENGTH: 132
<212> TYPE: PRT
<213> ORGANISM: Artificial Sequence
<220> FEATURE:
<223> OTHER INFORMATION: Synthetic: IL-2_V90[AzK]
<220> FEATURE:
<221> NAME/KEY: misc_feature
<222> LOCATION: (90)..(90)
<223> OTHER INFORMATION: Xaa is [AzK]

<400> SEQUENCE: 108

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Xaa Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 109
<211> LENGTH: 132
<212> TYPE: PRT
<213> ORGANISM: Artificial Sequence
<220> FEATURE:
<223> OTHER INFORMATION: Synthetic: IL-2_K8[AzK_L1_PEG]
<220> FEATURE:
<221> NAME/KEY: misc_feature
<222> LOCATION: (8)..(8)
<223> OTHER INFORMATION: Xaa is [AzK_L1_PEG]

<400> SEQUENCE: 109

Pro Thr Ser Ser Ser Thr Lys Xaa Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 110
<211> LENGTH: 132
<212> TYPE: PRT
<213> ORGANISM: Artificial Sequence
<220> FEATURE:
<223> OTHER INFORMATION: Synthetic: IL-2_H15[AzK_L1_PEG]
<220> FEATURE:
<221> NAME/KEY: misc_feature
<222> LOCATION: (15)..(15)
<223> OTHER INFORMATION: Xaa is [AzK_L1_PEG]

<400> SEQUENCE: 110

Pro Thr Ser Ser Ser Thr Lys Lys Thr Gln Leu Gln Leu Glu Xaa Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

```
Ile Val Glu Phe Leu Asn Arg Trp Ile Thr Phe Ser Gln Ser Ile Ile
            115                 120                 125

Ser Thr Leu Thr
        130

<210> SEQ ID NO 111
<211> LENGTH: 132
<212> TYPE: PRT
<213> ORGANISM: Artificial Sequence
<220> FEATURE:
<223> OTHER INFORMATION: Synthetic: IL-2_L18[AzK_L1_PEG]
<220> FEATURE:
<221> NAME/KEY: misc_feature
<222> LOCATION: (18)..(18)
<223> OTHER INFORMATION: Xaa is [AzK_L1_PEG]

<400> SEQUENCE: 111

Pro Thr Ser Ser Ser Thr Lys Lys Thr Gln Leu Gln Leu Glu His Leu
1               5                   10                  15

Leu Xaa Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 112
<211> LENGTH: 132
<212> TYPE: PRT
<213> ORGANISM: Artificial Sequence
<220> FEATURE:
<223> OTHER INFORMATION: Synthetic: IL-2_D19[AzK_L1_PEG]
<220> FEATURE:
<221> NAME/KEY: misc_feature
<222> LOCATION: (19)..(19)
<223> OTHER INFORMATION: Xaa is [AzK_L1_PEG]

<400> SEQUENCE: 112

Pro Thr Ser Ser Ser Thr Lys Lys Thr Gln Leu Gln Leu Glu His Leu
1               5                   10                  15

Leu Leu Xaa Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95
```

```
Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 113
<211> LENGTH: 132
<212> TYPE: PRT
<213> ORGANISM: Artificial Sequence
<220> FEATURE:
<223> OTHER INFORMATION: Synthetic: IL-2_M22[AzK_L1_PEG]
<220> FEATURE:
<221> NAME/KEY: misc_feature
<222> LOCATION: (22)..(22)
<223> OTHER INFORMATION: Xaa is [AzK_L1_PEG]

<400> SEQUENCE: 113

Pro Thr Ser Ser Thr Lys Lys Thr Gln Leu Gln Leu Glu His Leu
1               5                   10                  15

Leu Leu Asp Leu Gln Xaa Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 114
<211> LENGTH: 132
<212> TYPE: PRT
<213> ORGANISM: Artificial Sequence
<220> FEATURE:
<223> OTHER INFORMATION: Synthetic: IL-2_N25[AzK_L1_PEG]
<220> FEATURE:
<221> NAME/KEY: misc_feature
<222> LOCATION: (25)..(25)
<223> OTHER INFORMATION: Xaa is [AzK_L1_PEG]

<400> SEQUENCE: 114

Pro Thr Ser Ser Thr Lys Lys Thr Gln Leu Gln Leu Glu His Leu
1               5                   10                  15

Leu Leu Asp Leu Gln Met Ile Leu Xaa Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80
```

```
Pro Arg Asp Leu Ile Ser Asn Ile Asn Val Ile Val Leu Glu Leu Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130
```

<210> SEQ ID NO 115
<211> LENGTH: 132
<212> TYPE: PRT
<213> ORGANISM: Artificial Sequence
<220> FEATURE:
<223> OTHER INFORMATION: Synthetic: IL-2_N87[AzK_L1_PEG]
<220> FEATURE:
<221> NAME/KEY: misc_feature
<222> LOCATION: (87)..(87)
<223> OTHER INFORMATION: Xaa is [AzK_L1_PEG]

<400> SEQUENCE: 115

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Xaa Ile Asn Val Ile Val Leu Glu Leu Lys
            85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130
```

<210> SEQ ID NO 116
<211> LENGTH: 132
<212> TYPE: PRT
<213> ORGANISM: Artificial Sequence
<220> FEATURE:
<223> OTHER INFORMATION: Synthetic: IL-2_E99 [AzK_L1_PEG]
<220> FEATURE:
<221> NAME/KEY: misc_feature
<222> LOCATION: (99)..(99)
<223> OTHER INFORMATION: Xaa is [AzK_L1_PEG]

<400> SEQUENCE: 116

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
            50                  55                  60
```

```
Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Xaa Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 117
<211> LENGTH: 132
<212> TYPE: PRT
<213> ORGANISM: Artificial Sequence
<220> FEATURE:
<223> OTHER INFORMATION: Synthetic: IL-2_N118[AzK_L1_PEG]
<220> FEATURE:
<221> NAME/KEY: misc_feature
<222> LOCATION: (118)..(118)
<223> OTHER INFORMATION: Xaa is [AzK_L1_PEG]

<400> SEQUENCE: 117

Pro Thr Ser Ser Ser Thr Lys Lys Thr Gln Leu Gln Leu Glu His Leu
  1               5                  10                  15

Leu Leu Asp Leu Gln Met Ile Leu Asn Gly Ile Asn Asn Tyr Lys Asn
             20                  25                  30

Pro Lys Leu Thr Arg Met Leu Thr Phe Lys Phe Tyr Met Pro Lys Lys
         35                  40                  45

Ala Thr Glu Leu Lys His Leu Gln Cys Leu Glu Glu Leu Lys Pro
     50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Xaa Arg Trp Ile Thr Phe Ser Gln Ser Ile Ile
        115                 120                 125

Ser Thr Leu Thr
    130

<210> SEQ ID NO 118
<211> LENGTH: 132
<212> TYPE: PRT
<213> ORGANISM: Artificial Sequence
<220> FEATURE:
<223> OTHER INFORMATION: Synthetic: IL-2_T122[AzK_L1_PEG]
<220> FEATURE:
<221> NAME/KEY: misc_feature
<222> LOCATION: (122)..(122)
<223> OTHER INFORMATION: Xaa is [AzK_L1_PEG]

<400> SEQUENCE: 118

Pro Thr Ser Ser Ser Thr Lys Lys Thr Gln Leu Gln Leu Glu His Leu
  1               5                  10                  15

Leu Leu Asp Leu Gln Met Ile Leu Asn Gly Ile Asn Asn Tyr Lys Asn
             20                  25                  30

Pro Lys Leu Thr Arg Met Leu Thr Phe Lys Phe Tyr Met Pro Lys Lys
         35                  40                  45
```

```
Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Xaa Phe Ser Gln Ser Ile Ile
                115                 120                 125

Ser Thr Leu Thr
    130

<210> SEQ ID NO 119
<211> LENGTH: 132
<212> TYPE: PRT
<213> ORGANISM: Artificial Sequence
<220> FEATURE:
<223> OTHER INFORMATION: Synthetic: IL-2_Q125[AzK_L1_PEG]
<220> FEATURE:
<221> NAME/KEY: misc_feature
<222> LOCATION: (125)..(125)
<223> OTHER INFORMATION: Xaa is [AzK_L1_PEG]

<400> SEQUENCE: 119

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
                35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Xaa Ser Ile Ile
                115                 120                 125

Ser Thr Leu Thr
    130

<210> SEQ ID NO 120
<211> LENGTH: 132
<212> TYPE: PRT
<213> ORGANISM: Artificial Sequence
<220> FEATURE:
<223> OTHER INFORMATION: Synthetic: IL-2_S126[AzK_L1_PEG]
<220> FEATURE:
<221> NAME/KEY: misc_feature
<222> LOCATION: (126)..(126)
<223> OTHER INFORMATION: Xaa is [AzK_L1_PEG]

<400> SEQUENCE: 120

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
                20                  25                  30
```

```
Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Xaa Ile Ile
            115                 120                 125

Ser Thr Leu Thr
     130
```

<210> SEQ ID NO 121
<211> LENGTH: 132
<212> TYPE: PRT
<213> ORGANISM: Artificial Sequence
<220> FEATURE:
<223> OTHER INFORMATION: Synthetic: IL-2_T130[AzK_L1_PEG]
<220> FEATURE:
<221> NAME/KEY: misc_feature
<222> LOCATION: (130)..(130)
<223> OTHER INFORMATION: Xaa is [AzK_L1_PEG]

<400> SEQUENCE: 121

```
Pro Thr Ser Ser Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Xaa Leu Thr
     130
```

<210> SEQ ID NO 122
<211> LENGTH: 132
<212> TYPE: PRT
<213> ORGANISM: Artificial Sequence
<220> FEATURE:
<223> OTHER INFORMATION: Synthetic: IL-2_N87R_D108[AzK_L1_PEG]
<220> FEATURE:
<221> NAME/KEY: misc_feature
<222> LOCATION: (108)..(108)
<223> OTHER INFORMATION: Xaa is [AzK_L1_PEG]

<400> SEQUENCE: 122

```
Pro Thr Ser Ser Ser Thr Lys Lys Thr Gln Leu Gln Leu Glu His Leu
 1               5                  10                  15
```

```
Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Arg Ile Asn Val Ile Leu Glu Leu Lys
                85                  90                  95

Gly Ser Glu Thr Thr Phe Met Cys Glu Tyr Ala Xaa Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 123
<211> LENGTH: 132
<212> TYPE: PRT
<213> ORGANISM: Artificial Sequence
<220> FEATURE:
<223> OTHER INFORMATION: Synthetic: IL-2_V90[AzK_L1_PEG]
<220> FEATURE:
<221> NAME/KEY: misc_feature
<222> LOCATION: (90)..(90)
<223> OTHER INFORMATION: Xaa is [AzK_L1_PEG]

<400> SEQUENCE: 123

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Xaa Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 124
<211> LENGTH: 132
<212> TYPE: PRT
<213> ORGANISM: Artificial Sequence
<220> FEATURE:
<223> OTHER INFORMATION: Synthetic: IL-2_K8[AzK_L1_PEG50kDa]
<220> FEATURE:
<221> NAME/KEY: misc_feature
<222> LOCATION: (8)..(8)
<223> OTHER INFORMATION: Xaa is [AzK_L1_PEG50kDa]

<400> SEQUENCE: 124
```

```
Pro Thr Ser Ser Ser Thr Lys Xaa Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 125
<211> LENGTH: 132
<212> TYPE: PRT
<213> ORGANISM: Artificial Sequence
<220> FEATURE:
<223> OTHER INFORMATION: Synthetic: IL-2_H15[AzK_L1_PEG50kDa]
<220> FEATURE:
<221> NAME/KEY: misc_feature
<222> LOCATION: (15)..(15)
<223> OTHER INFORMATION: Xaa is [AzK_L1_PEG50kDa]

<400> SEQUENCE: 125

Pro Thr Ser Ser Thr Lys Lys Thr Gln Leu Gln Leu Glu Xaa Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 126
<211> LENGTH: 132
<212> TYPE: PRT
<213> ORGANISM: Artificial Sequence
<220> FEATURE:
<223> OTHER INFORMATION: Synthetic: IL-2_L18[AzK_L1_PEG50kDa]
<220> FEATURE:
<221> NAME/KEY: misc_feature
<222> LOCATION: (18)..(18)
<223> OTHER INFORMATION: Xaa is [AzK_L1_PEG50kDa]
```

<400> SEQUENCE: 126

Pro Thr Ser Ser Ser Thr Lys Lys Thr Gln Leu Gln Leu Glu His Leu
1               5                   10                  15

Leu Xaa Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 127
<211> LENGTH: 132
<212> TYPE: PRT
<213> ORGANISM: Artificial Sequence
<220> FEATURE:
<223> OTHER INFORMATION: Synthetic: IL-2_D19[AzK_L1_PEG50kDa]-1
<220> FEATURE:
<221> NAME/KEY: misc_feature
<222> LOCATION: (19)..(19)
<223> OTHER INFORMATION: Xaa is [AzK_L1_PEG50kDa]

<400> SEQUENCE: 127

Pro Thr Ser Ser Ser Thr Lys Lys Thr Gln Leu Gln Leu Glu His Leu
1               5                   10                  15

Leu Leu Xaa Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 128
<211> LENGTH: 132
<212> TYPE: PRT
<213> ORGANISM: Artificial Sequence
<220> FEATURE:
<223> OTHER INFORMATION: Synthetic: IL-2_M22[AzK_L1_PEG50kDa]
<220> FEATURE:

```
<221> NAME/KEY: misc_feature
<222> LOCATION: (22)..(22)
<223> OTHER INFORMATION: Xaa is [AzK_L1_PEG50kDa]

<400> SEQUENCE: 128

Pro Thr Ser Ser Ser Thr Lys Lys Thr Gln Leu Gln Leu Glu His Leu
1               5                   10                  15

Leu Leu Asp Leu Gln Xaa Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 129
<211> LENGTH: 132
<212> TYPE: PRT
<213> ORGANISM: Artificial Sequence
<220> FEATURE:
<223> OTHER INFORMATION: Synthetic: IL-2_N25[AzK_L1_PEG50kDa]
<220> FEATURE:
<221> NAME/KEY: misc_feature
<222> LOCATION: (25)..(25)
<223> OTHER INFORMATION: Xaa is [AzK_L1_PEG50kDa]

<400> SEQUENCE: 129

Pro Thr Ser Ser Ser Thr Lys Lys Thr Gln Leu Gln Leu Glu His Leu
1               5                   10                  15

Leu Leu Asp Leu Gln Met Ile Leu Xaa Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 130
<211> LENGTH: 132
<212> TYPE: PRT
<213> ORGANISM: Artificial Sequence
```

```
<220> FEATURE:
<223> OTHER INFORMATION: Synthetic: IL-2_N87[AzK_L1_PEG50kDa]
<220> FEATURE:
<221> NAME/KEY: misc_feature
<222> LOCATION: (87)..(87)
<223> OTHER INFORMATION: Xaa is [AzK_L1_PEG50kDa]

<400> SEQUENCE: 130
```

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Xaa Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

```
<210> SEQ ID NO 131
<211> LENGTH: 132
<212> TYPE: PRT
<213> ORGANISM: Artificial Sequence
<220> FEATURE:
<223> OTHER INFORMATION: Synthetic: IL-2_E99[AzK_L1_PEG50kDa]
<220> FEATURE:
<221> NAME/KEY: misc_feature
<222> LOCATION: (99)..(99)
<223> OTHER INFORMATION: Xaa is [AzK_L1_PEG50kDa]

<400> SEQUENCE: 131
```

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Xaa Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

```
<210> SEQ ID NO 132
```

```
<211> LENGTH: 132
<212> TYPE: PRT
<213> ORGANISM: Artificial Sequence
<220> FEATURE:
<223> OTHER INFORMATION: Synthetic: IL-2_N118[AzK_L1_PEG50kDa]
<220> FEATURE:
<221> NAME/KEY: misc_feature
<222> LOCATION: (118)..(118)
<223> OTHER INFORMATION: Xaa is [AzK_L1_PEG50kDa]

<400> SEQUENCE: 132

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Xaa Arg Trp Ile Thr Phe Ser Gln Ser Ile Ile
        115                 120                 125

Ser Thr Leu Thr
        130

<210> SEQ ID NO 133
<211> LENGTH: 132
<212> TYPE: PRT
<213> ORGANISM: Artificial Sequence
<220> FEATURE:
<223> OTHER INFORMATION: Synthetic: IL-2_T122[AzK_L1_PEG50kDa]
<220> FEATURE:
<221> NAME/KEY: misc_feature
<222> LOCATION: (122)..(122)
<223> OTHER INFORMATION: Xaa is [AzK_L1_PEG50kDa]

<400> SEQUENCE: 133

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Xaa Phe Ser Gln Ser Ile Ile
        115                 120                 125

Ser Thr Leu Thr
        130
```

<210> SEQ ID NO 134
<211> LENGTH: 132
<212> TYPE: PRT
<213> ORGANISM: Artificial Sequence
<220> FEATURE:
<223> OTHER INFORMATION: Synthetic: IL-2_Q125[AzK_L1_PEG50kDa]
<220> FEATURE:
<221> NAME/KEY: misc_feature
<222> LOCATION: (125)..(125)
<223> OTHER INFORMATION: Xaa is [AzK_L1_PEG50kDa]

<400> SEQUENCE: 134

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Xaa Ser Ile Ile
        115                 120                 125

Ser Thr Leu Thr
    130

<210> SEQ ID NO 135
<211> LENGTH: 132
<212> TYPE: PRT
<213> ORGANISM: Artificial Sequence
<220> FEATURE:
<223> OTHER INFORMATION: Synthetic: IL-2_S126[AzK_L1_PEG50kDa]
<220> FEATURE:
<221> NAME/KEY: misc_feature
<222> LOCATION: (126)..(126)
<223> OTHER INFORMATION: Xaa is [AzK_L1_PEG50kDa]

<400> SEQUENCE: 135

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Xaa Ile Ile
        115                 120                 125

Ser Thr Leu Thr
    130

<210> SEQ ID NO 136
<211> LENGTH: 132
<212> TYPE: PRT
<213> ORGANISM: Artificial Sequence
<220> FEATURE:
<223> OTHER INFORMATION: Synthetic: IL-2_T130[AzK_L1_PEG50kDa]
<220> FEATURE:
<221> NAME/KEY: misc_feature
<222> LOCATION: (130)..(130)
<223> OTHER INFORMATION: Xaa is [AzK_L1_PEG50kDa]

<400> SEQUENCE: 136

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Xaa Leu Thr
    130

<210> SEQ ID NO 137
<211> LENGTH: 132
<212> TYPE: PRT
<213> ORGANISM: Artificial Sequence
<220> FEATURE:
<223> OTHER INFORMATION: Synthetic: IL-2_N87R_D108[AzK_L1_PEG50kDa]
<220> FEATURE:
<221> NAME/KEY: misc_feature
<222> LOCATION: (108)..(108)
<223> OTHER INFORMATION: Xaa is [AzK_L1_PEG50kDa]

<400> SEQUENCE: 137

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Arg Ile Asn Val Ile Val Leu Glu Leu Lys
                85                  90                  95

Gly Ser Glu Thr Thr Phe Met Cys Glu Tyr Ala Xaa Glu Thr Ala Thr
            100                 105                 110

-continued

```
Ile Val Glu Phe Leu Asn Arg Trp Ile Thr Phe Ser Gln Ser Ile Ile
        115                 120                 125

Ser Thr Leu Thr
        130

<210> SEQ ID NO 138
<211> LENGTH: 132
<212> TYPE: PRT
<213> ORGANISM: Artificial Sequence
<220> FEATURE:
<223> OTHER INFORMATION: Synthetic: IL-2_V91[AzK_L1_PEG50kDa]-1
<220> FEATURE:
<221> NAME/KEY: misc_feature
<222> LOCATION: (90)..(90)
<223> OTHER INFORMATION: Xaa is [AzK_L1_PEG50kDa]

<400> SEQUENCE: 138

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Xaa Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 139
<211> LENGTH: 132
<212> TYPE: PRT
<213> ORGANISM: Artificial Sequence
<220> FEATURE:
<223> OTHER INFORMATION: Synthetic: IL-2_K8[AzK_L1_PEG30kDa]
<220> FEATURE:
<221> NAME/KEY: misc_feature
<222> LOCATION: (8)..(8)
<223> OTHER INFORMATION: Xaa is [AzK_L1_PEG30kDa]

<400> SEQUENCE: 139

Pro Thr Ser Ser Ser Thr Lys Xaa Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95
```

```
Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 140
<211> LENGTH: 132
<212> TYPE: PRT
<213> ORGANISM: Artificial Sequence
<220> FEATURE:
<223> OTHER INFORMATION: Synthetic: IL-2_H15[AzK_L1_PEG30kDa]
<220> FEATURE:
<221> NAME/KEY: misc_feature
<222> LOCATION: (15)..(15)
<223> OTHER INFORMATION: Xaa is [AzK_L1_PEG30kDa]

<400> SEQUENCE: 140

Pro Thr Ser Ser Ser Thr Lys Lys Thr Gln Leu Gln Leu Glu Xaa Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 141
<211> LENGTH: 132
<212> TYPE: PRT
<213> ORGANISM: Artificial Sequence
<220> FEATURE:
<223> OTHER INFORMATION: Synthetic: IL-2_L18[AzK_L1_PEG30kDa]
<220> FEATURE:
<221> NAME/KEY: misc_feature
<222> LOCATION: (18)..(18)
<223> OTHER INFORMATION: Xaa is [AzK_L1_PEG30kDa]

<400> SEQUENCE: 141

Pro Thr Ser Ser Ser Thr Lys Lys Thr Gln Leu Gln Leu Glu His Leu
1               5                   10                  15

Leu Xaa Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80
```

-continued

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 142
<211> LENGTH: 132
<212> TYPE: PRT
<213> ORGANISM: Artificial Sequence
<220> FEATURE:
<223> OTHER INFORMATION: Synthetic: IL-2_D19[AzK_L1_PEG30kDa]
<220> FEATURE:
<221> NAME/KEY: misc_feature
<222> LOCATION: (19)..(19)
<223> OTHER INFORMATION: Xaa is [AzK_L1_PEG30kDa]

<400> SEQUENCE: 142

Pro Thr Ser Ser Ser Thr Lys Lys Thr Gln Leu Gln Leu Glu His Leu
1               5                   10                  15

Leu Leu Xaa Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 143
<211> LENGTH: 132
<212> TYPE: PRT
<213> ORGANISM: Artificial Sequence
<220> FEATURE:
<223> OTHER INFORMATION: Synthetic: IL-2_M22[AzK_L1_PEG30kDa]
<220> FEATURE:
<221> NAME/KEY: misc_feature
<222> LOCATION: (22)..(22)
<223> OTHER INFORMATION: Xaa is [AzK_L1_PEG30kDa]

<400> SEQUENCE: 143

Pro Thr Ser Ser Ser Thr Lys Lys Thr Gln Leu Gln Leu Glu His Leu
1               5                   10                  15

Leu Leu Asp Leu Gln Xaa Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
50                  55                  60

```
Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 144
<211> LENGTH: 132
<212> TYPE: PRT
<213> ORGANISM: Artificial Sequence
<220> FEATURE:
<223> OTHER INFORMATION: Synthetic: IL-2_N25[AzK_L1_PEG30kDa]
<220> FEATURE:
<221> NAME/KEY: misc_feature
<222> LOCATION: (25)..(25)
<223> OTHER INFORMATION: Xaa is [AzK_L1_PEG30kDa]

<400> SEQUENCE: 144

Pro Thr Ser Ser Ser Thr Lys Lys Thr Gln Leu Gln Leu Glu His Leu
1               5                   10                  15

Leu Leu Asp Leu Gln Met Ile Leu Xaa Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 145
<211> LENGTH: 132
<212> TYPE: PRT
<213> ORGANISM: Artificial Sequence
<220> FEATURE:
<223> OTHER INFORMATION: Synthetic: IL-2_N87[AzK_L1_PEG30kDa]
<220> FEATURE:
<221> NAME/KEY: misc_feature
<222> LOCATION: (87)..(87)
<223> OTHER INFORMATION: Xaa is [AzK_L1_PEG30kDa]

<400> SEQUENCE: 145

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45
```

```
Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Xaa Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 146
<211> LENGTH: 132
<212> TYPE: PRT
<213> ORGANISM: Artificial Sequence
<220> FEATURE:
<223> OTHER INFORMATION: Synthetic: IL-2_E99[AzK_L1_PEG30kDa]
<220> FEATURE:
<221> NAME/KEY: misc_feature
<222> LOCATION: (99)..(99)
<223> OTHER INFORMATION: Xaa is [AzK_L1_PEG30kDa]

<400> SEQUENCE: 146

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Xaa Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 147
<211> LENGTH: 132
<212> TYPE: PRT
<213> ORGANISM: Artificial Sequence
<220> FEATURE:
<223> OTHER INFORMATION: Synthetic: IL-2_N118[AzK_L1_PEG30kDa]
<220> FEATURE:
<221> NAME/KEY: misc_feature
<222> LOCATION: (118)..(118)
<223> OTHER INFORMATION: Xaa is [AzK_L1_PEG30kDa]

<400> SEQUENCE: 147

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30
```

```
Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Xaa Arg Trp Ile Thr Phe Ser Gln Ser Ile Ile
            115                 120                 125

Ser Thr Leu Thr
            130

<210> SEQ ID NO 148
<211> LENGTH: 132
<212> TYPE: PRT
<213> ORGANISM: Artificial Sequence
<220> FEATURE:
<223> OTHER INFORMATION: Synthetic: IL-2_T122[AzK_L1_PEG30kDa]
<220> FEATURE:
<221> NAME/KEY: misc_feature
<222> LOCATION: (122)..(122)
<223> OTHER INFORMATION: Xaa is [AzK_L1_PEG30kDa]

<400> SEQUENCE: 148

Pro Thr Ser Ser Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Xaa Phe Ser Gln Ser Ile Ile
            115                 120                 125

Ser Thr Leu Thr
            130

<210> SEQ ID NO 149
<211> LENGTH: 132
<212> TYPE: PRT
<213> ORGANISM: Artificial Sequence
<220> FEATURE:
<223> OTHER INFORMATION: Synthetic: IL-2_Q125[AzK_L1_PEG30kDa]
<220> FEATURE:
<221> NAME/KEY: misc_feature
<222> LOCATION: (125)..(125)
<223> OTHER INFORMATION: Xaa is [AzK_L1_PEG30kDa]

<400> SEQUENCE: 149

Pro Thr Ser Ser Ser Thr Lys Lys Thr Gln Leu Gln Leu Glu His Leu
 1               5                  10                  15
```

```
Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Xaa Ser Ile Ile
                115                 120                 125

Ser Thr Leu Thr
    130

<210> SEQ ID NO 150
<211> LENGTH: 132
<212> TYPE: PRT
<213> ORGANISM: Artificial Sequence
<220> FEATURE:
<223> OTHER INFORMATION: Synthetic: IL-2_S126[AzK_L1_PEG30kDa]
<220> FEATURE:
<221> NAME/KEY: misc_feature
<222> LOCATION: (126)..(126)
<223> OTHER INFORMATION: Xaa is [AzK_L1_PEG30kDa]

<400> SEQUENCE: 150

Pro Thr Ser Ser Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Xaa Ile Ile
                115                 120                 125

Ser Thr Leu Thr
    130

<210> SEQ ID NO 151
<211> LENGTH: 132
<212> TYPE: PRT
<213> ORGANISM: Artificial Sequence
<220> FEATURE:
<223> OTHER INFORMATION: Synthetic: IL-2_T130[AzK_L1_PEG30kDa]
<220> FEATURE:
<221> NAME/KEY: misc_feature
<222> LOCATION: (130)..(130)
<223> OTHER INFORMATION: Xaa is [AzK_L1_PEG30kDa]

<400> SEQUENCE: 151
```

```
Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Xaa Leu Thr
    130

<210> SEQ ID NO 152
<211> LENGTH: 132
<212> TYPE: PRT
<213> ORGANISM: Artificial Sequence
<220> FEATURE:
<223> OTHER INFORMATION: Synthetic: IL-2_N87R_D108[AzK_L1_PEG30kDa]
<220> FEATURE:
<221> NAME/KEY: misc_feature
<222> LOCATION: (108)..(108)
<223> OTHER INFORMATION: Xaa is [AzK_L1_PEG30kDa]

<400> SEQUENCE: 152

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Arg Ile Asn Val Ile Val Leu Glu Leu Lys
                85                  90                  95

Gly Ser Glu Thr Thr Phe Met Cys Glu Tyr Ala Xaa Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 153
<211> LENGTH: 132
<212> TYPE: PRT
<213> ORGANISM: Artificial Sequence
<220> FEATURE:
<223> OTHER INFORMATION: Synthetic: IL-2_V90[AzK_L1_PEG30kDa]
<220> FEATURE:
<221> NAME/KEY: misc_feature
<222> LOCATION: (90)..(90)
```

<223> OTHER INFORMATION: Xaa is [AzK_L1_PEG30kDa]

<400> SEQUENCE: 153

```
Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Xaa Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
    130
```

<210> SEQ ID NO 154
<211> LENGTH: 133
<212> TYPE: PRT
<213> ORGANISM: Artificial Sequence
<220> FEATURE:
<223> OTHER INFORMATION: Synthetic: IL-2_K9[AzK_L1_PEG]
<220> FEATURE:
<221> NAME/KEY: misc_feature
<222> LOCATION: (9)..(9)
<223> OTHER INFORMATION: Xaa is [AzK_L1_PEG]

<400> SEQUENCE: 154

```
Ala Pro Thr Ser Ser Ser Thr Lys Xaa Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
    130
```

<210> SEQ ID NO 155
<211> LENGTH: 133
<212> TYPE: PRT
<213> ORGANISM: Artificial Sequence
<220> FEATURE:
<223> OTHER INFORMATION: Synthetic: IL-2_H16[AzK_L1_PEG]

<220> FEATURE:
<221> NAME/KEY: misc_feature
<222> LOCATION: (16)..(16)
<223> OTHER INFORMATION: Xaa is [AzK_L1_PEG]

<400> SEQUENCE: 155

Ala Pro Thr Ser Ser Ser Thr Lys Lys Thr Gln Leu Gln Leu Glu Xaa
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 156
<211> LENGTH: 133
<212> TYPE: PRT
<213> ORGANISM: Artificial Sequence
<220> FEATURE:
<223> OTHER INFORMATION: Synthetic: IL-2_L19[AzK_L1_PEG]
<220> FEATURE:
<221> NAME/KEY: misc_feature
<222> LOCATION: (19)..(19)
<223> OTHER INFORMATION: Xaa is [AzK_L1_PEG]

<400> SEQUENCE: 156

Ala Pro Thr Ser Ser Ser Thr Lys Lys Thr Gln Leu Gln Leu Glu His
1               5                   10                  15

Leu Leu Xaa Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 157
<211> LENGTH: 133
<212> TYPE: PRT

```
<213> ORGANISM: Artificial Sequence
<220> FEATURE:
<223> OTHER INFORMATION: Synthetic: IL-2_D20[AzK_L1_PEG]
<220> FEATURE:
<221> NAME/KEY: misc_feature
<222> LOCATION: (20)..(20)
<223> OTHER INFORMATION: Xaa is [AzK_L1_PEG]

<400> SEQUENCE: 157

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 158
<211> LENGTH: 133
<212> TYPE: PRT
<213> ORGANISM: Artificial Sequence
<220> FEATURE:
<223> OTHER INFORMATION: Synthetic: IL-2_M23[AzK_L1_PEG]
<220> FEATURE:
<221> NAME/KEY: misc_feature
<222> LOCATION: (23)..(23)
<223> OTHER INFORMATION: Xaa is [AzK_L1_PEG]

<400> SEQUENCE: 158

Ala Pro Thr Ser Ser Ser Thr Lys Lys Thr Gln Leu Gln Leu Glu His
1               5                   10                  15

Leu Leu Leu Asp Leu Gln Xaa Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130
```

```
<210> SEQ ID NO 159
<211> LENGTH: 133
<212> TYPE: PRT
<213> ORGANISM: Artificial Sequence
<220> FEATURE:
<223> OTHER INFORMATION: Synthetic: IL-2_N26[AzK_L1_PEG]
<220> FEATURE:
<221> NAME/KEY: misc_feature
<222> LOCATION: (26)..(26)
<223> OTHER INFORMATION: Xaa is [AzK_L1_PEG]

<400> SEQUENCE: 159
```

Ala Pro Thr Ser Ser Ser Thr Lys Lys Thr Gln Leu Gln Leu Glu His
1               5                   10                  15

Leu Leu Leu Asp Leu Gln Met Ile Leu Xaa Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

```
<210> SEQ ID NO 160
<211> LENGTH: 133
<212> TYPE: PRT
<213> ORGANISM: Artificial Sequence
<220> FEATURE:
<223> OTHER INFORMATION: Synthetic: IL-2_N88[AzK_L1_PEG]
<220> FEATURE:
<221> NAME/KEY: misc_feature
<222> LOCATION: (88)..(88)
<223> OTHER INFORMATION: Xaa is [AzK_L1_PEG]

<400> SEQUENCE: 160
```

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Xaa Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr

<210> SEQ ID NO 161
<211> LENGTH: 133
<212> TYPE: PRT
<213> ORGANISM: Artificial Sequence
<220> FEATURE:
<223> OTHER INFORMATION: Synthetic: IL-2_E100[AzK_L1_PEG]
<220> FEATURE:
<221> NAME/KEY: misc_feature
<222> LOCATION: (100)..(100)
<223> OTHER INFORMATION: Xaa is [AzK_L1_PEG]

<400> SEQUENCE: 161

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Xaa Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 162
<211> LENGTH: 133
<212> TYPE: PRT
<213> ORGANISM: Artificial Sequence
<220> FEATURE:
<223> OTHER INFORMATION: Synthetic: IL-2_N119[AzK_L1_PEG]
<220> FEATURE:
<221> NAME/KEY: misc_feature
<222> LOCATION: (119)..(119)
<223> OTHER INFORMATION: Xaa is [AzK_L1_PEG]

<400> SEQUENCE: 162

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Xaa Arg Trp Ile Thr Phe Ser Gln Ser Ile

-continued

```
                 115                 120                 125
Ile Ser Thr Leu Thr
        130

<210> SEQ ID NO 163
<211> LENGTH: 133
<212> TYPE: PRT
<213> ORGANISM: Artificial Sequence
<220> FEATURE:
<223> OTHER INFORMATION: Synthetic: IL-2_T123[AzK_L1_PEG]
<220> FEATURE:
<221> NAME/KEY: misc_feature
<222> LOCATION: (123)..(123)
<223> OTHER INFORMATION: Xaa is [AzK_L1_PEG]

<400> SEQUENCE: 163

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Xaa Phe Ser Gln Ser Ile
        115                 120                 125

Ile Ser Thr Leu Thr
        130

<210> SEQ ID NO 164
<211> LENGTH: 133
<212> TYPE: PRT
<213> ORGANISM: Artificial Sequence
<220> FEATURE:
<223> OTHER INFORMATION: Synthetic: IL-2_Q126[AzK_L1_PEG]
<220> FEATURE:
<221> NAME/KEY: misc_feature
<222> LOCATION: (126)..(126)
<223> OTHER INFORMATION: Xaa is [AzK_L1_PEG]

<400> SEQUENCE: 164

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
```

```
                    100                 105                 110
Thr Ile Val Glu Phe Leu Asn Arg Trp Ile Thr Phe Ser Xaa Ser Ile
            115                 120                 125

Ile Ser Thr Leu Thr
            130

<210> SEQ ID NO 165
<211> LENGTH: 133
<212> TYPE: PRT
<213> ORGANISM: Artificial Sequence
<220> FEATURE:
<223> OTHER INFORMATION: Synthetic: IL-2_S127[AzK_L1_PEG]
<220> FEATURE:
<221> NAME/KEY: misc_feature
<222> LOCATION: (127)..(127)
<223> OTHER INFORMATION: Xaa is [AzK_L1_PEG]

<400> SEQUENCE: 165

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Xaa Ile
            115                 120                 125

Ile Ser Thr Leu Thr
            130

<210> SEQ ID NO 166
<211> LENGTH: 133
<212> TYPE: PRT
<213> ORGANISM: Artificial Sequence
<220> FEATURE:
<223> OTHER INFORMATION: Synthetic: IL-2_T131[AzK_L1_PEG]
<220> FEATURE:
<221> NAME/KEY: misc_feature
<222> LOCATION: (131)..(131)
<223> OTHER INFORMATION: Xaa is [AzK_L1_PEG]

<400> SEQUENCE: 166

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
```

85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Xaa Leu Thr
        130

<210> SEQ ID NO 167
<211> LENGTH: 133
<212> TYPE: PRT
<213> ORGANISM: Artificial Sequence
<220> FEATURE:
<223> OTHER INFORMATION: Synthetic: IL-2_N88R_D109[AzK_L1_PEG]
<220> FEATURE:
<221> NAME/KEY: misc_feature
<222> LOCATION: (109)..(109)
<223> OTHER INFORMATION: Xaa is [AzK_L1_PEG]

<400> SEQUENCE: 167

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Xaa Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 168
<211> LENGTH: 133
<212> TYPE: PRT
<213> ORGANISM: Artificial Sequence
<220> FEATURE:
<223> OTHER INFORMATION: Synthetic: IL-2_V91[AzK_L1_PEG]
<220> FEATURE:
<221> NAME/KEY: misc_feature
<222> LOCATION: (91)..(91)
<223> OTHER INFORMATION: Xaa is [AzK_L1_PEG]

<400> SEQUENCE: 168

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu

-continued

```
                65                  70                  75                  80
Arg Pro Arg Asp Leu Ile Ser Asn Ile Asn Xaa Ile Val Leu Glu Leu
                    85                  90                  95
Lys Gly Ser Glu Thr Thr Phe Met Cys Glu Tyr Ala Asp Glu Thr Ala
                    100                 105                 110
Thr Ile Val Glu Phe Leu Asn Arg Trp Ile Thr Phe Ser Gln Ser Ile
                    115                 120                 125
Ile Ser Thr Leu Thr
                    130
```

<210> SEQ ID NO 169
<211> LENGTH: 133
<212> TYPE: PRT
<213> ORGANISM: Artificial Sequence
<220> FEATURE:
<223> OTHER INFORMATION: Synthetic: IL-2_K9[AzK_L1_PEG50kDa]
<220> FEATURE:
<221> NAME/KEY: misc_feature
<222> LOCATION: (9)..(9)
<223> OTHER INFORMATION: Xaa is [AzK_L1_PEG50kDa]

<400> SEQUENCE: 169

```
Ala Pro Thr Ser Ser Ser Thr Lys Xaa Thr Gln Leu Gln Leu Glu His
1               5                   10                  15
Leu Leu Leu Asp Leu Gln Met Ile Leu Asn Gly Ile Asn Asn Tyr Lys
                    20                  25                  30
Asn Pro Lys Leu Thr Arg Met Leu Thr Phe Lys Phe Tyr Met Pro Lys
                    35                  40                  45
Lys Ala Thr Glu Leu Lys His Leu Gln Cys Leu Glu Glu Glu Leu Lys
                    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                    85                  90                  95
Lys Gly Ser Glu Thr Thr Phe Met Cys Glu Tyr Ala Asp Glu Thr Ala
                    100                 105                 110
Thr Ile Val Glu Phe Leu Asn Arg Trp Ile Thr Phe Ser Gln Ser Ile
                    115                 120                 125
Ile Ser Thr Leu Thr
                    130
```

<210> SEQ ID NO 170
<211> LENGTH: 133
<212> TYPE: PRT
<213> ORGANISM: Artificial Sequence
<220> FEATURE:
<223> OTHER INFORMATION: Synthetic: IL-2_H16[AzK_L1_PEG50kDa]
<220> FEATURE:
<221> NAME/KEY: misc_feature
<222> LOCATION: (16)..(16)
<223> OTHER INFORMATION: Xaa is [AzK_L1_PEG50kDa]

<400> SEQUENCE: 170

```
Ala Pro Thr Ser Ser Ser Thr Lys Lys Thr Gln Leu Gln Leu Glu Xaa
1               5                   10                  15
Leu Leu Leu Asp Leu Gln Met Ile Leu Asn Gly Ile Asn Asn Tyr Lys
                    20                  25                  30
Asn Pro Lys Leu Thr Arg Met Leu Thr Phe Lys Phe Tyr Met Pro Lys
                    35                  40                  45
Lys Ala Thr Glu Leu Lys His Leu Gln Cys Leu Glu Glu Glu Leu Lys
```

```
                50                  55                  60
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 171
<211> LENGTH: 133
<212> TYPE: PRT
<213> ORGANISM: Artificial Sequence
<220> FEATURE:
<223> OTHER INFORMATION: Synthetic: IL-2_L19[AzK_L1_PEG50kDa]
<220> FEATURE:
<221> NAME/KEY: misc_feature
<222> LOCATION: (19)..(19)
<223> OTHER INFORMATION: Xaa is [AzK_L1_PEG50kDa]

<400> SEQUENCE: 171

Ala Pro Thr Ser Ser Ser Thr Lys Lys Thr Gln Leu Gln Leu Glu His
 1               5                  10                  15

Leu Leu Xaa Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Glu Leu Lys
         50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 172
<211> LENGTH: 133
<212> TYPE: PRT
<213> ORGANISM: Artificial Sequence
<220> FEATURE:
<223> OTHER INFORMATION: Synthetic: IL-2_D20[AzK_L1_PEG50kDa]-2
<220> FEATURE:
<221> NAME/KEY: misc_feature
<222> LOCATION: (20)..(20)
<223> OTHER INFORMATION: Xaa is [AzK_L1_PEG50kDa]

<400> SEQUENCE: 172

Ala Pro Thr Ser Ser Ser Thr Lys Lys Thr Gln Leu Gln Leu Glu His
 1               5                  10                  15

Leu Leu Leu Xaa Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
```

```
                35                  40                  45
Lys Ala Thr Glu Leu Lys His Leu Gln Cys Leu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
                130

<210> SEQ ID NO 173
<211> LENGTH: 133
<212> TYPE: PRT
<213> ORGANISM: Artificial Sequence
<220> FEATURE:
<223> OTHER INFORMATION: Synthetic: IL-2_M23[AzK_L1_PEG50kDa]
<220> FEATURE:
<221> NAME/KEY: misc_feature
<222> LOCATION: (23)..(23)
<223> OTHER INFORMATION: Xaa is [AzK_L1_PEG50kDa]

<400> SEQUENCE: 173

Ala Pro Thr Ser Ser Ser Thr Lys Lys Thr Gln Leu Gln Leu Glu His
 1               5                  10                  15

Leu Leu Leu Asp Leu Gln Xaa Ile Leu Asn Gly Ile Asn Asn Tyr Lys
                 20                  25                  30

Asn Pro Lys Leu Thr Arg Met Leu Thr Phe Lys Phe Tyr Met Pro Lys
                 35                  40                  45

Lys Ala Thr Glu Leu Lys His Leu Gln Cys Leu Glu Glu Leu Lys
 50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
                115                 120                 125

Ile Ser Thr Leu Thr
                130

<210> SEQ ID NO 174
<211> LENGTH: 133
<212> TYPE: PRT
<213> ORGANISM: Artificial Sequence
<220> FEATURE:
<223> OTHER INFORMATION: Synthetic: IL-2_N26[AzK_L1_PEG50kDa]
<220> FEATURE:
<221> NAME/KEY: misc_feature
<222> LOCATION: (26)..(26)
<223> OTHER INFORMATION: Xaa is [AzK_L1_PEG50kDa]

<400> SEQUENCE: 174

Ala Pro Thr Ser Ser Ser Thr Lys Lys Thr Gln Leu Gln Leu Glu His
 1               5                  10                  15

Leu Leu Leu Asp Leu Gln Met Ile Leu Xaa Gly Ile Asn Asn Tyr Lys
```

-continued

```
                20                  25                  30
Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 175
<211> LENGTH: 133
<212> TYPE: PRT
<213> ORGANISM: Artificial Sequence
<220> FEATURE:
<223> OTHER INFORMATION: Synthetic: IL-2_N88[AzK_L1_PEG50kDa]
<220> FEATURE:
<221> NAME/KEY: misc_feature
<222> LOCATION: (88)..(88)
<223> OTHER INFORMATION: Xaa is [AzK_L1_PEG50kDa]

<400> SEQUENCE: 175

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Xaa Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 176
<211> LENGTH: 133
<212> TYPE: PRT
<213> ORGANISM: Artificial Sequence
<220> FEATURE:
<223> OTHER INFORMATION: Synthetic: IL-2_E100[AzK_L1_PEG50kDa]
<220> FEATURE:
<221> NAME/KEY: misc_feature
<222> LOCATION: (100)..(100)
<223> OTHER INFORMATION: Xaa is [AzK_L1_PEG50kDa]

<400> SEQUENCE: 176

Ala Pro Thr Ser Ser Ser Thr Lys Lys Thr Gln Leu Gln Leu Glu His
```

```
1               5                   10                  15
Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
 65                 70                  75                  80

Arg Pro Arg Asp Leu Ile Ser Asn Ile Asn Val Ile Val Leu Glu Leu
                85                  90                  95

Lys Gly Ser Xaa Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
            130

<210> SEQ ID NO 177
<211> LENGTH: 133
<212> TYPE: PRT
<213> ORGANISM: Artificial Sequence
<220> FEATURE:
<223> OTHER INFORMATION: Synthetic: IL-2_N119[AzK_L1_PEG50kDa]
<220> FEATURE:
<221> NAME/KEY: misc_feature
<222> LOCATION: (119)..(119)
<223> OTHER INFORMATION: Xaa is [AzK_L1_PEG50kDa]

<400> SEQUENCE: 177

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
 65                 70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Xaa Arg Trp Ile Thr Phe Ser Gln Ser Ile
            115                 120                 125

Ile Ser Thr Leu Thr
            130

<210> SEQ ID NO 178
<211> LENGTH: 133
<212> TYPE: PRT
<213> ORGANISM: Artificial Sequence
<220> FEATURE:
<223> OTHER INFORMATION: Synthetic: IL-2_T123[AzK_L1_PEG50kDa]
<220> FEATURE:
<221> NAME/KEY: misc_feature
<222> LOCATION: (123)..(123)
<223> OTHER INFORMATION: Xaa is [AzK_L1_PEG50kDa]
```

<400> SEQUENCE: 178

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Xaa Phe Ser Gln Ser Ile
        115                 120                 125

Ile Ser Thr Leu Thr
    130

<210> SEQ ID NO 179
<211> LENGTH: 133
<212> TYPE: PRT
<213> ORGANISM: Artificial Sequence
<220> FEATURE:
<223> OTHER INFORMATION: Synthetic: IL-2_Q126[AzK_L1_PEG50kDa]
<220> FEATURE:
<221> NAME/KEY: misc_feature
<222> LOCATION: (126)..(126)
<223> OTHER INFORMATION: Xaa is [AzK_L1_PEG50kDa]

<400> SEQUENCE: 179

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Xaa Ser Ile
        115                 120                 125

Ile Ser Thr Leu Thr
    130

<210> SEQ ID NO 180
<211> LENGTH: 133
<212> TYPE: PRT
<213> ORGANISM: Artificial Sequence
<220> FEATURE:
<223> OTHER INFORMATION: Synthetic: IL-2_S127[AzK_L1_PEG50kDa]
<220> FEATURE:
<221> NAME/KEY: misc_feature
<222> LOCATION: (127)..(127)
<223> OTHER INFORMATION: Xaa is [AzK_L1_PEG50kDa]

<400> SEQUENCE: 180

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Xaa Ile
        115                 120                 125

Ile Ser Thr Leu Thr
        130
```

<210> SEQ ID NO 181
<211> LENGTH: 133
<212> TYPE: PRT
<213> ORGANISM: Artificial Sequence
<220> FEATURE:
<223> OTHER INFORMATION: Synthetic: IL-2_T131[AzK_L1_PEG50kDa]
<220> FEATURE:
<221> NAME/KEY: misc_feature
<222> LOCATION: (131)..(131)
<223> OTHER INFORMATION: Xaa is [AzK_L1_PEG50kDa]

<400> SEQUENCE: 181

```
Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Xaa Leu Thr
        130
```

<210> SEQ ID NO 182
<211> LENGTH: 133
<212> TYPE: PRT
<213> ORGANISM: Artificial Sequence
<220> FEATURE:

<223> OTHER INFORMATION: Synthetic: IL-2_N88R_D109[AzK_L1_PEG50kDa]
<220> FEATURE:
<221> NAME/KEY: misc_feature
<222> LOCATION: (109)..(109)
<223> OTHER INFORMATION: Xaa is [AzK_L1_PEG50kDa]

<400> SEQUENCE: 182

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Xaa Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130
```

<210> SEQ ID NO 183
<211> LENGTH: 133
<212> TYPE: PRT
<213> ORGANISM: Artificial Sequence
<220> FEATURE:
<223> OTHER INFORMATION: Synthetic: IL-2_V91[AzK_L1_PEG50kDa]
<220> FEATURE:
<221> NAME/KEY: misc_feature
<222> LOCATION: (91)..(91)
<223> OTHER INFORMATION: Xaa is [AzK_L1_PEG50kDa]

<400> SEQUENCE: 183

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Xaa Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130
```

<210> SEQ ID NO 184
<211> LENGTH: 133

```
<212> TYPE: PRT
<213> ORGANISM: Artificial Sequence
<220> FEATURE:
<223> OTHER INFORMATION: Synthetic: IL-2_K9[AzK_L1_PEG30kDa]
<220> FEATURE:
<221> NAME/KEY: misc_feature
<222> LOCATION: (9)..(9)
<223> OTHER INFORMATION: Xaa is [AzK_L1_PEG30kDa]

<400> SEQUENCE: 184
```

Ala Pro Thr Ser Ser Ser Thr Lys Xaa Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
    130

```
<210> SEQ ID NO 185
<211> LENGTH: 133
<212> TYPE: PRT
<213> ORGANISM: Artificial Sequence
<220> FEATURE:
<223> OTHER INFORMATION: Synthetic: IL-2_H16[AzK_L1_PEG30kDa]
<220> FEATURE:
<221> NAME/KEY: misc_feature
<222> LOCATION: (16)..(16)
<223> OTHER INFORMATION: Xaa is [AzK_L1_PEG30kDa]

<400> SEQUENCE: 185
```

Ala Pro Thr Ser Ser Ser Thr Lys Lys Thr Gln Leu Gln Leu Glu Xaa
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
    130

```
<210> SEQ ID NO 186
<211> LENGTH: 133
<212> TYPE: PRT
<213> ORGANISM: Artificial Sequence
<220> FEATURE:
<223> OTHER INFORMATION: Synthetic: IL-2_L19[AzK_L1_PEG30kDa]
<220> FEATURE:
<221> NAME/KEY: misc_feature
<222> LOCATION: (19)..(19)
<223> OTHER INFORMATION: Xaa is [AzK_L1_PEG30kDa]

<400> SEQUENCE: 186

Ala Pro Thr Ser Ser Ser Thr Lys Lys Thr Gln Leu Gln Leu Glu His
1               5                   10                  15

Leu Leu Xaa Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 187
<211> LENGTH: 133
<212> TYPE: PRT
<213> ORGANISM: Artificial Sequence
<220> FEATURE:
<223> OTHER INFORMATION: Synthetic: IL-2_D20[AzK_L1_PEG30kDa]
<220> FEATURE:
<221> NAME/KEY: misc_feature
<222> LOCATION: (20)..(20)
<223> OTHER INFORMATION: Xaa is [AzK_L1_PEG30kDa]

<400> SEQUENCE: 187

Ala Pro Thr Ser Ser Ser Thr Lys Lys Thr Gln Leu Gln Leu Glu His
1               5                   10                  15

Leu Leu Leu Xaa Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125
```

Ile Ser Thr Leu Thr
            130

<210> SEQ ID NO 188
<211> LENGTH: 133
<212> TYPE: PRT
<213> ORGANISM: Artificial Sequence
<220> FEATURE:
<223> OTHER INFORMATION: Synthetic: IL-2_M23[AzK_L1_PEG30kDa]
<220> FEATURE:
<221> NAME/KEY: misc_feature
<222> LOCATION: (23)..(23)
<223> OTHER INFORMATION: Xaa is [AzK_L1_PEG30kDa]

<400> SEQUENCE: 188

Ala Pro Thr Ser Ser Ser Thr Lys Lys Thr Gln Leu Gln Leu Glu His
1               5                   10                  15

Leu Leu Leu Asp Leu Gln Xaa Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
            130

<210> SEQ ID NO 189
<211> LENGTH: 133
<212> TYPE: PRT
<213> ORGANISM: Artificial Sequence
<220> FEATURE:
<223> OTHER INFORMATION: Synthetic: IL-2_N26[AzK_L1_PEG30kDa]
<220> FEATURE:
<221> NAME/KEY: misc_feature
<222> LOCATION: (26)..(26)
<223> OTHER INFORMATION: Xaa is [AzK_L1_PEG30kDa]

<400> SEQUENCE: 189

Ala Pro Thr Ser Ser Ser Thr Lys Lys Thr Gln Leu Gln Leu Glu His
1               5                   10                  15

Leu Leu Leu Asp Leu Gln Met Ile Leu Xaa Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

```
Thr Ile Val Glu Phe Leu Asn Arg Trp Ile Thr Phe Ser Gln Ser Ile
            115                 120                 125

Ile Ser Thr Leu Thr
        130

<210> SEQ ID NO 190
<211> LENGTH: 133
<212> TYPE: PRT
<213> ORGANISM: Artificial Sequence
<220> FEATURE:
<223> OTHER INFORMATION: Synthetic: IL-2_N88[AzK_L1_PEG30kDa]
<220> FEATURE:
<221> NAME/KEY: misc_feature
<222> LOCATION: (88)..(88)
<223> OTHER INFORMATION: Xaa is [AzK_L1_PEG30kDa]

<400> SEQUENCE: 190

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Xaa Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 191
<211> LENGTH: 133
<212> TYPE: PRT
<213> ORGANISM: Artificial Sequence
<220> FEATURE:
<223> OTHER INFORMATION: Synthetic: IL-2_E100[AzK_L1_PEG30kDa]
<220> FEATURE:
<221> NAME/KEY: misc_feature
<222> LOCATION: (100)..(100)
<223> OTHER INFORMATION: Xaa is [AzK_L1_PEG30kDa]

<400> SEQUENCE: 191

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95
```

```
Lys Gly Ser Xaa Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 192
<211> LENGTH: 133
<212> TYPE: PRT
<213> ORGANISM: Artificial Sequence
<220> FEATURE:
<223> OTHER INFORMATION: Synthetic: IL-2_N119[AzK_L1_PEG30kDa]
<220> FEATURE:
<221> NAME/KEY: misc_feature
<222> LOCATION: (119)..(119)
<223> OTHER INFORMATION: Xaa is [AzK_L1_PEG30kDa]

<400> SEQUENCE: 192

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Xaa Arg Trp Ile Thr Phe Ser Gln Ser Ile
        115                 120                 125

Ile Ser Thr Leu Thr
        130

<210> SEQ ID NO 193
<211> LENGTH: 133
<212> TYPE: PRT
<213> ORGANISM: Artificial Sequence
<220> FEATURE:
<223> OTHER INFORMATION: Synthetic: IL-2_T123[AzK_L1_PEG30kDa]
<220> FEATURE:
<221> NAME/KEY: misc_feature
<222> LOCATION: (123)..(123)
<223> OTHER INFORMATION: Xaa is [AzK_L1_PEG30kDa]

<400> SEQUENCE: 193

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Xaa Phe Ser Gln Ser Ile
        115                 120                 125

Ile Ser Thr Leu Thr
        130

<210> SEQ ID NO 194
<211> LENGTH: 133
<212> TYPE: PRT
<213> ORGANISM: Artificial Sequence
<220> FEATURE:
<223> OTHER INFORMATION: Synthetic: IL-2_Q126[AzK_L1_PEG30kDa]
<220> FEATURE:
<221> NAME/KEY: misc_feature
<222> LOCATION: (126)..(126)
<223> OTHER INFORMATION: Xaa is [AzK_L1_PEG30kDa]

<400> SEQUENCE: 194

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Xaa Ser Ile
        115                 120                 125

Ile Ser Thr Leu Thr
        130

<210> SEQ ID NO 195
<211> LENGTH: 133
<212> TYPE: PRT
<213> ORGANISM: Artificial Sequence
<220> FEATURE:
<223> OTHER INFORMATION: Synthetic: IL-2_S127[AzK_L1_PEG30kDa]
<220> FEATURE:
<221> NAME/KEY: misc_feature
<222> LOCATION: (127)..(127)
<223> OTHER INFORMATION: Xaa is [AzK_L1_PEG30kDa]

<400> SEQUENCE: 195

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60
```

```
Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Xaa Ile
        115                 120                 125

Ile Ser Thr Leu Thr
        130

<210> SEQ ID NO 196
<211> LENGTH: 133
<212> TYPE: PRT
<213> ORGANISM: Artificial Sequence
<220> FEATURE:
<223> OTHER INFORMATION: Synthetic: IL-2_T131[AzK_L1_PEG30kDa]
<220> FEATURE:
<221> NAME/KEY: misc_feature
<222> LOCATION: (131)..(131)
<223> OTHER INFORMATION: Xaa is [AzK_L1_PEG30kDa]

<400> SEQUENCE: 196

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45

Lys Ala Thr Glu Leu Lys His Leu Gln Cys Leu Glu Glu Glu Leu Lys
     50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Val Ile Val Leu Glu Leu
                 85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Xaa Leu Thr
        130

<210> SEQ ID NO 197
<211> LENGTH: 133
<212> TYPE: PRT
<213> ORGANISM: Artificial Sequence
<220> FEATURE:
<223> OTHER INFORMATION: Synthetic: IL-2_N88R_D109[AzK_L1_PEG30kDa]
<220> FEATURE:
<221> NAME/KEY: misc_feature
<222> LOCATION: (109)..(109)
<223> OTHER INFORMATION: Xaa is [AzK_L1_PEG30kDa]

<400> SEQUENCE: 197

Ala Pro Thr Ser Ser Ser Thr Lys Lys Thr Gln Leu Gln Leu Glu His
 1               5                  10                  15

Leu Leu Leu Asp Leu Gln Met Ile Leu Asn Gly Ile Asn Asn Tyr Lys
             20                  25                  30

Asn Pro Lys Leu Thr Arg Met Leu Thr Phe Lys Phe Tyr Met Pro Lys
         35                  40                  45
```

Lys Ala Thr Glu Leu Lys His Leu Gln Cys Leu Glu Glu Leu Lys
        50                  55                  60

Pro Leu Glu Glu Val Leu Asn Leu Ala Gln Ser Lys Asn Phe His Leu
 65                  70                  75                  80

Arg Pro Arg Asp Leu Ile Ser Arg Ile Val Lys Ile Val Leu Glu Leu
                85                  90                  95

Lys Gly Ser Glu Thr Thr Phe Met Cys Glu Tyr Ala Xaa Glu Thr Ala
            100                 105                 110

Thr Ile Val Glu Phe Leu Asn Arg Trp Ile Thr Phe Ser Gln Ser Ile
                115                 120                 125

Ile Ser Thr Leu Thr
        130

<210> SEQ ID NO 198
<211> LENGTH: 133
<212> TYPE: PRT
<213> ORGANISM: Artificial Sequence
<220> FEATURE:
<223> OTHER INFORMATION: Synthetic: IL-2_V91[AzK_L1_PEG30kDa]
<220> FEATURE:
<221> NAME/KEY: misc_feature
<222> LOCATION: (91)..(91)
<223> OTHER INFORMATION: Xaa is [AzK_L1_PEG30kDa]

<400> SEQUENCE: 198

Ala Pro Thr Ser Ser Thr Lys Lys Thr Gln Leu Gln Leu Glu His
  1               5                  10                  15

Leu Leu Leu Asp Leu Gln Met Ile Leu Asn Gly Ile Asn Asn Tyr Lys
                 20                  25                  30

Asn Pro Lys Leu Thr Arg Met Leu Thr Phe Lys Phe Tyr Met Pro Lys
             35                  40                  45

Lys Ala Thr Glu Leu Lys His Leu Gln Cys Leu Glu Glu Leu Lys
        50                  55                  60

Pro Leu Glu Glu Val Leu Asn Leu Ala Gln Ser Lys Asn Phe His Leu
 65                  70                  75                  80

Arg Pro Arg Asp Leu Ile Ser Asn Ile Asn Xaa Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
                115                 120                 125

Ile Ser Thr Leu Thr
        130

<210> SEQ ID NO 199
<211> LENGTH: 132
<212> TYPE: PRT
<213> ORGANISM: Artificial Sequence
<220> FEATURE:
<223> OTHER INFORMATION: Synthetic: IL-2_K8[AzK_PEG]
<220> FEATURE:
<221> NAME/KEY: misc_feature
<222> LOCATION: (8)..(8)
<223> OTHER INFORMATION: Xaa is [AzK_PEG]

<400> SEQUENCE: 199

Pro Thr Ser Ser Ser Thr Lys Xaa Thr Gln Leu Gln Leu Glu His Leu
  1               5                  10                  15

Leu Leu Asp Leu Gln Met Ile Leu Asn Gly Ile Asn Asn Tyr Lys Asn
                 20                  25                  30

```
Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
    130

<210> SEQ ID NO 200
<211> LENGTH: 132
<212> TYPE: PRT
<213> ORGANISM: Artificial Sequence
<220> FEATURE:
<223> OTHER INFORMATION: Synthetic: IL-2_H15[AzK_PEG]
<220> FEATURE:
<221> NAME/KEY: misc_feature
<222> LOCATION: (15)..(15)
<223> OTHER INFORMATION: Xaa is [AzK_PEG]

<400> SEQUENCE: 200

Pro Thr Ser Ser Ser Thr Lys Lys Thr Gln Leu Gln Leu Glu Xaa Leu
 1               5                  10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
            35                  40                  45

Ala Thr Glu Leu Lys His Leu Gln Cys Leu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
    130

<210> SEQ ID NO 201
<211> LENGTH: 132
<212> TYPE: PRT
<213> ORGANISM: Artificial Sequence
<220> FEATURE:
<223> OTHER INFORMATION: Synthetic: IL-2_L18[AzK_PEG]
<220> FEATURE:
<221> NAME/KEY: misc_feature
<222> LOCATION: (18)..(18)
<223> OTHER INFORMATION: Xaa is [AzK_PEG]

<400> SEQUENCE: 201

Pro Thr Ser Ser Ser Thr Lys Lys Thr Gln Leu Gln Leu Glu His Leu
 1               5                  10                  15
```

```
Leu Xaa Asp Leu Gln Met Ile Leu Asn Gly Ile Asn Asn Tyr Lys Asn
     20                  25                  30

Pro Lys Leu Thr Arg Met Leu Thr Phe Lys Phe Tyr Met Pro Lys Lys
         35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130
```

<210> SEQ ID NO 202
<211> LENGTH: 132
<212> TYPE: PRT
<213> ORGANISM: Artificial Sequence
<220> FEATURE:
<223> OTHER INFORMATION: Synthetic: IL-2_D19[AzK_PEG]
<220> FEATURE:
<221> NAME/KEY: misc_feature
<222> LOCATION: (19)..(19)
<223> OTHER INFORMATION: Xaa is [AzK_PEG]

<400> SEQUENCE: 202

```
Pro Thr Ser Ser Thr Lys Lys Thr Gln Leu Gln Leu Glu His Leu
 1               5                  10                  15

Leu Leu Xaa Leu Gln Met Ile Leu Asn Gly Ile Asn Asn Tyr Lys Asn
         20                  25                  30

Pro Lys Leu Thr Arg Met Leu Thr Phe Lys Phe Tyr Met Pro Lys Lys
         35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                 85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130
```

<210> SEQ ID NO 203
<211> LENGTH: 132
<212> TYPE: PRT
<213> ORGANISM: Artificial Sequence
<220> FEATURE:
<223> OTHER INFORMATION: Synthetic: IL-2_M22[AzK_PEG]
<220> FEATURE:
<221> NAME/KEY: misc_feature
<222> LOCATION: (22)..(22)
<223> OTHER INFORMATION: Xaa is [AzK_PEG]

<400> SEQUENCE: 203

```
Pro Thr Ser Ser Ser Thr Lys Lys Thr Gln Leu Gln Leu Glu His Leu
1               5                   10                  15

Leu Leu Asp Leu Gln Xaa Ile Leu Asn Gly Ile Asn Asn Tyr Lys Asn
            20              25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50              55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 204
<211> LENGTH: 132
<212> TYPE: PRT
<213> ORGANISM: Artificial Sequence
<220> FEATURE:
<223> OTHER INFORMATION: Synthetic: IL-2_N25[AzK_PEG]
<220> FEATURE:
<221> NAME/KEY: misc_feature
<222> LOCATION: (25)..(25)
<223> OTHER INFORMATION: Xaa is [AzK_PEG]

<400> SEQUENCE: 204

Pro Thr Ser Ser Ser Thr Lys Lys Thr Gln Leu Gln Leu Glu His Leu
1               5                   10                  15

Leu Leu Asp Leu Gln Met Ile Leu Xaa Gly Ile Asn Asn Tyr Lys Asn
            20              25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50              55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 205
<211> LENGTH: 132
<212> TYPE: PRT
<213> ORGANISM: Artificial Sequence
<220> FEATURE:
<223> OTHER INFORMATION: Synthetic: IL-2_N87[AzK_PEG]
<220> FEATURE:
<221> NAME/KEY: misc_feature
<222> LOCATION: (87)..(87)
<223> OTHER INFORMATION: Xaa is [AzK_PEG]
```

<400> SEQUENCE: 205

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Xaa Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 206
<211> LENGTH: 132
<212> TYPE: PRT
<213> ORGANISM: Artificial Sequence
<220> FEATURE:
<223> OTHER INFORMATION: Synthetic: IL-2_E99[AzK_PEG]
<220> FEATURE:
<221> NAME/KEY: misc_feature
<222> LOCATION: (99)..(99)
<223> OTHER INFORMATION: Xaa is [AzK_PEG]

<400> SEQUENCE: 206

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Xaa Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 207
<211> LENGTH: 132
<212> TYPE: PRT
<213> ORGANISM: Artificial Sequence
<220> FEATURE:
<223> OTHER INFORMATION: Synthetic: IL-2_N118[AzK_PEG]
<220> FEATURE:

<221> NAME/KEY: misc_feature
<222> LOCATION: (118)..(118)
<223> OTHER INFORMATION: Xaa is [AzK_PEG]

<400> SEQUENCE: 207

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Xaa Arg Trp Ile Thr Phe Ser Gln Ser Ile Ile
            115                 120                 125

Ser Thr Leu Thr
        130

<210> SEQ ID NO 208
<211> LENGTH: 132
<212> TYPE: PRT
<213> ORGANISM: Artificial Sequence
<220> FEATURE:
<223> OTHER INFORMATION: Synthetic: IL-2_T122[AzK_PEG]
<220> FEATURE:
<221> NAME/KEY: misc_feature
<222> LOCATION: (122)..(122)
<223> OTHER INFORMATION: Xaa is [AzK_PEG]

<400> SEQUENCE: 208

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Xaa Phe Ser Gln Ser Ile Ile
            115                 120                 125

Ser Thr Leu Thr
        130

<210> SEQ ID NO 209
<211> LENGTH: 132
<212> TYPE: PRT
<213> ORGANISM: Artificial Sequence

```
<220> FEATURE:
<223> OTHER INFORMATION: Synthetic: IL-2_Q125[AzK_PEG]
<220> FEATURE:
<221> NAME/KEY: misc_feature
<222> LOCATION: (125)..(125)
<223> OTHER INFORMATION: Xaa is [AzK_PEG]

<400> SEQUENCE: 209
```

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Xaa Ser Ile Ile
        115                 120                 125

Ser Thr Leu Thr
        130

```
<210> SEQ ID NO 210
<211> LENGTH: 132
<212> TYPE: PRT
<213> ORGANISM: Artificial Sequence
<220> FEATURE:
<223> OTHER INFORMATION: Synthetic: IL-2_S126[AzK_PEG]
<220> FEATURE:
<221> NAME/KEY: misc_feature
<222> LOCATION: (126)..(126)
<223> OTHER INFORMATION: Xaa is [AzK_PEG]

<400> SEQUENCE: 210
```

Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Xaa Ile Ile
        115                 120                 125

Ser Thr Leu Thr
        130

```
<210> SEQ ID NO 211
```

```
<211> LENGTH: 132
<212> TYPE: PRT
<213> ORGANISM: Artificial Sequence
<220> FEATURE:
<223> OTHER INFORMATION: Synthetic: IL-2_T130[AzK_PEG]
<220> FEATURE:
<221> NAME/KEY: misc_feature
<222> LOCATION: (130)..(130)
<223> OTHER INFORMATION: Xaa is [AzK_PEG]

<400> SEQUENCE: 211

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Xaa Leu Thr
    130

<210> SEQ ID NO 212
<211> LENGTH: 132
<212> TYPE: PRT
<213> ORGANISM: Artificial Sequence
<220> FEATURE:
<223> OTHER INFORMATION: Synthetic: IL-2_N87R_D109[AzK_PEG]-1
<220> FEATURE:
<221> NAME/KEY: misc_feature
<222> LOCATION: (108)..(108)
<223> OTHER INFORMATION: Xaa is [AzK_PEG]

<400> SEQUENCE: 212

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Arg Ile Asn Val Ile Val Leu Glu Leu Lys
                85                  90                  95

Gly Ser Glu Thr Thr Phe Met Cys Glu Tyr Ala Xaa Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 213
<211> LENGTH: 132
<212> TYPE: PRT
<213> ORGANISM: Artificial Sequence
<220> FEATURE:
<223> OTHER INFORMATION: Synthetic: IL-2_V90[AzK_PEG]
<220> FEATURE:
<221> NAME/KEY: misc_feature
<222> LOCATION: (90)..(90)
<223> OTHER INFORMATION: Xaa is [AzK_PEG]

<400> SEQUENCE: 213

```
Pro Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Xaa Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130
```

<210> SEQ ID NO 214
<211> LENGTH: 132
<212> TYPE: PRT
<213> ORGANISM: Artificial Sequence
<220> FEATURE:
<223> OTHER INFORMATION: Synthetic: IL-2_K8[AzK_PEG50kDa]
<220> FEATURE:
<221> NAME/KEY: misc_feature
<222> LOCATION: (8)..(8)
<223> OTHER INFORMATION: Xaa is [AzK_PEG50kDa]

<400> SEQUENCE: 214

```
Pro Thr Ser Ser Thr Lys Xaa Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125
```

```
Ser Thr Leu Thr
    130

<210> SEQ ID NO 215
<211> LENGTH: 132
<212> TYPE: PRT
<213> ORGANISM: Artificial Sequence
<220> FEATURE:
<223> OTHER INFORMATION: Synthetic: IL-2_H15[AzK_PEG50kDa]
<220> FEATURE:
<221> NAME/KEY: misc_feature
<222> LOCATION: (15)..(15)
<223> OTHER INFORMATION: Xaa is [AzK_PEG50kDa]

<400> SEQUENCE: 215

Pro Thr Ser Ser Ser Thr Lys Lys Thr Gln Leu Gln Leu Glu Xaa Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 216
<211> LENGTH: 132
<212> TYPE: PRT
<213> ORGANISM: Artificial Sequence
<220> FEATURE:
<223> OTHER INFORMATION: Synthetic: IL-2_L18[AzK_PEG50kDa]
<220> FEATURE:
<221> NAME/KEY: misc_feature
<222> LOCATION: (18)..(18)
<223> OTHER INFORMATION: Xaa is [AzK_PEG50kDa]

<400> SEQUENCE: 216

Pro Thr Ser Ser Ser Thr Lys Lys Thr Gln Leu Gln Leu Glu His Leu
1               5                   10                  15

Leu Xaa Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110
```

Ile Val Glu Phe Leu Asn Arg Trp Ile Thr Phe Ser Gln Ser Ile Ile
            115                 120                 125

Ser Thr Leu Thr
        130

<210> SEQ ID NO 217
<211> LENGTH: 132
<212> TYPE: PRT
<213> ORGANISM: Artificial Sequence
<220> FEATURE:
<223> OTHER INFORMATION: Synthetic: IL-2_D19[AzK_PEG50kDa]
<220> FEATURE:
<221> NAME/KEY: misc_feature
<222> LOCATION: (19)..(19)
<223> OTHER INFORMATION: Xaa is [AzK_PEG50kDa]

<400> SEQUENCE: 217

Pro Thr Ser Ser Ser Thr Lys Lys Thr Gln Leu Gln Leu Glu His Leu
1               5                   10                  15

Leu Leu Xaa Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 218
<211> LENGTH: 132
<212> TYPE: PRT
<213> ORGANISM: Artificial Sequence
<220> FEATURE:
<223> OTHER INFORMATION: Synthetic: IL-2_M22[AzK_PEG50kDa]
<220> FEATURE:
<221> NAME/KEY: misc_feature
<222> LOCATION: (22)..(22)
<223> OTHER INFORMATION: Xaa is [AzK_PEG50kDa]

<400> SEQUENCE: 218

Pro Thr Ser Ser Ser Thr Lys Lys Thr Gln Leu Gln Leu Glu His Leu
1               5                   10                  15

Leu Leu Asp Leu Gln Xaa Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 219
<211> LENGTH: 132
<212> TYPE: PRT
<213> ORGANISM: Artificial Sequence
<220> FEATURE:
<223> OTHER INFORMATION: Synthetic: IL-2_N25[AzK_PEG50kDa]
<220> FEATURE:
<221> NAME/KEY: misc_feature
<222> LOCATION: (25)..(25)
<223> OTHER INFORMATION: Xaa is [AzK_PEG50kDa]

<400> SEQUENCE: 219

Pro Thr Ser Ser Ser Thr Lys Lys Thr Gln Leu Gln Leu Glu His Leu
1               5                   10                  15

Leu Leu Asp Leu Gln Met Ile Leu Xaa Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 220
<211> LENGTH: 132
<212> TYPE: PRT
<213> ORGANISM: Artificial Sequence
<220> FEATURE:
<223> OTHER INFORMATION: Synthetic: IL-2_N87[AzK_PEG50kDa]
<220> FEATURE:
<221> NAME/KEY: misc_feature
<222> LOCATION: (87)..(87)
<223> OTHER INFORMATION: Xaa is [AzK_PEG50kDa]

<400> SEQUENCE: 220

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

```
Pro Arg Asp Leu Ile Ser Xaa Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 221
<211> LENGTH: 132
<212> TYPE: PRT
<213> ORGANISM: Artificial Sequence
<220> FEATURE:
<223> OTHER INFORMATION: Synthetic: IL-2_E99[AzK_PEG50kDa]-1
<220> FEATURE:
<221> NAME/KEY: misc_feature
<222> LOCATION: (99)..(99)
<223> OTHER INFORMATION: Xaa is [AzK_PEG50kDa]

<400> SEQUENCE: 221

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Xaa Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 222
<211> LENGTH: 132
<212> TYPE: PRT
<213> ORGANISM: Artificial Sequence
<220> FEATURE:
<223> OTHER INFORMATION: Synthetic: IL-2_N118[AzK_PEG50kDa]
<220> FEATURE:
<221> NAME/KEY: misc_feature
<222> LOCATION: (118)..(118)
<223> OTHER INFORMATION: Xaa is [AzK_PEG50kDa]

<400> SEQUENCE: 222

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60
```

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Xaa Arg Trp Ile Thr Phe Ser Gln Ser Ile Ile
        115                 120                 125

Ser Thr Leu Thr
    130

<210> SEQ ID NO 223
<211> LENGTH: 132
<212> TYPE: PRT
<213> ORGANISM: Artificial Sequence
<220> FEATURE:
<223> OTHER INFORMATION: Synthetic: IL-2_T122[AzK_PEG50kDa]
<220> FEATURE:
<221> NAME/KEY: misc_feature
<222> LOCATION: (122)..(122)
<223> OTHER INFORMATION: Xaa is [AzK_PEG50kDa]

<400> SEQUENCE: 223

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Xaa Phe Ser Gln Ser Ile Ile
        115                 120                 125

Ser Thr Leu Thr
    130

<210> SEQ ID NO 224
<211> LENGTH: 132
<212> TYPE: PRT
<213> ORGANISM: Artificial Sequence
<220> FEATURE:
<223> OTHER INFORMATION: Synthetic: IL-2_Q125[AzK_PEG50kDa]
<220> FEATURE:
<221> NAME/KEY: misc_feature
<222> LOCATION: (125)..(125)
<223> OTHER INFORMATION: Xaa is [AzK_PEG50kDa]

<400> SEQUENCE: 224

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

```
Ala Thr Glu Leu Lys His Leu Gln Cys Leu Glu Glu Glu Leu Lys Pro
        50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Xaa Ser Ile Ile
        115                 120                 125

Ser Thr Leu Thr
        130

<210> SEQ ID NO 225
<211> LENGTH: 132
<212> TYPE: PRT
<213> ORGANISM: Artificial Sequence
<220> FEATURE:
<223> OTHER INFORMATION: Synthetic: IL-2_S126[AzK_PEG50kDa]
<220> FEATURE:
<221> NAME/KEY: misc_feature
<222> LOCATION: (126)..(126)
<223> OTHER INFORMATION: Xaa is [AzK_PEG50kDa]

<400> SEQUENCE: 225

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Xaa Ile Ile
        115                 120                 125

Ser Thr Leu Thr
        130

<210> SEQ ID NO 226
<211> LENGTH: 132
<212> TYPE: PRT
<213> ORGANISM: Artificial Sequence
<220> FEATURE:
<223> OTHER INFORMATION: Synthetic: IL-2_T130[AzK_PEG50kDa]
<220> FEATURE:
<221> NAME/KEY: misc_feature
<222> LOCATION: (130)..(130)
<223> OTHER INFORMATION: Xaa is [AzK_PEG50kDa]

<400> SEQUENCE: 226

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30
```

```
Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                    85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Xaa Leu Thr
        130

<210> SEQ ID NO 227
<211> LENGTH: 132
<212> TYPE: PRT
<213> ORGANISM: Artificial Sequence
<220> FEATURE:
<223> OTHER INFORMATION: Synthetic: IL-2_N87R_D108[AzK_PEG50kDa]
<220> FEATURE:
<221> NAME/KEY: misc_feature
<222> LOCATION: (108)..(108)
<223> OTHER INFORMATION: Xaa is [AzK_PEG50kDa]

<400> SEQUENCE: 227

Pro Thr Ser Ser Ser Thr Lys Lys Thr Gln Leu Gln Leu Glu His Leu
 1               5                  10                  15

Leu Leu Asp Leu Gln Met Ile Leu Asn Gly Ile Asn Asn Tyr Lys Asn
                20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Arg Ile Asn Val Ile Val Leu Glu Leu Lys
                    85                  90                  95

Gly Ser Glu Thr Thr Phe Met Cys Glu Tyr Ala Xaa Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
        130

<210> SEQ ID NO 228
<211> LENGTH: 132
<212> TYPE: PRT
<213> ORGANISM: Artificial Sequence
<220> FEATURE:
<223> OTHER INFORMATION: Synthetic: IL-2_V90[AzK_PEG50kDa]
<220> FEATURE:
<221> NAME/KEY: misc_feature
<222> LOCATION: (90)..(90)
<223> OTHER INFORMATION: Xaa is [AzK_PEG50kDa]

<400> SEQUENCE: 228

Pro Thr Ser Ser Ser Thr Lys Lys Thr Gln Leu Gln Leu Glu His Leu
 1               5                  10                  15
```

```
Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Xaa Ile Val Leu Glu Leu Lys
                85                  90                  95

Gly Ser Glu Thr Thr Phe Met Cys Glu Tyr Ala Asp Glu Thr Ala Thr
             100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 229
<211> LENGTH: 132
<212> TYPE: PRT
<213> ORGANISM: Artificial Sequence
<220> FEATURE:
<223> OTHER INFORMATION: Synthetic: IL-2_K8[AzK_PEG30kDa]
<220> FEATURE:
<221> NAME/KEY: misc_feature
<222> LOCATION: (8)..(8)
<223> OTHER INFORMATION: Xaa is [AzK_PEG30kDa]

<400> SEQUENCE: 229

Pro Thr Ser Ser Ser Thr Lys Xaa Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
 50                  55                  60

Leu Glu Glu Val Leu Asn Leu Ala Gln Ser Lys Asn Phe His Leu Arg
 65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
             100                 105                 110

Ile Val Glu Phe Leu Asn Arg Trp Ile Thr Phe Ser Gln Ser Ile Ile
            115                 120                 125

Ser Thr Leu Thr
    130

<210> SEQ ID NO 230
<211> LENGTH: 132
<212> TYPE: PRT
<213> ORGANISM: Artificial Sequence
<220> FEATURE:
<223> OTHER INFORMATION: Synthetic: IL-2_H15[AzK_PEG30kDa]
<220> FEATURE:
<221> NAME/KEY: misc_feature
<222> LOCATION: (15)..(15)
<223> OTHER INFORMATION: Xaa is [AzK_PEG30kDa]

<400> SEQUENCE: 230
```

```
Pro Thr Ser Ser Ser Thr Lys Lys Thr Gln Leu Gln Leu Glu Xaa Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 231
<211> LENGTH: 132
<212> TYPE: PRT
<213> ORGANISM: Artificial Sequence
<220> FEATURE:
<223> OTHER INFORMATION: Synthetic: IL-2_L18[AzK_PEG30kDa]
<220> FEATURE:
<221> NAME/KEY: misc_feature
<222> LOCATION: (18)..(18)
<223> OTHER INFORMATION: Xaa is [AzK_PEG30kDa]

<400> SEQUENCE: 231

Pro Thr Ser Ser Ser Thr Lys Lys Thr Gln Leu Gln Leu Glu His Leu
1               5                   10                  15

Leu Xaa Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 232
<211> LENGTH: 132
<212> TYPE: PRT
<213> ORGANISM: Artificial Sequence
<220> FEATURE:
<223> OTHER INFORMATION: Synthetic: IL-2_D19[AzK_PEG30kDa]
<220> FEATURE:
<221> NAME/KEY: misc_feature
<222> LOCATION: (19)..(19)
```

<223> OTHER INFORMATION: Xaa is [AzK_PEG30kDa]

<400> SEQUENCE: 232

Pro Thr Ser Ser Ser Thr Lys Lys Thr Gln Leu Gln Leu Glu His Leu
1               5                   10                  15

Leu Leu Xaa Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
    130

<210> SEQ ID NO 233
<211> LENGTH: 132
<212> TYPE: PRT
<213> ORGANISM: Artificial Sequence
<220> FEATURE:
<223> OTHER INFORMATION: Synthetic: IL-2_M22[AzK_PEG30kDa]
<220> FEATURE:
<221> NAME/KEY: misc_feature
<222> LOCATION: (22)..(22)
<223> OTHER INFORMATION: Xaa is [AzK_PEG30kDa]

<400> SEQUENCE: 233

Pro Thr Ser Ser Ser Thr Lys Lys Thr Gln Leu Gln Leu Glu His Leu
1               5                   10                  15

Leu Leu Asp Leu Gln Xaa Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
                115                 120                 125

Ser Thr Leu Thr
    130

<210> SEQ ID NO 234
<211> LENGTH: 132
<212> TYPE: PRT
<213> ORGANISM: Artificial Sequence
<220> FEATURE:
<223> OTHER INFORMATION: Synthetic: IL-2_N25[AzK_PEG30kDa]

```
<220> FEATURE:
<221> NAME/KEY: misc_feature
<222> LOCATION: (25)..(25)
<223> OTHER INFORMATION: Xaa is [AzK_PEG30kDa]

<400> SEQUENCE: 234
```

Pro Thr Ser Ser Ser Thr Lys Lys Thr Gln Leu Gln Leu Glu His Leu
1               5                   10                  15

Leu Leu Asp Leu Gln Met Ile Leu Xaa Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Leu Arg
65              70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

```
<210> SEQ ID NO 235
<211> LENGTH: 132
<212> TYPE: PRT
<213> ORGANISM: Artificial Sequence
<220> FEATURE:
<223> OTHER INFORMATION: Synthetic: IL-2_N87[AzK_PEG30kDa]
<220> FEATURE:
<221> NAME/KEY: misc_feature
<222> LOCATION: (87)..(87)
<223> OTHER INFORMATION: Xaa is [AzK_PEG30kDa]

<400> SEQUENCE: 235
```

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
50                  55                  60

Leu Glu Glu Val Leu Asn Leu Ala Gln Ser Lys Asn Phe His Leu Arg
65              70                  75                  80

Pro Arg Asp Leu Ile Ser Xaa Ile Asn Val Ile Val Leu Glu Leu Lys
                85                  90                  95

Gly Ser Glu Thr Thr Phe Met Cys Glu Tyr Ala Asp Glu Thr Ala Thr
                100                 105                 110

Ile Val Glu Phe Leu Asn Arg Trp Ile Thr Phe Ser Gln Ser Ile Ile
            115                 120                 125

Ser Thr Leu Thr
        130

```
<210> SEQ ID NO 236
<211> LENGTH: 132
<212> TYPE: PRT
```

```
<213> ORGANISM: Artificial Sequence
<220> FEATURE:
<223> OTHER INFORMATION: Synthetic: IL-2_E99[AzK_PEG30kDa]
<220> FEATURE:
<221> NAME/KEY: misc_feature
<222> LOCATION: (99)..(99)
<223> OTHER INFORMATION: Xaa is [AzK_PEG30kDa]

<400> SEQUENCE: 236

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Xaa Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130

<210> SEQ ID NO 237
<211> LENGTH: 132
<212> TYPE: PRT
<213> ORGANISM: Artificial Sequence
<220> FEATURE:
<223> OTHER INFORMATION: Synthetic: IL-2_N118[AzK_PEG30kDa]
<220> FEATURE:
<221> NAME/KEY: misc_feature
<222> LOCATION: (118)..(118)
<223> OTHER INFORMATION: Xaa is [AzK_PEG30kDa]

<400> SEQUENCE: 237

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Xaa Arg Trp Ile Thr Phe Ser Gln Ser Ile Ile
            115                 120                 125

Ser Thr Leu Thr
        130
```

-continued

```
<210> SEQ ID NO 238
<211> LENGTH: 132
<212> TYPE: PRT
<213> ORGANISM: Artificial Sequence
<220> FEATURE:
<223> OTHER INFORMATION: Synthetic: IL-2_T122[AzK_PEG30kDa]
<220> FEATURE:
<221> NAME/KEY: misc_feature
<222> LOCATION: (122)..(122)
<223> OTHER INFORMATION: Xaa is [AzK_PEG30kDa]

<400> SEQUENCE: 238

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Xaa Phe Ser Gln Ser Ile Ile
        115                 120                 125

Ser Thr Leu Thr
    130

<210> SEQ ID NO 239
<211> LENGTH: 132
<212> TYPE: PRT
<213> ORGANISM: Artificial Sequence
<220> FEATURE:
<223> OTHER INFORMATION: Synthetic: IL-2_Q125[AzK_PEG30kDa]
<220> FEATURE:
<221> NAME/KEY: misc_feature
<222> LOCATION: (125)..(125)
<223> OTHER INFORMATION: Xaa is [AzK_PEG30kDa]

<400> SEQUENCE: 239

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Xaa Ser Ile Ile
        115                 120                 125

Ser Thr Leu Thr
```

<210> SEQ ID NO 240
<211> LENGTH: 132
<212> TYPE: PRT
<213> ORGANISM: Artificial Sequence
<220> FEATURE:
<223> OTHER INFORMATION: Synthetic: IL-2_S126[AzK_PEG30kDa]
<220> FEATURE:
<221> NAME/KEY: misc_feature
<222> LOCATION: (126)..(126)
<223> OTHER INFORMATION: Xaa is [AzK_PEG30kDa]

<400> SEQUENCE: 240

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Xaa Ile Ile
        115                 120                 125

Ser Thr Leu Thr
    130

<210> SEQ ID NO 241
<211> LENGTH: 132
<212> TYPE: PRT
<213> ORGANISM: Artificial Sequence
<220> FEATURE:
<223> OTHER INFORMATION: Synthetic: IL-2_T130[AzK_PEG30kDa]
<220> FEATURE:
<221> NAME/KEY: misc_feature
<222> LOCATION: (130)..(130)
<223> OTHER INFORMATION: Xaa is [AzK_PEG30kDa]

<400> SEQUENCE: 241

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile

-continued

```
                115                 120                 125
Ser Xaa Leu Thr
    130

<210> SEQ ID NO 242
<211> LENGTH: 132
<212> TYPE: PRT
<213> ORGANISM: Artificial Sequence
<220> FEATURE:
<223> OTHER INFORMATION: Synthetic: IL-2_N87R_D108[AzK_PEG30kDa]
<220> FEATURE:
<221> NAME/KEY: misc_feature
<222> LOCATION: (108)..(108)
<223> OTHER INFORMATION: Xaa is [AzK_PEG30kDa]

<400> SEQUENCE: 242

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Arg Ile Asn Val Ile Val Leu Glu Leu Lys
                85                  90                  95

Gly Ser Glu Thr Thr Phe Met Cys Glu Tyr Ala Xaa Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
    130

<210> SEQ ID NO 243
<211> LENGTH: 132
<212> TYPE: PRT
<213> ORGANISM: Artificial Sequence
<220> FEATURE:
<223> OTHER INFORMATION: Synthetic: IL-2_V90[AzK_PEG30kDa]
<220> FEATURE:
<221> NAME/KEY: misc_feature
<222> LOCATION: (90)..(90)
<223> OTHER INFORMATION: Xaa is [AzK_PEG30kDa]

<400> SEQUENCE: 243

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Xaa Ile Val Leu Glu Leu Lys
                85                  90                  95

Gly Ser Glu Thr Thr Phe Met Cys Glu Tyr Ala Asp Glu Thr Ala Thr
```

```
                100             105             110
Ile Val Glu Phe Leu Asn Arg Trp Ile Thr Phe Ser Gln Ser Ile Ile
            115             120             125
Ser Thr Leu Thr
    130

<210> SEQ ID NO 244
<211> LENGTH: 133
<212> TYPE: PRT
<213> ORGANISM: Artificial Sequence
<220> FEATURE:
<223> OTHER INFORMATION: Synthetic: IL-2_L12[AzK_PEG30kDa]
<220> FEATURE:
<221> NAME/KEY: misc_feature
<222> LOCATION: (12)..(12)
<223> OTHER INFORMATION: Xaa is [AzK_PEG30kDa]

<400> SEQUENCE: 244

Ala Pro Thr Ser Ser Ser Thr Lys Lys Thr Gln Xaa Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Tyr Ala Asp Glu Thr Ala
            100             105             110
Thr Ile Val Glu Phe Leu Asn Arg Trp Ile Thr Phe Ser Gln Ser Ile
            115             120             125
Ile Ser Thr Leu Thr
    130

<210> SEQ ID NO 245
<211> LENGTH: 133
<212> TYPE: PRT
<213> ORGANISM: Artificial Sequence
<220> FEATURE:
<223> OTHER INFORMATION: Synthetic: IL-2_E15[AzK_PEG30kDa]
<220> FEATURE:
<221> NAME/KEY: misc_feature
<222> LOCATION: (15)..(15)
<223> OTHER INFORMATION: Xaa is [AzK_PEG30kDa]

<400> SEQUENCE: 245

Ala Pro Thr Ser Ser Ser Thr Lys Lys Thr Gln Leu Gln Leu Xaa His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
```

```
                    85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 246
<211> LENGTH: 133
<212> TYPE: PRT
<213> ORGANISM: Artificial Sequence
<220> FEATURE:
<223> OTHER INFORMATION: Synthetic: IL-2_V91K_C125S

<400> SEQUENCE: 246

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Lys Ile Val Leu Glu Leu
                85                  90                  95

Lys Gly Ser Glu Thr Thr Phe Met Cys Glu Tyr Ala Asp Glu Thr Ala
                100                 105                 110

Thr Ile Val Glu Phe Leu Asn Arg Trp Ile Thr Phe Ser Gln Ser Ile
            115                 120                 125

Ile Ser Thr Leu Thr
        130

<210> SEQ ID NO 247
<211> LENGTH: 133
<212> TYPE: PRT
<213> ORGANISM: Artificial Sequence
<220> FEATURE:
<223> OTHER INFORMATION: Synthetic: IL-2_N88R_C125S

<400> SEQUENCE: 247

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Arg Ile Asn Val Ile Val Leu Glu Leu
                85                  90                  95

Lys Gly Ser Glu Thr Thr Phe Met Cys Glu Tyr Ala Asp Glu Thr Ala
                100                 105                 110
```

```
Thr Ile Val Glu Phe Leu Asn Arg Trp Ile Thr Phe Ser Gln Ser Ile
        115                 120                 125

Ile Ser Thr Leu Thr
    130

<210> SEQ ID NO 248
<211> LENGTH: 30
<212> TYPE: PRT
<213> ORGANISM: Artificial Sequence
<220> FEATURE:
<223> OTHER INFORMATION: Synthetic: CTP peptide
<220> FEATURE:
<221> NAME/KEY: MOD_RES
<222> LOCATION: (6)..(6)
<223> OTHER INFORMATION: O-glycosylation site
<220> FEATURE:
<221> NAME/KEY: MOD_RES
<222> LOCATION: (12)..(12)
<223> OTHER INFORMATION: O-glycosylation site
<220> FEATURE:
<221> NAME/KEY: MOD_RES
<222> LOCATION: (17)..(17)
<223> OTHER INFORMATION: O-glycosylation site
<220> FEATURE:
<221> NAME/KEY: MOD_RES
<222> LOCATION: (23)..(23)
<223> OTHER INFORMATION: O-glycosylation site

<400> SEQUENCE: 248

Phe Gln Ser Ser Ser Ser Lys Ala Pro Pro Pro Ser Leu Pro Ser Pro
1               5                   10                  15

Ser Arg Leu Pro Gly Pro Ser Asp Thr Pro Ile Leu Pro Gln
            20                  25                  30

<210> SEQ ID NO 249
<211> LENGTH: 31
<212> TYPE: PRT
<213> ORGANISM: Artificial Sequence
<220> FEATURE:
<223> OTHER INFORMATION: Synthetic: CTP peptide

<400> SEQUENCE: 249

Phe Gln Asp Ser Ser Ser Ser Lys Ala Pro Pro Pro Ser Leu Pro Ser
1               5                   10                  15

Pro Ser Arg Leu Pro Gly Pro Ser Asp Thr Pro Ile Leu Pro Gln
            20                  25                  30
```

UNITED STATES PATENT AND TRADEMARK OFFICE
CERTIFICATE OF CORRECTION

Page 1 of 3

PATENT NO. : 12,234,271 B2
APPLICATION NO. : 17/016003
DATED : February 25, 2025
INVENTOR(S) : Jerod Ptacin et al.

It is certified that error appears in the above-identified patent and that said Letters Patent is hereby corrected as shown below:

In the Claims

In Claim 1, Column 646, Lines 3-13, should read: -- 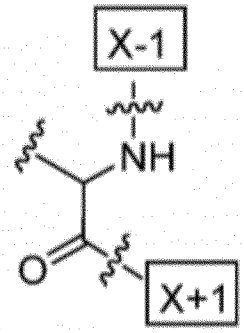 ; --;

In Claim 1, Column 646, Line 40, delete "[E60,]";

In Claim 12, Columns 647-648, should read:

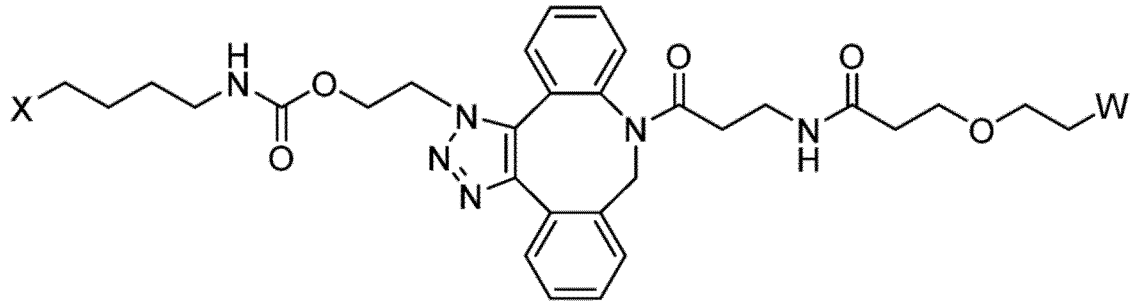

(III)

-- --;

Signed and Sealed this
Twenty-sixth Day of August, 2025

Coke Morgan Stewart
*Acting Director of the United States Patent and Trademark Office*

CERTIFICATE OF CORRECTION (continued)
U.S. Pat. No. 12,234,271 B2

In Claim 12, Column 649, Line 15, should read: -- 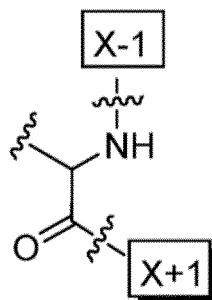 ; --;

In Claim 14, Columns 649-650, should read:

-- 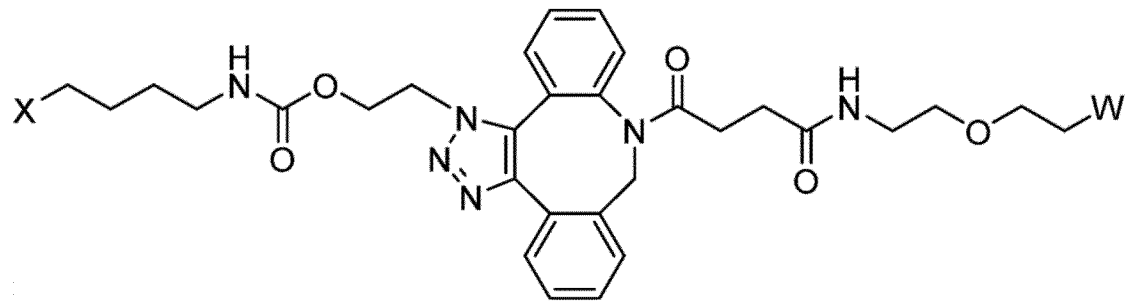

(V)

--;

In Claim 14, Column 651, Lines 8-18, should read: -- 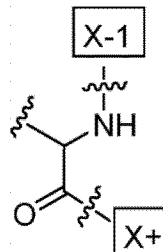 ; --;

In Claim 23, Column 656, Lines 17-27, should read: -- 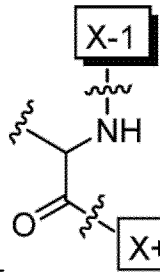 ; --;

CERTIFICATE OF CORRECTION (continued)
U.S. Pat. No. 12,234,271 B2

In Claim 29, Column 659, Lines 5-15, should read: -- 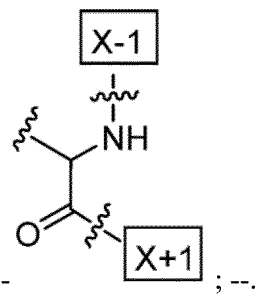 ; --.